US012173339B2

(12) United States Patent
Joung et al.

(10) Patent No.: US 12,173,339 B2
(45) Date of Patent: *Dec. 24, 2024

(54) VARIANTS OF CPF1 (CAS12a) WITH ALTERED PAM SPECIFICITY

(71) Applicant: The General Hospital Corporation, Boston, MA (US)

(72) Inventors: J. Keith Joung, Winchester, MA (US); Benjamin Kleinstiver, Medford, MA (US); Alexander Sousa, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 417 days.

This patent is subject to a terminal disclaimer.

(21) Appl. No.: 17/244,738

(22) Filed: Apr. 29, 2021

(65) Prior Publication Data

US 2021/0269788 A1 Sep. 2, 2021

Related U.S. Application Data

(63) Continuation of application No. 15/960,271, filed on Apr. 23, 2018, now Pat. No. 11,591,589.

(60) Provisional application No. 62/616,066, filed on Jan. 11, 2018, provisional application No. 62/488,426, filed on Apr. 21, 2017.

(51) Int. Cl.

| | |
|---|---|
| ***C12N 9/88*** | (2006.01) |
| ***C12N 9/22*** | (2006.01) |
| ***C12N 9/52*** | (2006.01) |
| ***C12N 15/62*** | (2006.01) |
| ***C12Q 1/6813*** | (2018.01) |

(52) U.S. Cl.

CPC ................ *C12N 9/88* (2013.01); *C12N 9/22* (2013.01); *C12N 9/52* (2013.01); *C12N 15/62* (2013.01); *C12N 2310/20* (2017.05); *C12Q 1/6813* (2013.01); *C12Y 401/99013* (2013.01)

(58) Field of Classification Search

None

See application file for complete search history.

(56) References Cited

U.S. PATENT DOCUMENTS

| | | | |
|---|---|---|---|
| 2011/0136895 | A1 | 6/2011 | Gregory et al. |
| 2014/0068797 | A1 | 3/2014 | Doudna et al. |
| 2014/0273226 | A1 | 9/2014 | Wu |
| 2014/0315985 | A1 | 10/2014 | May et al. |
| 2016/0208243 | A1 | 7/2016 | Zhang et al. |
| 2017/0058271 | A1 | 3/2017 | Joung et al. |
| 2017/0233756 | A1 | 8/2017 | Begemann et al. |
| 2017/0362644 | A1 | 12/2017 | Doudna et al. |
| 2018/0100148 | A1 | 4/2018 | Vakulskas et al. |
| 2018/0282714 | A1 | 10/2018 | Joung et al. |
| 2019/0106687 | A1 | 4/2019 | Joung et al. |
| 2019/0382775 | A1 | 12/2019 | Tan et al. |

FOREIGN PATENT DOCUMENTS

| | | |
|---|---|---|
| CN | 105543195 | 5/2016 |
| CN | 106244591 | 12/2016 |
| CN | 106479985 | 3/2017 |
| WO | WO 2015/089364 | 6/2015 |
| WO | WO 2016/115179 | 7/2016 |
| WO | WO 2016/115355 | 7/2016 |
| WO | WO 2016/141224 | 9/2016 |
| WO | WO 2017/015015 | 1/2017 |
| WO | WO 2017/040348 | 3/2017 |
| WO | WO 2017/070633 | 4/2017 |
| WO | WO 2017/127807 | 7/2017 |
| WO | WO 2017/184768 | 10/2017 |
| WO | WO 2017/219027 | 12/2017 |
| WO | WO 2018/022634 | 2/2018 |
| WO | WO 2018/226855 | 12/2018 |
| WO | WO 2019/040650 | 2/2019 |
| WO | WO 2019/126762 | 6/2019 |
| WO | WO 2021/151073 | 7/2021 |
| WO | WO 2021/151085 | 7/2021 |

OTHER PUBLICATIONS

Office Action in Chinese Appln. No. 201880042346.4, dated Feb. 18, 2023, 28 pages (with English translation).

Office Action in European Appln. No. 18788179.2, dated Apr. 11, 2022, 5 pages.

Notice of Acceptance in Australian Appln. No. 2018254619, dated Jul. 12, 2022, 4 pages.

Anders et al., "Structural basis of PAM-dependent target DNA recognition by the Cas9 endonuclease," Nature, Sep. 2014, 513(7519):569-573.

Bae et al., "Cas-OFFinder: a fast and versatile algorithm that searches for potential off-target sites of Cas9 RNA-guided endonucleases," Bioinformatics, 2014, 30: 1473-1475.

biorxiv.org [online], "Enhanced proofreading governs CRISPR-Cas9 targeting accuracy," Jul. 6, 2017, retrieved from the Internet: URL <https://www.biorxiv.org/content/biorxiv/early/2017/07/06/160036.full.pdf>, 22 pages.

Bolukbasi et al., "DNA-binding-domain fusions enhance the targeting range and precision of Cas9," Nat Methods, 2015, 12:1150-1156.

Chavez et al., "Highly-efficient Cas9-mediated transcriptional programming," Nat Methods., 2015, 12:326-8.

Chen et al., "CRISPR-Cas12a target binding unleashes indiscriminate single-stranded DNase activity," Science, 2018, 8 pages.

Chen et al., "Supplementary Materials for CRISPR-Cas12a target binding unleashes indiscriminate single-stranded DNase activity," Science, 2018, 28 pages.

(Continued)

*Primary Examiner* — Marsha Tsay

(74) *Attorney, Agent, or Firm* — Fish & Richardson P.C.

(57) ABSTRACT

Engineered CRISPR from *Prevotella* and *Francisella* 1 (Cpf1) nucleases with improved targeting range and enhanced on-target activity, and their use in genomic engineering, epigenomic engineering, base editing, genome targeting, genome editing, and in vitro diagnostics.

30 Claims, 96 Drawing Sheets

Specification includes a Sequence Listing.

(56) References Cited

OTHER PUBLICATIONS

CL Office Action in Chilean Appln. No. 201903004, dated Jun. 7, 2021, 34 pages (with English translation).
Cong et al., "Multiplex genome engineering using CRISPR/Cas systems," Science, 2013, 339:819-823.
Deltcheva et al., "CRISPR RNA maturation by trans-encoded small RNA and host factor RNase III," Nature, 2011, 471:602-607.
Dong et al., "The crystal structure of Cpf1 in complex with CRISPR RNA," Nature, 2016, 532(7600):522-6.
Doudna and Charpentier, "Genome editing. The new frontier of genome engineering with CRISPR-Cas9," Science, 2014, 346: 1258096 (11 pages).
East-Seletsky et al., "Two Distinct RNase Activities of CRISPR-C2c2 Enable Guide RNA Processing and RNA Detection," Nature, 2016, 538(7624): 270-273.
EP Extended European Search Report in European Appln. No. 18788179.2, dated Nov. 27, 2020, 10 pages.
EP Partial Supplementary European Search Report in European Appln. No. 17835126.8, dated Jan. 2, 2020, 12 pages.
EP Partial Supplementary European Search Report in European Appln. No. 17835126.8, dated Apr. 2, 2020, 9 pages.
Fagerlund et al., "The Cpf1 CRISPR-Cas protein expands genome-editing tools," Genome Biol, 2015, 16:251.
Fonfara et al., "The CRISPR-associated DNA-cleaving enzyme Cpf1 also processes precursor CRISPR RNA," Nature, 2016, 532(7600):517-21.
Friedland et al., "Characterization of Staphylococcus aureus Cas9: a smaller Cas9 for all-in-one adeno-associated virus delivery and paired nickase applications," Genome Biol, 2015, 16: 257 (10 pages).
Frock et al., "Genome-wide detection of DNA double-stranded breaks induced by engineered nucleases," Nat Biotechnol, 2015, 33:179-186.
Fu et al., "Improving CRISPR-Cas nuclease specificity using truncated guide RNAs," Nat Biotechnol, 2014, 32:279-284.
Gao et al., "Engineered Cpf1 Enzymes with Altered PAM Specificities," BioRxiv Preprint, 2016, 091611, 17 pages.
Gaudelli et al., "Programmable base editing of A•T to G•C in genomic DNA without DNA cleavage," Nature. 2017, 551(7681):464-471.
GenBank Accession No. EOS46485.1, "The Genome Sequence of Lachnospiraceae bacterium COE1," May 29, 2013, retrieved on Nov. 7, 2017, https://www.ncbi.nlm.nih.gov/protein/EOS46485, 2 pages.
Gootenberg et al., "Multiplexed and portable nucleic acid detection platform with Cas13, Cas12a, and Csm6," Science, 2018, 10 pages.
Gootenberg et al., "Nucleic acid detection with CRISPR-Cas13a/C2c2," Science, 2017, 356: 438-442.
Gootenberg et al., "Supplementary Materials for Multiplexed and portable nucleic acid detection platform with Cas13, Cas12a, and Csm6," Science, 2018, 85 pages.
Gootenberg et al., "Supplementary Materials for Nucleic acid detection with CRISPR-Cas13a/C2c2," Science, 2017, 45 pages.
Hsu et al., "Development and applications of CRISPR-Cas9 for genome engineering," Cell, 2014, 157:1262-1278.
International Preliminary Report on Patentability in International Appln. No. PCT/US2017/043753, mailed on Feb. 7, 2019, 10 pages.
International Preliminary Report on Patentability in International Appln. No. PCT/US2018/028919, dated Oct. 31, 2019, 9 pages.
International Search Report and Written Opinion in International Appln. No. PCT/US18/28919, mailed on Oct. 1, 2018, 17 pages.
International Search Report and Written Opinion in International Appln. No. PCT/US1 7/43753, mailed on Dec. 28, 2017, 18 pages.
International Search Report and Written Opinion in International Appln. No. PCT/US2016/020756, dated Jul. 26, 2016, 12 pages.
International Search Report and Written Opinion in International Appln. No. PCT/US2016/049147, dated on Dec. 23, 2016, 12 pages.
International Search Report and Written Opinion in International Appln. No. PCT/US2018/036293, dated Nov. 8, 2018, 12 pages.
International Search Report and Written Opinion in International Appln. No. PCT/US2018/047577, dated Jan. 29, 2019, 12 pages.
International Search Report and Written Opinion in International Appln. No. PCT/US2021/014900, dated Jul. 21, 2021, 12 pages.
International Search Report and Written Opinion in International Appln. No. PCT/US2021/014933, dated Jul. 20, 2021, 12 pages.
Invitation to Pay Additional Fees in International Appln. No. PCT/US2017/043753, dated Oct. 24, 2017, 2 pages.
Invitation to Pay Additional Fees in International Appln. No. PCT/US2018/028919, dated Aug. 7, 2018, 3 pages.
Jinek et al., "A programmable dual-RNA-guided DNA endonuclease in adaptive bacterial immunity," Science, 2012, 337: 816-821.
Jinek et al., "RNA-programmed genome editing in human cells," Elife, 2013, 2:e00471.
Kim et al., "Digenome-seq: genome-wide profiling of CRISPR-Cas9 off-target effects in human cells," Nat Methods, Mar. 2015, 12: 237-243.
Kim et al., "Erratum: Genome-wide analysis reveals specificities of Cpf1 endonucleases in human cells," Nat Biotechnol. 2016, 34(8): 888.
Kim et al., "Genome-wide analysis reveals specificities of Cpf1 endonucleases in human cells," Nat Biotechnol. 2016, 34(8):863-8.
Kim et al., "Increasing the genome-targeting scope and precision of base editing with engineered Cas9-cytidine deaminase fusions," Nat Biotechnol, 2017, 35(4):371-376.
Kleinstiver et al., "Broadening the targeting range of *Staphylococcus aureus* CRISPR-Cas9 by modifying PAM recognition," Nat Biotechnol, 2015, 33: 1293-1298.
Kleinstiver et al., "Engineered CRISPR-Cas9 nucleases with altered specificities," Nature, 2015, 523:481-485.
Kleinstiver et al., "Genome-wide specificities of CRISPR-Cas Cpf1 nucleases in human cells," Nat Biotechnol, 2016, 34(8):869-74.
Kleinstiver et al., "High-fidelity CRISPR-Cas9 nucleases with no detectable genome-wide off-target effects," Nature, 2016, 529:490-495.
Komor et al., "Improved base excision repair inhibition and bacteriophage Mu Gam protein yields C:G-to-T:A base editors with higher efficiency and product purity," Sci Adv, 2017, 3(8):eaao4774.
Komor et al., "Programmable editing of a target base in genomic DNA without double-stranded DNA cleavage," Nature, 2016, 533(7603):420-4.
Maeder and Gersbach, "Genome-editing Technologies for Gene and Cell Therapy," Mol Ther, 2016, 24: 430-446.
Makarova et al., "An updated evolutionary classification of CRISPR-Cas systems," Nat Rev Microbiol, 2015, 13:722-736.
Mali et al., "RNA-guided human genome engineering via Cas9," Science, 2013, 339: 823-826.
Moreno-Mateos et al., "CRISPR-Cpf1 mediates efficient homology-directed repair and temperature-controlled genome editing," Nat Commun., 2017, 8:2024.
Nishamasu et al., "Engineered CRISPR-Cas9 nuclease with expanded targeting space," Science, Aug. 2018, 361(6408):1259-1262.
Nishida et al., "Targeted nucleotide editing using hybrid prokaryotic and vertebrate adaptive immune systems," Science. 2016, 353(6305).
Protein Data Bank (PDB) [online], "4UN3-Crystal structure of Cas9 bound to PAM-containing DNA target," Sequence Display for the Entities in PDB 4UN3, Jul. 23, 2014, retrieved May 6, 2015, retrieved from URL <http://www.rcsb.org/pdb/explore/explore.do?structureid=4UN3>, 2 pages.
Reyon et al., FLASH assembly of TALENs for high-throughput genome editing, Nat Biotechnol, May 2012, 30: 460-465.
Rohland and Reich, "Cost-effective, high-throughput DNA sequencing libraries for multiplexed target capture," Genome Res, 2012, 22:939-46.
Sander and Joung, "CRISPR-Cas systems for editing, regulating and targeting genomes," Nat Biotechnol, 2014, 32:347-355.
Schunder et al., "First indication for a functional CRISPR/Cas system in Francisella tularensis," Int J Med Microbiol, 2013, 303:51-60.
Shmakov et al., "Discovery and Functional Characterization of Diverse Class 2 CRISPR-Cas Systems," Mol Cell, 2015, 60(3):385-97.

(56) References Cited

OTHER PUBLICATIONS

Slaymaker et al., "Rationally engineered Cas9 nucleases with improved specificity," Science, 2016, 351:84-88.
Tak et al., "Inducible and multiplex gene regulation using CRISPR-Cpf1-based transcription factors," Nat Methods, 2017, 14:1163-1166.
Tak et al., "Inducible, tunable and multiplex human gene regulation using CRISPR-Cpf1-based transcription factors," bioRxiv, 2017, 150656 (21 pages).
Tsai et al., "Dimeric CRISPR RNA-guided FokI nucleases for highly specific genome editing," Nat Biotechnol, 2014, 32:569-576.
Tsai et al., "GUIDE-seq enables genome-wide profiling of off-target cleavage by CRISPR-Cas nucleases," Nat Biotechnol, 2015, 33:187-197.
Tsai et al., "Open-source guideseq software for analysis of GUIDE-seq data," Nat Biotechnol, 2016, 34:483.
Wang et al., "Unbiased detection of off-target cleavage by CRISPR-Cas9 and TALENs using integrase-defective lentiviral vectors," Nat Biotechnol, 2015, 33:175-178.
Wright et al., "Biology and Applications of CRISPR Systems: Harnessing Nature's Toolbox for Genome Engineering," Cell, Jan. 2016, 164: 29-44.
Yamano et al., "Crystal Structure of Cpf1 in Complex with Guide RNA and Target DNA," Cell, 2016, 165(4):949-62.
Yin et al., "Therapeutic genome editing by combined viral and non-viral delivery of CRISPR system components in vivo," Nat Biotechnol, Mar. 2016, 34: 328-333.
Zetsche et al., "Cpf1 Is a Single RNA-Guided Endonuclease of a Class 2 CRISPR-Cas System," Cell, 2015, 163:759-771.
Zetsche et al., "Multiplex gene editing by CRISPR-Cpf1 through autonomous processing of a single crRNA array," Nat Biotechnol., 2017, 35:31-34.
Office Action in Australian Appln. No. 2018254619, dated Oct. 29, 2021, 5 pages.
Office Action in Chilean Appln. No. 201903004, dated Dec. 6, 2021, 26 pages (with English machine translation).
Office Action in Chinese Appln. No. 201880042346.4, dated Nov. 22, 2023, 8 pages (with English translation).
Office Action in Australian Appln. No. 2022246445, dated Oct. 6, 2023, 5 pages.
Office Action in Chilean Appln. No. 202102739, dated Jul. 14, 2023, 34 pages (with English machine translation).
Office Action in Chilean Appln. No. 202102740, dated Jul. 14, 2023, 34 pages (with English machine translation).
Office Action in Chilean Appln. No. 202102741, dated Jul. 14, 2023, 34 pages (with English machine translation).
Office Action in Chilean Appln. No. 202102742, dated Jul. 14, 2023, 36 pages (with English machine translation).
Office Action in Chilean Appln. No. 202102739, dated Jan. 3, 2024, 36 pages (with English machine translation).
Office Action in Chilean Appln. No. 202102740, dated Jan. 3, 2024, 36 pages (with English machine translation).
Office Action in Chilean Appln. No. 202102741, dated Jan. 3, 2024, 40 pages (with English machine translation).
Office Action in Chilean Appln. No. 202102742, dated Jan. 3, 2024, 38 pages (with English machine translation).
Office Action in Chilean Appln. No. 202201524, dated Jan. 2, 2024, 36 pages (with English machine translation).
Office Action in Chilean Appln. No. 202201525, dated Jan. 2, 2024, 42 pages (with English machine translation).

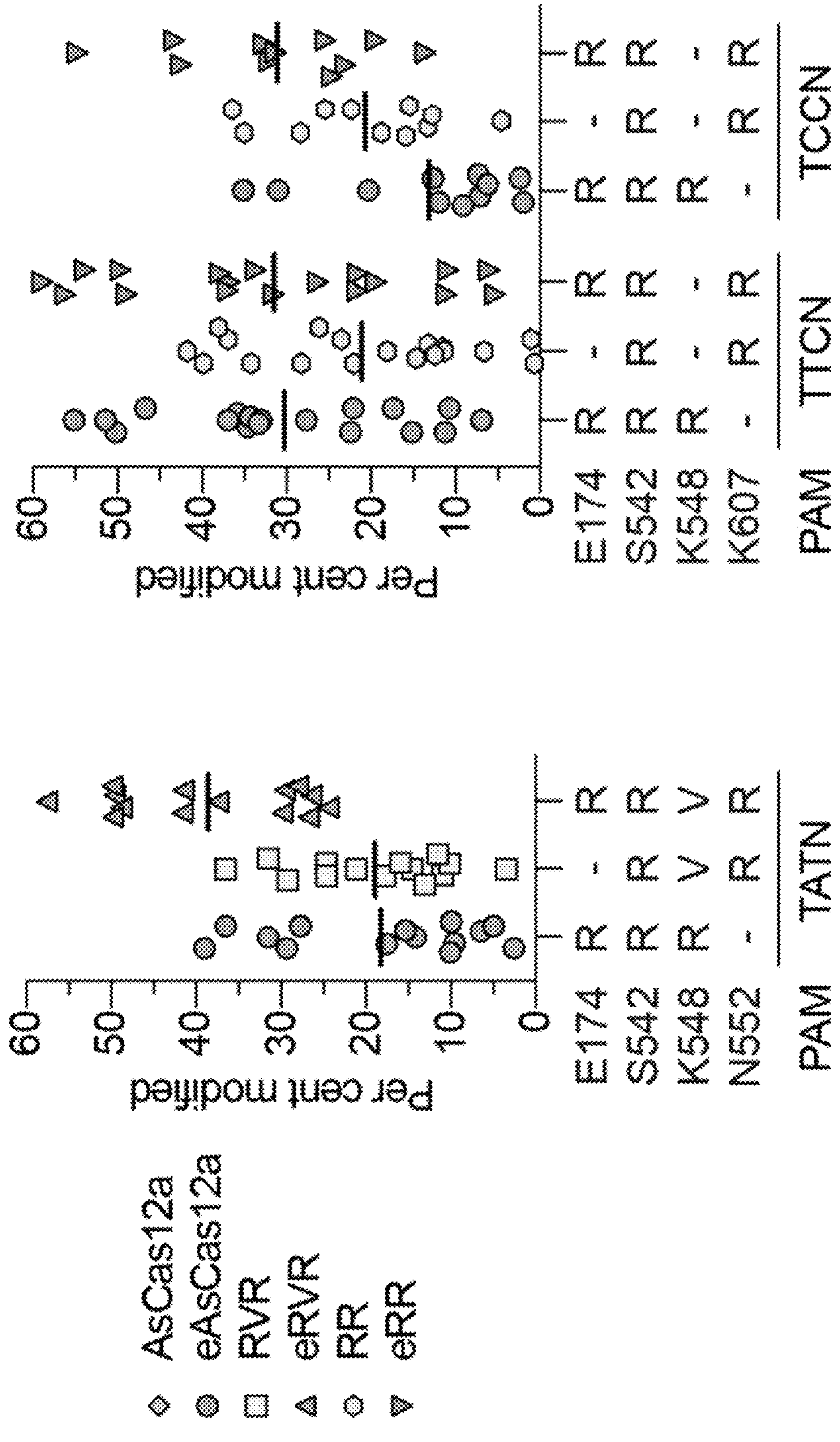
FIGs. 16C-D

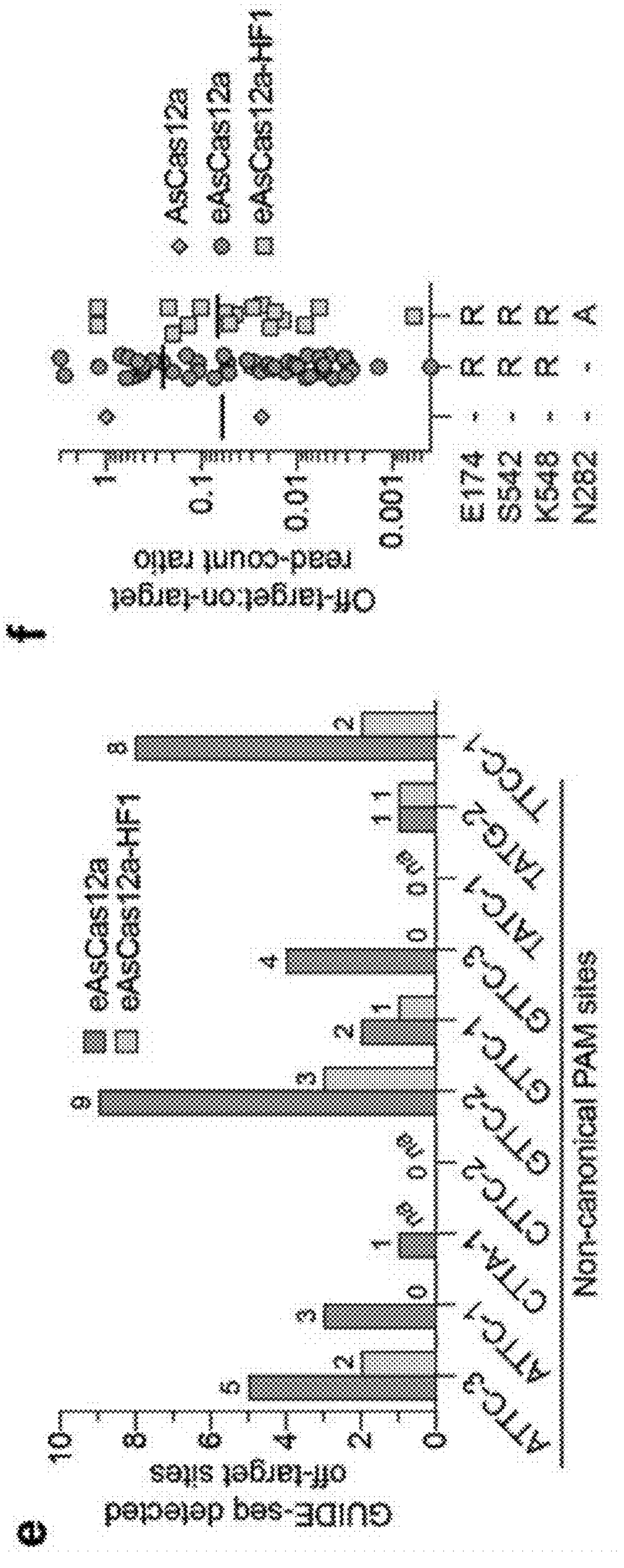
FIGs. 17E-F

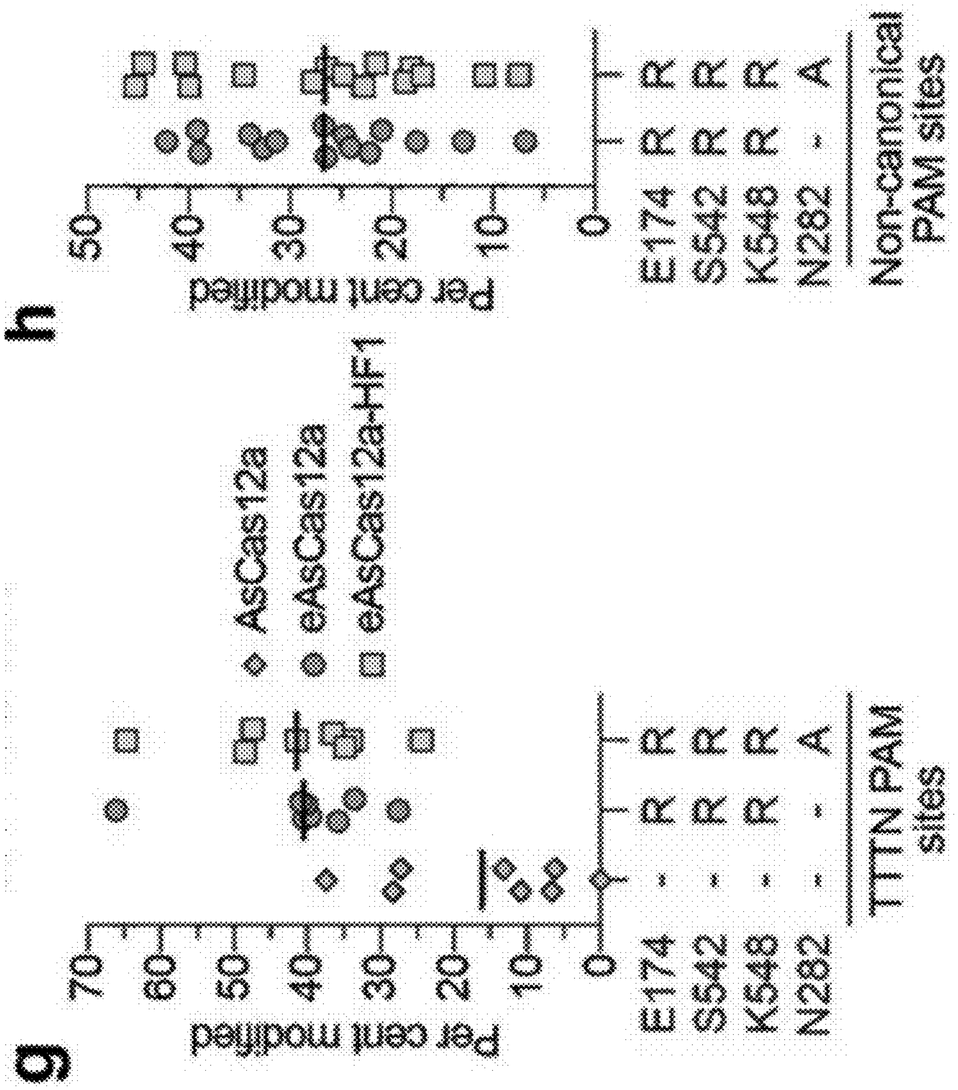
FIGs. 17G-H

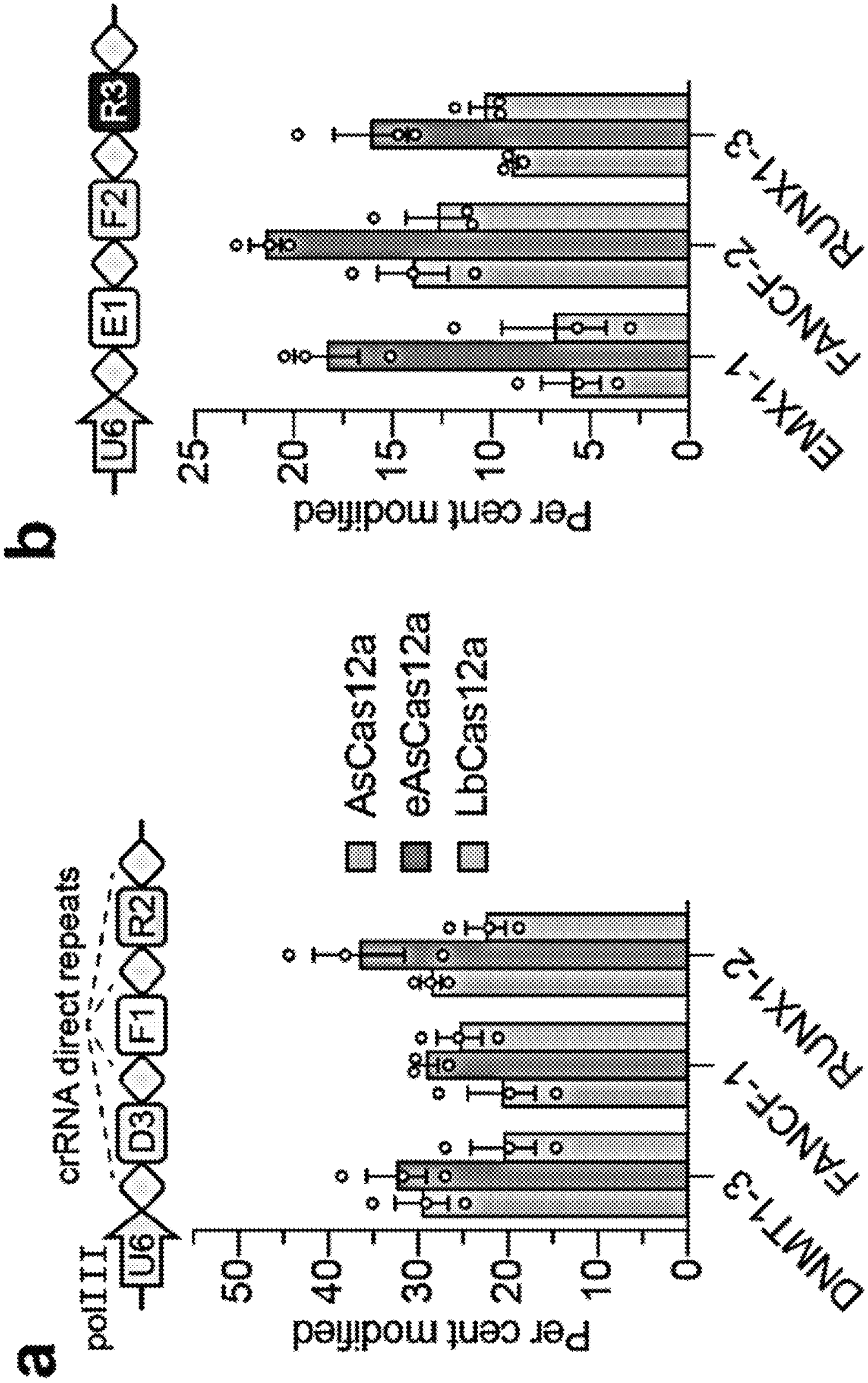
FIGs. 18A-B

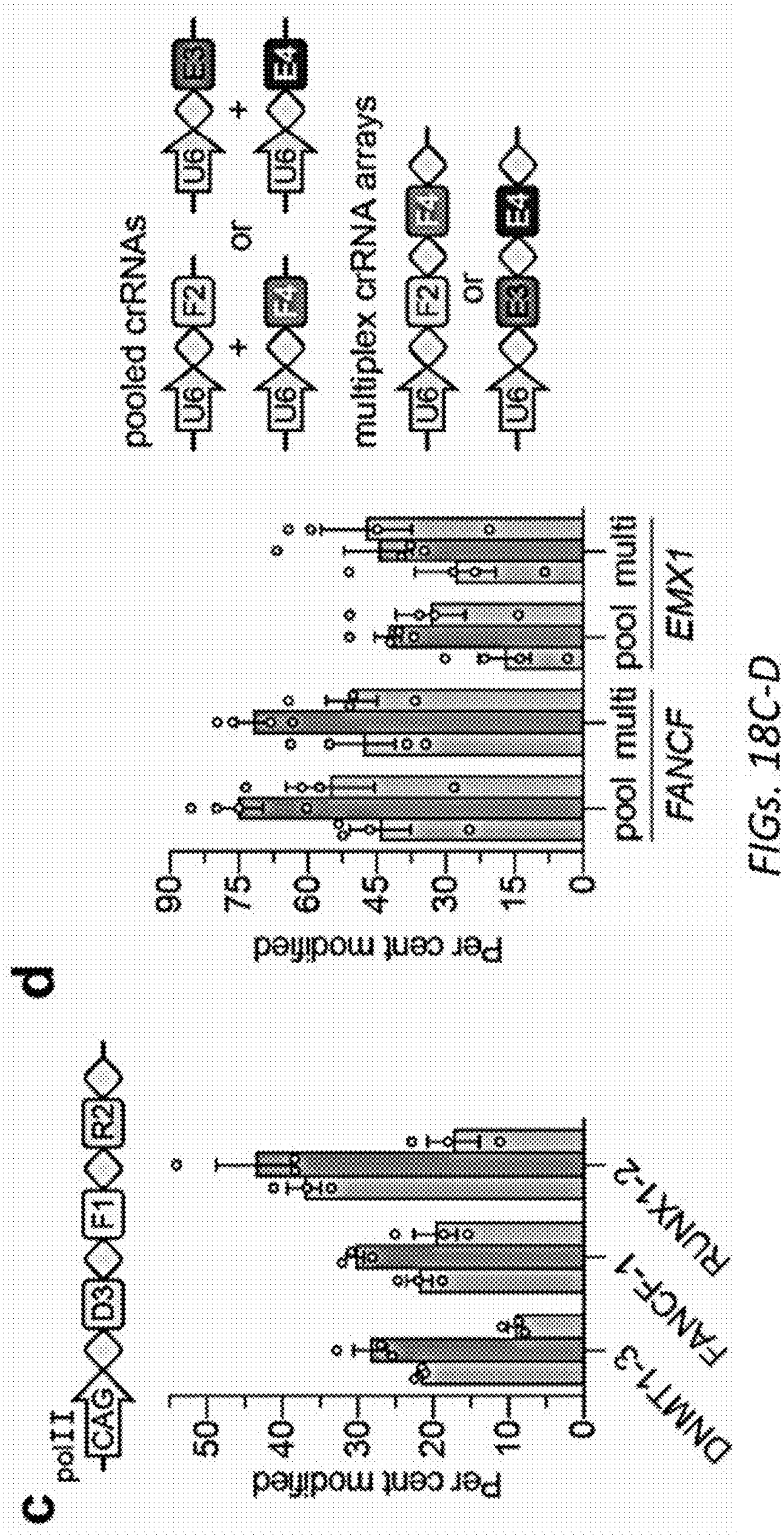
FIGs. 18C-D

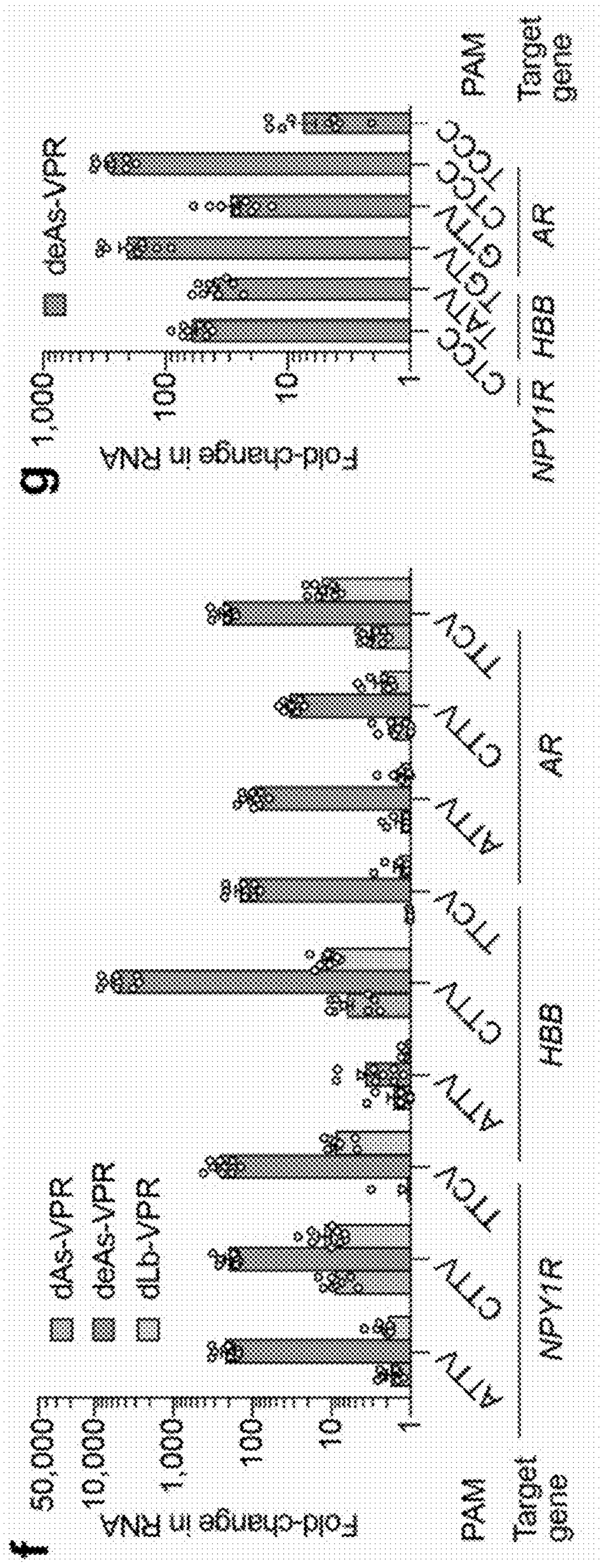
FIGs. 18F-G

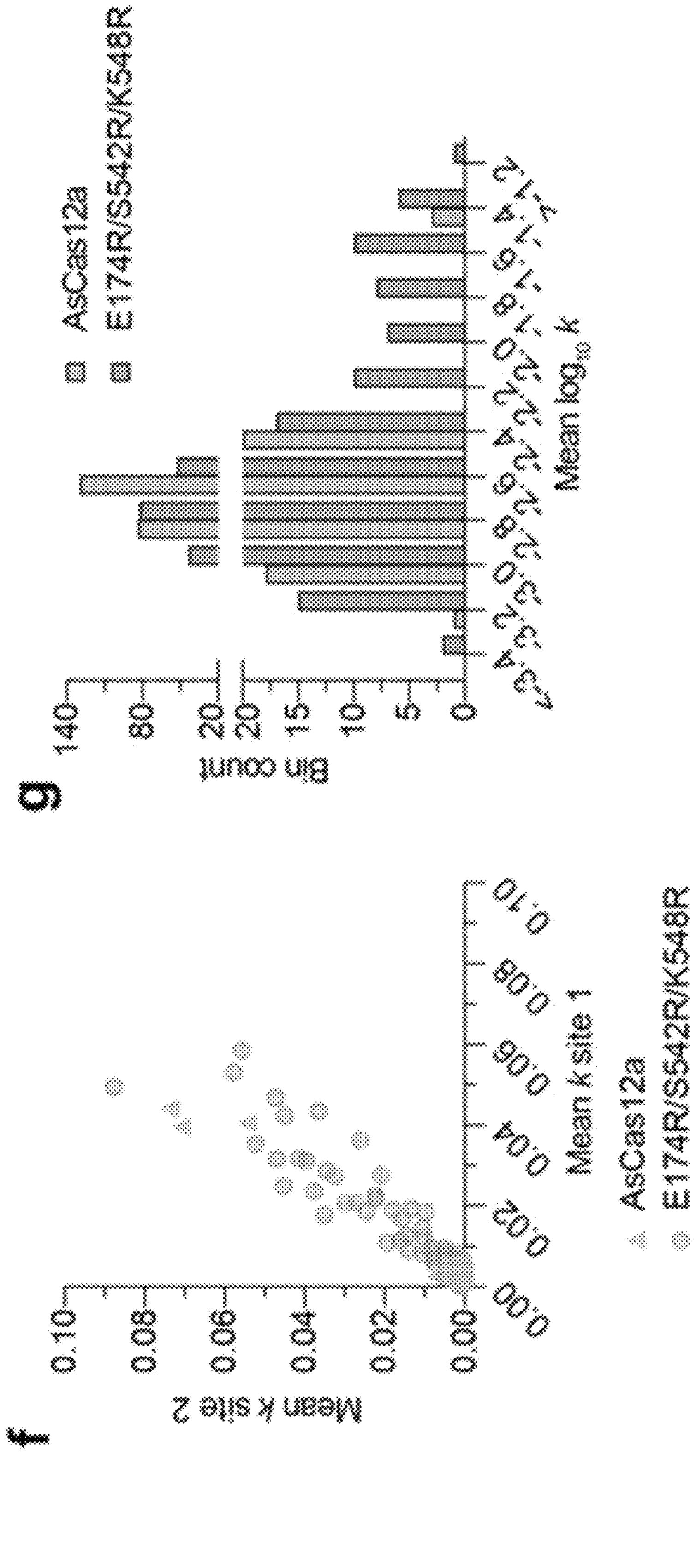
FIGs. 21F-G

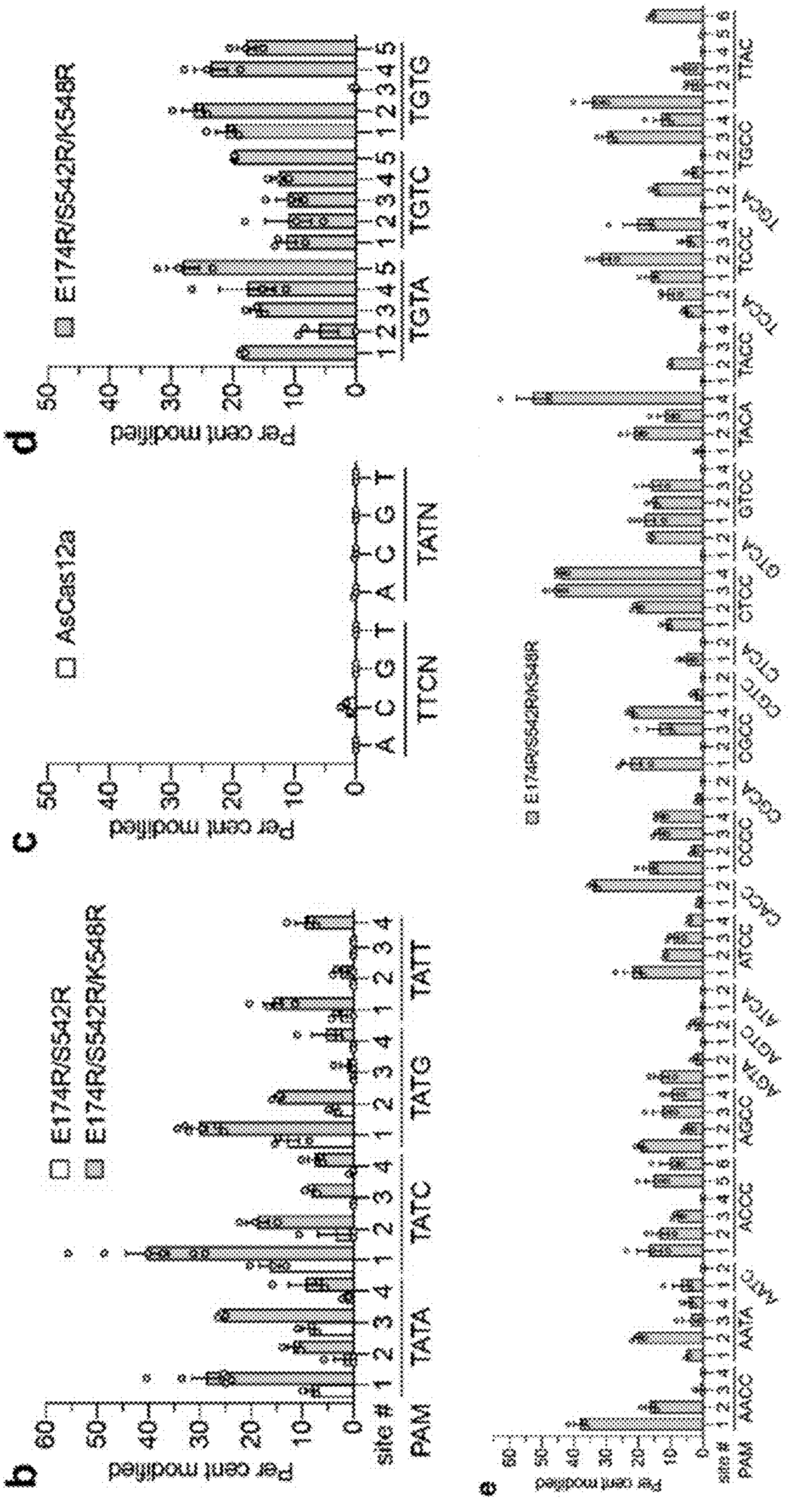
FIGS. 23B-E

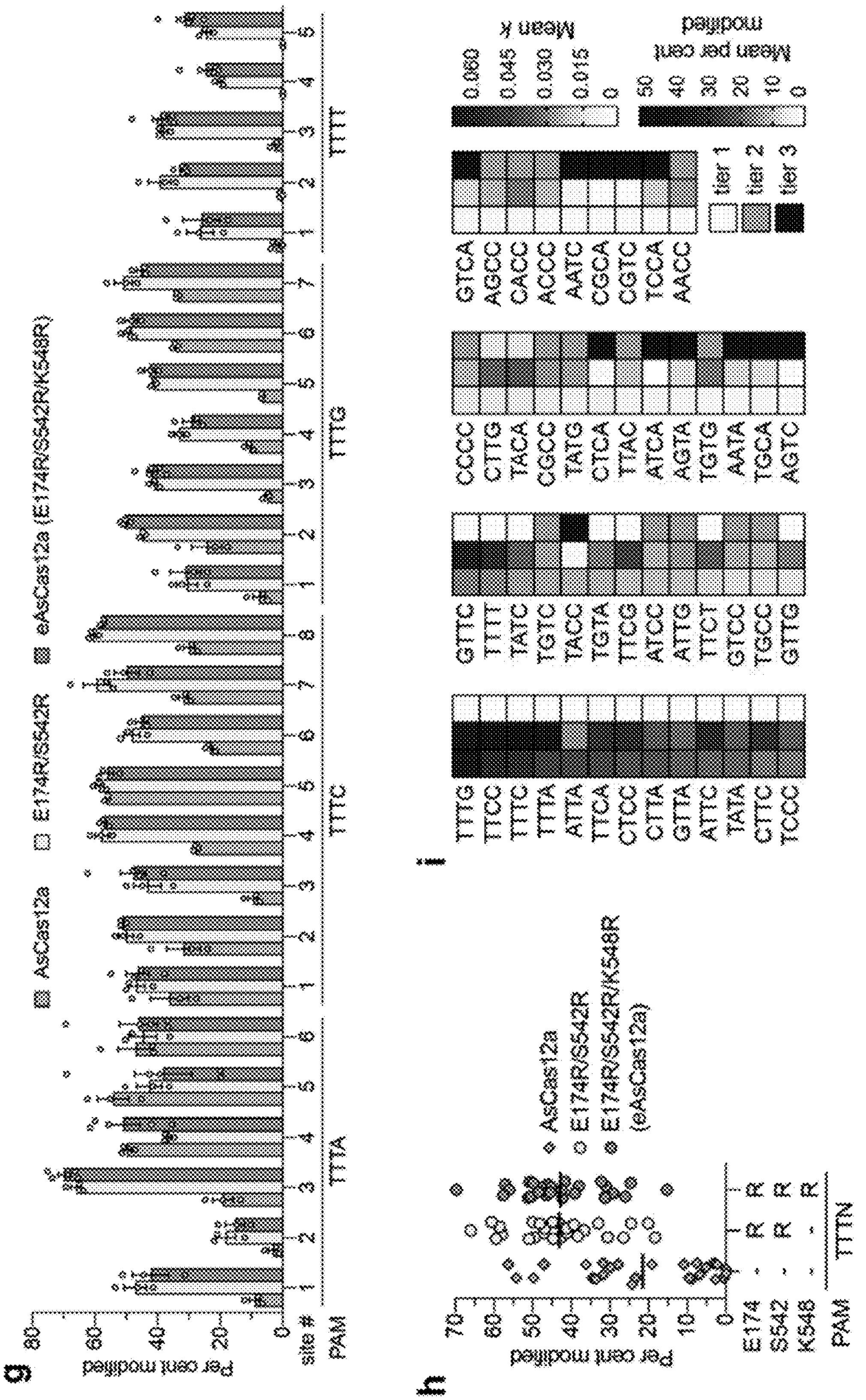
FIGs. 23G-I

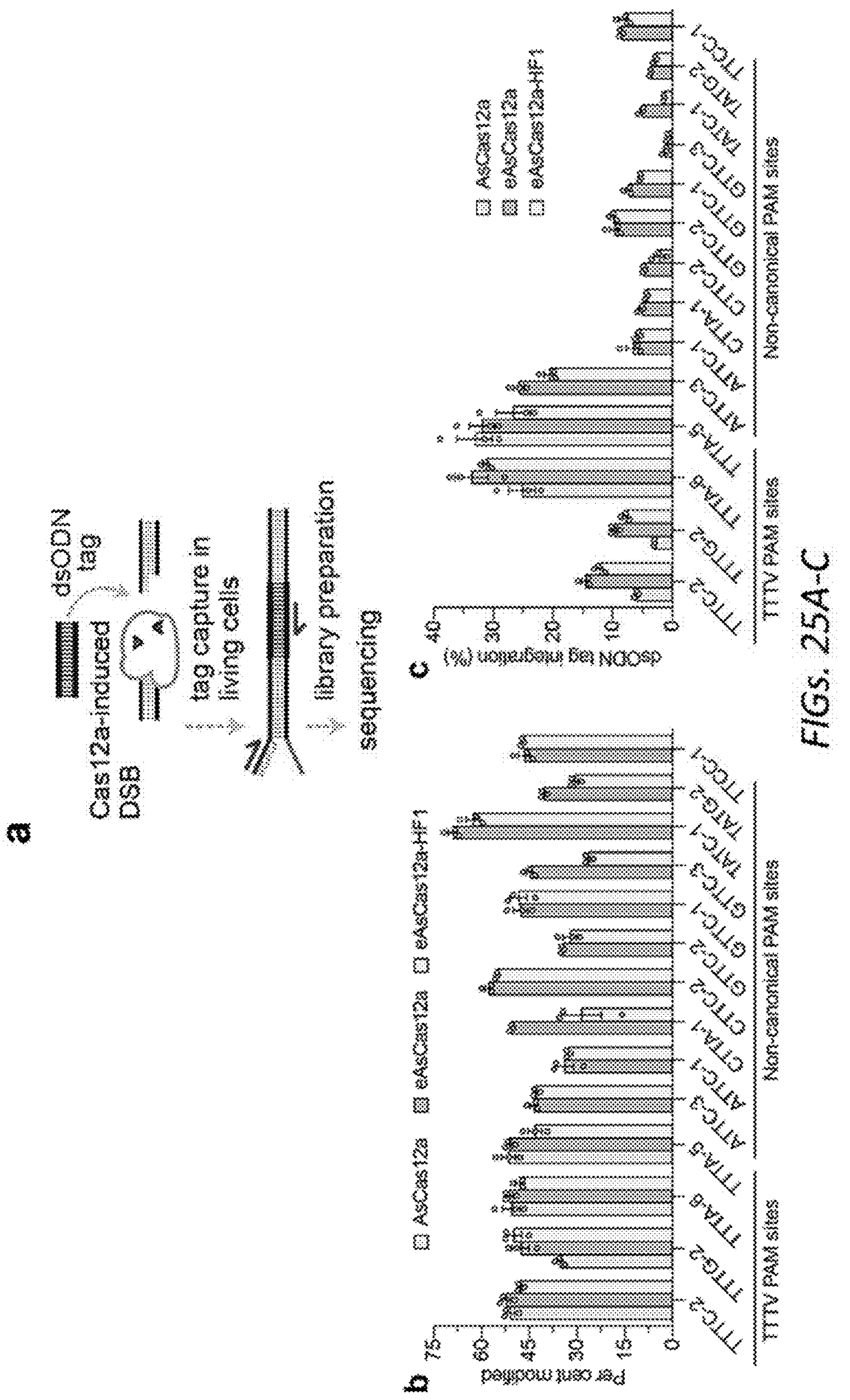
FIGs. 25A-C

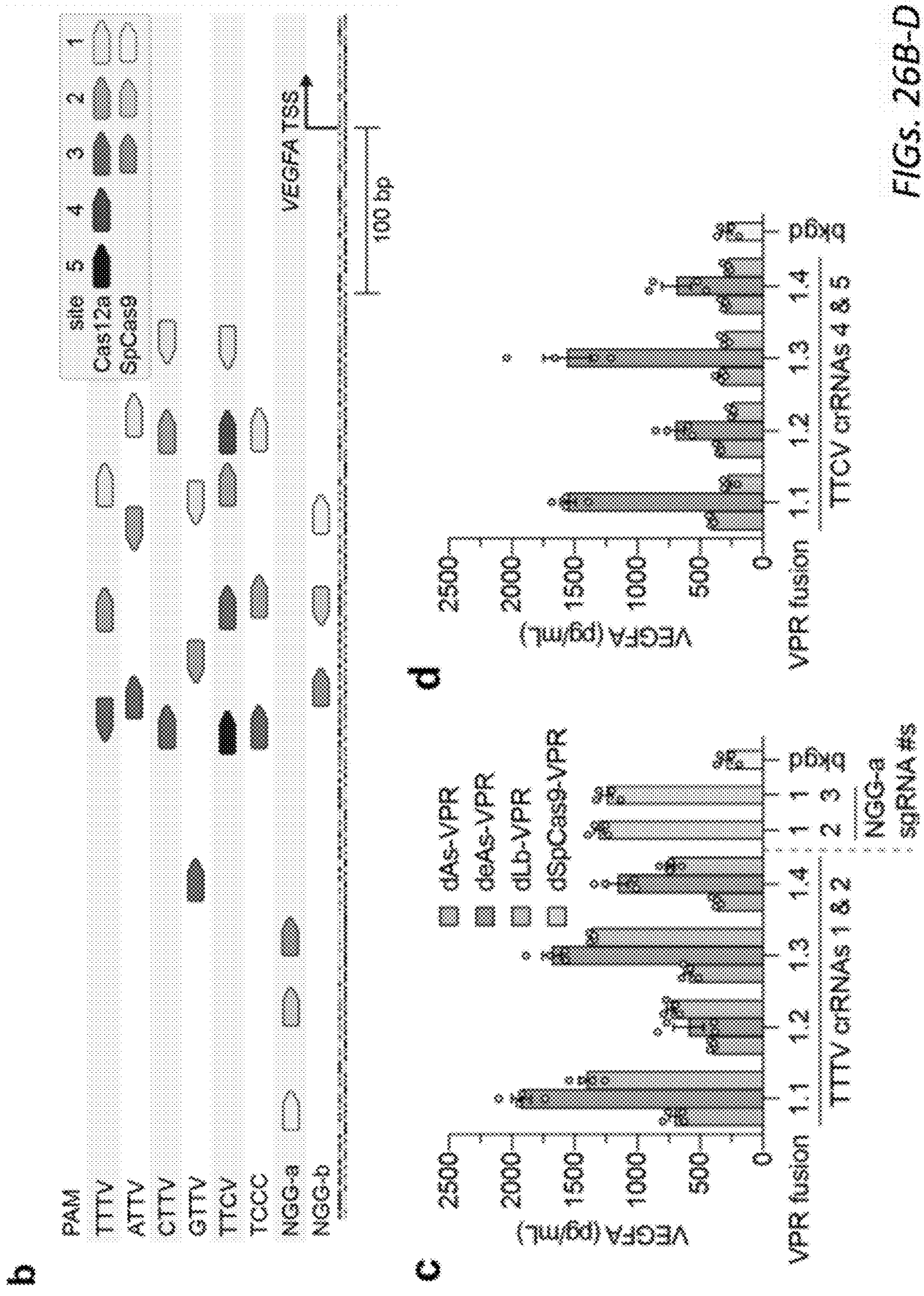
FIGs. 26B-D

VARIANTS OF CPF1 (CAS12a) WITH ALTERED PAM SPECIFICITY

CLAIM OF PRIORITY

This application is a continuation application of U.S. patent application Ser. No. 15/960,271, filed Apr. 23, 2018, which claims the benefit of U.S. Patent Application Ser. No. 62/616,066, filed on Jan. 11, 2018 and 62/488,426, filed on Apr. 21, 2017. The entire contents of the foregoing are hereby incorporated by reference.

FEDERALLY SPONSORED RESEARCH OR DEVELOPMENT

This invention was made with Government support under Grant No. GM105378, HG009490, and GM118158 awarded by the National Institutes of Health. The Government has certain rights in the invention.

TECHNICAL FIELD

The present invention relates, at least in part, to engineered CRISPR from *Prevotella* and *Francisella* 1 (Cpf1) nucleases with altered and improved target specificities and their use in genomic engineering, epigenomic engineering, genome targeting, genome editing, and in vitro diagnostics.

BACKGROUND

CRISPR-Cas Cpf1 nucleases (also referred to as Cas12a nucleases) have recently been described as an alternative to Cas9 nucleases for genome editing applications (Zetsche et al. *Cell* 163, 759-771 (2015): Shmakov et al., *Mol Cell.* 2015 Nov. 5; 60(3): 385-97; Kleinstiver et al., *Nat Biotechnol.* 2016 August; 34(8): 869-74; Kim et al., *Nat Biotechnol.* 2016 August; 34(8):863-8). Cpf1 nucleases possess a number of potentially advantageous properties that include, but are not limited to: recognition of T-rich protospacer-adjacent motif (PAM) sequences, relatively greater genome-wide specificities in human cells than wild-type *Streptococcus pyogenes* Cas9 (SpCas9), an endoribonuclease activity to process pre-crRNAs that simplifies the simultaneous targeting of multiple sites (multiplexing), DNA endonuclease activity that generates a 5' DNA overhang (rather than a blunt double-strand break as observed with SpCas9), and cleavage of the protospacer DNA sequence on the end most distal from the PAM (compared with cleavage at the PAM proximal end of the protospacer as is observed with SpCas9 and SaCas9). To date, Cpf1 orthologues from *Acidaminococcus* sp. BV3L6. Lachnospiraceae bacterium ND2006, and *Francisella tularensis* subsp. *novicida* U112 (AsCpf1, LbCpf1, and FnCpf1 respectively), are the only orthologues that have been described to robustly function in human cells. Despite these capabilities, Cpf1 nucleases have been adopted less rapidly for genome editing compared to SpCas9. One potential reason could be the requirement for a longer PAM that constrains targeting to roughly once in every 43 bps of random DNA sequence, compared to once in every 8 bps for SpCas9.

Here we addressed this targeting range limitation by utilizing a structure-guided engineering approach to generate AsCpf1 variants with not only greatly expanded targeting range, but also substantially improved on-target activities. In addition to improved potency and versatility as nucleases for genome editing, we demonstrate that these variants can be leveraged for other applications including multiplex nuclease targeting, epigenome editing, C-to-T base-editing, and Cpf1-mediated DNA detection, all at levels not previously possible with wild-type AsCpf1.

SUMMARY

Described herein are a series of AsCpf1, FnCpf1, and LbCpf1 variants that recognize a broader range of PAMs than their wild-type counterparts, thereby increasing the range of sites that can be targeted by this class of RNA-guided nucleases. In addition, these variants perform better than wild-type Cpf1 nucleases at recognizing and modifying target sites harboring canonical TTTN PAMs. The enhanced activities of the variants described herein improve the activities of AsCpf1 for genome editing, epigenome editing, base editing, and in vitro DNA detection.

Thus, provided herein are isolated CRISPR from *Prevotella* and *Francisella* 1 (Cpf1) proteins from *Acidaminococcus* sp. BV3L6 (AsCpf1), comprising a sequence that is at least 80% identical to the amino acid sequence of SEQ ID NO:2 with mutations at one or more of the following positions: E174, S170, K548, N551, T167, T539, N552, M604, and/or K607 of SEQ ID NO:2.

In some embodiments, the isolated Cpf1 proteins include a mutation at E174R, optionally with one or more additional mutations at S170R, K548, N551, T167, T539, S542, N552, M604, and/or K607. In some embodiments, the isolated Cpf1 proteins include a mutation at S170R, optionally with one or more additional mutations at E174R, K548, N551, T167, T539, S542, N552, M604, and/or K607.

In some embodiments, the isolated Cpf1 proteins include a mutation at S542.

In some embodiments, the isolated Cpf1 proteins include mutations S542Q, S542K, or S542R.

In some embodiments, the isolated Cpf1 proteins include a sequence that is at least 95% identical to the amino acid sequence of SEQ ID NO:2.

In some embodiments, the isolated Cpf1 proteins include one or more of the following mutations: E174R, S170R, K548R, S170K, E174K, T167A, T539K, T539R, K548V, N551R, N552R, M604A, K607Q, K607R, K607S, and/or K607H.

In some embodiments, the isolated Cpf1 proteins include the following mutations: S170R/E174R, E174R/K548R, S170R/K548R, E174R/S542R, S170R/S542R, E174R/S542R/K548R, E174R/N551R, S170R/N551R, S542R/K548R, S542R/N551R, S542R/N552R, K548R/N551R, S170R/S542R/K607R, E174R/S542R/K607R, E174R/S542R/K607H, E174R/S542R/K548R/N551R, S170R/S542R/K548V/N552R, E174R/S542R/K548V/N552R, S170R/S542R/K607R, or E174R/S542R/K607R of SEQ ID NO:2.

In some embodiments, the isolated Cpf1 proteins include one or more mutations that decrease nuclease activity, e.g., selected from the group consisting of mutations at D908, E993, R1226, D1235, and/or D1263, preferably D908A, E993A, R1226A, D1235A, and/or D1263A.

In some embodiments, the isolated Cpf1 proteins include a mutation at one or more of N282, N178, S186, N278, R301, T315, S376, N515, K523, K524, K603, K965, Q1013, Q1014, and/or K1054, preferably at N282, T315, N515, or N278, preferably wherein the mutation increases specificity of the protein. In some embodiments, the isolated Cpf1 proteins include a mutation selected from the group consisting of N282A, T315A, N515A, or N278A Also provided herein are isolated CRISPR from *Prevotella* and *Francisella* 1 (Cpf1) proteins from *Lachno-* spiraceae bacterium ND2006 (LbCpf1), comprising a sequence that is at least 80% identical to SEQ ID NO:11, with one or more of the following positions: T152, D156, G532, and/or K538 of SEQ ID NO:11.

In some embodiments, the isolated Cpf1 proteins include a sequence that is at least 95% identical to the amino acid sequence of SEQ ID NO:11.

In some embodiments, the isolated Cpf1 proteins include one or more of the following mutations: T152R, T152K, D156R, D156K, G532R, and/or K538R.

In some embodiments, the isolated Cpf1 proteins include the following mutations: D156R/G532R/K538R.

In some embodiments, the isolated Cpf1 proteins include one or more mutations that decrease nuclease activity, e.g., selected from the group consisting of mutations at D832, E925, R1138, D1148, and/or D1180, preferably D832A, E925A, R1138A, D1148A, and/or D1180A.

In some embodiments, the isolated Cpf1 proteins include mutations at one or more of S202, N274, N278, K290, K367, K532, K609, K915, Q962, K963, K966, K1002 and/or S1003, preferably wherein the mutation increases specificity of the protein. In some embodiments, the isolated Cpf1 proteins include one or more of the following mutations: S202A, N274A, N278A, K290A, K367A, K532A, K609A, K915A, Q962A, K963A, K966A, K1002A and/or S1003A.

Also provided herein are isolated CRISPR from *Prevotella* and *Francisella* 1 (Cpf1) proteins from *Francisella tularensis* (FnCpf1), comprising a sequence that is at least 80% identical to SEQ ID NO:4, with mutations at one or more of the following positions: K180, E184, N607, K613, D616, N617, and/or K671 of SEQ ID NO:4.

In some embodiments, the isolated Cpf1 proteins include a sequence that is at least 95% identical to the amino acid sequence of SEQ ID NO:4.

In some embodiments, the isolated Cpf1 proteins include one or more of the following mutations: K180R, E184R, N607R, K613R, K613V, D616R, N617R, K671H, and K671R.

In some embodiments, the isolated Cpf1 proteins include the following mutations: N607R/K613R, N607R/K613V, N607R/K613V/D616R, or N607R/K613R/D616R.

In some embodiments, the isolated Cpf1 proteins include one or more mutations that decrease nuclease activity, e.g., selected from the group consisting of mutations at D917, E1006, R1218, D1227, and/or D1255, preferably D917A, E1006A, R1218A, D1227A, and/or D1255A.

Also provided herein are fusion proteins comprising the Cpf1 proteins described herein, fused to a heterologous functional domain, with an optional intervening linker, wherein the linker does not interfere with activity of the fusion protein.

In some embodiments, the heterologous functional domain is a transcriptional activation domain, e.g., the tetrameric VP16 fusion termed VP64, Rta, NF-κB p65, or VPR (a VP64, p65, Rta fusion protein).

In some embodiments, the heterologous functional domain is a transcriptional silencer or transcriptional repression domain. In some embodiments, the transcriptional repression domain is a Krueppel-associated box (KRAB) domain, ERF repressor domain (ERD), or mSin3A interaction domain (SID). In some embodiments, the transcriptional silencer is Heterochromatin Protein 1 (HP1).

In some embodiments, the heterologous functional domain is an enzyme that modifies the methylation state of DNA, e.g., a DNA methyltransferase (DNMT) or a TET protein, e.g., TET1.

In some embodiments, the heterologous functional domain is an enzyme that modifies a histone subunit, e.g., a histone acetyltransferase (HAT), histone deacetylase (HDAC), histone methyltransferase (HMT), or histone demethylase.

In some embodiments, the heterologous functional domain is a deaminase that modifies cytosine DNA bases, e.g., a cytidine deaminase from the apolipoprotein B mRNA-editing enzyme, catalytic polypeptide-like (APOBEC) family of deaminases, including APOBEC1, APOBEC2, APOBEC3A, APOBEC3B, APOBEC3C, APOBEC3D/E, APOBEC3F, APOBEC3G, APOBEC3H, APOBEC4, activation-induced cytidine deaminase (AID), cytosine deaminase 1 (CDA1), and CDA2, and cytosine deaminase acting on tRNA (CDAT).

In some embodiments, the heterologous functional domain is a deaminase that modifies adenosine DNA bases, e.g., the deaminase is an adenosine deaminase 1 (ADA1), ADA2; adenosine deaminase acting on RNA 1 (ADAR1), ADAR2, ADAR3; adenosine deaminase acting on tRNA 1 (ADAT1), ADAT2, ADAT3; and naturally occurring or engineered tRNA-specific adenosine deaminase (TadA).

In some embodiments, the heterologous functional domain is an enzyme, domain, or peptide that inhibits or enhances endogenous DNA repair or base excision repair (BER) pathways, e.g., uracil DNA glycosylase inhibitor (UGI) that inhibits uracil DNA glycosylase (UDG, also known as uracil N-glycosylase, or UNG) mediated excision of uracil to initiate BER; or DNA end-binding proteins such as Gam from the bacteriophage Mu.

In some embodiments, the heterologous functional domain is a biological tether, e.g., MS2, Csy4 or lambda N protein.

In some embodiments, the heterologous functional domain is FokI.

Also provided herein are isolated nucleic acids encoding the Cpf1 variant proteins and fusion proteins described herein.

In addition, provided herein are vectors comprising the nucleic acids. In some embodiments, the isolated nucleic acid encodes an isolated CRISPR from *Prevotella* and *Francisella* 1 (Cpf1) protein from *Acidaminococcus* sp. BV3L6 (AsCpf1), with mutations at one or more of the following positions: T167, S170, E174, T539, K548, N551, N552, M604, and/or K607 of SEQ ID NO:2 and is operably linked to one or more regulatory domains for expressing an isolated CRISPR from *Prevotella* and *Francisella* 1 (Cpf1) protein from *Acidaminococcus* sp. BV3L6 (AsCpf1), with mutations at one or more of the following positions: T167, S170, E174, T539, K548, N551, N552, M604, and/or K607 of SEQ ID NO:2.

In some embodiments, the isolated nucleic acid encodes an isolated CRISPR from *Prevotella* and *Francisella* 1 (Cpf1) protein from Lachnospiraceae bacterium ND2006 (LbCpf1), with mutations at one or more of the following positions: T152, D156, G532, and/or K538 of SEQ ID NO: 11 and is operably linked to one or more regulatory domains for expressing an isolated CRISPR from *Prevotella* and *Francisella* 1 (Cpf1) protein from Lachnospiraceae bacterium ND2006 (LbCpf1), with mutations at one or more of the following positions: T152, D156, G532, and/or K538 of SEQ ID NO:11.

In some embodiments, the isolated nucleic acid encodes an isolated CRISPR CRISPR from *Prevotella* and *Francisella* 1 (Cpf1) protein from *Francisella tularensis* (FnCpf1), comprising a sequence that is at least 80% identical to SEQ ID NO:4, with mutations at one or more of the following positions: K180, E184, N607, K613, D616, N617, and/or K671 of SEQ ID NO:4 and is operably linked to one or more regulatory domains for expressing an isolated CRISPR CRISPR from *Prevotella* and *Francisella* 1 (Cpf1) protein from *Francisella tularensis* (FnCpf1), comprising a sequence that is at least 80% identical to SEQ ID NO:4, with mutations at one or more of the following positions: K180, E184, N607, K613, D616, N617, and/or K671 of SEQ ID NO:4.

Also provided herein are host cells, preferably mammalian host cells, comprising the nucleic acids described herein, and optionally expressing a protein or fusion protein described herein.

In addition, provided herein are method for altering the genome of a cell, the method comprising expressing in the cell, or contacting the cell with, an isolated protein or fusion protein as described herein, and at least one guide RNA having a region complementary to a selected portion of the genome of the cell, i.e., wherein the complementary region is adjacent to a PAM sequence that corresponds to the protein or fusion protein, e.g., as shown in Table B. In some embodiments, the isolated protein or fusion protein comprises one or more of a nuclear localization sequence, cell penetrating peptide sequence, and/or affinity tag. In some embodiments, the cell is a stem cell. In some embodiments, the cell is an embryonic stem cell, mesenchymal stem cell, or induced pluripotent stem cell; is in a living animal; or is in an embryo.

Also provided are methods of altering a double stranded DNA (dsDNA) molecule, the method comprising contacting the dsDNA molecule with an isolated protein or fusion protein as described herein, and a guide RNA having a region complementary to a selected portion of the dsDNA molecule, i.e., wherein the complementary region is adjacent to a PAM sequence that corresponds to the protein or fusion protein, e.g., as shown in Table B. In some embodiments, the dsDNA molecule is in vitro.

Also provided are methods for detecting a target ssDNA or dsDNA in vitro in a sample. The methods include contacting the sample with (i) the isolated protein or fusion protein as described in any of the above embodiments, (ii) a guide RNA having a region complementary to a selected portion of the target ssDNA or dsDNA molecule, and (iii) a labeled detector DNA, wherein the isolated protein or fusion protein cleaves the detector DNA upon binding to the target ssDNA or dsDNA; and measuring a detectable signal produced by cleavage of the labeled detector DNA, thereby detecting the target ssDNA or dsDNA.

In some embodiments, measuring the labeled detector DNA comprises detecting one or more of a gold nanoparticle, a fluorophore, fluorescence polarization, colloid phase transition/dispersion, electrochemical signals, and semiconductor-based signals.

In some embodiments, the labeled detector DNA produces an amount of detectable signal prior to being cleaved, and the amount of detectable signal is reduced when the labeled detector DNA is cleaved. In some embodiments, the labeled detector DNA produces a first detectable signal prior to being cleaved and a second detectable signal when the labeled detector DNA is cleaved.

In some embodiments, the labeled detector DNA comprises a quencher/fluor pair or a FRET pair.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 16A-16E: Enhanced activities of AsCas12a variants. (A), Quantification of time-course in vitro cleavage reactions of Cas12a orthologs and variants on linearized plasmid substrates encoding PAMDA site 1 target, conducted at 37, 32, and 25° C. (left, middle, and right panels, respectively). Curves were fit using a one phase exponential decay equation; error bars represent s.e.m for n=3. (B-D), Summaries of the activities of wild-type and variant AsCas12a nucleases across sites encoding TTTN PAMs (panel B), TATN PAMs (panel C) and TYCN PAMs (panel D) (see also FIGS. 24A-C, respectively). (E), Scatterplots of the PAMDA determined rate constants for each NNNN PAM to compare the PAM preferences of AsCas12a variants (RVR to eRVR, left panel; RR to eRR, right panel). Variants encode the following substitutions: eAsCas12a, E174R/S542R/K548R; RVR, S542R/K548V/N552R; eRVR, E174R/S542R/K548V/N552R; RR, S542R/K607R; eRR, E174R/S542R/K607R.

FIGS. 17A-17H: Characterization and improvement of eAsCas12a specificity. (A), GUIDE-seq genome-wide specificity profiles for AsCas12a, eAsCas12a, and eAsCas12a-HF 1 each paired with crRNAs targeting sites with TTTV PAMs. Mismatched positions in off-target sites are highlighted; GUIDE-seq read counts are shown to the right of the sequences; yellow circles indicate off-target sites that are only supported by asymmetric GUIDE-seq reads; green circles indicate off-target sites previously identified for LbCas12a (Kleinstiver et al., Nat Biotechnol., 2016, 34:869-74); alternate nucleotides in non-canonical PAMs with mean PAMDA ks>0.005 for eAsCas12a are not coloured/highlighted as mismatches. SEQ ID NOs. 449-477, in order of appearance. (B), Histogram of the number of GUIDE-seq detected off-target sites for AsCas12a variants from the sites examined in panel A. (C), Scatterplot of the PAMDA determined rate constants for each NNNN PAM to compare the PAM preferences of eAsCas12a and eAsCas12a-HF1. (D), GUIDE-seq genome-wide specificity profiles for eAsCas12a and eAsCas12a-HF1 for crRNAs targeting sites with non-canonical PAMs. Illustrations as described for panel a; eAsCas12a-HF1 not assessed on CTTA-1, CTTC-2, or TATC-1. SEQ ID NOs. 478-530, in order of appearance. (E), Histogram of the number of GUIDE-seq detected off-target sites for eAsCas12a and eAsCas12a-HF1 from the sites examined in panel a; na, not assessed. (F), Off-target efficiency ratio calculated by normalizing off-target GUIDE-seq read counts against counts observed at the on-target site. (G, H), On-target activity summaries of wild-type, eAsCas12a, and eAsCas12a-HF1 across sites encoding TTTN PAMs (panel G) or non-canonical PAMs (panel H) (see FIGS. 251 and 25J, respectively).

FIGS. 18A-18K: Applications of eAsCas12a for multiplex targeting, gene activation, and base editing. (A-C), Comparison of the multiplex on-target modification efficiencies of AsCas12a, eAsCas12a, and LbCas12a, when programmed with TTTV PAM targeted crRNA arrays encoding 3 separate crRNAs expressed either from a polymerase III promoter (U6, panels A and B) or a polymerase II promoter (CAG, panel C). The activities at three separate loci were assessed by T7E1 assay using the same genomic DNA samples; mean, s.e.m., and individual data points shown for n=3. (D), Assessment of the editing efficiencies when using pooled crRNA plasmids or multiplex crRNA arrays expressing two crRNAs targeted to nearby (~100 bp) genomic loci. Activities assessed by T7E1 assay; mean, s.e.m., and individual data points shown for n=4. (E-G), Activation of endogenous human genes with dCas12a-VPR(1.1) fusions (see FIG. 26A) using pools of three crRNAs targeted to canonical PAM sites (panel E) and non-canonical PAM sites (panels F and G). Activities assessed by RT-qPCR and fold-changes in RNA were normalized to HPRT1 levels; mean, s.e.m., and individual data points shown for technical triplicates of three biological replicates (n=9). (H), Schematic of dCas12a base editor (BE) constructs with varying NLS and linker compositions. (I), Cytosine to thymine (C-to-T) conversion efficiencies directed by dCas12a-BEs across eight different target sites, assessed by targeted deep sequencing. The mean percent C-to-T editing of three biological replicates was examined within a −5 to +25 window; all Cs in this window are highlighted in green for each target site; the position of the C within the target site is indicated below the heat map. SEQ ID NOs. 531-538, in order of appearance. (J), Aggregate summary of C-to-T editing efficiency within the 20 nt target site spacer sequence with dCas12a-BEs across all eight target sites. (K), Summary of fold-change in the percent of sequencing reads that contain insertion or deletion mutations (indels) for each dCas12a-BE experiment (eight target sites and three replicates), normalized relative to the percent indels observed in the control sample (LbBE1.4 and an empty U6 plasmid). VPR, synthetic VP64-p65-Rta activation domain (Chavez et al., Nat Methods., 2015, 12:326-8); NLS(sv), SV40 nuclear localization signal; NLS(nuc), nucleoplasmin nuclear localization signal; rAPO1, rat APOBEC1; gs, glycine-serine peptide linker; UGI, uracil glycosylase inhibitor.

FIGS. 21A-21H: Optimization of an in vitro PAM characterization assay. (A), Representative SDS-PAGE gel images of purified Cas12a orthologs and AsCas12a variants; s.m, size marker in kDa. (B), Schematic of linearized plasmid bearing combinations of PAMs and spacers used as substrates for in vitro cleavage reactions. SEQ ID NOs. 539-540. (C), Time-course in vitro cleavage reaction profiles of wild-type AsCas12a (left panel) and the E174R/S542R/

K548R variant (right panel) on the substrates illustrated in panel b. Curves were fit using a one phase exponential decay equation; error bars represent s.e.m for n=3. (D), Schematic of the PAM determination assay (PAMDA). Linearized plasmid libraries harboring 8 randomized nucleotides in place of the PAM were subjected to in vitro cleavage reactions with Cas12a ribonucleoprotein (RNP) complexes. Aliquots of the reaction were stopped at various time-points, and subsequently used as template for PCR. Substrates harboring incompletely targetable PAMs were amplified and sequenced to enable quantification of the rate of PAM depletion from the starting library over time. (E), Correlation between PAMDA rate constants (k) across replicates of wild-type AsCas12a (left panel) and the E174R/S542R/K548R variant (right panel). (F), Correlation between rate constants from mean PAMDA values across two spacer sequences. (G), Histogram of PAMDA rate constants for wild-type and E174R/S542R/K548R AsCas12a. (H), Depletion profiles of substrates encoding the indicated PAM sequences over time. Curves were fit using a one phase exponential decay equation; error bars represent s.e.m for n=4.

Figure 21A:
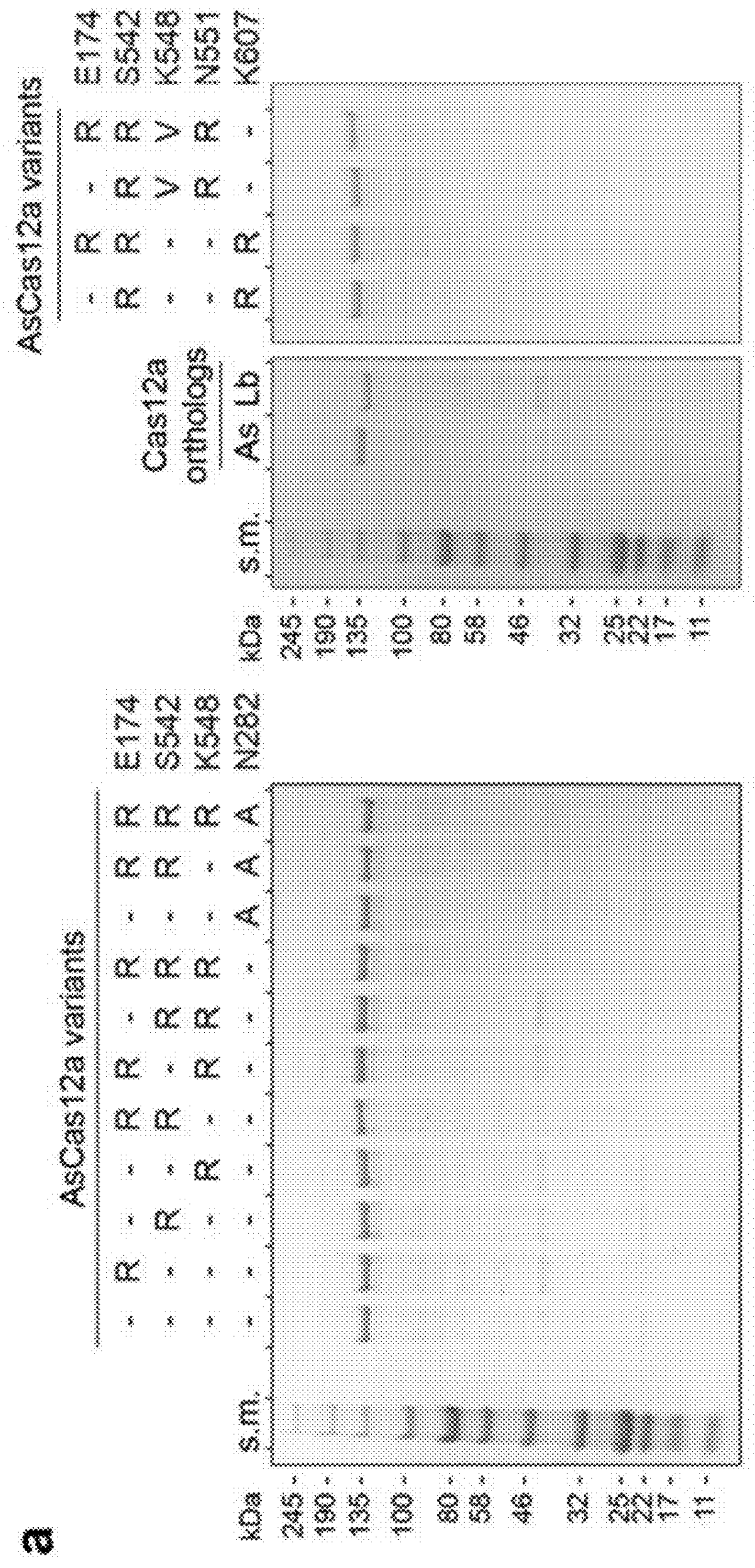
Figure 21B:
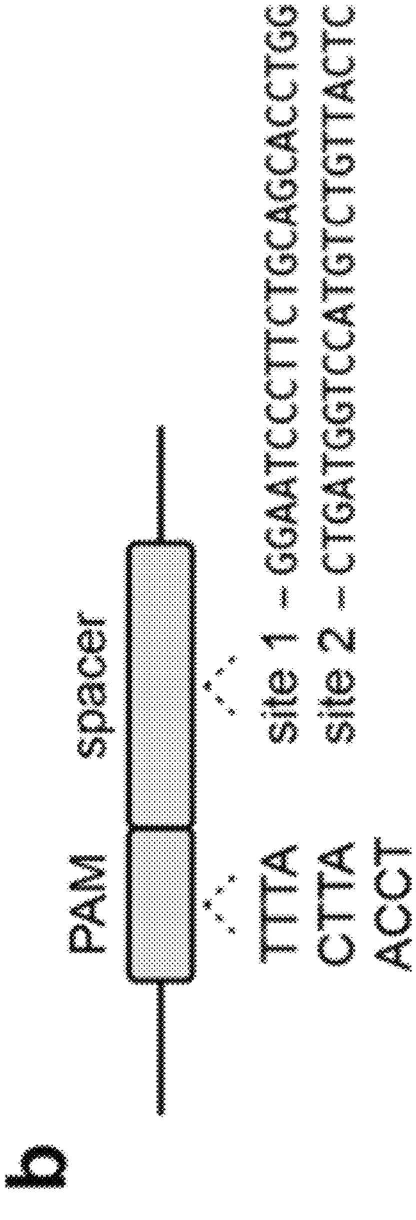
Figure 21C:
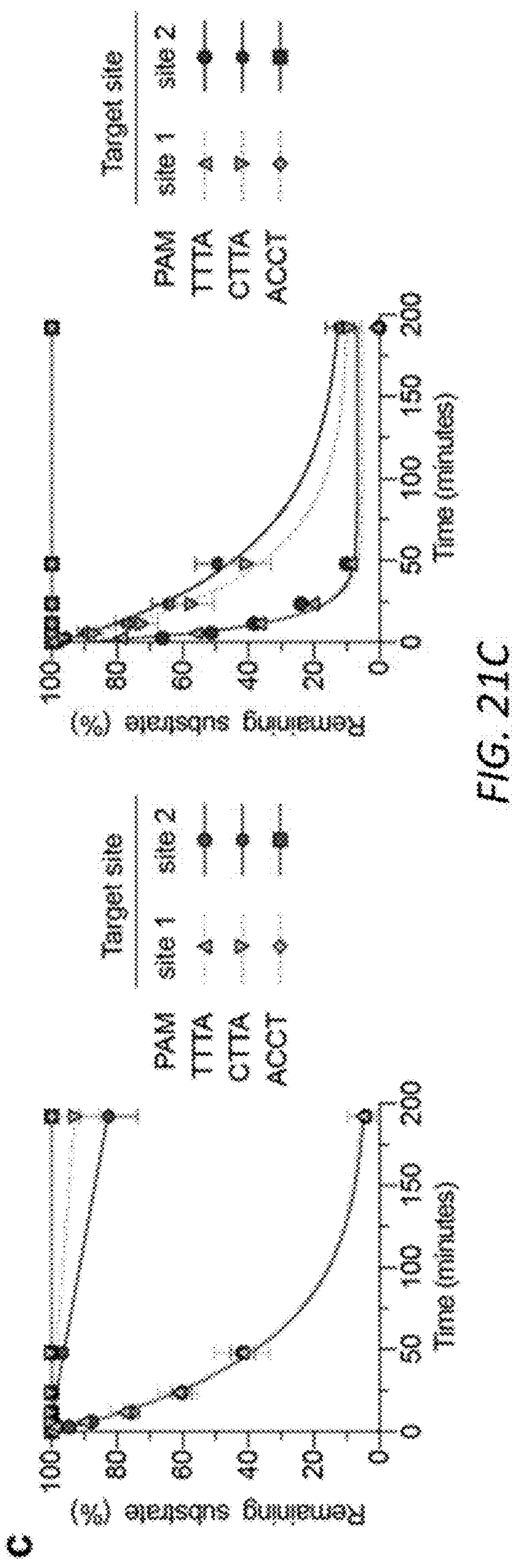
Figure 21D:
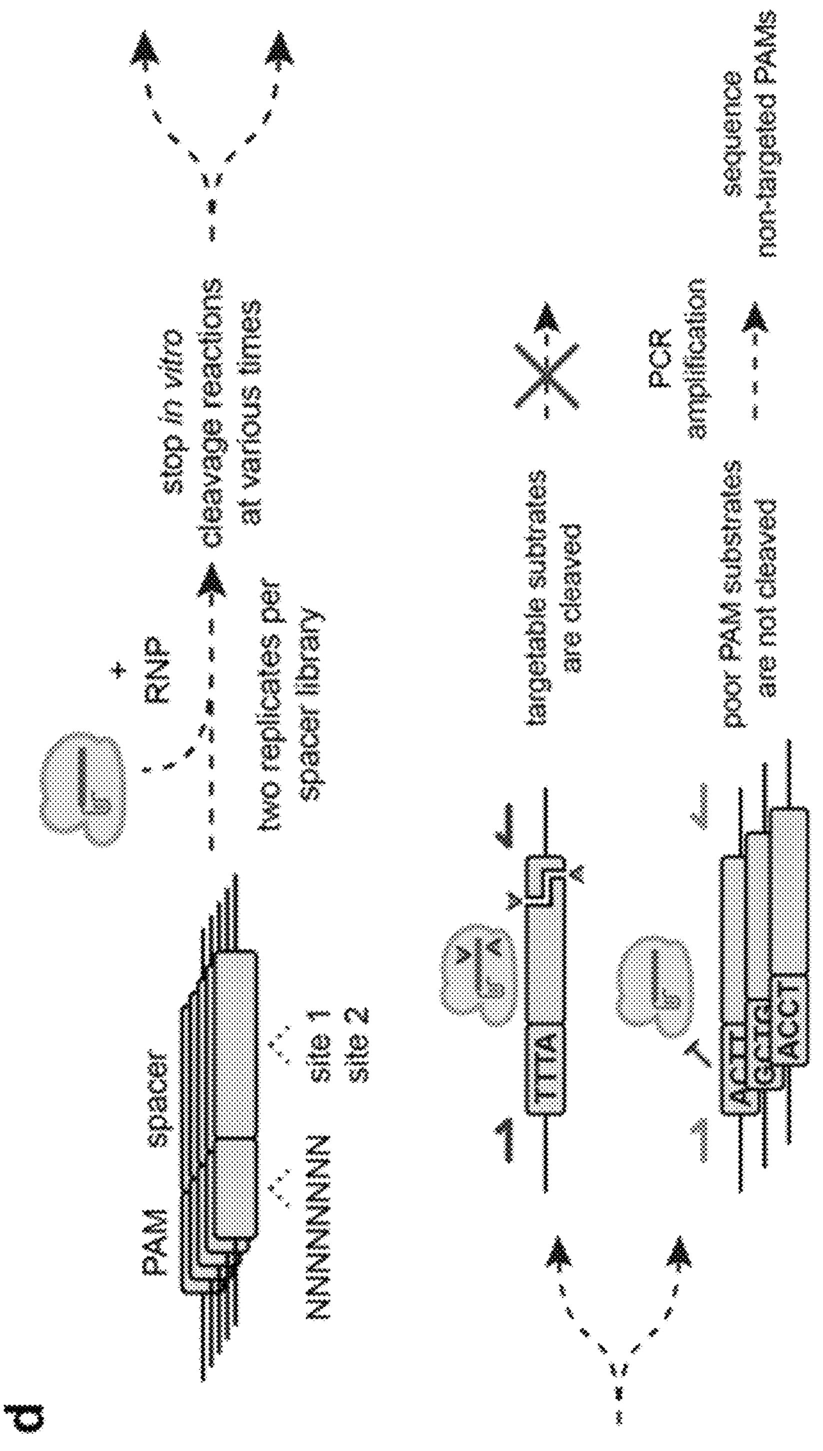
Figure 21E:
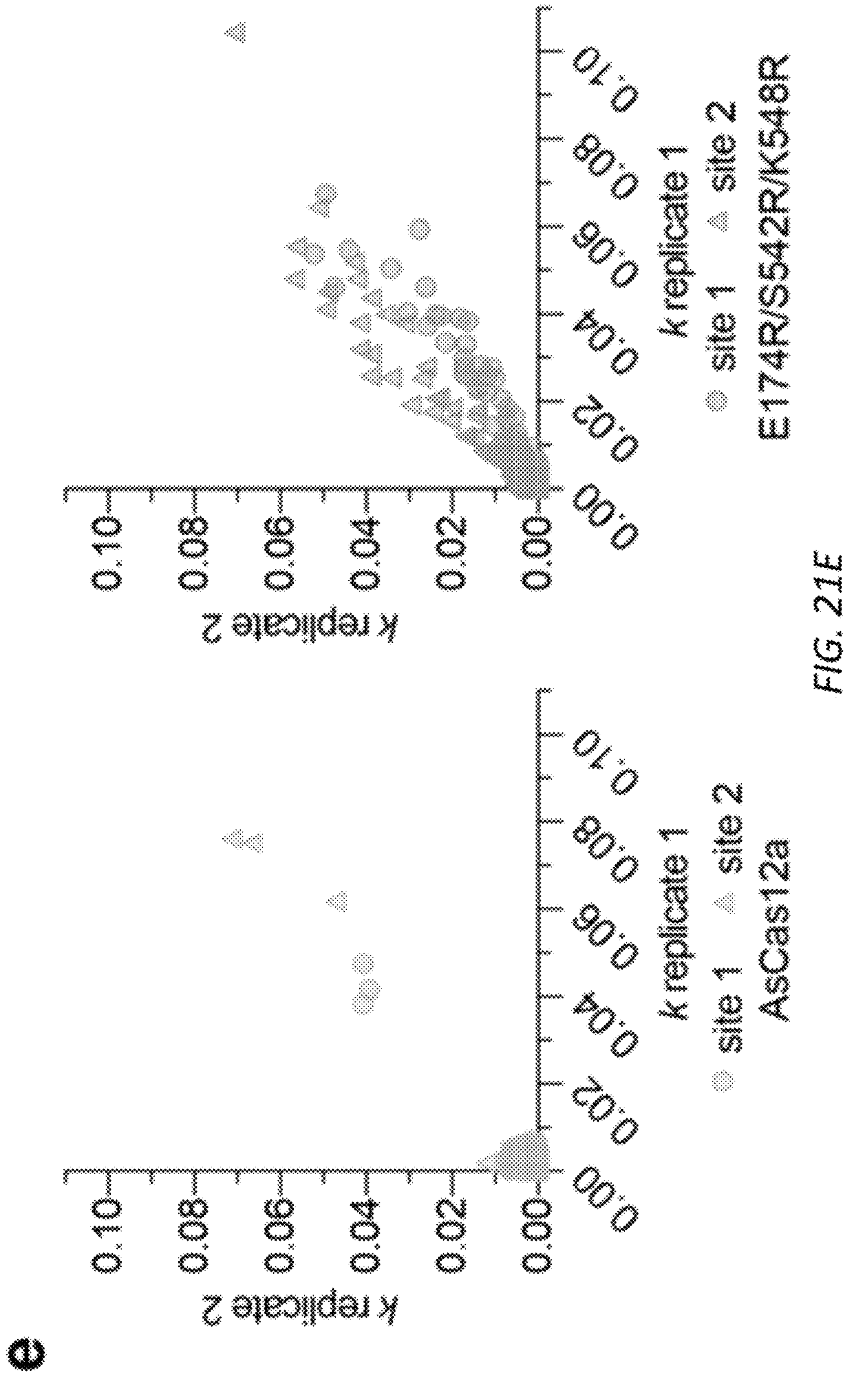
Figure 21H:
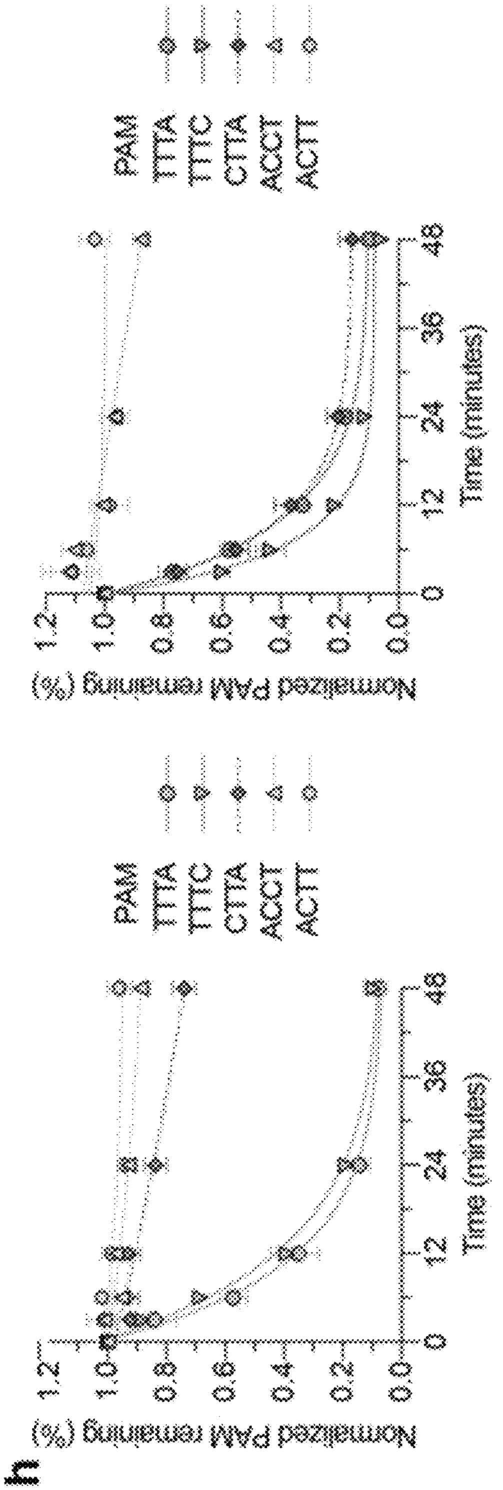
Figure 22A:
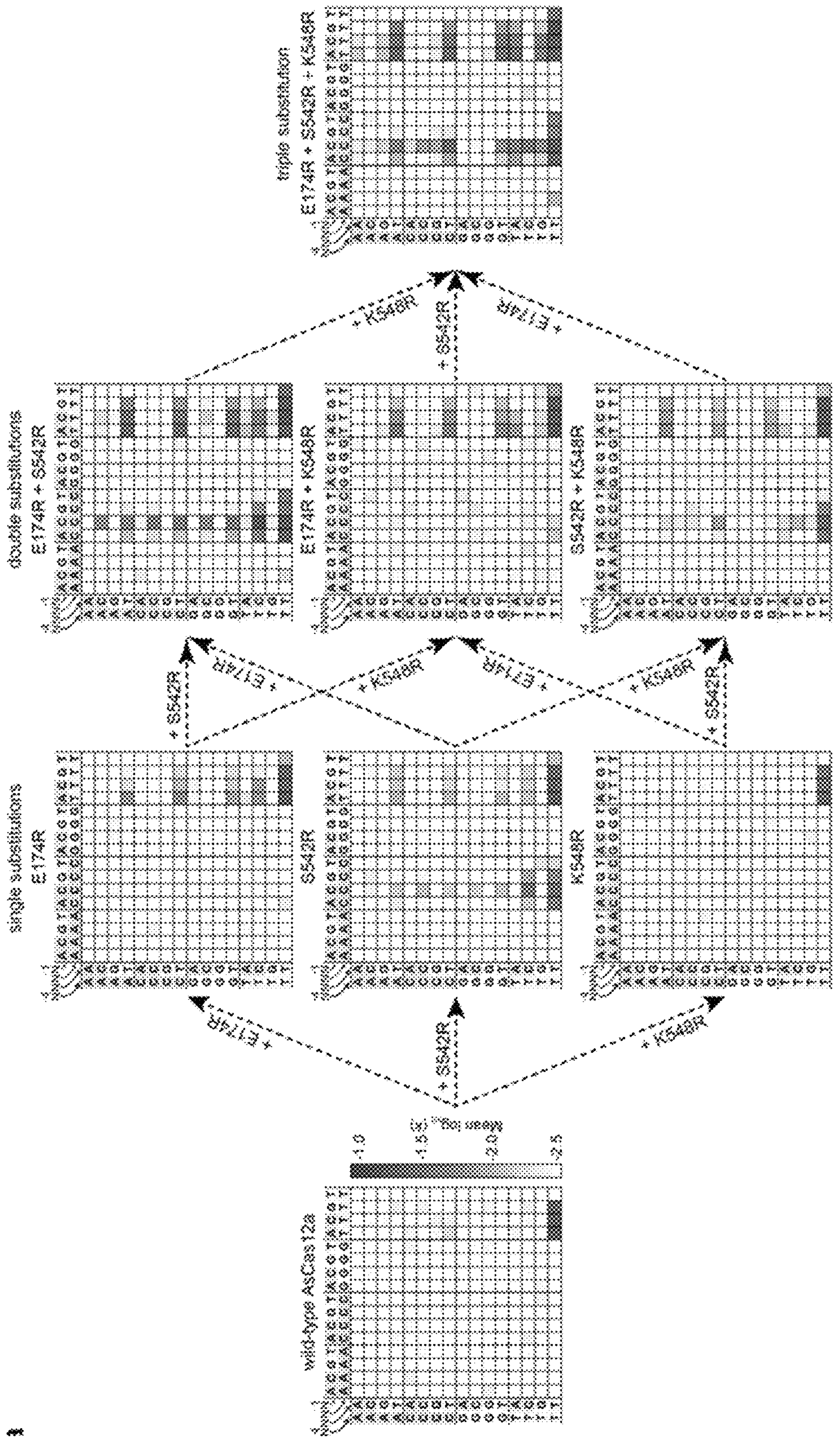
Figure 22B:
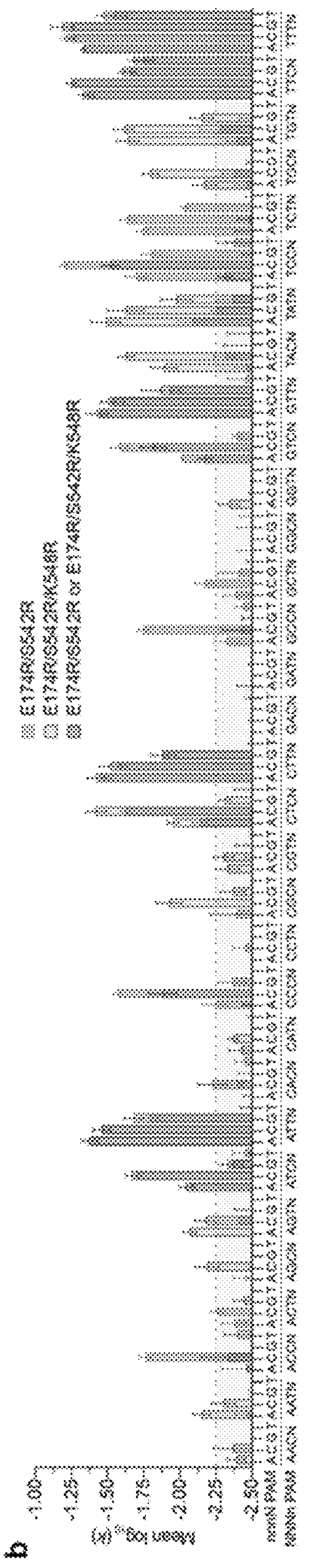
Figure 22C:
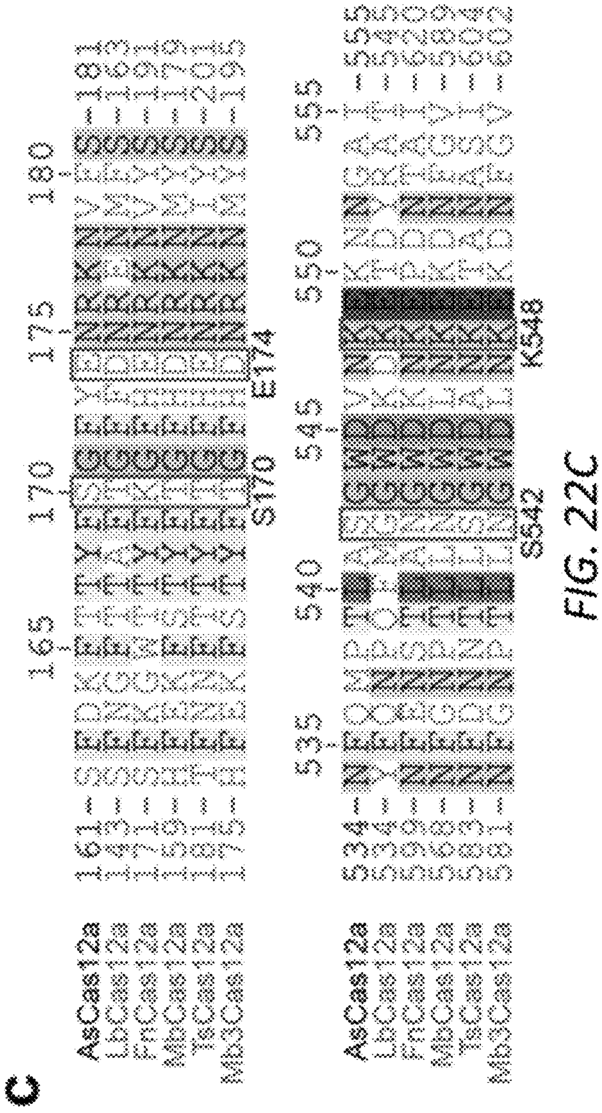

FIGS. 22A-22C: Deconvolution of the PAM specificities of eAsCas12a derivative variants. (A), PAM preference profiles for wild-type AsCas12a, the E174R/S542R/K548R variant, and all intermediate single and double substitution variants, assessed by PAMDA. The $\log_{10}$ rate constants (k) are the mean of four replicates, two each against two distinct spacer sequences (see FIG. 21A-21H). (B), Comparison of the PAM preference profiles of the E174R/S542R and E174R/S542R/K548R variants across all 128 NNYN PAMs. (C), Alignment of Cas12a orthologs with residues important for altering PAM preference in this study highlighted with a red border. (SEQ ID NOs.: 541-552).

FIGS. 23A-23I: Assessment of the improved targeting range of eAsCas12a. (A, B), Comparison of the activities of E174R/S542R and E174R/S542R/K548R AsCas12a on endogenous sites in human cells bearing non-canonical VTTN and TTCN PAMs (panel a), or TATN PAMs (panel b). (C), Activity of wild-type AsCas12a on sites with TTCN or TATN PAMs. (D, E), Activity of the E174R/S542R/K548R variant against sites with TGTV PAMs (panel D) or additional sites with various non-canonical PAMs (panel E). (F), Correlation between the PAMDA rate constant and mean modification in human cells for the PAMs tested in panels A-E. The grey shaded box indicates an arbitrary PAMDA rate constant threshold of 0.005 (or 10-2.25) roughly predictive of activity in human cells. (G), Comparison of the activities of wild-type, E174R/S542R, and E174R/S542R/K548R AsCas12a on sites with TTTN PAMs. (H), Summary of the mean activities of AsCas12a, the E174R/S542R variant, and eAsCas12a across 26 sites encoding TTTN PAMs (see also FIG. 23G). (I), Summary of targetable PAMs for eAsCas12a. Tiers of PAMs: 1, high confidence PAM (mean k>0.01, mean percent modified >13%); 2, medium confidence PAM (mean k>0.005, mean percent modified >10%); 3, low activity or discrepant PAM (mean percent modified <10% or discrepancy between mean k and percent modified). For all panels, percent modification assessed by T7E1 assay; mean, s.e.m., and individual data points shown for n≥3.

FIGS. 24A-24E: Activities of enhanced Cas12a PAM variants. (A-C), Comparison of the endogenous site modification activities of AsCas12a variants on sites with TTTN PAMs (panel A), TATN PAMs (panel B), and TYCN PAMs (panel C). Percent modification assessed by T7E1 assay; mean, s.e.m., and individual data points shown for n=3. (D), PAM preference profiles for original and enhanced RVR and RR AsCas12a variants assessed by PAMDA. The $\log_{10}$ rate constants are the mean of four replicates, two each against two distinct spacer sequences (see FIG. 21A-21H). (E), Comparison of the PAM preference profiles of the RVR/eRVR (top panel) and RR/eRR (bottom panel) variants across all 128 NNYN PAMs. AsCas12a variants encode the following substitutions: eAsCas12a, E174R/S542R/K548R; RVR, S542R/K548V/N552R; eRVR, E174R/S542R/K548V/N552R; RR, S542R/K607R; eRR, E174R/S542R/K607R.

FIGS. 25A-25K: Assessment and improvement of AsCas12a and eAsCas12a specificities. (A), Schematic of the GUIDE-seq method. (B, C), Comparison of the on-target mutagenesis (panel b) and GUIDE-seq dsODN tag integration (panel c) activities of AsCas12a nucleases for GUIDE-seq samples. Percent modification and tag integration assessed by T7E1 and RFLP assays, respectively; mean, s.e.m., and individual data points shown for n=3. (D), Ratio of GUIDE-seq dsODN tag integration to overall mutagenesis for AsCas12a nucleases; data from panels b and c. (E), Activities of wild-type AsCas12a or variants bearing single substitutions when using crRNAs that perfectly match the on-target site, or that encode single nucleotide mismatches. Percent modification assessed by T7E1 assay; mean, s.e.m., and individual data points shown for n=3. SEQ ID NOs.553-554. (F), Activities of eAsCas12a variants bearing single amino acid substitutions, assessed as in panel e. Percent modification assessed by T7E1 assay; mean, s.e.m., and individual data points shown for n=3. (G), PAM preference profiles of eAsCas12a and eAsCas12a-HF1 assessed by PAMDA. The $\log_{10}$ rate constants are the mean of four replicates, two each against two distinct spacer sequences (see FIG. 21A-21H). (H), Comparison of the PAM preference profiles of eAsCas12a and eAsCas12a-HF1 across all 128 NNYN PAMs. (I, J), Assessment of the on-target activities of AsCas12a, eAsCas12a, and eAsCas12a-HF1 on target sites harboring TTTN PAMs (panel i) or non-canonical VTTV, TATV, and TTCV PAMs (panel j). Percent modification assessed by T7E1 assay; mean, s.e.m., and individual data points shown for n=3. (K), Time-course in vitro cleavage reactions of Cas12a orthologs and variants on the PAMDA site 1 substrate, conducted at 37, 32, and 25° C. (left, middle, and right panels, respectively). Curves were fit using a one phase exponential decay equation; error bars represent s.e.m for n=3. AsCas12a variants encode the following substitutions: eAsCas12a, E174R/S542R/K548R; eAsCas12a-HF1, E174R/N282A/S542R/K548R.

FIGS. 26A-26F: Gene activation with Cas12a fusions. (A), Schematic of VPR activation domain fusions to DNase-inactive Cas12a (dCas12a) orthologs and variants. (B), Illustration of the sequence window encompassing roughly 700 bp upstream of the VEGEA transcription start site (TSS), with target sites for SpCas) and Cas12a indicated. (C, D), Comparison of the activities of dCas12a-VPR and dSpCas9-VPR architectures (using pairs of crRNAs or sgRNAs, respectively); crRNAs were targeted to sites with TTTV PAMs (panel C) or TTCV PAMs (panel D) in the VEGFA promoter. Activities assessed via changes in VEGFA production compared to a control transfection containing deAs-VPR(1.3) and a mock crRNA plasmid; mean, s.e.m., and individual data points shown for n=4. (E, F), VEGFA activation by dCas12a-VPR(1.1) or dSpCas9-VPR fusion proteins using pools of three or two (panels e and f, respectively) crRNAs or sgRNAs across a range of sites with canonical and non-canonical PAMs for the dCas12a-VPR fusions; mean, s.e.m., and individual data points shown for n≥3. VPR, synthetic VP64-p65-Rta activation domain (Chavez et al., Nat Methods., 2015, 12:326-8); NLS(sv), SV40 nuclear localization signal; NLS(nuc), nucleoplasmin nuclear localization signal; HA, Human influenza hemagglutinin tag; gs, glycine-serine peptide linker.

FIGS. 27A-D: Base editing with Cas12a. (A), Fold-change in C-to-T editing compared to the untreated control across all Cs in the 20 nt spacers of 8 target sites. (B), Influence of identity of the preceding (5') base on the conversion of cytosine to thymine (C-to-T). The C-to-T editing efficiency across eight target sites (see FIG. 18I) is plotted for all Cs in the window encompassing the −14 to +30 region of each target site (an additional 10 nt upstream of the 4 nt PAM and 10 nt downstream of the 20 nt spacer sequence). (C), Analysis of edit purity at six selected cytosines across five target sites. The fraction of each non-C identity is plotted over the sum of all non-C occurrences at that position for each BE construct. (D), Insertion or deletion mutation (indel) activities of Cas12a-BEs were calculated for each BE/crRNA pair by determining the percentage of alleles encoding an indel within the −14 to +30 window, not counting alleles with substitutions only.

Figure 28A:
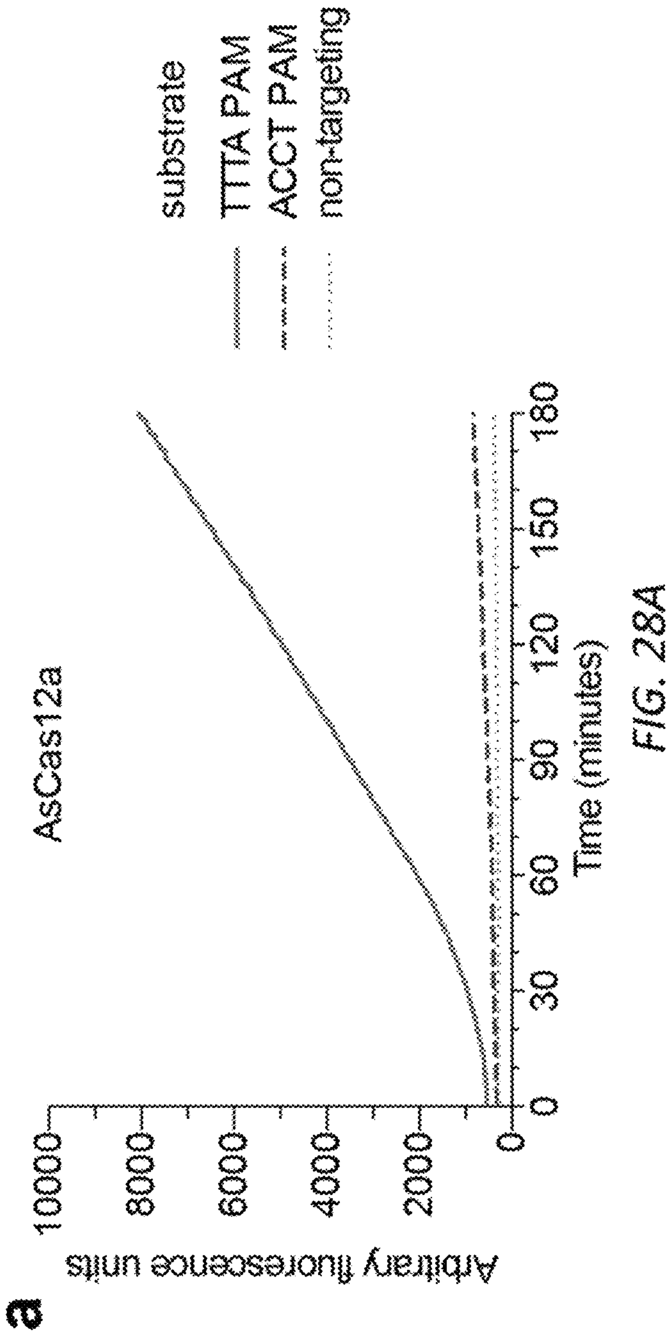
Figure 28B:
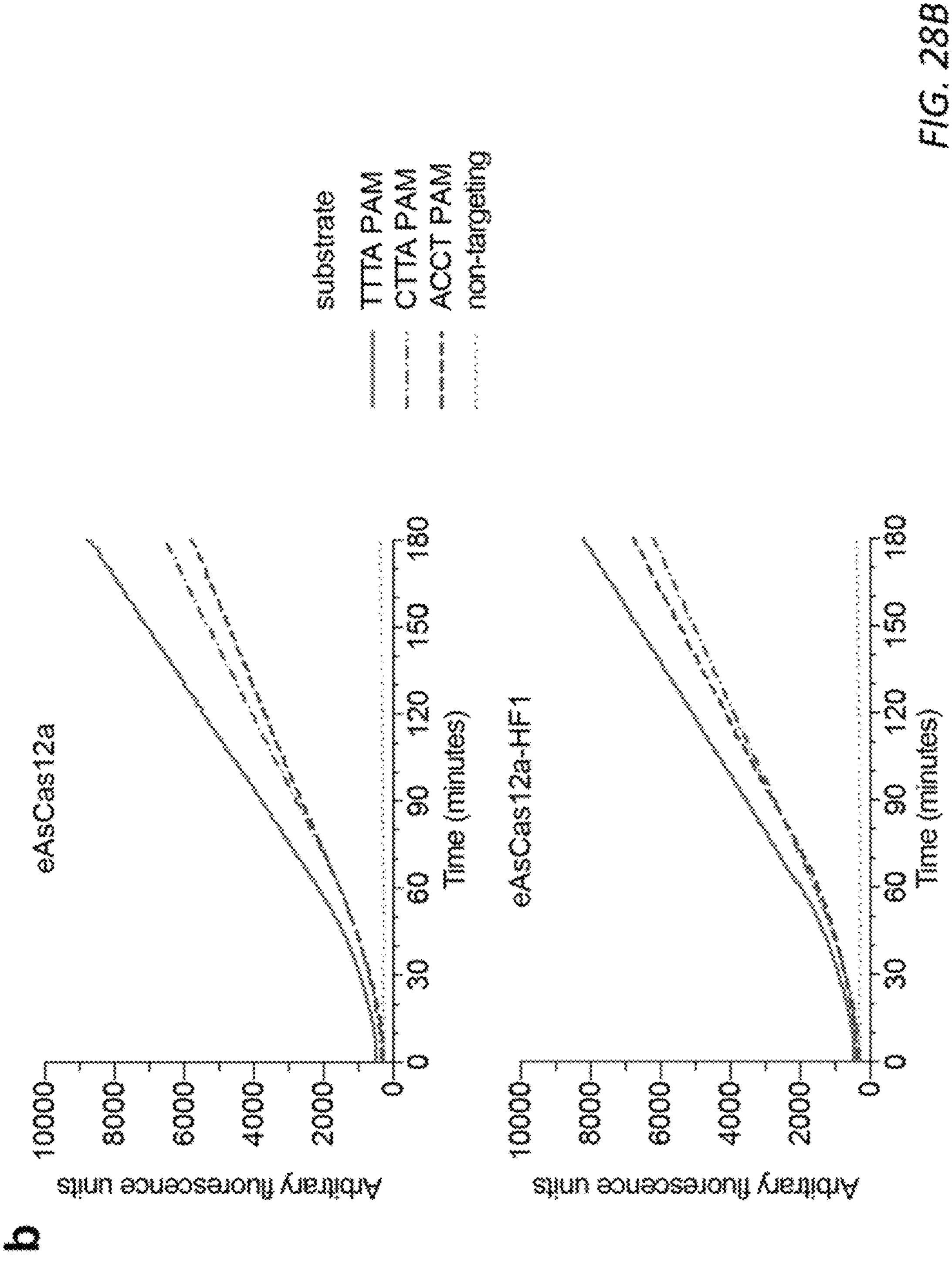

FIGS. 28A-28B: DNA detection with AsCas12 and eAsCas12a. (A), Time-course DNA-detection with wild-type AsCas12a via DNase-induced reporter molecule fluorescence. Activities assessed when programmed with different active and inactive substrates. (B), DNA-detection activities of eAsCas12a and eAsCas12a-HF1 (top and bottom panels, respectively) over time. Activities assessed when programmed with substrates bearing canonical PAM, non-canonical PAM, and non-targetable sequences. Measurements of fluorescence were taken every 60 seconds for three hours with with $\lambda_{ex}$=485 nm and $\lambda_{em}$=528 nm.

DETAILED DESCRIPTION

Figure 1:
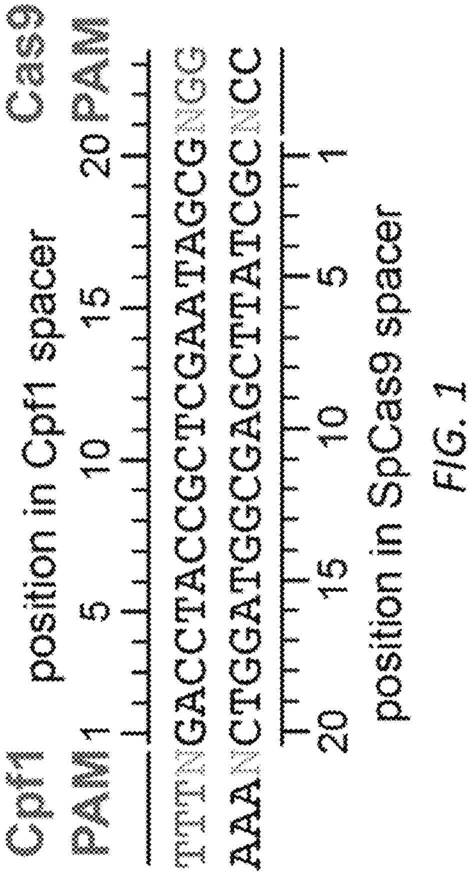
FIG. 1: Representative target sites for Cpf1 and SpCas9 nucleases. AsCpf1 and LbCpf1 recognize a TTTN PAM sequence at the 5' end of the target site spacer, whereas SpCas9 recognizes an NGG PAM at the 3' end of the spacer. Sense sequence: SEQ ID NO:1.

Cpf1 enzymes characterized to date recognize T-rich PAMs that are positioned 5' to the spacer sequence (FIG. 1). Both AsCpf1 and LbCpf1 have been reported to recognize a PAM of the form TTTN but strongly prefer TTTV (where V=A, C, or G). A TTTV PAM sequence is expected to occur roughly once in every 43 bases of random DNA, potentially limiting the targeting range (and utility) of AsCpf1 and LbCpf1 for genome editing. The targeting range of engineered nucleases is particularly important for applications that require precise targeting or placement of the DNA double-strand break (DSB), including but not limited to: 1) generation of insertion or deletion mutations (indels) in small genetic elements such as: short open reading frames (ORFs), transcription factor binding sites, micropeptides, miRNAs, etc.; 2) homology-directed repair (HDR), where proximity of the DSB to the desired sequence change can dramatically influence efficiency of repair, 3) allele-specific editing achieved by placing the SNP variation within the protospacer or PAM; 4) generating genomic deletions of defined length or translocations by introduction of pairs of DSBs; 5) performing saturation mutagenesis of genes or gene regulatory elements; and 6) use of engineered RNA-guided nucleases or nickases fused to DNA modifying enzymes for performing base editing. Given these clear advantages of an increased targeting range, we sought to alter or relax the PAM specificities of AsCpf1 and LbCpf1 to improve their capabilities to recognize a more diverse range of DNA sequences.

Herein we demonstrate that substitutions at or near PAM-proximal amino acid residues can alter the PAM preferences of both AsCpf1 and LbCpf1, generating variants of these nucleases that can recognize non-cognate PAM sequences, thereby increasing the targeting range of this platform. These engineered CRISPR-Cas12a variants have dramatically improved properties, exhibiting simultaneously broadened targeting range and enhanced targeting activity. To the best of our knowledge, this is the first description of amino acid substitutions that can improve the on-target activity of a CRISPR nuclease. The enhanced properties of eAsCas12a offer major advantages over currently available Cas12a orthologs and variants, exhibiting greater than an 8-fold improvement in targeting range, while also enabling more potent multiplex editing, gene activation, DNA detection, and base editing applications at efficiencies previously unachievable with wild-type AsCas12a. The development of eAsCas12a base editor technologies expands the scope of targetable bases in the genome and does so with little evidence of collateral indel mutations. Importantly, the targeting range of eAsCas12a is comparable to previously described engineered SpCas9 nucleases, providing greater target site density for Cas12a applications that require broadened PAM recognition (eg., for targeting within defined or small genomic windows, multiplex genome or epigenome editing, focused coding or non-coding crRNA-tiling screens, or when conceiving of complex combinatorial library screens). The improved properties of the variants described herein, including eAsCas12a, make them some of the most broadly targetable and active Cas12a enzymes described to-date.

Cpf1

Clustered, regularly interspaced, short palindromic repeat (CRISPR) systems encode RNA-guided endonucleases that are essential for bacterial adaptive immunity (Wright et al., Cell 164, 29-44 (2016)). CRISPR-associated (Cas) nucleases can be readily programmed to cleave target DNA sequences for genome editing in various organisms[2-5]. One class of these nucleases, referred to as Cas9 proteins, complex with two short RNAs: a crRNA and a trans-activating crRNA (tracrRNA)[7,8]. The most commonly used Cas9 ortholog, SpCas9, uses a crRNA that has 20 nucleotides (nt) at its 5' end that are complementary to the "protospacer" region of the target DNA site. Efficient cleavage also requires that SpCas9 recognizes a protospacer adjacent motif (PAM). The crRNA and tracrRNA are usually combined into a single ~100-nt guide RNA (gRNA)[7,9-11] that directs the DNA cleavage activity of SpCas9. The genome-wide specificities of SpCas9 nucleases paired with different gRNAs have been characterized using many different approaches[12-15]. SpCas9 variants with substantially improved genome-wide specificities have also been engineered[16,17].

Recently, a Cas protein named Cpf1 has been identified that can also be programmed to cleave target DNA sequences[1, 18-20]. Unlike SpCas9, Cpf1 requires only a single 42-nt crRNA, which has 23 nt at its 3' end that are complementary to the protospacer of the target DNA sequence[1]. Furthermore, whereas SpCas9 recognizes an NGG PAM sequence that is 3' of the protospacer, AsCpf1 and LbCp1 recognize TTTN PAMs that are positioned 5' of the protospacer[1]. Early experiments with AsCpf1 and LbCpf1 showed that these nucleases can be programmed to edit target sites in human cells[1] but they were tested on only a small number of sites. Recent studies have demonstrated that both AsCpf1 and LbCpf1 possess robust on-target activities and high genome-wide specificities in human cells (see, e.g., Kleinstiver & Tsai et al., Nature Biotechnology 2016; and Kim et al., Nat Biotechnol. 2016). See also US20160208243.

The present findings provide support for engineered AsCpf1 and LbCpf1 variants, referred to collectively herein as “variants” or “the variants”.

All of the variants described herein can be rapidly incorporated into existing and widely used vectors, e.g., by simple site-directed mutagenesis.

Thus, provided herein are AsCpf1 variants. The AsCpf1 wild type protein sequence is as follows:

AsCpf1—Type V CRISPR-Associated Protein Cpf1 [*Acidaminococcus* sp. BV3L6], NCBI Reference Sequence: WU 021736722.1

NO:2 (or at positions analogous thereto, e.g., of SEQ ID NO:9). In some embodiments, the AsCpf1 variants are at least 80%, e.g., at least 85%, 90%, or 95% identical to the amino acid sequence of SEQ ID NO:2, e.g., have differences at up to 5%, 10%, 15%, or 20% of the residues of SEQ ID NO:2 replaced, e.g., with conservative mutations, in addition to the mutations described herein. In preferred embodiments, the variant retains desired activity of the parent, e.g., the nuclease activity (except where the parent is a nickase or (SEQ ID NO: 2)

1 MTQFEGFTNL YQVSKTLRFE LIPQGKTLKH IQEQGFIEED KARNDHYKEL KPIIDRIYKT

61 YADQCLQLVQ LDWENLSAAI DSYRKEKTEE TRNALIEEQA TYRNAIHDYF IGRTDNLTDA

121 INKRHAEIYK GLFKAELFNG KVLKQLGTVT TTEHENALLR SFDKFTTYFS GFYENRKNVE

181 SAEDISTAIP HRIVQDNFPK FKENCHIFTR LITAVPSLRE HFENVKKAIG IFVSTSIEEV

241 FSFPFYNQLL TQTQIDLYNQ LLGGISREAG TEKIKGLNEV LNLAIQKNDE TAHIIASLPH

301 RFIPLEKQIL SDRNTLSFIL EEFKSDEEVI QSFCKYKTLL RNENVLETAE ALFNELNSID

361 LTHIFISHKK LETISSALCD HWDTLRNALY ERRISELTGK ITKSAKEKVQ RSLKHEDINL

421 QEIISAAGKE LSEAFKQKTS EILSHAHAAL DQPLPTTLKK QEEKEILKSQ LDSLLGLYHL

481 LDWFAVDESN EVDPEFSARL TGIKLEMEPS LSFYNKARNY ATKKPYSVEK FKLNFQMPTL

541 ASGWDVNKEK NNGAILFVKN GLYYLGIMPK QKGRYKALSF EPTEKTSEGF DKMYYDYFPD

601 AAKMIPKCST QLKAVTAHFQ THTTPILLSN NFIEPLEITK EIYDLNNPEK EPKKFQTAYA

661 KKTGDQKGYR EALCKWIDFT RDFLSKYTKT TSIDLSSLRP SSQYKDLGEY YAELNPLLYH

721 ISFQRIAEKE IMDAVETGKL YLFQIYNKDF AKGHHGKPNL HTLYWTGLES PENLAKTSIK

781 INGQARTFYR PKSRMKRMAH RLGEKMLNKK LKDQKTPIPD TLYQELYDYV NHRLSHDLSD

841 EARALLPNVI TKEVSHEIIK DRRFTSDKFF FHVPITLNYQ AANSPSKFNQ RVNAYLKEHP

901 ETPIIGIDRG ERNLIYITVI DSTGKILEQR SLNTIQQFDY QKKLDNREKE RVAARQAWSV

961 VGTIKDLKQG YLSQVIHEIV DLMIHYQAVV VLENLNFGFK SKRTGIAEKA VYQQFEKMLI

1021 DKLNCLVLKD YPAEKVGGVL NPYQLTDQFT SFAKMGTQSG FLFYVPAPYT SKIDPLTGFV

1081 DPFVWKTIKN HESRKHFLEG FDFLHYDVKT GDFILHFKMN RNLSFQRGLP GFMPAWDIVE

1141 EKNETQFDAK GTPFIAGKRI VPVIENHRFT GRYRDLYPAN ELIALLEEKG IVERDGSNIL

1201 PKLLENDDSH AIDTMVALIR SVLQMRNSNA ATGEDYINSP VRDLNGVCFD SRFQNPEWPM

1261 DADANGAYHI ALKGQLLLNH LKESKDLKLQ NGISNQDWLA YIQELRN

The AsCpf1 variants described herein can include the amino acid sequence of SEQ ID NO:2, e.g., at least comprising amino acids 1-1307 of SEQ ID NO:2, with mutations (i.e., replacement of the native amino acid with a different amino acid, e.g., alanine, glycine, or serine (except where the native amino acid is serine)), at one or more positions in Table 1, e.g., at the following positions: T167, S170, E174, T539, K548, N551, N552, M604, and/or K607 of SEQ ID a dead Cpf1), and/or the ability to interact with a guide RNA and target DNA).

Also provided herein are LbCpf1 variants. The LbCpf1 wild type protein sequence is as follows:

LbCpF1—Type V CRISPR-Associated Protein Cpf1 [*Lachnospiraceae bacterium* ND2006], GenBank Acc No. WP_051666128.1

(SEQ ID NO: 3)

1 MLKNVGIDRL DVEKGRKNMS KLEKFTNCYS LSKTLRFKAI PVGKTQENID NKRLLVEDEK

61 RAEDYKGVKK LLDRYYLSFI NDVLHSIKLK NLNNYISLFR KKTRTEKENK ELENLEINLR

121 KEIAKAFKGN EGYKSLFKKD IIETILPEFL DDKDEIALVN SENGFTTAFT GFFDNRENME

181 SEEAKSTSIA FRCINENLTR YISNMDIFEK VDAIFDKHEV QEIKEKILNS DYDVEDFFEG

-continued

```
 241 EFFNFVLTQE GIDVYNAIIG GFVTESGEKI KGLNEYINLY NQKTKQKLPK FKPLYKQVLS
 301 DRESLSFYGE GYTSDEEVLE VERNTLNKNS EIFSSIKKLE KLFKNFDEYS SAGIFVKNGP
 361 AISTISKDIF GEWNVIRDKW NAEYDDIHLK KKAVVTEKYE DDRRKSFKKI GSFSLEQLQE
 421 YADADLSVVE KLKEIIIQKV DEIYKVYGSS EKLFDADFVL EKSLKKNDAV VAIMKDLLDS
 481 VKSFENYIKA FFGEGKETNR DESFYGDFVL AYDILLKVDH IYDAIRNYVT QKPYSKDKFK
 541 LYFQNPQFMG GWDKDKETDY RATILRYGSK YYLAIMDKKY AKCLQKIDKD DVNGNYEKIN
 601 YKLLPGPNKM LPKVFFSKKW MAYYNPSEDI QKIYKNGTFK KGDMFNLNDC HKLIDFFKDS
 661 ISRYPKWSNA YDENFSETEK YKDIAGFYRE VEEQGYKVSF ESASKKEVDK LVEEGKLYMF
 721 QIYNKDESDK SHGTPNLHTM YFKLLFDENN HGQIRLSGGA ELFMRRASLK KEELVVHPAN
 781 SPIANKNPDN PKKTTTLSYD VYKDKRFSED QYELHIPIAI NKCPKNIFKI NTEVRVLLKH
 841 DDNPYVIGID RGERNLLYIV VVDGKGNIVE QYSLNEIINN FNGIRIKTDY HSLLDKKEKE
 901 RFEARQNWTS IENIKELKAG YISQVVHKIC ELVEKYDAVI ALEDLNSGFK NSRVKVEKQV
 961 YQKFEKMLID KLNYMVDKKS NPCATGGALK GYQITNKFES FKSMSTQNGF IFYIPAWLTS
1021 KIDPSTGFVN LLKTKYTSIA DSKKFISSFD RIMYVPEEDL FEFALDYKNF SRTDADYIKK
1081 WKLYSYGNRI RIFRNPKKNN VEDWEEVCLT SAYKELFNKY GINYQQGDIR ALLCEQSDKA
1141 FYSSFMALMS LMLQMRNSIT GRTDVDFLIS PVKNSDGIFY DSRNYEAQEN AILPKNADAN
1201 GAYNIARKVL WAIGQFKKAE DEKLDKVKIA ISNKEWLEYA QTSVKH
```

The LbCpf1 variants described herein can include the amino acid sequence of SEQ ID NO:3, e.g., at least comprising amino acids 23-1246 of SEQ ID NO:3, with mutations (i.e., replacement of the native amino acid with a different amino acid, e.g., alanine, glycine, or serine), at one or more of the following positions: T152, D156, G532, and/or K538 of SEQ ID NO: 11 (or at positions analogous thereto, e.g., T170, D174, G550, and/or K556 of SEQ ID NO:3); amino acids 19-1246 of SEQ ID NO:3 are identical to amino acids 1-1228 of SEQ ID NO: 11 (amino acids 1-1228 of SEQ ID NO:11 are also referred to herein as LbCPF1 (−18)). In some embodiments, the LbCpf1 variants are at least 80%, e.g., at least 85%, 90%, or 95% identical to the amino acid sequence of SEQ ID NO:3, e.g., have differences at up to 5%, 10%, 15%, or 20% of the residues of SEQ ID NO:3 replaced, e.g., with conservative mutations, in addition to the mutations described herein. In preferred embodiments, the variant retains desired activity of the parent, e.g., the nuclease activity (except where the parent is a nickase or a dead Cpf1), and/or the ability to interact with a guide RNA and target DNA). The version of LbCpf1 used in the present working examples starts at the MSKLEK motif, omitting the first 18 amino acids boxed above as described in Zetsche et al. Cell 163, 759-771 (2015).

Also provided herein are FnCpf1 variants. The FnCpf1 wild type protein sequence is as follows:

FnCPf1—type V CRISPR-Associated Protein Cpf1 [*Francisella tularensis*], GenBank Acc No. WP-003040289.1

```
                                                        (SEQ ID NO: 4)
  1 MSIYQEFVNK YSLSKTLRFE LIPQGKTLEN IKARGLILDD EKRAKDYKKA KQIIDKYHQF
 61 FIEEILSSVC ISEDLLQNYS DVYFKLKKSD DDNLQKDFKS AKDTIKKQIS EYIKDSEKFK
121 NLFNQNLIDA KKGQESDLIL WLKQSKDNGI ELFKANSDIT DIDEALEIIK SFKGWTTYFK
181 GFHENRKNVY SSNDIPTSII YRIVDDNLPK FLENKAKYES LKDKAPEAIN YEQIKKDLAE
241 ELTFDIDYKT SEVNQRVFSL DEVFEIANFN NYLNQSGITK FNTIIGGKFV NGENTKRKGI
301 NEYINLYSQQ INDKTLKKYK MSVLFKQILS DTESKSFVID KLEDDSDVVT TMQSFYEQIA
361 AFKTVEEKSI KETLSLLEDD LKAQKLDLSK IYFKNDKSLT DLSQQVFDDY SVIGTAVLEY
421 ITQQIAPKNL DNPSKKEQEL IAKKTEKAKY LSLETIKLAL EEFNKHRDID KQCRFEEILA
481 NFAAIPMIFD EIAQNKDNLA QISIKYQNQG KKDLLQASAE DDVKAIKDLL DQTNNLLHKL
541 KIFHISQSED KANILDKDEH FYLVFEECYF ELANIVPLYN KIRNYITQKP YSDEKFKLNF
601 ENSTLANGWD KNKEPDNTAI LFIKDDKYYL GVMNKKNNKI FDDKAIKENK GEGYKKIVYK
```

-continued

```
 661 LLPGANKMLP KVFFSAKSIK FYNPSEDILR IRNHSTHTKN GSPQKGYEKF EFNIEDCRKF

 721 IDFYKQSISK HPEWKDFGFR FSDTQRYNSI DEFYREVENQ GYKLTFENIS ESYIDSVVNQ

 781 GKLYLFQIYN KDFSAYSKGR PNLHTLYWKA LFDERNLQDV VYKLNGEAEL FYRKQSIPKK

 841 ITHPAKEAIA NKNKDNPKKE SVFEYDLIKD KRFTEDKFFF HCPITINFKS SGANKENDEI

 901 NLLLKEKAND VHILSIDRGE RHLAYYTLVD GKGNIIKQDT FNIIGNDRMK TNYHDKLAAI

 961 EKDRDSARKD WKKINNIKEM KEGYLSQVVH EIAKLVIEYN AIVVFEDLNF GFKRGRFKVE

1021 KQVYQKLEKM LIEKLNYLVF KDNEFDKTGG VLRAYQLTAP FETFKKMGKQ TGIIYYVPAG

1081 FTSKICPVTG FVNQLYPKYE SVSKSQEFFS KEDKICYNLD KGYFEFSFDY KNFGDKAAKG

1141 KWTIASFGSR LINFRNSDKN HNWDTREVYP TKELEKLLKD YSIEYGHGEC IKAAICGESD

1201 KKFFAKLTSV LNTILQMRNS KTGTELDYLI SPVADVNGNF FDSRQAPKNM PQDADANGAY

1261 HIGLKGLMLL GRIKNNQEGK KLNLVIKNEE YFEFVQNRNN
```

The FnCpf1 variants described herein can include the amino acid sequence of SEQ ID NO:4, with mutations (i.e., replacement of the native amino acid with a different amino acid, e.g., alanine, glycine, or serine), at one or more of the following positions: K180, E184, N607, K613, D616, N617, and/or K671 of SEQ ID NO:4. In some embodiments, the FnCpf1 variants are at least 80%, e.g., at least 85%, 90%, or 95% identical to the amino acid sequence of SEQ ID NO:4, e.g., have differences at up to 5%, 10%, 15%, or 20% of the residues of SEQ ID NO:4 replaced, e.g., with conservative mutations, in addition to the mutations described herein. In preferred embodiments, the variant retains desired activity of the parent, e.g., the nuclease activity (except where the parent is a nickase or a dead Cpf1), and/or the ability to interact with a guide RNA and target DNA).

To determine the percent identity of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The nucleotides at corresponding amino acid positions or nucleotide positions are then compared. When a position in the first sequence is occupied by the same nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences. Percent identity between two polypeptides or nucleic acid sequences is determined in various ways that are within the skill in the art, for instance, using publicly available computer software such as Smith Waterman Alignment (Smith, T. F. and M. S. Waterman (1981) J Mol Biol 147: 195-7); "BestFit" (Smith and Waterman, Advances in Applied Mathematics, 482-489 (1981)) as incorporated into GeneMatcher Plus™, Schwarz and Dayhof (1979) Atlas of Protein Sequence and Structure, Dayhof, M. O., Ed, pp 353-358; BLAST program (Basic Local Alignment Search Tool; (Altschul, S. F., W. Gish, et al. (1990) J Mol Biol 215: 403-10), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins or nucleic acids, the length of comparison can be any length, up to and including full length (e.g., 5%, 10%, 20%, 30%, 40%, 50%, 60%, 70%, 80%, 90%, 95%, or 100%). For purposes of the present compositions and methods, at least 80% of the full length of the sequence is aligned.

For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

In some embodiments, the mutants have alanine in place of the wild type amino acid. In some embodiments, the mutants have any amino acid other than arginine or lysine (or the native amino acid).

In some embodiments, the Cpf1 variants also include one of the following mutations listed in Table A, which reduce or destroy the nuclease activity of the Cpf1:

TABLE A

| Residues involved in DNA and RNA catalysis | | | | |
|---|---|---|---|---|
| | AsCpf1 | LbCpf1 (+18) | LbCpf1 | FnCpf1 |
| DNA targeting | D908 | D850 | D832 | D917 |
| | E911 | E853 | E835 | E920 |
| | N913 | N855 | N837 | H922 |
| | Y916 | Y858 | Y840 | Y925 |
| | E993 | E943 | E925 | E1006 |
| | R1226 | R1156 | R1138 | R1218 |
| | S1228 | S1158 | S1140 | S1220 |
| | D1235 | D1166 | D1148 | D1227 |
| | D1263 | D1198 | D1180 | D1255 |
| RNA processing | H800 | H777 | H759 | H843 |
| | K809 | K786 | K768 | K852 |
| | K860 | K803 | K785 | K869 |
| | F864 | F807 | F789 | F873 |
| Mutations that turn Cpf1 into a nickase | | | | |
| | R1226A | R1156A | R1138A | R1218A |

See, e.g., Yamano et al., Cell. 2016 May 5; 165(4):949-62; Fonfara et al., Nature. 2016 Apr. 28; 532(7600):517-21; Dong et al., Nature. 2016 Apr. 28; 532(7600):522-6; and Zetsche et al., Cell. 2015 Oct. 22; 163(3):759-71. Note that "LbCpf1 (+18)" refers to the full sequence of amino acids 1-1246 of SEQ ID NO:3, while the LbCpf1 refers to the sequence of LbCpf1 in Zetsche et al., also shown herein as amino acids 1-1228 of SEQ ID NO:11 and amino acids 19-1246 of SEQ ID NO:3.

Thus, in some embodiments, for AsCpf1, catalytic activity-destroying mutations are made at D908 and E993, e.g., D908A and E993A; and for LbCpf1 catalytic activity-destroying mutations at D832 and E925, e.g., D832A and E925A.

In some embodiments, the Cpf1 variants also include mutations that increase specificity (i.e., induce substantially fewer off target effects), e.g., as described in WO2018/022634. For example, LbCpf1 variant proteins can include one or more mutations at one, two, three, four, five, six or all seven of the following positions: S202, N274, N278, K290, K367, K532, K609, K915, Q962, K963, K966, K1002 and/or S1003, e.g., S202A, N274A, N278A, K290A, K367A, K532A, K609A, K915A, Q962A, K963A, K966A, K1002A and/or S1003A. AsCpf1 variant proteins can include one or more mutations at one, two, three, four, five, or six of the following positions: N178, N278, N282, R301, T315, S376, N515, K523, K524, K603, K965, Q1013, and/or K1054, e.g., N178A, N278A, N282A, R301A, T315A, S376A, N515A, K523A, K524A, K603A, K965A, Q1013A, and/or K1054A. In some embodiments, the AsCpf1 variants comprise mutations at N282A, T315A, N515A, or N278A.

Also provided herein are isolated nucleic acids encoding the Cpf1 variants, vectors comprising the isolated nucleic acids, optionally operably linked to one or more regulatory domains for expressing the variant proteins, and host cells, e.g., mammalian host cells, comprising the nucleic acids, and optionally expressing the variant proteins.

The variants described herein can be used for altering the genome of a cell; the methods generally include expressing the variant proteins in the cells, along with a guide RNA having a region complementary to a selected portion of the genome of the cell. Methods for selectively altering the genome of a cell are known in the art, see, e.g., U.S. Pat. No. 8,993,233; US 20140186958; U.S. Pat. No. 9,023,649; WO/2014/099744; WO 2014/089290; WO2014/144592; WO144288; WO2014/204578; WO2014/152432; WO2115/099850; U.S. Pat. No. 8,697,359; US20160024529; US20160024524; US20160024523; US20160024510; US20160017366; US20160017301; US20150376652; US20150356239; US20150315576; US20150291965; US20150252358; US20150247150; US20150232883; US20150232882; US20150203872; US20150191744; US20150184139; US20150176064; US20150167000; US20150166969; US20150159175; US20150159174; US20150093473; US20150079681; US20150067922; US20150056629; US20150044772; US20150024500; US20150024499; US20150020223; US20140356867; US20140295557; US20140273235; US20140273226; US20140273037; US20140189896; US20140113376; US20140093941; US20130330778; US20130288251; US20120088676; US20110300538; US20110236530; US20110217739; US20110002889; US20100076057; US20110189776; US20110223638; US20130130248; US20150050699; US20150071899; US20150045546; US20150031134; US20150024500; US20140377868; US20140357530; US20140349400; US20140335620; US20140335063; US20140315985; US20140310830; US20140310828; US20140309487; US20140304853; US20140298547; US20140295556; US20140294773; US20140287938; US20140273234; US20140273232; US20140273231; US20140273230; US20140271987; US20140256046; US20140248702; US20140242702; US20140242700; US20140242699; US20140242664; US20140234972; US20140227787; US20140212869; US20140201857; US20140199767: US20140189896; US20140186958; US20140186919; US20140186843; US20140179770; US20140179006; US20140170753; WO/2008/108989; WO/2010/054108; WO/2012/164565; WO/2013/098244; WO/2013/176772; Makarova et al., "Evolution and classification of the CRISPR-Cas systems" 9(6) Nature Reviews Microbiology 467-477 (1-23) (June 2011); Wiedenheft et al., "RNA-guided genetic silencing systems in bacteria and archaea" 482 Nature 331-338 (Feb. 16, 2012); Gasiunas et al., "Cas9-crRNA ribonucleoprotein complex mediates specific DNA cleavage for adaptive immunity in bacteria" 109(39) Proceedings of the National Academy of Sciences USA E2579-E2586 (Sep. 4, 2012); Jinek et al., "A Programmable Dual-RNA-Guided DNA Endonuclease in Adaptive Bacterial Immunity" 337 Science 816-821 (Aug. 17, 2012); Carroll, "A CRISPR Approach to Gene Targeting" 20(9) Molecular Therapy 1658-1660 (September 2012); U.S. Appl. No. 61/652,086, filed May 25, 2012; Al-Attar et al., Clustered Regularly Interspaced Short Palindromic Repeats (CRISPRs): The Hallmark of an Ingenious Antiviral Defense Mechanism in Prokaryotes, Biol Chem. (2011) vol. 392, Issue 4, pp. 277-289; Hale et al., Essential Features and Rational Design of CRISPR RNAs That Function With the Cas RAMP Module Complex to Cleave RNAs, Molecular Cell, (2012) vol. 45, Issue 3, 292-302.

The variant proteins described herein can be used in place of or in addition to any of the Cas9 or Cpf1 proteins described in the foregoing references, or in combination with analogous mutations described therein, with a guide RNA appropriate for the selected Cpf1, i.e., with guide RNAs that target sequences other than the wild type PAM, e.g., that have PAM sequences according to the following Table B.

TABLE B

| Variant protein | Stronger PAM | Weaker PAM |
|---|---|---|
| AsCpf1 S170R | TTTN, CTTN, GTTN | TATN, TCTN, TTAN, TTCN, TTGN |
| AsCpf1 E174R | TTTN, CTTN, GTTN, TTCN | TATN, TCTN, TTAN, TTGN |
| AsCpf1 S542K | TTTN, GTTN, TTCN | CTTN, TCTN, TTAN |
| AsCpf1 S542Q | TTTN | TTCN |
| AsCpf1 S542R | TTTN, ATTN, CTTN, GTTN, TCTN, TTCN, ATCN, CCCN, CCTN, GCTN, GGTN, TCCN | TGTN, TATN, CTCN, TGCN |
| AsCpf1 N551R | TTTN | GTTN |
| AsCpf1 N552R | | TTTN |
| AsCpf1 T167A/T539K | TTTN, GTTN | |
| AsCpf1 T167A/T539R | TTTN, GTTN | |
| AsCpf1 E174R/S542R | TTTN, CTTN, TTCN | |
| AsCpf1 S542R/K548R | TTTN, CTTN, GTTN, TTCN | TATN, TGTN, TTAN |
| AsCpf1 S542R/N551R | TTTN, GTTN, TTCN | CTTN |
| AsCpf1 S542R/N552R | TTTN | GTTN |
| AsCpf1 K548R/N551R | TTTN, GTTN | |
| AsCpf1 K548R/N552R | | TTTN |
| AsCpf1 S542R/M604A | TTTN | TTCN |
| AsCpf1 S542R/K607H | TTTN, TTCN | |
| AsCpf1 E174R/S542R/K548R | TTTN, CTTN, GTTN, ATTN, TATN, TGTN, TTAN, TTCN, AGTN, CATN, CCCN, CGTN, | TCTN, TTGN, AAAN, ACTN, ATCN, CCTN, CTAN |

TABLE B-continued

| Variant protein | Stronger PAM | Weaker PAM |
|---|---|---|
| | CTCN, GATN, GCTN, GGTN, GTCN, TACN, TCCN, TGCN, ACCN | |
| AsCpf1 S542R/K548R/N551R | TTTN, GTTN, TTCN | CTTN, TATN, TGTN, TTAN |
| AsCpf1 S170R/S542R/K607R | TTTN, TTCN, TCCN, TCTN, ACCN | GTTN, TTAN |
| AsCpf1 E174R/S542R/K607H | CTTN, TCTN, TTCN, TCCN, TTTN | CCCN, ACCN |
| AsCpf1 E174R/S542R/K607R | TTTN, TTCN, TCCN, CCCN, ACCN, GCCN | CTTN, GTTN, TCTN, TTAN, TTGN |
| AsCpf1 E174R/S542R/K548R/N551R | TTTN, CTTN, GTTN, TTCN, TCCN, CCCN, ACCN | TATN |
| AsCpf1 E174R/S542R/K548R/N552R | TTTN, CTTN, GTTN | TATN |
| AsCpf1 E174R/S542R/K548V/N552R | TTTN, CTTN, GTTN, TATN | TCTN, TGTN, TTCN, TCCN |
| AsCpf1 S170R/S542R/K548V/N552R | TTTN, GTTN, TATN, | CTTN, TGTN, TTCN |
| LbCpf1 T152R | TTTN, TTCN | |
| LbCpf1 T152K | TTTN, TTCN | |
| LbCpf1 D156R | TTTN, TTCN | |
| LbCpf1 D156K | TTTN, TTCN | |
| LbCpf1 G532R | TTTN, TTCN | |
| LbCpf1 K538R | TTTN | TTCN |
| LbCpf1 D156R/G532R/K538R | TTTN, CTTN, GTTN, TTAN, TTCN, TTGN, TCCN | TATN, TCTN |
| FnCpf1 K180R | TTTN, CTTN, GTTN, NTTN, TCTN | TTAN, TTCN |
| FnCpf1 N607R | TTTN, CTTN, GTTN, NTTN, TCTN, TTCN | TTAN |
| FnCpf1 K613R | TTTN, CTTN, GTTN, NTTN, | TTCN, TGTN |
| FnCpf1 K613V | TTTN, CTTN, GTTN, NTTN, | TATN, TGTN, TTCN |
| FnCpf1 D616R | TTTN, CTTN, GTTN, NTTN, TCTN, TTCN | TTAN |
| FnCpf1 N617R | TTTN, CTTN, GTTN, NTTN, TCTN | TTCN |
| FnCpf1 K671R | TTTN, TCTN | CTTN, GTTN, NTTN, TTCN |
| FnCpf1 K671H | TTTN, CTTN, GTTN, TCTN, NTTN | TTCN |
| FnCpf1 K607R/K613V | TTTN, CTTN, GTTN, NTTN, TGTN, TTCN | TATN, TCTN, TTAN |
| FnCpf1 K607R/K613V/D616R | TTTN, GTTN, GTTN, NTTN, TATN, TCTN, TGTN, TTAN, TTCN | |
| FnCpf1 K607R/K613R/D616R | TTTN, GTTN, GTTN, NTTN, TGTN, TTAN, TTCN | TCTN, |

The variants described herein can also be used in methods of detecting a target ssDNA or dsDNA in a sample in vitro, e.g., as described in US20170362644; East-Seletsky et al., Nature. 2016 Oct. 13; 538(7624): 270-273; Gootenberg et al., Science. 2017 Apr. 28; 356(6336): 438-442; Gootenberg et al., Science 10.1126/science.aaq0179 (2018); Chen et al., Science. 2018 Feb. 15. pii: eaar6245: Science. 2018 Feb. 15. pii: eaaq0179; and WO2017219027A1. In these methods, the binding of the variant to its target induces a non-specific DNase activity against other targets. The methods include contacting a sample known or suspected to include a target ssDNA or dsDNA with the fusion protein (or a plurality of fusion proteins), cognate guide RNAs that work with that fusion proteins, and labeled detector DNAs (e.g., a reporter ssDNA that is, eg., 3-30 nts, 3-20, 5-20, 5-15, or other suitable length). When a fusion protein binds its target the non-specific DNAse activity cleaves the detector DNAs, producing a signal. Methods for measuring the signal from the labeled detector DNA are known in the art, and can include, for example, detecting one or more of a gold nanoparticle, a fluorophore, fluorescence polarization, colloid phase transition/dispersion, electrochemical signals, and semiconductor-based signals. In some embodiments, the labeled detector DNA produces an amount of detectable signal prior to being cleaved, and the amount of detectable signal is reduced when the labeled detector DNA is cleaved. Alternatively, the labeled detector DNA can produce a first detectable signal prior to being cleaved and a second detectable signal when the labeled detector DNA is cleaved. In some embodiments, the labeled detector DNA comprises a quencher/fluor pair. In some embodiments, Csm6, an auxiliary CRISPR-associated enzyme, is also included.

In addition, the variants described herein can be used in fusion proteins in place of the wild-type Cas9 or other Cas9 mutations (such as the dCas) or Cas9 nickase) as known in the art, e.g., a fusion protein with a heterologous functional domains as described in U.S. Pat. No. 8,993,233; US 20140186958; U.S. Pat. No. 9,023,649; WO/2014/099744; WO 2014/089290; WO2014/144592; WO144288; WO2014/204578; WO2014/152432; WO2115/099850; U.S. Pat. No. 8,697,359; US2010/0076057; US2011/0189776; US2011/0223638; US2013/0130248; WO/2008/108989; WO/2010/054108; WO/2012/164565; WO/2013/098244; WO/2013/176772; US20150050699; US 20150071899 and WO 2014/124284. For example, the variants, preferably comprising one or more nuclease-reducing or killing mutation, can be fused on the N or C terminus of the Cpf1 to a transcriptional activation domain (e.g., a transcriptional activation domain from the VP16 domain form herpes simplex virus (Sadowski et al., 1988, Nature, 335:563-564) or VP64; the p65 domain from the cellular transcription factor NF-kappaB (Ruben et al., 1991, Science, 251:1490-93); or a tripartite effector fused to dCas9, composed of activators VP64, p65, and Rta (VPR) linked in tandem, Chavez et al., Nat Methods. 2015 April; 12(4):326-8) or other heterologous functional domains (e.g., transcriptional repressors (e.g., KRAB, ERD, SID, and others, e.g., amino acids 473-530 of the ets2 repressor factor (ERF) repressor domain (ERD), amino acids 1-97 of the KRAB domain of KOX1, or amino acids 1-36 of the Mad mSIN3 interaction domain (SID); see Beerli et al., PNAS USA 95:14628-14633 (1998)) or silencers such as Heterochromatin Protein 1 (HP1, also known as swi6), e.g., HP1α or HP1β; proteins or peptides that could recruit long non-coding RNAs (lncRNAs) fused to a fixed RNA binding sequence such as those bound by the MS2 coat protein, endoribonuclease Csy4, or the lambda N protein; base editors (enzymes that modify the methylation state of DNA (e.g., DNA methyltransferase (DNMT) or TET proteins); or enzymes that modify histone subunits (e.g., histone acetyltransferases (HAT), histone deacetylases (HDAC), histone methyltransferases (e.g., for methylation of lysine or arginine residues) or histone demethylases (e.g., for demethylation of lysine or arginine residues)) as are known in the art can also be used. A number of sequences for such domains are known in the art, e.g., a domain that catalyzes hydroxylation of methylated cytosines in DNA. Exemplary proteins include the Ten-Eleven-Translocation (TET) 1-3 family, enzymes that converts 5-methylcytosine (5-mC) to 5-hydroxymethylcytosine (5-hmC) in DNA.

Sequences for human TET1-3 are known in the art and are shown in the following table:

| GenBank Accession Nos. | | |
| --- | --- | --- |
| Gene | Amino Acid | Nucleic Acid |
| TET1 | NP_085128.2 | NM_030625.2 |
| TET2* | NP_001120680.1 (var 1) | NM_001127208.2 |
|  | NP_060098.3 (var 2) | NM_017628.4 |
| TET3 | NP_659430.1 | NM_144993.1 |

*Variant (1) represents the longer transcript and encodes the longer isoform (a). Variant (2) differs in the 5' UTR and in the 3' UTR and coding sequence compared to variant 1. The resulting isoform (b) is shorter and has a distinct C-terminus compared to isoform a.

In some embodiments, all or part of the full-length sequence of the catalytic domain can be included, e.g., a catalytic module comprising the cysteine-rich extension and the 2OGFeDO domain encoded by 7 highly conserved exons, e.g., the Tet1 catalytic domain comprising amino acids 1580-2052, Tet2 comprising amino acids 1290-1905 and Tet3 comprising amino acids 966-1678. See, e.g., FIG. 1 of Iyer et al., Cell Cycle. 2009 Jun. 1; 8(11): 1698-710. Epub 2009 Jun. 27, for an alignment illustrating the key catalytic residues in all three Tet proteins, and the supplementary materials thereof (available at ftp site ftp.ncbi.nih.gov/pub/aravind/DONS/supplementary_material_DONS.html) for full length sequences (see, e.g., seq 2c); in some embodiments, the sequence includes amino acids 1418-2136 of Tet 1 or the corresponding region in Tet2/3.

Other catalytic modules can be from the proteins identified in Iyer et al., 2009.

In some embodiments, the heterologous functional domain is a base editor, e.g., a deaminase that modifies cytosine DNA bases, e.g., a cytidine deaminase from the apolipoprotein B mRNA-editing enzyme, catalytic polypeptide-like (APOBEC) family of deaminases, including APOBEC1, APOBEC2, APOBEC3A, APOBEC3B, APOBEC3C, APOBEC3D/E, APOBEC3F, APOBEC3G, APOBEC3H, APOBEC4 (see, e.g., Yang et al., J Genet Genomics. 2017 Sep. 20; 44(9):423-437); activation-induced cytidine deaminase (AID), e.g., activation induced cytidine deaminase (AICDA), cytosine deaminase 1 (CDA1), and CDA2, and cytosine deaminase acting on tRNA (CDAT). The following table provides exemplary sequences; other sequences can also be used.

| GenBank Accession Nos. | | |
| --- | --- | --- |
| Deaminase | Nucleic Acid | Amino Acid |
| hAID/AICDA | NM_020661.3 isoform 1 | NP_065712.1 variant 1 |
|  | NM_020661.3 isoform 2 | NP_065712.1 variant 2 |
| APOBEC1 | NM_001644.4 isoform a | NP_001635.2 variant 1 |
|  | NM_005889.3 isoform b | NP_005880.2 variant 3 |
| APOBEC2 | NM_006789.3 | NP_006780.1 |
| APOBEC3A | NM_145699.3 isoform a | NP_663745.1 variant 1 |
|  | NM_001270406.1 isoform b | NP_001257335.1 variant 2 |
| APOBEC3B | NM_004900.4 isoform a | NP_004891.4 variant 1 |
|  | NM_001270411.1 isoform b | NP_001257340.1 variant 2 |
| APOBEC3C | NM_014508.2 | NP_055323.2 |
| APOBEC3D/E | NM_152426.3 | NP_689639.2 |
| APOBEC3F | NM_145298.5 isoform a | NP_660341.2 variant 1 |
|  | NM_001006666.1 isoform b | NP_001006667.1 variant 2 |
| APOBEC3G | NM_021822.3 (isoform a) | NP_068594.1 (variant 1) |
| APOBEC3H | NM_001166003.2 | NP_001159475.2 (variant SV-200) |
| APOBEC4 | NM_203454.2 | NP_982279.1 |
| CDA1* | NM_127515.4 | NP_179547.1 |

*from Saccharomyces cerevisiae S288C

In some embodiments, the heterologous functional domain is a deaminase that modifies adenosine DNA bases, e.g., the deaminase is an adenosine deaminase 1 (ADA1), ADA2; adenosine deaminase acting on RNA 1 (ADAR1), ADAR2, ADAR3 (see, e.g., Savva et al., Genome Biol. 2012 Dec. 28; 13(12):252); adenosine deaminase acting on tRNA 1 (ADAT1), ADAT2, ADAT3 (see Keegan et al., RNA. 2017 September; 23(9):1317-1328 and Schaub and Keller, Biochimie. 2002 August; 84(8):791-803); and naturally occurring or engineered tRNA-specific adenosine deaminase (TadA) (see, e.g., Gaudelli et al., Nature. 2017 Nov. 23; 551(7681):464-471) (NP_417054.2 (*Escherichia coli* str. K-12 substr. MG1655); See, e.g., Wolf et al., EMBO J. 2002 Jul. 15; 21(14):3841-51). The following table provides exemplary sequences; other sequences can also be used.

| GenBank Accession Nos. | | |
| --- | --- | --- |
| Deaminase | Nucleic Acid | Amino Acid |
| ADA (ADA1) | NM_000022.3 variant 1 | NP_000013.2 isoform 1 |
| ADA2 | NM_001282225.1 | NP_001269154.1 |
| ADAR | NM_001111.4 | NP_001102.2 |
| ADAR2 (ADARB1) | NM_001112.3 variant 1 | NP_001103.1 isoform 1 |
| ADAR3 (ADARB2) | NM_018702.3 | NP_061172.1 |
| ADAT1 | NM_012091.4 variant 1 | NP_036223.2 isoform 1 |
| ADAT2 | NM_182503.2 variant 1 | NP_872309.2 isoform 1 |
| ADAT3 | NM_138422.3 variant 1 | NP_612431.2 isoform 1 |

In some embodiments, the heterologous functional domain is an enzyme, domain, or peptide that inhibits or enhances endogenous DNA repair or base excision repair (BER) pathways, e.g., thymine DNA glycosylase (TDG; GenBank Acc Nos. NM_003211.4 (nucleic acid) and NP_003202.3 (protein)) or uracil DNA glycosylase (UDG, also known as uracil N-glycosylase, or UNG; GenBank Acc Nos. NM 003362.3 (nucleic acid) and NP_003353.1 (protein)) or uracil DNA glycosylase inhibitor (UGI) that inhibits UNG mediated excision of uracil to initiate BER (see, e.g., Mol et al., Cell 82, 701-708 (1995); Komor et al., Nature. 2016 May 19; 533(7603)); or DNA end-binding proteins such as Gam, which is a protein from the bacteriophage Mu that binds free DNA ends, inhibiting DNA repair enzymes and leading to more precise editing (less unintended base edits; Komor et al., Sci Adv. 2017 Aug. 30; 3(8): eaao4774).

In some embodiments, all or part of the protein, e.g., at least a catalytic domain that retains the intended function of the enzyme, can be used.

In some embodiments, the heterologous functional domain is a biological tether, and comprises all or part of (e.g., DNA binding domain from) the MS2 coat protein, endoribonuclease Csy4, or the lambda N protein. These proteins can be used to recruit RNA molecules containing a specific stem-loop structure to a locale specified by the dCpf1 gRNA targeting sequences. For example, a dCpf1 variant fused to MS2 coat protein, endoribonuclease Csy4, or lambda N can be used to recruit a long non-coding RNA (lncRNA) such as XIST or HOTAIR; see, e.g., Keryer-Bibens et al., Biol. Cell 100:125-138 (2008), that is linked to the Csy4, MS2 or lambda N binding sequence. Alternatively, the Csy4, MS2 or lambda N protein binding sequence can be linked to another protein, e.g., as described in Keryer-Bibens et al., supra, and the protein can be targeted to the dCpf1 variant binding site using the methods and compositions described herein. In some embodiments, the Csy4 is catalytically inactive. In some embodiments, the Cpf1 variant, preferably a dCpf1 variant, is fused to FokI as described in U.S. Pat. No. 8,993,233; US 20140186958; U.S. Pat. No. 9,023,649; WO/2014/099744; WO 2014/089290; WO2014/144592; WO144288; WO2014/204578;

WO2014/152432; WO2115/099850; U.S. Pat. No. 8,697,359; US2010/0076057; US2011/0189776; US2011/0223638; US2013/0130248; WO/2008/108989; WO/2010/054108; WO/2012/164565; WO/2013/098244; WO/2013/176772; US20150050699; US 20150071899 and WO 2014/204578.

In some embodiments, the fusion proteins include a linker between the Cpf1 variant and the heterologous functional domains. Linkers that can be used in these fusion proteins (or between fusion proteins in a concatenated structure) can include any sequence that does not interfere with the function of the fusion proteins. In preferred embodiments, the linkers are short, e.g., 2-20 amino acids, and are typically flexible (i.e., comprising amino acids with a high degree of freedom such as glycine, alanine, and serine). In some embodiments, the linker comprises one or more units consisting of GGGS (SEQ ID NO:12) or GGGGS (SEQ ID NO: 13), e.g., two, three, four, or more repeats of the GGGS (SEQ ID NO: 12) or GGGGS (SEQ ID NO:13) unit. Other linker sequences can also be used.

In some embodiments, the variant protein includes a cell-penetrating peptide sequence that facilitates delivery to the intracellular space, e.g., HIV-derived TAT peptide, penetratins, transportans, or hCT derived cell-penetrating peptides, see, e.g., Caron et al., (2001) Mol Ther. 3(3):310-8; Langel, Cell-Penetrating Peptides: Processes and Applications (CRC Press, Boca Raton FL 2002); El-Andaloussi et al., (2005) Curr Pharm Des. 11(28):3597-611; and Deshayes et al., (2005) Cell Mol Life Sci. 62(16): 1839-49.

Cell penetrating peptides (CPPs) are short peptides that facilitate the movement of a wide range of biomolecules across the cell membrane into the cytoplasm or other organelles, e.g. the mitochondria and the nucleus. Examples of molecules that can be delivered by CPPs include therapeutic drugs, plasmid DNA, oligonucleotides, siRNA, peptide-nucleic acid (PNA), proteins, peptides, nanoparticles, and liposomes. CPPs are generally 30 amino acids or less, are derived from naturally or non-naturally occurring protein or chimeric sequences, and contain either a high relative abundance of positively charged amino acids, e.g. lysine or arginine, or an alternating pattern of polar and non-polar amino acids. CPPs that are commonly used in the art include Tat (Frankel et al., (1988) Cell. 55:1189-1193, Vives et al., (1997) J. Biol. Chem. 272:16010-16017), penetratin (Derossi et al., (1994) J. Biol. Chem. 269:10444-10450), polyarginine peptide sequences (Wender et al., (2000) Proc. Natl. Acad. Sci. USA 97:13003-13008, Futaki et al., (2001) J. Biol. Chem. 276:5836-5840), and transportan (Pooga et al., (1998) Nat. Biotechnol. 16:857-861).

CPPs can be linked with their cargo through covalent or non-covalent strategies. Methods for covalently joining a CPP and its cargo are known in the art, e.g. chemical cross-linking (Stetsenko et al., (2000) J. Org. Chem. 65:4900-4909, Gait et al. (2003) Cell. Mol. Life. Sci. 60:844-853) or cloning a fusion protein (Nagahara et al., (1998) Nat. Med. 4:1449-1453). Non-covalent coupling between the cargo and short amphipathic CPPs comprising polar and non-polar domains is established through electrostatic and hydrophobic interactions.

CPPs have been utilized in the art to deliver potentially therapeutic biomolecules into cells. Examples include cyclosporine linked to polyarginine for immunosuppression (Rothbard et al., (2000) Nature Medicine 6(11): 1253-1257), siRNA against cyclin B1 linked to a CPP called MPG for inhibiting tumorigenesis (Crombez et al., (2007) Biochem Soc. Trans. 35:44-46), tumor suppressor p53 peptides linked to CPPs to reduce cancer cell growth (Takenobu et al., (2002) Mol. Cancer Ther. 1(12):1043-1049, Snyder et al., (2004) PLOS Biol. 2:E36), and dominant negative forms of Ras or phosphoinositol 3 kinase (PI3K) fused to Tat to treat asthma (Myou et al., (2003) J. Immunol. 171:4399-4405).

CPPs have been utilized in the art to transport contrast agents into cells for imaging and biosensing applications. For example, green fluorescent protein (GFP) attached to Tat has been used to label cancer cells (Shokolenko et al., (2005) DNA Repair 4(4):511-518). Tat conjugated to quantum dots have been used to successfully cross the blood-brain barrier for visualization of the rat brain (Santra et al., (2005) Chem. Commun. 3144-3146). CPPs have also been combined with magnetic resonance imaging techniques for cell imaging (Liu et al., (2006) Biochem. and Biophys. Res. Comm. 347(1): 133-140). See also Ramsey and Flynn, Pharmacol Ther. 2015 Jul. 22. pii: S0163-7258(15)00141-2.

In some embodiments, alternatively or in addition, the variant proteins can include a nuclear localization sequence, e.g., SV40 large T antigen NLS (PKKKRRV (SEQ ID NO:16)) and nucleoplasmin NLS (KRPAATKKAGQAKKKK (SEQ ID NO:7)). Other NLSs are known in the art; see, e.g., Cokol et al., EMBO Rep. 2000 Nov. 15; 1(5): 411-415; Freitas and Cunha, Curr Genomics. 2009 December; 10(8): 550-557.

In some embodiments, the variants include a moiety that has a high affinity for a ligand, for example GST, FLAG or hexahistidine sequences. Such affinity tags can facilitate the purification of recombinant variant proteins.

For methods in which the variant proteins are delivered to cells, the proteins can be produced using any method known in the art, e.g., by in vitro translation, or expression in a suitable host cell from nucleic acid encoding the variant protein; a number of methods are known in the art for producing proteins. For example, the proteins can be produced in and purified from yeast, *E. coli*, insect cell lines, plants, transgenic animals, or cultured mammalian cells; see, e.g., Palomares et al., "Production of Recombinant Proteins: Challenges and Solutions," Methods Mol Biol. 2004; 267: 15-52. In addition, the variant proteins can be linked to a moiety that facilitates transfer into a cell, e.g., a lipid nanoparticle, optionally with a linker that is cleaved once the protein is inside the cell. See, e.g., LaFountaine et al., Int J Pharm. 2015 Aug. 13; 494(1): 180-194.

Expression Systems

To use the Cpf1 variants described herein, it may be desirable to express them from a nucleic acid that encodes them. This can be performed in a variety of ways. For example, the nucleic acid encoding the Cpf1 variant can be cloned into an intermediate vector for transformation into prokaryotic or eukaryotic cells for replication and/or expression. Intermediate vectors are typically prokaryote vectors, e.g., plasmids, or shuttle vectors, or insect vectors, for storage or manipulation of the nucleic acid encoding the Cpf1 variant for production of the Cpf1 variant. The nucleic acid encoding the Cpf1 variant can also be cloned into an expression vector, for administration to a plant cell, animal cell, preferably a mammalian cell or a human cell, fungal cell, bacterial cell, or protozoan cell.

To obtain expression, a sequence encoding a Cpf1 variant is typically subcloned into an expression vector that contains a promoter to direct transcription. Suitable bacterial and eukaryotic promoters are well known in the art and described, e.g., in Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 2010). Bacterial expression systems for expressing the engineered protein are available in, e.g., *E. coli, Bacillus* sp., and *Salmonella* (Palva et al., 1983, Gene 22:229-235). Kits for such expression systems are commercially available. Eukaryotic expression systems for mammalian cells, yeast, and insect cells are well known in the art and are also commercially available.

The promoter used to direct expression of a nucleic acid depends on the particular application. For example, a strong constitutive promoter is typically used for expression and purification of fusion proteins. In contrast, when the Cpf1 variant is to be administered in vivo for gene regulation, either a constitutive or an inducible promoter can be used, depending on the particular use of the Cpf1 variant. In addition, a preferred promoter for administration of the Cpf1 variant can be a weak promoter, such as HSV TK or a promoter having similar activity. The promoter can also include elements that are responsive to transactivation, e.g., hypoxia response elements, Gal4 response elements, lac repressor response element, and small molecule control systems such as tetracycline-regulated systems and the RU-486 system (see, e.g., Gossen & Bujard, 1992, Proc. Natl. Acad. Sci. USA, 89:5547; Oligino et al., 1998, Gene Ther., 5:491-496; Wang et al., 1997, Gene Ther., 4:432-441; Neering et al., 1996, Blood, 88:1147-55; and Rendahl et al., 1998, Nat. Biotechnol., 16:757-761).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the Cpf1 variant, and any signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the Cpf1 variant, e.g., expression in plants, animals, bacteria, fungus, protozoa, etc. Standard bacterial expression vectors include plasmids such as pBR322 based plasmids, pSKF, pET23D, and commercially available tag-fusion expression systems such as GST and LacZ.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

The vectors for expressing the Cpf1 variants can include RNA Pol III promoters to drive expression of the guide RNAs, e.g., the HI, U6 or 7SK promoters. These human promoters allow for expression of Cpf1 variants in mammalian cells following plasmid transfection.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with the gRNA encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., 1989, J. Biol. Chem., 264:17619-22; Guide to Protein Purification, in Methods in Enzymology, vol. 182 (Deutscher, ed., 1990)). Transformation of eukaryotic and prokaryotic cells are performed according to standard techniques (see, e.g., Morrison, 1977, J. Bacteriol. 132:349-351; Clark-Curtiss & Curtiss, Methods in Enzymology 101:347-362 (Wu et al., eds, 1983).

Any of the known procedures for introducing foreign nucleotide sequences into host cells may be used. These include the use of calcium phosphate transfection, poly brene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the Cpf1 variant.

The present invention also includes the vectors and cells comprising the vectors.

Also provided herein are compositions and kits comprising the variants described herein. In some embodiments, the kits include the fusion proteins and a cognate guide RNA (i.e., a guide RNA that binds to the protein and directs it to a target sequence appropriate for that protein). In some embodiments, the kits also include labeled detector DNA, e.g., for use in a method of detecting a target ssDNA or dsDNA. Labeled detector DNAs are known in the art, e.g., as described in US20170362644; East-Seletsky et al., Nature. 2016 Oct. 13; 538(7624): 270-273; Gootenberg et al., Science. 2017 Apr. 28; 356(6336): 438-442, and WO2017219027A1, and can include labeled detector DNAs comprising a fluorescence resonance energy transfer (FRET) pair or a quencher/fluor pair, or both. The kits can also include one or more additional reagents, e.g., additional enzymes (such as RNA polymerases) and buffers, e.g., for use in a method described herein.

EXAMPLES

The invention is further described in the following examples, which do not limit the scope of the invention described in the claims.

Methods

The following materials and methods were used in the Examples below, unless otherwise noted.

Plasmids and Oligonucleotides.

The target site sequences for crRNAs and oligonucleotide sequences used in Examples 1B, 4B, and 5-8 are available in Tables 2A-2D and 3A-3D respectively. Human expression plasmids for wild-type AsCas12a, LbCas12a, FnCas12a, and MbCas12a (SQT1659, SQT1665, AAS1472, AAS2134, respectively) were generated by sub-cloning the nuclease open-reading frames from plasmids pY010, pY016, pY004, and pY014, respectively (Addgene plasmids 69982, 69988, 69976, and 69986; gifts from Feng Zhang) into the Not and AgeI sites of pCAG-CFP (Addgene plasmid 11179; a gift from Connie Cepko). Protein expression plasmids were generated by cloning the human codon-optimized open reading frames of As, Fn, and MbCas12a, and the bacterial codon-optimized LbCas12a open reading frame (from Addgene plasmid 79008; a gift from Jin Soo Kim) into the NcoI and FseI sites of pET28b-Cas9 (Addgene plasmid 47327; a gift from Alex Schier) to generate BPK3541, RTW656, RTW660, and RTW645, respectively. All Cas12a variants, activator constructs, and base editor fusions were generated via standard molecular cloning and isothermal assembly. Human cell expression plasmids for Cas12a crRNAs were generated by annealing and ligating oligonucleotides corresponding to spacer sequence duplexes into BsmBI-digested BPK3079, BPK3082, BPK4446, and BPK4449 for U6 promoter-driven transcription of As, Lb, Fn, and MbCas12a crRNAs, respectively. Substrate plasmids for in vitro cleavage reactions were generated by cloning target sites into the NheI and HindIII sites of pUC19. Plasmids for in vitro transcription of Cas12a crRNAs were generated by annealing and ligating oligonucleotides corresponding to spacer sequence duplexes into BsaI-digested MSP3491, MSP3495, RTW763, and RTW767 for T7 promoter-driven transcription of As, Lb, Fn, and MbCas12a crRNAs, respectively.

TABLE 2A

Cas12a crRNAs for nuclease experiments

| crRNA ID | gene name | 4 nt PAM | 20 nt Spacer | SEQ ID NO: |
|---|---|---|---|---|
| AACC-1 | FANCF | AACC | AGTGGAGGCAAGAGGGCGGC | 26. |
| AACC-2 | RUNX1 | AACC | AAGACAGGTCACTGTTTCAG | 27. |
| AACC-3 | EMX1 | AACC | ACACCTTCACCTGGGCCAGG | 28. |
| AACC-4 | EMX1 | AACC | GGTGGCGCATTGCCACGAAG | 29. |
| AATA-1 | FANCF | AATA | GCATTGCAGAGAGGCGTATC | 30. |
| AATA-2 | RUNX1 | AATA | TGCTGTCTGAAGCCATCGCT | 31. |
| AATA-3 | DNMT1 | AATA | AGTGGCAGAGTGCTAAGGGA | 32. |
| AATA-4 | EMX1 (amplicon 2) | AATA | TGGAGCCTGCTCCAGGTGGG | 33. |
| AATC-1 | FANCF | AATC | AGTACGCAGAGAGTCGCCGT | 34. |
| AATC-2 | CFTR | AATC | CTAACTGAGACCTTACACCG | 35. |
| AATG-1 | EMX1 | AATG | CGCCACCGGTTGATGTGATG | 36. |
| ACCC-1 | VEGFA | ACCC | CGGCTCTGGCTAAAGAGGGA | 37. |
| ACCC-2 | VEGFA | ACCC | CCTATTTCTGACCTCCCAAA | 38. |
| ACCC-3 | DNMT1 | ACCC | AGAGGCTCAAGTGAGCAGCT | 39. |
| ACCC-4 | EMX1 | ACCC | TAGTCATTGGAGGTGACATC | 40. |
| ACCC-5 | EMX1 | ACCC | ACGAGGGCAGAGTGCTGCTT | 41. |
| ACCC-6 | DNMT1 | ACCC | AATAAGTGGCAGAGTGCTAA | 42. |
| AGCC-1 | FANCF | AGCC | GCCCTCTTGCCTCCACTGGT | 43. |
| AGCC-2 | RUNX1 | AGCC | ATCGCTTCCTCCTGAAAATG | 44. |
| AGCC-3 | RUNX1 | AGCC | TCACCCCTCTAGCCCTACAT | 45. |
| AGCC-4 | EMX1 (amplicon 2) | AGCC | TGCTCCAGGTGGGGAATAAG | 46. |
| AGTA-1 | DNMT1 | AGTA | ACAGACATGGACCATCAGGA | 47. |
| AGTA-2 | CFTR | AGTA | CCAGATTCTGAGCAGGGAGA | 48. |
| AGTC-1 | DNMT1 | AGTC | TCCGTGAACGTTCCCTTAGC | 49. |
| AGTC-2 | CFTR | AGTC | TGTCCTGAACCTGATGACAC | 50. |
| ATCA-1 | DNMT1 | ATCA | GGAAACATTAACGTACTGAT | 51. |
| ATCA-2 | CFTR | ATCA | GAATCCTCTTCGATGCCATT | 52. |
| ATCC-1 | DNMT1 | ATCC | TCACAGCAGCCCCTTGAGAA | 53. |
| ATCC-2 | CFTR | ATCC | AATCAACTCTATACGAAAAT | 54. |

TABLE 2A-continued

Cas12a crRNAs for nuclease experiments

| crRNA ID | gene name | 4 nt PAM | 20 nt Spacer | SEQ ID NO: |
|---|---|---|---|---|
| ATCC-3 | DNMT1 | ATCC | CCAACATGCACTGATGTTGT | 55. |
| ATCC-4 | FANCF | ATCC | ATCGGCGCTTTGGTCGGCAT | 56. |
| ATTA-1 | DNMT1 | ATTA | ACGTACTGATGTTAACAGCT | 57. |
| ATTA-2 | EMX1 (amplicon 2) | ATTA | ACATTAACAAGAAGCATTTG | 58. |
| ATTA-3 | EMX1 (amplicon 2) | ATTA | TTCAAGTGGCGCAGATCTAG | 59. |
| ATTA-4 | CFTR | ATTA | GAAGGAGATGCTCCTGTCTC | 60. |
| ATTC-1 | DNMT1 | ATTC | ACCGAGCAGGAGTGAGGGAA | 61. |
| ATTC-2 | EMX1 (amplicon 2) | ATTC | CCCACCTGGAGCAGGCTCCA | 62. |
| ATTC-3 | CFTR | ATTC | TGATGAGCCTTTAGAGAGAA | 63. |
| ATTC-4 | VEGFA | ATTC | CCTCTTTAGCCAGAGCCGGG | 64. |
| ATTC-5 | FANCF | ATTC | GCACGGCTCTGGAGCGGCGG | 65. |
| ATTG-1 | DNMT1 | ATTG | GGTCAGCTGTTAACATCAGT | 66. |
| ATTG-2 | EMX1 (amplicon 2) | ATTG | TTATGAACCTGGGTGAAGTC | 67. |
| ATTG-3 | VEGFA | ATTG | GAATCCTGGAGTGACCCCTG | 68. |
| ATTG-4 | CFTR | ATTG | GATTGAGAATAGAATTCTTC | 69. |
| ATTG-5 | FANCF | ATTG | GAACATCCGCGAAATGATAC | 70. |
| ATTT-1 | DNMT1 | ATTT | GGCTCAGCAGGCACCTGCCT | 71. |
| ATTT-2 | EMX1 (amplicon 2) | ATTT | GCTTTCCACCCACCTTTCCC | 72. |
| ATTT-3 | VEGFA | ATTT | CTGACCTCCCAAACAGCTAC | 73. |
| ATTT-4 | CFTR | ATTT | CTTCTTTCTGCACTAAATTG | 74. |
| ATTT-5 | FANCF | ATTT | CGCGGATGTTCCAATCAGTA | 75. |
| CACC-1 | FANCF | CACC | GTGCGCCGGGCCTTGCAGTG | 76. |
| CACC-2 | RUNX1 | CACC | GAGGCATCTCTGCACCGAGG | 77. |
| CCCC-1 | FANCF | CCCC | GCCCAAAGCCGCCCTCTTGC | 78. |
| CCCC-2 | RUNX1 | CCCC | GCCTTCAGAAGAGGGTGCAT | 79. |
| CCCC-3 | DNMT1 | CCCC | AGAGGGTTCTAGACCCAGAG | 80. |
| CCCC-4 | DNMT1 | CCCC | AGGGCCAGCCCAGCAGCCAA | 81. |
| CGCA-1 | FANCF | CGCA | CGGCTCTGGAGCGGCGGCTG | 82. |
| CGCA-2 | EMX1 | CGCA | TTGCCACGAAGCAGGCCAAT | 83. |
| CGCC-1 | FANCF | CGCC | GCTCCAGAGCCGTGCGAATG | 84. |
| CGCC-2 | EMX1 | CGCC | ACCGGTTGATGTGATGGGAG | 85. |
| CGCC-3 | FANCF | CGCC | ACATCCATCGGCGCTTTGGT | 86. |
| CGCC-4 | FANCF | CGCC | GATGGATGTGGCGCAGGTAG | 87. |
| CGTC-1 | FANCF | CGTC | AGCACCTGGGACCCCGCCAC | 88. |
| CGTC-2 | FANCF | CGTC | TCCAAGGTGAAAGCGGAAGT | 89. |
| CTCA-1 | DNMT1 | CTCA | AACGGTCCCCAGAGGGTTCT | 90. |
| CTCA-2 | CFTR | CTCA | AAACTCATGGGATGTGATTC | 91. |
| CTCC-1 | DNMT1 | CTCC | GTGAACGTTCCCTTAGCACT | 92. |

TABLE 2A-continued

Cas12a crRNAs for nuclease experiments

| crRNA ID | gene name | 4 nt PAM | 20 nt Spacer | SEQ ID NO: |
|---|---|---|---|---|
| CTCC-2 | CFTR | CTCC | TTCTAATGAGAAACGGTGTA | 93. |
| CTCC-3 | FANCF | CTCC | ACTGGTTGTGCAGCCGCCGC | 94. |
| CTCC-4 | FANCF | CTCC | AGAGCCGTGCGAATGGGGCC | 95. |
| CTCT-1 | DNMT1 | CTCT | GGGGAACACGCCCGGTGTCA | 96. |
| CTTA-1 | DNMT1 | CTTA | TTGGGTCAGCTGTTAACATC | 97. |
| CTTA-2 | EMX1 (amplicon 2) | CTTA | TTCCCCACCTGGAGCAGGCT | 98. |
| CTTA-3 | RUNX1 | CTTA | CTAATCAGATGGAAGCTCTT | 99. |
| CTTA-4 | CFTR | CTTA | CACCGTTTCTCATTAGAAGG | 100. |
| CTTC-1 | FANCF | CTTC | CGCTTTCACCTTGGAGACGG | 101. |
| CTTC-2 | EMX1 (amplicon 2) | CTTC | ACCCAGGTTCATAACAATGT | 102. |
| CTTC-3 | VEGFA | CTTC | TCCCCGCTCCAACGCCCTCA | 103. |
| CTTC-4 | CFTR | CTTC | TAATGAGAAACGGTGTAAGG | 104. |
| CTTC-5 | FANCF | CTTC | GCGCACCTCATGGAATCCCT | 105. |
| CTTG-1 | DNMT1 | CTTG | ACAGGCGAGTAACAGACATG | 106. |
| CTTG-2 | EMX1 (amplicon 2) | CTTG | TTAATGTTAATAACTTGCTT | 107. |
| CTTG-3 | CFTR | CTTG | GTTAACTGAGTGTGTCATCA | 108. |
| CTTG-4 | RUNX1 | CTTG | GGGAGTCCCAGAGGTATCCA | 109. |
| CTTT-1 | DNMT1 | CTTT | GGTCAGGTTGGCTGCTGGGC | 110. |
| CTTT-2 | EMX1 (amplicon 2) | CTTT | CCCTGGCCTACCTCACTGGC | 111. |
| CTTT-3 | VEGFA | CTTT | AGCCAGAGCCGGGGTGTGCA | 112. |
| CTTT-4 | CFTR | CTTT | AGAGAGAAGGCTGTCCTTAG | 113. |
| CTTT-5 | FANCF | CTTT | GGTCGGCATGGCCCCATTCG | 114. |
| GCCC-1 | DNMT1 | GCCC | GGTGTCACGCCACTTGACAG | 115. |
| GCCC-2 | CFTR | GCCC | CACGCTTCAGGCACGAAGGA | 116. |
| GTCA-1 | DNMT1 | GTCA | CGCCACTTGACAGGCGAGTA | 117. |
| GTCA-2 | CFTR | GTCA | TCAGGTTCAGGACAGACTGC | 118. |
| GTCC-1 | DNMT1 | GTCC | CCAGAGGGTTCTAGACCCAG | 119. |
| GTCC-2 | CFTR | GTCC | AGGAGACAGGAGCATCTCCT | 120. |
| GTCC-3 | FANCF | GTCC | CAGGTGCTGACGTAGGTAGT | 121. |
| GTCC-4 | EMX1 | GTCC | TCCCCATTGGCCTGCTTCGT | 122. |
| GTTA-1 | DNMT1 | GTTA | CTCGCCTGTCAAGTGGCGTG | 123. |
| GTTA-2 | EMX1 (amplicon 2) | GTTA | TGAACCTGGGTGAAGTCCCA | 124. |
| GTTA-3 | EMX1 (amplicon 2) | GTTA | ATGTTAATAACTTGCTTCAA | 125. |
| GTTA-4 | CFTR | GTTA | ACCAAGGTCAGAACATTCAC | 126. |
| GTTC-1 | DNMT1 | GTTC | CCTTAGCACTCTGCCACTTA | 127. |
| GTTC-2 | EMX1 (amplicon 2) | GTTC | ATTTGTCCAGAGGAAACCAC | 128. |
| GTTC-3 | RUNX1 | GTTC | CCTGTCTTGTTTGTGAGAGG | 129. |

TABLE 2A-continued

Cas12a crRNAs for nuclease experiments

| crRNA ID | gene name | 4 nt PAM | 20 nt Spacer | SEQ ID NO: |
|---|---|---|---|---|
| GTTC-4 | CFTR | GTTC | AGGACAGACTGCCTCCTTCG | 130. |
| GTTG-1 | DNMT1 | GTTG | GGGATTCCTGGTGCCAGAAA | 131. |
| GTTG-2 | EMX1 (amplicon 2) | GTTG | GGACTTCACCCAGGTTCATA | 132. |
| GTTG-3 | VEGFA | GTTG | AGGGCGTTGGAGCGGGGAGA | 133. |
| GTTG-4 | CFTR | GTTG | ATTGGATTGAGAATAGAATT | 134. |
| GTTG-5 | FANCF | GTTG | TGCAGCCGCCGCTCCAGAGC | 135. |
| GTTT-1 | DNMT1 | GTTT | CCTGATGGTCCATGTCTGTT | 136. |
| GTTT-2 | EMX1 (amplicon 2) | GTTT | GACTTGGGATAGTGGAATAG | 137. |
| GTTT-3 | VEGFA | GTTT | GGGAGGTCAGAAATAGGGGG | 138. |
| GTTT-4 | CFTR | GTTT | CTCATTAGAAGGAGATGCTC | 139. |
| GTTT-5 | RUNX1 | GTTT | CACCTCGGTGCAGAGATGCC | 140. |
| TACA-1 | RUNX1 | TACA | TCTCTCTTTCTTCTCCCCTC | 141. |
| TACA-2 | RUNX1 | TACA | GGCAAAGCTGAGCAAAAGTA | 142. |
| TACA-3 | EMX1 | TACA | AACGGCAGAAGCTGGAGGAG | 143. |
| TACA-4 | RUNX1 | TACA | AGACCAGCATGTACTCACCT | 144. |
| TACC-1 | DNMT1 | TACC | CACGTTCGTGGCCCCATCTT | 145. |
| TACC-2 | CFTR | TACC | AGATTCTGAGCAGGGAGAGG | 146. |
| TACC-3 | EMX1 (amplicon 2) | TACC | TCACTGGCCCCACCCCAGAG | 147. |
| TACC-4 | FANCF | TACC | TGCGCCACATCCATCGGCGC | 148. |
| TATA-1 | CFTR | TATA | GAGTTGATTGGATTGAGAAT | 149. |
| TATA-2 | CFTR | TATA | TTCAAGAAGGTTATCTCAAG | 150. |
| TATA-3 | CFTR | TATA | TATTCAAGAAGGTTATCTCA | 151. |
| TATA-4 | VEGFA (amplicon 2) | TATA | GACATGTCCCATTTGTGGGA | 152. |
| TATC-1 | CFTR | TATC | GCCTCTCCCTGCTCAGAATC | 153. |
| TATC-2 | CFTR | TATC | TCAAGAAACTGGCTTGGAAA | 154. |
| TATC-3 | CFTR | TATC | CAGTTCAGTCAAGTTTGCCT | 155. |
| TATC-4 | EMX1 (amplicon 2) | TATC | CCAAGTCAAACTTCTCTTCA | 156. |
| TATG-1 | VEGFA (amplicon 2) | TATG | TTCGGGTGCTGTGAACTTCC | 157. |
| TATG-2 | EMX1 (amplicon 2) | TATG | AACCTGGGTGAAGTCCCAAC | 158. |
| TATG-3 | VEGFA | TATG | TAGCTGTTTGGGAGGTCAGA | 159. |
| TATG-4 | CFTR | TATG | GGACATTTTCAGAACTCCAA | 160. |
| TATT-1 | DNMT1 | TATT | GGGTCAGCTGTTAACATCAG | 161. |
| TATT-2 | VEGFA | TATT | TCTGACCTCCCAAACAGCTA | 162. |
| TATT-3 | CFTR | TATT | CTCAATCCAATCAACTCTAT | 163. |
| TATT-4 | FANCF | TATT | GGTCGAAATGCATGTCAATC | 164. |
| TCCA-1 | DNMT1 | TCCA | TGTCTGTTACTCGCCTGTCA | 165. |
| TCCA-2 | CFTR | TCCA | GGAGACAGGAGCATCTCCTT | 166. |
| TCCA-3 | VEGFA | TCCA | GTCCCAAATATGTAGCTGTT | 167. |

TABLE 2A-continued

| Cas12a crRNAs for nuclease experiments | | | | |
|---|---|---|---|---|
| crRNA ID | gene name | 4 nt PAM | 20 nt Spacer | SEQ ID NO: |
| TCCC-1 | DNMT1 | TCCC | CAGAGGGTTCTAGACCCAGA | 168. |
| TCCC-2 | CFTR | TCCC | CAAACTCTCCAGTCTGTTTA | 169. |
| TCCC-3 | DNMT1 | TCCC | GTCACCCCTGTTTCTGGCAC | 170. |
| TCCC-4 | FANCF | TCCC | AGGTGCTGACGTAGGTAGTG | 171. |
| TCCC-5 | VEGFA | TCCC | TCTTTAGCCAGAGCCGGGGT | 172. |
| TCCG-1 | DNMT1 | TCCG | TGAACGTTCCCTTAGCACTC | 173. |
| TCCG-2 | FANCF | TCCG | AGCTTCTGGCGGTCTCAAGC | 174. |
| TCCG-3 | VEGFA | TCCG | CACGTAACCTCACTTTCCTG | 175. |
| TCCT-1 | DNMT1 | TCCT | GATGGTCCATGTCTGTTACT | 176. |
| TGCA-1 | DNMT1 | TGCA | CACAGCAGGCCTTTGGTCAG | 177. |
| TGCA-2 | CFTR | TGCA | GAAAGAAGAAATTCAATCCT | 178. |
| TGCC-1 | DNMT1 | TGCC | ACTTATTGGGTCAGCTGTTA | 179. |
| TGCC-2 | CFTR | TGCC | TCGCATCAGCGTGATCAGCA | 180. |
| TGCC-3 | FANCF | TGCC | TCCACTGGTTGTGCAGCCGC | 181. |
| TGCC-4 | FANCF | TGCC | GACCAAAGCGCCGATGGATG | 182. |
| TGTA-1 | RUNX1 | TGTA | ATGAAATGGCAGCTTGTTTC | 183. |
| TGTA-2 | EMX1 | TGTA | CTTTGTCCTCCGGTTCTGGA | 184. |
| TGTA-3 | Matched Site 5 | TGTA | CCTCACCACTGACATTAATT | 185. |
| TGTA-4 | Matched Site 5 | TGTA | ACCACAGTCAAGTAGTTAAT | 186. |
| TGTA-5 | CFTR | TGTA | AGGTCTCAGTTAGGATTGAA | 187. |
| TGTC-1 | FANCF | TGTC | AATCTCCCAGCGTCTTTATC | 188. |
| TGTC-2 | RUNX1 | TGTC | TTGTTTGTGAGAGGAATTCA | 189. |
| TGTC-3 | EMX1 (amplicon 2) | TGTC | CAGAGGAAACCACTGTTGGG | 190. |
| TGTC-4 | EMX1 (amplicon 2) | TGTC | TATTCCACTATCCCAAGTCA | 191. |
| TGTC-5 | EMX1 (amplicon 2) | TGTC | CCTCACCCATCTCCCTGTGA | 192. |
| TGTG-1 | FANCF | TGTG | CAGCCGCCGCTCCAGAGCCG | 193. |
| TGTG-2 | RUNX1 | TGTG | AGAGGAATTCAAACTGAGGC | 194. |
| TGTG-3 | FANCF | TGTG | GCGCAGGTAGCGCGCCCACT | 195. |
| TGTG-4 | EMX1 | TGTG | GTTCCAGAACCGGAGGACAA | 196. |
| TGTG-5 | EMX1 | TGTG | ATGGGAGCCCTTCTTCTTCT | 197. |
| TTAC-2 | RUNX1 | TTAC | AGGCAAAGCTGAGCAAAAGT | 198. |
| TTAC-3 | EMX1 (amplicon 2) | TTAC | TCATCTCTGCCAGACCACCT | 199. |
| TTAC-4 | Matched Site 5 | TTAC | TGATTCTGGGGTCAACATCT | 200. |
| TTAC-5 | CFTR | TTAC | AAATGAATGGCATCGAAGAG | 201. |
| TTAC-6 | CFTR | TTAC | ACCGTTTCTCATTAGAAGGA | 202. |
| TTAC-7 | Matched Site 5 | TTAC | TAGGGCAATAAGCAACACCT | 203. |
| TTCA-1 | DNMT1 | TTCA | GTCTCCGTGAACGTTCCCTT | 204. |

TABLE 2A-continued

| Cas12a crRNAs for nuclease experiments | | | | |
|---|---|---|---|---|
| crRNA ID | gene name | 4 nt PAM | 20 nt Spacer | SEQ ID NO: |
| TTCA-2 | EMX1 (amplicon 2) | TTCA | CCCAGGTTCATAACAATGTT | 205. |
| TTCA-3 | VEGFA | TTCA | CCCAGCTTCCCTGTGGTGGC | 206. |
| TTCA-4 | CFTR | TTCA | ATCCTAACTGAGACCTTACA | 207. |
| TTCA-5 | FANCF | TTCA | CCTTGGAGACGGCGACTCTC | 208. |
| TTCC-1 | DNMT1 | TTCC | TGATGGTCCATGTCTGTTAC | 209. |
| TTCC-2 | EMX1 (amplicon 2) | TTCC | CTGGCCTACCTCACTGGCCC | 210. |
| TTCC-3 | VEGFA | TTCC | AAAGCCCATTCCCTCTTTAG | 211. |
| TTCC-4 | CFTR | TTCC | ATTGTGCAAAAGACTCCCTT | 212. |
| TTCC-5 | FANCF | TTCC | GAGCTTCTGGCGGTCTCAAG | 213. |
| TTCG-1 | DNMT1 | TTCG | TGGCCCCATCTTTCTCAAGG | 214. |
| TTCG-2 | VEGFA | TTCG | AGAGTGAGGACGTGTGTGTC | 215. |
| TTCG-3 | RUNX1 | TTCG | GAGCGAAAACCAAGACAGGT | 216. |
| TTCG-4 | CFTR | TTCG | ACCAATTTAGTGCAGAAAGA | 217. |
| TTCG-5 | FANCF | TTCG | CACGGCTCTGGAGCGGCGGC | 218. |
| TTCT-1 | DNMT1 | TTCT | GCCCTCCCGTCACCCCTGTT | 219. |
| TTCT-2 | EMX1 (amplicon 2) | TTCT | GCCCTTTACTCATCTCTGCC | 220. |
| TTCT-3 | VEGFA | TTCT | GACCTCCCAAACAGCTACAT | 221. |
| TTCT-4 | CFTR | TTCT | TTCGACCAATTTAGTGCAGA | 222. |
| TTCT-5 | FANCF | TTCT | GGCGGTCTCAAGCACTACCT | 223. |
| TTTA-1 | DNMT1 | TTTA | TTTCCCTTCAGCTAAAATAA | 224. |
| TTTA-2 | DNMT1 | TTTA | TTTTAGCTGAAGGGAAATAA | 225. |
| TTTA-3 | FANCF | TTTA | TCCGTGTTCCTTGACTCTGG | 226. |
| TTTA-4 | RUNX1 | TTTA | CCTTCGGAGCGAAAACCAAG | 227. |
| TTTA-5 | Matched site 5 | TTTA | GGATGCCACTAAAAGGGAAA | 228. |
| TTTA-6 | Matched site 1 | TTTA | GATTGAAGGAAAAGTTACAA | 229. |
| TTTC-1 | DNMT1 | TTTC | CCTCACTCCTGCTCGGTGAA | 230. |
| TTTC-2 | DNMT1 | TTTC | CTGATGGTCCATGTCTGTTA | 231. |
| TTTC-3 | EMX1 | TTTC | TCATCTGTGCCCCTCCCTCC | 232. |
| TTTC-4 | FANCF | TTTC | ACCTTGGAGACGGCGACTCT | 233. |
| TTTC-5 | RUNX1 | TTTC | GCTCCGAAGGTAAAAGAAAT | 234. |
| TTTC-6 | RUNX1 | TTTC | AGCCTCACCCCTCTAGCCCT | 235. |
| TTTC-7 | RUNX1 | TTTC | TTCTCCCCTCTGCTGGATAC | 236. |
| TTTC-8 | FANCF | TTTC | CGAGCTTCTGGCGGTCTCAA | 237. |
| TTTG-1 | DNMT1 | TTTG | AGGAGTGTTCAGTCTCCGTG | 238. |
| TTTG-2 | DNMT1 | TTTG | GCTCAGCAGGCACCTGCCTC | 239. |
| TTTG-3 | EMX1 | TTTG | TCCTCCGGTTCTGGAACCAC | 240. |
| TTTG-4 | EMX1 | TTTG | TGGTTGCCCACCCTAGTCAT | 241. |
| TTTG-5 | EMX1 | TTTG | TACTTTGTCCTCCGGTTCTG | 242. |

TABLE 2A-continued

Cas12a crRNAs for nuclease experiments

| crRNA ID | gene name | 4 nt PAM | 20 nt Spacer | SEQ ID NO: |
|---|---|---|---|---|
| TTTG-6 | FANCF | TTTG | GGCGGGGTCCAGTTCCGGGA | 243. |
| TTTG-7 | FANCF | TTTG | GTCGGCATGGCCCCATTCGC | 244. |
| TTTT-1 | DNMT1 | TTTT | ATTTCCCTTCAGCTAAAATA | 245. |
| TTTT-2 | RUNX1 | TTTT | CAGGAGGAAGCGATGGCTTC | 246. |
| TTTT-3 | FANCF | TTTT | CCGAGCTTCTGGCGGTCTCA | 247. |
| TTTT-4 | CFTR | TTTT | CGTATAGAGTTGATTGGATT | 248. |
| TTTT-5 | CFTR | TTTT | GAGCTAAAGTCTGGCTGTAG | 249. |

TABLE 2B

Cas12a crRNAs for gene activation experiments

| crRNA ID | gene name | 4 nt PAM | 20 nt Spacer | SEQ ID NO: | Distance from TSS (bp)‡ | Strand |
|---|---|---|---|---|---|---|
| AR-TTTV-a-1 | AR | TTTG | AGAGTCTGGATGAGAAATGC | 250. | 639 | C |
| AR-TTTV-a-2 | AR | TTTC | TACCCTCTTCTCTGCCTTTC | 251. | 588 | T |
| AR-TTTV-a-3 | AR | TTTG | CTCTAGGAACCCTCAGCCCC | 252. | 550 | T |
| AR-TTTV-b-1 | AR | TTTC | TCCAAAGCCACTAGGCAGGC | 253. | 141 | C |
| AR-TTTV-b-2 | AR | TTTA | GGAAAGCAGGAGCTATTCAG | 254. | 231 | C |
| AR-TTTV-b-3 | AR | TTTG | GAACCAAATTTGGTGAGTGC | 255. | 296 | C |
| AR-ATTV-1 | AR | ATTC | AGGAAGCAGGGGTCCTCCAG | 256. | 142 | C |
| AR-ATTV-2 | AR | ATTG | GGCTTTGGAACCAAATTTGG | 257. | 303 | C |
| AR-ATTV-3 | AR | ATTC | CGTCATAGGGATAGATCGGG | 258. | 508 | T |
| AR-CTTV-1 | AR | CTTG | TTTCTCCAAAGCCACTAGGC | 259. | 145 | C |
| AR-CTTV-2 | AR | CTTC | CTGAATAGCTCCTGCTTTCC | 260. | 227 | T |
| AR-CTTV-3 | AR | CTTA | TCAGTCCTGAAAAGAACCCC | 261. | 398 | C |
| AR-GTTV-1 | AR | GTTG | CATTTGCTCTCCACCTCCCA | 262. | 9 | C |
| AR-GTTV-2 | AR | GTTA | GCGCGCGGTGAGGGGAGGGG | 263. | 117 | C |
| AR-GTTV-3 | AR | GTTC | CAAAGCCCAATCTAAAAAAC | 264. | 312 | T |
| AR-TTCV-1 | AR | TTCA | GGAAGCAGGGGTCCTCCAGG | 265. | 212 | C |
| AR-TTCV-2 | AR | TTCC | TGGAGGCCAGCACTCACCAA | 266. | 283 | T |
| AR-TTCV-3 | AR | TTCA | GGACTGATAAGAGCGCGCAG | 267. | 407 | T |
| AR-CTCC-1 | AR | CTCC | AAAGCCACTAGGCAGGCGTT | 268. | 138 | C |
| AR-CTCC-2 | AR | CTCC | AGGAAATCTGGAGCCCTGGC | 269. | 268 | C |
| AR-CTCC-3 | AR | CTCC | CTCCCTCGCCTCCACCCTGT | 270. | 338 | C |
| AR-TCCC-1 | AR | TCCC | GCCCCCACCGGGCCGGCCTC | 271. | 48 | T |
| AR-TCCC-2 | AR | TCCC | CTCACCGCGCGCTAACGCCT | 272. | 121 | T |
| AR-TCCC-3 | AR | TCCC | TCGCCTCCACCCTGTTGGTT | 273. | 333 | C |
| HBB-TTTV-1 | NBB | TTTG | TACTGATGGTATGGGGCCAA | 274. | 203 | C |

TABLE 2B-continued

| Cas12a crRNAs for gene activation experiments | | | | | | |
|---|---|---|---|---|---|---|
| crRNA ID | gene name | 4 nt PAM | 20 nt Spacer | SEQ ID NO: | Distance from TSS (bp)‡ | Strand |
| HBB-TTTV-2 | NBB | TTTG | AAGTCCAACTCCTAAGCCAG | 275. | 150 | C |
| HBB-TTTV-3 | NBB | TTTG | CAAGTGTATTTACGTAATAT | 276. | 248 | T |
| HBB-ATTV-1 | NBB | ATTG | GCCAACCCTAGGGTGTGGCT | 277. | 71 | T |
| HBB-ATTV-2 | NBB | ATTG | CTACTAAAAACATCCTCCTT | 278. | 226 | T |
| HBB-ATTV-3 | NBB | ATTG | GGAAAACGATCTTCAATATG | 279. | 293 | T |
| HBB-CTTV-1 | NBB | CTTA | GACCTCACCCTGTGGAGCCA | 280. | 90 | C |
| HBB-CTTV-2 | NBB | CTTA | GGAGTTGGACTTCAAACCCT | 281. | 154 | T |
| HBB-CTTV-3 | NBB | CTTA | CCAAGCTGTGATTCCAAATA | 282. | 269 | C |
| HBB-TATV-1 | NBB | TATG | CCCAGCCCTGGCTCCTGCCC | 283. | 28 | T |
| HBB-TATV-2 | NBB | TATC | TCTTGGCCCCATACCATCAG | 284. | 197 | T |
| HBB-TATV-3 | NBB | TATC | CCAAAGCTGAATTATGGTAG | 285. | 369 | C |
| HBB-TGTV-1 | NBB | TGTC | ATCACTTAGACCTCACCCTG | 286. | 98 | C |
| HBB-TGTV-2 | NBB | TGTA | CTGATGGTATGGGGCCAAGA | 287. | 203 | C |
| HBB-TGTV-4 | NBB | TGTA | GATGGATCTCTTCCTGCGTC | 288. | 393 | T |
| HBB-TTCV-1 | NBB | TTCA | AACCCTCAGCCCTCCCTCTA | 289. | 167 | T |
| HBB-TTCV-2 | NBB | TTCC | AAATATTACGTAAATACACT | 290. | 254 | C |
| HBB-TTCV-3 | NBB | TTCA | GCTTTGGGATATGTAGATGG | 291. | 378 | T |
| HBB-CTCC-1 | NBB | CTCC | CTGCTCCTGGGAGTAGATTG | 292. | 51 | T |
| HBB-CTCC-2 | NBB | CTCC | CTCTAAGATATATCTCTTGG | 293. | 183 | T |
| HBB-CTCC-3 | NBB | CTCC | AGAATATGCAAAATACTTAC | 294. | 417 | T |
| HBB-TACC-1 | NBB | TACC | TGTCCTTGGCTCTTCTGGCA | 295. | 126 | T |
| HBB-TACC-2 | NBB | TACC | ATCAGTACAAATTGCTACTA | 296. | 212 | T |
| HBB-TACC-3 | NBB | TACC | ATAATTCAGCTTTGGGATAT | 297. | 370 | T |
| NPY1R-TTTV-1 | NPY1R | TTTC | AAGCCTCGGGAAACTGCCCT | 298. | 256 | C |
| NPY1R-TTTV-2 | NPY1R | TTTC | TTTGTTTGCAGGTCAGTGCC | 299. | 299 | T |
| NPY1R-TTTV-3 | NPY1R | TTTG | GGCTGGCGCTCGAGCTCTCC | 300. | 350 | C |
| NPY1R-ATTV-1 | NPY1R | ATTC | CTGGTTTGGGCTGGCGCTCG | 301. | 382 | C |
| NPY1R-ATTV-2 | NPY1R | ATTA | GTGCCATTATTGTGGCGAAT | 302. | 407 | C |
| NPY1R-ATTV-3 | NPY1R | ATTC | TCGGCACTGGCGTGAGAGTT | 303. | 464 | C |
| NPY1R-CTTV-1 | NPY1R | CTTC | CCCGGAGTCGAGGACTGTGG | 304. | 230 | C |
| NPY1R-CTTV-2 | NPY1R | CTTC | GGCCACAAGATGGCACTGAC | 305. | 314 | C |
| NPY1R-CTTV-3 | NPY1R | CTTA | TAAAGTGAGGAAAACAAATT | 306. | 485 | C |
| NPY1R-TTCV-1 | NPY1R | TTCC | CCGGAGTCGAGGACTGTGGG | 307. | 229 | C |
| NPY1R-TTCV-2 | NPY1R | TTCG | GCCACAAGATGGCACTGACC | 308. | 313 | C |
| NPY1R-TTCV-3 | NPY1R | TTCC | CAGCGAGCCUTTGATTCCT | 309. | 376 | C |
| NPY1R-CTCC-1 | NPY1R | CTCC | GGGGAAGGCAGGGCAUTTC | 310. | 243 | T |
| NPY1R-CTCC-2 | NPY1R | CTCC | AGCCGGGTATGACTTCGGCC | 311. | 330 | C |

TABLE 2B-continued

| Cas12a crRNAs for gene activation experiments | | | | | | |
|---|---|---|---|---|---|---|
| crRNA ID | gene name | 4 nt PAM | 20 nt Spacer | SEQ ID NO: | Distance from TSS (bp)‡ | Strand |
| NPY1R-CTCC-3 | NPY1R | CTCC | TTICTITGGCCCACTGAGAA | 312. | 554 | T |
| VEGFA-TTTV-1 | VEGFA | TTTC | AGGCTGTGAACCTTGGTGGG | 313. | 200 | C |
| VEGFA-TTTV-2 | VEGFA | TTTC | CTGCTCCCTCCTCGCCAATG | 314. | 274 | C |
| VEGFA-TTTV-3 | VEGFA | TTTG | CTAGGAATATTGAAGGGGGC | 315. | 338 | T |
| VEGFA-ATTV-1 | VEGFA | ATTG | CGGCGGGCTGCGGGCCAGGC | 316. | 159 | C |
| VEGFA-ATTV-2 | VEGFA | ATTA | CCCATCCGCCCCCGGAAACT | 317. | 274 | T |
| VEGFA-ATTV-3 | VEGFA | ATTC | CTAGCAAAGAGGGAACGGCT | 318. | 326 | C |
| VEGFA-CTTV-1 | VEGFA | CTTC | CCCTTCATTGCGGCGGGCTG | 319. | 114 | T |
| VEGFA-CTTV-2 | VEGFA | CTTC | CCCTTCATTGCGGCGGGCTG | 320. | 169 | C |
| VEGFA-CTTV-3 | VEGFA | CTTC | CCCTGCCCCCTTCAATATTC | 321. | 346 | C |
| VEGFA-GTTV-1 | VEGFA | GTTC | ACAGCCTGAAAATTACCCAT | 322. | 209 | T |
| VEGFA-GTTV-2 | VEGFA | GTTA | CGTGCGGACAGGGCCTGAGA | 323. | 303 | T |
| VEGFA-GTTV-3 | VEGFA | GTTG | GAGCGGGGAGAAGGCCAGGG | 324. | 435 | C |
| VEGFA-TTCV-1 | VEGFA | TTCC | ACACGCGGCTCGGGCCCGGG | 325. | 115 | T |
| VEGFA-TTCV-2 | VEGFA | TTCA | GGCTGTGAACCTIGGIGGGG | 326. | 199 | C |
| VEGFA-TTCV-3 | VEGFA | TTCC | TGCTCCCTCCTCGCCAATGC | 327. | 213 | C |
| VEGFA-TTCV-4 | VEGFA | TTCC | CCTTCATTGCGGCGGGCTGC | 328. | 185 | C |
| VEGFA-TTCV-5 | VEGFA | TTCC | CCTGCCCCCTICAATATTCC | 329. | 362 | C |
| VEGFA-TCCC-1 | VEGFA | TCCC | CTTCATTGCGGCGGGCTGCG | 330. | 167 | C |
| VEGFA-TCCC-2 | VEGFA | TCCC | TCCTCGCCAATGCCCCGCGG | 331. | 266 | C |
| VEGFA-TCCC-3 | VEGFA | TCCC | CTGCCCCCTICAATATTCCT | 332. | 344 | C |
| VEGFA-CTCC-1 | VEGFA | CTCC | TCGCCAATGCCCCGCGGGCG | 333. | 263 | C |
| VEGFA-CTCC-2 | VEGFA | CTCC | CTCCTCGCCAATGCCCCGCG | 334. | 267 | C |
| VEGFA-CTCC-3 | VEGFA | CTCC | AGGATTCCAATAGATCTGTG | 335. | 407 | C |

C, Coding; T, template; ‡, measured from the TSS to the -4 position of the PAM for template-strand guides or the 20th nt of the spacer for coding-strand guides

TABLE 2C

| SpCas9 sgRNAs for VEGFA gene activation experiments | | | | | |
|---|---|---|---|---|---|
| guide ID | 3 nt PAM | 20 nt Spacer | SEQ ID NO: | Distance from TSS (bp)‡ | Strand |
| VEGFA-NGG-a-1 | AGG | GTGTGCAGACGGCAGTCACT | 336. | 571 | coding |
| VEGFA-NGG-a-2 | AGG | GAGCAGCGTCTTCGAGAGTG | 337. | 509 | coding |
| VEGFA-NGG-a-3 | TGG | GGTGAGTGAGTGTGTGCGTG | 338. | 469 | coding |
| VEGFA-NGG-b-4 | AGG | GGGGCGGATGGGTAATTTTC | 339. | 217 | coding |

TABLE 2C-continued

SpCas9 sgRNAs for VEGFA gene activation experiments

| guide ID | 3 nt PAM | 20 nt Spacer | SEQ ID NO: | Distance from TSS (bp)‡ | Strand |
|---|---|---|---|---|---|
| VEGFA-NGG-b-5 | AGG | GGCATTGGCGAGGAGGGAGC | 340. | 272 | template |
| VEGFA-NGG-b-6 | AGG | GCAAAGAGGGAACGGCTCTC | 341. | 320 | coding |

‡, measured from the TS S to the -3 position of the PAM for coding-strand guides or the 20th nt of the spacer for template-strand guides

TABLE 2D

Cas12a crRNAs for base editor experiments

| crRNA ID | gene name | 4 nt PAM | 20 nt Spacer | SEQ ID NO: |
|---|---|---|---|---|
| TTTA-3 | FANCF | TTTA | TCCGTGTTCCTTGACTCTGG | 342. |
| TTTC-1 | DNMT1 | TTTC | CCTCACTCCTGCTCGGTGAA | 343. |
| TTTC-3 | EMX1 | TTTC | TCATCTGTGCCCCTCCCTCC | 344. |
| TTTC-6 | RUNX1 | TTTC | AGCCTCACCCCTCTAGCCCT | 345. |

TABLE 2D-continued

Cas12a crRNAs for base editor experiments

| crRNA ID | gene name | 4 nt PAM | 20 nt Spacer | SEQ ID NO: |
|---|---|---|---|---|
| TTTC-7 | RUNX1 | TTTC | TTCTCCCCTCTGCTGGATAC | 346. |
| TTTC-8 | FANCF | TTTC | CGAGCTTCTGGCGGTCTCAA | 347. |
| TTTG-4 | EMX1 | TTTG | TGGTTGCCCACCCTAGTCAT | 348. |
| TTTG-7 | FANCF | TTTG | GTCGGCATGGCCCCATTCGC | 349. |

TABLE 3A

Oligonucleotides used in this study-For T7E1 and RFLP experiments

| description | sequence | SEQ ID NO: |
|---|---|---|
| forward PCR primer to amplify DNMT1 locus in human cells | CCAGAATGCACAAAGTACTGCAC | 350. |
| reverse PCR primer to amplify DNMT1 locus in human cells | GCCAAAGCCCGAGAGAGTGCC | 351. |
| forward PCR primer to amplify CFTR locus in human cells | GCTGTGTCTGTAAACTGATGGCTAACA | 352. |
| reverse PCR primer to amplify CFTR locus in human cells | TTGCATTCTACTCAATTGCATTCTGTGGG | 353. |
| forward PCR primer to amplify EMX1 locus in human cells | GGAGCAGCTGGTCAGAGGGG | 354. |
| reverse PCR primer to amplify EMX1 locus in human cells | CCATAGGGAAGGGGGACACTGG | 355. |
| forward PCR primer to amplify EMX1 (amplicon 2) locus in human cells | CTGCCTCCTATTCATACACACTTACGGG | 356. |
| reverse PCR primer to amplify EMX1 (amplicon 2) locus in human cells | CTCTGTTGGTGGAAACTCCCTGACC | 357. |
| forward PCR primer to amplify FANCF locus in human cells | GGGCCGGGAAAGAGTTGCTG | 358. |
| reverse PCR primer to amplify FANCF locus in human cells | GCCCTACATCTGCTCTCCCTCC | 359. |
| forward PCR primer to amplify RUNX1 locus in human cells | CCAGCACAACTTACTCGCACTTGAC | 360. |
| reverse PCR primer to amplify RUNX1 locus in human cells | CATCACCAACCCACAGCCAAGG | 361. |
| forward PCR primer to amplify VEGFA locus in human cells | CAGCTCCACAAACTTGGTGCCAAATTC | 362. |

TABLE 3A-continued

| Oligonucleotides used in this study-For T7E1 and RFLP experiments | | |
|---|---|---|
| description | sequence | SEQ ID NO: |
| reverse PCR primer to amplify VEGFA locus in human cells | CCGCAATGAAGGGGAAGCTCGAC | 363. |
| forward PCR primer to amplify VEGFA (amplicon 2) locus in human cells | CGCTGTTCAGGTCTCTGCTAGAAGTAGG | 364. |
| reverse PCR primer to amplify VEGFA (amplicon 2) locus in human cells | CCAGACCAGAGACCACTGGGAAG | 365. |
| forward PCR primer to amplify Matched Site 1 locus in human cells | GACAAATGTATCATGCTATTATAAGATGTTGAC | 366. |
| reverse PCR primer to amplify Matched Site 1 locus in human cells | CCATTTACTGAGAGTAATTATAATTGTGC | 367. |
| forward PCR primer to amplify Matched Site 5 locus in human cells | CCAAGGACAGGAATATCTTATACCCTCTGT | 368. |
| reverse PCR primer to amplify Matched Site 5 locus in human cells | TGTCATTGTCCTTGTCCTTTAGCTACCG | 369. |

TABLE 3B

| Oligonucleotides used in this study-For PAM determination assay (PAMDA) and other in vitro cleavage experiments | | |
|---|---|---|
| description | sequence | SEQ ID NO: |
| reverse PCR primer for amplifying randomized PAM locus | CAAAACAGCCAAGCTTGCATGC | 370. |
| forward PCR primer for amplifying randomized PAM locus, adding CCAT barcode | AGCTGCCATCGGTATTTCACACCGCATACG TAC | 371. |
| forward PCR primer for amplifying randomized PAM locus, adding GCAA barcode | AGCTGGCAACGGTATTTCACACCGCATACG TAC | 372. |
| forward PCR primer for amplifying randomized PAM locus, adding ATGC barcode | AGCTGATGCCGGTATTTCACACCGCATACG TAC | 373. |
| forward PCR primer for amplifying randomized PAM locus, adding GATG barcode | AGCTGGATGCGGTATTTCACACCGCATACG TAC | 374. |
| forward PCR primer for amplifying randomized PAM locus, adding CGAT barcode | AGCTGCGATCGGTATTTCACACCGCATACG TAC | 375. |
| top strand oligo for NNNNNNNN PAM depletion library spacer 1 to be cloned into EcoRI/SphI of p11-lacY-wtx1 | AGACCGGAATTCNNNGTNNNNNNNNNNGGA ATCCCTTCTGCAGCACCTGGGCGCAGGTCA CGAGGCATG | 376. |
| top strand oligo for NNNNNNNN PAM depletion library spacer 2 to be cloned into EcoRI/SphI of p11-lacY-wtx1 | AGACCGGAATTCNNNGTNNNNNNNNNNCTG ATGGTCCATGTCTGTTACTCGCGCAGGTCA CGAGGCATG | 377. |
| reverse primer to fill in library oligos | /5Phos/CCTCGTGACCTGCGC | 378. |
| top strand for spacer 1 with TTTA PAM target to be cloned into EcoRI/SphI of p11-lacY-wtx1 | AATTCTTTAGGAATCCCTTCTGCAGCACCT GGGCATG | 379. |

TABLE 3B-continued

Oligonucleotides used in this study-For PAM determination assay (PAMDA) and other in vitro cleavage experiments

| description | sequence | SEQ ID NO: |
|---|---|---|
| bottom strand for spacer 1 with TTTA PAM target to be cloned into EcoRI/SphI of p11-lacY-wtx1 | CCCAGGTGCTGCAGAAGGGATTCCTAAAG | 380. |
| top strand for spacer 1 with CTTA PAM target to be cloned into EcoRI/SphI of p11-lacY-wtx1 | AATTCCTTAGGAATCCCTTCTGCAGCACCTGGGCATG | 381. |
| bottom strand for spacer 1 with CTTA PAM target to be cloned into EcoRI/SphI of p11-lacY-wtx1 | CCCAGGTGCTGCAGAAGGGATTCCTAAGG | 382. |
| top strand for spacer 1 with ACCT PAM target to be cloned into EcoRI/SphI of p11-lacY-wtx1 | AATTCACCTGGAATCCCTTCTGCAGCACCTGGGCATG | 383. |
| bottom strand for spacer 1 with ACCT PAM target to be cloned into EcoRI/SphI of p11-lacY-wtx1 | CCCAGGTGCTGCAGAAGGGATTCCAGGTG | 384. |
| top strand for spacer 2 with TTTA PAM target to be cloned into EcoRI/SphI of p11-lacY-wtx1 | AATTCTTTACTGATGGTCCATGTCTGTTACTCGCATG | 385. |
| bottom strand for spacer 2 with TTTA PAM target to be cloned into EcoRI/SphI of p11-lacY-wtx1 | CGAGTAACAGACATGGACCATCAGTAAAG | 386. |
| top strand for spacer 2 with CTTA PAM target to be cloned into EcoRI/SphI of p11-lacY-wtx1 | AATTCCTTACTGATGGTCCATGTCTGTTACTCGCATG | 387. |
| bottom strand for spacer 2 with CTTA PAM target to be cloned into EcoRI/SphI of p11-lacY-wtx1 | CGAGTAACAGACATGGACCATCAGTAAGG | 388. |
| top strand for spacer 2 with ACCT PAM target to be cloned into EcoRI/SphI of p11-lacY-wtx1 | AATTCACCTCTGATGGTCCATGTCTGTTACTCGCATG | 389. |
| bottom strand for spacer 2 with ACCT PAM target to be cloned into EcoRI/SphI of p11-lacY-wtx1 | CGAGTAACAGACATGGACCATCAGAGGTG | 390. |

TABLE 3C

Oligonucleotides used in this study-For activator RT-qPCR experiments

| description | sequence | SEQ ID NO: |
|---|---|---|
| forward RT-qPCR primer for the human NPY1R gene | ATGGTGAGCAGAGTGCCCTATC | 391. |
| reverse RT-qPCR primer for the human NPY1R gene | ATGGTCCCTGGCAGTCTCCAAA | 392. |
| forward RT-qPCR primer for the human AR gene | CCATCGGACTCTCATAGGTTGTC | 393. |
| reverse RT-qPCR primer for the human AR gene | GACCTGTACTTATTGTCTCTCATC | 394. |
| forward RT-qPCR primer for the human HBB gene | GCACGTGGATCCTGAGAACT | 395. |
| reverse RT-qPCR primer for the human HBB gene | ATTGGACAGCAAGAAAGCGAG | 396. |

TABLE 3C-continued

| Oligonucleotides used in this study-For activator RT-qPCR experiments | | |
|---|---|---|
| description | sequence | SEQ ID NO: |
| forward RT-qPCR primer for the human HPRT1 gene | CATTATGCTGAGGATTTGGAAAGG | 397. |
| reverse RT-qPCR primer for the human HPRT1 gene | CTTGAGCACACAGAGGGCTACA | 398. |

TABLE 3D

| Oligonucleotides used in this study-For base editor deep sequencing experiments | | |
|---|---|---|
| description | sequence | SEQ ID NO: |
| forward PCR primer to amplify TTTA PAM site 3 in human cells | GCTCCAGAGCCGTGCGAATGG | 399. |
| reverse PCR primer to amplify TTTA PAM site 3 in human cells | GCCCTACATCTGCTCTCCCTCC | 400. |
| forward PCR primer to amplify TTTC PAM site 1 in human cells | CAGCTGACCCAATAAGTGGCAGAGTG | 401. |
| reverse PCR primer to amplify TTTC PAM site 1 in human cells | TCAGGTTGGCTGCTGGGCTGG | 402. |
| forward PCR primer to amplify TTTC PAM site 3 in human cells | CCCCAGTGGCTGCTCTGGG | 403. |
| reverse PCR primer to amplify TTTC PAM site 3 in human cells | CATCGATGTCCTCCCCATTGGC | 404. |
| forward PCR primer to amplify TTTC PAM site 6 in human cells | GCTGTCTGAAGCCATCGCTTCC | 405. |
| reverse PCR primer to amplify TTTC PAM site 6 in human cells | CAGAGGTATCCAGCAGAGGGGAG | 406. |
| forward PCR primer to amplify TTTC PAM site 7 in human cells | CCTTCGGAGCGAAAACCAAGACAG | 407. |
| reverse PCR primer to amplify TTTC PAM site 7 in human cells | CAGGCAGGACGAATCACACTGAATG | 408. |
| forward PCR primer to amplify TTTC PAM site 8 in human cells | GCTCCAGAGCCGTGCGAATGG | 409. |
| reverse PCR primer to amplify TTTC PAM site 8 in human cells | GCACCTCATGGAATCCCTTCTGC | 410. |
| forward PCR primer to amplify TTTG PAM site 4 in human cells | GAAGCTGGAGGAGGAAGGGC | 411. |
| reverse PCR primer to amplify TTTG PAM site 4 in human cells | CAGCAGCAAGCAGCACTCTGC | 412. |
| forward PCR primer to amplify TTTG PAM site 7 in human cells | GCCCTCTTGCCTCCACTGGTTG | 413. |
| reverse PCR primer to amplify TTTG PAM site 7 in human cells | CCAATAGCATTGCAGAGAGGCGT | 414. |

Cell Culture Conditions.

Human U2OS (from Toni Cathomen, Freiburg) and HEK293 cells (Invitrogen) were cultured in Advanced Dulbecco's Modified Eagle Medium (A-DMEM) and DMEM, respectively, supplemented with 10% heat-inactivated FBS, 1% and penicillin and streptomycin, and 2 mM GlutaMax (with the exception that HEK293 cells cultured for experiments analyzed by RT-qPCR use media containing 0.1% penicillin and streptomycin that lacked GlutaMax). All cell culture reagents were purchased from Life Technologies, and cells were grown at 37° C. in 5% $CO_2$. Media supernatant was analyzed biweekly for the presence of *Myco-*

*plasma*, and cell line identities were confirmed by STR profiling (ATCC). Unless otherwise indicated, negative control transfections included Cas12a expression and U6-null plasmids.

Assessment of Gene and Base Editing by T7E1 or Deep-Sequencing.

For nuclease and base editor experiments, Cas12a and crRNA expression plasmids (500 ng and 250 ng, respectively) were electroporated into approximately $2\times10^5$ U2OS cells via the DN-100 program with the SE Cell Line Nucleofector Kit using a 4D-Nucleofector (Lonza). Genomic DNA (gDNA) was extracted approximately 72 or 120 hours post-nucleofection (for nuclease or base editing experiments, respectively) using the Agencourt DNAdvance Nucleic Acid Isolation Kit (Beckman Coulter), or by custom lysis and paramagnetic bead extraction. Paramagnetic beads prepared similar to as previously described (Rohland et al., Genome Res., 2012, 22:939-46)(GE Healthcare Sera-Mag SpeedBeads (Fisher Scientific) washed in 0.1×TE and suspended in 20% PEG-8000 (w/v), 1.5 M NaCl, 10 mM Tris-HCl pH 8, 1 mM EDTA pH 8, and 0.05% Tween20). For cell lysis, media supernatant was removed, a 500 μL PBS wash was performed, and the cells were treated with 200 μL lysis buffer (100 mM Tris HCl pH 8.0, 200 mM NaCl, 5 mM EDTA, 0.05% SDS, 1.4 mg/mL Proteinase K (NEB), and 12.5 mM DTT) for 12-20 hours at 55° C. To extract gDNA, the lysate was combined with 165 μL paramagnetic beads, mixed thoroughly, incubated for 5 minutes, separated on a magnetic plate and washed 3 times with 70% EtOH, allowed to dry for 5 minutes, and eluted in 65 μL elution buffer (1.2 mM Tris-HCl pH 8.0). Genomic loci were amplified by PCR with Phusion Hot Start Flex DNA Polymerase (New England Biolabs; NEB) using 100 ng of gDNA as a template and the primers listed in Table 3. Following analysis on a QIAxcel capillary electrophoresis machine (Qiagen), PCR products were purified with using paramagnetic beads.

For nuclease experiments, the percent modification of endogenous human target sites was determined by T7 Endonuclease I (T7EI) assays, similar to as previously described (Reyon et al., Nat Biotechnol., 2012, 30:460-5). Briefly, 200 ng of purified PCR products were denatured, annealed, and digested with 10 U T7EI (NEB) at 37° C. for 25 minutes. Digests were purified with paramagnetic beads and analyzed using a QIAxcel to estimate target site modification.

For base editing experiments, targeted deep sequencing was performed essentially as previously described (Kleinstiver et al., Nature, 2016, 529:490-5). Dual-indexed Tru-seq libraries were generated from purified and pooled PCR products using a KAPA HTP Library Preparation Kit (KAPA BioSystems) and sequenced on an Illumina MiSeq Sequencer. Samples were sequenced to an average read count of 55,000 and a minimum of 8,500 reads. Nucleotide substitutions and insertion or deletion mutations (indels) were analyzed using a modified version of CRISPResso (Pinello et al., Nat Biotechnol., 2016, 34:695-7), with an additional custom analysis performed to examine indel percentages (defined as [modified reads−substitution only reads]/total reads*100), in a 44 nt window encompassing the −14 to +30 region of each target site (an additional 10 nt upstream of the 4 nt PAM and 10 nt downstream of the 20 nt spacer sequence).

GUIDE-seq.

GUIDE-seq experiments were performed as previously described (Tsai et al., Nat Biotechnol., 2015, 33:187-197). Briefly, U2OS cells were electroporated as described above but including 100 pmol of the double-stranded oligodeoxynucleotide (dsODN) GUIDE-seq tag. Restriction-fragment length polymorphisms (RFLP) assays (performed as previously described; Kleinstiver et al., Nature, 2015, 523:481-5) and T7E1 assays (as described above) were performed to assess GUIDE-seq tag integration and on-target modification percentages, respectively. GUIDE-seq libraries were sequenced using an Illumina MiSeq sequencer, and data was analyzed using guideseq (Tsai et al., Nat Biotechnol., 2016, 34:483) v1.1 with a 75 bp window and allowing up to 9 mismatches prior to downstream data processing. High-confidence, cell-type-specific, single-nucleotide polymorphisms (SNPs) were identified using SAMTools.

Gene Activation Experiments.

For experiments with crRNAs or sgRNAs targeting the VEGFA promoter, $1.6\times10^5$ HEK293 cells per well were seeded in 24-well plates roughly 24 hours prior to transfection with plasmids encoding Cas12a or Cas9 activators and pools of crRNAs or sgRNAs (750 ng and 250 ng, respectively), 1.5 μL TransIT-LTI (Mirus), and Opti-MEM to a total volume of 50 μL. The cell culture media was changed 22 hours post-transfection, and aliquots of the media supernatant were collected 44 hours post-transfection to determine VEGFA concentration using a Human VEGF Quantikine ELISA Kit (R&D Systems).

For experiments with crRNAs targeting the AR, HBB, or NPYIR promoters, $8.6\times10^4$ HEK293 cells per well were seeded in 12-well plates roughly 24 hours prior to transfection with 750 ng Cas12a activator expression plasmid, 250 ng crRNA plasmid pools, 3 μL TransIT-LTI (Mirus), and 100 μL Opti-MEM. Total RNA was extracted from the transfected cells 72 hours post-transfection using the NucleoSpin RNA Plus Kit (Clontech). cDNA synthesis using a High-Capacity RNA-to-cDNA kit (ThermoFisher) was performed with 250 ng of purified RNA, and 3 μL of 1:20 diluted cDNA was amplified by quantitative reverse transcription PCR (RT-qPCR) using Fast SYBR Green Master Mix (ThermoFisher) and the primers listed in Table 3. RT-qPCR reactions were performed on a LightCycler480 (Roche) with the following cycling program: initial denaturation at 95° C. for 20 seconds (s) followed by 45 cycles of 95° C. for 3 s and 60° C. for 30 s. If sample amplification did not reach the detection threshold after 35 cycles, Ct (Cycles to threshold) values are considered as 35 due to Ct fluctuations typical of transcripts expressed at very low levels. Gene expression levels over negative controls experiments (Cas12a activator and empty crRNA plasmids) were normalized to the expression of HPRT1.

Expression and Purification of Cas12a Proteins.

Plasmids encoding Cas12a-SV40NLS-6×His fusion proteins were transformed into Rosetta 2 (DE3) *E. coli*, and single colonies were inoculated into 25 mL LB medium cultures containing 50 mg/L kanamycin and 25 mg/L chloramphenicol (Kan/Cm) prior to growth at 25° C. for 16 hours. Starter cultures were then diluted 1:100 into 150 mL LB medium containing Kan/Cm and grown at 37° C. until the $OD_{600}$ reached 0.4. Cultures were then induced with 0.2 mM isopropyl B-D-thiogalactopyranoside prior to shaking at 18° C. for 23 hours. Cell pellets from 50 mL of the culture were harvested by centrifugation at 1200 g for 15 minutes and suspended in 1 mL lysis buffer containing 20 mM Hepes pH 7.5, 100 mM KCl, 5 mM MgCl2, 5% glycerol, 1 mM DTT, Sigmafast protease inhibitor (Sigma-Aldrich), and 0.1% Triton X-100. The cell suspension was loaded into a 1 mL AFA fiber milliTUBE (Covaris) and was lysed using an E220evolution focused-ultrasonicator (Covaris) according to the following conditions: peak intensity power of 150 W, 200 cycles per burst, duty factor of 10%, and treatment for 20 minutes at 5° C. The cell lysate was centrifuged for 20 minutes at 21,000 g and 4° C., and the supernatant was mixed with an equal volume of binding buffer (lysis buffer+10 mM imidazole), added to 400 μL of HisPur Ni-NTA Resin (Thermo Fisher Scientific) that was pre-equilibrated in binding buffer, and rocked at 4° C. for 8 hours. The protein-bound resin was washed three times with 1 mL wash buffer (20 mM Hepes pH 7.5, 500 mM KCl, 5 mM MgCl2, 5% glycerol, 25 mM imidazole, and 0.1% Triton X-100), washed once with 1 mL binding buffer, and then three sequential elutions were performed with 500 μL elution buffer (20 mM Hepes pH 7.5, 100 mM KCl, 5 mM MgCl2, 10% glycerol, and 500 mM imidazole). Select elutions were pooled and dialyzed using Spectra/Por 4 Standard Cellulose Dialysis Tubing (Spectrum Chemical Manufacturing Corp) in three sequential 1:500 buffer exchanges, the first two into dialysis buffer (300 mM NaCl, 10 mM Tris-HCl pH 7.4, 0.1 mM EDTA, and 1 mM DTT) and the last into dialysis buffer containing 20% glycerol. Proteins were then concentrated with Amicon Ultra-0.5 mL Centrifugal Filter Units (Millipore Sigma), diluted with an equal volume of dialysis buffer with 80% glycerol, and stored at −20° C.

In Vitro Cleavage Reactions.

Cas12a crRNAs were in vitro transcribed from roughly 1 μg of HindIII linearized crRNA transcription plasmid using the T7 RiboMAX Express Large Scale RNA Production kit (Promega) at 37° C. for 16 hours. The DNA template was degraded by the addition of 1 μL RQI DNase at 37° C. for 15 minutes, and the RNA was subsequently purified with the miRNeasy Mini Kit (Qiagen). In vitro cleavage reactions consisted of 25 nM PvuI-linearized substrate plasmid, 300 nM crRNA, and 200 nM purified Cas12a protein in cleavage buffer (10 mM Hepes pH 7.5, 150 mM NaCl and 5 mM $MgCl_2$), and were performed at 37° C. unless otherwise indicated. Plasmid substrates for temperature tolerance assays encoded the PAMDA site 2 spacer with a TTTA PAM. Cleavage reaction master-mixes were prepared and then aliquoted into 5 μL volumes for each time point, incubated in a thermal cycler, and halted by the addition of 10 μL of stop buffer (0.5% SDS, 50 mM EDTA). Stopped aliquots were purified with paramagnetic beads, and the percent cleavage was quantified by QIAxcel ScreenGel Software (v1.4).

PAM Determination Assay.

Plasmid libraries encoding target sites with randomized sequences were cloned using Klenoq(-exo) (NEB) to fill in the bottom strands of two separate oligos harboring 10 nt randomized sequences 5' of two distinct spacer sequences (Table 3). The double-stranded product was digested with EcoRI and ligated into EcoRI and SphI digested p11-lacY-wtx1 (Addgene plasmid 69056; a gift from Huimin Zhao). Ligations were transformed into electrocompetent XLI Blue *E. coli*, recovered in 9 mL of SOC at 37° C. for 1 hour, and then grown for 16 hours in 150 mL of LB medium with 100 mg/L carbenicillin. The complexity of each library was estimated to be greater than $10^6$ based on the number of transformants observed.

Cleavage reactions of the randomized PAM plasmid libraries were performed as described above, with aliquots being stopped at 3, 6, 12, 24, and 48 minutes. Reactions were purified with magnetic beads and approximately 1-5 ng was used as template for PCR amplification of uncleaved molecules with Phusion Hot Start Flex DNA Polymerase (NEB) for 15 cycles. During the PCR reactions, a 4 nt unique molecular index (UMI) was added upstream of the PAM to enable demultiplexing of the time-point samples, and products were also generated from an undigested plasmid to determine initial PAM representation in the libraries. Purified PCR products were quantified with QuantiFluor dsDNA System (Promega), normalized, and pooled for library preparation with Illumina dual-indexed adapters using a KAPA HTP PCR-free Library Preparation Kit (KAPA BioSystems). Libraries were quantified using the Universal KAPA Illumina Library qPCR Quantification Kit (KAPA Biosystems) and sequenced on an Illumina MiSeq sequencer using a 300-cycle v2 kit (Illumina).

Sequencing reads were analyzed using a custom Python script to estimate cleavage rates on each PAM for a given protein. Paired-end reads were filtered by Phred score (≥Q30) and then merged with the requirement of perfect matches of time point UMIs, PAM, and spacer sequence. Counts were generated for every 4 and 5 nt PAM for all time points, protein, and spacer. PAM counts were then corrected for inter-sample differences in sequencing depth, converted to a fraction of the initial representation of that PAM in the original plasmid library (as determined by the undigested control), and then normalized to account for the increased fractional representation of uncleaved substrates over time due to depletion of cleaved substrates (by selecting the 5 PAMs with the highest average counts across all time points to represent the profile of uncleavable substrates). The depletion of each PAM over time was then fit to an exponential decay model (y(t)=Ae^(−kt), where y(t) is the normalized PAM count, t is the time (minutes), k is the rate constant, and A is a constant), by linear least squares regression.

Targeting Range Calculations.

The targeting ranges of wild-type and variant AsCas12a nucleases were assessed on various annotated genomic elements using GENCODE's Release 27 GTF file. Complete occurrences of targetable 4 nt PAMs were enumerated within regions encompassing 1 kb upstream of all transcription start sites (TSSs), within the first exon of all genes, and within all annotated miRNAs. Parameter value(s) for each element in the GTF file were: Exon1, feature-type exon, exon_number 1, gene_type protein_coding; TSS, feature-type transcript, gene_type protein_coding or miRNA; miRNA, feature-type gene, gene_type miRNA. For each element, PAM counts were normalized by length and were visualized through a boxplot. The PAM identification and enumeration script will be made available upon request. Targetable PAMs for Cas12a nucleases included: TTTV, for wild-type AsCas12a; TTYN, RTTC, CTTV, TATM, CTCC, TCCC, TACA (tier 1), and RTTS, TATA, TGTV, ANCC, CVCC, TGCC, GTCC, TTAC (tier 2) PAMs for eAsCas12a (see FIG. 1*g* and Extended Data FIG. 5*h*); TATV, AsCas12a-RVR; and TYCV for AsCas12a-RR.

DNA Detection Assays.

Cas12a-crRNA RNP complexes were formed by incubating 500 nM purified AsCas12a protein and 750 nM chemically synthesized crRNA (IDT) at 4° C. for 5 minutes. All reactions were carried out in 10 mM Hepes pH 7.5, 150 mM NaCl, and 5 mM $MgCl_2$. Next, RNPs were diluted to 100 nM and mixed with 250 nM linearized activating plasmid DNA harboring a matched target site with a canonical (TTTA) or non-canonical (CTTA or ACCT) PAM or an unrelated target site (negative control) in a total volume of 15 μL. Reactions were allowed to proceed at 37° C. for 30 minutes, prior to incubation at 4° C. For fluorescent detection, 10 μL of the RNP/target-DNA reaction was then mixed with an equal volume of 100 nM custom fluorescent-quenched reporter (IDT) in a low-volume 384-well black plate (Corning). Detection reactions were conducted at 37° C. for three hours with measurements taken every 60 seconds with $\mu_{ex}$=485 nm and $\mu_{em}$=528 nm, using a Synergy HTX Microplate Reader (BTX).

Sequences

The following constructs were used in the Examples below.

BPK3079: U6-AsCas12a-crRNA-BsmBIcassette

U6 promoter in black, AsCas12a crRNA in italics, guanine necessary for U6 transcription in bold, spacer entry cassette in lower case with BsmBI sites doubleunderlined, U6 terminator (TTTTTTT) doubleunderlinedinbold (SEQ ID NO: 415)

TGTACAAAAAAGCAGGCTTTAAAGGAACCAATTCAGTCGACTGGATCCGGTACCAAGGTCGG

GCAGGAAGAGGGCCTATTTCCCATGATTCCTTCATATTTGCATATACGATACAAGGCTGTTA

GAGAGATAATTAGAATTAATTTGACTGTAAACACAAAGATATTAGTACAAAATACGTGACGTA

GAAAGTAATAATTTCTTGGGTAGTTTGCAGTTTTAAAATTATGTTTTAAAATGGACTATCATAT

GCTTACCGTAACTTGAAAGTATTTCGATTTCTTGGCTTTATATATCTTGTGGAAAGGACGAAA

CACCG*TAATTTCTACTCTTGTAGAT*ggagacgattaatgcgtctccTTTTTTT

BPK3082: U6-LbCas12a-crRNA-BsmBIcassette

U6 promoter in green, LbCas12a crRNA colored in italics, guanine necessary for U6 transcription in bold, spacer entry cassette in lower case with BsmBI sites doubleunderlined, U6 terminator (TTTTTTT)doubleunderlinedinbold (SEQ ID NO: 416)

TGTACAAAAAAGCAGGCTTTAAAGGAACCAATTCAGTCGACTGGATCCGGTACCAAGGTCGG

GCAGGAAGAGGGCCTATTTCCCATGATTCCTTCATATTTGCATATACGATACAAGGCTGTTA

GAGAGATAATTAGAATTAATTTGACTGTAAACACAAAGATATTAGTACAAAATACGTGACGTA

GAAAGTAATAATTTCTTGGGTAGTTTGCAGTTTTAAAATTATGTTTTAAAATGGACTATCATAT

GCTTACCGTAACTTGAAAGTATTTCGATTTCTTGGCTTTATATATCTTGTGGAAAGGACGAAA

CACCG*AATTTCTACTAAGTGTAGAT*ggagacgattaatgcgtctccTTTTTTT

BPK4446: U6-FnCas12a-crRNA-BsmBIcassette

U6 promoter in black, FnCas12a crRNA colored in italics, guanine necessary for U6 transcription in bold, spacer entry cassette in lower case with BsmBI sites doubleunderlined, U6 terminator (TTTTTTT)doubleunderlinedinbold (SEQ ID NO: 417)

TGTACAAAAAAGCAGGCTTTAAAGGAACCAATTCAGTCGACTGGATCCGGTACCAAGGTCGG

GCAGGAAGAGGGCCTATTTCCCATGATTCCTTCATATTTGCATATACGATACAAGGCTGTTA

GAGAGATAATTAGAATTAATTTGACTGTAAACACAAAGATATTAGTACAAAATACGTGACGTA

GAAAGTAATAATTTCTTGGGTAGTTTGCAGTTTTAAAATTATGTTTTAAAATGGACTATCATAT

GCTTACCGTAACTTGAAAGTATTTCGATTTCTTGGCTTTATATATCTTGTGGAAAGGACGAAA

CACCG*AATTTCTACTGTTGTAGAT*ggagacgattaatgcgtctccTTTTTTT

BPK4449: U6-MbCas12a-crRNA-BsmBIcassette

U6 promoter in black, MbCas12a crRNA colored in italics, guanine necessary for U6 transcription in bold, spacer entry cassette in lower case with BsmBI sites doubleunderlined, U6 terminator (TTTTTTT)doubleunderlinedinbold (SEQ ID NO: 418)
TGTACAAAAAAGCAGGCTTTAAAGGAACCAATTCAGTCGACTGGATCCGGTACCAAGGTCGG

GCAGGAAGAGGGCCTATTTCCCATGATTCCTTCATATTTGCATATACGATACAAGGCTGTTA

GAGAGATAATTAGAATTAATTTGACTGTAAACACAAAGATATTAGTACAAAATACGTGACGTA

GAAAGTAATAATTTCTTGGGTAGTTTGCAGTTTTAAAATTATGTTTTAAAATGGACTATCATAT

GCTTACCGTAACTTGAAAGTATTTCGATTTCTTGGCTTTATATATCTTGTGGAAAGGACGAAA

CACCG*AATTTCTACTGTTTGTAGAT*ggagacgattaatgcgtctccTTTTTTT

MSP3491: T7-AsCas12a-crRNA-BsaIcassette

T7 promoter in black, guanine necessary for T7 transcription in bold, AsCas12a crRNA in italics, spacer entry cassette in lower case with BsaI sites doubleunderlined, restriction sites for DraI (tttaaa) in lower case bold and Hindill ( AAGCTT)doubleunderlinedinbold for linearization (SEQ ID NO: 419)
TAATACGACTCACTATAG*TAATTTCTACTCTTGTAGAT*ggagacccatgc catagcgttgttcggaatatgaatttttgaacagattcaccaacacctag tggtctcctttaaaAAGCTT MSP3495: T7-LbCas12a-crRNA-BsaIcassette T7 promoter in black, guanine necessary for T7 transcription in bold, LbCas12a crRNA in italics, spacer entry cassette in lower case with BsaI sites doubleunderlined, restriction sites for DraI (tttaaa) in lower case bold and HindIII ( √AAGCTT)doubleunderlinedinbold for linearization:

(SEQ ID NO: 420)
TAATACGACTCACTATAG*AATTTCTACTAAGTGTAGAT*ggagacccatgc catagcgttgttcggaatatgaatttttgaacagattcaccaacacctag tggtctcctttaaaAAGCTT Nucleotide Sequence of pCAG-humanAsCpf1-NLS-3×HA Human codon optimized AsCpf1 in normal font (NTs 1-3921), NLS in lower case (aaaaggccggcggccacgaaaaaggccggccaggcaaaaaagaaaaag, SEQ ID NO: 21), 3xHA tag (TACCCATACGATGTTCCAGATTACGCTTATCCCTACGACGTGCCTGATTATGCATACCCATAT GATGTCCCCGACTATGCC, SEQ ID NO: 5) in bold (SEQ ID NO: 6)
ATGACACAGTTCGAGGGCTTTACCAACCTGTATCAGGTGAGCAAGACACTGCGGTTT

GAGCTGATCCCACAGGGCAAGACCCTGAAGCACATCCAGGAGCAGGGCTTCATCGAGGAGG

ACAAGGCCCGCAATGATCACTACAAGGAGCTGAAGCCCATCATCGATCGGATCTACAAGACC

TATGCCGACCAGTGCCTGCAGCTGGTGCAGCTGGATTGGGAGAACCTGAGCGCCGCCATCG

ACTCCTATAGAAAGGAGAAAACCGAGGAGACAAGGAACGCCCTGATCGAGGAGCAGGCCACA

TATCGCAATGCCATCCACGACTACTTCATCGGCCGGACAGACAACCTGACCGATGCCATCAAT

AAGAGACACGCCGAGATCTACAAGGGCCTGTTCAAGGCCGAGCTGTTTAATGGCAAGGTGCT

GAAGCAGCTGGGCACCGTGACCACAACCGAGCACGAGAACGCCCTGCTGCGGAGCTTCGAC

AAGTTTACAACCTACTTCTCCGGCTTTTATGAGAACAGGAAGAACGTGTTCAGCGCCGAGGAT

ATCAGCACAGCCATCCCACACCGCATCGTGCAGGACAACTTCCCCAAGTTTAAGGAGAATTGT

CACATCTTCACACGCCTGATCACCGCCGTGCCCAGCCTGCGGGAGCACTTTGAGAACGTGAA

GAAGGCCATCGGCATCTTCGTGAGCACCTCCATCGAGGAGGTGTTTTCCTTCCCTTTTTATAA

CCAGCTGCTGACACAGACCCAGATCGACCTGTATAACCAGCTGCTGGGAGGAATCTCTCGGG

AGGCAGGCACCGAGAAGATCAAGGGCCTGAACGAGGTGCTGAATCTGGCCATCCAGAAGAAT

GATGAGACAGCCCACATCATCGCCTCCCTGCCACACAGATTCATCCCCCTGTTTAAGCAGATC

CTGTCCGATAGGAACACCCTGTCTTTCATCCTGGAGGAGTTTAAGAGCGACGAGGAAGTGAT

CCAGTCCTTCTGCAAGTACAAGACACTGCTGAGAAACGAGAACGTGCTGGAGACAGCCGAGG

CCCTGTTTAACGAGCTGAACAGCATCGACCTGACACACATCTTCATCAGCCACAAGAAGCTGG

-continued

AGACAATCAGCAGCGCCCTGTGCGACCACTGGGATACACTGAGGAATGCCCTGTATGAGCGG

AGAATCTCCGAGCTGACAGGCAAGATCACCAAGTCTGCCAAGGAGAAGGTGCAGCGCAGCCT

GAAGCACGAGGATATCAACCTGCAGGAGATCATCTCTGCCGCAGGCAAGGAGCTGAGCGAG

GCCTTCAAGCAGAAAACCAGCGAGATCCTGTCCCACGCACACGCCGCCCTGGATCAGCCACT

GCCTACAACCCTGAAGAAGCAGGAGGAGAAGGAGATCCTGAAGTCTCAGCTGGACAGCCTGC

TGGGCCTGTACCACCTGCTGGACTGGTTTGCCGTGGATGAGTCCAACGAGGTGGACCCCGA

GTTCTCTGCCCGGCTGACCGGCATCAAGCTGGAGATGGAGCCTTCTCTGAGCTTCTACAACA

AGGCCAGAAATTATGCCACCAAGAAGCCCTACTCCGTGGAGAAGTTCAAGCTGAACTTTCAGA

TGCCTACACTGGCCTCTGGCTGGGACGTGAATAAGGAGAAGAACAATGGCGCCATCCTGTTT

GTGAAGAACGGCCTGTACTATCTGGGCATCATGCCAAAGCAGAAGGGCAGGTATAAGGCCCT

GAGCTTCGAGCCCACAGAGAAAACCAGCGAGGGCTTTGATAAGATGTACTATGACTACTTCCC

TGATGCCGCCAAGATGATCCCAAAGTGCAGCACCCAGCTGAAGGCCGTGACAGCCCACTTTC

AGACCCACACAACCCCCATCCTGCTGTCCAACAATTTCATCGAGCCTCTGGAGATCACAAAGG

AGATCTACGACCTGAACAATCCTGAGAAGGAGCCAAAGAAGTTTCAGACAGCCTACGCCAAG

AAAACCGGCGACCAGAAGGGCTACAGAGAGGCCCTGTGCAAGTGGATCGACTTCACAAGGG

ATTTTCTGTCCAAGTATACCAAGACAACCTCTATCGATCTGTCTAGCCTGCGGCCATCCTCTCA

GTATAAGGACCTGGGCGAGTACTATGCCGAGCTGAATCCCCTGCTGTACCACATCAGCTTCC

AGAGAATCGCCGAGAAGGAGATCATGGATGCCGTGGAGACAGGCAAGCTGTACCTGTTCCAG

ATCTATAACAAGGACTTTGCCAAGGGCCACCACGGCAAGCCTAATCTGCACACACTGTATTGG

ACCGGCCTGTTTTCTCCAGAGAACCTGGCCAAGACAAGCATCAAGCTGAATGGCCAGGCCGA

GCTGTTCTACCGCCCTAAGTCCAGGATGAAGAGGATGGCACACCGGCTGGGAGAGAAGATG

CTGAACAAGAAGCTGAAGGATCAGAAAACCCCAATCCCCGACACCCTGTACCAGGAGCTGTA

CGACTATGTGAATCACAGACTGTCCCACGACCTGTCTGATGAGGCCAGGGCCCTGCTGCCCA

ACGTGATCACCAAGGAGGTGTCTCACGAGATCATCAAGGATAGGCGCTTTACCAGCGACAAG

TTCTTTTTCCACGTGCCTATCACACTGAACTATCAGGCCGCCAATTCCCCATCTAAGTTCAACC

AGAGGGTGAATGCCTACCTGAAGGAGCACCCCGAGACACCTATCATCGGCATCGATCGGGG

CGAGAGAAACCTGATCTATATCACAGTGATCGACTCCACCGGCAAGATCCTGGAGCAGCGGA

GCCTGAACACCATCCAGCAGTTTGATTACCAGAAGAAGCTGGACAACAGGGAGAAGGAGAGG

GTGGCAGCAAGGCAGGCCTGGTCTGTGGTGGGCACAATCAAGGATCTGAAGCAGGGCTATC

TGAGCCAGGTCATCCACGAGATCGTGGACCTGATGATCCACTACCAGGCCGTGGTGGTGCTG

GAGAACCTGAATTTCGGCTTTAAGAGCAAGAGGACCGGCATCGCCGAGAAGGCCGTGTACCA

GCAGTTCGAGAAGATGCTGATCGATAAGCTGAATTGCCTGGTGCTGAAGGACTATCCAGCAG

AGAAAGTGGGAGGCGTGCTGAACCCATACCAGCTGACAGACCAGTTCACCTCCTTTGCCAAG

ATGGGCACCCAGTCTGGCTTCCTGTTTTACGTGCCTGCCCCATATACATCTAAGATCGATCCC

CTGACCGGCTTCGTGGACCCCTTCGTGTGGAAAACCATCAAGAATCACGAGAGCCGCAAGCA

CTTCCTGGAGGGCTTCGACTTTCTGCACTACGACGTGAAAACCGGCGACTTCATCCTGCACTT

TAAGATGAACAGAAATCTGTCCTTCCAGAGGGGCCTGCCCGGCTTTATGCCTGCATGGGATAT

CGTGTTCGAGAAGAACGAGACACAGTTTGACGCCAAGGGCACCCCTTTCATCGCCGGCAAGA

GAATCGTGCCAGTGATCGAGAATCACAGATTCACCGGCAGATACCGGGACCTGTATCCTGCC

AACGAGCTGATCGCCCTGCTGGAGGAGAAGGGCATCGTGTTCAGGGATGGCTCCAACATCCT

GCCAAAGCTGCTGGAGAATGACGATTCTCACGCCATCGACACCATGGTGGCCCTGATCCGCA

-continued

GCGTGCTGCAGATGCGGAACTCCAATGCCGCCACAGGCGAGGACTATATCAACAGCCCCGT

GCGCGATCTGAATGGCGTGTGCTTCGACTCCCGGTTTCAGAACCCAGAGTGGCCCATGGACG

CCGATGCCAATGGCGCCTACCACATCGCCCTGAAGGGCCAGCTGCTGCTGAATCACCTGAAG

GAGAGCAAGGATCTGAAGCTGCAGAACGGCATCTCCAATCAGGACTGGCTGGCCTACATCCA

GGAGCTGCGCAACaaaaggccggcggccacgaaaaaggccggccaggcaaaaaagaaaaagGGATCCTACCC

ATACGATGTTCCAGATTACGCTTATCCCTACGACGTGCCTGATTATGCATACCCATATGATGT

CCCCGACTATGCCTAA

Amino Acid Sequence of AsCpf1-NLS-3×HA

AsCpf1 in normal font (AAs 1-1306), NLS (krpaatkkagqakkkk, SEQ ID NO:7) in lower case, 3xHA tag (YPYDVPDYAYPYDVPDYAYPYDVPDYA, SEQ ID NO: 8) in bold (SEQ ID NO: 9)

MTQFEGFTNLYQVSKTLRFELIPQGKTLKHIQEQGFIEEDKARNDHYKELKPIIDRIYKTYAD

QCLQLVQLDWENLSAAIDSYRKEKTEETRNALIEEQATYRNAIHDYFIGRTDNLTDAINKRHAEIYK

GLFKAELFNGKVLKQLGTVTTTEHENALLRSFDKFTTYFSGFYENRKNVFSAEDISTAIPHRIVQDN

FPKFKENCHIFTRLITAVPSLREHFENVKKAIGIFVSTSIEEVFSFPFYNQLLTQTQIDLYNQLLGGISR

EAGTEKIKGLNEVLNLAIQKNDETAHIIASLPHRFIPLFKQILSDRNTLSFILEEFKSDEEVIQSFCKYK

TLLRNENVLETAEALFNELNSIDLTHIFISHKKLETISSALCDHWDTLRNALYERRISELTGKITKSAKE

KVQRSLKHEDINLQEIISAAGKELSEAFKQKTSEILSHAHAALDQPLPTTLKKQEEKEILKSQLDSLL

GLYHLLDWFAVDESNEVDPEFSARLTGIKLEMEPSLSFYNKARNYATKKPYSVEKFKLNFQMPTLA

SGWDVNKEKNNGAILFVKNGLYYLGIMPKQKGRYKALSFEPTEKTSEGFDKMYYDYFPDAAKMIP

KCSTQLKAVTAHFQTHTTPILLSNNFIEPLEITKEIYDLNNPEKEPKKFQTAYAKKTGDQKGYREALC

KWIDFTRDFLSKYTKTTSIDLSSLRPSSQYKDLGEYYAELNPLLYHISFQRIAEKEIMDAVETGKLYL

FQIYNKDFAKGHHGKPNLHTLYWTGLFSPENLAKTSIKLNGQAELFYRPKSRMKRMAHRLGEKML

NKKLKDQKTPIPDTLYQELYDYVNHRLSHDLSDEARALLPNVITKEVSHEIIKDRRFTSDKFFFHVPI

TLNYQAANSPSKFNQRVNAYLKEHPETPIIGIDRGERNLIYITVIDSTGKILEQRSLNTIQQFDYQKKL

DNREKERVAARQAWSVVGTIKDLKQGYLSQVIHEIVDLMIHYQAVVVLENLNFGFKSKRTGIAEKA

VYQQFEKMLIDKLNCLVLKDYPAEKVGGVLNPYQLTDQFTSFAKMGTQSGFLFYVPAPYTSKIDPL

TGFVDPFVWKTIKNHESRKHFLEGFDFLHYDVKTGDFILHFKMNRNLSFQRGLPGFMPAWDIVFE

KNETQFDAKGTPFIAGKRIVPVIENHRFTGRYRDLYPANELIALLEEKGIVFRDGSNILPKLLENDDS

HAIDTMVALIRSVLQMRNSNAATGEDYINSPVRDLNGVCFDSRFQNPEWPMDADANGAYHIALKG

QLLLNHLKESKDLKLQNGISNQDWLAYIQELRNkrpaatkkagqakkkkGSYPYDVPDYAYPYDVPDYA

YPYDVPDYA

SQT1659: pCAG-hAsCas12a-NLS-3×HA

Human codon optimized *Acidaminococcus* sp. BV3L6 Cas12a (AsCas12a) in black, nucleoplasmin NLS (aaaaggccggcggccacgaaaaaggccggccaggcaaaaaagaaaaag, SEQ ID NO:21) in lower case, linker sequences in italics. 3×HA tag (TACCCATACGATGTTCCAGATTACGCTTATCCCTACGACGTGCCTGATTATGCATACCCATA
TGATGTCCCCGACTATGCC, SEQ ID NO: 5) in BOLD (SEQ ID NO: 421)

ATGACACAGTTCGAGGGCTTTACCAACCTGTATCAGGTGAGCAAGACACTGCGGTTT
GAGCTGATCCCACAGGGCAAGACCCTGAAGCACATCCAGGAGCAGGGCTTCATCGAGGAGGA
CAAGGCCCGCAATGATCACTACAAGGAGCTGAAGCCCATCATCGATCGGATCTACAAGACCT
ATGCCGACCAGTGCCTGCAGCTGGTGCAGCTGGATTGGGAGAACCTGAGCGCCGCCATCGAC
TCCTATAGAAAGGAGAAAACCGAGGAGACAAGGAACGCCCTGATCGAGGAGCAGGCCACAT
ATCGCAATGCCATCCACGACTACTTCATCGGCCGGACAGACAACCTGACCGATGCCATCAATA
AGAGACACGCCGAGATCTACAAGGGCCTGTTCAAGGCCGAGCTGTTTAATGGCAAGGTGCTG
AAGCAGCTGGGCACCGTGACCACAACCGAGCACGAGAACGCCCTGCTGCGGAGCTTCGACAA
GTTTACAACCTACTTCTCCGGCTTTTATGAGAACAGGAAGAACGTGTTCAGCGCCGAGGATAT
CAGCACAGCCATCCCACACCGCATCGTGCAGGACAACTTCCCCAAGTTTAAGGAGAATTGTCA
CATCTTCACACGCCTGATCACCGCCGTGCCCAGCCTGCGGGAGCACTTTGAGAACGTGAAGAA
GGCCATCGGCATCTTCGTGAGCACCTCCATCGAGGAGGTGTTTTCCTTCCCTTTTTATAACCAG
CTGCTGACACAGACCCAGATCGACCTGTATAACCAGCTGCTGGGAGGAATCTCTCGGGAGGC
AGGCACCGAGAAGATCAAGGGCCTGAACGAGGTGCTGAATCTGGCCATCCAGAAGAATGATG
AGACAGCCCACATCATCGCCTCCCTGCCACACAGATTCATCCCCCTGTTTAAGCAGATCCTGT
CCGATAGGAACACCCTGTCTTTCATCCTGGAGGAGTTTAAGAGCGACGAGGAAGTGATCCAGT
CCTTCTGCAAGTACAAGACACTGCTGAGAAACGAGAACGTGCTGGAGACAGCCGAGGCCCTG
TTTAACGAGCTGAACAGCATCGACCTGACACACATCTTCATCAGCCACAAGAAGCTGGAGAC
AATCAGCAGCGCCCTGTGCGACCACTGGGATACACTGAGGAATGCCCTGTATGAGCGGAGAA
TCTCCGAGCTGACAGGCAAGATCACCAAGTCTGCCAAGGAGAAGGTGCAGCGCAGCCTGAAG
CACGAGGATATCAACCTGCAGGAGATCATCTCTGCCGCAGGCAAGGAGCTGAGCGAGGCCTT
CAAGCAGAAAACCAGCGAGATCCTGTCCCACGCACACGCCGCCCTGGATCAGCCACTGCCTA
CAACCCTGAAGAAGCAGGAGGAGAAGGAGATCCTGAAGTCTCAGCTGGACAGCCTGCTGGGC
CTGTACCACCTGCTGGACTGGTTTGCCGTGGATGAGTCCAACGAGGTGGACCCCGAGTTCTCT
GCCCGGCTGACCGGCATCAAGCTGGAGATGGAGCCTTCTCTGAGCTTCTACAACAAGGCCAG
AAATTATGCCACCAAGAAGCCCTACTCCGTGGAGAAGTTCAAGCTGAACTTTCAGATGCCTAC
ACTGGCCTCTGGCTGGGACGTGAATAAGGAGAAGAACAATGGCGCCATCCTGTTTGTGAAGA
ACGGCCTGTACTATCTGGGCATCATGCCAAAGCAGAAGGGCAGGTATAAGGCCCTGAGCTTC
GAGCCCACAGAGAAAACCAGCGAGGGCTTTGATAAGATGTACTATGACTACTTCCCTGATGCC
GCCAAGATGATCCCAAAGTGCAGCACCCAGCTGAAGGCCGTGACAGCCCACTTTCAGACCCA
CACAACCCCCATCCTGCTGTCCAACAATTTCATCGAGCCTCTGGAGATCACAAAGGAGATCTA
CGACCTGAACAATCCTGAGAAGGAGCCAAAGAAGTTTCAGACAGCCTACGCCAAGAAAACCG
GCGACCAGAAGGGCTACAGAGAGGCCCTGTGCAAGTGGATCGACTTCACAAGGGATTTTCTG
TCCAAGTATACCAAGACAACCTCTATCGATCTGTCTAGCCTGCGGCCATCCTCTCAGTATAAG
GACCTGGGCGAGTACTATGCCGAGCTGAATCCCCTGCTGTACCACATCAGCTTCCAGAGAATC
GCCGAGAAGGAGATCATGGATGCCGTGGAGACAGGCAAGCTGTACCTGTTCCAGATCTATAA
CAAGGACTTTGCCAAGGGCCACCACGGCAAGCCTAATCTGCACACACTGTATTGGACCGGCCT
GTTTTCTCCAGAGAACCTGGCCAAGACAAGCATCAAGCTGAATGGCCAGGCCGAGCTGTTCTA

-continued

CCGCCCTAAGTCCAGGATGAAGAGGATGGCACACCGGCTGGGAGAGAAGATGCTGAACAAG

AAGCTGAAGGATCAGAAAACCCCAATCCCCGACACCCTGTACCAGGAGCTGTACGACTATGT

GAATCACAGACTGTCCCACGACCTGTCTGATGAGGCCAGGGCCCTGCTGCCCAACGTGATCAC

CAAGGAGGTGTCTCACGAGATCATCAAGGATAGGCGCTTTACCAGCGACAAGTTCTTTTTCCA

CGTGCCTATCACACTGAACTATCAGGCCGCCAATTCCCCATCTAAGTTCAACCAGAGGGTGAA

TGCCTACCTGAAGGAGCACCCCGAGACACCTATCATCGGCATCGATCGGGGCGAGAGAAACC

TGATCTATATCACAGTGATCGACTCCACCGGCAAGATCCTGGAGCAGCGGAGCCTGAACACC

ATCCAGCAGTTTGATTACCAGAAGAAGCTGGACAACAGGGAGAAGGAGAGGGTGGCAGCAA

GGCAGGCCTGGTCTGTGGTGGGCACAATCAAGGATCTGAAGCAGGGCTATCTGAGCCAGGTC

ATCCACGAGATCGTGGACCTGATGATCCACTACCAGGCCGTGGTGGTGCTGGAGAACCTGAAT

TTCGGCTTTAAGAGCAAGAGGACCGGCATCGCCGAGAAGGCCGTGTACCAGCAGTTCGAGAA

GATGCTGATCGATAAGCTGAATTGCCTGGTGCTGAAGGACTATCCAGCAGAGAAAGTGGGAG

GCGTGCTGAACCCATACCAGCTGACAGACCAGTTCACCTCCTTTGCCAAGATGGGCACCCAGT

CTGGCTTCCTGTTTTACGTGCCTGCCCCATATACATCTAAGATCGATCCCCTGACCGGCTTCGT

GGACCCCTTCGTGTGGAAAACCATCAAGAATCACGAGAGCCGCAAGCACTTCCTGGAGGGCT

TCGACTTTCTGCACTACGACGTGAAAACCGGCGACTTCATCCTGCACTTTAAGATGAACAGAA

ATCTGTCCTTCCAGAGGGGCCTGCCCGGCTTTATGCCTGCATGGGATATCGTGTTCGAGAAGA

ACGAGACACAGTTTGACGCCAAGGGCACCCCTTTCATCGCCGGCAAGAGAATCGTGCCAGTG

ATCGAGAATCACAGATTCACCGGCAGATACCGGGACCTGTATCCTGCCAACGAGCTGATCGCC

CTGCTGGAGGAGAAGGGCATCGTGTTCAGGGATGGCTCCAACATCCTGCCAAAGCTGCTGGA

GAATGACGATTCTCACGCCATCGACACCATGGTGGCCCTGATCCGCAGCGTGCTGCAGATGCG

GAACTCCAATGCCGCCACAGGCGAGGACTATATCAACAGCCCCGTGCGCGATCTGAATGGCG

TGTGCTTCGACTCCCGGTTTCAGAACCCAGAGTGGCCCATGGACGCCGATGCCAATGGCGCCT

ACCACATCGCCCTGAAGGGCCAGCTGCTGCTGAATCACCTGAAGGAGAGCAAGGATCTGAAG

CTGCAGAACGGCATCTCCAATCAGGACTGGCTGGCCTACATCCAGGAGCTGCGCAACaaaaggcc ggcggccacgaaaaaggccggccaggcaaaaaagaaaaag*GGATCC*TACCCATACGATGTTCCAGATTACGCTTA

TCCCTACGACGTGCCTGATTATGCATACCCATATGATGTCCCCGACTATGCCTAA

AAS826: pCAG-hAsCas12a(E174R/S542R)-NLS-3xHA
Human codon optimized *Acidaminococcus* sp. BV3L6 Cas12a (AsCas12a) in black, modified codons (E174R/S542R) double underlined, nucleoplasmin NLS (aaaaggccggcggccacgaaaaaggccggccaggcaaaaaagaaaaag, SEQ ID NO: 21) in lower case, linker sequences in italics, 3xHA tag (TACCCATACGATGTTCCAGATTACGCTTATCCCTACGACGTGCCTGATTATGCATACCCATA TGATGTCCCCGACTATGCC, SEQ ID NO: 5) in BOLD (SEQ ID NO: 422)

ATGACACAGTTCGAGGGCTTTACCAACCTGTATCAGGTGAGCAAGACACTGCGGTTTGAGCT

GATCCCACAGGGCAAGACCCTGAAGCACATCCAGGAGCAGGGCTTCATCGAGGAGGACAA

GGCCCGCAATGATCACTACAAGGAGCTGAAGCCCATCATCGATCGGATCTACAAGACCTAT

GCCGACCAGTGCCTGCAGCTGGTGCAGCTGGATTGGGAGAACCTGAGCGCCGCCATCGAC

TCCTATAGAAAGGAGAAAACCGAGGAGACAAGGAACGCCCTGATCGAGGAGCAGGCCACAT

ATCGCAATGCCATCCACGACTACTTCATCGGCCGGACAGACAACCTGACCGATGCCATCAAT

AAGAGACACGCCGAGATCTACAAGGGCCTGTTCAAGGCCGAGCTGTTTAATGGCAAGGTGC

TGAAGCAGCTGGGCACCGTGACCACAACCGAGCACGAGAACGCCCTGCTGCGGAGCTTCG

-continued

ACAAGTTTACAACCTACTTCTCCGGCTTTTATAGAAACAGGAAGAACGTGTTCAGCGCCGAG

GATATCAGCACAGCCATCCCACACCGCATCGTGCAGGACAACTTCCCCAAGTTTAAGGAGA

ATTGTCACATCTTCACACGCCTGATCACCGCCGTGCCCAGCCTGCGGGAGCACTTTGAGAA

CGTGAAGAAGGCCATCGGCATCTTCGTGAGCACCTCCATCGAGGAGGTGTTTTCCTTCCCTT

TTTATAACCAGCTGCTGACACAGACCCAGATCGACCTGTATAACCAGCTGCTGGGAGGAATC

TCTCGGGAGGCAGGCACCGAGAAGATCAAGGGCCTGAACGAGGTGCTGAATCTGGCCATC

CAGAAGAATGATGAGACAGCCCACATCATCGCCTCCCTGCCACACAGATTCATCCCCCTGTT

TAAGCAGATCCTGTCCGATAGGAACACCCTGTCTTTCATCCTGGAGGAGTTTAAGAGCGACG

AGGAAGTGATCCAGTCCTTCTGCAAGTACAAGACACTGCTGAGAAACGAGAACGTGCTGGA

GACAGCCGAGGCCCTGTTTAACGAGCTGAACAGCATCGACCTGACACACATCTTCATCAGC

CACAAGAAGCTGGAGACAATCAGCAGCGCCCTGTGCGACCACTGGGATACACTGAGGAATG

CCCTGTATGAGCGGAGAATCTCCGAGCTGACAGGCAAGATCACCAAGTCTGCCAAGGAGAA

GGTGCAGCGCAGCCTGAAGCACGAGGATATCAACCTGCAGGAGATCATCTCTGCCGCAGG

CAAGGAGCTGAGCGAGGCCTTCAAGCAGAAAACCAGCGAGATCCTGTCCCACGCACACGC

CGCCCTGGATCAGCCACTGCCTACAACCCTGAAGAAGCAGGAGGAGAAGGAGATCCTGAA

GTCTCAGCTGGACAGCCTGCTGGGCCTGTACCACCTGCTGGACTGGTTTGCCGTGGATGAG

TCCAACGAGGTGGACCCCGAGTTCTCTGCCCGGCTGACCGGCATCAAGCTGGAGATGGAG

CCTTCTCTGAGCTTCTACAACAAGGCCAGAAATTATGCCACCAAGAAGCCCTACTCCGTGGA

GAAGTTCAAGCTGAACTTTCAGATGCCTACACTGGCCAGAGGCTGGGACGTGAATAAGGAG

AAGAACAATGGCGCCATCCTGTTTGTGAAGAACGGCCTGTACTATCTGGGCATCATGCCAAA

GCAGAAGGGCAGGTATAAGGCCCTGAGCTTCGAGCCCACAGAGAAAACCAGCGAGGGCTT

TGATAAGATGTACTATGACTACTTCCCTGATGCCGCCAAGATGATCCCAAAGTGCAGCACCC

AGCTGAAGGCCGTGACAGCCCACTTTCAGACCCACACAACCCCCATCCTGCTGTCCAACAA

TTTCATCGAGCCTCTGGAGATCACAAAGGAGATCTACGACCTGAACAATCCTGAGAAGGAGC

CAAAGAAGTTTCAGACAGCCTACGCCAAGAAAACCGGCGACCAGAAGGGCTACAGAGAGGC

CCTGTGCAAGTGGATCGACTTCACAAGGGATTTTCTGTCCAAGTATACCAAGACAACCTCTA

TCGATCTGTCTAGCCTGCGGCCATCCTCTCAGTATAAGGACCTGGGCGAGTACTATGCCGA

GCTGAATCCCCTGCTGTACCACATCAGCTTCCAGAGAATCGCCGAGAAGGAGATCATGGAT

GCCGTGGAGACAGGCAAGCTGTACCTGTTCCAGATCTATAACAAGGACTTTGCCAAGGGCC

ACCACGGCAAGCCTAATCTGCACACACTGTATTGGACCGGCCTGTTTTCTCCAGAGAACCTG

GCCAAGACAAGCATCAAGCTGAATGGCCAGGCCGAGCTGTTCTACCGCCCTAAGTCCAGGA

TGAAGAGGATGGCACACCGGCTGGGAGAGAAGATGCTGAACAAGAAGCTGAAGGATCAGA

AAACCCCAATCCCCGACACCCTGTACCAGGAGCTGTACGACTATGTGAATCACAGACTGTCC

CACGACCTGTCTGATGAGGCCAGGGCCCTGCTGCCCAACGTGATCACCAAGGAGGTGTCTC

ACGAGATCATCAAGGATAGGCGCTTTACCAGCGACAAGTTCTTTTTCCACGTGCCTATCACA

CTGAACTATCAGGCCGCCAATTCCCCATCTAAGTTCAACCAGAGGGTGAATGCCTACCTGAA

GGAGCACCCCGAGACACCTATCATCGGCATCGATCGGGGCGAGAGAAACCTGATCTATATC

ACAGTGATCGACTCCACCGGCAAGATCCTGGAGCAGCGGAGCCTGAACACCATCCAGCAGT

TTGATTACCAGAAGAAGCTGGACAACAGGGAGAAGGAGAGGGTGGCAGCAAGGCAGGCCT

GGTCTGTGGTGGGCACAATCAAGGATCTGAAGCAGGGCTATCTGAGCCAGGTCATCCACGA

GATCGTGGACCTGATGATCCACTACCAGGCCGTGGTGGTGCTGGAGAACCTGAATTTCGGC

-continued

TTTAAGAGCAAGAGGACCGGCATCGCCGAGAAGGCCGTGTACCAGCAGTTCGAGAAGATGC

TGATCGATAAGCTGAATTGCCTGGTGCTGAAGGACTATCCAGCAGAGAAAGTGGGAGGCGT

GCTGAACCCATACCAGCTGACAGACCAGTTCACCTCCTTTGCCAAGATGGGCACCCAGTCT

GGCTTCCTGTTTTACGTGCCTGCCCCATATACATCTAAGATCGATCCCCTGACCGGCTTCGT

GGACCCCTTCGTGTGGAAAACCATCAAGAATCACGAGAGCCGCAAGCACTTCCTGGAGGGC

TTCGACTTTCTGCACTACGACGTGAAAACCGGCGACTTCATCCTGCACTTTAAGATGAACAG

AAATCTGTCCTTCCAGAGGGGCCTGCCCGGCTTTATGCCTGCATGGGATATCGTGTTCGAG

AAGAACGAGACACAGTTTGACGCCAAGGGCACCCCTTTCATCGCCGGCAAGAGAATCGTGC

CAGTGATCGAGAATCACAGATTCACCGGCAGATACCGGGACCTGTATCCTGCCAACGAGCT

GATCGCCCTGCTGGAGGAGAAGGGCATCGTGTTCAGGGATGGCTCCAACATCCTGCCAAAG

CTGCTGGAGAATGACGATTCTCACGCCATCGACACCATGGTGGCCCTGATCCGCAGCGTGC

TGCAGATGCGGAACTCCAATGCCGCCACAGGCGAGGACTATATCAACAGCCCCGTGCGCG

ATCTGAATGGCGTGTGCTTCGACTCCCGGTTTCAGAACCCAGAGTGGCCCATGGACGCCGA

TGCCAATGGCGCCTACCACATCGCCCTGAAGGGCCAGCTGCTGCTGAATCACCTGAAGGAG

AGCAAGGATCTGAAGCTGCAGAACGGCATCTCCAATCAGGACTGGCTGGCCTACATCCAGG

AGCTGCGCAACaaaaggccggcggccacgaaaaaggccggccaggcaaaaaagaaaaag*GGATCC*TACCCA

TACGATGTTCCAGATTACGCTTATCCCTACGACGTGCCTGATTATGCATACCCATATGATGT

CCCCGACTATGCCTAA

AAS848: pCAG-heAsCas12a(E174R/S542R/K548R)-NLS-3xHA

Human codon optimized *Acidaminococcus* sp. BV3L6 Cas12a (AsCas12a) in black, modified codons for eAsCas12a (E174R/S542R/K548R) doubleunderlined, nucleoplasmin NLS (aaaaggccogcggccacgaaaaaggc-cogccaggcaaaaaagaaaaag, SEQ ID NO:21) in lower case, linker sequences in italics, 3×HA tag (TACCCATACGATGTTCCAGATTACGCTTATCCCTACGACGTGCCTGATTATGCATACCCATA TGATGTCCCCGACTATGCC, SEQ ID NO: 5) in BOLD (SEQ ID NO: 423)

ATGACACAGTTCGAGGGCTTTACCAACCTGTATCAGGTGAGCAAGACACTGCGGTTTGAGCT

GATCCCACAGGGCAAGACCCTGAAGCACATCCAGGAGCAGGGCTTCATCGAGGAGGACAA

GGCCCGCAATGATCACTACAAGGAGCTGAAGCCCATCATCGATCGGATCTACAAGACCTAT

GCCGACCAGTGCCTGCAGCTGGTGCAGCTGGATTGGGAGAACCTGAGCGCCGCCATCGAC

TCCTATAGAAAGGAGAAAACCGAGGAGACAAGGAACGCCCTGATCGAGGAGCAGGCCACAT

ATCGCAATGCCATCCACGACTACTTCATCGGCCGGACAGACAACCTGACCGATGCCATCAAT

AAGAGACACGCCGAGATCTACAAGGGCCTGTTCAAGGCCGAGCTGTTTAATGGCAAGGTGC

TGAAGCAGCTGGGCACCGTGACCACAACCGAGCACGAGAACGCCCTGCTGCGGAGCTTCG

ACAAGTTTACAACCTACTTCTCCGGCTTTTATAGAAACAGGAAGAACGTGTTCAGCGCCGAG

GATATCAGCACAGCCATCCCACACCGCATCGTGCAGGACAACTTCCCCAAGTTTAAGGAGA

ATTGTCACATCTTCACACGCCTGATCACCGCCGTGCCCAGCCTGCGGGAGCACTTTGAGAA

CGTGAAGAAGGCCATCGGCATCTTCGTGAGCACCTCCATCGAGGAGGTGTTTTCCTTCCCTT

TTTATAACCAGCTGCTGACACAGACCCAGATCGACCTGTATAACCAGCTGCTGGGAGGAATC

TCTCGGGAGGCAGGCACCGAGAAGATCAAGGGCCTGAACGAGGTGCTGAATCTGGCCATC

CAGAAGAATGATGAGACAGCCCACATCATCGCCTCCCTGCCACACAGATTCATCCCCCTGTT

TAAGCAGATCCTGTCCGATAGGAACACCCTGTCTTTCATCCTGGAGGAGTTTAAGAGCGACG

-continued

AGGAAGTGATCCAGTCCTTCTGCAAGTACAAGACACTGCTGAGAAACGAGAACGTGCTGGA

GACAGCCGAGGCCCTGTTTAACGAGCTGAACAGCATCGACCTGACACACATCTTCATCAGC

CACAAGAAGCTGGAGACAATCAGCAGCGCCCTGTGCGACCACTGGGATACACTGAGGAATG

CCCTGTATGAGCGGAGAATCTCCGAGCTGACAGGCAAGATCACCAAGTCTGCCAAGGAGAA

GGTGCAGCGCAGCCTGAAGCACGAGGATATCAACCTGCAGGAGATCATCTCTGCCGCAGG

CAAGGAGCTGAGCGAGGCCTTCAAGCAGAAAACCAGCGAGATCCTGTCCCACGCACACGC

CGCCCTGGATCAGCCACTGCCTACAACCCTGAAGAAGCAGGAGGAGAAGGAGATCCTGAA

GTCTCAGCTGGACAGCCTGCTGGGCCTGTACCACCTGCTGGACTGGTTTGCCGTGGATGAG

TCCAACGAGGTGGACCCCGAGTTCTCTGCCCGGCTGACCGGCATCAAGCTGGAGATGGAG

CCTTCTCTGAGCTTCTACAACAAGGCCAGAAATTATGCCACCAAGAAGCCCTACTCCGTGGA

GAAGTTCAAGCTGAACTTTCAGATGCCTACACTGGCCAGAGGCTGGGACGTGAATAGAGAG

AAGAACAATGGCGCCATCCTGTTTGTGAAGAACGGCCTGTACTATCTGGGCATCATGCCAAA

GCAGAAGGGCAGGTATAAGGCCCTGAGCTTCGAGCCCACAGAGAAAACCAGCGAGGGCTT

TGATAAGATGTACTATGACTACTTCCCTGATGCCGCCAAGATGATCCCAAAGTGCAGCACCC

AGCTGAAGGCCGTGACAGCCCACTTTCAGACCCACACAACCCCCATCCTGCTGTCCAACAA

TTTCATCGAGCCTCTGGAGATCACAAAGGAGATCTACGACCTGAACAATCCTGAGAAGGAGC

CAAAGAAGTTTCAGACAGCCTACGCCAAGAAAACCGGCGACCAGAAGGGCTACAGAGAGGC

CCTGTGCAAGTGGATCGACTTCACAAGGGATTTTCTGTCCAAGTATACCAAGACAACCTCTA

TCGATCTGTCTAGCCTGCGGCCATCCTCTCAGTATAAGGACCTGGGCGAGTACTATGCCGA

GCTGAATCCCCTGCTGTACCACATCAGCTTCCAGAGAATCGCCGAGAAGGAGATCATGGAT

GCCGTGGAGACAGGCAAGCTGTACCTGTTCCAGATCTATAACAAGGACTTTGCCAAGGGCC

ACCACGGCAAGCCTAATCTGCACACACTGTATTGGACCGGCCTGTTTTCTCCAGAGAACCTG

GCCAAGACAAGCATCAAGCTGAATGGCCAGGCCGAGCTGTTCTACCGCCCTAAGTCCAGGA

TGAAGAGGATGGCACACCGGCTGGGAGAGAAGATGCTGAACAAGAAGCTGAAGGATCAGA

AAACCCCAATCCCCGACACCCTGTACCAGGAGCTGTACGACTATGTGAATCACAGACTGTCC

CACGACCTGTCTGATGAGGCCAGGGCCCTGCTGCCCAACGTGATCACCAAGGAGGTGTCTC

ACGAGATCATCAAGGATAGGCGCTTTACCAGCGACAAGTTCTTTTTCCACGTGCCTATCACA

CTGAACTATCAGGCCGCCAATTCCCCATCTAAGTTCAACCAGAGGGTGAATGCCTACCTGAA

GGAGCACCCCGAGACACCTATCATCGGCATCGATCGGGGCGAGAGAAACCTGATCTATATC

ACAGTGATCGACTCCACCGGCAAGATCCTGGAGCAGCGGAGCCTGAACACCATCCAGCAGT

TTGATTACCAGAAGAAGCTGGACAACAGGGAGAAGGAGAGGGTGGCAGCAAGGCAGGCCT

GGTCTGTGGTGGGCACAATCAAGGATCTGAAGCAGGGCTATCTGAGCCAGGTCATCCACGA

GATCGTGGACCTGATGATCCACTACCAGGCCGTGGTGGTGCTGGAGAACCTGAATTTCGGC

TTTAAGAGCAAGAGGACCGGCATCGCCGAGAAGGCCGTGTACCAGCAGTTCGAGAAGATGC

TGATCGATAAGCTGAATTGCCTGGTGCTGAAGGACTATCCAGCAGAGAAAGTGGGAGGCGT

GCTGAACCCATACCAGCTGACAGACCAGTTCACCTCCTTTGCCAAGATGGGCACCCAGTCT

GGCTTCCTGTTTTACGTGCCTGCCCCATATACATCTAAGATCGATCCCCTGACCGGCTTCGT

GGACCCCTTCGTGTGGAAAACCATCAAGAATCACGAGAGCCGCAAGCACTTCCTGGAGGGC

TTCGACTTTCTGCACTACGACGTGAAAACCGGCGACTTCATCCTGCACTTTAAGATGAACAG

AAATCTGTCCTTCCAGAGGGGCCTGCCCGGCTTTATGCCTGCATGGGATATCGTGTTCGAG

-continued

AAGAACGAGACACAGTTTGACGCCAAGGGCACCCCTTTCATCGCCGGCAAGAGAATCGTGC

CAGTGATCGAGAATCACAGATTCACCGGCAGATACCGGGACCTGTATCCTGCCAACGAGCT

GATCGCCCTGCTGGAGGAGAAGGGCATCGTGTTCAGGGATGGCTCCAACATCCTGCCAAAG

CTGCTGGAGAATGACGATTCTCACGCCATCGACACCATGGTGGCCCTGATCCGCAGCGTGC

TGCAGATGCGGAACTCCAATGCCGCCACAGGCGAGGACTATATCAACAGCCCCGTGCGCG

ATCTGAATGGCGTGTGCTTCGACTCCCGGTTTCAGAACCCAGAGTGGCCCATGGACGCCGA

TGCCAATGGCGCCTACCACATCGCCCTGAAGGGCCAGCTGCTGCTGAATCACCTGAAGGAG

AGCAAGGATCTGAAGCTGCAGAACGGCATCTCCAATCAGGACTGGCTGGCCTACATCCAGG

AGCTGCGCAACaaaaggccggcggccacgaaaaaggccggccaggcaaaaaagaaaaag*GGATCC*TACCCA

TACGATGTTCCAGATTACGCTTATCCCTACGACGTGCCTGATTATGCATACCCATATGATGT

CCCCGACTATGCCTAA

AAS1815: pCAG-heAsCas128-HF1(E174R/N282A/S542R/K548R)-NLS-3×HA Human codon optimized *Acidaminococcus* sp. BV3L6 Cas12a (AsCas12a) in black, modified codons (E174R/N282A/S542R/K548R) in doubleunderlined, nucleoplasmin NLS (aaaaggccogcggc-cacgassaeggccogcceggcasagang, SEQ ID NO:21) in lower case, linker sequences in italics, 3×HA tag (TACCCATACGATGTTCCAGATTACGCTTATCCCTACGACGTGCCTGATTATGCATACCCATA TGATGTCCCCGACTATGCC, SEQ ID NO: 5) in BOLD (SEQ ID NO: 424)

ATGACACAGTTCGAGGGCTTTACCAACCTGTATCAGGTGAGCAAGACACTGCGGTTTGAGCT

GATCCCACAGGGCAAGACCCTGAAGCACATCCAGGAGCAGGGCTTCATCGAGGAGGACAA

GGCCCGCAATGATCACTACAAGGAGCTGAAGCCCATCATCGATCGGATCTACAAGACCTAT

GCCGACCAGTGCCTGCAGCTGGTGCAGCTGGATTGGGAGAACCTGAGCGCCGCCATCGAC

TCCTATAGAAAGGAGAAAACCGAGGAGACAAGGAACGCCCTGATCGAGGAGCAGGCCACAT

ATCGCAATGCCATCCACGACTACTTCATCGGCCGGACAGACAACCTGACCGATGCCATCAAT

AAGAGACACGCCGAGATCTACAAGGGCCTGTTCAAGGCCGAGCTGTTTAATGGCAAGGTGC

TGAAGCAGCTGGGCACCGTGACCACAACCGAGCACGAGAACGCCCTGCTGCGGAGCTTCG

ACAAGTTTACAACCTACTTCTCCGGCTTTTATAGAAACAGGAAGAACGTGTTCAGCGCCGAG

GATATCAGCACAGCCATCCCACACCGCATCGTGCAGGACAACTTCCCCAAGTTTAAGGAGA

ATTGTCACATCTTCACACGCCTGATCACCGCCGTGCCCAGCCTGCGGGAGCACTTTGAGAA

CGTGAAGAAGGCCATCGGCATCTTCGTGAGCACCTCCATCGAGGAGGTGTTTTCCTTCCCTT

TTTATAACCAGCTGCTGACACAGACCCAGATCGACCTGTATAACCAGCTGCTGGGAGGAATC

TCTCGGGAGGCAGGCACCGAGAAGATCAAGGGCCTGAACGAGGTGCTGGCCCTGGCCATC

CAGAAGAATGATGAGACAGCCCACATCATCGCCTCCCTGCCACACAGATTCATCCCCCTGTT

TAAGCAGATCCTGTCCGATAGGAACACCCTGTCTTTCATCCTGGAGGAGTTTAAGAGCGACG

AGGAAGTGATCCAGTCCTTCTGCAAGTACAAGACACTGCTGAGAAACGAGAACGTGCTGGA

GACAGCCGAGGCCCTGTTTAACGAGCTGAACAGCATCGACCTGACACACATCTTCATCAGC

CACAAGAAGCTGGAGACAATCAGCAGCGCCCTGTGCGACCACTGGGATACACTGAGGAATG

CCCTGTATGAGCGGAGAATCTCCGAGCTGACAGGCAAGATCACCAAGTCTGCCAAGGAGAA

GGTGCAGCGCAGCCTGAAGCACGAGGATATCAACCTGCAGGAGATCATCTCTGCCGCAGG

CAAGGAGCTGAGCGAGGCCTTCAAGCAGAAAACCAGCGAGATCCTGTCCCACGCACACGC

CGCCCTGGATCAGCCACTGCCTACAACCCTGAAGAAGCAGGAGGAGAAGGAGATCCTGAA

-continued

GTCTCAGCTGGACAGCCTGCTGGGCCTGTACCACCTGCTGGACTGGTTTGCCGTGGATGAG

TCCAACGAGGTGGACCCCGAGTTCTCTGCCCGGCTGACCGGCATCAAGCTGGAGATGGAG

CCTTCTCTGAGCTTCTACAACAAGGCCAGAAATTATGCCACCAAGAAGCCCTACTCCGTGGA

GAAGTTCAAGCTGAACTTTCAGATGCCTACACTGGCCAGAGGCTGGGACGTGAATAGAGAG

AAGAACAATGGCGCCATCCTGTTTGTGAAGAACGGCCTGTACTATCTGGGCATCATGCCAAA

GCAGAAGGGCAGGTATAAGGCCCTGAGCTTCGAGCCCACAGAGAAAACCAGCGAGGGCTT

TGATAAGATGTACTATGACTACTTCCCTGATGCCGCCAAGATGATCCCAAAGTGCAGCACCC

AGCTGAAGGCCGTGACAGCCCACTTTCAGACCCACACAACCCCCATCCTGCTGTCCAACAA

TTTCATCGAGCCTCTGGAGATCACAAAGGAGATCTACGACCTGAACAATCCTGAGAAGGAGC

CAAAGAAGTTTCAGACAGCCTACGCCAAGAAAACCGGCGACCAGAAGGGCTACAGAGAGGC

CCTGTGCAAGTGGATCGACTTCACAAGGGATTTTCTGTCCAAGTATACCAAGACAACCTCTA

TCGATCTGTCTAGCCTGCGGCCATCCTCTCAGTATAAGGACCTGGGCGAGTACTATGCCGA

GCTGAATCCCCTGCTGTACCACATCAGCTTCCAGAGAATCGCCGAGAAGGAGATCATGGAT

GCCGTGGAGACAGGCAAGCTGTACCTGTTCCAGATCTATAACAAGGACTTTGCCAAGGGCC

ACCACGGCAAGCCTAATCTGCACACACTGTATTGGACCGGCCTGTTTTCTCCAGAGAACCTG

GCCAAGACAAGCATCAAGCTGAATGGCCAGGCCGAGCTGTTCTACCGCCCTAAGTCCAGGA

TGAAGAGGATGGCACACCGGCTGGGAGAGAAGATGCTGAACAAGAAGCTGAAGGATCAGA

AAACCCCAATCCCCGACACCCTGTACCAGGAGCTGTACGACTATGTGAATCACAGACTGTCC

CACGACCTGTCTGATGAGGCCAGGGCCCTGCTGCCCAACGTGATCACCAAGGAGGTGTCTC

ACGAGATCATCAAGGATAGGCGCTTTACCAGCGACAAGTTCTTTTTCCACGTGCCTATCACA

CTGAACTATCAGGCCGCCAATTCCCCATCTAAGTTCAACCAGAGGGTGAATGCCTACCTGAA

GGAGCACCCCGAGACACCTATCATCGGCATCGATCGGGGCGAGAGAAACCTGATCTATATC

ACAGTGATCGACTCCACCGGCAAGATCCTGGAGCAGCGGAGCCTGAACACCATCCAGCAGT

TTGATTACCAGAAGAAGCTGGACAACAGGGAGAAGGAGAGGGTGGCAGCAAGGCAGGCCT

GGTCTGTGGTGGGCACAATCAAGGATCTGAAGCAGGGCTATCTGAGCCAGGTCATCCACGA

GATCGTGGACCTGATGATCCACTACCAGGCCGTGGTGGTGCTGGAGAACCTGAATTTCGGC

TTTAAGAGCAAGAGGACCGGCATCGCCGAGAAGGCCGTGTACCAGCAGTTCGAGAAGATGC

TGATCGATAAGCTGAATTGCCTGGTGCTGAAGGACTATCCAGCAGAGAAAGTGGGAGGCGT

GCTGAACCCATACCAGCTGACAGACCAGTTCACCTCCTTTGCCAAGATGGGCACCCAGTCT

GGCTTCCTGTTTTACGTGCCTGCCCCATATACATCTAAGATCGATCCCCTGACCGGCTTCGT

GGACCCCTTCGTGTGGAAAACCATCAAGAATCACGAGAGCCGCAAGCACTTCCTGGAGGGC

TTCGACTTTCTGCACTACGACGTGAAAACCGGCGACTTCATCCTGCACTTTAAGATGAACAG

AAATCTGTCCTTCCAGAGGGGCCTGCCCGGCTTTATGCCTGCATGGGATATCGTGTTCGAG

AAGAACGAGACACAGTTTGACGCCAAGGGCACCCCTTTCATCGCCGGCAAGAGAATCGTGC

CAGTGATCGAGAATCACAGATTCACCGGCAGATACCGGGACCTGTATCCTGCCAACGAGCT

GATCGCCCTGCTGGAGGAGAAGGGCATCGTGTTCAGGGATGGCTCCAACATCCTGCCAAAG

CTGCTGGAGAATGACGATTCTCACGCCATCGACACCATGGTGGCCCTGATCCGCAGCGTGC

TGCAGATGCGGAACTCCAATGCCGCCACAGGCGAGGACTATATCAACAGCCCCGTGCGCG

ATCTGAATGGCGTGTGCTTCGACTCCCGGTTTCAGAACCCAGAGTGGCCCATGGACGCCGA

TGCCAATGGCGCCTACCACATCGCCCTGAAGGGCCAGCTGCTGCTGAATCACCTGAAGGAG

AGCAAGGATCTGAAGCTGCAGAACGGCATCTCCAATCAGGACTGGCTGGCCTACATCCAGG

-continued

AGCTGCGCAACaaaaggccggcggccacgaaaaaggccggccaggcaaaaaagaaaaag*GGATCC*TACCC

ATACGATGTTCCAGATTACGCTTATCCCTACGACGTGCCTGATTATGCATACCCATATGA

TGTCCCCGACTATGCCTAA

BPK3541: pET-28b-hAsCas12a-NLS-6×His

Human codon optimized *Acidaminococcus* sp. BV3L6 Cas12a (AsCas12a) in black, codons with silent mutations to remove NcoI sites doubleunderlined, inserted glycine dash-underlined , nucleoplasmin NLS (aaaaggccggcggccacgaaaaaggccggccaggcaaaaaagaaaaag, SEQ ID NO:21) in lower case, linker sequences in italics, 6×His in bold (SEQ ID NO: 425)

ATGGGGACACAGTTCGAGGGCTTTACCAACCTGTATCAGTGAGCAAGACACTGCGGTTTG

AGCTGATCCCACAGGGCAAGACCCTGAAGCACATCCAGGAGCAGGGCTTCATCGAGGAGG

ACAAGGCCCGCAATGATCACTACAAGGAGCTGAAGCCCATCATCGATCGGATCTACAAGAC

CTATGCCGACCAGTGCCTGCAGCTGGTGCAGCTGGATTGGGAGAACCTGAGCGCCGCCAT

CGACTCCTATAGAAAGGAGAAAACCGAGGAGACAAGGAACGCCCTGATCGAGGAGCAGGC

CACATATCGCAATGCCATCCACGACTACTTCATCGGCCGGACAGACAACCTGACCGATGCC

ATCAATAAGAGACACGCCGAGATCTACAAGGGCCTGTTCAAGGCCGAGCTGTTTAATGGCA

AGGTGCTGAAGCAGCTGGGCACCGTGACCACAACCGAGCACGAGAACGCCCTGCTGCGGA

GCTTCGACAAGTTTACAACCTACTTCTCCGGCTTTTATGAGAACAGGAAGAACGTGTTCAGC

GCCGAGGATATCAGCACAGCCATCCCACACCGCATCGTGCAGGACAACTTCCCCAAGTTTA

AGGAGAATTGTCACATCTTCACACGCCTGATCACCGCCGTGCCCAGCCTGCGGGAGCACTT

TGAGAACGTGAAGAAGGCCATCGGCATCTTCGTGAGCACCTCCATCGAGGAGGTGTTTTCC

TTCCCTTTTTATAACCAGCTGCTGACACAGACCCAGATCGACCTGTATAACCAGCTGCTGGG

AGGAATCTCTCGGGAGGCAGGCACCGAGAAGATCAAGGGCCTGAACGAGGTGCTGAATCT

GGCCATCCAGAAGAATGATGAGACAGCCCACATCATCGCCTCCCTGCCACACAGATTCATC

CCCCTGTTTAAGCAGATCCTGTCCGATAGGAACACCCTGTCTTTCATCCTGGAGGAGTTTAA

GAGCGACGAGGAAGTGATCCAGTCCTTCTGCAAGTACAAGACACTGCTGAGAAACGAGAAC

GTGCTGGAGACAGCCGAGGCCCTGTTTAACGAGCTGAACAGCATCGACCTGACACACATCT

TCATCAGCCACAAGAAGCTGGAGACAATCAGCAGCGCCCTGTGCGACCACTGGGATACACT

GAGGAATGCCCTGTATGAGCGGAGAATCTCCGAGCTGACAGGCAAGATCACCAAGTCTGCC

AAGGAGAAGGTGCAGCGCAGCCTGAAGCACGAGGATATCAACCTGCAGGAGATCATCTCTG

CCGCAGGCAAGGAGCTGAGCGAGGCCTTCAAGCAGAAAACCAGCGAGATCCTGTCCCACG

CACACGCCGCCCTGGATCAGCCACTGCCTACAACCCTGAAGAAGCAGGAGGAGAAGGAGA

TCCTGAAGTCTCAGCTGGACAGCCTGCTGGGCCTGTACCACCTGCTGGACTGGTTTGCCGT

GGATGAGTCCAACGAGGTGGACCCCGAGTTCTCTGCCCGGCTGACCGGCATCAAGCTGGA

GATGGAGCCTTCTCTGAGCTTCTACAACAAGGCCAGAAATTATGCCACCAAGAAGCCCTACT

CCGTGGAGAAGTTCAAGCTGAACTTTCAGATGCCTACACTGGCCTCTGGCTGGGACGTGAA

TAAGGAGAAGAACAATGGCGCCATCCTGTTTGTGAAGAACGGCCTGTACTATCTGGGCATCA

TGCCAAAGCAGAAGGGCAGGTATAAGGCCCTGAGCTTCGAGCCCACAGAGAAAACCAGCG

AGGGCTTTGATAAGATGTACTATGACTACTTCCCTGATGCCGCCAAGATGATCCCAAAGTGC

AGCACCCAGCTGAAGGCCGTGACAGCCCACTTTCAGACCCACACAACCCCCATCCTGCTGT

CCAACAATTTCATCGAGCCTCTGGAGATCACAAAGGAGATCTACGACCTGAACAATCCTGAG

AAGGAGCCAAAGAAGTTTCAGACAGCCTACGCCAAGAAAACCGGCGACCAGAAGGGCTACA

-continued

GAGAGGCCCTGTGCAAGTGGATCGACTTCACAAGGGATTTTCTGTCCAAGTATACCAAGACA

ACCTCTATCGATCTGTCTAGCCTGCGGCCATCCTCTCAGTATAAGGACCTGGGCGAGTACTA

TGCCGAGCTGAATCCCCTGCTGTACCACATCAGCTTCCAGAGAATCGCCGAGAAGGAGATC

ATGGATGCCGTGGAGACAGGCAAGCTGTACCTGTTCCAGATCTATAACAAGGACTTTGCCAA

GGGCCACCACGGCAAGCCTAATCTGCACACACTGTATTGGACCGGCCTGTTTTCTCCAGAG

AACCTGGCCAAGACAAGCATCAAGCTGAATGGCCAGGCCGAGCTGTTCTACCGCCCTAAGT

CCAGGATGAAGAGGATGGCACACCGGCTGGGAGAGAAGATGCTGAACAAGAAGCTGAAGG

ATCAGAAAACCCCAATCCCCGACACCCTGTACCAGGAGCTGTACGACTATGTGAATCACAGA

CTGTCCCACGACCTGTCTGATGAGGCCAGGGCCCTGCTGCCCAACGTGATCACCAAGGAG

GTGTCTCACGAGATCATCAAGGATAGGCGCTTTACCAGCGACAAGTTCTTTTTCCACGTGCC

TATCACACTGAACTATCAGGCCGCCAATTCCCCATCTAAGTTCAACCAGAGGGTGAATGCCT

ACCTGAAGGAGCACCCCGAGACACCTATCATCGGCATCGATCGGGGCGAGAGAAACCTGAT

CTATATCACAGTGATCGACTCCACCGGCAAGATCCTGGAGCAGCGGAGCCTGAACACCATC

CAGCAGTTTGATTACCAGAAGAAGCTGGACAACAGGGAGAAGGAGAGGGTGGCAGCAAGG

CAGGCCTGGTCTGTGGTGGGCACAATCAAGGATCTGAAGCAGGGCTATCTGAGCCAGGTCA

TCCACGAGATCGTGGACCTGATGATCCACTACCAGGCCGTGGTGGTGCTGGAGAACCTGAA

TTTCGGCTTTAAGAGCAAGAGGACCGGCATCGCCGAGAAGGCCGTGTACCAGCAGTTCGAG

AAGATGCTGATCGATAAGCTGAATTGCCTGGTGCTGAAGGACTATCCAGCAGAGAAAGTGG

GAGGCGTGCTGAACCCATACCAGCTGACAGACCAGTTCACCTCCTTTGCCAAGATGGGCAC

CCAGTCTGGCTTCCTGTTTTACGTGCCTGCCCCATATACATCTAAGATCGATCCCCTGACCG

GCTTCGTGGACCCCTTCGTGTGGAAAACCATCAAGAATCACGAGAGCCGCAAGCACTTCCT

GGAGGGCTTCGACTTTCTGCACTACGACGTGAAAACCGGCGACTTCATCCTGCACTTTAAGA

TGAACAGAAATCTGTCCTTCCAGAGGGGCCTGCCCGGCTTTATGCCTGCATGGGATATCGT

GTTCGAGAAGAACGAGACACAGTTTGACGCCAAGGGCACCCCTTTCATCGCCGGCAAGAGA

ATCGTGCCAGTGATCGAGAATCACAGATTCACCGGCAGATACCGGGACCTGTATCCTGCCA

ACGAGCTGATCGCCCTGCTGGAGGAGAAGGGCATCGTGTTCAGGGATGGCTCCAACATCCT

GCCAAAGCTGCTGGAGAATGACGATTCTCACGCCATCGACACGATGGTGGCCCTGATCCGC

AGCGTGCTGCAGATGCGGAACTCCAATGCCGCCACAGGCGAGGACTATATCAACAGCCCC

GTGCGCGATCTGAATGGCGTGTGCTTCGACTCCCGGTTTCAGAACCCAGAGTGGCCAATGG

ACGCCGATGCCAATGGCGCCTACCACATCGCCCTGAAGGGCCAGCTGCTGCTGAATCACCT

GAAGGAGAGCAAGGATCTGAAGCTGCAGAACGGCATCTCCAATCAGGACTGGCTGGCCTAC

ATCCAGGAGCTGCGCAACaaaaggccggcggccacgaaaaaggccggccaggcaaaaaagaaaaag*GGAGC*

*GGCCGCACTCGAG*CACCACCACCACCACCACTGA

RTW645: pET-28b-bLbCas12a-NLS-6×His

Bacterial codon optimized Lachnospiraceae bacterium ND2006 Cas12a (LbCas12a) in black, inserted glycine dash-underlined, nucleoplasmin NLS (aaaaggccogcogc-cacgassaeggccggcceggcassasagaaaaag, SEQ ID NO:21) in lower case, linker sequences in italics, 6×His in bold (SEQ ID NO: 426)

ATGGGGAGCAAACTGGAAAAATTTACGAATTGTTATAGCCTGTCCCAAGACCCTGCGTTTCAA

AGCCATCCCCGTTGGCAAAACCCAGGAGAATATTGATAATAAACGTCTGCTGGTTGAGGATG

AAAAAAGAGCAGAAGACTATAAGGGAGTCAAAAAACTGCTGGATCGGTACTACCTGAGCTTT

-continued
ATAAATGACGTGCTGCATAGCATTAAACTGAAAAATCTGAATAACTATATTAGTCTGTTCCGC
AAGAAAACCCGAACAGAGAAAGAAAATAAAGAGCTGGAAAACCTGGAGATCAATCTGCGTAA
AGAGATCGCAAAAGCTTTTAAAGGAAATGAAGGTTATAAAAGCCTGTTCAAAAAAGACATTAT
TGAAACCATCCTGCCGGAATTTCTGGATGATAAAGACGAGATAGCGCTCGTGAACAGCTTCA
ACGGGTTCACGACCGCCTTCACGGGCTTTTTCGATAACAGGGAAAATATGTTTTCAGAGGAA
GCCAAAAGCACCTCGATAGCGTTCCGTTGCATTAATGAAAATTTGACAAGATATATCAGCAAC
ATGGATATTTTCGAGAAAGTTGATGCGATCTTTGACAAACATGAAGTGCAGGAGATTAAGGA
AAAAATTCTGAACAGCGATTATGATGTTGAGGATTTTTTCGAGGGGGAATTTTTTAACTTTGT
ACTGACACAGGAAGGTATAGATGTGTATAATGCTATTATCGGCGGGTTCGTTACCGAATCCG
GCGAGAAAATTAAGGGTCTGAATGAGTACATCAATCTGTATAACCAAAAGACCAAACAGAAA
CTGCCAAAATTCAAACCGCTGTACAAGCAAGTCCTGAGCGATCGGGAAAGCTTGAGCTTTTA
CGGTGAAGGTTATACCAGCGACGAGGAGGTACTGGAGGTCTTTCGCAATACCCTGAACAAG
AACAGCGAAATTTTCAGCTCCATTAAAAAGCTGGAGAAACTGTTTAAGAATTTTGACGAGTAC
AGCAGCGCAGGTATTTTTGTGAAGAACGGACCTGCCATAAGCACCATTAGCAAGGATATTTT
TGGAGAGTGGAATGTTATCCGTGATAAATGGAACGCGGAATATGATGACATACACCTGAAAA
AGAAGGCTGTGGTAACTGAGAAATATGAAGACGATCGCCGCAAAAGCTTTAAAAAAATCGGC
AGCTTTAGCCTGGAGCAGCTGCAGGAATATGCGGACGCCGACCTGAGCGTGGTCGAGAAA
CTGAAGGAAATTATTATCCAAAAAGTGGATGAGATTTACAAGGTATATGGTAGCAGCGAAAAA
CTGTTTGATGCGGACTTCGTTCTGGAAAAAAGCCTGAAAAAAAATGATGCTGTTGTTGCGAT
CATGAAAGACCTGCTCGATAGCGTTAAGAGCTTTGAAAATTACATTAAAGCATTCTTTGGCGA
GGGCAAAGAAACAAACAGAGACGAAAGCTTTTATGGCGACTTCGTCCTGGCTTATGACATCC
TGTTGAAGGTAGATCATATATATGATGCAATTCGTAATTACGTAACCCAAAAGCCGTACAGCA
AAGATAAGTTCAAACTGTATTTCCAGAACCCGCAGTTTATGGGTGGCTGGGACAAAGACAAG
GAGACAGACTATCGCGCCACTATTCTGCGTTACGGCAGCAAGTACTATCTCGCCATCATGGA
CAAAAAATATGCAAAGTGTCTGCAGAAAATCGATAAAGACGACGTGAACGGAAATTACGAAA
AGATTAATTATAAGCTGCTGCCAGGGCCCAACAAGATGTTACCGAAAGTATTTTTTTCCAAAA
AATGGATGGCATACTATAACCCGAGCGAGGATATACAGAAGATTTACAAAAATGGGACCTTC
AAAAAGGGGGATATGTTCAATCTGAATGACTGCCACAAACTGATCGATTTTTTTAAAGATAGC
ATCAGCCGTTATCCTAAATGGTCAAACGCGTATGATTTTAATTTCTCCGAAACGGAGAAATAT
AAAGACATTGCTGGTTTCTATCGCGAAGTCGAAGAACAGGGTTATAAAGTTAGCTTTGAATC
GGCCAGCAAGAAAGAGGTTGATAAACTGGTGGAGGAGGGTAAGCTGTATATGTTTCAGATTT
ATAACAAAGACTTTAGCGACAAAAGCCACGGTACTCCTAATCTGCATACGATGTACTTTAAAC
TGCTGTTTGATGAGAATAACCACGGCCAAATCCGTCTCTCCGGTGGAGCAGAACTTTTTATG
CGGCGTGCGAGCCTAAAAAAGGAAGAACTGGTGGTGCATCCCGCCAACAGCCCGATTGCTA
ACAAAAATCCAGATAATCCTAAGAAGACCACCACACTGTCGTACGATGTCTATAAGGATAAAC
GTTTCTCGGAAGACCAGTATGAATTGCATATACCGATAGCAATTAATAAATGCCCAAAAAACA
TTTTCAAAATCAACACTGAAGTTCGTGTGCTGCTGAAACATGATGATAATCCGTATGTGATCG
GAATTGACCGTGGGGAGAGAAATCTGCTGTATATTGTAGTCGTTGATGGCAAGGGCAACATC
GTTGAGCAGTATAGCCTGAATGAAATAATTAATAATTTTAACGGTATACGTATTAAAACCGAC
TATCATAGCCTGCTGGATAAAAAGGAGAAAGAGCGTTTTGAGGCACGCCAAAATTGGACGA
GCATCGAAAACATCAAGGAACTGAAGGCAGGATATATCAGCCAAGTAGTCCATAAAATCTGT -continued

GAACTGGTGGAGAAGTACGACGCTGTCATTGCCCTGGAAGACCTCAATAGCGGCTTTAAAA

ACAGCCGGGTGAAGGTGGAGAAACAGGTATACCAAAAGTTTGAAAAGATGCTCATTGATAAG

CTGAACTATATGGTTGATAAAAAGAGCAACCCGTGCGCCACTGGCGGTGCACTGAAAGGGT

ACCAAATTACCAATAAATTTGAAAGCTTTAAAAGCATGAGCACGCAGAATGGGTTTATTTTTTA

TATACCAGCATGGCTGACGAGCAAGATTGACCCCAGCACTGGTTTTGTCAATCTGCTGAAAA

CCAAATACACAAGCATTGCGGATAGCAAAAAATTTATTTCGAGCTTCGACCGTATTATGTATG

TTCCGGAGGAAGATCTGTTTGAATTTGCCCTGGATTATAAAAACTTCAGCCGCACCGATGCA

GATTATATCAAAAAATGGAAGCTGTACAGTTATGGTAATCGTATACGTATCTTCCGTAATCCG

AAGAAAAACAATGTGTTCGATTGGGAAGAGGTCTGTCTGACCAGCGCGTATAAAGAACTGTT

CAACAAGTACGGAATAAATTATCAGCAAGGTGACATTCGCGCACTGCTGTGTGAACAGTCAG

ATAAAGCATTTTATAGCAGCTTTATGGCGCTGATGAGCCTGATGCTCCAGATGCGCAACAGC

ATAACCGGTCGCACAGATGTTGACTTTCTGATCAGCCCTGTGAAGAATAGCGACGGCATCTT

CTACGATTCCAGGAACTATGAAGCACAGGAAAACGCTATTCTGCCTAAAAATGCCGATGCCA

ACGGCGCCTATAATATTGCACGGAAGGTTCTGTGGGCGATTGGACAGTTCAAGAAAGCGGA

AGATGAGAAGCTGGATAAGGTAAAAATTGCTATTAGCAATAAGGAATGGCTGGAGTACGCAC

AGACATCGGTTAAACAC*GGTAGT*aaaaggccggcggccacgaaaaaggccggccaggcaaaaaagaaaaag*G*

*GAGCGGCCGCACTCGAG*CACCACCACCACCACCACTGA

AAS1885: pET-28b-heAsCas12a(E174R/S542R/K548R)-NLS-6×His

Human codon optimized *Acidaminococcus* sp. BV3L6 Cas12a (AsCas12a) in black, modified codons for eAsCas12a (E174R/S542R/K548R) in doubleunderlinedlower case, codons with silent mutations to remove NcoI sites doubleunderlinedUPPERCASE, inserted glycine dash-underlined, nucleoplasmin NLS (aaaaggccggcggccacgaaaaaggccggccaggcaaaaaagaaaaag, SEQ ID NO:21) in lower case, linker sequences in italics, 6×His in bold

SEQ ID NO: 427)

ATGGGGACACAGTTCGAGGGCTTTACCAACCTGTATCAGGTGAGCAAGACACTGCG

GTTTGAGCTGATCCCACAGGGCAAGACCCTGAAGCACATCCAGGAGCAGGGCTTCATCGAG

GAGGACAAGGCCCGCAATGATCACTACAAGGAGCTGAAGCCCATCATCGATCGGATCTACA

AGACCTATGCCGACCAGTGCCTGCAGCTGGTGCAGCTGGATTGGGAGAACCTGAGCGCCG

CCATCGACTCCTATAGAAAGGAGAAAACCGAGGAGACAAGGAACGCCCTGATCGAGGAGCA

GGCCACATATCGCAATGCCATCCACGACTACTTCATCGGCCGGACAGACAACCTGACCGAT

GCCATCAATAAGAGACACGCCGAGATCTACAAGGGCCTGTTCAAGGCCGAGCTGTTTAATG

GCAAGGTGCTGAAGCAGCTGGGCACCGTGACCACAACCGAGCACGAGAACGCCCTGCTGC

GGAGCTTCGACAAGTTTACAACCTACTTCTCCGGCTTTTATagaAACAGGAAGAACGTGTTCA

GCGCCGAGGATATCAGCACAGCCATCCCACACCGCATCGTGCAGGACAACTTCCCCAAGTT

TAAGGAGAATTGTCACATCTTCACACGCCTGATCACCGCCGTGCCCAGCCTGCGGGAGCAC

TTTGAGAACGTGAAGAAGGCCATCGGCATCTTCGTGAGCACCTCCATCGAGGAGGTGTTTT

CCTTCCCTTTTTATAACCAGCTGCTGACACAGACCCAGATCGACCTGTATAACCAGCTGCTG

GGAGGAATCTCTCGGGAGGCAGGCACCGAGAAGATCAAGGGCCTGAACGAGGTGCTGAAT

CTGGCCATCCAGAAGAATGATGAGACAGCCCACATCATCGCCTCCCTGCCACACAGATTCAT

CCCCCTGTTTAAGCAGATCCTGTCCGATAGGAACACCCTGTCTTTCATCCTGGAGGAGTTTA

AGAGCGACGAGGAAGTGATCCAGTCCTTCTGCAAGTACAAGACACTGCTGAGAAACGAGAA

-continued

CGTGCTGGAGACAGCCGAGGCCCTGTTTAACGAGCTGAACAGCATCGACCTGACACACATC

TTCATCAGCCACAAGAAGCTGGAGACAATCAGCAGCGCCCTGTGCGACCACTGGGATACAC

TGAGGAATGCCCTGTATGAGCGGAGAATCTCCGAGCTGACAGGCAAGATCACCAAGTCTGC

CAAGGAGAAGGTGCAGCGCAGCCTGAAGCACGAGGATATCAACCTGCAGGAGATCATCTCT

GCCGCAGGCAAGGAGCTGAGCGAGGCCTTCAAGCAGAAAACCAGCGAGATCCTGTCCCAC

GCACACGCCGCCCTGGATCAGCCACTGCCTACAACCCTGAAGAAGCAGGAGGAGAAGGAG

ATCCTGAAGTCTCAGCTGGACAGCCTGCTGGGCCTGTACCACCTGCTGGACTGGTTTGCCG

TGGATGAGTCCAACGAGGTGGACCCCGAGTTCTCTGCCCGGCTGACCGGCATCAAGCTGG

AGATGGAGCCTTCTCTGAGCTTCTACAACAAGGCCAGAAATTATGCCACCAAGAAGCCCTAC

TCCGTGGAGAAGTTCAAGCTGAACTTTCAGATGCCTACACTGGCCagaGGCTGGGACGTGAA

TagaGAGAAGAACAATGGCGCCATCCTGTTTGTGAAGAACGGCCTGTACTATCTGGGCATCA

TGCCAAAGCAGAAGGGCAGGTATAAGGCCCTGAGCTTCGAGCCCACAGAGAAAACCAGCG

AGGGCTTTGATAAGATGTACTATGACTACTTCCCTGATGCCGCCAAGATGATCCCAAAGTGC

AGCACCCAGCTGAAGGCCGTGACAGCCCACTTTCAGACCCACACAACCCCCATCCTGCTGT

CCAACAATTTCATCGAGCCTCTGGAGATCACAAAGGAGATCTACGACCTGAACAATCCTGAG

AAGGAGCCAAAGAAGTTTCAGACAGCCTACGCCAAGAAAACCGGCGACCAGAAGGGCTACA

GAGAGGCCCTGTGCAAGTGGATCGACTTCACAAGGGATTTTCTGTCCAAGTATACCAAGACA

ACCTCTATCGATCTGTCTAGCCTGCGGCCATCCTCTCAGTATAAGGACCTGGGCGAGTACTA

TGCCGAGCTGAATCCCCTGCTGTACCACATCAGCTTCCAGAGAATCGCCGAGAAGGAGATC

ATGGATGCCGTGGAGACAGGCAAGCTGTACCTGTTCCAGATCTATAACAAGGACTTTGCCAA

GGGCCACCACGGCAAGCCTAATCTGCACACACTGTATTGGACCGGCCTGTTTTCTCCAGAG

AACCTGGCCAAGACAAGCATCAAGCTGAATGGCCAGGCCGAGCTGTTCTACCGCCCTAAGT

CCAGGATGAAGAGGATGGCACACCGGCTGGGAGAGAAGATGCTGAACAAGAAGCTGAAGG

ATCAGAAAACCCCAATCCCCGACACCCTGTACCAGGAGCTGTACGACTATGTGAATCACAGA

CTGTCCCACGACCTGTCTGATGAGGCCAGGGCCCTGCTGCCCAACGTGATCACCAAGGAG

GTGTCTCACGAGATCATCAAGGATAGGCGCTTTACCAGCGACAAGTTCTTTTTCCACGTGCC

TATCACACTGAACTATCAGGCCGCCAATTCCCCATCTAAGTTCAACCAGAGGGTGAATGCCT

ACCTGAAGGAGCACCCCGAGACACCTATCATCGGCATCGATCGGGGCGAGAGAAACCTGAT

CTATATCACAGTGATCGACTCCACCGGCAAGATCCTGGAGCAGCGGAGCCTGAACACCATC

CAGCAGTTTGATTACCAGAAGAAGCTGGACAACAGGGAGAAGGAGAGGGTGGCAGCAAGG

CAGGCCTGGTCTGTGGTGGGCACAATCAAGGATCTGAAGCAGGGCTATCTGAGCCAGGTCA

TCCACGAGATCGTGGACCTGATGATCCACTACCAGGCCGTGGTGGTGCTGGAGAACCTGAA

TTTCGGCTTTAAGAGCAAGAGGACCGGCATCGCCGAGAAGGCCGTGTACCAGCAGTTCGAG

AAGATGCTGATCGATAAGCTGAATTGCCTGGTGCTGAAGGACTATCCAGCAGAGAAAGTGG

GAGGCGTGCTGAACCCATACCAGCTGACAGACCAGTTCACCTCCTTTGCCAAGATGGGCAC

CCAGTCTGGCTTCCTGTTTTACGTGCCTGCCCCATATACATCTAAGATCGATCCCCTGACCG

GCTTCGTGGACCCCTTCGTGTGGAAAACCATCAAGAATCACGAGAGCCGCAAGCACTTCCT

GGAGGGCTTCGACTTTCTGCACTACGACGTGAAAACCGGCGACTTCATCCTGCACTTTAAGA

TGAACAGAAATCTGTCCTTCCAGAGGGGCCTGCCCGGCTTTATGCCTGCATGGGATATCGT

GTTCGAGAAGAACGAGACACAGTTTGACGCCAAGGGCACCCCTTTCATCGCCGGCAAGAGA

ATCGTGCCAGTGATCGAGAATCACAGATTCACCGGCAGATACCGGGACCTGTATCCTGCCA

-continued

```
ACGAGCTGATCGCCCTGCTGGAGGAGAAGGGCATCGTGTTCAGGGATGGCTCCAACATCCT
GCCAAAGCTGCTGGAGAATGACGATTCTCACGCCATCGACACGATGGTGGCCCTGATCCGC
AGCGTGCTGCAGATGCGGAACTCCAATGCCGCCACAGGCGAGGACTATATCAACAGCCCC
GTGCGCGATCTGAATGGCGTGTGCTTCGACTCCCGGTTTCAGAACCCAGAGTGGCCAATGG
ACGCCGATGCCAATGGCGCCTACCACATCGCCCTGAAGGGCCAGCTGCTGCTGAATCACCT
GAAGGAGAGCAAGGATCTGAAGCTGCAGAACGGCATCTCCAATCAGGACTGGCTGGCCTAC
ATCCAGGAGCTGCGCAACaaaaggccggcggccacgaaaaaggccggccaggcaaaaaagaaaaagGGAGC
GGCCGCACTCGAGCACCACCACCACCACCACTGA
```

AAS1880: pET-28b-hAsCas12a(E174R/S542R)-NLS-6×His

Human codon optimized *Acidaminococcus* sp. BV3L6 Cas12a (AsCas12a) in black, modified codons (E174R/S542R) in doubleunderlinedlower case, codons with silent mutations to remove NcoI sites doubleunderlinedUPPERCASE, inserted glycine dash-underlined, nucleoplasmin NLS (aaaaggccggcggccacgaaaaaggccggccaggcaaaaaagaaaaag, SEQ ID NO:21) in lower case, linker sequences in italics, 6×His in bold (SEQ ID NO: 428)

```
ATGGGGACACAGTTCGAGGGCTTTACCAACCTGTATCAGGTGAGCAAGACACTGCG
GTTTGAGCTGATCCCACAGGGCAAGACCCTGAAGCACATCCAGGAGCAGGGCTTCATCGAG
GAGGACAAGGCCCGCAATGATCACTACAAGGAGCTGAAGCCCATCATCGATCGGATCTACA
AGACCTATGCCGACCAGTGCCTGCAGCTGGTGCAGCTGGATTGGGAGAACCTGAGCGCCG
CCATCGACTCCTATAGAAAGGAGAAAACCGAGGAGACAAGGAACGCCCTGATCGAGGAGCA
GGCCACATATCGCAATGCCATCCACGACTACTTCATCGGCCGGACAGACAACCTGACCGAT
GCCATCAATAAGAGACACGCCGAGATCTACAAGGGCCTGTTCAAGGCCGAGCTGTTTAATG
GCAAGGTGCTGAAGCAGCTGGGCACCGTGACCACAACCGAGCACGAGAACGCCCTGCTGC
GGAGCTTCGACAAGTTTACAACCTACTTCTCCGGCTTTTATagaAACAGGAAGAACGTGTTCA
GCGCCGAGGATATCAGCACAGCCATCCCACACCGCATCGTGCAGGACAACTTCCCCAAGTT
TAAGGAGAATTGTCACATCTTCACACGCCTGATCACCGCCGTGCCCAGCCTGCGGGAGCAC
TTTGAGAACGTGAAGAAGGCCATCGGCATCTTCGTGAGCACCTCCATCGAGGAGGTGTTTT
CCTTCCCTTTTTATAACCAGCTGCTGACACAGACCCAGATCGACCTGTATAACCAGCTGCTG
GGAGGAATCTCTCGGGAGGCAGGCACCGAGAAGATCAAGGGCCTGAACGAGGTGCTGAAT
CTGGCCATCCAGAAGAATGATGAGACAGCCCACATCATCGCCTCCCTGCCACACAGATTCAT
CCCCCTGTTTAAGCAGATCCTGTCCGATAGGAACACCCTGTCTTTCATCCTGGAGGAGTTTA
AGAGCGACGAGGAAGTGATCCAGTCCTTCTGCAAGTACAAGACACTGCTGAGAAACGAGAA
CGTGCTGGAGACAGCCGAGGCCCTGTTTAACGAGCTGAACAGCATCGACCTGACACACATC
TTCATCAGCCACAAGAAGCTGGAGACAATCAGCAGCGCCCTGTGCGACCACTGGGATACAC
TGAGGAATGCCCTGTATGAGCGGAGAATCTCCGAGCTGACAGGCAAGATCACCAAGTCTGC
CAAGGAGAAGGTGCAGCGCAGCCTGAAGCACGAGGATATCAACCTGCAGGAGATCATCTCT
GCCGCAGGCAAGGAGCTGAGCGAGGCCTTCAAGCAGAAAACCAGCGAGATCCTGTCCCAC
GCACACGCCGCCCTGGATCAGCCACTGCCTACAACCCTGAAGAAGCAGGAGGAGAAGGAG
ATCCTGAAGTCTCAGCTGGACAGCCTGCTGGGCCTGTACCACCTGCTGGACTGGTTTGCCG
TGGATGAGTCCAACGAGGTGGACCCCGAGTTCTCTGCCCGGCTGACCGGCATCAAGCTGG
AGATGGAGCCTTCTCTGAGCTTCTACAACAAGGCCAGAAATTATGCCACCAAGAAGCCCTAC
TCCGTGGAGAAGTTCAAGCTGAACTTTCAGATGCCTACACTGGCCagaGGCTGGGACGTGAA
```

-continued

TAAGGAGAAGAACAATGGCGCCATCCTGTTTGTGAAGAACGGCCTGTACTATCTGGGCATCA

TGCCAAAGCAGAAGGGCAGGTATAAGGCCCTGAGCTTCGAGCCCACAGAGAAAACCAGCG

AGGGCTTTGATAAGATGTACTATGACTACTTCCCTGATGCCGCCAAGATGATCCCAAAGTGC

AGCACCCAGCTGAAGGCCGTGACAGCCCACTTTCAGACCCACACAACCCCCATCCTGCTGT

CCAACAATTTCATCGAGCCTCTGGAGATCACAAAGGAGATCTACGACCTGAACAATCCTGAG

AAGGAGCCAAAGAAGTTTCAGACAGCCTACGCCAAGAAAACCGGCGACCAGAAGGGCTACA

GAGAGGCCCTGTGCAAGTGGATCGACTTCACAAGGGATTTTCTGTCCAAGTATACCAAGACA

ACCTCTATCGATCTGTCTAGCCTGCGGCCATCCTCTCAGTATAAGGACCTGGGCGAGTACTA

TGCCGAGCTGAATCCCCTGCTGTACCACATCAGCTTCCAGAGAATCGCCGAGAAGGAGATC

ATGGATGCCGTGGAGACAGGCAAGCTGTACCTGTTCCAGATCTATAACAAGGACTTTGCCAA

GGGCCACCACGGCAAGCCTAATCTGCACACACTGTATTGGACCGGCCTGTTTTCTCCAGAG

AACCTGGCCAAGACAAGCATCAAGCTGAATGGCCAGGCCGAGCTGTTCTACCGCCCTAAGT

CCAGGATGAAGAGGATGGCACACCGGCTGGGAGAGAAGATGCTGAACAAGAAGCTGAAGG

ATCAGAAAACCCCAATCCCCGACACCCTGTACCAGGAGCTGTACGACTATGTGAATCACAGA

CTGTCCCACGACCTGTCTGATGAGGCCAGGGCCCTGCTGCCCAACGTGATCACCAAGGAG

GTGTCTCACGAGATCATCAAGGATAGGCGCTTTACCAGCGACAAGTTCTTTTTCCACGTGCC

TATCACACTGAACTATCAGGCCGCCAATTCCCCATCTAAGTTCAACCAGAGGGTGAATGCCT

ACCTGAAGGAGCACCCCGAGACACCTATCATCGGCATCGATCGGGGCGAGAGAAACCTGAT

CTATATCACAGTGATCGACTCCACCGGCAAGATCCTGGAGCAGCGGAGCCTGAACACCATC

CAGCAGTTTGATTACCAGAAGAAGCTGGACAACAGGGAGAAGGAGAGGGTGGCAGCAAGG

CAGGCCTGGTCTGTGGTGGGCACAATCAAGGATCTGAAGCAGGGCTATCTGAGCCAGGTCA

TCCACGAGATCGTGGACCTGATGATCCACTACCAGGCCGTGGTGGTGCTGGAGAACCTGAA

TTTCGGCTTTAAGAGCAAGAGGACCGGCATCGCCGAGAAGGCCGTGTACCAGCAGTTCGAG

AAGATGCTGATCGATAAGCTGAATTGCCTGGTGCTGAAGGACTATCCAGCAGAGAAAGTGG

GAGGCGTGCTGAACCCATACCAGCTGACAGACCAGTTCACCTCCTTTGCCAAGATGGGCAC

CCAGTCTGGCTTCCTGTTTTACGTGCCTGCCCCATATACATCTAAGATCGATCCCCTGACCG

GCTTCGTGGACCCCTTCGTGTGGAAAACCATCAAGAATCACGAGAGCCGCAAGCACTTCCT

GGAGGGCTTCGACTTTCTGCACTACGACGTGAAAACCGGCGACTTCATCCTGCACTTTAAGA

TGAACAGAAATCTGTCCTTCCAGAGGGGCCTGCCCGGCTTTATGCCTGCATGGGATATCGT

GTTCGAGAAGAACGAGACACAGTTTGACGCCAAGGGCACCCCTTTCATCGCCGGCAAGAGA

ATCGTGCCAGTGATCGAGAATCACAGATTCACCGGCAGATACCGGGACCTGTATCCTGCCA

ACGAGCTGATCGCCCTGCTGGAGGAGAAGGGCATCGTGTTCAGGGATGGCTCCAACATCCT

GCCAAAGCTGCTGGAGAATGACGATTCTCACGCCATCGACACGATGGTGGCCCTGATCCGC

AGCGTGCTGCAGATGCGGAACTCCAATGCCGCCACAGGCGAGGACTATATCAACAGCCCC

GTGCGCGATCTGAATGGCGTGTGCTTCGACTCCCGGTTTCAGAACCCAGAGTGGCCAATGG

ACGCCGATGCCAATGGCGCCTACCACATCGCCCTGAAGGGCCAGCTGCTGCTGAATCACCT

GAAGGAGAGCAAGGATCTGAAGCTGCAGAACGGCATCTCCAATCAGGACTGGCTGGCCTAC

ATCCAGGAGCTGCGCAACaaaaggccggcggccacgaaaaaggccggccaggcaaaaaagaaaaag*GGAGC*

*GGCCGCACTCGAG*CACCACCACCACCACCACTGA

AAS1935: pET-28b-heAsCas12a-HF1(E174R/N282A/S542R/K548R)-NLS-6×His

Human codon optimized *Acidaminococcus* sp. BV3L6 Cas12a (AsCas12a) in black, modified codons for eAsCas12a-HF1 (E174R/N282A/S542R/K548R) in doubleunderlinedlower case, codons with silent mutations to remove NcoI sites doubleunderlinedUPPERCASE, inserted glycine dash-underlined, nucleoplasmin NLS (aaaaggccggcggccacgaaaaaggccggccaggcaaaaaagaaaaag, SEQ ID NO:21) in lower case, linker sequences in italics, 6×His in bold

SEQ ID NO: 429)

ATGGGGACACAGTTCGAGGGCTTTACCAACCTGTATCAGGTGAGCAAGACACTGCG

GTTTGAGCTGATCCCACAGGGCAAGACCCTGAAGCACATCCAGGAGCAGGGCTTCATCGAG

GAGGACAAGGCCCGCAATGATCACTACAAGGAGCTGAAGCCCATCATCGATCGGATCTACA

AGACCTATGCCGACCAGTGCCTGCAGCTGGTGCAGCTGGATTGGGAGAACCTGAGCGCCG

CCATCGACTCCTATAGAAAGGAGAAAACCGAGGAGACAAGGAACGCCCTGATCGAGGAGCA

GGCCACATATCGCAATGCCATCCACGACTACTTCATCGGCCGGACAGACAACCTGACCGAT

GCCATCAATAAGAGACACGCCGAGATCTACAAGGGCCTGTTCAAGGCCGAGCTGTTTAATG

GCAAGGTGCTGAAGCAGCTGGGCACCGTGACCACAACCGAGCACGAGAACGCCCTGCTGC

GGAGCTTCGACAAGTTTACAACCTACTTCTCCGGCTTTTATagaAACAGGAAGAACGTGTTCA

GCGCCGAGGATATCAGCACAGCCATCCCACACCGCATCGTGCAGGACAACTTCCCCAAGTT

TAAGGAGAATTGTCACATCTTCACACGCCTGATCACCGCCGTGCCCAGCCTGCGGGAGCAC

TTTGAGAACGTGAAGAAGGCCATCGGCATCTTCGTGAGCACCTCCATCGAGGAGGTGTTTT

CCTTCCCTTTTTATAACCAGCTGCTGACACAGACCCAGATCGACCTGTATAACCAGCTGCTG

GGAGGAATCTCTCGGGAGGCAGGCACCGAGAAGATCAAGGGCCTGAACGAGGTGCTGgccC

TGGCCATCCAGAAGAATGATGAGACAGCCCACATCATCGCCTCCCTGCCACACAGATTCATC

CCCCTGTTTAAGCAGATCCTGTCCGATAGGAACACCCTGTCTTTCATCCTGGAGGAGTTTAA

GAGCGACGAGGAAGTGATCCAGTCCTTCTGCAAGTACAAGACACTGCTGAGAAACGAGAAC

GTGCTGGAGACAGCCGAGGCCCTGTTTAACGAGCTGAACAGCATCGACCTGACACACATCT

TCATCAGCCACAAGAAGCTGGAGACAATCAGCAGCGCCCTGTGCGACCACTGGGATACACT

GAGGAATGCCCTGTATGAGCGGAGAATCTCCGAGCTGACAGGCAAGATCACCAAGTCTGCC

AAGGAGAAGGTGCAGCGCAGCCTGAAGCACGAGGATATCAACCTGCAGGAGATCATCTCTG

CCGCAGGCAAGGAGCTGAGCGAGGCCTTCAAGCAGAAAACCAGCGAGATCCTGTCCCACG

CACACGCCGCCCTGGATCAGCCACTGCCTACAACCCTGAAGAAGCAGGAGGAGAAGGAGA

TCCTGAAGTCTCAGCTGGACAGCCTGCTGGGCCTGTACCACCTGCTGGACTGGTTTGCCGT

GGATGAGTCCAACGAGGTGGACCCCGAGTTCTCTGCCCGGCTGACCGGCATCAAGCTGGA

GATGGAGCCTTCTCTGAGCTTCTACAACAAGGCCAGAAATTATGCCACCAAGAAGCCCTACT

CCGTGGAGAAGTTCAAGCTGAACTTTCAGATGCCTACACTGGCCagaGGCTGGGACGTGAAT agaGAGAAGAACAATGGCGCCATCCTGTTTGTGAAGAACGGCCTGTACTATCTGGGCATCAT

GCCAAAGCAGAAGGGCAGGTATAAGGCCCTGAGCTTCGAGCCCACAGAGAAAACCAGCGA

GGGCTTTGATAAGATGTACTATGACTACTTCCCTGATGCCGCCAAGATGATCCCAAAGTGCA

GCACCCAGCTGAAGGCCGTGACAGCCCACTTTCAGACCCACACAACCCCCATCCTGCTGTC

CAACAATTTCATCGAGCCTCTGGAGATCACAAAGGAGATCTACGACCTGAACAATCCTGAGA

AGGAGCCAAAGAAGTTTCAGACAGCCTACGCCAAGAAAACCGGCGACCAGAAGGGCTACAG

AGAGGCCCTGTGCAAGTGGATCGACTTCACAAGGGATTTTCTGTCCAAGTATACCAAGACAA

CCTCTATCGATCTGTCTAGCCTGCGGCCATCCTCTCAGTATAAGGACCTGGGCGAGTACTAT

GCCGAGCTGAATCCCCTGCTGTACCACATCAGCTTCCAGAGAATCGCCGAGAAGGAGATCA

-continued

TGGATGCCGTGGAGACAGGCAAGCTGTACCTGTTCCAGATCTATAACAAGGACTTTGCCAA

GGGCCACCACGGCAAGCCTAATCTGCACACACTGTATTGGACCGGCCTGTTTTCTCCAGAG

AACCTGGCCAAGACAAGCATCAAGCTGAATGGCCAGGCCGAGCTGTTCTACCGCCCTAAGT

CCAGGATGAAGAGGATGGCACACCGGCTGGGAGAGAAGATGCTGAACAAGAAGCTGAAGG

ATCAGAAAACCCCAATCCCCGACACCCTGTACCAGGAGCTGTACGACTATGTGAATCACAGA

CTGTCCCACGACCTGTCTGATGAGGCCAGGGCCCTGCTGCCCAACGTGATCACCAAGGAG

GTGTCTCACGAGATCATCAAGGATAGGCGCTTTACCAGCGACAAGTTCTTTTTCCACGTGCC

TATCACACTGAACTATCAGGCCGCCAATTCCCCATCTAAGTTCAACCAGAGGGTGAATGCCT

ACCTGAAGGAGCACCCCGAGACACCTATCATCGGCATCGATCGGGGCGAGAGAAACCTGAT

CTATATCACAGTGATCGACTCCACCGGCAAGATCCTGGAGCAGCGGAGCCTGAACACCATC

CAGCAGTTTGATTACCAGAAGAAGCTGGACAACAGGGAGAAGGAGAGGGTGGCAGCAAGG

CAGGCCTGGTCTGTGGTGGGCACAATCAAGGATCTGAAGCAGGGCTATCTGAGCCAGGTCA

TCCACGAGATCGTGGACCTGATGATCCACTACCAGGCCGTGGTGGTGCTGGAGAACCTGAA

TTTCGGCTTTAAGAGCAAGAGGACCGGCATOGCCGAGAAGGCCGTGTACCAGCAGTTCGAG

AAGATGCTGATCGATAAGCTGAATTGCCTGGTGCTGAAGGACTATCCAGCAGAGAAAGTGG

GAGGCGTGCTGAACCCATACCAGCTGACAGACCAGTTCACCTCCTTTGCCAAGATGGGCAC

CCAGTCTGGCTTCCTGTTTTACGTGCCTGCCCCATATACATCTAAGATCGATCCCCTGACCG

GCTTCGTGGACCCCTTCGTGTGGAAAACCATCAAGAATCACGAGAGCCGCAAGCACTTCCT

GGAGGGCTTCGACTTTCTGCACTACGACGTGAAAACCGGCGACTTCATCCTGCACTTTAAGA

TGAACAGAAATCTGTCCTTCCAGAGGGGCCTGCCCGGCTTTATGCCTGCATGGGATATCGT

GTTCGAGAAGAACGAGACACAGTTTGACGCCAAGGGCACCCCTTTCATCGCCGGCAAGAGA

ATCGTGCCAGTGATCGAGAATCACAGATTCACCGGCAGATACCGGGACCTGTATCCTGCCA

ACGAGCTGATCGCCCTGCTGGAGGAGAAGGGCATCGTGTTCAGGGATGGCTCCAACATCCT

GCCAAAGCTGCTGGAGAATGACGATTCTCACGCCATCGACACGATGGTGGCCCTGATCCGC

AGCGTGCTGCAGATGCGGAACTCCAATGCCGCCACAGGCGAGGACTATATCAACAGCCCC

GTGCGCGATCTGAATGGCGTGTGCTTCGACTCCCGGTTTCAGAACCCAGAGTGGCCAATGG

ACGCCGATGCCAATGGCGCCTACCACATCGCCCTGAAGGGCCAGCTGCTGCTGAATCACCT

GAAGGAGAGCAAGGATCTGAAGCTGCAGAACGGCATCTCCAATCAGGACTGGCTGGCCTAC

ATCCAGGAGCTGCGCAACaaaaggccggcggccacgaaaaaggccggccaggcaaaaaagaaaaag*GGAGC*

*GGCCGCACTCGAG*CACCACCACCACCACCACTGA

Nucleotide Sequence of SQT1665 pCAG-humanLbCpf1-NLS-3×HA

Human codon optimized LbCpf1 in normal font, nts 1-3684), NLS (aaaaggccggcggc-cacgaaaaaggccggccaggcaaaaaagaaaaag, SEQ ID NO:21) in lower case, 3×HA tag (TACCCATACGATGTTCCAGATTACGCTTATCCCTACGACGTGCCTGATTATGCATACCCATAT GATGTCCCCGACTATGCC, SEQ ID NO: 5) in BOLD, linker sequence in italics (SEQ ID NO: 10)

ATGAGCAAGCTGGAGAAGTTTACAAACTGCTACTCCCTGTCTAAGACCCTGAGGTTCA

AGGCCATCCCTGTGGGCAAGACCCAGGAGAACATCGACAATAAGCGGCTGCTGGTGGAGGA

CGAGAAGAGAGCCGAGGATTATAAGGGCGTGAAGAAGCTGCTGGATCGCTACTATCTGTCTT

-continued

TTATCAACGACGTGCTGCACAGCATCAAGCTGAAGAATCTGAACAATTACATCAGCCTGTTCC

GGAAGAAAACCAGAACCGAGAAGGAGAATAAGGAGCTGGAGAACCTGGAGATCAATCTGCGG

AAGGAGATCGCCAAGGCCTTCAAGGGCAACGAGGGCTACAAGTCCCTGTTTAAGAAGGATAT

CATOGAGACAATCCTGCCAGAGTTCCTGGACGATAAGGACGAGATCGCCCTGGTGAACAGCT

TCAATGGCTTTACCACAGCCTTCACCGGCTTCTTTGATAACAGAGAGAATATGTTTTCCGAGGA

GGCCAAGAGCACATCCATCGCCTTCAGGTGTATCAACGAGAATCTGACCCGCTACATCTCTAA

TATGGACATCTTCGAGAAGGTGGACGCCATCTTTGATAAGCACGAGGTGCAGGAGATCAAGG

AGAAGATCCTGAACAGCGACTATGATGTGGAGGATTTCTTTGAGGGCGAGTTCTTTAACTTTG

TGCTGACACAGGAGGGCATCGACGTGTATAACGCCATCATCGGCGGCTTCGTGACCGAGAGC

GGCGAGAAGATCAAGGGCCTGAACGAGTACATCAACCTGTATAATCAGAAAACCAAGCAGAA

GCTGCCTAAGTTTAAGCCACTGTATAAGCAGGTGCTGAGCGATCGGGAGTCTCTGAGCTTCTA

CGGCGAGGGCTATACATCCGATGAGGAGGTGCTGGAGGTGTTTAGAAACACCCTGAACAAGA

ACAGCGAGATCTTCAGCTCCATCAAGAAGCTGGAGAAGCTGTTCAAGAATTTTGACGAGTACT

CTAGCGCCGGCATCTTTGTGAAGAACGGCCCCGCCATCAGCACAATCTCCAAGGATATCTTC

GGCGAGTGGAACGTGATCCGGGACAAGTGGAATGCCGAGTATGACGATATCCACCTGAAGAA

GAAGGCCGTGGTGACCGAGAAGTACGAGGACGATCGGAGAAAGTCCTTCAAGAAGATCGGC

TCCTTTTCTCTGGAGCAGCTGCAGGAGTACGCCGACGCCGATCTGTCTGTGGTGGAGAAGCT

GAAGGAGATCATCATCCAGAAGGTGGATGAGATCTACAAGGTGTATGGCTCCTCTGAGAAGC

TGTTCGACGCCGATTTTGTGCTGGAGAAGAGCCTGAAGAAGAACGACGCCGTGGTGGCCATC

ATGAAGGACCTGCTGGATTCTGTGAAGAGCTTCGAGAATTACATCAAGGCCTTCTTTGGCGAG

GGCAAGGAGACAAACAGGGACGAGTCCTTCTATGGCGATTTTGTGCTGGCCTACGACATCCT

GCTGAAGGTGGACCACATCTACGATGCCATCCGCAATTATGTGACCCAGAAGCCCTACTCTAA

GGATAAGTTCAAGCTGTATTTTCAGAACCCTCAGTTCATGGGCGGCTGGGACAAGGATAAGGA

GACAGACTATCGGGCCACCATCCTGAGATACGGCTCCAAGTACTATCTGGCCATCATGGATAA

GAAGTACGCCAAGTGCCTGCAGAAGATCGACAAGGACGATGTGAACGGCAATTACGAGAAGA

TCAACTATAAGCTGCTGCCCGGCCCTAATAAGATGCTGCCAAAGGTGTTCTTTTCTAAGAAGT

GGATGGCCTACTATAACCCCAGCGAGGACATCCAGAAGATCTACAAGAATGGCACATTCAAGA

AGGGCGATATGTTTAACCTGAATGACTGTCACAAGCTGATCGACTTCTTTAAGGATAGCATCTC

CCGGTATCCAAAGTGGTCCAATGCCTACGATTTCAACTTTTCTGAGACAGAGAAGTATAAGGA

CATCGCCGGCTTTTACAGAGAGGTGGAGGAGCAGGGCTATAAGGTGAGCTTCGAGTCTGCCA

GCAAGAAGGAGGTGGATAAGCTGGTGGAGGAGGGCAAGCTGTATATGTTCCAGATCTATAAC

AAGGACTTTTCCGATAAGTCTCACGGCACACCCAATCTGCACACCATGTACTTCAAGCTGCTG

TTTGACGAGAACAATCACGGACAGATCAGGCTGAGCGGAGGAGCAGAGCTGTTCATGAGGCG

CGCCTCCCTGAAGAAGGAGGAGCTGGTGGTGCACCCAGCCAACTCCCCTATCGCCAACAAGA

ATCCAGATAATCCCAAGAAAACCACAACCCTGTCCTACGACGTGTATAAGGATAAGAGGTTTT

CTGAGGACCAGTACGAGCTGCACATCCCAATCGCCATCAATAAGTGCCCCAAGAACATCTTCA

AGATCAATACAGAGGTGCGCGTGCTGCTGAAGCACGACGATAACCCCTATGTGATCGGCATC

GATAGGGGCGAGCGCAATCTGCTGTATATCGTGGTGGTGGACGGCAAGGGCAACATCGTGG

AGCAGTATTCCCTGAACGAGATCATCAACAACTTCAACGGCATCAGGATCAAGACAGATTACC

ACTCTCTGCTGGACAAGAAGGAGAAGGAGAGGTTCGAGGCCCGCCAGAACTGGACCTCCATC

-continued

GAGAATATCAAGGAGCTGAAGGCCGGCTATATCTCTCAGGTGGTGCACAAGATCTGCGAGCT

GGTGGAGAAGTACGATGCCGTGATCGCCCTGGAGGACCTGAACTCTGGCTTTAAGAATAGCC

GCGTGAAGGTGGAGAAGCAGGTGTATCAGAAGTTCGAGAAGATGCTGATCGATAAGCTGAAC

TACATGGTGGACAAGAAGTCTAATCCTTGTGCAACAGGCGGCGCCCTGAAGGGCTATCAGAT

CACCAATAAGTTCGAGAGCTTTAAGTCCATGTCTACCCAGAACGGCTTCATCTTTTACATCCCT

GCCTGGCTGACATCCAAGATCGATCCATCTACCGGCTTTGTGAACCTGCTGAAAACCAAGTAT

ACCAGCATCGCCGATTCCAAGAAGTTCATCAGCTCCTTTGACAGGATCATGTACGTGCCCGAG

GAGGATCTGTTCGAGTTTGCCCTGGACTATAAGAACTTCTCTCGCACAGACGCCGATTACATC

AAGAAGTGGAAGCTGTACTCCTACGGCAACCGGATCAGAATCTTCCGGAATCCTAAGAAGAAC

AACGTGTTCGACTGGGAGGAGGTGTGCCTGACCAGCGCCTATAAGGAGCTGTTCAACAAGTA

CGGCATCAATTATCAGCAGGGCGATATCAGAGCCCTGCTGTGCGAGCAGTCCGACAAGGCCT

TCTACTCTAGCTTTATGGCCCTGATGAGCCTGATGCTGCAGATGCGGAACAGCATCACAGGC

CGCACCGACGTGGATTTTCTGATCAGCCCTGTGAAGAACTCCGACGGCATCTTCTACGATAGC

CGGAACTATGAGGCCCAGGAGAATGCCATCCTGCCAAAGAACGCCGACGCCAATGGCGCCT

ATAACATCGCCAGAAAGGTGCTGTGGGCCATCGGCCAGTTCAAGAAGGCCGAGGACGAGAA

GCTGGATAAGGTGAAGATCGCCATCTCTAACAAGGAGTGGCTGGAGTACGCCCAGACCAGCG

TGAAGCACaaaaggccggcggccacgaaaaaggccggccaggcaaaaaagaaaaag*GGATCC*TACCCATACGA

TGTTCCAGATTACGCTTATCCCTACGACGTGCCTGATTATGCATACCCATATGATGTCCCCG

ACTATGCCTAA

Amino Acid Sequence of LbCpf1-NLS-3×HA

LbCpf1 in normal text (AAs 1-1228), NLS (krpaatkk-agqakkkk, SEQ ID NO:7) in lower case, 3×HA taa (YPYDVPDYAYPYDVPDYAYPYDVPDYA. SEQ ID NO:8) in bold (SEQ ID NO: 11)

MSKLEKFTNCYSLSKTLRFKAIPVGKTQENIDNKRLLVEDEKRAEDYKGVKKLLDRYYLSFI

NDVLHSIKLKNLNNYISLFRKKTRTEKENKELENLEINLRKEIAKAFKGNEGYKSLFKKDIIETILPEFL

DDKDEIALVNSFNGFTTAFTGFFDNRENMFSEEAKSTSIAFRCINENLTRYISNMDIFEKVDAIFDKH

EVQEIKEKILNSDYDVEDFFEGEFFNFVLTQEGIDVYNAIIGGFVTESGEKIKGLNEYINLYNQKTKQ

KLPKFKPLYKQVLSDRESLSFYGEGYTSDEEVLEVFRNTLNKNSEIFSSIKKLEKLFKNFDEYSSAGI

FVKNGPAISTISKDIFGEWNVIRDKWNAEYDDIHLKKKAVVTEKYEDDRRKSFKKIGSFSLEQLQEY

ADADLSVVEKLKEIIIQKVDEIYKVYGSSEKLFDADFVLEKSLKKNDAVVAIMKDLLDSVKSFENYIKA

FFGEGKETNRDESFYGDFVLAYDILLKVDHIYDAIRNYVTQKPYSKDKFKLYFQNPQFMGGWDKD

KETDYRATILRYGSKYYLAIMDKKYAKCLQKIDKDDVNGNYEKINYKLLPGPNKMLPKVFFSKKWM

AYYNPSEDIQKIYKNGTFKKGDMFNLNDCHKLIDFFKDSISRYPKWSNAYDFNFSETEKYKDIAGFY

REVEEQGYKVSFESASKKEVDKLVEEGKLYMFQIYNKDFSDKSHGTPNLHTMYFKLLFDENNHGQ

IRLSGGAELFMRRASLKKEELVVHPANSPIANKNPDNPKKTTTLSYDVYKDKRFSEDQYELHIPIAIN

KCPKNIFKINTEVRVLLKHDDNPYVIGIDRGERNLLYIVVVDGKGNIVEQYSLNEIINNFNGIRIKTDYH

SLLDKKEKERFEARQNVVTSIENIKELKAGYISQVVHKICELVEKYDAVIALEDLNSGFKNSRVKVEK

QVYQKFEKMLIDKLNYMVDKKSNPCATGGALKGYQITNKFESFKSMSTQNGFIFYIPAWLTSKIDPS

TGFVNLLKTKYTSIADSKKFISSFDRIMYVPEEDLFEFALDYKNFSRTDADYIKKWKLYSYGNRIRIF

RNPKKNNVFDWEEVCLTSAYKELFNKYGINYQQGDIRALLCEQSDKAFYSSFMALMSLMLQMRNS

-continued

ITGRTDVDFLISPVKNSDGIFYDSRNYEAQENAILPKNADANGAYNIARKVLWAIGQFKKAEDEKLD

KVKIAISNKEWLEYAQTSVKHkrpaatkkagqakkkkGSYPYDVPDYAYPYDVPDYAYPYDVPDYA

Nucleotide Sequence of AAS1472 pCAG-humanFnCpf1-NLS-3×HA

Human codon optimized FnCnf1 in normal font, nts 1-3900) NLS (aaaaggccggcggccacgaaaaaggccggccaggcaaaaaagaaaag. SEQ ID NO:21) in lower case, 3xHA tag (TACCCATACGATGTTCCAGATTACGCTTATCCCTACGACGTGCCTGATTATGCATACCCATAT GATGTCCCCGACTATGCC, SEQ ID NO: 5) in BOLD (SEQ ID NO: 17)

ATGAGCATCTACCAGGAGTTCGTCAACAAGTATTCACTGAGTAAGACACTGCGGTTCG

AGCTGATCCCACAGGGCAAGACACTGGAGAACATCAAGGCCCGAGGCCTGATTCTGGACGAT

GAGAAGCGGGCAAAAGACTATAAGAAAGCCAAGCAGATCATTGATAAATACCACCAGTTCTTT

ATCGAGGAAATTCTGAGCTCCGTGTGCATCAGTGAGGATCTGCTGCAGAATTACTCAGACGTG

TACTTCAAGCTGAAGAAGAGCGACGATGACAACCTGCAGAAGGACTTCAAGTCCGCCAAGGA

CACCATCAAGAAACAGATTAGCGAGTACATCAAGGACTCCGAAAAGTTTAAAAATCTGTTCAAC

CAGAATCTGATCGATGCTAAGAAAGGCCAGGAGTCCGACCTGATCCTGTGGCTGAAACAGTC

TAAGGACAATGGGATTGAACTGTTCAAGGCTAACTCCGATATCACTGATATTGACGAGGCACT

GGAAATCATCAAGAGCTTCAAGGGATGGACCACATACTTTAAAGGCTTCCACGAGAACCGCAA

GAACGTGTACTCCAGCAACGACATTCCTACCTCCATCATCTACCGAATCGTCGATGACAATCT

GCCAAAGTTCCTGGAGAACAAGGCCAAATATGAATCTCTGAAGGACAAAGCTCCCGAGGCAA

TTAATTACGAACAGATCAAGAAAGATCTGGCTGAGGAACTGACATTCGATATCGACTATAAGAC

TAGCGAGGTGAACCAGAGGGTCTTTTCCCTGGACGAGGTGTTTGAAATCGCCAATTTCAACAA

TTACCTGAACCAGTCCGGCATTACTAAATTCAATACCATCATTGGCGGGAAGTTTGTGAACGG

GGAGAATACCAAGCGCAAGGGAATTAACGAATACATCAATCTGTATAGCCAGCAGATCAACGA

CAAAACTCTGAAGAAATACAAGATGTCTGTGCTGTTCAAACAGATCCTGAGTGATACCGAGTC

CAAGTCTTTTGTCATTGATAAACTGGAAGATGACTCAGACGTGGTCACTACCATGCAGAGCTTT

TATGAGCAGATCGCCGCTTTCAAGACAGTGGAGGAAAAATCTATTAAGGAAACTCTGAGTCTG

CTGTTCGATGACCTGAAAGCCCAGAAGCTGGACCTGAGTAAGATCTACTTCAAAAACGATAAG

AGTCTGACAGACCTGTCACAGCAGGTGTTTGATGACTATTCCGTGATTGGGACCGCCGTCCT

GGAGTACATTACACAGCAGATCGCTCCAAAGAACCTGGATAATCCCTCTAAGAAAGAGCAGGA

ACTGATCGCTAAGAAAACCGAGAAGGCAAAATATCTGAGTCTGGAAACAATTAAGCTGGCACT

GGAGGAGTTCAACAAGCACAGGGATATTGACAAACAGTGCCGCTTTGAGGAAATCCTGGCCA

ACTTCGCAGCCATCCCCATGATTTTTGATGAGATCGCCCAGAACAAAGACAATCTGGCTCAGA

TCAGTATTAAGTACCAGAACCAGGGCAAGAAAGACCTGCTGCAGGCTTCAGCAGAAGATGAC

GTGAAAGCCATCAAGGATCTGCTGGACCAGACCAACAATCTGCTGCACAAGCTGAAAATCTTC

CATATTAGTCAGTCAGAGGATAAGGCTAATATCCTGGATAAAGACGAACACTTCTACCTGGTG

TTCGAGGAATGTTACTTCGAGCTGGCAAACATTGTCCCCCTGTATAACAAGATTAGGAACTAC

ATCACACAGAAGCCTTACTCTGACGAGAAGTTTAAACTGAACTTCGAAAATAGTACCCTGGCC

AACGGGTGGGATAAGAACAAGGAGCCTGACAACACAGCTATCCTGTTCATCAAGGATGACAA

GTACTATCTGGGAGTGATGAATAAGAAAAACAATAAGATCTTCGATGACAAAGCCATTAAGGA

-continued

GAACAAAGGGGAAGGATACAAGAAAATCGTGTATAAGCTGCTGCCCGGCGCAAATAAGATGC

TGCCTAAGGTGTTCTTCAGCGCCAAGAGTATCAAATTCTACAACCCATCCGAGGACATCCTGC

GGATTAGAAATCACTCAACACATACTAAGAACGGGAGCCCCCAGAAGGGATATGAGAAATTTG

AGTTCAACATCGAGGATTGCAGGAAGTTTATTGACTTCTACAAGCAGAGCATCTCCAAACACC

CTGAATGGAAGGATTTTGGCTTCCGGTTTTCCGACACACAGAGATATAACTCTATCGACGAGT

TCTACCGCGAGGTGGAAAATCAGGGGTATAAGCTGACTTTTGAGAACATTTCTGAAAGTTACA

TCGACAGCGTGGTCAATCAGGGAAAGCTGTACCTGTTCCAGATCTATAACAAAGATTTTTCAG

CATACAGCAAGGGCAGACCAAACCTGCATACACTGTACTGGAAGGCCCTGTTCGATGAGAGG

AATCTGCAGGACGTGGTCTATAAACTGAACGGAGAGGCCGAACTGTTTTACCGGAAGCAGTC

TATTCCTAAGAAAATCACTCACCCAGCTAAGGAGGCCATCGCTAACAAGAACAAGGACAATCC

TAAGAAAGAGAGCGTGTTCGAATACGATCTGATTAAGGACAAGCGGTTCACCGAAGATAAGTT

CTTTTTCCATTGTCCAATCACCATTAACTTCAAGTCAAGCGGCGCTAACAAGTTCAACGACGAG

ATCAATCTGCTGCTGAAGGAAAAAGCAAACGATGTGCACATCCTGAGCATTGACCGAGGAGA

GCGGCATCTGGCCTACTATACCCTGGTGGATGGCAAAGGGAATATCATTAAGCAGGATACATT

CAACATCATTGGCAATGACCGGATGAAAACCAACTACCACGATAAACTGGCTGCAATCGAGAA

GGATAGAGACTCAGCTAGGAAGGACTGGAAGAAAATCAACAACATTAAGGAGATGAAGGAAG

GCTATCTGAGCCAGGTGGTCCATGAGATTGCAAAGCTGGTCATCGAATACAATGCCATTGTGG

TGTTCGAGGATCTGAACTTCGGCTTTAAGAGGGGGCGCTTTAAGGTGGAAAAACAGGTCTATC

AGAAGCTGGAGAAAATGCTGATCGAAAAGCTGAATTACCTGGTGTTTAAAGATAACGAGTTCG

ACAAGACCGGAGGCGTCCTGAGAGCCTACCAGCTGACAGCTCCCTTTGAAACTTTCAAGAAA

ATGGGAAAACAGACAGGCATCATCTACTATGTGCCAGCCGGATTCACTTCCAAGATCTGCCCC

GTGACCGGCTTTGTCAACCAGCTGTACCCTAAATATGAGTCAGTGAGCAAGTCCCAGGAATTT

TTCAGCAAGTTCGATAAGATCTGTTATAATCTGGACAAGGGGTACTTCGAGTTTTCCTTCGATT

ACAAGAACTTCGGCGACAAGGCCGCTAAGGGGAAATGGACCATTGCCTCCTTCGGATCTCGC

CTGATCAACTTTCGAAATTCCGATAAAAACCACAATTGGGACACTAGGGAGGTGTACCCAACC

AAGGAGCTGGAAAAGCTGCTGAAAGACTACTCTATCGAGTATGGACATGGCGAATGCATCAA

GGCAGCCATCTGTGGCGAGAGTGATAAGAAATTTTTCGCCAAGCTGACCTCAGTGCTGAATAC

AATCCTGCAGATGCGGAACTCAAAGACCGGGACAGAACTGGACTATCTGATTAGCCCCGTGG

CTGATGTCAACGGAAACTTCTTCGACAGCAGACAGGCACCCAAAAATATGCCTCAGGATGCAG

ACGCCAACGGGGCCTACCACATCGGGCTGAAGGGACTGATGCTGCTGGGCCGGATCAAGAA

CAATCAGGAGGGGAAGAAGCTGAACCTGGTCATTAAGAACGAGGAATACTTCGAGTTTGTCCA

GAATAGAAATAACaaaaggccggcggccacgaaaaaggccggccaggcaaaaaagaaaaag*GGATCC*TACCCA

TACGATGTTCCAGATTACGCTTATCCCTACGACGTGCCTGATTATGCATACCCATATGATGTC

CCCGACTATGCCTAA

Amino Acid Sequence of FnCpf1-NLS-3×HA

FnCpf1 in normal text (AAs 1-1300), NLS (krpaatkkagqakkkk, SEQ ID NO:7) in lower case, 3×HA tag (YPYDVPDYAYPYDVPDYAYPYDVPDYA, SEQ ID NO:8) in bold (SEQ ID NO: 18)

MSIYQEFVNKYSLSKTLRFELIPQGKTLENIKARGLILDDEKRAKDYKKAKQIIDKYHQFFI

EEILSSVCISEDLLQNYSDVYFKLKKSDDDNLQKDFKSAKDTIKKQISEYIKDSEKFKNLFNQNLID

AKKGQESDLILWLKQSKIDNGIELFKANSDITDIDEALEIIKSFKGVVTTYFKGFHENRKNVYSSNDIP

TSIIYRIVDDNLPKFLENKAKYESLKDKAPEAINYEQIKKDLAEELTFDIDYKTSEVNQRVFSLDEVF

EIANFNNYLNQSGITKFNTIIGGKFVNGENTKRKGINEYINLYSQQINDKTLKKYKMSVLFKQILSDT

ESKSFVIDKLEDDSDVVTTMQSFYEQIAAFKTVEEKSIKETLSLLFDDLKAQKLDLSKIYFKNDKSL

TDLSQQVFDDYSVIGTAVLEYITQQIAPKNLDNPSKKEQELIAKKTEKAKYLSLETIKLALEEFNKH

RDIDKQCRFEEILANFAAIPMIFDEIAQNKDNLAQISIKYQNQGKKDLLQASAEDDVKAIKDLLDQT

NNLLHKLKIFHISQSEDKANILDKDEHFYLVFEECYFELANIVPLYNKIRNYITQKPYSDEKFKLNFE

NSTLANGWDKNKEPDNTAILFIKDDKYYLGVMNKKNNKIFDDKAIKENKGEGYKKIVYKLLPGANK

MLPKVFFSAKSIKFYNPSEDILRIRNHSTHTKNGSPQKGYEKFEFNIEDCRKFIDFYKQSISKHPE

WKDFGFRFSDTQRYNSIDEFYREVENQGYKLTFENISESYIDSVVNQGKLYLFQIYNKDFSAYSK

GRPNLHTLYWKALFDERNLQDVVYKLNGEAELFYRKQSIPKKITHPAKEAIANKNKDNPKKESVF

EYDLIKDKRFTEDKFFFHCPITINFKSSGANKFNDEINLLLKEKANDVHILSIDRGERHLAYYTLVDG

KGNIIKQDTFNIIGNDRMKTNYHDKLAAIEKDRDSARKDWKKINNIKEMKEGYLSQVVHEIAKLVIE

YNAIVVFEDLNFGFKRGRFKVEKQVYQKLEKMLIEKLNYLVFKDNEFDKTGGVLRAYQLTAPFET

FKKMGKQTGIIYYVPAGFTSKICPVTGFVNQLYPKYESVSKSQEFFSKFDKICYNLDKGYFEFSFD

YKNFGDKAAKGKVVTIASFGSRLINFRNSDKNHNWDTREVYPTKELEKLLKDYSIEYGHGECIKAA

ICGESDKKFFAKLTSVLNTILQMRNSKTGTELDYLISPVADVNGNFFDSRQAPKNMPQDADANGA

YHIGLKGLMLLGRIKNNQEGKKLNLVIKNEEYFEFVQNRNNkrpaatkkagqakkkkGSYPYDVPDYAY

PYDVPDYAYPYDVPDYA

AAS2134: pCAG-hMbCas12a-NLS-3×HA

Human codon optimized *Moraxella bovoculi* 237 Cas12a (MbCas12a) in black, nucleoplasmin nucleoplasmin NLS (aaaaggccggcggccacgaaaaaggccggccaggcaaaaaagaaaaag, SEQ ID NO:21) in lower case, linker sequences in italics, 3×HA tag (TACCCATACGATGTTCCAGATTACGCTTATCCCTACGACGTGCCTGATTATGCATACCCATA TGATGTCCCCGACTATGCC, SEQ ID NO: 5) in BOLD (SEQ ID NO: 430)

ATGCTGTTCCAGGACTTTACCCACCTGTATCCACTGTCCAAGACAGTGAGATTTGAG

CTGAAGCCCATCGATAGGACCCTGGAGCACATCCACGCCAAGAACTTCCTGTCTCAGGACG

AGACAATGGCCGATATGCACCAGAAGGTGAAAGTGATCCTGGACGATTACCACCGCGACTT

CATCGCCGATATGATGGGCGAGGTGAAGCTGACCAAGCTGGCCGAGTTCTATGACGTGTAC

CTGAAGTTTCGGAAGAACCCAAAGGACGATGAGCTGCAGAAGCAGCTGAAGGATCTGCAGG

CCGTGCTGAGAAAGGAGATCGTGAAGCCCATCGGCAATGGCGGCAAGTATAAGGCCGGCT

ACGACAGGCTGTTCGGCGCCAAGCTGTTTAAGGACGGCAAGGAGCTGGGCGATCTGGCCA

AGTTCGTGATCGCACAGGAGGGAGAGAGCTCCCCAAAGCTGGCCCACCTGGCCCACTTCG

AGAAGTTTTCCACCTATTTCACAGGCTTTCACGATAACCGGAAGAATATGTATTCTGACGAGG

ATAAGCACACCGCCATCGCCTACCGCCTGATCCACGAGAACCTGCCCCGGTTTATCGACAA

-continued

TCTGCAGATCCTGACCACAATCAAGCAGAAGCACTCTGCCCTGTACGATCAGATCATCAACG

AGCTGACCGCCAGCGGCCTGGACGTGTCTCTGGCCAGCCACCTGGATGGCTATCACAAGC

TGCTGACACAGGAGGGCATCACCGCCTACAATACACTGCTGGGAGGAATCTCCGGAGAGG

CAGGCTCTCCTAAGATCCAGGGCATCAACGAGCTGATCAATTCTCACCACAACCAGCACTGC

CACAAGAGCGAGAGAATCGCCAAGCTGAGGCCACTGCACAAGCAGATCCTGTCCGACGGC

ATGAGCGTGTCCTTCCTGCCCTCTAAGTTTGCCGACGATAGCGAGATGTGCCAGGCCGTGA

ACGAGTTCTATCGCCACTACGCCGACGTGTTCGCCAAGGTGCAGAGCCTGTTCGACGGCTT

TGACGATCACCAGAAGGATGGCATCTACGTGGAGCACAAGAACCTGAATGAGCTGTCCAAG

CAGGCCTTCGGCGACTTTGCACTGCTGGGACGCGTGCTGGACGGATACTATGTGGATGTGG

TGAATCCAGAGTTCAACGAGCGGTTTGCCAAGGCCAAGACCGACAATGCCAAGGCCAAGCT

GACAAAGGAGAAGGATAAGTTCATCAAGGGCGTGCACTCCCTGGCCTCTCTGGAGCAGGCC

ATCGAGCACTATACCGCAAGGCACGACGATGAGAGCGTGCAGGCAGGCAAGCTGGGACAG

TACTTCAAGCACGGCCTGGCCGGAGTGGACAACCCCATCCAGAAGATCCACAACAATCACA

GCACCATCAAGGGCTTTCTGGAGAGGGAGCGCCCTGCAGGAGAGAGAGCCCTGCCAAAGA

TCAAGTCCGGCAAGAATCCTGAGATGACACAGCTGAGGCAGCTGAAGGAGCTGCTGGATAA

CGCCCTGAATGTGGCCCACTTCGCCAAGCTGCTGACCACAAAGACCACACTGGACAATCAG

GATGGCAACTTCTATGGCGAGTTTGGCGTGCTGTACGACGAGCTGGCCAAGATCCCCACCC

TGTATAACAAGGTGAGAGATTACCTGAGCCAGAAGCCTTTCTCCACCGAGAAGTACAAGCTG

AACTTTGGCAATCCAACACTGCTGAATGGCTGGGACCTGAACAAGGAGAAGGATAATTTCGG

CGTGATCCTGCAGAAGGACGGCTGCTACTATCTGGCCCTGCTGGACAAGGCCCACAAGAAG

GTGTTTGATAACGCCCCTAATACAGGCAAGAGCATCTATCAGAAGATGATCTATAAGTACCT

GGAGGTGAGGAAGCAGTTCCCCAAGGTGTTCTTTTCCAAGGAGGCCATCGCCATCAACTAC

CACCCTTCTAAGGAGCTGGTGGAGATCAAGGACAAGGGCCGGCAGAGATCCGACGATGAG

CGCCTGAAGCTGTATCGGTTTATCCTGGAGTGTCTGAAGATCCACCCTAAGTACGATAAGAA

GTTCGAGGGCGCCATCGGCGACATCCAGCTGTTTAAGAAGGATAAGAAGGGCAGAGAGGT

GCCAATCAGCGAGAAGGACCTGTTCGATAAGATCAACGGCATCTTTTCTAGCAAGCCTAAGC

TGGAGATGGAGGACTTCTTTATCGGCGAGTTCAAGAGGTATAACCCAAGCCAGGACCTGGT

GGATCAGTATAATATCTACAAGAAGATCGACTCCAACGATAATCGCAAGAAGGAGAATTTCTA

CAACAATCACCCCAAGTTTAAGAAGGATCTGGTGCGGTACTATTACGAGTCTATGTGCAAGC

ACGAGGAGTGGGAGGAGAGCTTCGAGTTTTCCAAGAAGCTGCAGGACATCGGCTGTTACGT

GGATGTGAACGAGCTGTTTACCGAGATCGAGACACGGAGACTGAATTATAAGATCTCCTTCT

GCAACATCAATGCCGACTACATCGATGAGCTGGTGGAGCAGGGCCAGCTGTATCTGTTCCA

GATCTACAACAAGGACTTTTCCCCAAAGGCCCACGGCAAGCCCAATCTGCACACCCTGTACT

TCAAGGCCCTGTTTTCTGAGGACAACCTGGCCGATCCTATCTATAAGCTGAATGGCGAGGC

CCAGATCTTCTACAGAAAGGCCTCCCTGGACATGAACGAGACAACAATCCACAGGGCCGGC

GAGGTGCTGGAGAACAAGAATCCCGATAATCCTAAGAAGAGACAGTTCGTGTACGACATCAT

CAAGGATAAGAGGTACACACAGGACAAGTTCATGCTGCACGTGCCAATCACCATGAACTTTG

GCGTGCAGGGCATGACAATCAAGGAGTTCAATAAGAAGGTGAACCAGTCTATCCAGCAGTA

TGACGAGGTGAACGTGATCGGCATCGATCGGGGCGAGAGACACCTGCTGTACCTGACCGT

GATCAATAGCAAGGGCGAGATCCTGGAGCAGTGTTCCCTGAACGACATCACCACAGCCTCT

-continued

GCCAATGGCACACAGATGACCACACCTTACCACAAGATCCTGGATAAGAGGGAGATCGAGC

GCCTGAACGCCCGGGTGGGATGGGGCGAGATCGAGACAATCAAGGAGCTGAAGTCTGGCT

ATCTGAGCCACGTGGTGCACCAGATCAGCCAGCTGATGCTGAAGTACAACGCCATCGTGGT

GCTGGAGGACCTGAATTTCGGCTTTAAGAGGGGCCGCTTTAAGGTGGAGAAGCAGATCTAT

CAGAACTTCGAGAATGCCCTGATCAAGAAGCTGAACCACCTGGTGCTGAAGGACAAGGCCG

ACGATGAGATCGGCTCTTACAAGAATGCCCTGCAGCTGACCAACAATTTCACAGATCTGAAG

AGCATCGGCAAGCAGACCGGCTTCCTGTTTTATGTGCCCGCCTGGAACACCTCTAAGATCG

ACCCTGAGACAGGCTTTGTGGATCTGCTGAAGCCAAGATACGAGAACATCGCCCAGAGCCA

GGCCTTCTTTGGCAAGTTCGACAAGATCTGCTATAATGCCGACAAGGATTACTTCGAGTTTC

ACATCGACTACGCCAAGTTTACCGATAAGGCCAAGAATAGCCGCCAGATCTGGACAATCTGT

TCCCACGGCGACAAGCGGTACGTGTACGATAAGACAGCCAACCAGAATAAGGGCGCCGCC

AAGGGCATCAACGTGAATGATGAGCTGAAGTCCCTGTTCGCCCGCCACCACATCAACGAGA

AGCAGCCCAACCTGGTCATGGACATCTGCCAGAACAATGATAAGGAGTTTCACAAGTCTCTG

ATGTACCTGCTGAAAACCCTGCTGGCCCTGCGGTACAGCAACGCCTCCTCTGACGAGGATT

TCATCCTGTCCCCCGTGGCAAACGACGAGGGCGTGTTCTTTAATAGCGCCCTGGCCGACGA

TACACAGCCTCAGAATGCCGATGCCAACGGCGCCTACCACATCGCCCTGAAGGGCCTGTGG

CTGCTGAATGAGCTGAAGAACTCCGACGATCTGAACAAGGTGAAGCTGGCCATCGACAATC

AGACCTGGCTGAATTTCGCCCAGAACAGGaaaaggccggcggccacgaaaaaggccggccaggcaaaaaa gaaaaag*GGATCC*TACCCATACGATGTTCCAGATTACGCTTATCCCTACGACGTGCCTGAT

TATGCATACCCATATGATGTCCCCGACTATGCCTAA

Nucleotide Sequence of (RTW876) pCAG-human-dAsCpf1 (D908A)-NLS(nucleoplasmin)-3×HA-VPR Human codon optimized dAsCpf1(D908A) in normal font (NTs 1-3921), Nucleoplasmin NLS in lower case (aaaaggccggcggccacgaaaaaggccggccaggcaaaaaagaaaaag, SEQ ID NO:21), 3×HA tag (TACCCATACGATGTTCCAGATTACGCTTATCCCTACGACGTGCCTGATTATGCATACCCATAT GATGTCCCCGACTATGCC, SEQ ID NO: 5) in bold, and VPR double underlined

SEQ ID NO: 431)

ATGACACAGTTCGAGGGCTTTACCAACCTGTATCAGGTGAGCAAGACACTGCGGTT

TGAGCTGATCCCACAGGGCAAGACCCTGAAGCACATCCAGGAGCAGGGCTTCATCGAGGA

GGACAAGGCCCGCAATGATCACTACAAGGAGCTGAAGCCCATCATCGATCGGATCTACAAG

ACCTATGCCGACCAGTGCCTGCAGCTGGTGCAGCTGGATTGGGAGAACCTGAGCGCCGCC

ATCGACTCCTATAGAAAGGAGAAAACCGAGGAGACAAGGAACGCCCTGATCGAGGAGCAGG

CCACATATCGCAATGCCATCCACGACTACTTCATCGGCCGGACAGACAACCTGACCGATGC

CATCAATAAGAGACACGCCGAGATCTACAAGGGCCTGTTCAAGGCCGAGCTGTTTAATGGC

AAGGTGCTGAAGCAGCTGGGCACCGTGACCACAACCGAGCACGAGAACGCCCTGCTGCGG

AGCTTCGACAAGTTTACAACCTACTTCTCCGGCTTTTATGAGAACAGGAAGAACGTGTTCAG

CGCCGAGGATATCAGCACAGCCATCCCACACCGCATCGTGCAGGACAACTTCCCCAAGTTT

AAGGAGAATTGTCACATCTTCACACGCCTGATCACCGCCGTGCCCAGCCTGCGGGAGCACT

TTGAGAACGTGAAGAAGGCCATCGGCATCTTCGTGAGCACCTCCATCGAGGAGGTGTTTTC

CTTCCCTTTTTATAACCAGCTGCTGACACAGACCCAGATCGACCTGTATAACCAGCTGCTGG

-continued

GAGGAATCTCTCGGGAGGCAGGCACCGAGAAGATCAAGGGCCTGAACGAGGTGCTGAATC

TGGCCATCCAGAAGAATGATGAGACAGCCCACATCATCGCCTCCCTGCCACACAGATTCATC

CCCCTGTTTAAGCAGATCCTGTCCGATAGGAACACCCTGTCTTTCATCCTGGAGGAGTTTAA

GAGCGACGAGGAAGTGATCCAGTCCTTCTGCAAGTACAAGACACTGCTGAGAAACGAGAAC

GTGCTGGAGACAGCCGAGGCCCTGTTTAACGAGCTGAACAGCATCGACCTGACACACATCT

TCATCAGCCACAAGAAGCTGGAGACAATCAGCAGCGCCCTGTGCGACCACTGGGATACACT

GAGGAATGCCCTGTATGAGCGGAGAATCTCCGAGCTGACAGGCAAGATCACCAAGTCTGCC

AAGGAGAAGGTGCAGCGCAGCCTGAAGCACGAGGATATCAACCTGCAGGAGATCATCTCTG

CCGCAGGCAAGGAGCTGAGCGAGGCCTTCAAGCAGAAAACCAGCGAGATCCTGTCCCACG

CACACGCCGCCCTGGATCAGCCACTGCCTACAACCCTGAAGAAGCAGGAGGAGAAGGAGA

TCCTGAAGTCTCAGCTGGACAGCCTGCTGGGCCTGTACCACCTGCTGGACTGGTTTGCCGT

GGATGAGTCCAACGAGGTGGACCCCGAGTTCTCTGCCCGGCTGACCGGCATCAAGCTGGA

GATGGAGCCTTCTCTGAGCTTCTACAACAAGGCCAGAAATTATGCCACCAAGAAGCCCTACT

CCGTGGAGAAGTTCAAGCTGAACTTTCAGATGCCTACACTGGCCTCTGGCTGGGACGTGAA

TAAGGAGAAGAACAATGGCGCCATCCTGTTTGTGAAGAACGGCCTGTACTATCTGGGCATCA

TGCCAAAGCAGAAGGGCAGGTATAAGGCCCTGAGCTTCGAGCCCACAGAGAAAACCAGCG

AGGGCTTTGATAAGATGTACTATGACTACTTCCCTGATGCCGCCAAGATGATCCCAAAGTGC

AGCACCCAGCTGAAGGCCGTGACAGCCCACTTTCAGACCCACACAACCCCCATCCTGCTGT

CCAACAATTTCATCGAGCCTCTGGAGATCACAAAGGAGATCTACGACCTGAACAATCCTGAG

AAGGAGCCAAAGAAGTTTCAGACAGCCTACGCCAAGAAAACCGGCGACCAGAAGGGCTACA

GAGAGGCCCTGTGCAAGTGGATCGACTTCACAAGGGATTTTCTGTCCAAGTATACCAAGACA

ACCTCTATCGATCTGTCTAGCCTGCGGCCATCCTCTCAGTATAAGGACCTGGGCGAGTACTA

TGCCGAGCTGAATCCCCTGCTGTACCACATCAGCTTCCAGAGAATCGCCGAGAAGGAGATC

ATGGATGCCGTGGAGACAGGCAAGCTGTACCTGTTCCAGATCTATAACAAGGACTTTGCCAA

GGGCCACCACGGCAAGCCTAATCTGCACACACTGTATTGGACCGGCCTGTTTTCTCCAGAG

AACCTGGCCAAGACAAGCATCAAGCTGAATGGCCAGGCCGAGCTGTTCTACCGCCCTAAGT

CCAGGATGAAGAGGATGGCACACCGGCTGGGAGAGAAGATGCTGAACAAGAAGCTGAAGG

ATCAGAAAACCCCAATCCCCGACACCCTGTACCAGGAGCTGTACGACTATGTGAATCACAGA

CTGTCCCACGACCTGTCTGATGAGGCCAGGGCCCTGCTGCCCAACGTGATCACCAAGGAG

GTGTCTCACGAGATCATCAAGGATAGGCGCTTTACCAGCGACAAGTTCTTTTTCCACGTGCC

TATCACACTGAACTATCAGGCCGCCAATTCCCCATCTAAGTTCAACCAGAGGGTGAATGCCT

ACCTGAAGGAGCACCCCGAGACACCTATCATCGGCATCGCCCGGGGCGAGAGAAACCTGA

TCTATATCACAGTGATCGACTCCACCGGCAAGATCCTGGAGCAGCGGAGCCTGAACACCAT

CCAGCAGTTTGATTACCAGAAGAAGCTGGACAACAGGGAGAAGGAGAGGGTGGCAGCAAG

GCAGGCCTGGTCTGTGGTGGGCACAATCAAGGATCTGAAGCAGGGCTATCTGAGCCAGGT

CATCCACGAGATCGTGGACCTGATGATCCACTACCAGGCCGTGGTGGTGCTGGAGAACCTG

AATTTCGGCTTTAAGAGCAAGAGGACCGGCATCGCCGAGAAGGCCGTGTACCAGCAGTTCG

AGAAGATGCTGATCGATAAGCTGAATTGCCTGGTGCTGAAGGACTATCCAGCAGAGAAAGT

GGGAGGCGTGCTGAACCCATACCAGCTGACAGACCAGTTCACCTCCTTTGCCAAGATGGGC

ACCCAGTCTGGCTTCCTGTTTTACGTGCCTGCCCCATATACATCTAAGATCGATCCCCTGAC

-continued

CGGCTTCGTGGACCCCTTCGTGTGGAAAACCATCAAGAATCACGAGAGCCGCAAGCACTTC

CTGGAGGGCTTCGACTTTCTGCACTACGACGTGAAAACCGGCGACTTCATCCTGCACTTTAA

GATGAACAGAAATCTGTCCTTCCAGAGGGGCCTGCCCGGCTTTATGCCTGCATGGGATATC

GTGTTCGAGAAGAACGAGACACAGTTTGACGCCAAGGGCACCCCTTTCATCGCCGGCAAGA

GAATCGTGCCAGTGATCGAGAATCACAGATTCACCGGCAGATACCGGGACCTGTATCCTGC

CAACGAGCTGATCGCCCTGCTGGAGGAGAAGGGCATCGTGTTCAGGGATGGCTCCAACATC

CTGCCAAAGCTGCTGGAGAATGACGATTCTCACGCCATCGACACCATGGTGGCCCTGATCC

GCAGCGTGCTGCAGATGCGGAACTCCAATGCCGCCACAGGCGAGGACTATATCAACAGCC

CCGTGCGCGATCTGAATGGCGTGTGCTTCGACTCCCGGTTTCAGAACCCAGAGTGGCCCAT

GGACGCCGATGCCAATGGCGCCTACCACATCGCCCTGAAGGGCCAGCTGCTGCTGAATCA

CCTGAAGGAGAGCAAGGATCTGAAGCTGCAGAACGGCATCTCCAATCAGGACTGGCTGGCC

TACATCCAGGAGCTGCGCAACaaaaggccggcggccacgaaaaaggccggccaggcaaaaaagaaaaagGGA

TCCTACCCATACGATGTTCCAGATTACGCTTATCCCTACGACGTGCCTGATTATGCATACC

CATATGATGTCCCCGACTATGCCGGAAGCGAGGCCAGCGGTTCCGGACGGGCTGACGCAT

TGGACGATTTTGATCTGGATATGCTGGGAAGTGACGCCCTCGATGATTTTGACCTTGACATG

CTTGGTTCGGATGCCCTTGATGACTTTGACCTCGACATGCTCGGCAGTGACGCCCTTGATGA

TTTCGACCTGGACATGCTGATTAACTCTAGAAGTTCCGGATCTCCGAAAAAGAAACGCAAAG

TTGGTAGCCAGTACCTGCCCGACACCGACGACCGGCACCGGATCGAGGAAAAGCGGAAGC

GGACCTACGAGACATTCAAGAGCATCATGAAGAAGTCCCCCTTCAGCGGCCCCACCGACCC

TAGACCTCCACCTAGAAGAATCGCCGTGCCCAGCAGATCCAGCGCCAGCGTGCCAAAACCT

GCCCCCCAGCCTTACCCCTTCACCAGCAGCCTGAGCACCATCAACTACGACGAGTTCCCTA

CCATGGTGTTCCCCAGCGGCCAGATCTCTCAGGCCTCTGCTCTGGCTCCAGCCCCTCCTCA

GGTGCTGCCTCAGGCTCCTGCTCCTGCACCAGCTCCAGCCATGGTGTCTGCACTGGCTCAG

GCACCAGCACCCGTGCCTGTGCTGGCTCCTGGACCTCCACAGGCTGTGGCTCCACCAGCC

CCTAAACCTACACAGGCCGGCGAGGGCACACTGTCTGAAGCTCTGCTGCAGCTGCAGTTCG

ACGACGAGGATCTGGGAGCCCTGCTGGGAAACAGCACCGATCCTGCCGTGTTCACCGACC

TGGCCAGCGTGGACAACAGCGAGTTCCAGCAGCTGCTGAACCAGGGCATCCCTGTGGCCC

CTCACACCACCGAGCCCATGCTGATGGAATACCCCGAGGCCATCACCCGGCTCGTGACAG

GCGCTCAGAGGCCTCCTGATCCAGCTCCTGCCCCTCTGGGAGCACCAGGCCTGCCTAATG

GACTGCTGTCTGGCGACGAGGACTTCAGCTCTATCGCCGATATGGATTTCTCAGCCTTGCTG

GGCTCTGGCAGCGGCAGCCGGGATTCCAGGGAAGGGATGTTTTTGCCGAAGCCTGAGGCC

GGCTCCGCTATTAGTGACGTGTTTGAGGGCCGCGAGGTGTGCCAGCCAAAACGAATCCGG

CCATTTCATCCTCCAGGAAGTCCATGGGCCAACCGCCCACTCCCCGCCAGCCTCGCACCAA

CACCAACCGGTCCAGTACATGAGCCAGTCGGGTCACTGACCCCGGCACCAGTCCCTCAGC

CACTGGATCCAGCGCCCGCAGTGACTCCCGAGGCCAGTCACCTGTTGGAGGATCCCGATG

AAGAGACGAGCCAGGCTGTCAAAGCCCTTCGGGAGATGGCCGATACTGTGATTCCCCAGAA

GGAAGAGGCTGCAATCTGTGGCCAAATGGACCTTTCCCATCCGCCCCCAAGGGGCCATCTG

GATGAGCTGACAACCACACTTGAGTCCATGACCGAGGATCTGAACCTGGACTCACCCCTGA

CCCCGGAATTGAACGAGATTCTGGATACCTTCCTGAACGACGAGTGCCTCTTGCATGCCATG

CATATCAGCACAGGACTGTCCATCTTCGACACATCTCTGTTTTAA

Amino Acid Sequence of dAsCpf1(D908A)-NLS(Nucleoplasmin)-3×HA-VPR

AsCpf1 in normal font (AAs 1-1306), NLS(nucleoplasmin) (krpaatkkagqakkkk, SEQ ID NO:7) in lower case, 3×HA tag (YPYDVPDYAYPYDVPDYAYPYDVPDYA, SEQ ID NO:8) in bold, and VPR doubleunderlined

SEQ ID NO: 432)

MTQFEGFTNLYQVSKTLRFELIPQGKTLKHIQEQGFIEEDKARNDHYKELKPIIDRIYKTYA

DQCLQLVQLDWENLSAAIDSYRKEKTEETRNALIEEQATYRNAIHDYFIGRTDNLTDAINKRHAEI

YKGLFKAELFNGKVLKQLGTVTTTEHENALLRSFDKFTTYFSGFYENRKNVFSAEDISTAIPHRIV

QDNFPKFKENCHIFTRLITAVPSLREHFENVKKAIGIFVSTSIEEVFSFPFYNQLLTQTQIDLYNQLL

GGISREAGTEKIKGLNEVLNLAIQKNDETAHIIASLPHRFIPLFKQILSDRNTLSFILEEFKSDEEVIQ

SFCKYKTLLRNENVLETAEALFNELNSIDLTHIFISHKKLETISSALCDHWDTLRNALYERRISELTG

KITKSAKEKVQRSLKHEDINLQEIISAAGKELSEAFKQKTSEILSHAHAALDQPLPTTLKKQEEKEIL

KSQLDSLLGLYHLLDWFAVDESNEVDPEFSARLTGIKLEMEPSLSFYNKARNYATKKPYSVEKFK

LNFQMPTLASGWDVNKEKNNGAILFVKNGLWLGIMPKQKGRYKALSFEPTEKTSEGFDKMYYD

YFPDAAKMIPKCSTQLKAVTAHFQTHTTPILLSNNFIEPLEITKEIYDLNNPEKEPKKFQTAYAKKT

GDQKGYREALCKWIDFIRDFLSKYTKITSIDLSSLRPSSQYKDLGEYYAELNPLLYHISFQRIAEK

EIMDAVETGKLYLFQIYNKDFAKGHHGKPNLHTLYVVTGLFSPENLAKTSIKLNGQAELFYRPKSR

MKRMAHRLGEKMLNKKLKDQKTPIPDTLYQELYDYVNHRLSHDLSDEARALLPNVITKEVSHEIIK

DRRFTSDKFFFHVPITLNYQAANSPSKFNQRVNAYLKEHPETPIIGIARGERNLIYITVIDSTGKILE

QRSLNTIQQFDYQKKLDNREKERVAARQAWSVVGTIKDLKQGYLSQVIHEIVDLMIHYQAVVVLE

NLNFGFKSKRTGIAEKAVYQQFEKMLIDKLNCLVLKDYPAEKVGGVLNPYQLTDQFTSFAKMGT

QSGFLFYVPAPYTSKIDPLIGFVDPFVWKTIKNHESRKHFLEGFDFLHYDVKTGDFILHFKMNRN

LSFQRGLPGFMPAWDIVFEKNETQFDAKGTPFIAGKRIVPVIENHRFTGRYRDLYPANELIALLEE

KGIVFRDGSNILPKLLENDDSHAIDTMVALIRSVLQMRNSNAATGEDYINSPVRDLNGVCFDSRF

QNPEWPMDADANGAYHIALKGQLLLNHLKESKDLKLQNGISNQDWLAYIQELRNkrpaatkkagqakk kkGSYPYDVPDYAYPYDVPDYAYPYDVPDYAGSEASGSGRADALDDFDLDMLGSDALDDFDLD

MLGSDALDDFDLDMLGSDALDDFDLDMLINSRSSGSPKKKRKVGSQYLPDTDDRHRIEEKRKRT

YETFKSIMKKSPFSGPTDPRPPPRRIAVPSRSSASVPKPAPQPYPFTSSLSTINYDEFPTMVFPS

GQISQASALAPAPPQVLPQAPAPAPAPAMVSALAQAPAPVPVLAPGPPQAVAPPAPKPTQAGEG

TLSEALLQLQFDDEDLGALLGNSTDPAVFTDLASVDNSEFQQLLNQGIPVAPHTTEPMLMEYPEA

ITRLVTGAQRPPDPAPAPLGAPGLPNGLLSGDEDFSSIADMDFSALLGSGSGSRDSREGMFLPK

PEAGSAISDVFEGREVCQPKRIRPFHPPGSPWANRPLPASLAPTPTGPVHEPVGSLTPAPVPQP

LDPAPAVTPEASHLLEDPDEETSQAVKALREMADTVIPQKEEAAICGQMDLSHPPPRGHLDELTT

TLESMTEDLNLDSPLTPELNEILDTFLNDECLLHAMHISTGLSIFDTSLF

Nucleotide sequence of (RTW776) pCAG-human-dAsCpf (D008A)triplovariant(E174R/S542R/K648R)-NILS (nucleoplasmin)-3×HA-VPR Human codon optimized dAsCpr1 (D908A) in normal font (NTs 1-3921), Nucleoplasmin NILS in lower case (aaaaggccogcogccacgaaaaaggccogccaggcaaaaaagaaaaag, SEQ ID NO:21), 3×HA tag (TACCCATACGATGTTCCAGATTACGCTTATCCCTACGACGTGCCTGATTATGCATACCCATAT
GATGTCCCCGACTATGCC, SEQ ID NO: 5) in bold, and VPR double underlined

SEQ ID NO: 433)

ATGACACAGTTCGAGGGCTTTACCAACCTGTATCAGGTGAGCAAGACACTGCGGTT
TGAGCTGATCCCACAGGGCAAGACCCTGAAGCACATCCAGGAGCAGGGCTTCATCGAGGA
GGACAAGGCCCGCAATGATCACTACAAGGAGCTGAAGCCCATCATCGATCGGATCTACAAG
ACCTATGCCGACCAGTGCCTGCAGCTGGTGCAGCTGGATTGGGAGAACCTGAGCGCCGCC
ATCGACTCCTATAGAAAGGAGAAAACCGAGGAGACAAGGAACGCCCTGATCGAGGAGCAGG
CCACATATCGCAATGCCATCCACGACTACTTCATCGGCCGGACAGACAACCTGACCGATGC
CATCAATAAGAGACACGCCGAGATCTACAAGGGCCTGTTCAAGGCCGAGCTGTTTAATGGC
AAGGTGCTGAAGCAGCTGGGCACCGTGACCACAACCGAGCACGAGAACGCCCTGCTGCGG
AGCTTCGACAAGTTTACAACCTACTTCTCCGGCTTTTATAGAAACAGGAAGAACGTGTTCAG
CGCCGAGGATATCAGCACAGCCATCCCACACCGCATCGTGCAGGACAACTTCCCCAAGTTT
AAGGAGAATTGTCACATCTTCACACGCCTGATCACCGCCGTGCCCAGCCTGCGGGAGCACT
TTGAGAACGTGAAGAAGGCCATCGGCATCTTCGTGAGCACCTCCATCGAGGAGGTGTTTTC
CTTCCCTTTTTATAACCAGCTGCTGACACAGACCCAGATCGACCTGTATAACCAGCTGCTGG
GAGGAATCTCTCGGGAGGCAGGCACCGAGAAGATCAAGGGCCTGAACGAGGTGCTGAATC
TGGCCATCCAGAAGAATGATGAGACAGCCCACATCATCGCCTCCCTGCCACACAGATTCATC
CCCCTGTTTAAGCAGATCCTGTCCGATAGGAACACCCTGTCTTTCATCCTGGAGGAGTTTAA
GAGCGACGAGGAAGTGATCCAGTCCTTCTGCAAGTACAAGACACTGCTGAGAAACGAGAAC
GTGCTGGAGACAGCCGAGGCCCTGTTTAACGAGCTGAACAGCATCGACCTGACACACATCT
TCATCAGCCACAAGAAGCTGGAGACAATCAGCAGCGCCCTGTGCGACCACTGGGATACACT
GAGGAATGCCCTGTATGAGCGGAGAATCTCCGAGCTGACAGGCAAGATCACCAAGTCTGCC
AAGGAGAAGGTGCAGCGCAGCCTGAAGCACGAGGATATCAACCTGCAGGAGATCATCTCTG
CCGCAGGCAAGGAGCTGAGCGAGGCCTTCAAGCAGAAAACCAGCGAGATCCTGTCCCACG
CACACGCCGCCCTGGATCAGCCACTGCCTACAACCCTGAAGAAGCAGGAGGAGAAGGAGA
TCCTGAAGTCTCAGCTGGACAGCCTGCTGGGCCTGTACCACCTGCTGGACTGGTTTGCCGT
GGATGAGTCCAACGAGGTGGACCCCGAGTTCTCTGCCCGGCTGACCGGCATCAAGCTGGA
GATGGAGCCTTCTCTGAGCTTCTACAACAAGGCCAGAAATTATGCCACCAAGAAGCCCTACT
CCGTGGAGAAGTTCAAGCTGAACTTTCAGATGCCTACACTGGCCAGAGGCTGGGACGTGAA
TAGAGAGAAGAACAATGGCGCCATCCTGTTTGTGAAGAACGGCCTGTACTATCTGGGCATCA
TGCCAAAGCAGAAGGGCAGGTATAAGGCCCTGAGCTTCGAGCCCACAGAGAAAACCAGCG
AGGGCTTTGATAAGATGTACTATGACTACTTCCCTGATGCCGCCAAGATGATCCCAAAGTGC
AGCACCCAGCTGAAGGCCGTGACAGCCCACTTTCAGACCCACACAACCCCCATCCTGCTGT
CCAACAATTTCATCGAGCCTCTGGAGATCACAAAGGAGATCTACGACCTGAACAATCCTGAG
AAGGAGCCAAAGAAGTTTCAGACAGCCTACGCCAAGAAAACCGGCGACCAGAAGGGCTACA
GAGAGGCCCTGTGCAAGTGGATCGACTTCACAAGGGATTTTCTGTCCAAGTATACCAAGACA
ACCTCTATCGATCTGTCTAGCCTGCGGCCATCCTCTCAGTATAAGGACCTGGGCGAGTACTA
TGCCGAGCTGAATCCCCTGCTGTACCACATCAGCTTCCAGAGAATCGCCGAGAAGGAGATC
ATGGATGCCGTGGAGACAGGCAAGCTGTACCTGTTCCAGATCTATAACAAGGACTTTGCCAA
GGGCCACCACGGCAAGCCTAATCTGCACACACTGTATTGGACCGGCCTGTTTTCTCCAGAG

-continued

AACCTGGCCAAGACAAGCATCAAGCTGAATGGCCAGGCCGAGCTGTTCTACCGCCCTAAGT

CCAGGATGAAGAGGATGGCACACCGGCTGGGAGAGAAGATGCTGAACAAGAAGCTGAAGG

ATCAGAAAACCCCAATCCCCGACACCCTGTACCAGGAGCTGTACGACTATGTGAATCACAGA

CTGTCCCACGACCTGTCTGATGAGGCCAGGGCCCTGCTGCCCAACGTGATCACCAAGGAG

GTGTCTCACGAGATCATCAAGGATAGGCGCTTTACCAGCGACAAGTTCTTTTTCCACGTGCC

TATCACACTGAACTATCAGGCCGCCAATTCCCCATCTAAGTTCAACCAGAGGGTGAATGCCT

ACCTGAAGGAGCACCCCGAGACACCTATCATCGGCATCGCCCGGGGCGAGAGAAACCTGA

TCTATATCACAGTGATCGACTCCACCGGCAAGATCCTGGAGCAGCGGAGCCTGAACACCAT

CCAGCAGTTTGATTACCAGAAGAAGCTGGACAACAGGGAGAAGGAGAGGGTGGCAGCAAG

GCAGGCCTGGTCTGTGGTGGGCACAATCAAGGATCTGAAGCAGGGCTATCTGAGCCAGGT

CATCCACGAGATCGTGGACCTGATGATCCACTACCAGGCCGTGGTGGTGCTGGAGAACCTG

AATTTCGGCTTTAAGAGCAAGAGGACCGGCATCGCCGAGAAGGCCGTGTACCAGCAGTTCG

AGAAGATGCTGATCGATAAGCTGAATTGCCTGGTGCTGAAGGACTATCCAGCAGAGAAAGT

GGGAGGCGTGCTGAACCCATACCAGCTGACAGACCAGTTCACCTCCTTTGCCAAGATGGGC

ACCCAGTCTGGCTTCCTGTTTTACGTGCCTGCCCCATATACATCTAAGATCGATCCCCTGAC

CGGCTTCGTGGACCCCTTCGTGTGGAAAACCATCAAGAATCACGAGAGCCGCAAGCACTTC

CTGGAGGGCTTCGACTTTCTGCACTACGACGTGAAAACCGGCGACTTCATCCTGCACTTTAA

GATGAACAGAAATCTGTCCTTCCAGAGGGGCCTGCCCGGCTTTATGCCTGCATGGGATATC

GTGTTCGAGAAGAACGAGACACAGTTTGACGCCAAGGGCACCCCTTTCATCGCCGGCAAGA

GAATCGTGCCAGTGATCGAGAATCACAGATTCACCGGCAGATACCGGGACCTGTATCCTGC

CAACGAGCTGATCGCCCTGCTGGAGGAGAAGGGCATCGTGTTCAGGGATGGCTCCAACATC

CTGCCAAAGCTGCTGGAGAATGACGATTCTCACGCCATCGACACCATGGTGGCCCTGATCC

GCAGCGTGCTGCAGATGCGGAACTCCAATGCCGCCACAGGCGAGGACTATATCAACAGCC

CCGTGCGCGATCTGAATGGCGTGTGCTTCGACTCCCGGTTTCAGAACCCAGAGTGGCCCAT

GGACGCCGATGCCAATGGCGCCTACCACATCGCCCTGAAGGGCCAGCTGCTGCTGAATCA

CCTGAAGGAGAGCAAGGATCTGAAGCTGCAGAACGGCATCTCCAATCAGGACTGGCTGGCC

TACATCCAGGAGCTGCGCAACaaaaggccggcggccacgaaaaaggccggccaggcaaaaaagaaaaagGGA

TCCTACCCATACGATGTTCCAGATTACGCTTATCCCTACGACGTGCCTGATTATGCATACC

CATATGATGTCCCCGACTATGCCGGAAGCGAGGCCAGCGGTTCCGGACGGGCTGACGCAT

TGGACGATTTTGATCTGGATATGCTGGGAAGTGACGCCCTCGATGATTTTGACCTTGACATG

CTTGGTTCGGATGCCCTTGATGACTTTGACCTCGACATGCTCGGCAGTGACGCCCTTGATGA

TTTCGACCTGGACATGCTGATTAACTCTAGAAGTTCCGGATCTCCGAAAAAGAAACGCAAAG

TTGGTAGCCAGTACCTGCCCGACACCGACGACCGGCACCGGATCGAGGAAAAGCGGAAGC

GGACCTACGAGACATTCAAGAGCATCATGAAGAAGTCCCCCTTCAGCGGCCCCACCGACCC

TAGACCTCCACCTAGAAGAATCGCCGTGCCCAGCAGATCCAGCGCCAGCGTGCCAAAACCT

GCCCCCCAGCCTTACCCCTTCACCAGCAGCCTGAGCACCATCAACTACGACGAGTTCCCTA

CCATGGTGTTCCCCAGCGGCCAGATCTCTCAGGCCTCTGCTCTGGCTCCAGCCCCTCCTCA

GGTGCTGCCTCAGGCTCCTGCTCCTGCACCAGCTCCAGCCATGGTGTCTGCACTGGCTCAG

GCACCAGCACCCGTGCCTGTGCTGGCTCCTGGACCTCCACAGGCTGTGGCTCCACCAGCC

CCTAAACCTACACAGGCCGGCGAGGGCACACTGTCTGAAGCTCTGCTGCAGCTGCAGTTCG

ACGACGAGGATCTGGGAGCCCTGCTGGGAAACAGCACCGATCCTGCCGTGTTCACCGACC

-continued

TGGCCAGCGTGGACAACAGCGAGTTCCAGCAGCTGCTGAACCAGGGCATCCCTGTGGCCC

CTCACACCACCGAGCCCATGCTGATGGAATACCCCGAGGCCATCACCCGGCTCGTGACAG

GCGCTCAGAGGCCTCCTGATCCAGCTCCTGCCCCTCTGGGAGCACCAGGCCTGCCTAATG

GACTGCTGTCTGGCGACGAGGACTTCAGCTCTATCGCCGATATGGATTTCTCAGCCTTGCTG

GGCTCTGGCAGCGGCAGCCGGGATTCCAGGGAAGGGATGTTTTTGCCGAAGCCTGAGGCC

GGCTCCGCTATTAGTGACGTGTTTGAGGGCCGCGAGGTGTGCCAGCCAAAACGAATCCGG

CCATTTCATCCTCCAGGAAGTCCATGGGCCAACCGCCCACTCCCCGCCAGCCTCGCACCAA

CACCAACCGGTCCAGTACATGAGCCAGTCGGGTCACTGACCCCGGCACCAGTCCCTCAGC

CACTGGATCCAGCGCCCGCAGTGACTCCCGAGGCCAGTCACCTGTTGGAGGATCCCGATG

AAGAGACGAGCCAGGCTGTCAAAGCCCTTCGGGAGATGGCCGATACTGTGATTCCCCAGAA

GGAAGAGGCTGCAATCTGTGGCCAAATGGACCTTTCCCATCCGCCCCCAAGGGGCCATCTG

GATGAGCTGACAACCACACTTGAGTCCATGACCGAGGATCTGAACCTGGACTCACCCCTGA

CCCCGGAATTGAACGAGATTCTGGATACCTTCCTGAACGACGAGTGCCTCTTGCATGCCATG

CATATCAGCACAGGACTGTCCATCTTCGACACATCTCTGTTT

Amino Acid Sequence of dAsCpf1(D008A)triplovariant (E174R/S642R/K648R)-NLS(nucleoplasmin)-3×HA-VPR AsCpf in normal font (AAs 1-1307), NLS(nucleoplasmin) (krpesikkaggakkkk, SEQ ID NO:7) in lower case, 3×HA tag (YPYDVPDYAYPYDVPDYAYPYDVPDYA, SEQ ID NO:8) in bold, and VPR doubleunderlined

SEQ ID NO: 434)

MTQFEGFTNLYQVSKTLRFELIPQGKTLKHIQEQGFIEEDKARNDHYKELKPIIDRIYKTYA

DQCLQLVQLDWENLSAAIDSYRKEKTEETRNALIEEQATYRNAIHDYFIGRTDNLTDAINKRHAEI

YKGLFKAELFNGKVLKQLGTVTTTEHENALLRSFDKFTTYFSGFYRNRKNVFSAEDISTAIPHRIV

QDNFPKFKENCHIFTRLITAVPSLREHFENVKKAIGIFVSTSIEEVFSFPFYNQLLTQTQIDLYNQLL

GGISREAGTEKIKGLNEVLNLAIQKNDETAHIIASLPHRFIPLFKQILSDRNTLSFILEEFKSDEEVIQ

SFCKYKTLLRNENVLETAEALFNELNSIDLTHIFISHKKLETISSALCDHWDTLRNALYERRISELTG

KITKSAKEKVQRSLKHEDINLQEIISAAGKELSEAFKQKTSEILSHAHAALDQPLPTTLKKQEEKEIL

KSQLDSLLGLYHLLDWFAVDESNEVDPEFSARLTGIKLEMEPSLSFYNKARNYATKKPYSVEKFK

LNFQMPTLARGWDVNKEKNNGAILFVKNGLYYLGIMPKQKGRYKALSFEPTEKTSEGFDKMYYD

YFPDAAKMIPKCSTQLKAVTAHFQTHTTPILLSNNFIEPLEITKEIYDLNNPEKEPKKFQTAYAKKT

GDQKGYREALCKWIDFIRDFLSKYTKITSIDLSSLRPSSQYKDLGEYYAELNPLLYHISFQRIAEK

EIMDAVETGKLYLFQIYNKDFAKGHHGKPNLHTLYVVTGLFSPENLAKTSIKLNGQAELFYRPKSR

MKRMAHRLGEKMLNKKLKDQKTPIPDTLYQELYDYVNHRLSHDLSDEARALLPNVITKEVSHEIIK

DRRFTSDKFFFHVPITLNYQAANSPSKFNQRVNAYLKEHPETPIIGIARGERNLIYITVIDSTGKILE

QRSLNTIQQFDYQKKLDNREKERVAARQAWSVVGTIKDLKQGYLSQVIHEIVDLMIHYQAVVVLE

NLNFGFKSKRTGIAEKAVYQQFEKMLIDKLNCLVLKDYPAEKVGGVLNPYQLTDQFTSFAKMGT

QSGFLFYVPAPYTSKIDPLIGFVDPFVWKTIKNHESRKHFLEGFDFLHYDVKTGDFILHFKMNRN

LSFQRGLPGFMPAWDIVFEKNETQFDAKGTPFIAGKRIVPVIENHRFTGRYRDLYPANELIALLEE

KGIVFRDGSNILPKLLENDDSHAIDTMVALIRSVLQMRNSNAATGEDYINSPVRDLNGVCFDSRF

QNPEWPMDADANGAYHIALKGQLLLNHLKESKDLKLQNGISNQDWLAYIQELRNkrpaatkkagqakk kkGSYPYDVPDYAYPYDVPDYAYPYDVPDYAGSEASGSGRADALDDFDLDMLGSDALDDFDLD -continued

MLGSDALDDFDLDMLGSDALDDFDLDMLINSRSSGSPKKKRKVGSQYLPDTDDRHRIEEKRKRT

YETFKSIMKKSPFSGPTDPRPPPRRIAVPSRSSASVPKPAPQPYPFTSSLSTINYDEFPTMVFPS

GQISQASALAPAPPQVLPQAPAPAPAPAMVSALAQAPAPVPVLAPGPPQAVAPPAPKPTQAGEG

TLSEALLQLQFDDEDLGALLGNSTDPAVFTDLASVDNSEFQQLLNQGIPVAPHTTEPMLMEYPEA

ITRLVTGAQRPPDPAPAPLGAPGLPNGLLSGDEDFSSIADMDFSALLGSGSGSRDSREGMFLPK

PEAGSAISDVFEGREVCQPKRIRPFHPPGSPWANRPLPASLAPTPTGPVHEPVGSLTPAPVPQP

LDPAPAVTPEASHLLEDPDEETSQAVKALREMADTVIPQKEEAAICGQMDLSHPPPRGHLDELTT

TLESMTEDLNLDSPLTPELNEILDTFLNDECLLHAMHISTGLSIFDTSLF

RTW1017: pCAG-2×NLS-hdeAsCas12a(E174R/S542R/K548R/D908A)-NLS-gs-3×HA-gs-VPR(deAs-VPR(1.2)) Human codon optimized *Acidaminococcus* sp. BV3L6 Cas12a (AsCas12a) in black, modified codons for DNase inactive (D908A) eAsCas12a (E174R/S542R/K548R) in doubleunderlined lowercase, codons with silent mutations to remove NcoI sites doubleunderlinedUPPERCASE, inserted glycine dash-underlined, nucleoplasmin NLS (aaaaggccggcggccacgaaaaaggccggccaggcaaaaaagaaaaag, SEQ ID NO:21) in lower case, linker sequences in italics, 3×HA tag (YPYDVPDYAYPYDVPDYAYPYDVPDYA, SEQ ID NO:8) in bold, SV40 NLS in lower case italics, VP64-p65-RTA (VPR) in doubleunderlineditalics (SEQ ID NO: 435)

ATGGGC*ccaaagaaaaagaggaaagtcGGCAGTGGAcctaaaaagaaacgaaaggttGGGTCAGGT*ACAC

AGTTCGAGGGCTTTACCAACCTGTATCAGGTGAGCAAGACACTGCGGTTTGAGCTGATCCC

ACAGGGCAAGACCCTGAAGCACATCCAGGAGCAGGGCTTCATCGAGGAGGACAAGGCCCG

CAATGATCACTACAAGGAGCTGAAGCCCATCATCGATCGGATCTACAAGACCTATGCCGACC

AGTGCCTGCAGCTGGTGCAGCTGGATTGGGAGAACCTGAGCGCCGCCATCGACTCCTATAG

AAAGGAGAAAACCGAGGAGACAAGGAACGCCCTGATCGAGGAGCAGGCCACATATCGCAAT

GCCATCCACGACTACTTCATCGGCCGGACAGACAACCTGACCGATGCCATCAATAAGAGAC

ACGCCGAGATCTACAAGGGCCTGTTCAAGGCCGAGCTGTTTAATGGCAAGGTGCTGAAGCA

GCTGGGCACCGTGACCACAACCGAGCACGAGAACGCCCTGCTGCGGAGCTTCGACAAGTT

TACAACCTACTTCTCCGGCTTTTATagaAACAGGAAGAACGTGTTCAGCGCCGAGGATATCAG

CACAGCCATCCCACACCGCATCGTGCAGGACAACTTCCCCAAGTTTAAGGAGAATTGTCACA

TCTTCACACGCCTGATCACCGCCGTGCCCAGCCTGCGGGAGCACTTTGAGAACGTGAAGAA

GGCCATCGGCATCTTCGTGAGCACCTCCATCGAGGAGGTGTTTTCCTTCCCTTTTTATAACC

AGCTGCTGACACAGACCCAGATCGACCTGTATAACCAGCTGCTGGGAGGAATCTCTCGGGA

GGCAGGCACCGAGAAGATCAAGGGCCTGAACGAGGTGCTGAATCTGGCCATCCAGAAGAA

TGATGAGACAGCCCACATCATCGCCTCCCTGCCACACAGATTCATCCCCCTGTTTAAGCAGA

TCCTGTCCGATAGGAACACCCTGTCTTTCATCCTGGAGGAGTTTAAGAGCGACGAGGAAGT

GATCCAGTCCTTCTGCAAGTACAAGACACTGCTGAGAAACGAGAACGTGCTGGAGACAGCC

GAGGCCCTGTTTAACGAGCTGAACAGCATCGACCTGACACACATCTTCATCAGCCACAAGAA

GCTGGAGACAATCAGCAGCGCCCTGTGCGACCACTGGGATACACTGAGGAATGCCCTGTAT

GAGCGGAGAATCTCCGAGCTGACAGGCAAGATCACCAAGTCTGCCAAGGAGAAGGTGCAG

CGCAGCCTGAAGCACGAGGATATCAACCTGCAGGAGATCATCTCTGCCGCAGGCAAGGAG

CTGAGCGAGGCCTTCAAGCAGAAAACCAGCGAGATCCTGTCCCACGCACACGCCGCCCTG

GATCAGCCACTGCCTACAACCCTGAAGAAGCAGGAGGAGAAGGAGATCCTGAAGTCTCAGC

TGGACAGCCTGCTGGGCCTGTACCACCTGCTGGACTGGTTTGCCGTGGATGAGTCCAACGA

GGTGGACCCCGAGTTCTCTGCCCGGCTGACCGGCATCAAGCTGGAGATGGAGCCTTCTCT

-continued

GAGCTTCTACAACAAGGCCAGAAATTATGCCACCAAGAAGCCCTACTCCGTGGAGAAGTTCA

AGCTGAACTTTCAGATGCCTACACTGGCCagaGGCTGGGACGTGAATagaGAGAAGAACAAT

GGCGCCATCCTGTTTGTGAAGAACGGCCTGTACTATCTGGGCATCATGCCAAAGCAGAAGG

GCAGGTATAAGGCCCTGAGCTTCGAGCCCACAGAGAAAACCAGCGAGGGCTTTGATAAGAT

GTACTATGACTACTTCCCTGATGCCGCCAAGATGATCCCAAAGTGCAGCACCCAGCTGAAG

GCCGTGACAGCCCACTTTCAGACCCACACAACCCCCATCCTGCTGTCCAACAATTTCATCGA

GCCTCTGGAGATCACAAAGGAGATCTACGACCTGAACAATCCTGAGAAGGAGCCAAAGAAG

TTTCAGACAGCCTACGCCAAGAAAACCGGCGACCAGAAGGGCTACAGAGAGGCCCTGTGCA

AGTGGATCGACTTCACAAGGGATTTTCTGTCCAAGTATACCAAGACAACCTCTATCGATCTGT

CTAGCCTGCGGCCATCCTCTCAGTATAAGGACCTGGGCGAGTACTATGCCGAGCTGAATCC

CCTGCTGTACCACATCAGCTTCCAGAGAATCGCCGAGAAGGAGATCATGGATGCCGTGGAG

ACAGGCAAGCTGTACCTGTTCCAGATCTATAACAAGGACTTTGCCAAGGGCCACCACGGCA

AGCCTAATCTGCACACACTGTATTGGACCGGCCTGTTTTCTCCAGAGAACCTGGCCAAGACA

AGCATCAAGCTGAATGGCCAGGCCGAGCTGTTCTACCGCCCTAAGTCCAGGATGAAGAGGA

TGGCACACCGGCTGGGAGAGAAGATGCTGAACAAGAAGCTGAAGGATCAGAAAACCCCAAT

CCCCGACACCCTGTACCAGGAGCTGTACGACTATGTGAATCACAGACTGTCCCACGACCTG

TCTGATGAGGCCAGGGCCCTGCTGCCCAACGTGATCACCAAGGAGGTGTCTCACGAGATCA

TCAAGGATAGGCGCTTTACCAGCGACAAGTTCTTTTTCCACGTGCCTATCACACTGAACTAT

CAGGCCGCCAATTCCCCATCTAAGTTCAACCAGAGGGTGAATGCCTACCTGAAGGAGCACC

CCGAGACACCTATCATCGGCATCgccCGGGGCGAGAGAAACCTGATCTATATCACAGTGATC

GACTCCACCGGCAAGATCCTGGAGCAGCGGAGCCTGAACACCATCCAGCAGTTTGATTACC

AGAAGAAGCTGGACAACAGGGAGAAGGAGAGGGTGGCAGCAAGGCAGGCCTGGTCTGTGG

TGGGCACAATCAAGGATCTGAAGCAGGGCTATCTGAGCCAGGTCATCCACGAGATCGTGGA

CCTGATGATCCACTACCAGGCCGTGGTGGTGCTGGAGAACCTGAATTTCGGCTTTAAGAGC

AAGAGGACCGGCATCGCCGAGAAGGCCGTGTACCAGCAGTTCGAGAAGATGCTGATCGATA

AGCTGAATTGCCTGGTGCTGAAGGACTATCCAGCAGAGAAAGTGGGAGGCGTGCTGAACCC

ATACCAGCTGACAGACCAGTTCACCTCCTTTGCCAAGATGGGCACCCAGTCTGGCTTCCTGT

TTTACGTGCCTGCCCCATATACATCTAAGATCGATCCCCTGACCGGCTTCGTGGACCCCTTC

GTGTGGAAAACCATCAAGAATCACGAGAGCCGCAAGCACTTCCTGGAGGGCTTCGACTTTC

TGCACTACGACGTGAAAACCGGCGACTTCATCCTGCACTTTAAGATGAACAGAAATCTGTCC

TTCCAGAGGGGCCTGCCCGGCTTTATGCCTGCATGGGATATCGTGTTCGAGAAGAACGAGA

CACAGTTTGACGCCAAGGGCACCCCTTTCATCGCCGGCAAGAGAATCGTGCCAGTGATCGA

GAATCACAGATTCACCGGCAGATACCGGGACCTGTATCCTGCCAACGAGCTGATCGCCCTG

CTGGAGGAGAAGGGCATCGTGTTCAGGGATGGCTCCAACATCCTGCCAAAGCTGCTGGAGA

ATGACGATTCTCACGCCATCGACACGATGGTGGCCCTGATCCGCAGCGTGCTGCAGATGCG

GAACTCCAATGCCGCCACAGGCGAGGACTATATCAACAGCCCCGTGCGCGATCTGAATGGC

GTGTGCTTCGACTCCCGGTTTCAGAACCCAGAGTGGCCAATGGACGCCGATGCCAATGGCG

CCTACCACATCGCCCTGAAGGGCCAGCTGCTGCTGAATCACCTGAAGGAGAGCAAGGATCT

GAAGCTGCAGAACGGCATCTCCAATCAGGACTGGCTGGCCTACATCCAGGAGCTGCGCAAC aaaaggccggcggccacgaaaaaggccggccaggcaaaaaagaaaaag*GGATCC*TACCCATACGATGTTCCA

-continued

GATTACGCTTATCCCTACGACGTGCCTGATTATGCATACCCATATGATGTCCCCGACTATG

CC*GGAAGC*GAGGCCAGCGGTTCCGGACGGGCTGACGCATTGGACGATTTTGATCTGGATAT

GCTGGGAAGTGACGCCCTCGATGATTTTGACCTTGACATGCTTGGTTCGGATGCCCTTGATG

ACTTTGACCTCGACATGCTCGGCAGTGACGCCCTTGATGATTTCGACCTGGACATGCTGATT

AACTCTAGAAGTFCCGGATCTCCGAAAAAGAAACGCAAAGTTGGTAGCCAGTACCTGCCCGA

CACCGACGACCGGCACCGGATCGAGGAAAAGCGGAAGCGGACCTACGAGACATTCAAGAG

CATCATGAAGAAGTCCCCCTTCAGCGGCCCCACCGACCCTAGACCTCCACCTAGAAGAATC

GCCGTGCCCAGCAGATCCAGCGCCAGCGTGCCAAAACCTGCCCCCCAGCCTTACCCCTTCA

CCAGCAGCCTGAGCACCATCAACTACGACGAGTTCCCTACCATGGTGTTCCCCAGCGGCCA

GATCTCTCAGGCCTCTGCTCTGGCTCCAGCCCCTCCTCAGGTGCTGCCTCAGGCTCCTGCT

CCTGCACCAGCTCCAGCCATGGTGTCTGCACTGGCTCAGGCACCAGCACCCGTGCCTGTG

CTGGCTCCTGGACCTCCACAGGCTGTGGCTCCACCAGCCCCTAAACCTACACAGGCCGGC

GAGGGCACACTGTCTGAAGCTCTGCTGCAGCTGCAGTTCGACGACGAGGATCTGGGAGCC

CTGCTGGGAAACAGCACCGATCCTGCCGTGTTCACCGACCTGGCCAGCGTGGACAACAGC

GAGTTCCAGCAGCTGCTGAACCAGGGCATCCCTGTGGCCCCTCACACCACCGAGCCCATG

CTGATGGAATACCCCGAGGCCATCACCCGGCTCGTGACAGGCGCTCAGAGGCCTCCTGAT

CCAGCTCCTGCCCCTCTGGGAGCACCAGGCCTGCCTAATGGACTGCTGTCTGGCGACGAG

GACTTCAGCTCTATCGCCGATATGGATTTCTCAGCCTTGCTGGGCTCTGGCAGCGGCAGCC

GGGATTCCAGGGAAGGGATGTTTTTGCCGAAGCCTGAGGCCGGCTCCGCTATTAGTGACGT

GTTTGAGGGCCGCGAGGTGTGCCAGCCAAAACGAATCCGGCCATTTCATCCTCCAGGAAGT

CCATGGGCCAACCGCCCACTCCCCGCCAGCCTCGCACCAACACCAACCGGTCCAGTACAT

GAGCCAGTCGGGTCACTGACCCCGGCACCAGTCCCTCAGCCACTGGATCCAGCGCCCGCA

GTGACTCCCGAGGCCAGTCACCTGTTGGAGGATCCCGATGAAGAGACGAGCCAGGCTGTC

AAAGCCCTTCGGGAGATGGCCGATACTGTGATTCCCCAGAAGGAAGAGGCTGCAATCTGTG

GCCAAATGGACCTTTCCCATCCGCCCCCAAGGGGCCATCTGGATGAGCTGACAACCACACT

TGAGTCCATGACCGAGGATCTGAACCTGGACTCACCCCTGACCCCGGAATTGAACGAGATT

CTGGATACCTTCCTGAACGACGAGTGCCTCTTGCATGCCATGCATATCAGCACAGGACTGTC

CATCTTCGACACATCTCTGTTTTAA

RTW1130: pCAG-hdeAsCas12a(E174R/S542R/K548R/D908A)-gs-NLS-gs-VPR(deAs-VPR(1.3)) Human codon optimized *Acidaminococcus* sp. BV3L6 Cas12a (AsCas12a) in black, modified codons for DNase inactive (D908A) eAsCas12a (E174R/S542R/K548R) in doubleunderlinedlowercase, codons with silent mutations to remove NcoI sites doubleunderlinedUPPERCASE, linker sequences in italics, SV40 NLS in lower case italics, VP64-p65-RTA (VPR) in doubleunderlineditalics (SEQ ID NO: 436)

ATGACACAGTTCGAGGGCTTTACCAACCTGTATCAGGTGAGCAAGACACTGCGGTTTGAGCT

GATCCCACAGGGCAAGACCCTGAAGCACATCCAGGAGCAGGGCTTCATCGAGGAGGACAA

GGCCCGCAATGATCACTACAAGGAGCTGAAGCCCATCATCGATCGGATCTACAAGACCTAT

GCCGACCAGTGCCTGCAGCTGGTGCAGCTGGATTGGGAGAACCTGAGCGCCGCCATCGAC

TCCTATAGAAAGGAGAAAACCGAGGAGACAAGGAACGCCCTGATCGAGGAGCAGGCCACAT

ATCGCAATGCCATCCACGACTACTTCATCGGCCGGACAGACAACCTGACCGATGCCATCAAT

AAGAGACACGCCGAGATCTACAAGGGCCTGTTCAAGGCCGAGCTGTTTAATGGCAAGGTGC

TGAAGCAGCTGGGCACCGTGACCACAACCGAGCACGAGAACGCCCTGCTGCGGAGCTTCG

-continued

ACAAGTTTACAACCTACTTCTCCGGCTTTTATagaAACAGGAAGAACGTGTTCAGCGCCGAGG
ATATCAGCACAGCCATCCCACACCGCATCGTGCAGGACAACTTCCCCAAGTTTAAGGAGAAT
TGTCACATCTTCACACGCCTGATCACCGCCGTGCCCAGCCTGCGGGAGCACTTTGAGAACG
TGAAGAAGGCCATCGGCATCTTCGTGAGCACCTCCATCGAGGAGGTGTTTTCCTTCCCTTTT
TATAACCAGCTGCTGACACAGACCCAGATCGACCTGTATAACCAGCTGCTGGGAGGAATCT
CTCGGGAGGCAGGCACCGAGAAGATCAAGGGCCTGAACGAGGTGCTGAATCTGGCCATCC
AGAAGAATGATGAGACAGCCCACATCATCGCCTCCCTGCCACACAGATTCATCCCCCTGTTT
AAGCAGATCCTGTCCGATAGGAACACCCTGTCTTTCATCCTGGAGGAGTTTAAGAGCGACGA
GGAAGTGATCCAGTCCTTCTGCAAGTACAAGACACTGCTGAGAAACGAGAACGTGCTGGAG
ACAGCCGAGGCCCTGTTTAACGAGCTGAACAGCATCGACCTGACACACATCTTCATCAGCC
ACAAGAAGCTGGAGACAATCAGCAGCGCCCTGTGCGACCACTGGGATACACTGAGGAATGC
CCTGTATGAGCGGAGAATCTCCGAGCTGACAGGCAAGATCACCAAGTCTGCCAAGGAGAAG
GTGCAGCGCAGCCTGAAGCACGAGGATATCAACCTGCAGGAGATCATCTCTGCCGCAGGCA
AGGAGCTGAGCGAGGCCTTCAAGCAGAAAACCAGCGAGATCCTGTCCCACGCACACGCCG
CCCTGGATCAGCCACTGCCTACAACCCTGAAGAAGCAGGAGGAGAAGGAGATCCTGAAGTC
TCAGCTGGACAGCCTGCTGGGCCTGTACCACCTGCTGGACTGGTTTGCCGTGGATGAGTCC
AACGAGGTGGACCCCGAGTTCTCTGCCCGGCTGACCGGCATCAAGCTGGAGATGGAGCCT
TCTCTGAGCTTCTACAACAAGGCCAGAAATTATGCCACCAAGAAGCCCTACTCCGTGGAGAA
GTTCAAGCTGAACTTTCAGATGCCTACACTGGCCagaGGCTGGGACGTGAATagaGAGAAGA
ACAATGGCGCCATCCTGTTTGTGAAGAACGGCCTGTACTATCTGGGCATCATGCCAAAGCA
GAAGGGCAGGTATAAGGCCCTGAGCTTCGAGCCCACAGAGAAAACCAGCGAGGGCTTTGAT
AAGATGTACTATGACTACTTCCCTGATGCCGCCAAGATGATCCCAAAGTGCAGCACCCAGCT
GAAGGCCGTGACAGCCCACTTTCAGACCCACACAACCCCCATCCTGCTGTCCAACAATTTCA
TCGAGCCTCTGGAGATCACAAAGGAGATCTACGACCTGAACAATCCTGAGAAGGAGCCAAA
GAAGTTTCAGACAGCCTACGCCAAGAAAACCGGCGACCAGAAGGGCTACAGAGAGGCCCT
GTGCAAGTGGATCGACTTCACAAGGGATTTTCTGTCCAAGTATACCAAGACAACCTCTATCG
ATCTGTCTAGCCTGCGGCCATCCTCTCAGTATAAGGACCTGGGCGAGTACTATGCCGAGCT
GAATCCCCTGCTGTACCACATCAGCTTCCAGAGAATCGCCGAGAAGGAGATCATGGATGCC
GTGGAGACAGGCAAGCTGTACCTGTTCCAGATCTATAACAAGGACTTTGCCAAGGGCCACC
ACGGCAAGCCTAATCTGCACACACTGTATTGGACCGGCCTGTTTTCTCCAGAGAACCTGGC
CAAGACAAGCATCAAGCTGAATGGCCAGGCCGAGCTGTTCTACCGCCCTAAGTCCAGGATG
AAGAGGATGGCACACCGGCTGGGAGAGAAGATGCTGAACAAGAAGCTGAAGGATCAGAAAA
CCCCAATCCCCGACACCCTGTACCAGGAGCTGTACGACTATGTGAATCACAGACTGTCCCA
CGACCTGTCTGATGAGGCCAGGGCCCTGCTGCCCAACGTGATCACCAAGGAGGTGTCTCAC
GAGATCATCAAGGATAGGCGCTTTACCAGCGACAAGTTCTTTTTCCACGTGCCTATCACACT
GAACTATCAGGCCGCCAATTCCCCATCTAAGTTCAACCAGAGGGTGAATGCCTACCTGAAG
GAGCACCCCGAGACACCTATCATCGGCATCgccCGGGGCGAGAGAAACCTGATCTATATCAC
AGTGATCGACTCCACCGGCAAGATCCTGGAGCAGCGGAGCCTGAACACCATCCAGCAGTTT
GATTACCAGAAGAAGCTGGACAACAGGGAGAAGGAGAGGGTGGCAGCAAGGCAGGCCTGG
TCTGTGGTGGGCACAATCAAGGATCTGAAGCAGGGCTATCTGAGCCAGGTCATCCACGAGA -continued
TCGTGGACCTGATGATCCACTACCAGGCCGTGGTGGTGCTGGAGAACCTGAATTTCGGCTT
TAAGAGCAAGAGGACCGGCATCGCCGAGAAGGCCGTGTACCAGCAGTTCGAGAAGATGCT
GATCGATAAGCTGAATTGCCTGGTGCTGAAGGACTATCCAGCAGAGAAAGTGGGAGGCGTG
CTGAACCCATACCAGCTGACAGACCAGTTCACCTCCTTTGCCAAGATGGGCACCCAGTCTG
GCTTCCTGTTTTACGTGCCTGCCCCATATACATCTAAGATCGATCCCCTGACCGGCTTCGTG
GACCCCTTCGTGTGGAAAACCATCAAGAATCACGAGAGCCGCAAGCACTTCCTGGAGGGCT
TCGACTTTCTGCACTACGACGTGAAAACCGGCGACTTCATCCTGCACTTTAAGATGAACAGA
AATCTGTCCTTCCAGAGGGGCCTGCCCGGCTTTATGCCTGCATGGGATATCGTGTTCGAGA
AGAACGAGACACAGTTTGACGCCAAGGGCACCCCTTTCATCGCCGGCAAGAGAATCGTGCC
AGTGATCGAGAATCACAGATTCACCGGCAGATACCGGGACCTGTATCCTGCCAACGAGCTG
ATCGCCCTGCTGGAGGAGAAGGGCATCGTGTTCAGGGATGGCTCCAACATCCTGCCAAAGC
TGCTGGAGAATGACGATTCTCACGCCATCGACACGATGGTGGCCCTGATCCGCAGCGTGCT
GCAGATGCGGAACTCCAATGCCGCCACAGGCGAGGACTATATCAACAGCCCCGTGCGCGA
TCTGAATGGCGTGTGCTTCGACTCCCGGTTTCAGAACCCAGAGTGGCCAATGGACGCCGAT
GCCAATGGCGCCTACCACATCGCCCTGAAGGGCCAGCTGCTGCTGAATCACCTGAAGGAGA
GCAAGGATCTGAAGCTGCAGAACGGCATCTCCAATCAGGACTGGCTGGCCTACATCCAGGA
GCTGCGCAAC*GGTGGAAGCGGAGGGAGTcccaagaagaagaggaaagtcGGGGGTTCCGGAGGAA*
*GC*GAGGCCAGCGGTTCCGGACGGGCTGACGCATTGGACGATTTTGATCTGGATATGCTGG
GAAGTGACGCCCTCGATGATTTTGACCTTGACATGCTTGGTTCGGATGCCCTTGATGACTTT
GACCTCGACATGCTCGGCAGTGACGCCCTTGATGATTTCGACCTGGACATGCTGATTAACTC
TAGAAGTTCCGGATCTCCGAAAAAGAAACGCAAAGTTGGTAGCCAGTACCTGCCCGACACC
GACGACCGGCACCGGATCGAGGAAAAGCGGAAGCGGACCTACGAGACATTCAAGAGCATC
ATGAAGAAGTCCCCCTTCAGCGGCCCCACCGACCCTAGACCTCCACCTAGAAGAATCGCCG
TGCCCAGCAGATCCAGCGCCAGCGTGCCAAAACCTGCCCCCCAGCCTTACCCCTTCACCAG
CAGCCTGAGCACCATCAACTACGACGAGTTCCCTACCATGGTGTTCCCCAGCGGCCAGATC
TCTCAGGCCTCTGCTCTGGCTCCAGCCCCTCCTCAGGTGCTGCCTCAGGCTCCTGCTCCTG
CACCAGCTCCAGCCATGGTGTCTGCACTGGCTCAGGCACCAGCACCCGTGCCTGTGCTGG
CTCCTGGACCTCCACAGGCTGTGGCTCCACCAGCCCCTAAACCTACACAGGCCGGCGAGG
GCACACTGTCTGAAGCTCTGCTGCAGCTGCAGTTCGACGACGAGGATCTGGGAGCCCTGCT
GGGAAACAGCACCGATCCTGCCGTGTTCACCGACCTGGCCAGCGTGGACAACAGCGAGTT
CCAGCAGCTGCTGAACCAGGGCATCCCTGTGGCCCCTCACACCACCGAGCCCATGCTGAT
GGAATACCCCGAGGCCATCACCCGGCTCGTGACAGGCGCTCAGAGGCCTCCTGATCCAGC
TCCTGCCCCTCTGGGAGCACCAGGCCTGCCTAATGGACTGCTGTCTGGCGACGAGGACTTC
AGCTCTATCGCCGATATGGATTTCTCAGCCTTGCTGGGCTCTGGCAGCGGCAGCCGGGATT
CCAGGGAAGGGATGTTTTTGCCGAAGCCTGAGGCCGGCTCCGCTATTAGTGACGTGTTTGA
GGGCCGCGAGGTGTGCCAGCCAAAACGAATCCGGCCATTTCATCCTCCAGGAAGTCCATGG
GCCAACCGCCCACTCCCCGCCAGCCTCGCACCAACACCAACCGGTCCAGTACATGAGCCA
GTCGGGTCACTGACCCCGGCACCAGTCCCTCAGCCACTGGATCCAGCGCCCGCAGTGACT
CCCGAGGCCAGTCACCTGTTGGAGGATCCCGATGAAGAGACGAGCCAGGCTGTCAAAGCC
CTTCGGGAGATGGCCGATACTGTGATTCCCCAGAAGGAAGAGGCTGCAATCTGTGGCCAAA
TGGACCTTTCCCATCCGCCCCCAAGGGGCCATCTGGATGAGCTGACAACCACACTTGAGTC -continued

CATGACCGAGGATCTGAACCTGGACTCACCCCTGACCCCGGAATTGAACGAGATTCTGGAT

ACCTTCCTGAACGACGAGTGCCTCTTGCATGCCATGCATATCAGCACAGGACTGTCCATCTT

CGACACATCTCTGTTTTAA

RTW1319: pCAG-2×NLS-hdeAsCas12a(E174R/S542R/K548R/D908A)-gs-NLS-gs-VPR(deAs-VPR(1.4))
Human codon optimized *Acidaminococcus* sp. BV3L6 Cas12a (AsCas12a) in black, modified codons for DNase inactive (D908A) eAsCas12a (E174R/S542R/K548R) in doubleunderlinedlowercase, codons with silent mutations to remove NcoI sites doubleunderlinedUPPERCASE, inserted glycine dash-underlined, linker sequences in italics, 3×HA tag (YPYDVPDYAYPYDVPDYAYPYDVPDYA, SEQ ID NO:8) in bold, SV40 NLS in lower case italics, VP64-p65-RTA (VPR) in doubleunderlineditalics (SEQ ID NO: 437)
ATGGGC*ccaaagaaaaagaggaaagtc*GGCAGTGGA*cctaaaaagaaacgaaaggtt*GGGTCAGGTACACA

GTTCGAGGGCTTTACCAACCTGTATCAGGTGAGCAAGACACTGCGGTTTGAGCTGATCCCA

CAGGGCAAGACCCTGAAGCACATCCAGGAGCAGGGCTTCATCGAGGAGGACAAGGCCCGC

AATGATCACTACAAGGAGCTGAAGCCCATCATCGATCGGATCTACAAGACCTATGCCGACCA

GTGCCTGCAGCTGGTGCAGCTGGATTGGGAGAACCTGAGCGCCGCCATCGACTCCTATAGA

AAGGAGAAAACCGAGGAGACAAGGAACGCCCTGATCGAGGAGCAGGCCACATATCGCAAT

GCCATCCACGACTACTTCATCGGCCGGACAGACAACCTGACCGATGCCATCAATAAGAGAC

ACGCCGAGATCTACAAGGGCCTGTTCAAGGCCGAGCTGTTTAATGGCAAGGTGCTGAAGCA

GCTGGGCACCGTGACCACAACCGAGCACGAGAACGCCCTGCTGCGGAGCTTCGACAAGTT

TACAACCTACTTCTCCGGCTTTTATagaAACAGGAAGAACGTGTTCAGCGCCGAGGATATCAG

CACAGCCATCCCACACCGCATCGTGCAGGACAACTTCCCCAAGTTTAAGGAGAATTGTCACA

TCTTCACACGCCTGATCACCGCCGTGCCCAGCCTGCGGGAGCACTTTGAGAACGTGAAGAA

GGCCATCGGCATCTTCGTGAGCACCTCCATCGAGGAGGTGTTTTCCTTCCCTTTTTATAACC

AGCTGCTGACACAGACCCAGATCGACCTGTATAACCAGCTGCTGGGAGGAATCTCTCGGGA

GGCAGGCACCGAGAAGATCAAGGGCCTGAACGAGGTGCTGAATCTGGCCATCCAGAAGAA

TGATGAGACAGCCCACATCATCGCCTCCCTGCCACACAGATTCATCCCCCTGTTTAAGCAGA

TCCTGTCCGATAGGAACACCCTGTCTTTCATCCTGGAGGAGTTTAAGAGCGACGAGGAAGT

GATCCAGTCCTTCTGCAAGTACAAGACACTGCTGAGAAACGAGAACGTGCTGGAGACAGCC

GAGGCCCTGTTTAACGAGCTGAACAGCATCGACCTGACACACATCTTCATCAGCCACAAGAA

GCTGGAGACAATCAGCAGCGCCCTGTGCGACCACTGGGATACACTGAGGAATGCCCTGTAT

GAGCGGAGAATCTCCGAGCTGACAGGCAAGATCACCAAGTCTGCCAAGGAGAAGGTGCAG

CGCAGCCTGAAGCACGAGGATATCAACCTGCAGGAGATCATCTCTGCCGCAGGCAAGGAG

CTGAGCGAGGCCTTCAAGCAGAAAACCAGCGAGATCCTGTCCCACGCACACGCCGCCCTG

GATCAGCCACTGCCTACAACCCTGAAGAAGCAGGAGGAGAAGGAGATCCTGAAGTCTCAGC

TGGACAGCCTGCTGGGCCTGTACCACCTGCTGGACTGGTTTGCCGTGGATGAGTCCAACGA

GGTGGACCCCGAGTTCTCTGCCCGGCTGACCGGCATCAAGCTGGAGATGGAGCCTTCTCT

GAGCTTCTACAACAAGGCCAGAAATTATGCCACCAAGAAGCCCTACTCCGTGGAGAAGTTCA

AGCTGAACTTTCAGATGCCTACACTGGCCagaGGCTGGGACGTGAATAGAGAGAAGAACAAT

GGCGCCATCCTGTTTGTGAAGAACGGCCTGTACTATCTGGGCATCATGCCAAAGCAGAAGG

GCAGGTATAAGGCCCTGAGCTTCGAGCCCACAGAGAAAACCAGCGAGGGCTTTGATAAGAT

GTACTATGACTACTTCCCTGATGCCGCCAAGATGATCCCAAAGTGCAGCACCCAGCTGAAG

-continued

GCCGTGACAGCCCACTTTCAGACCCACACAACCCCCATCCTGCTGTCCAACAATTTCATCGA

GCCTCTGGAGATCACAAAGGAGATCTACGACCTGAACAATCCTGAGAAGGAGCCAAAGAAG

TTTCAGACAGCCTACGCCAAGAAAACCGGCGACCAGAAGGGCTACAGAGAGGCCCTGTGCA

AGTGGATCGACTTCACAAGGGATTTTCTGTCCAAGTATACCAAGACAACCTCTATCGATCTGT

CTAGCCTGCGGCCATCCTCTCAGTATAAGGACCTGGGCGAGTACTATGCCGAGCTGAATCC

CCTGCTGTACCACATCAGCTTCCAGAGAATCGCCGAGAAGGAGATCATGGATGCCGTGGAG

ACAGGCAAGCTGTACCTGTTCCAGATCTATAACAAGGACTTTGCCAAGGGCCACCACGGCA

AGCCTAATCTGCACACACTGTATTGGACCGGCCTGTTTTCTCCAGAGAACCTGGCCAAGACA

AGCATCAAGCTGAATGGCCAGGCCGAGCTGTTCTACCGCCCTAAGTCCAGGATGAAGAGGA

TGGCACACCGGCTGGGAGAGAAGATGCTGAACAAGAAGCTGAAGGATCAGAAAACCCCAAT

CCCCGACACCCTGTACCAGGAGCTGTACGACTATGTGAATCACAGACTGTCCCACGACCTG

TCTGATGAGGCCAGGGCCCTGCTGCCCAACGTGATCACCAAGGAGGTGTCTCACGAGATCA

TCAAGGATAGGCGCTTTACCAGCGACAAGTTCTTTTTCCACGTGCCTATCACACTGAACTAT

CAGGCCGCCAATTCCCCATCTAAGTTCAACCAGAGGGTGAATGCCTACCTGAAGGAGCACC

CCGAGACACCTATCATCGGCATCgccCGGGGCGAGAGAAACCTGATCTATATCACAGTGATC

GACTCCACCGGCAAGATCCTGGAGCAGCGGAGCCTGAACACCATCCAGCAGTTTGATTACC

AGAAGAAGCTGGACAACAGGGAGAAGGAGAGGGTGGCAGCAAGGCAGGCCTGGTCTGTGG

TGGGCACAATCAAGGATCTGAAGCAGGGCTATCTGAGCCAGGTCATCCACGAGATCGTGGA

CCTGATGATCCACTACCAGGCCGTGGTGGTGCTGGAGAACCTGAATTTCGGCTTTAAGAGC

AAGAGGACCGGCATCGCCGAGAAGGCCGTGTACCAGCAGTTCGAGAAGATGCTGATCGATA

AGCTGAATTGCCTGGTGCTGAAGGACTATCCAGCAGAGAAAGTGGGAGGCGTGCTGAACCC

ATACCAGCTGACAGACCAGTTCACCTCCTTTGCCAAGATGGGCACCCAGTCTGGCTTCCTGT

TTTACGTGCCTGCCCCATATACATCTAAGATCGATCCCCTGACCGGCTTCGTGGACCCCTTC

GTGTGGAAAACCATCAAGAATCACGAGAGCCGCAAGCACTTCCTGGAGGGCTTCGACTTTC

TGCACTACGACGTGAAAACCGGCGACTTCATCCTGCACTTTAAGATGAACAGAAATCTGTCC

TTCCAGAGGGGCCTGCCCGGCTTTATGCCTGCATGGGATATCGTGTTCGAGAAGAACGAGA

CACAGTTTGACGCCAAGGGCACCCCTTTCATCGCCGGCAAGAGAATCGTGCCAGTGATCGA

GAATCACAGATTCACCGGCAGATACCGGGACCTGTATCCTGCCAACGAGCTGATCGCCCTG

CTGGAGGAGAAGGGCATCGTGTTCAGGGATGGCTCCAACATCCTGCCAAAGCTGCTGGAGA

ATGACGATTCTCACGCCATCGACACGATGGTGGCCCTGATCCGCAGCGTGCTGCAGATGCG

GAACTCCAATGCCGCCACAGGCGAGGACTATATCAACAGCCCCGTGCGCGATCTGAATGGC

GTGTGCTTCGACTCCCGGTTTCAGAACCCAGAGTGGCCAATGGACGCCGATGCCAATGGCG

CCTACCACATCGCCCTGAAGGGCCAGCTGCTGCTGAATCACCTGAAGGAGAGCAAGGATCT

GAAGCTGCAGAACGGCATCTCCAATCAGGACTGGCTGGCCTACATCCAGGAGCTGCGCAAC

*GGTGGAAGCGGAGGGAGT*cccaagaagaagaggaaagtc*GGGGGTTCCGGAGGAAGC*GAGGCCA

GCGGTTCCGGACGGGCTGACGCATTGGACGATTTTGATCTGGATATGCTGGGAAGTGACGC

CCTCGATGATTTTGACCTTGACATGCTTGGTTCGGATGCCCTTGATGACTTTGACCTCGACA

TGCTCGGCAGTGACGCCCTTGATGATTTCGACCTGGACATGCTGATTAACTCTAGAAGTTCC

GGATCTCCGAAAAAGAAACGCAAAGTTGGTAGCCAGTACCTGCCCGACACCGACGACCGGC

ACCGGATCGAGGAAAAGCGGAAGCGGACCTACGAGACATTCAAGAGCATCATGAAGAAGTC

CCCCTTCAGCGGCCCCACCGACCCTAGACCTCCACCTAGAAGAATCGCCGTGCCCAGCAGA

-continued

TCCAGCGCCAGCGTGCCAAAACCTGCCCCCCAGCCTTACCCCTTCACCAGCAGCCTGAGCA

CCATCAACTACGACGAGTTCCCTACCATGGTGTTCCCCAGCGGCCAGATCTCTCAGGCCTC

TGCTCTGGCTCCAGCCCCTCCTCAGGTGCTGCCTCAGGCTCCTGCTCCTGCACCAGCTCCA

GCCATGGTGTCTGCACTGGCTCAGGCACCAGCACCCGTGCCTGTGCTGGCTCCTGGACCT

CCACAGGCTGTGGCTCCACCAGCCCCTAAACCTACACAGGCCGGCGAGGGCACACTGTCT

GAAGCTCTGCTGCAGCTGCAGTTCGACGACGAGGATCTGGGAGCCCTGCTGGGAAACAGC

ACCGATCCTGCCGTGTTCACCGACCTGGCCAGCGTGGACAACAGCGAGTTCCAGCAGCTG

CTGAACCAGGGCATCCCTGTGGCCCCTCACACCACCGAGCCCATGCTGATGGAATACCCCG

AGGCCATCACCCGGCTCGTGACAGGCGCTCAGAGGCCTCCTGATCCAGCTCCTGCCCCTCT

GGGAGCACCAGGCCTGCCTAATGGACTGCTGTCTGGCGACGAGGACTTCAGCTCTATCGCC

GATATGGATTTCTCAGCCTTGCTGGGCTCTGGCAGCGGCAGCCGGGATTCCAGGGAAGGG

ATGTTTTTGCCGAAGCCTGAGGCCGGCTCCGCTATTAGTGACGTGTTTGAGGGCCGCGAGG

TGTGCCAGCCAAAACGAATCCGGCCATTTCATCCTCCAGGAAGTCCATGGGCCAACCGCCC

ACTCCCCGCCAGCCTCGCACCAACACCAACCGGTCCAGTACATGAGCCAGTCGGGTCACTG

ACCCCGGCACCAGTCCCTCAGCCACTGGATCCAGCGCCCGCAGTGACTCCCGAGGCCAGT

CACCTGTTGGAGGATCCCGATGAAGAGACGAGCCAGGCTGTCAAAGCCCTTCGGGAGATG

GCCGATACTGTGATTCCCCAGAAGGAAGAGGCTGCAATCTGTGGCCAAATGGACCTTTCCC

ATCCGCCCCCAAGGGGCCATCTGGATGAGCTGACAACCACACTTGAGTCCATGACCGAGGA

TCTGAACCTGGACTCACCCCTGACCCCGGAATTGAACGAGATTCTGGATACCTTCCTGAACG

ACGAGTGCCTCTTGCATGCCATGCATATCAGCACAGGACTGTCCATCTTCGACACATCTCTG

TTTTAA

RTW1351: pCAG-rAPOBEC1-gs-XTEN-gs-hdAsCas12a (D908A)-NLS-gs-UGI-NLS(AsBE1.1)

Rat APOBEC1 (rAPOBEC1) in bold upper case, inserted glycine dash-underlined glycine/serine linkers in italics, XTEN linker in lower case italics, human codon optimized *Acidaminococcus* sp. BV3L6 Cas12a (AsCas12a) in black, modified codon for DNase inactive (D908A) AsCas12a in doubleunderlinedlowercase, codons with silent mutations to remove NcoI sites doubleunderlinedUPPERCASE, nucleoplasmin NLS in lower case bold, UGI in BOLD UPPER CASE WITH HYPHEN-UNDERLINING, SV40 NLS in doubleunderlineditalics (SEQ ID NO: 438)

ATGGGCAGCTCAGAGACTGGCCCAGTGGCTGTGGACCCCACATTGAGACGGCGGATCGA

GCCCCATGAGTTTGAGGTATTCTTCGATCCGAGAGAGCTCCGCAAGGAGACCTGCCTGCT

TTACGAAATTAATTGGGGGGGCCGGCACTCCATTTGGCGACATACATCACAGAACACTAA

CAAGCACGTCGAAGTCAACTTCATCGAGAAGTTCACGACAGAAAGATATTTCTGTCCGAA

CACAAGGTGCAGCATTACCTGGTTTCTCAGCTGGAGCCCATGCGGCGAATGTAGTAGGGC

CATCACTGAATTCCTGTCAAGGTATCCCCACGTCACTCTGTTTATTTACATCGCAAGGCTGT

ACCACCACGCTGACCCCCGCAATCGACAAGGCCTGCGGGATTTGATCTCTTCAGGTGTGA

CTATCCAAATTATGACTGAGCAGGAGTCAGGATACTGCTGGAGAAACTTTGTGAATTATAG

CCCGAGTAATGAAGCCCACTGGCCTAGGTATCCCCATCTGTGGGTACGACTGTACGTTCTT

GAACTGTACTGCATCATACTGGGCCTGCCTCCTTGTCTCAACATTCTGAGAAGGAAGCAGC

CACAGCTGACATTCTTTACCATCGCTCTTCAGTCTTGTCATTACCAGCGACTGCCCCCACA

CATTCTCTGGGCCACCGGGTTGAAA*TCTGGTGGTTCTTCTGGTGGTTCTagcggcagcgagactcc*

*cgggacctcagagtccgccacacccgaaagtTCCGGAGGGAGTAGCGGCGGGTCT*ACACAGTTCGAGGG

-continued

CTTTACCAACCTGTATCAGGTGAGCAAGACACTGCGGTTTGAGCTGATCCCACAGGGCAAG

ACCCTGAAGCACATCCAGGAGCAGGGCTTCATCGAGGAGGACAAGGCCCGCAATGATCACT

ACAAGGAGCTGAAGCCCATCATCGATCGGATCTACAAGACCTATGCCGACCAGTGCCTGCA

GCTGGTGCAGCTGGATTGGGAGAACCTGAGCGCCGCCATCGACTCCTATAGAAAGGAGAAA

ACCGAGGAGACAAGGAACGCCCTGATCGAGGAGCAGGCCACATATCGCAATGCCATCCAC

GACTACTTCATCGGCCGGACAGACAACCTGACCGATGCCATCAATAAGAGACACGCCGAGA

TCTACAAGGGCCTGTTCAAGGCCGAGCTGTTTAATGGCAAGGTGCTGAAGCAGCTGGGCAC

CGTGACCACAACCGAGCACGAGAACGCCCTGCTGCGGAGCTTCGACAAGTTTACAACCTAC

TTCTCCGGCTTTTATGAGAACAGGAAGAACGTGTTCAGCGCCGAGGATATCAGCACAGCCAT

CCCACACCGCATCGTGCAGGACAACTTCCCCAAGTTTAAGGAGAATTGTCACATCTTCACAC

GCCTGATCACCGCCGTGCCCAGCCTGCGGGAGCACTTTGAGAACGTGAAGAAGGCCATCG

GCATCTTCGTGAGCACCTCCATCGAGGAGGTGTTTTCCTTCCCTTTTTATAACCAGCTGCTG

ACACAGACCCAGATCGACCTGTATAACCAGCTGCTGGGAGGAATCTCTCGGGAGGCAGGCA

CCGAGAAGATCAAGGGCCTGAACGAGGTGCTGAATCTGGCCATCCAGAAGAATGATGAGAC

AGCCCACATCATCGCCTCCCTGCCACACAGATTCATCCCCCTGTTTAAGCAGATCCTGTCCG

ATAGGAACACCCTGTCTTTCATCCTGGAGGAGTTTAAGAGCGACGAGGAAGTGATCCAGTC

CTTCTGCAAGTACAAGACACTGCTGAGAAACGAGAACGTGCTGGAGACAGCCGAGGCCCTG

TTTAACGAGCTGAACAGCATCGACCTGACACACATCTTCATCAGCCACAAGAAGCTGGAGAC

AATCAGCAGCGCCCTGTGCGACCACTGGGATACACTGAGGAATGCCCTGTATGAGCGGAGA

ATCTCCGAGCTGACAGGCAAGATCACCAAGTCTGCCAAGGAGAAGGTGCAGCGCAGCCTGA

AGCACGAGGATATCAACCTGCAGGAGATCATCTCTGCCGCAGGCAAGGAGCTGAGCGAGG

CCTTCAAGCAGAAAACCAGCGAGATCCTGTCCCACGCACACGCCGCCCTGGATCAGCCACT

GCCTACAACCCTGAAGAAGCAGGAGGAGAAGGAGATCCTGAAGTCTCAGCTGGACAGCCTG

CTGGGCCTGTACCACCTGCTGGACTGGTTTGCCGTGGATGAGTCCAACGAGGTGGACCCC

GAGTTCTCTGCCCGGCTGACCGGCATCAAGCTGGAGATGGAGCCTTCTCTGAGCTTCTACA

ACAAGGCCAGAAATTATGCCACCAAGAAGCCCTACTCCGTGGAGAAGTTCAAGCTGAACTTT

CAGATGCCTACACTGGCCTCTGGCTGGGACGTGAATAAGGAGAAGAACAATGGCGCCATCC

TGTTTGTGAAGAACGGCCTGTACTATCTGGGCATCATGCCAAAGCAGAAGGGCAGGTATAA

GGCCCTGAGCTTCGAGCCCACAGAGAAAACCAGCGAGGGCTTTGATAAGATGTACTATGAC

TACTTCCCTGATGCCGCCAAGATGATCCCAAAGTGCAGCACCCAGCTGAAGGCCGTGACAG

CCCACTTTCAGACCCACACAACCCCCATCCTGCTGTCCAACAATTTCATCGAGCCTCTGGAG

ATCACAAAGGAGATCTACGACCTGAACAATCCTGAGAAGGAGCCAAAGAAGTTTCAGACAGC

CTACGCCAAGAAAACCGGCGACCAGAAGGGCTACAGAGAGGCCCTGTGCAAGTGGATCGA

CTTCACAAGGGATTTTCTGTCCAAGTATACCAAGACAACCTCTATCGATCTGTCTAGCCTGC

GGCCATCCTCTCAGTATAAGGACCTGGGCGAGTACTATGCCGAGCTGAATCCCCTGCTGTA

CCACATCAGCTTCCAGAGAATCGCCGAGAAGGAGATCATGGATGCCGTGGAGACAGGCAAG

CTGTACCTGTTCCAGATCTATAACAAGGACTTTGCCAAGGGCCACCACGGCAAGCCTAATCT

GCACACACTGTATTGGACCGGCCTGTTTTCTCCAGAGAACCTGGCCAAGACAAGCATCAAG

CTGAATGGCCAGGCCGAGCTGTTCTACCGCCCTAAGTCCAGGATGAAGAGGATGGCACACC

GGCTGGGAGAGAAGATGCTGAACAAGAAGCTGAAGGATCAGAAAACCCCAATCCCCGACAC

-continued

CCTGTACCAGGAGCTGTACGACTATGTGAATCACAGACTGTCCCACGACCTGTCTGATGAG

GCCAGGGCCCTGCTGCCCAACGTGATCACCAAGGAGGTGTCTCACGAGATCATCAAGGATA

GGCGCTTTACCAGCGACAAGTTCTTTTTCCACGTGCCTATCACACTGAACTATCAGGCCGCC

AATTCCCCATCTAAGTTCAACCAGAGGGTGAATGCCTACCTGAAGGAGCACCCCGAGACAC

CTATCATCGGCATCgccCGGGGCGAGAGAAACCTGATCTATATCACAGTGATCGACTCCACC

GGCAAGATCCTGGAGCAGCGGAGCCTGAACACCATCCAGCAGTTTGATTACCAGAAGAAGC

TGGACAACAGGGAGAAGGAGAGGGTGGCAGCAAGGCAGGCCTGGTCTGTGGTGGGCACAA

TCAAGGATCTGAAGCAGGGCTATCTGAGCCAGGTCATCCACGAGATCGTGGACCTGATGAT

CCACTACCAGGCCGTGGTGGTGCTGGAGAACCTGAATTTCGGCTTTAAGAGCAAGAGGACC

GGCATCGCCGAGAAGGCCGTGTACCAGCAGTTCGAGAAGATGCTGATCGATAAGCTGAATT

GCCTGGTGCTGAAGGACTATCCAGCAGAGAAAGTGGGAGGCGTGCTGAACCCATACCAGCT

GACAGACCAGTTCACCTCCTTTGCCAAGATGGGCACCCAGTCTGGCTTCCTGTTTTACGTGC

CTGCCCCATATACATCTAAGATCGATCCCCTGACCGGCTTCGTGGACCCCTTCGTGTGGAAA

ACCATCAAGAATCACGAGAGCCGCAAGCACTTCCTGGAGGGCTTCGACTTTCTGCACTACG

ACGTGAAAACCGGCGACTTCATCCTGCACTTTAAGATGAACAGAAATCTGTCCTTCCAGAGG

GGCCTGCCCGGCTTTATGCCTGCATGGGATATCGTGTTCGAGAAGAACGAGACACAGTTTG

ACGCCAAGGGCACCCCTTTCATCGCCGGCAAGAGAATCGTGCCAGTGATCGAGAATCACAG

ATTCACCGGCAGATACCGGGACCTGTATCCTGCCAACGAGCTGATCGCCCTGCTGGAGGAG

AAGGGCATCGTGTTCAGGGATGGCTCCAACATCCTGCCAAAGCTGCTGGAGAATGACGATT

CTCACGCCATCGACACGATGGTGGCCCTGATCCGCAGCGTGCTGCAGATGCGGAACTCCA

ATGCCGCCACAGGCGAGGACTATATCAACAGCCCCGTGCGCGATCTGAATGGCGTGTGCTT

CGACTCCCGGTTTCAGAACCCAGAGTGGCCAATGGACGCCGATGCCAATGGCGCCTACCA

CATCGCCCTGAAGGGCCAGCTGCTGCTGAATCACCTGAAGGAGAGCAAGGATCTGAAGCTG

CAGAACGGCATCTCCAATCAGGACTGGCTGGCCTACATCCAGGAGCTGCGCAACaaaaggcc ggcggccacgaaaaaggccggccaggcaaaaaagaaaaag*GGATCCTCTGGTGGTTCTGGAGGATCTG*

*GTGGTTCT*ACTAATCTGTCAGATATTATTGAAAAGGAGACCGGTAAGCAACTGGTTATCCA

GGAATCCATCCTCATGCTCCCAGAGGAGGTGGAAGAAGTCATTGGGAACAAGCCGGAAA

GCGATATACTCGTGCACACCGCCTACGACGAGAGCACCGACGAGAATGTCATGCTTCTGA

CTAGCGACGCCCCTGAATACAAGCCTTGGGCTCTGGTCATACAGGATAGCAACGGTGAGA

ACAAGATTAAGATGCTC*TCTGGTGGTTCTCCCAAGAAGAAGAGGAAAGTC*TAA

RTW1295: pCAG-rAPOBEC1-gs-XTEN-gs-hdLbCas12a (D832A)-NLS-gs-UGI-NLS(LbBE1.1)

Rat APOBEC1 (rAPOBEC1) in bold upper case, inserted glycine dash-underlined glycine/serine linkers in italics, XTEN linker in lower case italics, human codon optimized Lachnospiraceae bacterium ND2006 Cas12a (LbCas12a) in black, modified codon for DNase inactive (D832A) LbCas12a in doubleunderlinedlowercase, codons with silent mutations to remove NcoI sites in doubleunderlinedUPPERCASE, nucleoplasmin NLS lower case bold, UGI in BOLD UPPER CASE WITH HYPHEN-UNDERLINING, SV40 NLS in *doubleunderlineditalics*

(SEQ ID NO:439)

ATGGGC

AGCTCAGAGACTGGCCCAGTGGCTGTGGACCCCACATTGAGACGGCGGATCGA

GCCCCATGAGTTTGAGGTATTCTTCGATCCGAGAGAGCTCCGCAAGGAGACCTGCCTGCT

TTACGAAATTAATTGGGGGGGCCGGCACTCCATTTGGCGACATACATCACAGAACACTAA

CAAGCACGTCGAAGTCAACTTCATCGAGAAGTTCACGACAGAAAGATATTTCTGTCCGAA

CACAAGGTGCAGCATTACCTGGTTTCTCAGCTGGAGCCCATGCGGCGAATGTAGTAGGGC

CATCACTGAATTCCTGTCAAGGTATCCCCACGTCACTCTGTTTATTTACATCGCAAGGCTGT

ACCACCACGCTGACCCCCGCAATCGACAAGGCCTGCGGGATTTGATCTCTTCAGGTGTGA

CTATCCAAATTATGACTGAGCAGGAGTCAGGATACTGCTGGAGAAACTTTGTGAATTATAG

CCCGAGTAATGAAGCCCACTGGCCTAGGTATCCCCATCTGTGGGTACGACTGTACGTTCTT

GAACTGTACTGCATCATACTGGGCCTGCCTCCTTGTCTCAACATTCTGAGAAGGAAGCAGC

CACAGCTGACATTCTTTACCATCGCTCTTCAGTCTTGTCATTACCAGCGACTGCCCCCACA

CATTCTCTGGGCCACCGGGTTGAAA*TCTGGTGGTTCTTCTGGTGGTTCTagcggcagcgagactcc*

*cgggacctcagagtccgccacacccgaaagtTCCGGAGGGAGTAGCGGCGGGTCT*AGCAAGCTGGAGAA

GTTTACAAACTGCTACTCCCTGTCTAAGACCCTGAGGTTCAAGGCCATCCCTGTGGGCAAGA

CCCAGGAGAACATCGACAATAAGCGGCTGCTGGTGGAGGACGAGAAGAGAGCCGAGGATT

ATAAGGGCGTGAAGAAGCTGCTGGATCGCTACTATCTGTCTTTTATCAACGACGTGCTGCAC

AGCATCAAGCTGAAGAATCTGAACAATTACATCAGCCTGTTCCGGAAGAAAACCAGAACCGA

GAAGGAGAATAAGGAGCTGGAGAACCTGGAGATCAATCTGCGGAAGGAGATCGCCAAGGC

CTTCAAGGGCAACGAGGGCTACAAGTCCCTGTTTAAGAAGGATATCATCGAGACAATCCTGC

CAGAGTTCCTGGACGATAAGGACGAGATCGCCCTGGTGAACAGCTTCAATGGCTTTACCAC

AGCCTTCACCGGCTTCTTTGATAACAGAGAGAATATGTTTTCCGAGGAGGCCAAGAGCACAT

CCATCGCCTTCAGGTGTATCAACGAGAATCTGACCCGCTACATCTCTAATATGGACATCTTC

GAGAAGGTGGACGCCATCTTTGATAAGCACGAGGTGCAGGAGATCAAGGAGAAGATCCTGA

ACAGCGACTATGATGTGGAGGATTTCTTTGAGGGCGAGTTCTTTAACTTTGTGCTGACACAG

GAGGGCATCGACGTGTATAACGCCATCATCGGCGGCTTCGTGACCGAGAGCGGCGAGAAG

ATCAAGGGCCTGAACGAGTACATCAACCTGTATAATCAGAAAACCAAGCAGAAGCTGCCTAA

GTTTAAGCCACTGTATAAGCAGGTGCTGAGCGATCGGGAGTCTCTGAGCTTCTACGGCGAG

GGCTATACATCCGATGAGGAGGTGCTGGAGGTGTTTAGAAACACCCTGAACAAGAACAGCG

AGATCTTCAGCTCCATCAAGAAGCTGGAGAAGCTGTTCAAGAATTTTGACGAGTACTCTAGC

GCCGGCATCTTTGTGAAGAACGGCCCCGCCATCAGCACAATCTCCAAGGATATCTTCGGCG

AGTGGAACGTGATCCGGGACAAGTGGAATGCCGAGTATGACGATATCCACCTGAAGAAGAA

GGCCGTGGTGACCGAGAAGTACGAGGACGATCGGAGAAAGTCCTTCAAGAAGATCGGCTC

CTTTTCTCTGGAGCAGCTGCAGGAGTACGCCGACGCCGATCTGTCTGTGGTGGAGAAGCTG

AAGGAGATCATCATCCAGAAGGTGGATGAGATCTACAAGGTGTATGGCTCCTCTGAGAAGCT

GTTCGACGCCGATTTTGTGCTGGAGAAGAGCCTGAAGAAGAACGACGCCGTGGTGGCCATC

ATGAAGGACCTGCTGGATTCTGTGAAGAGCTTCGAGAATTACATCAAGGCCTTCTTTGGCGA

GGGCAAGGAGACAAACAGGGACGAGTCCTTCTATGGCGATTTTGTGCTGGCCTACGACATC

CTGCTGAAGGTGGACCACATCTACGATGCCATCCGCAATTATGTGACCCAGAAGCCCTACTC

TAAGGATAAGTTCAAGCTGTATTTTCAGAACCCTCAGTTCATGGGCGGCTGGGACAAGGATA

-continued

AGGAGACAGACTATCGGGCCACCATCCTGAGATACGGCTCCAAGTACTATCTGGCCATCAT

GGATAAGAAGTACGCCAAGTGCCTGCAGAAGATCGACAAGGACGATGTGAACGGCAATTAC

GAGAAGATCAACTATAAGCTGCTGCCCGGCCCTAATAAGATGCTGCCAAAGGTGTTCTTTTC

TAAGAAGTGGATGGCCTACTATAACCCCAGCGAGGACATCCAGAAGATCTACAAGAATGGC

ACATTCAAGAAGGGCGATATGTTTAACCTGAATGACTGTCACAAGCTGATCGACTTCTTTAAG

GATAGCATCTCCCGGTATCCAAAGTGGTCCAATGCCTACGATTTCAACTTTTCTGAGACAGA

GAAGTATAAGGACATCGCCGGCTTTTACAGAGAGGTGGAGGAGCAGGGCTATAAGGTGAGC

TTCGAGTCTGCCAGCAAGAAGGAGGTGGATAAGCTGGTGGAGGAGGGCAAGCTGTATATGT

TCCAGATCTATAACAAGGACTTTTCCGATAAGTCTCACGGCACACCCAATCTGCACACCATG

TACTTCAAGCTGCTGTTTGACGAGAACAATCACGGACAGATCAGGCTGAGCGGAGGAGCAG

AGCTGTTCATGAGGCGCGCCTCCCTGAAGAAGGAGGAGCTGGTGGTGCACCCAGCCAACT

CCCCTATCGCCAACAAGAATCCAGATAATCCCAAGAAAACCACAACCCTGTCCTACGACGTG

TATAAGGATAAGAGGTTTTCTGAGGACCAGTACGAGCTGCACATCCCAATCGCCATCAATAA

GTGCCCCAAGAACATCTTCAAGATCAATACAGAGGTGCGCGTGCTGCTGAAGCACGACGAT

AACCCCTATGTGATCGGCATCgccAGGGGCGAGCGCAATCTGCTGTATATCGTGGTGGTGGA

CGGCAAGGGCAACATCGTGGAGCAGTATTCCCTGAACGAGATCATCAACAACTTCAACGGC

ATCAGGATCAAGACAGATTACCACTCTCTGCTGGACAAGAAGGAGAAGGAGAGGTTCGAGG

CCCGCCAGAACTGGACCTCCATCGAGAATATCAAGGAGCTGAAGGCCGGCTATATCTCTCA

GGTGGTGCACAAGATCTGCGAGCTGGTGGAGAAGTACGATGCCGTGATCGCCCTGGAGGA

CCTGAACTCTGGCTTTAAGAATAGCCGCGTGAAGGTGGAGAAGCAGGTGTATCAGAAGTTC

GAGAAGATGCTGATCGATAAGCTGAACTACATGGTGGACAAGAAGTCTAATCCTTGTGCAAC

AGGCGGCGCCCTGAAGGGCTATCAGATCACCAATAAGTTCGAGAGCTTTAAGTCCATGTCTA

CCCAGAACGGCTTCATCTTTTACATCCCTGCCTGGCTGACATCCAAGATCGATCCATCTACC

GGCTTTGTGAACCTGCTGAAAACCAAGTATACCAGCATCGCCGATTCCAAGAAGTTCATCAG

CTCCTTTGACAGGATCATGTACGTGCCCGAGGAGGATCTGTTCGAGTTTGCCCTGGACTATA

AGAACTTCTCTCGCACAGACGCCGATTACATCAAGAAGTGGAAGCTGTACTCCTACGGCAAC

CGGATCAGAATCTTCCGGAATCCTAAGAAGAACAACGTGTTCGACTGGGAGGAGGTGTGCC

TGACCAGCGCCTATAAGGAGCTGTTCAACAAGTACGGCATCAATTATCAGCAGGGCGATATC

AGAGCCCTGCTGTGCGAGCAGTCCGACAAGGCCTTCTACTCTAGCTTTATGGCCCTGATGA

GCCTGATGCTGCAGATGCGGAACAGCATCACAGGCCGCACCGACGTGGATTTTCTGATCAG

CCCTGTGAAGAACTCCGACGGCATCTTCTACGATAGCCGGAACTATGAGGCCCAGGAGAAT

GCCATCCTGCCAAAGAACGCCGACGCCAATGGCGCCTATAACATCGCCAGAAAGGTGCTGT

GGGCCATCGGCCAGTTCAAGAAGGCCGAGGACGAGAAGCTGGATAAGGTGAAGATCGCCA

TCTCTAACAAGGAGTGGCTGGAGTACGCCCAGACCAGCGTGAAGCACaaaaggccggcggccac gaaaaaggccggccaggcaaaaaagaaaaag*GGATCCTCTGGTGGTTCTGGAGGATCTGGTGGTTCT*

ACTAATCTGTCAGATATTATTGAAAAGGAGACCGGTAAGCAACTGGTTATCCAGGAATCCA

TCCTCATGCTCCCAGAGGAGGTGGAAGAAGTCATTGGGAACAAGCCGGAAAGCGATATA

CTCGTGCACACCGCCTACGACGAGAGCACCGACGAGAATGTCATGCTTCTGACTAGCGAC

-continued

GCCCCTGAATACAAGCCTTGGGCTCTGGTCATACAGGATAGCAACGGTGAGAACAAGATT

AAGATGCTC

TCTGGTGGTTCTCCCAAGAAGAAGAGGAAAGTCTAA

RTW1352: pCAG-rAPOBEC1-gs-XTEN-gs-hdeAsCas12a (E174R/S542R/K548R/D908A)-NLS-gs-UGI-NLS (eAsBE1.1)

Rat APOBEC1 (rAPOBEC1) in bold upper case, inserted glycine dash-underlined, glycine/serine linkers in italics, XTEN linker in lower case italics, human codon optimized *Acidaminococcus* sp. BV3L6 Cas12a (AsCas12a) in black, modified codons for DNase inactive (D908A) eAsCas12a (E174R/S542R/K548R) in doubleunderlinedlowercase, codons with silent mutations to remove NcoI sites in doubleunderlinedUPPERCASE, nucleoplasmin NLS lower case bold, UGI in BOLD UPPER CASE WITH HYPHEN-UNDERLINING, SV40 NLS in doubleunderlineditalics (SEQ ID NO: 440)

ATGGGCAGCTCAGAGACTGGCCCAGTGGCTGTGGACCCCACATTGAGACGGCGGATCGA

GCCCCATGAGTTTGAGGTATTCTTCGATCCGAGAGAGCTCCGCAAGGAGACCTGCCTGCT

TTACGAAATTAATTGGGGGGGCCGGCACTCCATTTGGCGACATACATCACAGAACACTAA

CAAGCACGTCGAAGTCAACTTCATCGAGAAGTTCACGACAGAAAGATATTTCTGTCCGAA

CACAAGGTGCAGCATTACCTGGTTTCTCAGCTGGAGCCCATGCGGCGAATGTAGTAGGGC

CATCACTGAATTCCTGTCAAGGTATCCCCACGTCACTCTGTTTATTTACATCGCAAGGCTGT

ACCACCACGCTGACCCCCGCAATCGACAAGGCCTGCGGGATTTGATCTCTTCAGGTGTGA

CTATCCAAATTATGACTGAGCAGGAGTCAGGATACTGCTGGAGAAACTTTGTGAATTATAG

CCCGAGTAATGAAGCCCACTGGCCTAGGTATCCCCATCTGTGGGTACGACTGTACGTTCTT

GAACTGTACTGCATCATACTGGGCCTGCCTCCTTGTCTCAACATTCTGAGAAGGAAGCAGC

CACAGCTGACATTCTTTACCATCGCTCTTCAGTCTTGTCATTACCAGCGACTGCCCCCACA

CATTCTCTGGGCCACCGGGTTGAAA*TCTGGTGGTTCTTCTGGTGGTTCTagcggcagcgagactcc*

*cgggacctcagagtccgccacacccgaaagtTCCGGAGGGAGTAGCGGCGGGTCT*ACACAGTTCGAGGG

CTTTACCAACCTGTATCAGGTGAGCAAGACACTGCGGTTTGAGCTGATCCCACAGGGCAAG

ACCCTGAAGCACATCCAGGAGCAGGGCTTCATCGAGGAGGACAAGGCCCGCAATGATCACT

ACAAGGAGCTGAAGCCCATCATCGATCGGATCTACAAGACCTATGCCGACCAGTGCCTGCA

GCTGGTGCAGCTGGATTGGGAGAACCTGAGCGCCGCCATCGACTCCTATAGAAAGGAGAAA

ACCGAGGAGACAAGGAACGCCCTGATCGAGGAGCAGGCCACATATCGCAATGCCATCCAC

GACTACTTCATCGGCCGGACAGACAACCTGACCGATGCCATCAATAAGAGACACGCCGAGA

TCTACAAGGGCCTGTTCAAGGCCGAGCTGTTTAATGGCAAGGTGCTGAAGCAGCTGGGCAC

CGTGACCACAACCGAGCACGAGAACGCCCTGCTGCGGAGCTTCGACAAGTTTACAACCTAC

TTCTCCGGCTTTTATagaAACAGGAAGAACGTGTTCAGCGCCGAGGATATCAGCACAGCCAT

CCCACACCGCATCGTGCAGGACAACTTCCCCAAGTTTAAGGAGAATTGTCACATCTTCACAC

GCCTGATCACCGCCGTGCCCAGCCTGCGGGAGCACTTTGAGAACGTGAAGAAGGCCATCG

GCATCTTCGTGAGCACCTCCATCGAGGAGGTGTTTTCCTTCCCTTTTTATAACCAGCTGCTG

ACACAGACCCAGATCGACCTGTATAACCAGCTGCTGGGAGGAATCTCTCGGGAGGCAGGCA

CCGAGAAGATCAAGGGCCTGAACGAGGTGCTGAATCTGGCCATCCAGAAGAATGATGAGAC

AGCCCACATCATCGCCTCCCTGCCACACAGATTCATCCCCCTGTTTAAGCAGATCCTGTCCG

ATAGGAACACCCTGTCTTTCATCCTGGAGGAGTTTAAGAGCGACGAGGAAGTGATCCAGTC

-continued

CTTCTGCAAGTACAAGACACTGCTGAGAAACGAGAACGTGCTGGAGACAGCCGAGGCCCTG

TTTAACGAGCTGAACAGCATCGACCTGACACACATCTTCATCAGCCACAAGAAGCTGGAGAC

AATCAGCAGCGCCCTGTGCGACCACTGGGATACACTGAGGAATGCCCTGTATGAGCGGAGA

ATCTCCGAGCTGACAGGCAAGATCACCAAGTCTGCCAAGGAGAAGGTGCAGCGCAGCCTGA

AGCACGAGGATATCAACCTGCAGGAGATCATCTCTGCCGCAGGCAAGGAGCTGAGCGAGG

CCTTCAAGCAGAAAACCAGCGAGATCCTGTCCCACGCACACGCCGCCCTGGATCAGCCACT

GCCTACAACCCTGAAGAAGCAGGAGGAGAAGGAGATCCTGAAGTCTCAGCTGGACAGCCTG

CTGGGCCTGTACCACCTGCTGGACTGGTTTGCCGTGGATGAGTCCAACGAGGTGGACCCC

GAGTTCTCTGCCCGGCTGACCGGCATCAAGCTGGAGATGGAGCCTTCTCTGAGCTTCTACA

ACAAGGCCAGAAATTATGCCACCAAGAAGCCCTACTCCGTGGAGAAGTTCAAGCTGAACTTT

CAGATGCCTACACTGGCCagaGGCTGGGACGTGAATagaGAGAAGAACAATGGCGCCATCCT

GTTTGTGAAGAACGGCCTGTACTATCTGGGCATCATGCCAAAGCAGAAGGGCAGGTATAAG

GCCCTGAGCTTCGAGCCCACAGAGAAAACCAGCGAGGGCTTTGATAAGATGTACTATGACT

ACTTCCCTGATGCCGCCAAGATGATCCCAAAGTGCAGCACCCAGCTGAAGGCCGTGACAGC

CCACTTTCAGACCCACACAACCCCCATCCTGCTGTCCAACAATTTCATCGAGCCTCTGGAGA

TCACAAAGGAGATCTACGACCTGAACAATCCTGAGAAGGAGCCAAAGAAGTTTCAGACAGC

CTACGCCAAGAAAACCGGCGACCAGAAGGGCTACAGAGAGGCCCTGTGCAAGTGGATCGA

CTTCACAAGGGATTTTCTGTCCAAGTATACCAAGACAACCTCTATCGATCTGTCTAGCCTGC

GGCCATCCTCTCAGTATAAGGACCTGGGCGAGTACTATGCCGAGCTGAATCCCCTGCTGTA

CCACATCAGCTTCCAGAGAATCGCCGAGAAGGAGATCATGGATGCCGTGGAGACAGGCAAG

CTGTACCTGTTCCAGATCTATAACAAGGACTTTGCCAAGGGCCACCACGGCAAGCCTAATCT

GCACACACTGTATTGGACCGGCCTGTTTTCTCCAGAGAACCTGGCCAAGACAAGCATCAAG

CTGAATGGCCAGGCCGAGCTGTTCTACCGCCCTAAGTCCAGGATGAAGAGGATGGCACACC

GGCTGGGAGAGAAGATGCTGAACAAGAAGCTGAAGGATCAGAAAACCCCAATCCCCGACAC

CCTGTACCAGGAGCTGTACGACTATGTGAATCACAGACTGTCCCACGACCTGTCTGATGAG

GCCAGGGCCCTGCTGCCCAACGTGATCACCAAGGAGGTGTCTCACGAGATCATCAAGGATA

GGCGCTTTACCAGCGACAAGTTCTTTTTCCACGTGCCTATCACACTGAACTATCAGGCCGCC

AATTCCCCATCTAAGTTCAACCAGAGGGTGAATGCCTACCTGAAGGAGCACCCCGAGACAC

CTATCATCGGCATCgccCGGGGCGAGAGAAACCTGATCTATATCACAGTGATCGACTCCACC

GGCAAGATCCTGGAGCAGCGGAGCCTGAACACCATCCAGCAGTTTGATTACCAGAAGAAGC

TGGACAACAGGGAGAAGGAGAGGGTGGCAGCAAGGCAGGCCTGGTCTGTGGTGGGCACAA

TCAAGGATCTGAAGCAGGGCTATCTGAGCCAGGTCATCCACGAGATCGTGGACCTGATGAT

CCACTACCAGGCCGTGGTGGTGCTGGAGAACCTGAATTTCGGCTTTAAGAGCAAGAGGACC

GGCATCGCCGAGAAGGCCGTGTACCAGCAGTTCGAGAAGATGCTGATCGATAAGCTGAATT

GCCTGGTGCTGAAGGACTATCCAGCAGAGAAAGTGGGAGGCGTGCTGAACCCATACCAGCT

GACAGACCAGTTCACCTCCTTTGCCAAGATGGGCACCCAGTCTGGCTTCCTGTTTTACGTGC

CTGCCCCATATACATCTAAGATCGATCCCCTGACCGGCTTCGTGGACCCCTTCGTGTGGAAA

ACCATCAAGAATCACGAGAGCCGCAAGCACTTCCTGGAGGGCTTCGACTTTCTGCACTACG

ACGTGAAAACCGGCGACTTCATCCTGCACTTTAAGATGAACAGAAATCTGTCCTTCCAGAGG

GGCCTGCCCGGCTTTATGCCTGCATGGGATATCGTGTTCGAGAAGAACGAGACACAGTTTG

ACGCCAAGGGCACCCCTTTCATCGCCGGCAAGAGAATCGTGCCAGTGATCGAGAATCACAG

-continued

ATTCACCGGCAGATACCGGGACCTGTATCCTGCCAACGAGCTGATCGCCCTGCTGGAGGAG

AAGGGCATCGTGTTCAGGGATGGCTCCAACATCCTGCCAAAGCTGCTGGAGAATGACGATT

CTCACGCCATCGACACGATGGTGGCCCTGATCCGCAGCGTGCTGCAGATGCGGAACTCCAA

TGCCGCCACAGGCGAGGACTATATCAACAGCCCCGTGCGCGATCTGAATGGCGTGTGCTTC

GACTCCCGGTTTCAGAACCCAGAGTGGCCAATGGACGCCGATGCCAATGGCGCCTACCACA

TCGCCCTGAAGGGCCAGCTGCTGCTGAATCACCTGAAGGAGAGCAAGGATCTGAAGCTGCA

GAACGGCATCTCCAATCAGGACTGGCTGGCCTACATCCAGGAGCTGCGCAACaaaaggccggc ggccacgaaaaaggccggccaggcaaaaaagaaaaag*GGATCCTCTGGTGGTTCTGGAGGATCTGGTG*

*GTTCT*ACTAATCTGTCAGATATTATTGAAAAGGAGACCGGTAAGCAACTGGTTATCCAGGA

ATCCATCCTCATGCTCCCAGAGGAGGTGGAAGAAGTCATTGGGAACAAGCCCGGAAAGCG

ATATACTCGTGCACACCGCCTACGACGAGAGCACCGACGAGAATGTCATGCTTCTGACTA

GCGACGCCCCTGAATACAAGCCTTGGGCTCTGGTCATACAGGATAGCAACGGTGAGAACA

AGATTAAGATGCTC*TCTGGTGGTTCTCCCAAGAAGAAGAGGAAAGTC*TAA

RTW1348: pCAG-2×NLS-rAPOBEC1-gs-XTEN-gs-hdeAsCas12a(E174R/S542R/K548R/D908A)-NLS-gs-UGI-NLS(eAsBE1.2)

Rat APOBEC1 (rAPOBEC1) in bold upper case, inserted glycine dash-underlined SV40 NLS in doubleunderlineditalics, glycine/serine linkers in italics, XTEN linker in lower case italics, human codon optimized *Acidaminococcus* sp. BV3L6 Cas12a (AsCas12a) in black, modified codons for DNase inactive (D908A) eAsCas12a (E174R/S542R/K548R) in doubleunderlinedlowercase, codons with silent mutations to remove NcoI sites double underlined UPPER CASE, nucleoplasmin NLS lower case bold, UGI in BOLD UPPER CASE WITH HYPHEN-UNDERLINING.

(SEQ ID NO: 441)

ATGGGC*CCAAAGAAAAAGAGGAAAGTCGGCAGTGGACCTAAAAAGAAACGAAAGGTTGGGT*

*CAGGT*AGCTCAGAGACTGGCCCAGTGGCTGTGGACCCCACATTGAGACGGCGGATCGAG

CCCCATGAGTTTGAGGTATTCTTCGATCCGAGAGAGCTCCGCAAGGAGACCTGCCTGCTTT

ACGAAATTAATTGGGGGGGCCGGCACTCCATTTGGCGACATACATCACAGAACACTAACA

AGCACGTCGAAGTCAACTTCATCGAGAAGTTCACGACAGAAAGATATTTCTGTCCGAACA

CAAGGTGCAGCATTACCTGGTTTCTCAGCTGGAGCCCATGCGGCGAATGTAGTAGGGCCA

TCACTGAATTCCTGTCAAGGTATCCCCACGTCACTCTGTTTATTTACATCGCAAGGCTGTAC

CACCACGCTGACCCCCGCAATCGACAAGGCCTGCGGGATTTGATCTCTTCAGGTGTGACT

ATCCAAATTATGACTGAGCAGGAGTCAGGATACTGCTGGAGAAACTTTGTGAATTATAGCC

CGAGTAATGAAGCCCACTGGCCTAGGTATCCCCATCTGTGGGTACGACTGTACGTTCTTGA

ACTGTACTGCATCATACTGGGCCTGCCTCCTTGTCTCAACATTCTGAGAAGGAAGCAGCCA

CAGCTGACATTCTTTACCATCGCTCTTCAGTCTTGTCATTACCAGCGACTGCCCCCACACA

TTCTCTGGGCCACCGGGTTGAAA*TCTGGTGGTTCTTCTGGTGGTTCTagcggcagcgagactcccg*

*ggacctcagagtccgccacacccgaaagtTCCGGAGGGAGTAGCGGCGGGTCT*ACACAGTTCGAGGGC

TTTACCAACCTGTATCAGGTGAGCAAGACACTGCGGTTTGAGCTGATCCCACAGGGCAAGA

CCCTGAAGCACATCCAGGAGCAGGGCTTCATCGAGGAGGACAAGGCCCGCAATGATCACTA

CAAGGAGCTGAAGCCCATCATCGATCGGATCTACAAGACCTATGCCGACCAGTGCCTGCAG

CTGGTGCAGCTGGATTGGGAGAACCTGAGCGCCGCCATCGACTCCTATAGAAAGGAGAAAA

-continued

CCGAGGAGACAAGGAACGCCCTGATCGAGGAGCAGGCCACATATCGCAATGCCATCCACG

ACTACTTCATCGGCCGGACAGACAACCTGACCGATGCCATCAATAAGAGACACGCCGAGAT

CTACAAGGGCCTGTTCAAGGCCGAGCTGTTTAATGGCAAGGTGCTGAAGCAGCTGGGCACC

GTGACCACAACCGAGCACGAGAACGCCCTGCTGCGGAGCTTCGACAAGTTTACAACCTACT

TCTCCGGCTTTTATAGAAACAGGAAGAACGTGTTCAGCGCCGAGGATATCAGCACAGCCATC

CCACACCGCATCGTGCAGGACAACTTCCCCAAGTTTAAGGAGAATTGTCACATCTTCACACG

CCTGATCACCGCCGTGCCCAGCCTGCGGGAGCACTTTGAGAACGTGAAGAAGGCCATCGG

CATCTTCGTGAGCACCTCCATCGAGGAGGTGTTTTCCTTCCCTTTTTATAACCAGCTGCTGA

CACAGACCCAGATCGACCTGTATAACCAGCTGCTGGGAGGAATCTCTCGGGAGGCAGGCAC

CGAGAAGATCAAGGGCCTGAACGAGGTGCTGAATCTGGCCATCCAGAAGAATGATGAGACA

GCCCACATCATCGCCTCCCTGCCACACAGATTCATCCCCCTGTTTAAGCAGATCCTGTCCGA

TAGGAACACCCTGTCTTTCATCCTGGAGGAGTTTAAGAGCGACGAGGAAGTGATCCAGTCCT

TCTGCAAGTACAAGACACTGCTGAGAAACGAGAACGTGCTGGAGACAGCCGAGGCCCTGTT

TAACGAGCTGAACAGCATCGACCTGACACACATCTTCATCAGCCACAAGAAGCTGGAGACAA

TCAGCAGCGCCCTGTGCGACCACTGGGATACACTGAGGAATGCCCTGTATGAGCGGAGAAT

CTCCGAGCTGACAGGCAAGATCACCAAGTCTGCCAAGGAGAAGGTGCAGCGCAGCCTGAA

GCACGAGGATATCAACCTGCAGGAGATCATCTCTGCCGCAGGCAAGGAGCTGAGCGAGGC

CTTCAAGCAGAAAACCAGCGAGATCCTGTCCCACGCACACGCCGCCCTGGATCAGCCACTG

CCTACAACCCTGAAGAAGCAGGAGGAGAAGGAGATCCTGAAGTCTCAGCTGGACAGCCTGC

TGGGCCTGTACCACCTGCTGGACTGGTTTGCCGTGGATGAGTCCAACGAGGTGGACCCCG

AGTTCTCTGCCCGGCTGACCGGCATCAAGCTGGAGATGGAGCCTTCTCTGAGCTTCTACAA

CAAGGCCAGAAATTATGCCACCAAGAAGCCCTACTCCGTGGAGAAGTTCAAGCTGAACTTTC

AGATGCCTACACTGGCCagaGGCTGGGACGTGAATagaGAGAAGAACAATGGCGCCATCCTG

TTTGTGAAGAACGGCCTGTACTATCTGGGCATCATGCCAAAGCAGAAGGGCAGGTATAAGG

CCCTGAGCTTCGAGCCCACAGAGAAAACCAGCGAGGGCTTTGATAAGATGTACTATGACTA

CTTCCCTGATGCCGCCAAGATGATCCCAAAGTGCAGCACCCAGCTGAAGGCCGTGACAGCC

CACTTTCAGACCCACACAACCCCCATCCTGCTGTCCAACAATTTCATCGAGCCTCTGGAGAT

CACAAAGGAGATCTACGACCTGAACAATCCTGAGAAGGAGCCAAAGAAGTTTCAGACAGCC

TACGCCAAGAAAACCGGCGACCAGAAGGGCTACAGAGAGGCCCTGTGCAAGTGGATCGAC

TTCACAAGGGATTTTCTGTCCAAGTATACCAAGACAACCTCTATCGATCTGTCTAGCCTGCG

GCCATCCTCTCAGTATAAGGACCTGGGCGAGTACTATGCCGAGCTGAATCCCCTGCTGTAC

CACATCAGCTTCCAGAGAATCGCCGAGAAGGAGATCATGGATGCCGTGGAGACAGGCAAGC

TGTACCTGTTCCAGATCTATAACAAGGACTTTGCCAAGGGCCACCACGGCAAGCCTAATCTG

CACACACTGTATTGGACCGGCCTGTTTTCTCCAGAGAACCTGGCCAAGACAAGCATCAAGCT

GAATGGCCAGGCCGAGCTGTTCTACCGCCCTAAGTCCAGGATGAAGAGGATGGCACACCG

GCTGGGAGAGAAGATGCTGAACAAGAAGCTGAAGGATCAGAAAACCCCAATCCCCGACACC

CTGTACCAGGAGCTGTACGACTATGTGAATCACAGACTGTCCCACGACCTGTCTGATGAGG

CCAGGGCCCTGCTGCCCAACGTGATCACCAAGGAGGTGTCTCACGAGATCATCAAGGATAG

GCGCTTTACCAGCGACAAGTTCTTTTTCCACGTGCCTATCACACTGAACTATCAGGCCGCCA

ATTCCCCATCTAAGTTCAACCAGAGGGTGAATGCCTACCTGAAGGAGCACCCCGAGACACC

-continued

TATCATCGGCATCgccCGGGGCGAGAGAAACCTGATCTATATCACAGTGATCGACTCCACCG

GCAAGATCCTGGAGCAGCGGAGCCTGAACACCATCCAGCAGTTTGATTACCAGAAGAAGCT

GGACAACAGGGAGAAGGAGAGGGTGGCAGCAAGGCAGGCCTGGTCTGTGGTGGGCACAAT

CAAGGATCTGAAGCAGGGCTATCTGAGCCAGGTCATCCACGAGATCGTGGACCTGATGATC

CACTACCAGGCCGTGGTGGTGCTGGAGAACCTGAATTTCGGCTTTAAGAGCAAGAGGACCG

GCATCGCCGAGAAGGCCGTGTACCAGCAGTTCGAGAAGATGCTGATCGATAAGCTGAATTG

CCTGGTGCTGAAGGACTATCCAGCAGAGAAAGTGGGAGGCGTGCTGAACCCATACCAGCTG

ACAGACCAGTTCACCTCCTTTGCCAAGATGGGCACCCAGTCTGGCTTCCTGTTTTACGTGCC

TGCCCCATATACATCTAAGATCGATCCCCTGACCGGCTTCGTGGACCCCTTCGTGTGGAAAA

CCATCAAGAATCACGAGAGCCGCAAGCACTTCCTGGAGGGCTTCGACTTTCTGCACTACGA

CGTGAAAACCGGCGACTTCATCCTGCACTTTAAGATGAACAGAAATCTGTCCTTCCAGAGGG

GCCTGCCCGGCTTTATGCCTGCATGGGATATCGTGTTCGAGAAGAACGAGACACAGTTTGA

CGCCAAGGGCACCCCTTTCATCGCCGGCAAGAGAATCGTGCCAGTGATCGAGAATCACAGA

TTCACCGGCAGATACCGGGACCTGTATCCTGCCAACGAGCTGATCGCCCTGCTGGAGGAGA

AGGGCATCGTGTTCAGGGATGGCTCCAACATCCTGCCAAAGCTGCTGGAGAATGACGATTC

TCACGCCATCGACACGATGGTGGCCCTGATCCGCAGCGTGCTGCAGATGCGGAACTCCAAT

GCCGCCACAGGCGAGGACTATATCAACAGCCCCGTGCGCGATCTGAATGGCGTGTGCTTC

GACTCCCGGTTTCAGAACCCAGAGTGGCCAATGGACGCCGATGCCAATGGCGCCTACCACA

TCGCCCTGAAGGGCCAGCTGCTGCTGAATCACCTGAAGGAGAGCAAGGATCTGAAGCTGCA

GAACGGCATCTCCAATCAGGACTGGCTGGCCTACATCCAGGAGCTGCGCAACaaaaggccggc ggccacgaaaaaggccggccaggcaaaaaagaaaaag*GGATCCTCTGGTGGTTCTGGAGGATCTGGTG*

*GTTCT*ACTAATCTGTCAGATATTATTGAAAAGGAGACCGGTAAGCAACTGGTTATCCAGGA

ATCCATCCTCATGCTCCCAGAGGAGGTGGAAGAAGTCATTGGGAACAAGCCCGGAAAGCG

ATATACTCGTGCACACCGCCTACGACGAGAGCACCGACGAGAATGTCATGCTTCTGACTA

GCGACGCCCCTGAATACAAGCCTTGGGCTCTGGTCATACAGGATAGCAACGGTGAGAACA

AGATTAAGATGCTC*TCTGGTGGTTCTCCCAAGAAGAAGAGGAAAGTC*TAA

RTW1296: pCAG-rAPOBEC1-gs-XTEN-gs-hdeAsCas12a (E174R/S542R/K548R/D908A)-gs-UGI-NLS(eAsBE1.3)

Rat APOBEC1 (rAPOBEC1) in bold upper case, inserted glycine dash-underlined glycine/serine linkers in italics, XTEN linker lower case italics, human codon optimized *Acidaminococcus* sp. BV3L6 Cas12a (AsCas12a) in black, modified codons for DNase inactive (D908A) eAsCas12a (E174R/S542R/K548R) in doubleunderlinedlowercase, codons with silent mutations to remove NcoI sites in bold underlined black, UGI in BOLD UPPER CASE WITH HYPHEN-UNDERLINING, SV40 NLS in doubleunderlineditalics (SEQ ID NO: 442)

ATGGGCAGCTCAGAGACTGGCCCAGTGGCTGTGGACCCCACATTGAGACGGCGGATCGA

GCCCCATGAGTTTGAGGTATTCTTCGATCCGAGAGAGCTCCGCAAGGAGACCTGCCTGCT

TTACGAAATTAATTGGGGGGGCCGGCACTCCATTTGGCGACATACATCACAGAACACTAA

CAAGCACGTCGAAGTCAACTTCATCGAGAAGTTCACGACAGAAAGATATTTCTGTCCGAA

CACAAGGTGCAGCATTACCTGGTTTCTCAGCTGGAGCCCATGCGGCGAATGTAGTAGGGC

CATCACTGAATTCCTGTCAAGGTATCCCCACGTCACTCTGTTTATTTACATCGCAAGGCTGT

-continued

ACCACCACGCTGACCCCCGCAATCGACAAGGCCTGCGGGATTTGATCTCTTCAGGTGTGA

CTATCCAAATTATGACTGAGCAGGAGTCAGGATACTGCTGGAGAAACTTTGTGAATTATAG

CCCGAGTAATGAAGCCCACTGGCCTAGGTATCCCCATCTGTGGGTACGACTGTACGTTCTT

GAACTGTACTGCATCATACTGGGCCTGCCTCCTTGTCTCAACATTCTGAGAAGGAAGCAGC

CACAGCTGACATTCTTTACCATCGCTCTTCAGTCTTGTCATTACCAGCGACTGCCCCCACA

CATTCTCTGGGCCACCGGGTTGAAA*TCTGGTGGTTCTTCTGGTGGTTCT*AGCGGCAGCGAG

ACTCCCGGGACCTCAGAGTCCGCCACACCCGAAAGT*TCCGGAGGGAGTAGCGGCGGGTCT*

ACACAGTTCGAGGGCTTTACCAACCTGTATCAGGTGAGCAAGACACTGCGGTTTGAGCTGAT

CCCACAGGGCAAGACCCTGAAGCACATCCAGGAGCAGGGCTTCATCGAGGAGGACAAGGC

CCGCAATGATCACTACAAGGAGCTGAAGCCCATCATCGATCGGATCTACAAGACCTATGCC

GACCAGTGCCTGCAGCTGGTGCAGCTGGATTGGGAGAACCTGAGCGCCGCCATCGACTCC

TATAGAAAGGAGAAAACCGAGGAGACAAGGAACGCCCTGATCGAGGAGCAGGCCACATATC

GCAATGCCATCCACGACTACTTCATCGGCCGGACAGACAACCTGACCGATGCCATCAATAA

GAGACACGCCGAGATCTACAAGGGCCTGTTCAAGGCCGAGCTGTTTAATGGCAAGGTGCTG

AAGCAGCTGGGCACCGTGACCACAACCGAGCACGAGAACGCCCTGCTGCGGAGCTTCGAC

AAGTTTACAACCTACTTCTCCGGCTTTTATagaAACAGGAAGAACGTGTTCAGCGCCGAGGAT

ATCAGCACAGCCATCCCACACCGCATCGTGCAGGACAACTTCCCCAAGTTTAAGGAGAATTG

TCACATCTTCACACGCCTGATCACCGCCGTGCCCAGCCTGCGGGAGCACTTTGAGAACGTG

AAGAAGGCCATCGGCATCTTCGTGAGCACCTCCATCGAGGAGGTGTTTTCCTTCCCTTTTTA

TAACCAGCTGCTGACACAGACCCAGATCGACCTGTATAACCAGCTGCTGGGAGGAATCTCT

CGGGAGGCAGGCACCGAGAAGATCAAGGGCCTGAACGAGGTGCTGAATCTGGCCATCCAG

AAGAATGATGAGACAGCCCACATCATCGCCTCCCTGCCACACAGATTCATCCCCCTGTTTAA

GCAGATCCTGTCCGATAGGAACACCCTGTCTTTCATCCTGGAGGAGTTTAAGAGCGACGAG

GAAGTGATCCAGTCCTTCTGCAAGTACAAGACACTGCTGAGAAACGAGAACGTGCTGGAGA

CAGCCGAGGCCCTGTTTAACGAGCTGAACAGCATCGACCTGACACACATCTTCATCAGCCA

CAAGAAGCTGGAGACAATCAGCAGCGCCCTGTGCGACCACTGGGATACACTGAGGAATGCC

CTGTATGAGCGGAGAATCTCCGAGCTGACAGGCAAGATCACCAAGTCTGCCAAGGAGAAGG

TGCAGCGCAGCCTGAAGCACGAGGATATCAACCTGCAGGAGATCATCTCTGCCGCAGGCAA

GGAGCTGAGCGAGGCCTTCAAGCAGAAAACCAGCGAGATCCTGTCCCACGCACACGCCGC

CCTGGATCAGCCACTGCCTACAACCCTGAAGAAGCAGGAGGAGAAGGAGATCCTGAAGTCT

CAGCTGGACAGCCTGCTGGGCCTGTACCACCTGCTGGACTGGTTTGCCGTGGATGAGTCCA

ACGAGGTGGACCCCGAGTTCTCTGCCCGGCTGACCGGCATCAAGCTGGAGATGGAGCCTT

CTCTGAGCTTCTACAACAAGGCCAGAAATTATGCCACCAAGAAGCCCTACTCCGTGGAGAAG

TTCAAGCTGAACTTTCAGATGCCTACACTGGCCagaGGCTGGGACGTGAATagaGAGAAGAAC

AATGGCGCCATCCTGTTTGTGAAGAACGGCCTGTACTATCTGGGCATCATGCCAAAGCAGAA

GGGCAGGTATAAGGCCCTGAGCTTCGAGCCCACAGAGAAAACCAGCGAGGGCTTTGATAAG

ATGTACTATGACTACTTCCCTGATGCCGCCAAGATGATCCCAAAGTGCAGCACCCAGCTGAA

GGCCGTGACAGCCCACTTTCAGACCCACACAACCCCCATCCTGCTGTCCAACAATTTCATCG

AGCCTCTGGAGATCACAAAGGAGATCTACGACCTGAACAATCCTGAGAAGGAGCCAAAGAA

GTTTCAGACAGCCTACGCCAAGAAAACCGGCGACCAGAAGGGCTACAGAGAGGCCCTGTG

CAAGTGGATCGACTTCACAAGGGATTTTCTGTCCAAGTATACCAAGACAACCTCTATCGATCT

-continued

GTCTAGCCTGCGGCCATCCTCTCAGTATAAGGACCTGGGCGAGTACTATGCCGAGCTGAAT

CCCCTGCTGTACCACATCAGCTTCCAGAGAATCGCCGAGAAGGAGATCATGGATGCCGTGG

AGACAGGCAAGCTGTACCTGTTCCAGATCTATAACAAGGACTTTGCCAAGGGCCACCACGG

CAAGCCTAATCTGCACACACTGTATTGGACCGGCCTGTTTTCTCCAGAGAACCTGGCCAAGA

CAAGCATCAAGCTGAATGGCCAGGCCGAGCTGTTCTACCGCCCTAAGTCCAGGATGAAGAG

GATGGCACACCGGCTGGGAGAGAAGATGCTGAACAAGAAGCTGAAGGATCAGAAAACCCCA

ATCCCCGACACCCTGTACCAGGAGCTGTACGACTATGTGAATCACAGACTGTCCCACGACC

TGTCTGATGAGGCCAGGGCCCTGCTGCCCAACGTGATCACCAAGGAGGTGTCTCACGAGAT

CATCAAGGATAGGCGCTTTACCAGCGACAAGTTCTTTTTCCACGTGCCTATCACACTGAACT

ATCAGGCCGCCAATTCCCCATCTAAGTTCAACCAGAGGGTGAATGCCTACCTGAAGGAGCA

CCCCGAGACACCTATCATCGGCATCgccCGGGGCGAGAGAAACCTGATCTATATCACAGTGA

TCGACTCCACCGGCAAGATCCTGGAGCAGCGGAGCCTGAACACCATCCAGCAGTTTGATTA

CCAGAAGAAGCTGGACAACAGGGAGAAGGAGAGGGTGGCAGCAAGGCAGGCCTGGTCTGT

GGTGGGCACAATCAAGGATCTGAAGCAGGGCTATCTGAGCCAGGTCATCCACGAGATCGTG

GACCTGATGATCCACTACCAGGCCGTGGTGGTGCTGGAGAACCTGAATTTCGGCTTTAAGA

GCAAGAGGACCGGCATCGCCGAGAAGGCCGTGTACCAGCAGTTCGAGAAGATGCTGATCG

ATAAGCTGAATTGCCTGGTGCTGAAGGACTATCCAGCAGAGAAAGTGGGAGGCGTGCTGAA

CCCATACCAGCTGACAGACCAGTTCACCTCCTTTGCCAAGATGGGCACCCAGTCTGGCTTC

CTGTTTTACGTGCCTGCCCCATATACATCTAAGATCGATCCCCTGACCGGCTTCGTGGACCC

CTTCGTGTGGAAAACCATCAAGAATCACGAGAGCCGCAAGCACTTCCTGGAGGGCTTCGAC

TTTCTGCACTACGACGTGAAAACCGGCGACTTCATCCTGCACTTTAAGATGAACAGAAATCT

GTCCTTCCAGAGGGGCCTGCCCGGCTTTATGCCTGCATGGGATATCGTGTTCGAGAAGAAC

GAGACACAGTTTGACGCCAAGGGCACCCCTTTCATCGCCGGCAAGAGAATCGTGCCAGTGA

TCGAGAATCACAGATTCACCGGCAGATACCGGGACCTGTATCCTGCCAACGAGCTGATCGC

CCTGCTGGAGGAGAAGGGCATCGTGTTCAGGGATGGCTCCAACATCCTGCCAAAGCTGCTG

GAGAATGACGATTCTCACGCCATCGACACGATGGTGGCCCTGATCCGCAGCGTGCTGCAGA

TGCGGAACTCCAATGCCGCCACAGGCGAGGACTATATCAACAGCCCCGTGCGCGATCTGAA

TGGCGTGTGCTTCGACTCCCGGTTTCAGAACCCAGAGTGGCCAATGGACGCCGATGCCAAT

GGCGCCTACCACATCGCCCTGAAGGGCCAGCTGCTGCTGAATCACCTGAAGGAGAGCAAG

GATCTGAAGCTGCAGAACGGCATCTCCAATCAGGACTGGCTGGCCTACATCCAGGAGCTGC

GCAAC*TCTGGTGGTTCTGGAGGATCTGGTGGTTCT*ACTAATCTGTCAGATATTATTGAAAAG

GAGACCGGTAAGCAACTGGTTATCCAGGAATCCATCCTCATGCTCCCAGAGGAGGTGGAA

GAAGTCATTGGGAACAAGCCGGAAAGCGATATACTCGTGCACACCGCCTACGACGAGAG

CACCGACGAGAATGTCATGCTTCTGACTAGCGACGCCCCTGAATACAAGCCTTGGGCTCT

GGTCATACAGGATAGCAACGGTGAGAACAAGATTAAGATGCTC*TCTGGTGGTTCTCCCAA*

*GAAGAAGAGGAAAGTCT*AA

Nucleotide Sequence of (JG1211) pCAG-human-dLbCpf1 (D832A)-NLS(nucleoplasmin)-3×HA-VPR Human codon optimized dLbCpf1(D832A) in normal font (NTs 1-3921), Nucleoplasmin NLS in lower case (aaaaggccggcggccacgaaaaaggccggccaggcaaaaaagaaaaag, SEQ ID NO:21), 3×HA tag (TACCCATACGATGTTCCAGATTACGCTTATCCCTACGACGTGCCTGATTATGCATACCCATA
TGATGTCCCCGACTATGCC, SEQ ID NO: 5) in bold, and VPR double underlined

SEQ ID NO: 443)

```
ATGAGCAAGCTGGAGAAGTTTACAAACTGCTACTCCCTGTCTAAGACCCTGAGGTTC
AAGGCCATCCCTGTGGGCAAGACCCAGGAGAACATCGACAATAAGCGGCTGCTGGTGGAG
GACGAGAAGAGAGCCGAGGATTATAAGGGCGTGAAGAAGCTGCTGGATCGCTACTATCTGT
CTTTTATCAACGACGTGCTGCACAGCATCAAGCTGAAGAATCTGAACAATTACATCAGCCTG
TTCCGGAAGAAAACCAGAACCGAGAAGGAGAATAAGGAGCTGGAGAACCTGGAGATCAATC
TGCGGAAGGAGATCGCCAAGGCCTTCAAGGGCAACGAGGGCTACAAGTCCCTGTTTAAGAA
GGATATCATCGAGACAATCCTGCCAGAGTTCCTGGACGATAAGGACGAGATCGCCCTGGTG
AACAGCTTCAATGGCTTTACCACAGCCTTCACCGGCTTCTTTGATAACAGAGAGAATATGTTT
TCCGAGGAGGCCAAGAGCACATCCATCGCCTTCAGGTGTATCAACGAGAATCTGACCCGCT
ACATCTCTAATATGGACATCTTCGAGAAGGTGGACGCCATCTTTGATAAGCACGAGGTGCAG
GAGATCAAGGAGAAGATCCTGAACAGCGACTATGATGTGGAGGATTTCTTTGAGGGCGAGT
TCTTTAACTTTGTGCTGACACAGGAGGGCATCGACGTGTATAACGCCATCATCGGCGGCTTC
GTGACCGAGAGCGGCGAGAAGATCAAGGGCCTGAACGAGTACATCAACCTGTATAATCAGA
AAACCAAGCAGAAGCTGCCTAAGTTTAAGCCACTGTATAAGCAGGTGCTGAGCGATCGGGA
GTCTCTGAGCTTCTACGGCGAGGGCTATACATCCGATGAGGAGGTGCTGGAGGTGTTTAGA
AACACCCTGAACAAGAACAGCGAGATCTTCAGCTCCATCAAGAAGCTGGAGAAGCTGTTCAA
GAATTTTGACGAGTACTCTAGCGCCGGCATCTTTGTGAAGAACGGCCCCGCCATCAGCACA
ATCTCCAAGGATATCTTCGGCGAGTGGAACGTGATCCGGGACAAGTGGAATGCCGAGTATG
ACGATATCCACCTGAAGAAGAAGGCCGTGGTGACCGAGAAGTACGAGGACGATCGGAGAAA
GTCCTTCAAGAAGATCGGCTCCTTTTCTCTGGAGCAGCTGCAGGAGTACGCCGACGCCGAT
CTGTCTGTGGTGGAGAAGCTGAAGGAGATCATCATCCAGAAGGTGGATGAGATCTACAAGG
TGTATGGCTCCTCTGAGAAGCTGTTCGACGCCGATTTTGTGCTGGAGAAGAGCCTGAAGAA
GAACGACGCCGTGGTGGCCATCATGAAGGACCTGCTGGATTCTGTGAAGAGCTTCGAGAAT
TACATCAAGGCCTTCTTTGGCGAGGGCAAGGAGACAAACAGGGACGAGTCCTTCTATGGCG
ATTTTGTGCTGGCCTACGACATCCTGCTGAAGGTGGACCACATCTACGATGCCATCCGCAAT
TATGTGACCCAGAAGCCCTACTCTAAGGATAAGTTCAAGCTGTATTTTCAGAACCCTCAGTTC
ATGGGCGGCTGGGACAAGGATAAGGAGACAGACTATCGGGCCACCATCCTGAGATACGGC
TCCAAGTACTATCTGGCCATCATGGATAAGAAGTACGCCAAGTGCCTGCAGAAGATCGACAA
GGACGATGTGAACGGCAATTACGAGAAGATCAACTATAAGCTGCTGCCCGGCCCTAATAAG
ATGCTGCCAAAGGTGTTCTTTTCTAAGAAGTGGATGGCCTACTATAACCCCAGCGAGGACAT
CCAGAAGATCTACAAGAATGGCACATTCAAGAAGGGCGATATGTTTAACCTGAATGACTGTC
ACAAGCTGATCGACTTCTTTAAGGATAGCATCTCCCGGTATCCAAAGTGGTCCAATGCCTAC
GATTTCAACTTTTCTGAGACAGAGAAGTATAAGGACATCGCCGGCTTTTACAGAGAGGTGGA
GGAGCAGGGCTATAAGGTGAGCTTCGAGTCTGCCAGCAAGAAGGAGGTGGATAAGCTGGT
```

-continued

GGAGGAGGGCAAGCTGTATATGTTCCAGATCTATAACAAGGACTTTTCCGATAAGTCTCACG

GCACACCCAATCTGCACACCATGTACTTCAAGCTGCTGTTTGACGAGAACAATCACGGACAG

ATCAGGCTGAGCGGAGGAGCAGAGCTGTTCATGAGGCGCGCCTCCCTGAAGAAGGAGGAG

CTGGTGGTGCACCCAGCCAACTCCCCTATCGCCAACAAGAATCCAGATAATCCCAAGAAAAC

CACAACCCTGTCCTACGACGTGTATAAGGATAAGAGGTTTTCTGAGGACCAGTACGAGCTGC

ACATCCCAATCGCCATCAATAAGTGCCCCAAGAACATCTTCAAGATCAATACAGAGGTGCGC

GTGCTGCTGAAGCACGACGATAACCCCTATGTGATCGGCATCGCCAGGGGCGAGCGCAAT

CTGCTGTATATCGTGGTGGTGGACGGCAAGGGCAACATCGTGGAGCAGTATTCCCTGAACG

AGATCATCAACAACTTCAACGGCATCAGGATCAAGACAGATTACCACTCTCTGCTGGACAAG

AAGGAGAAGGAGAGGTTCGAGGCCCGCCAGAACTGGACCTCCATCGAGAATATCAAGGAG

CTGAAGGCCGGCTATATCTCTCAGGTGGTGCACAAGATCTGCGAGCTGGTGGAGAAGTACG

ATGCCGTGATCGCCCTGGAGGACCTGAACTCTGGCTTTAAGAATAGCCGCGTGAAGGTGGA

GAAGCAGGTGTATCAGAAGTTCGAGAAGATGCTGATCGATAAGCTGAACTACATGGTGGAC

AAGAAGTCTAATCCTTGTGCAACAGGCGGCGCCCTGAAGGGCTATCAGATCACCAATAAGTT

CGAGAGCTTTAAGTCCATGTCTACCCAGAACGGCTTCATCTTTTACATCCCTGCCTGGCTGA

CATCCAAGATCGATCCATCTACCGGCTTTGTGAACCTGCTGAAAACCAAGTATACCAGCATC

GCCGATTCCAAGAAGTTCATCAGCTCCTTTGACAGGATCATGTACGTGCCCGAGGAGGATCT

GTTCGAGTTTGCCCTGGACTATAAGAACTTCTCTCGCACAGACGCCGATTACATCAAGAAGT

GGAAGCTGTACTCCTACGGCAACCGGATCAGAATCTTCCGGAATCCTAAGAAGAACAACGT

GTTCGACTGGGAGGAGGTGTGCCTGACCAGCGCCTATAAGGAGCTGTTCAACAAGTACGGC

ATCAATTATCAGCAGGGCGATATCAGAGCCCTGCTGTGCGAGCAGTCCGACAAGGCCTTCT

ACTCTAGCTTTATGGCCCTGATGAGCCTGATGCTGCAGATGCGGAACAGCATCACAGGCCG

CACCGACGTGGATTTTCTGATCAGCCCTGTGAAGAACTCCGACGGCATCTTCTACGATAGCC

GGAACTATGAGGCCCAGGAGAATGCCATCCTGCCAAAGAACGCCGACGCCAATGGCGCCT

ATAACATCGCCAGAAAGGTGCTGTGGGCCATCGGCCAGTTCAAGAAGGCCGAGGACGAGA

AGCTGGATAAGGTGAAGATCGCCATCTCTAACAAGGAGTGGCTGGAGTACGCCCAGACCAG

CGTGAAGCACaaaaggccggcggccacgaaaaaggccggccaggcaaaaaagaaaaagGGATCCTACCCATA

CGATGTTCCAGATTACGCTTATCCCTACGACGTGCCTGATTATGCATACCCATATGATGTC

CCCGACTATGCCGGAAGCGAGGCCAGCGGTTCCGGACGGGCTGACGCATTGGACGATTTT

GATCTGGATATGCTGGGAAGTGACGCCCTCGATGATTTTGACCTTGACATGCTTGGTTCGGA

TGCCCTTGATGACTTTGACCTCGACATGCTCGGCAGTGACGCCCTTGATGATTTCGACCTGG

ACATGCTGATTAACTCTAGAAGTTCCGGATCTCCGAAAAAGAAACGCAAAGTTGGTAGCCAG

TACCTGCCCGACACCGACGACCGGCACCGGATCGAGGAAAAGCGGAAGCGGACCTACGAG

ACATTCAAGAGCATCATGAAGAAGTCCCCCTTCAGCGGCCCCACCGACCCTAGACCTCCAC

CTAGAAGAATCGCCGTGCCCAGCAGATCCAGCGCCAGCGTGCCAAAACCTGCCCCCCAGC

CTTACCCCTTCACCAGCAGCCTGAGCACCATCAACTACGACGAGTTCCCTACCATGGTGTTC

CCCAGCGGCCAGATCTCTCAGGCCTCTGCTCTGGCTCCAGCCCCTCCTCAGGTGCTGCCTC

AGGCTCCTGCTCCTGCACCAGCTCCAGCCATGGTGTCTGCACTGGCTCAGGCACCAGCACC

CGTGCCTGTGCTGGCTCCTGGACCTCCACAGGCTGTGGCTCCACCAGCCCCTAAACCTACA

CAGGCCGGCGAGGGCACACTGTCTGAAGCTCTGCTGCAGCTGCAGTTCGACGACGAGGAT

CTGGGAGCCCTGCTGGGAAACAGCACCGATCCTGCCGTGTTCACCGACCTGGCCAGCGTG

-continued

GACAACAGCGAGTTCCAGCAGCTGCTGAACCAGGGCATCCCTGTGGCCCCTCACACCACC

GAGCCCATGCTGATGGAATACCCCGAGGCCATCACCCGGCTCGTGACAGGCGCTCAGAGG

CCTCCTGATCCAGCTCCTGCCCCTCTGGGAGCACCAGGCCTGCCTAATGGACTGCTGTCTG

GCGACGAGGACTTCAGCTCTATCGCCGATATGGATTTCTCAGCCTTGCTGGGCTCTGGCAG

CGGCAGCCGGGATTCCAGGGAAGGGATGTTTTTGCCGAAGCCTGAGGCCGGCTCCGCTAT

TAGTGACGTGTTTGAGGGCCGCGAGGTGTGCCAGCCAAAACGAATCCGGCCATTTCATCCT

CCAGGAAGTCCATGGGCCAACCGCCCACTCCCCGCCAGCCTCGCACCAACACCAACCGGT

CCAGTACATGAGCCAGTCGGGTCACTGACCCCGGCACCAGTCCCTCAGCCACTGGATCCAG

CGCCCGCAGTGACTCCCGAGGCCAGTCACCTGTTGGAGGATCCCGATGAAGAGACGAGCC

AGGCTGTCAAAGCCCTTCGGGAGATGGCCGATACTGTGATTCCCCAGAAGGAAGAGGCTGC

AATCTGTGGCCAAATGGACCTTTCCCATCCGCCCCCAAGGGGCCATCTGGATGAGCTGACA

ACCACACTTGAGTCCATGACCGAGGATCTGAACCTGGACTCACCCCTGACCCCGGAATTGA

ACGAGATTCTGGATACCTTCCTGAACGACGAGTGCCTCTTGCATGCCATGCATATCAGCACA

GGACTGTCCATCTTCGACACATCTCTGTTTTAA

Amino Acid Sequence of dLbCpf1(D832A)-NLS(nucleoplasmin)-3×HA-VPR

LbCpf1 in normal font (AAs 1-1228), NLS(nucleoplasmin) (krpaatkkagqakkkk, SEQ ID NO:7) in lower case, 3×HA tag (YPYDVPDYAYPYDVPDYAYPYDVPDYA, SEQ ID NO:8) in bold, and VPR doubleunderlined

SEQ ID NO: 444)

MSKLEKFTNCYSLSKTLRFKAIPVGKTQENIDNKRLLVEDEKRAEDYKGVKKLLDRYYLS

FINDVLHSIKLKNLNNYISLFRKKTRTEKENKELENLEINLRKEIAKAFKGNEGYKSLFKKDIIETILPE

FLDDKDEIALVNSFNGFTTAFTGFFDNRENMFSEEAKSTSIAFRCINENLTRYISNMDIFEKVDAIF

DKHEVQEIKEKILNSDYDVEDFFEGEFFNFVLTQEGIDVYNAIIGGFVTESGEKIKGLNEYINLYNQ

KTKQKLPKFKPLYKQVLSDRESLSFYGEGYTSDEEVLEVFRNTLNKNSEIFSSIKKLEKLFKNFDE

YSSAGIFVKNGPAISTISKDIFGEWNVIRDKWNAEYDDIHLKKKAVVTEKYEDDRRKSFKKIGSFSL

EQLQEYADADLSVVEKLKEIIIQKVDEIYKVYGSSEKLFDADFVLEKSLKKNDAVVAIMKDLLDSVK

SFENYIKAFFGEGKETNRDESFYGDFVLAYDILLKVDHIYDAIRNYVTQKPYSKDKFKLYFQNPQF

MGGWDKDKETDYRATILRYGSKYYLAIMDKKYAKCLQKIDKDDVNGNYEKINYKLLPGPNKMLP

KVFFSKKWMAYYNPSEDIQKIYKNGTFKKGDMFNLNDCHKLIDFFKDSISRYPKWSNAYDFNFSE

TEKYKDIAGFYREVEEQGYKVSFESASKKEVDKLVEEGKLYMFQIYNKDFSDKSHGTPNLHTMY

FKLLFDENNHGQIRLSGGAELFMRRASLKKEELVVHPANSPIANKNPDNPKKTTTLSYDVYKDKR

FSEDQYELHIPIAINKCPKNIFKINTEVRVLLKHDDNPYVIGIARGERNLLYIVVVDGKGNIVEQYSL

NEIINNFNGIRIKTDYHSLLDKKEKERFEARQNVVTSIENIKELKAGYISQVVHKICELVEKYDAVIAL

EDLNSGFKNSRVKVEKQVYQKFEKMLIDKLNYMVDKKSNPCATGGALKGYQITNKFESFKSMST

QNGFIFYIPAWLTSKIDPSTGFVNLLKTKYTSIADSKKFISSFDRIMYVPEEDLFEFALDYKNFSRTD

ADYIKKWKLYSYGNRIRIFRNPKKNNVFDWEEVCLTSAYKELFNKYGINYQQGDIRALLCEQSDK

AFYSSFMALMSLMLQMRNSITGRTDVDFLISPVKNSDGIFYDSRNYEAQENAILPKNADANGAYN

IARKVLWAIGQFKKAEDEKLDKVKIAISNKEWLEYAQTSVKHkrpaatkkagqakkkkGSYPYDVPDYA

YPYDVPDYAYPYDVPDYAGSEASGSGRADALDDFDLDMLGSDALDDFDLDMLGSDALDDFDLD

MLGSDALDDFDLDMLINSRSSGSPKKKRKVGSQYLPDTDDRHRIEEKRKRTYETFKSIMKKSPFS

-continued

GPTDPRPPPRRIAVPSRSSASVPKPAPQPYPFTSSLSTINYDEFPTMVFPSGQISQASALAPAPP

QVLPQAPAPAPAPAMVSALAQAPAPVPVLAPGPPQAVAPPAPKPTQAGEGTLSEALLQLQFDDE

DLGALLGNSTDPAVFTDLASVDNSEFQQLLNQGIPVAPHTTEPMLMEYPEAITRLVTGAQRPPDP

APAPLGAPGLPNGLLSGDEDFSSIADMDFSALLGSGSGSRDSREGMFLPKPEAGSAISDVFEGR

EVCQPKRIRPFHPPGSPWANRPLPASLAPTPTGPVHEPVGSLTPAPVPQPLDPAPAVTPEASHL

LEDPDEETSQAVKALREMADTVIPQKEEAAICGQMDLSHPPPRGHLDELTTTLESMTEDLNLDSP

LTPELNEILDTFLNDECLLHAMHISTGLSIFDTSLF

Nucleotide Sequence of (RTW1008) pCAG-NLS(SV40)×2-rAPOBEC1-gsXTENgslinker-human-dAsCpf1(D908A)-NLS(nucleoplasmin)-GSlinker-UGI-NLS(SV40)

Human codon optimized dAsCpf1(D908A) in normal font (NTs 844-4764), rAPOBEC1 in bold (NTs 67-750), Nucleoplasmin NLS in lower case (aaaaggccggcggc-cacgaaaaaggccggccaggcaaaaaagaaaaag, SEQ ID NO:21), SV40 NLS in lower case (ccaaagaaaaagaggaaagtc, cctaaaaagaaacgaaaggtt, or cccaagaagaagaggaaagtc, SEQ ID NOs:19, 20, or 22, respectively), gsXTENgs linker (tctggtggttcttctggtggttctagcggcagcga-gactcccgggacctcagagtccgccacacccgaaagttccggagggagtagcggcggg, SEQ ID NO:23) in lower case, and UGI doubleunderlined (SEQ ID NO: 445)

ATGGGCccaaagaaaaagaggaaagteGGCAGTGGAcctaaaaagaaacgaaaggttGGGTCAGGT

AGCTCAGAGACTGGCCCAGTGGCTGTGGACCCCACATTGAGACGGCGGATCGAGCCCCA

TGAGTTTGAGGTATTCTTCGATCCGAGAGAGCTCCGCAAGGAGACCTGCCTGCTTTACGA

AATTAATTGGGGGGGCCGGCACTCCATTTGGCGACATACATCACAGAACACTAACAAGCA

CGTCGAAGTCAACTTCATCGAGAAGTTCACGACAGAAAGATATTTCTGTCCGAACACAAG

GTGCAGCATTACCTGGTTTCTCAGCTGGAGCCCATGCGGCGAATGTAGTAGGGCCATCAC

TGAATTCCTGTCAAGGTATCCCCACGTCACTCTGTTTATTTACATCGCAAGGCTGTACCAC

CACGCTGACCCCCGCAATCGACAAGGCCTGCGGGATTTGATCTCTTCAGGTGTGACTATC

CAAATTATGACTGAGCAGGAGTCAGGATACTGCTGGAGAAACTTTGTGAATTATAGCCCG

AGTAATGAAGCCCACTGGCCTAGGTATCCCCATCTGTGGGTACGACTGTACGTTCTTGAAC

TGTACTGCATCATACTGGGCCTGCCTCCTTGTCTCAACATTCTGAGAAGGAAGCAGCCACA

GCTGACATTCTTTACCATCGCTCTTCAGTCTTGTCATTACCAGCGACTGCCCCCACACATTC

TCTGGGCCACCGGGTTGAAAtctggtggttcttctggtggttctagcggcagcgagactcccgggacctcagagtccgcca cacccgaaagttccggagggagtagcggcgggTCTACACAGTTCGAGGGCTTTACCAACCTGTATCAGGT

GAGCAAGACACTGCGGTTTGAGCTGATCCCACAGGGCAAGACCCTGAAGCACATCCAGGAG

CAGGGCTTCATCGAGGAGGACAAGGCCCGCAATGATCACTACAAGGAGCTGAAGCCCATCA

TCGATCGGATCTACAAGACCTATGCCGACCAGTGCCTGCAGCTGGTGCAGCTGGATTGGGA

GAACCTGAGCGCCGCCATCGACTCCTATAGAAAGGAGAAAACCGAGGAGACAAGGAACGC

CCTGATCGAGGAGCAGGCCACATATCGCAATGCCATCCACGACTACTTCATCGGCCGGACA

GACAACCTGACCGATGCCATCAATAAGAGACACGCCGAGATCTACAAGGGCCTGTTCAAGG

CCGAGCTGTTTAATGGCAAGGTGCTGAAGCAGCTGGGCACCGTGACCACAACCGAGCACG

AGAACGCCCTGCTGCGGAGCTTCGACAAGTTTACAACCTACTTCTCCGGCTTTTATGAGAAC

AGGAAGAACGTGTTCAGCGCCGAGGATATCAGCACAGCCATCCCACACCGCATCGTGCAGG

ACAACTTCCCCAAGTTTAAGGAGAATTGTCACATCTTCACACGCCTGATCACCGCCGTGCCC

AGCCTGCGGGAGCACTTTGAGAACGTGAAGAAGGCCATCGGCATCTTCGTGAGCACCTCCA

TCGAGGAGGTGTTTTCCTTCCCTTTTTATAACCAGCTGCTGACACAGACCCAGATCGACCTG

TATAACCAGCTGCTGGGAGGAATCTCTCGGGAGGCAGGCACCGAGAAGATCAAGGGCCTG

-continued

AACGAGGTGCTGAATCTGGCCATCCAGAAGAATGATGAGACAGCCCACATCATCGCCTCCC
TGCCACACAGATTCATCCCCCTGTTTAAGCAGATCCTGTCCGATAGGAACACCCTGTCTTTC
ATCCTGGAGGAGTTTAAGAGCGACGAGGAAGTGATCCAGTCCTTCTGCAAGTACAAGACAC
TGCTGAGAAACGAGAACGTGCTGGAGACAGCCGAGGCCCTGTTTAACGAGCTGAACAGCAT
CGACCTGACACACATCTTCATCAGCCACAAGAAGCTGGAGACAATCAGCAGCGCCCTGTGC
GACCACTGGGATACACTGAGGAATGCCCTGTATGAGCGGAGAATCTCCGAGCTGACAGGCA
AGATCACCAAGTCTGCCAAGGAGAAGGTGCAGCGCAGCCTGAAGCACGAGGATATCAACCT
GCAGGAGATCATCTCTGCCGCAGGCAAGGAGCTGAGCGAGGCCTTCAAGCAGAAAACCAG
CGAGATCCTGTCCCACGCACACGCCGCCCTGGATCAGCCACTGCCTACAACCCTGAAGAAG
CAGGAGGAGAAGGAGATCCTGAAGTCTCAGCTGGACAGCCTGCTGGGCCTGTACCACCTG
CTGGACTGGTTTGCCGTGGATGAGTCCAACGAGGTGGACCCCGAGTTCTCTGCCCGGCTGA
CCGGCATCAAGCTGGAGATGGAGCCTTCTCTGAGCTTCTACAACAAGGCCAGAAATTATGC
CACCAAGAAGCCCTACTCCGTGGAGAAGTTCAAGCTGAACTTTCAGATGCCTACACTGGCCT
CTGGCTGGGACGTGAATAAGGAGAAGAACAATGGCGCCATCCTGTTTGTGAAGAACGGCCT
GTACTATCTGGGCATCATGCCAAAGCAGAAGGGCAGGTATAAGGCCCTGAGCTTCGAGCCC
ACAGAGAAAACCAGCGAGGGCTTTGATAAGATGTACTATGACTACTTCCCTGATGCCGCCAA
GATGATCCCAAAGTGCAGCACCCAGCTGAAGGCCGTGACAGCCCACTTTCAGACCCACACA
ACCCCCATCCTGCTGTCCAACAATTTCATCGAGCCTCTGGAGATCACAAAGGAGATCTACGA
CCTGAACAATCCTGAGAAGGAGCCAAAGAAGTTTCAGACAGCCTACGCCAAGAAAACCGGC
GACCAGAAGGGCTACAGAGAGGCCCTGTGCAAGTGGATCGACTTCACAAGGGATTTTCTGT
CCAAGTATACCAAGACAACCTCTATCGATCTGTCTAGCCTGCGGCCATCCTCTCAGTATAAG
GACCTGGGCGAGTACTATGCCGAGCTGAATCCCCTGCTGTACCACATCAGCTTCCAGAGAA
TCGCCGAGAAGGAGATCATGGATGCCGTGGAGACAGGCAAGCTGTACCTGTTCCAGATCTA
TAACAAGGACTTTGCCAAGGGCCACCACGGCAAGCCTAATCTGCACACACTGTATTGGACC
GGCCTGTTTTCTCCAGAGAACCTGGCCAAGACAAGCATCAAGCTGAATGGCCAGGCCGAGC
TGTTCTACCGCCCTAAGTCCAGGATGAAGAGGATGGCACACCGGCTGGGAGAGAAGATGCT
GAACAAGAAGCTGAAGGATCAGAAAACCCCAATCCCCGACACCCTGTACCAGGAGCTGTAC
GACTATGTGAATCACAGACTGTCCCACGACCTGTCTGATGAGGCCAGGGCCCTGCTGCCCA
ACGTGATCACCAAGGAGGTGTCTCACGAGATCATCAAGGATAGGCGCTTTACCAGCGACAA
GTTCTTTTTCCACGTGCCTATCACACTGAACTATCAGGCCGCCAATTCCCCATCTAAGTTCAA
CCAGAGGGTGAATGCCTACCTGAAGGAGCACCCCGAGACACCTATCATCGGCATCGCCCG
GGGCGAGAGAAACCTGATCTATATCACAGTGATCGACTCCACCGGCAAGATCCTGGAGCAG
CGGAGCCTGAACACCATCCAGCAGTTTGATTACCAGAAGAAGCTGGACAACAGGGAGAAGG
AGAGGGTGGCAGCAAGGCAGGCCTGGTCTGTGGTGGGCACAATCAAGGATCTGAAGCAGG
GCTATCTGAGCCAGGTCATCCACGAGATCGTGGACCTGATGATCCACTACCAGGCCGTGGT
GGTGCTGGAGAACCTGAATTTCGGCTTTAAGAGCAAGAGGACCGGCATCGCCGAGAAGGC
CGTGTACCAGCAGTTCGAGAAGATGCTGATCGATAAGCTGAATTGCCTGGTGCTGAAGGAC
TATCCAGCAGAGAAAGTGGGAGGCGTGCTGAACCCATACCAGCTGACAGACCAGTTCACCT
CCTTTGCCAAGATGGGCACCCAGTCTGGCTTCCTGTTTTACGTGCCTGCCCCATATACATCT
AAGATCGATCCCCTGACCGGCTTCGTGGACCCCTTCGTGTGGAAAACCATCAAGAATCACG

-continued

AGAGCCGCAAGCACTTCCTGGAGGGCTTCGACTTTCTGCACTACGACGTGAAAACCGGCGA

CTTCATCCTGCACTTTAAGATGAACAGAAATCTGTCCTTCCAGAGGGGCCTGCCCGGCTTTA

TGCCTGCATGGGATATCGTGTTCGAGAAGAACGAGACACAGTTTGACGCCAAGGGCACCCC

TTTCATCGCCGGCAAGAGAATCGTGCCAGTGATCGAGAATCACAGATTCACCGGCAGATAC

CGGGACCTGTATCCTGCCAACGAGCTGATCGCCCTGCTGGAGGAGAAGGGCATCGTGTTCA

GGGATGGCTCCAACATCCTGCCAAAGCTGCTGGAGAATGACGATTCTCACGCCATCGACAC

GATGGTGGCCCTGATCCGCAGCGTGCTGCAGATGCGGAACTCCAATGCCGCCACAGGCGA

GGACTATATCAACAGCCCCGTGCGCGATCTGAATGGCGTGTGCTTCGACTCCCGGTTTCAG

AACCCAGAGTGGCCAATGGACGCCGATGCCAATGGCGCCTACCACATCGCCCTGAAGGGC

CAGCTGCTGCTGAATCACCTGAAGGAGAGCAAGGATCTGAAGCTGCAGAACGGCATCTCCA

ATCAGGACTGGCTGGCCTACATCCAGGAGCTGCGCAACaaaaggccggcggccacgaaaaaggccggc caggcaaaaaagaaaaagGGATCCTCTGGTGGTTCTGGAGGATCTGGTGGTTCTACTAATCTGTCA

GATATTATTGAAAAGGAGACCGGTAAGCAACTGGTTATCCAGGAATCCATCCTCATGCTCCC

AGAGGAGGTGGAAGAAGTCATTGGGAACAAGCCGGAAAGCGATATACTCGTGCACACCGCC

TACGACGAGAGCACCGACGAGAATGTCATGCTTCTGACTAGCGACGCCCCTGAATACAAGC

CTTGGGCTCTGGTCATACAGGATAGCAACGGTGAGAACAAGATTAAGATGCTCTCTGGTGGT

TCTcccaagaagaagaggaaagtc

Amino Acid Sequence of NLS(SV40)×2-rAPOBEC1-g&XTENgslinker-human-dAsCpf1(D908A)-NLS(nucleoplasmin)-GSlinker-UGI-NLS(SV40)

AsCpf1 in normal font (AAs x-xxxx), rAPOBEC1 in bold (AAs 23-250), NLS(nucleoplasmin) (krpaatkkaggakkkk, SEQ ID NO:7) in lower case, SV40 NLS in lower case (pkkkrkv, SEQ ID NO:24), gsXTENgs linker (sggssggssg-setpgtsesatpessggssgg, SEQ ID NO:25) in lower case, and UGI doubleunderlined (SEQ ID NO: 446)

MGpkkkrkvGSGpkkkrkvGSGSSETGPVAVDPTLRRRIEPHEFEVFFDPRELRKETCLLYEI

NWGGRHSIWRHTSQNTNKHVEVNFIEKFTTERYFCPNTRCSITINFLSWSPCGECSRAITEFLSR

YPHVTLFIYIARLYHHADPRNRQGLRDLISSGVTIQIMTEQESGYCWRNFVNYSPSNEAHWPRY

PHLVVVRLYVLELYCIILGLPPCLNILRRKQPQLTFFTIALQSCHYQRLPPHILWATGLKsggssggss gsetpgtsesatpessggssggSTQFEGFTNLYQVSKTLRFELIPQGKTLKHIQEQGFIEEDKARNDHYKE

LKPIIDRIYKTYADQCLQLVQLDWENLSAAIDSYRKEKTEETRNALIEEQATYRNAIHDYFIGRTDN

LTDAINKRHAEIYKGLFKAELFNGKVLKQLGTVTTTEHENALLRSFDKFTTYFSGFYENRKNVFSA

EDISTAIPHRIVQDNFPKFKENCHIFTRLITAVPSLREHFENVKKAIGIFVSTSIEEVFSFPFYNQLLT

QTQIDLYNQLLGGISREAGTEKIKGLNEVLNLAIQKNDETAHIIASLPHRFIPLFKQILSDRNTLSFIL

EEFKSDEEVIQSFCKYKTLLRNENVLETAEALFNELNSIDLTHIFISHKKLETISSALCDHWDTLRNA

LYERRISELTGKITKSAKEKVQRSLKHEDINLQEIISAAGKELSEAFKQKTSEILSHAHAALDQPLPT

TLKKQEEKEILKSQLDSLLGLYHLLDWFAVDESNEVDPEFSARLTGIKLEMEPSLSFYNKARNYAT

KKPYSVEKFKLNFQMPTLASGWDVNKEKNNGAILFVKNGLYYLGIMPKQKGRYKALSFEPTEKT

SEGFDKMYYDYFPDAAKMIPKCSTQLKAVTAHFQTHTTPILLSNNFIEPLEITKEIYDLNNPEKEPK

KFQTAYAKKTGDQKGYREALCKWIDFTRDFLSKYTKTTSIDLSSLRPSSQYKDLGEYYAELNPLL

YHISFQRIAEKEIMDAVETGKLYLFQIYNKDFAKGHHGKPNLHTLYVVTGLFSPENLAKTSIKLNGQ

AELFYRPKSRMKRMAHRLGEKMLNKKLKDQKTPIPDTLYQELYDYVNHRLSHDLSDEARALLPN

VITKEVSHEIIKDRRFTSDKFFFHVPITLNYQAANSPSKFNQRVNAYLKEHPETPIIGIARGERNLIYI

TVIDSTGKILEQRSLNTIQQFDYQKKLDNREKERVAARQAWSVVGTIKDLKQGYLSQVIHEIVDLM

-continued

IHYQAVVVLENLNFGFKSKRTGIAEKAVYQQFEKMLIDKLNCLVLKDYPAEKVGGVLNPYQLTDQ

FTSFAKMGTQSGFLFYVPAPYTSKIDPLTGFVDPFVWKTIKNHESRKHFLEGFDFLHYDVKTGDFI

LHFKMNRNLSFQRGLPGFMPAWDIVFEKNETQFDAKGTPFIAGKRIVPVIENHRFTGRYRDLYPA

NELIALLEEKGIVFRDGSNILPKLLENDDSHAIDTMVALIRSVLQMRNSNAATGEDYINSPVRDLNG

VCFDSRFQNPEWPMDADANGAYHIALKGQLLLNHLKESKDLKLQNGISNQDWLAYIQELRNkrpa atkkaggakkkkGSSGGSGGSGGSTNLSDIIEKETGKQLVIQESILMLPEEVEEVIGNKPESDILVHTA YDESTDENVMLLTSDAPEYKPWALVIQDSNGENKIKMLSGGSpkkkrky Nucleotide Sequence of (RTW1028) pCAG-NLS(SV40)×2-rAPOBEC1-gsXTENgslinker-human-dAsCpf1(D908A)triplevariant(E174R/S542R/K548R)-NLS(nucleoplasmin)-GSlinker-UGI-NLS(SV40)

Human codon optimized dAsCpf1(D908A) in normal font (NTs 844-4764), rAPOBEC1 in bold (NTs 67-750), Nucleoplasmin NLS in lower case (aaaaggccggcggccacgaaaaaggccggccaggcaaaaaagaaaaag, SEQ ID NO: 21), SV40 NLS in lower case (ccaaagaaaaagaggaaagtc, cctaaaaagaaacgaaaggtt, or cccaagaagaagaggaaagtc, SEQ ID NOs: 19, 20, or 22, respectively), gsXTENgs linker (tctggtggttcttctggtggttctagcggcagcgagactcccgggacctcagagtccgccacacccgaaagttccggagggagtagcggcggg, SEQ ID NO: 23) in lower case, and UGI double underlined (SEQ ID NO: 447)

ATGGGCccaaagaaaaagaggaaagteGGCAGTGGAcctaaaaagaaacgaaaggttGGGTCAGGT

AGCTCAGAGACTGGCCCAGTGGCTGTGGACCCCACATTGAGACGGCGGATCGAGCCCCA

TGAGTTTGAGGTATTCTTCGATCCGAGAGAGCTCCGCAAGGAGACCTGCCTGCTTTACGA

AATTAATTGGGGGGGCCGGCACTCCATTTGGCGACATACATCACAGAACACTAACAAGCA

CGTCGAAGTCAACTTCATCGAGAAGTTCACGACAGAAAGATATTTCTGTCCGAACACAAG

GTGCAGCATTACCTGGTTTCTCAGCTGGAGCCCATGCGGCGAATGTAGTAGGGCCATCAC

TGAATTCCTGTCAAGGTATCCCCACGTCACTCTGTTTATTTACATCGCAAGGCTGTACCAC

CACGCTGACCCCCGCAATCGACAAGGCCTGCGGGATTTGATCTCTTCAGGTGTGACTATC

CAAATTATGACTGAGCAGGAGTCAGGATACTGCTGGAGAAACTTTGTGAATTATAGCCCG

AGTAATGAAGCCCACTGGCCTAGGTATCCCCATCTGTGGGTACGACTGTACGTTCTTGAAC

TGTACTGCATCATACTGGGCCTGCCTCCTTGTCTCAACATTCTGAGAAGGAAGCAGCCACA

GCTGACATTCTTTACCATCGCTCTTCAGTCTTGTCATTACCAGCGACTGCCCCCACACATTC

TCTGGGCCACCGGGTTGAAAtctggtggttcttctggtggttctagcggcagcgagactcccgggacctcagagtccgcca cacccgaaagttccggagggagtagcggcgggTCTACACAGTTCGAGGGCTTTACCAACCTGTATCAGGT

GAGCAAGACACTGCGGTTTGAGCTGATCCCACAGGGCAAGACCCTGAAGCACATCCAGGAG

CAGGGCTTCATCGAGGAGGACAAGGCCCGCAATGATCACTACAAGGAGCTGAAGCCCATCA

TCGATCGGATCTACAAGACCTATGCCGACCAGTGCCTGCAGCTGGTGCAGCTGGATTGGGA

GAACCTGAGCGCCGCCATCGACTCCTATAGAAAGGAGAAAACCGAGGAGACAAGGAACGC

CCTGATCGAGGAGCAGGCCACATATCGCAATGCCATCCACGACTACTTCATCGGCCGGACA

GACAACCTGACCGATGCCATCAATAAGAGACACGCCGAGATCTACAAGGGCCTGTTCAAGG

CCGAGCTGTTTAATGGCAAGGTGCTGAAGCAGCTGGGCACCGTGACCACAACCGAGCACG

AGAACGCCCTGCTGCGGAGCTTCGACAAGTTTACAACCTACTTCTCCGGCTTTTATGCCAAC

AGGAAGAACGTGTTCAGCGCCGAGGATATCAGCACAGCCATCCCACACCGCATCGTGCAGG

ACAACTTCCCCAAGTTTAAGGAGAATTGTCACATCTTCACACGCCTGATCACCGCCGTGCCC

AGCCTGCGGGAGCACTTTGAGAACGTGAAGAAGGCCATCGGCATCTTCGTGAGCACCTCCA

TCGAGGAGGTGTTTTCCTTCCCTTTTTATAACCAGCTGCTGACACAGACCCAGATCGACCTG

-continued

TATAACCAGCTGCTGGGAGGAATCTCTCGGGAGGCAGGCACCGAGAAGATCAAGGGCCTG

AACGAGGTGCTGAATCTGGCCATCCAGAAGAATGATGAGACAGCCCACATCATCGCCTCCC

TGCCACACAGATTCATCCCCCTGTTTAAGCAGATCCTGTCCGATAGGAACACCCTGTCTTTC

ATCCTGGAGGAGTTTAAGAGCGACGAGGAAGTGATCCAGTCCTTCTGCAAGTACAAGACAC

TGCTGAGAAACGAGAACGTGCTGGAGACAGCCGAGGCCCTGTTTAACGAGCTGAACAGCAT

CGACCTGACACACATCTTCATCAGCCACAAGAAGCTGGAGACAATCAGCAGCGCCCTGTGC

GACCACTGGGATACACTGAGGAATGCCCTGTATGAGCGGAGAATCTCCGAGCTGACAGGCA

AGATCACCAAGTCTGCCAAGGAGAAGGTGCAGCGCAGCCTGAAGCACGAGGATATCAACCT

GCAGGAGATCATCTCTGCCGCAGGCAAGGAGCTGAGCGAGGCCTTCAAGCAGAAAACCAG

CGAGATCCTGTCCCACGCACACGCCGCCCTGGATCAGCCACTGCCTACAACCCTGAAGAAG

CAGGAGGAGAAGGAGATCCTGAAGTCTCAGCTGGACAGCCTGCTGGGCCTGTACCACCTG

CTGGACTGGTTTGCCGTGGATGAGTCCAACGAGGTGGACCCCGAGTTCTCTGCCCGGCTGA

CCGGCATCAAGCTGGAGATGGAGCCTTCTCTGAGCTTCTACAACAAGGCCAGAAATTATGC

CACCAAGAAGCCCTACTCCGTGGAGAAGTTCAAGCTGAACTTTCAGATGCCTACACTGGCC

GCCGGCTGGGACGTGAATAAGGCCAAGAACAATGGCGCCATCCTGTTTGTGAAGAACGGCC

TGTACTATCTGGGCATCATGCCAAAGCAGAAGGGCAGGTATAAGGCCCTGAGCTTCGAGCC

CACAGAGAAAACCAGCGAGGGCTTTGATAAGATGTACTATGACTACTTCCCTGATGCCGCCA

AGATGATCCCAAAGTGCAGCACCCAGCTGAAGGCCGTGACAGCCCACTTTCAGACCCACAC

AACCCCCATCCTGCTGTCCAACAATTTCATCGAGCCTCTGGAGATCACAAAGGAGATCTACG

ACCTGAACAATCCTGAGAAGGAGCCAAAGAAGTTTCAGACAGCCTACGCCAAGAAAACCGG

CGACCAGAAGGGCTACAGAGAGGCCCTGTGCAAGTGGATCGACTTCACAAGGGATTTTCTG

TCCAAGTATACCAAGACAACCTCTATCGATCTGTCTAGCCTGCGGCCATCCTCTCAGTATAA

GGACCTGGGCGAGTACTATGCCGAGCTGAATCCCCTGCTGTACCACATCAGCTTCCAGAGA

ATCGCCGAGAAGGAGATCATGGATGCCGTGGAGACAGGCAAGCTGTACCTGTTCCAGATCT

ATAACAAGGACTTTGCCAAGGGCCACCACGGCAAGCCTAATCTGCACACACTGTATTGGAC

CGGCCTGTTTTCTCCAGAGAACCTGGCCAAGACAAGCATCAAGCTGAATGGCCAGGCCGAG

CTGTTCTACCGCCCTAAGTCCAGGATGAAGAGGATGGCACACCGGCTGGGAGAGAAGATGC

TGAACAAGAAGCTGAAGGATCAGAAAACCCCAATCCCCGACACCCTGTACCAGGAGCTGTA

CGACTATGTGAATCACAGACTGTCCCACGACCTGTCTGATGAGGCCAGGGCCCTGCTGCCC

AACGTGATCACCAAGGAGGTGTCTCACGAGATCATCAAGGATAGGCGCTTTACCAGCGACA

AGTTCTTTTTCCACGTGCCTATCACACTGAACTATCAGGCCGCCAATTCCCCATCTAAGTTCA

ACCAGAGGGTGAATGCCTACCTGAAGGAGCACCCCGAGACACCTATCATCGGCATCGCCCG

GGGCGAGAGAAACCTGATCTATATCACAGTGATCGACTCCACCGGCAAGATCCTGGAGCAG

CGGAGCCTGAACACCATCCAGCAGTTTGATTACCAGAAGAAGCTGGACAACAGGGAGAAGG

AGAGGGTGGCAGCAAGGCAGGCCTGGTCTGTGGTGGGCACAATCAAGGATCTGAAGCAGG

GCTATCTGAGCCAGGTCATCCACGAGATCGTGGACCTGATGATCCACTACCAGGCCGTGGT

GGTGCTGGAGAACCTGAATTTCGGCTTTAAGAGCAAGAGGACCGGCATCGCCGAGAAGGC

CGTGTACCAGCAGTTCGAGAAGATGCTGATCGATAAGCTGAATTGCCTGGTGCTGAAGGAC

TATCCAGCAGAGAAAGTGGGAGGCGTGCTGAACCCATACCAGCTGACAGACCAGTTCACCT

CCTTTGCCAAGATGGGCACCCAGTCTGGCTTCCTGTTTTACGTGCCTGCCCCATATACATCT

-continued

AAGATCGATCCCCTGACCGGCTTCGTGGACCCCTTCGTGTGGAAAACCATCAAGAATCACG

AGAGCCGCAAGCACTTCCTGGAGGGCTTCGACTTTCTGCACTACGACGTGAAAACCGGCGA

CTTCATCCTGCACTTTAAGATGAACAGAAATCTGTCCTTCCAGAGGGGCCTGCCCGGCTTTA

TGCCTGCATGGGATATCGTGTTCGAGAAGAACGAGACACAGTTTGACGCCAAGGGCACCCC

TTTCATCGCCGGCAAGAGAATCGTGCCAGTGATCGAGAATCACAGATTCACCGGCAGATAC

CGGGACCTGTATCCTGCCAACGAGCTGATCGCCCTGCTGGAGGAGAAGGGCATCGTGTTCA

GGGATGGCTCCAACATCCTGCCAAAGCTGCTGGAGAATGACGATTCTCACGCCATCGACAC

GATGGTGGCCCTGATCCGCAGCGTGCTGCAGATGCGGAACTCCAATGCCGCCACAGGCGA

GGACTATATCAACAGCCCCGTGCGCGATCTGAATGGCGTGTGCTTCGACTCCCGGTTTCAG

AACCCAGAGTGGCCAATGGACGCCGATGCCAATGGCGCCTACCACATCGCCCTGAAGGGC

CAGCTGCTGCTGAATCACCTGAAGGAGAGCAAGGATCTGAAGCTGCAGAACGGCATCTCCA

ATCAGGACTGGCTGGCCTACATCCAGGAGCTGCGCAACaaaaggccggcggccacgaaaaaggccggc caggcaaaaaaagaaaaagGGATCCTCTGGTGGTTCTGGAGGATCTGGTGGTTCTACTAATCTGTCA

GATATTATTGAAAAGGAGACCGGTAAGCAACTGGTTATCCAGGAATCCATCCTCATGCTCCC

AGAGGAGGTGGAAGAAGTCATTGGGAACAAGCCGGAAAGCGATATACTCGTGCACACCGCC

TACGACGAGAGCACCGACGAGAATGTCATGCTTCTGACTAGCGACGCCCCTGAATACAAGC

CTTGGGCTCTGGTCATACAGGATAGCAACGGTGAGAACAAGATTAAGATGCTCTCTGGTGGT

TCTcccaagaagaagaggaaagtc

Amino Acid Sequence of NLS(SV40)×2-rAPOBEC1-gsXTENgslinker-human-dAsCpf1(D908A) triplevariant (E174R/S542R/K548R)-NLS(nucleoplasmin)-GSlinker-UGI-NLS(SV40)

AsCpf1 in normal font (AAs x-xxxx), rAPOBEC1 in bold (AAs 23-250), NLS(nucleoplasmin) (krpaatkkagqakkkk, SEQ ID NO:7) in lower case, SV40 NLS in lower case (pkkkrkv, SEQ ID NO:24), gsXTENgs linker (sggssggssg-setpgtsesatpessggssgg, SEQ ID NO:25) in lower case, and UGI doubleunderlined (SEQ ID NO: 448)

MGpkkkrkvGSGpkkkrkvGSGSSETGPVAVDPTLRRRIEPHEFEVFFDPRELRKETCLLYEI

NWGGRHSIWRHTSQNTNKHVEVNFIEKFTTERYFCPNTRCSITINFLSWSPCGECSRAITEFLSR

YPHVTLFIYIARLYHHADPRNRQGLRDLISSGVTIQIMTEQESGYCWRNFVNYSPSNEAHWPRY

PHLVVVRLYVLELYCIILGLPPCLNILRRKQPQLTFFTIALQSCHYQRLPPHILWATGLKsggssggss gsetpgtsesatpessggssggSTQFEGFTNLYQVSKTLRFELIPQGKTLKHIQEQGFIEEDKARNDHYKE

LKPIIDRIYKTYADQCLQLVQLDWENLSAAIDSYRKEKTEETRNALIEEQATYRNAIHDYFIGRTDN

LTDAINKRHAEIYKGLFKAELFNGKVLKQLGTVTTTEHENALLRSFDKFTTYFSGFYRNRKNVFSA

EDISTAIPHRIVQDNFPKFKENCHIFTRLITAVPSLREHFENVKKAIGIFVSTSIEEVFSFPFYNQLLT

QTQIDLYNQLLGGISREAGTEKIKGLNEVLNLAIQKNDETAHIIASLPHRFIPLFKQILSDRNTLSFIL

EEFKSDEEVIQSFCKYKTLLRNENVLETAEALFNELNSIDLTHIFISHKKLETISSALCDHWDTLRNA

LYERRISELTGKITKSAKEKVQRSLKHEDINLQEIISAAGKELSEAFKQKTSEILSHAHAALDQPLPT

TLKKQEEKEILKSQLDSLLGLYHLLDWFAVDESNEVDPEFSARLTGIKLEMEPSLSFYNKARNYAT

KKPYSVEKFKLNFQMPTLARGWDVNREKNNGAILFVKNGLYYLGIMPKQKGRYKALSFEPTEKT

SEGFDKMYYDYFPDAAKMIPKCSTQLKAVTAHFQTHTTPILLSNNFIEPLEITKEIYDLNNPEKEPK

KFQTAYAKKTGDQKGYREALCKWIDFTRDFLSKYTKTTSIDLSSLRPSSQYKDLGEYYAELNPLL

-continued

YHISFQRIAEKEIMDAVETGKLYLFQIYNKDFAKGHHGKPNLHTLYVVTGLFSPENLAKTSIKLNGQ

AELFYRPKSRMKRMAHRLGEKMLNKKLKDQKTPIPDTLYQELYDYVNHRLSHDLSDEARALLPN

VITKEVSHEIIKDRRFTSDKFFFHVPITLNYQAANSPSKFNQRVNAYLKEHPETPIIGIARGERNLIYI

TVIDSTGKILEQRSLNTIQQFDYQKKLDNREKERVAARQAWSVVGTIKDLKQGYLSQVIHEIVDLM

IHYQAVVVLENLNFGFKSKRTGIAEKAVYQQFEKMLIDKLNCLVLKDYPAEKVGGVLNPYQLTDQ

FTSFAKMGTQSGFLFYVPAPYTSKIDPLTGFVDPFVWKTIKNHESRKHFLEGFDFLHYDVKTGDFI

LHFKMNRNLSFQRGLPGFMPAWDIVFEKNETQFDAKGTPFIAGKRIVPVIENHRFTGRYRDLYPA

NELIALLEEKGIVFRDGSNILPKLLENDDSHAIDTMVALIRSVLQMRNSNAATGEDYINSPVRDLNG

VCFDSRFQNPEWPMDADANGAYHIALKGQLLLNHLKESKDLKLQNGISNQDWLAYIQELRNkrpa atkkaggakkkkGSSGGSGGSGGSTNLSDIIEKETGKQLVIQESILMLPEEVEEVIGNKPESDILVHTA YDESTDENVMLLTSDAPEYKPWALVIQDSNGENKIKMLSGGSpkkkrkv

Example 1. Variants of AsCpf1 with Altered PAM Specificity

To attempt to alter the targeting range of Cpf1 nucleases, we first examined the available crystal structures of AsCpf1 and LbCpf1 (Dong, Nature 2016; Yamano, Cell 2016). Among other observations, these structures demonstrate that PAM specificity is mediated by a combination of electrostatic interactions and indirect base readout. We therefore hypothesized that certain combinations of amino acid substitutions at residues in close spatial proximity to the DNA bases of the PAM bases might yield variants with altered or relaxed PAM recognition preferences. To test this, we examined regions of AsCpf1 in the vicinity of the PAM that span residues G131-L137, S161-S181, N534-I555, Y595-T616, L628-F632, and S685-1693 (Table 1). We focused on amino acids in the reference AsCpf1 sequence whose three-dimensional position met at least one of the following criteria: 1) spatial proximity to PAM DNA bases (on either the target or non-target strand), 2) positioning within the DNA major or minor groove, and/or 3) residues positioned such that substitution of the existing amino acid with a positively charged alternative such as arginine, lysine, or histidine might be expected to increase proximity (and presumably interaction) of the side chain with the phosphodiester backbone. Because crystal structures that contain the crRNA and PAM-containing DNA are only available for AsCpf1, homologous positions in LbCpf1 and FnCpf1 were identified based on sequence alignment (Table 1) between the three orthologues.

TABLE 1

Comparison of candidate residues for mutation from AsCpf1 and LbCpf1 to create altered PAM recognition specificity variants. Alignments were performed with or without FnCpf1.

| | AsCpf1 | LbCpf1 | LbCpf1(+18) | FnCpf1 | alignment parameters |
|---|---|---|---|---|---|
| G131-L137 | G131 | S117* | S135* | G133** | * means LbCpf1 residues, from alignment with AsCpf1 only ** means FnCpf1 residues, from alignment with AsCpf1 only residues from |
| | L132 | L118* | L136* | L142** | |
| | F133 | F119* | F137* | K143** | |
| | K134 | K120* | K138* | Q144** | |
| | A135 | K121* | K139* | S145** | |
| | E136 | D122* | D140* | K146** | |
| | L137 | I123* | I141* | D147** | |

TABLE 1-continued

Comparison of candidate residues for mutation from AsCpf1 and LbCpf1 to create altered PAM recognition specificity variants. Alignments were performed with or without FnCpf1.

| | AsCpf1 | LbCpf1 | LbCpf1(+18) | FnCpf1 | alignment parameters |
|---|---|---|---|---|---|
| | | | | | alignment with all 3 Cpf1 orthologs (AsCpf1 as reference) |
| S161-S181 | S161 | S143 | S161 | s171 | residues from alignment with all 3 Cpf1 orthologs |
| | F162 | F144 | F162 | F172 | |
| | D163 | N145 | N163 | K173 | |
| | K164 | G146 | G164 | G174 | |
| | F165 | F147 | F165 | W175 | |
| | T166 | T148 | T166 | T176 | |
| | T167 | T149 | T167 | T177 | |
| | Y168 | A150 | A168 | Y178 | |
| | F169 | F151 | F169 | F179 | |
| | S170 | T152 | T170 | K180 | |
| | G171 | G153 | G171 | G181 | |
| | F172 | F154 | F172 | F182 | |
| | Y173 | F155 | F173 | H183 | |
| | E174 | D156 | D174 | E184 | |
| | N175 | N157 | N175 | N185 | |
| | R176 | R158 | R176 | R186 | |
| | K177 | E159 | E177 | K187 | |
| | N178 | N160 | N178 | N188 | |
| | V179 | M161 | M179 | V189 | |
| | F180 | F162 | F180 | Y190 | |
| | S181 | S163 | S181 | S191 | |
| N534-I555 | N534 | Y524 | Y542 | N599 | residues from alignment with all 3 Cpf1 orthologs |
| | F535 | F525 | F543 | F600 | |
| | Q536 | Q526 | Q544 | E601 | |
| | M537 | N527 | N545 | N602 | |
| | P538 | P528 | P546 | S603 | |
| | T539 | Q529 | Q547 | T604 | |
| | L540 | F530 | F548 | L605 | |
| | A541 | M531 | M549 | A606 | |
| | S542 | G532 | G550 | N607 | |
| | G543 | G533 | G551 | G608 | |
| | W544 | W534 | W552 | W609 | |
| | D545 | D535 | D553 | D610 | |
| | V546 | K536 | K554 | K611 | |
| | N547 | D537 | D555 | N612 | |
| | K548 | K538 | K556 | K613 | |
| | E549 | E539 | E557 | E614 | |
| | K550 | T540 | T558 | P615 | |
| | N551 | D541 | D559 | D616 | |
| | N552 | Y542 | Y560 | N617 | |

TABLE 1-continued

Comparison of candidate residues for mutation from AsCpf1 and LbCpf1 to create altered PAM recognition specificity variants. Alignments were performed with or without FnCpf1.

| | AsCpf1 | LbCpf1 | LbCpf1(+18) | FnCpf1 | alignment parameters |
|---|---|---|---|---|---|
| | G553 | R543 | R561 | T618 | |
| | A554 | A544 | A562 | A619 | |
| | I555 | T545 | T563 | I620 | |
| Y595-T616 | Y595 | Y583 | Y601 | Y659 | residues from alignment with all 3 Cpf1 orthologs |
| | D596 | K584 | K602 | K660 | |
| | Y597 | L585 | L603 | L661 | |
| | F598 | L586 | L604 | L662 | |
| | P599 | P587 | P605 | P663 | |
| | D600 | G588 | G606 | G664 | |
| | A601 | P589 | P607 | A665 | |
| | A602 | N590 | N608 | N666 | |
| | K603 | K591 | K609 | K667 | |
| | M604 | M592 | M610 | M668 | |
| | I605 | L593 | L611 | L669 | |
| | P606 | P594 | P612 | P670 | |
| | K607 | K595 | K613 | K671 | |
| | C608 | V596 | V614 | V672 | |
| | S609 | F597 | F615 | F673 | |
| | T610 | F598 | F616 | F674 | |
| | Q611 | S599 | S617 | S675 | |
| | L612 | K600 | K618 | A676 | |
| | K613 | K601 | K619 | K677 | |
| | A614 | W602 | W620 | S678 | |
| | V615 | M603 | M621 | I679 | |
| | T616 | A604 | A622 | K680 | |
| L628-F632 | L628 | F598* | F616* | R690** | * means LbCpf1 residues, from alignment with AsCpf1 only ** means FnCpf1 residues, from alignment with AsCpf1 only if alignment performed with AsCpf1, LbCpf1, and FnCpf1, both LbCpf1 and FnCpf1 don't align in this region with AsCpf1 |
| | S629 | S599* | S617* | I691** | |
| | N630 | K600* | K618* | R692** | |
| | N631 | K601* | K619* | N693** | |
| | F632 | W602* | W620* | H694** | |
| S685-1693 | S685 | S644 | S662 | S729 | residues from alignment with all 3 Cpf1 orthologs ** means FnCpf1 residues, from alignment with AsCpf1 only |
| | K686 | R645 | R663 | K730 | |
| | Y687 | Y646 | Y664 | H731 | |
| | T688 | P647 | P665 | P732 | |
| | K689 | K648 | K666 | E733 | |
| | T690 | W649 | W667 | W734 | |
| | T691 | S650 | S668 | K735 | |
| | S692 | N651 | N669 | D736 | |
| | I693 | A652 | A670 | F737** | |

Figure 2:
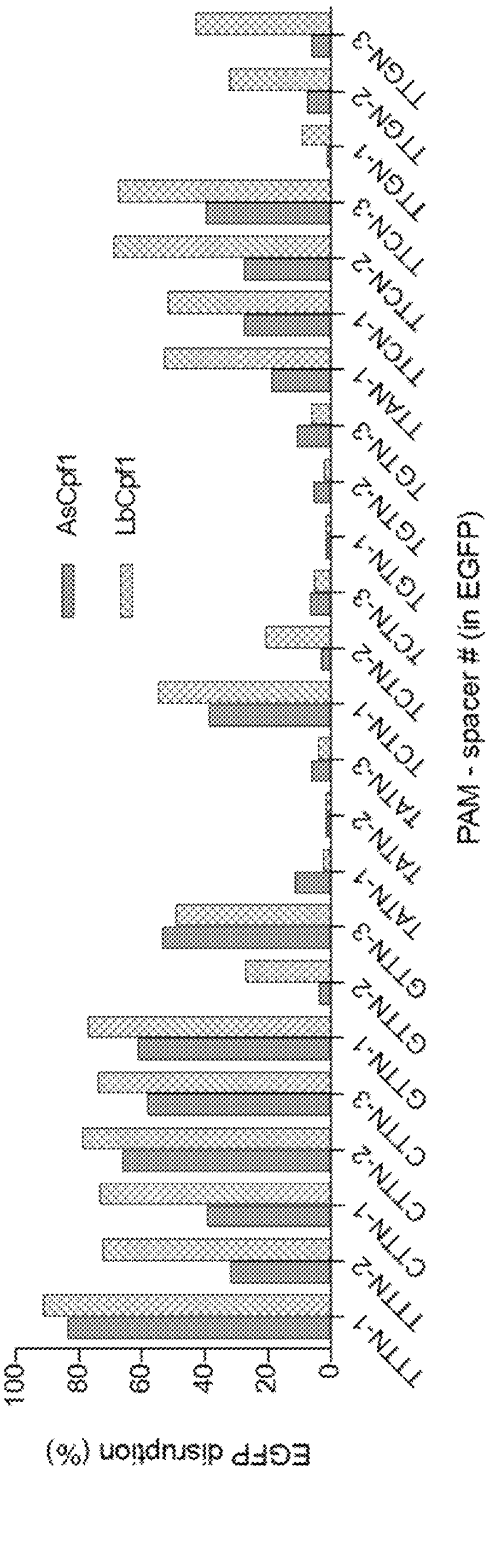
FIG. 2: PAM recognition profiles of wild-type AsCpf1 and LbCpf1 nucleases. The abilities of wild-type AsCpf1 and LbCpf1 to recognize target sites in the human cell-based EGFP disruption assay were determined using crRNAs targeted to sites with either a canonical TTTN PAM, or sites with non-canonical PAMs bearing single base differences. Three sites for each non-canonical PAM were examined, with the exception of ATTN and TTAN due to lack of target sites in the EGFP reporter gene.
Figure 3:
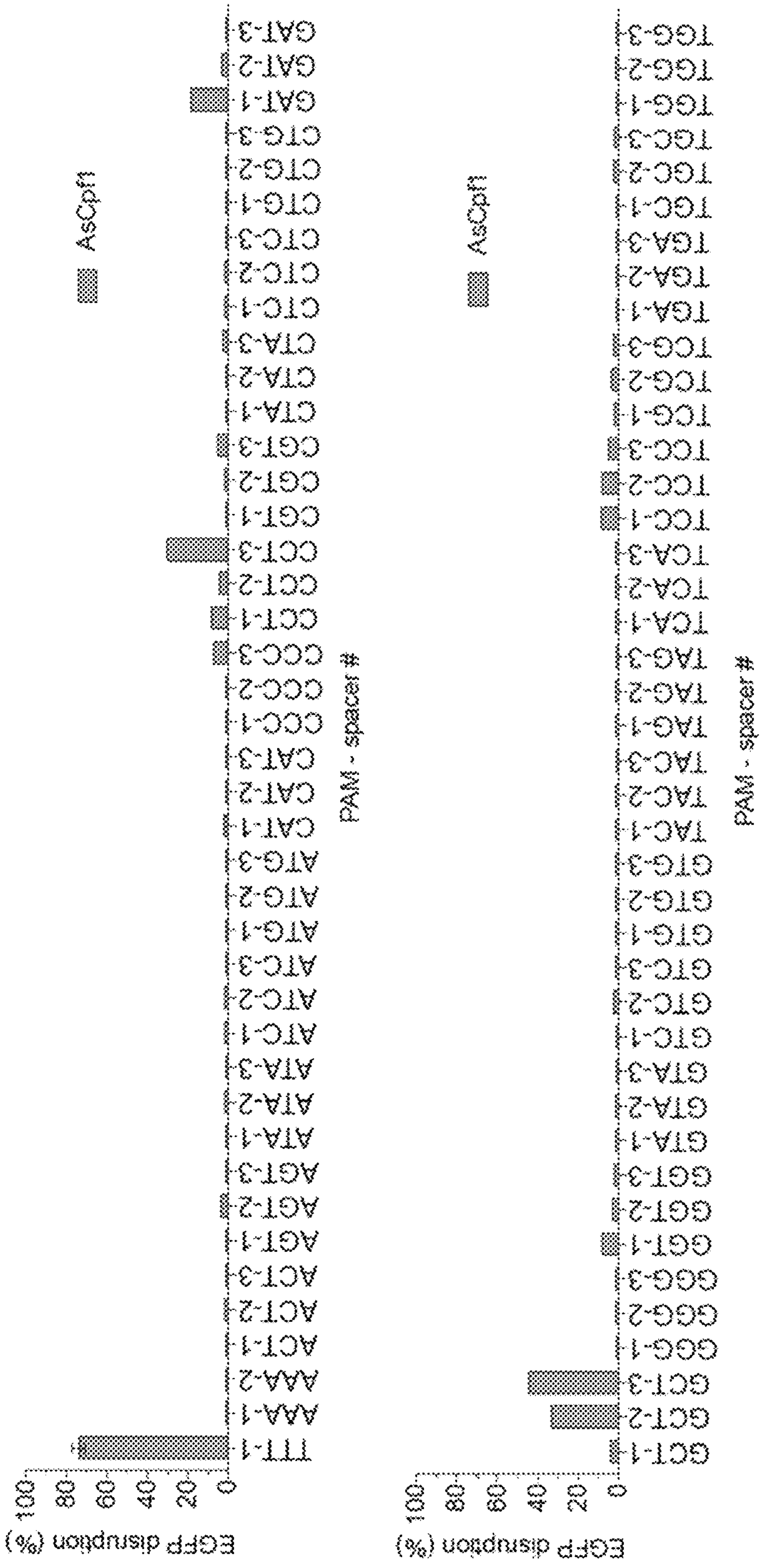
FIG. 3: PAM recognition profiles of wild-type AsCpf1 for sites with canonical PAMs and non-canonical PAMs bearing double and triple base differences. The ability of AsCpf1 to recognize and disrupt target sites in the human cell-based EGFP disruption assay was determined using crRNAs targeted to sites with the indicated PAM. Where possible, three sites for each non-canonical PAM were examined, with the exception of ATTN and TTAN due to the lack of target sites in the EGFP reporter gene. Error bars, s.e.m. for n=3, otherwise n=1.

In initial experiments, we first sought to carefully define the PAM preferences of wild-type AsCpf1 and LbCpf1 by testing the activities of these nucleases in human cells against alternative PAM target sites that have base differences within the TTTN motif defined in initial characterization of these enzymes (Zetsche. Cell 2015). Using our well-established human cell-based EGFP disruption assay, we first tested the abilities of AsCpf1 and LbCpf1 to mutagenize various target sites harboring a canonical TTTN or non-canonical PAMs bearing a range of different single base mismatches within the TTT motif. We determined that although both AsCpf1 and LbCpf1 could tolerate non-canonical bases in the PAM, recognition by LbCpf1 was more promiscuous (FIG. 2). Both Cpf1 enzymes efficiently and consistently targeted sites in our EGFP disruption assay with alternative CTTN, GTTN, and TTCN PAMs. (The EGFP disruption assay measures loss of EGFP expression as a surrogate for targeting of sites within the EGFP sequence by genome-editing nucleases (Reyon. Nature Biotechnology 2012). We also examined the ability of AsCpf1 to recognize sites that contain more divergent PAM sequences in EGFP, with either two or three base differences in the TTT sequence of a TTTN PAM. With the exception of some slight and variable activity against sites containing CCCN, CCTN, GATN, GCTN, and TCCN PAMs, we found that the wild-type AsCpf1 nuclease did not efficiently target any of these alternative PAMs (FIG. 3).

Figure 4:
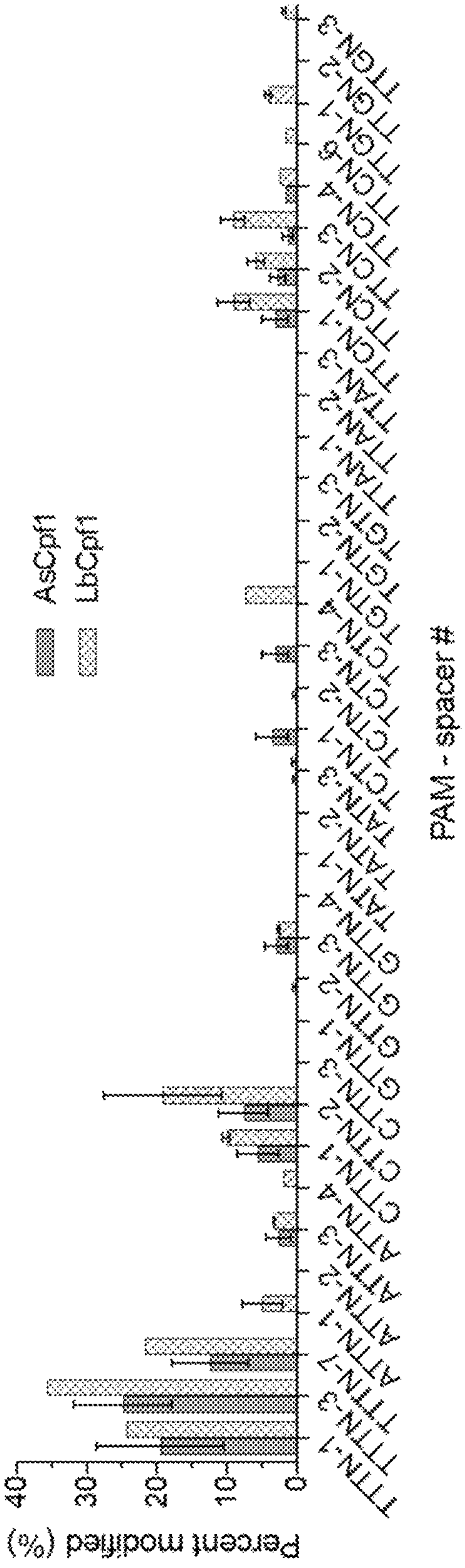
FIG. 4: PAM recognition profiles of AsCpf1 and LbCpf1 for canonical and non-canonical (single base difference) PAM sites. The abilities of wild-type AsCpf1 and LbCpf1 to recognize and disrupt endogenous target sites in U2OS human cells was determined by T7E1 assay using crRNAs targeted to sites with either a canonical TTTN PAM or with a non-canonical PAM bearing a single base difference. Where possible, three sites for each non-canonical PAM were examined. Error bars, s.e.m. for n=2 or 3, otherwise n=1.

However, because activity observed in the EGFP disruption assay might represent a combination of nuclease mediated gene disruption and transcriptional repression mediated by DNA-binding (without cleavage), we tested the activities of AsCpf1 and LbCpf1 on endogenous human gene target sites that contain alternative PAM sequences with single base differences relative to the canonical PAM, because the read-out from this assay quantifies bona fide gene disruption events (FIG. 4). We found that even though modest activities were observed with AsCpf1 and LbCpf1 on sites harboring certain non-canonical PAM sites in our EGFP disruption assay, we did not observe comparable induction of indel mutations on endogenous gene sites bearing these alternative PAM sequences. This result suggests that although wild-type AsCpf1 and LbCpf1 nucleases may efficiently bind alternative PAM sequences with single base differences, in some cases they may not efficiently cleave these sites.

Given the limited capability of wild-type Cpf1 nucleases to cleave non-TTTN PAMs, we sought to engineer Cpf1 variants that could target and disrupt sites harboring such alternative PAMs. In initial experiments, we attempted to engineer Cpf1 nucleases with relaxed PAM recognition specificities. We used the EGFP disruption assay to rapidly identify and screen single amino acid substitutions in AsCpf1 that could alter PAM recognition, reasoning that we would need to ultimately validate any variants we identified for their abilities to cleave sites within actual endogenous genes in human cells given the limitations of the EGFP-based assay described above. To test the hypothesis of whether rational substitutions of AsCpf1 could alter PAM specificity, we focused on testing the effect of amino acid substitutions at positions: T167, S170, E174, T539, S542, K548, N551, N552, M604, and K607.

Note that the subsequent PAM numbering is based on the TTTN PAM being numbered $T_4T_3T_2N_1$, and only a small subset of all possible PAMs were examined for the initial tests of each AsCpf1 variant, with subsequent more extensive testing for combinations of variants.

Figure 5A:
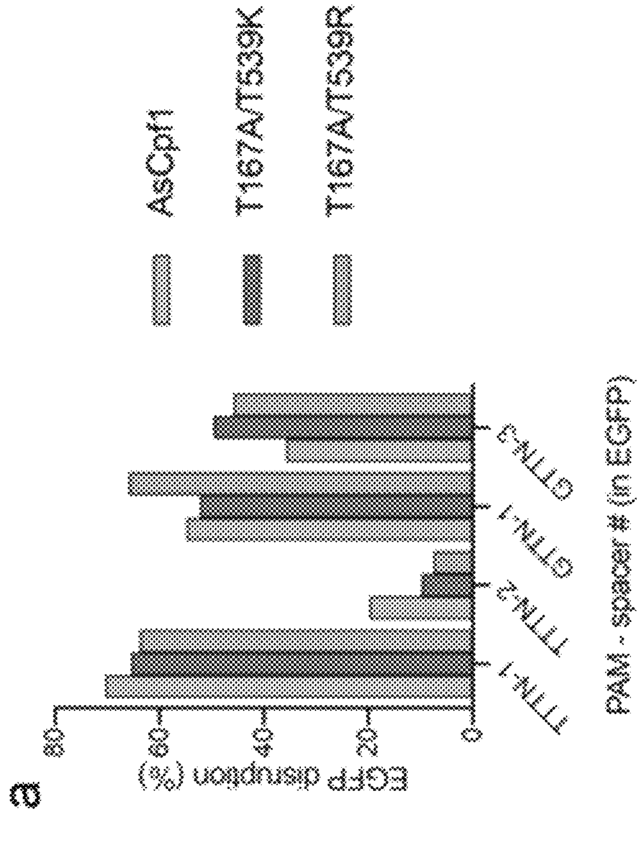
FIGS. 5A-5H: Alteration of AsCpf1 PAM recognition specificity by rational mutation of residues physically proximal to PAM DNA bases. The activities of wild-type AsCpf1 and variants bearing single or double mutations were assessed with crRNAs targeted to sites bearing canonical TTTN or non-canonical PAM sites using either the human cell EGFP disruption assay or by quantifying indel mutation frequencies induced at endogenous gene sites in human U2OS cells. Wild-type AsCpf1 was compared to: (A) T167/T539 variants using crRNAs targeted to sites in EGFP; (B) S170 and E174 variants using crRNAs targeted to sites in EGFP; (C and D) S542 variants using crRNAs targeted to sites in EGFP (panel C) or endogenous human gene sites (panel D); (E) N551 and N552 variants using crRNAs targeted to sites in EGFP; (F) K607 variants using crRNAs targeted to sites in EGFP; (G and H) S542/K607 variants using crRNAs targeted to sites in EGFP (panel G) and endogenous human gene sites (panel H).

T167/T539: Based on the proximity of T539 to $T_4$ of the PAM in the AsCpf1 co-crystal structure, we envisioned that concurrent substitutions of T539K/T167A or T539R/T167A might enable base specific recognition of a G at the fourth position of the PAM by: 1) the T539 substitution to K or R enabling base specific readout of a guanine, and/or 2) the T167A substitution alleviating other interfering or unfavorable contacts induced by alteration of the T539 residue. Relative to wild-type AsCpf1, both the T539K/T167A and T539R/T167A variants show improved activity in the EGFP disruption assay on sites harboring GTTN PAMs with minimal or only modest reductions in activity on sites harboring canonical TTTN PAMs (FIG. 5A).

Figure 5B:
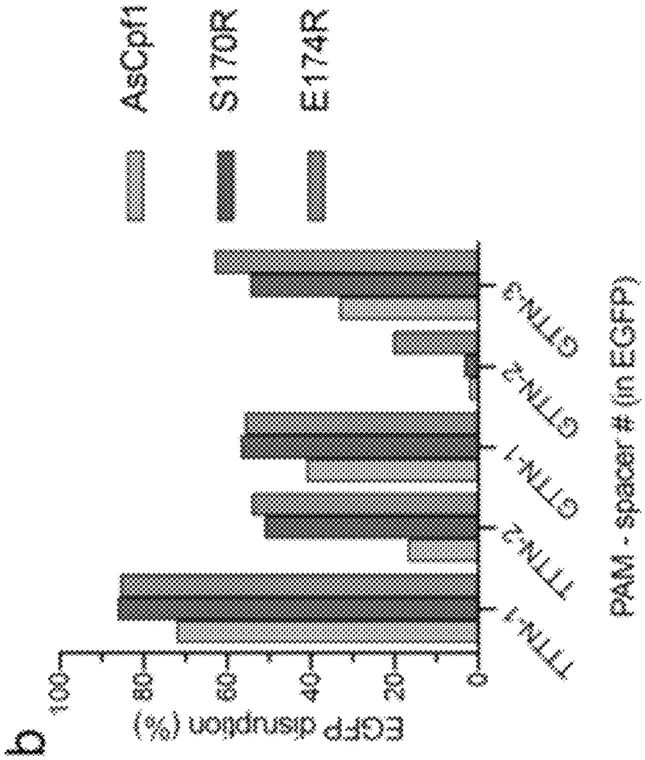
Figure 8A:
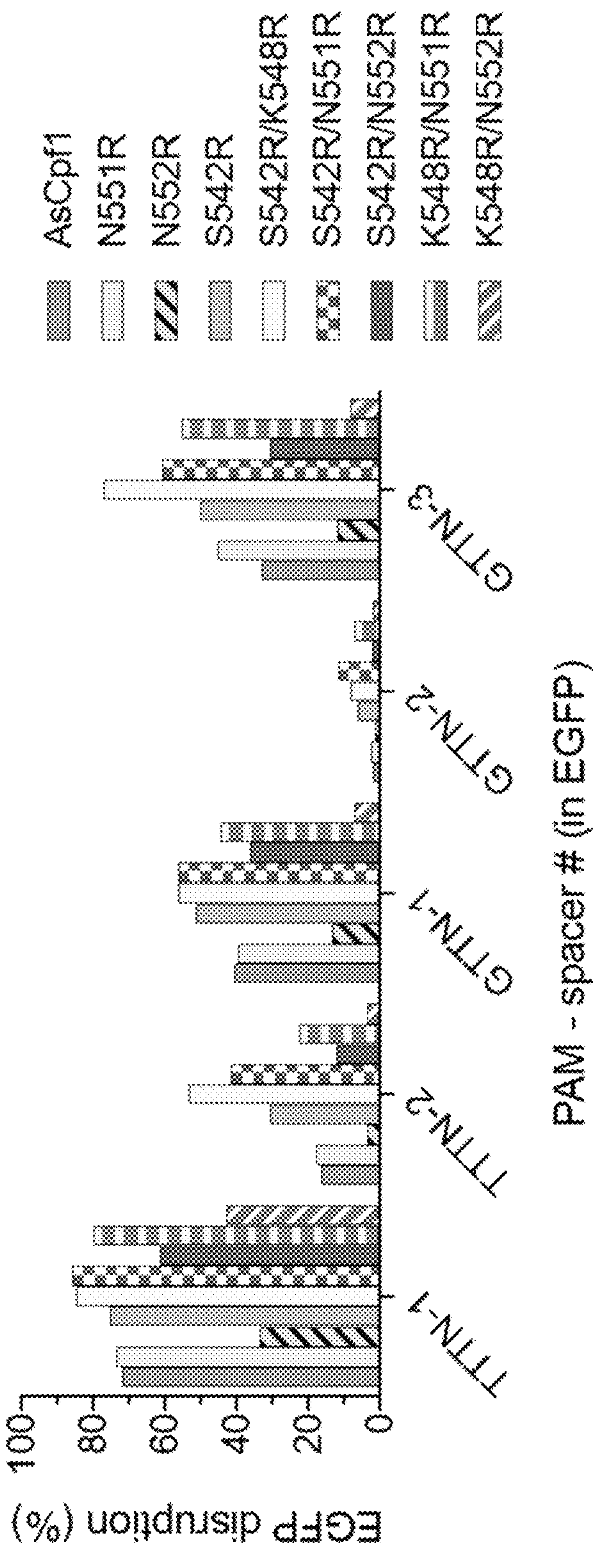
FIGS. 8A-8C: PAM recognition profiles of rationally designed AsCpf1 variants bearing additional mutations at residues positioned near PAM DNA bases. In separate experiments shown in panels A, B, and C, single amino acid substitutions and double or triple combinations of amino acid substitutions were tested using the human cell-based EGFP reporter assay to assess their abilities to recognize target sites bearing canonical TTTN or non-canonical PAM sites.
Figure 8B:
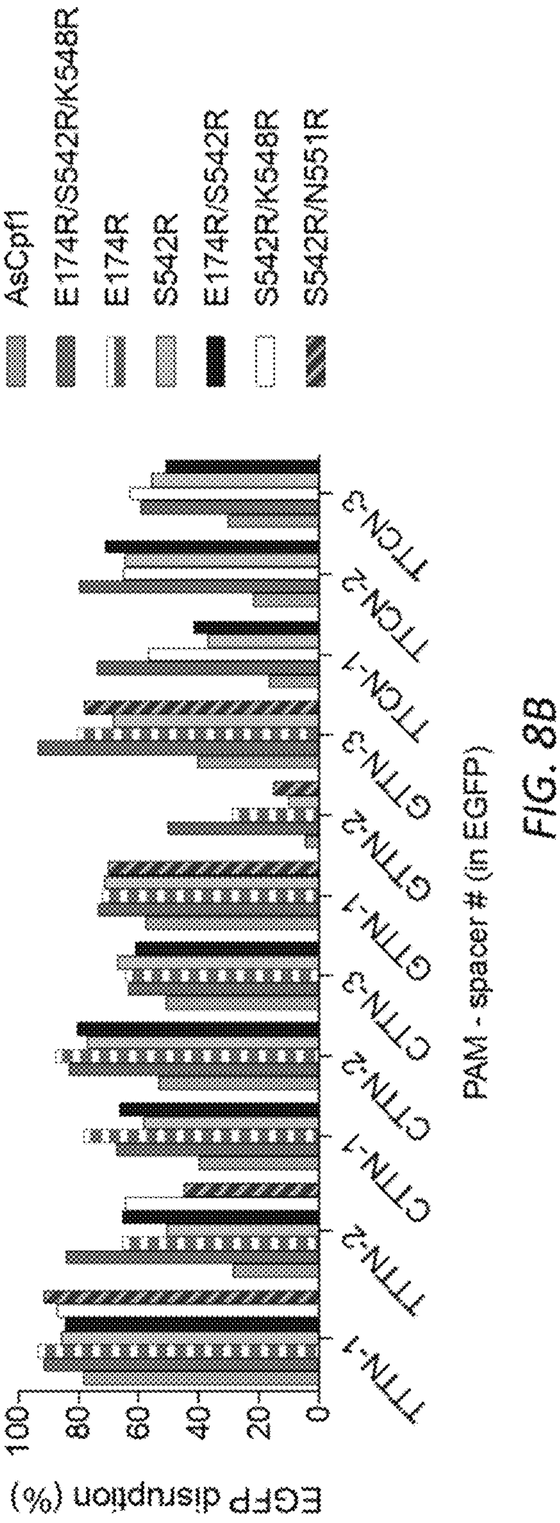
Figure 8C:
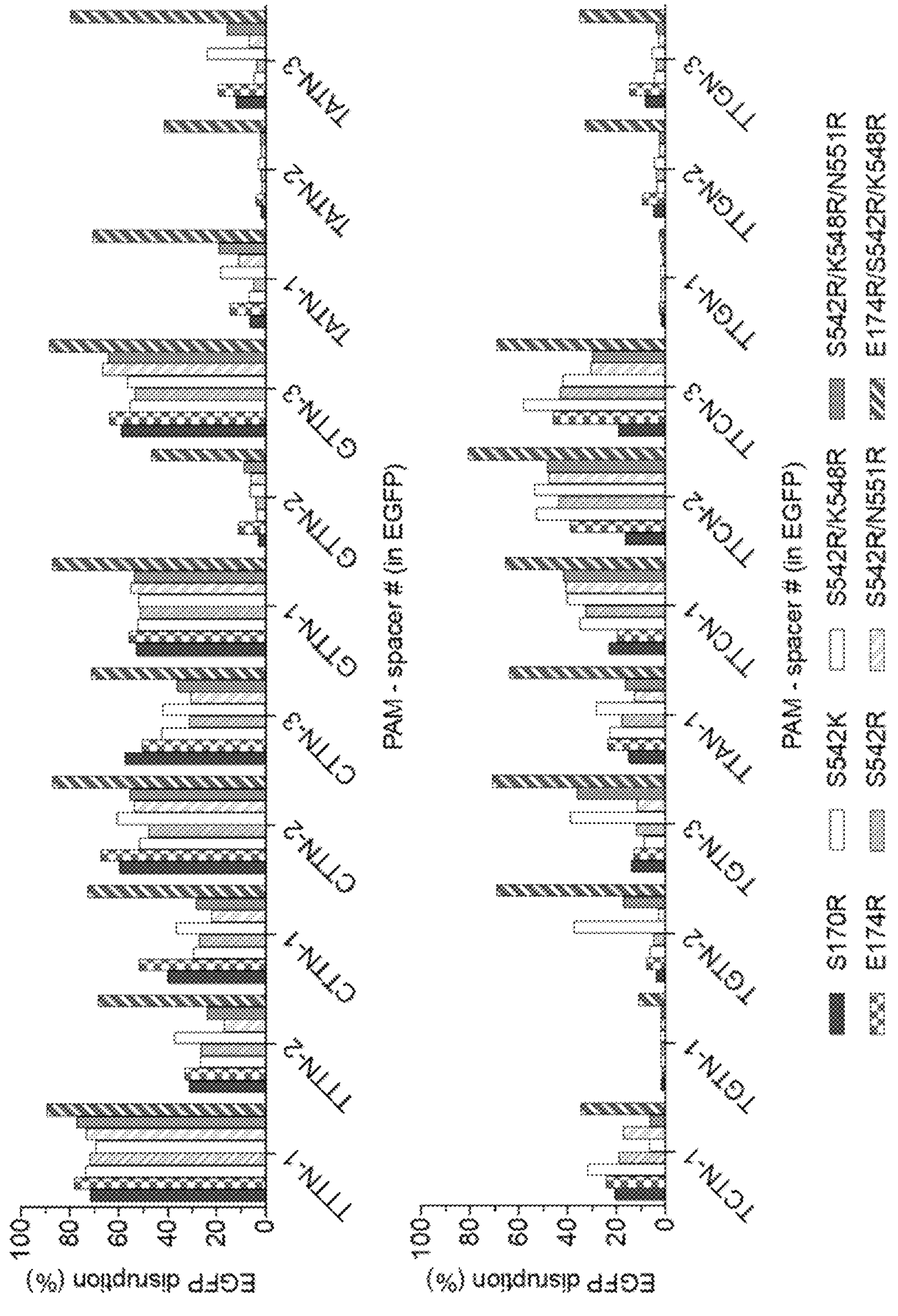

S170/E174: Both residues lie within the DNA major groove with S170 near $T_2$ of the PAM and E174 positioned near the $T_2$ or $N_1$ position of the PAM and near the target strand DNA backbone. We envisioned that arginine substitutions at these positions might relax PAM specificity, enabling the creation of non-specific contacts to the DNA backbone or potentially establishing base specific recognition of TTGN or TTTG PAMs. Both the S170R and E174R variants increase activity at canonical TTTN PAMs in the EGFP disruption assay while also increasing activity on sites bearing GTTN PAMs (FIG. 5B). We also show that both the S170R and E174R variants confer an increased ability to target CTTN and TTCN PAM sites (FIG. 8C).

Figure 5C:
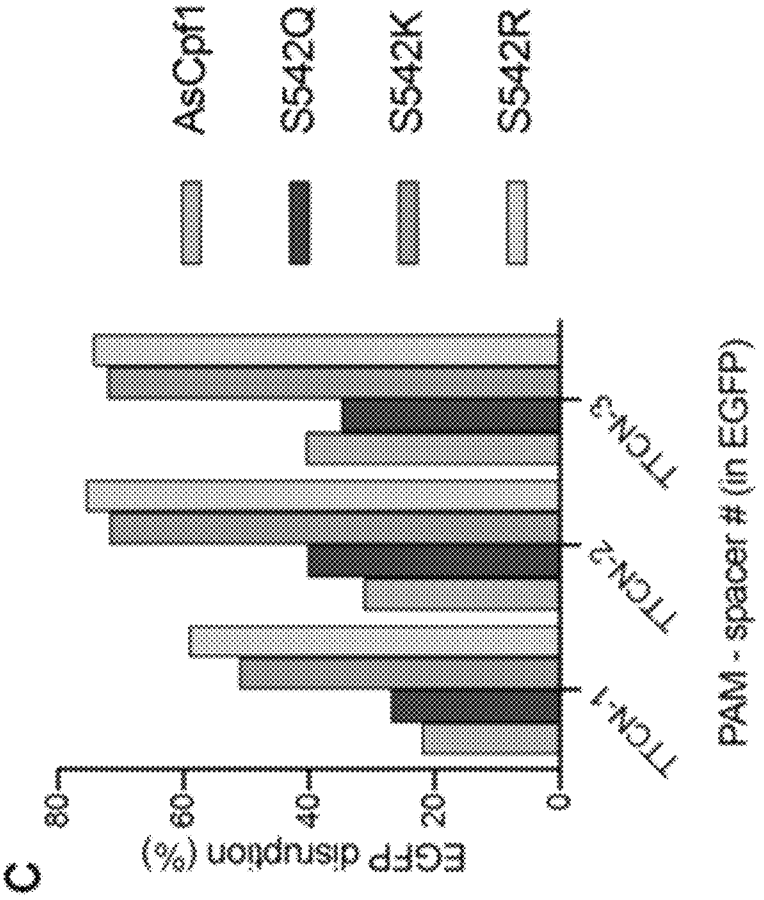
Figure 5E:
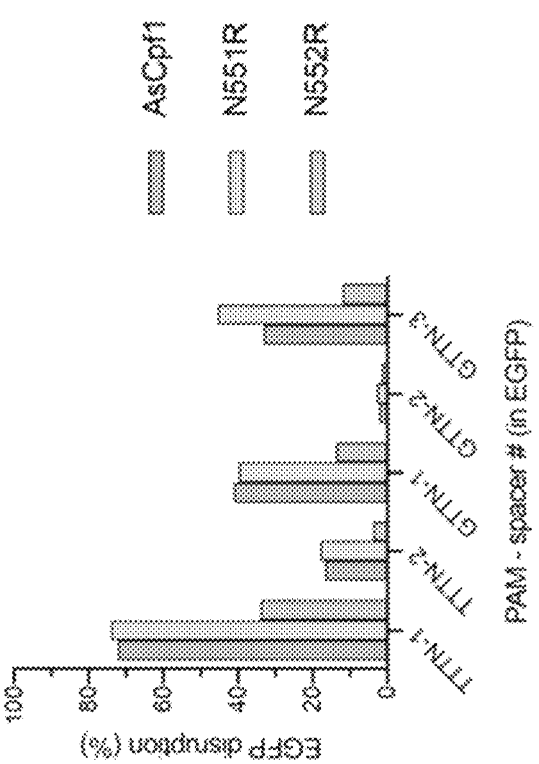
Figure 5D:
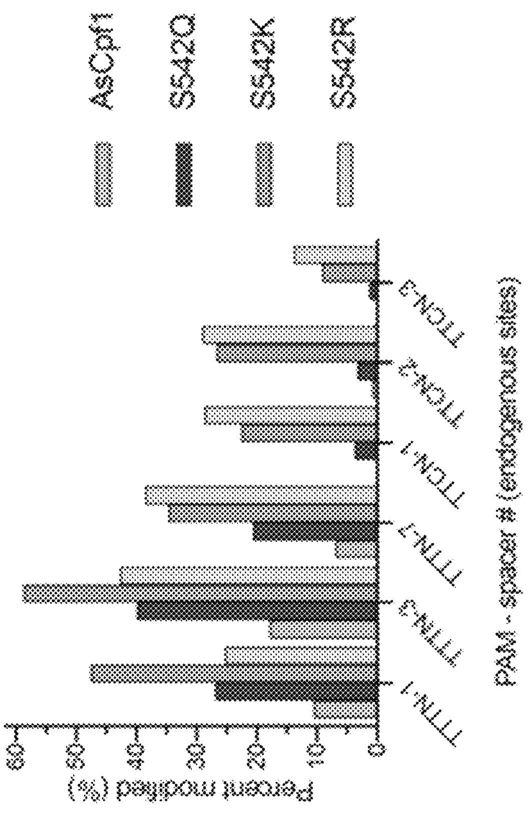
Figure 7A:
FIGS. 7A-7B: PAM recognition profiles of wild-type AsCpf1 and the AsCpf1-S542R variant on endogenous human gene target sites. Nucleases were assessed for their abilities to mutagenize endogenous gene target sites in human U2OS cells using crRNAs targeted to sites bearing either a canonical TTTN PAM or a non-canonical PAM with a single base difference (panel A) or double or triple base differences (panel B). Where possible, three sites for each non-canonical PAM were examined.

S542: This residue is positioned in the major groove in close proximity to the $T_3$ and $T_2$ bases of the PAM. Therefore, we hypothesized that S542K or S542R mutations might function to relax PAM specificity by: 1) providing additional non-specific energy in the PAM binding interface to accommodate non-canonical bases, and/or 2) creating a base-specific contact that might potentially recognize a $G_3$ or $G_2$ on the non-target strand, or perhaps a $G_3$ or $G_2$ on the target strand which would be a $C_3$ or $C_2$ on the non-target strand of the PAM. Our hypotheses would predict that variants bearing substitutions at S542 might be expected to enable recognition of sites harboring TGTN, TTGN, TCTN, or TTCN PAMs. Using the EGFP reporter assay, we found that AsCpf1 variants with either an S542K or an S542R substitution (but not with a S542Q substitution) exhibit increase activities on target sites with non-canonical TTCN PAMs (FIG. 5C). Interestingly, when tested for their abilities to cleave and mutagenize endogenous human gene targets, AsCpf1 variants bearing an S542Q, S542K, or S542R mutation all show increased abilities to induce indel mutations on target sites bearing TTTN PAMs (FIG. 5D) but only the S542K and S542R variants show increased activities on target sites bearing non-canonical TTCN PAMs (FIG. 5D). Recognition of additional non-canonical PAMs by these variants is also further examined in FIG. 7 (see below).

Figure 9A:
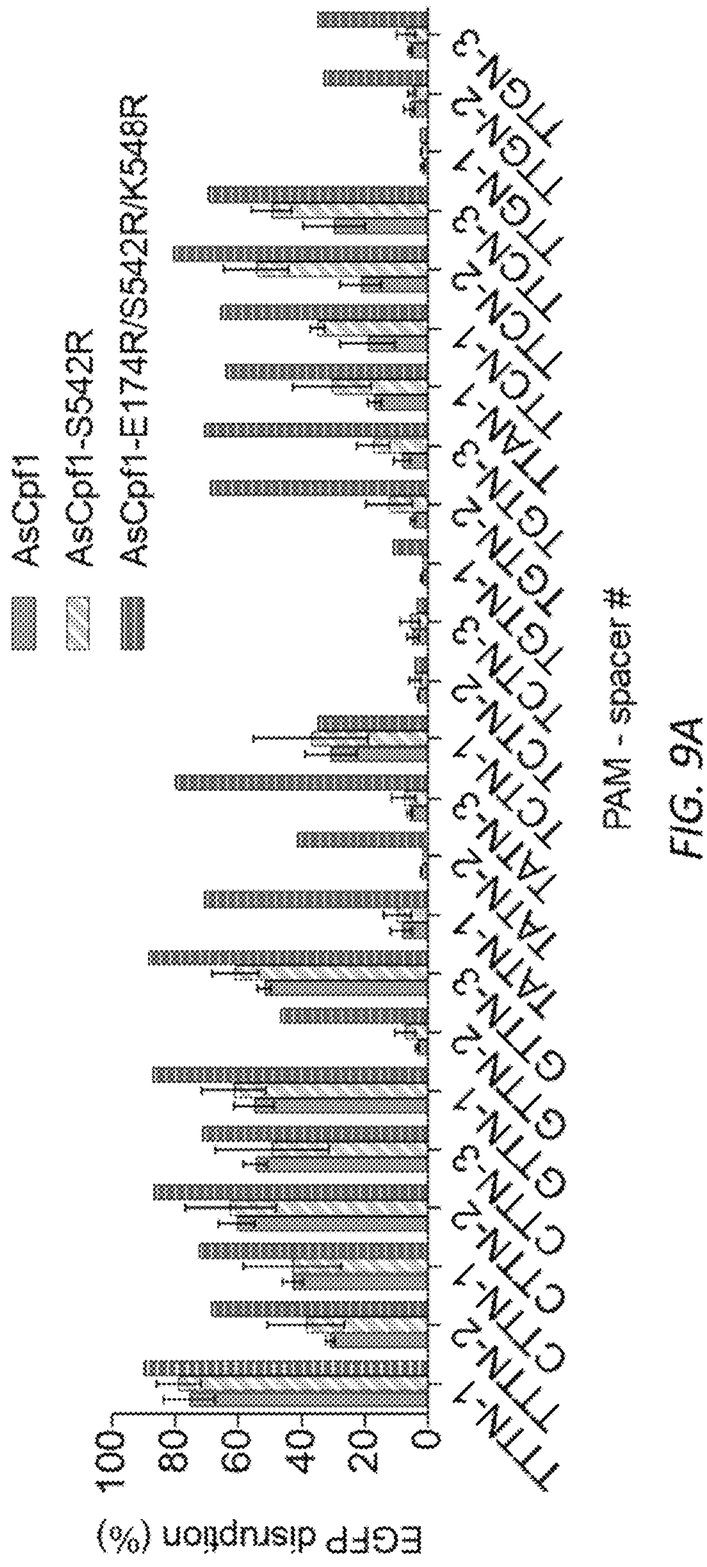
FIGS. 9A-9B: PAM of wild-type AsCpf1 and AsCpf1 variants. (A) The activity of wild-type AsCpf1 was compared to the activities of variants bearing a single S542R substitution or a combination of the E174R, S542R, and K548R substitutions. Activities of these nucleases were tested using human cell-based EGFP disruption assay using crRNAs targeted to sites bearing either a canonical TTTN PAM or PAMs with single base differences. (B) The activity of wild-type AsCpf1 was also compared to the E174R/S542R/K548R variant using the human cell-based EGFP reporter assay with crRNAs targeting sites with a canonical TTTN PAM or PAM bearing double or triple base differences. Where possible, three sites for each non-canonical PAM were examined. Error bars, s.e.m. for n=2 or 3, otherwise n=1.

K548: This residue is positioned near $A_4$ and $A_3$ of the non-PAM DNA strand and near the backbone of the target strand DNA. We therefore hypothesized that substitutions at this position might potentially increase activity against target sites with non-canonical CTTN, TCTN, or CCTN PAMs. We found that introduction of a K548R mutation appears to confer no substantial alteration in PAM specificity on its own but does contribute to relaxing PAM recognition in the context of other substitutions at positions S542, N551, and N552 (see below in FIG. 9).

N551/N552: The residues N551 and N552 are both positioned in the major groove between the target and non-target DNA strand backbones, but N552 is also very near $A_3$ of the non-PAM DNA strand and near the target strand DNA backbone. Whereas an N551R substitution appears to have no detrimental effect or in one case perhaps slightly improve AsCpf1 activity on target sites with non-canonical GTTN PAM sequences (without impacting recognition of sites with canonical TTTN PAMs), an N552R substitution appears to abrogate activity on target sites with either TTTN or GTTN PAMs (FIG. 5E). We also explored the N551R and N552R substitutions in combination with the S542R mutation and other combinations of mutations (see FIG. 8B and FIG. 11 below)

Figure 5F:
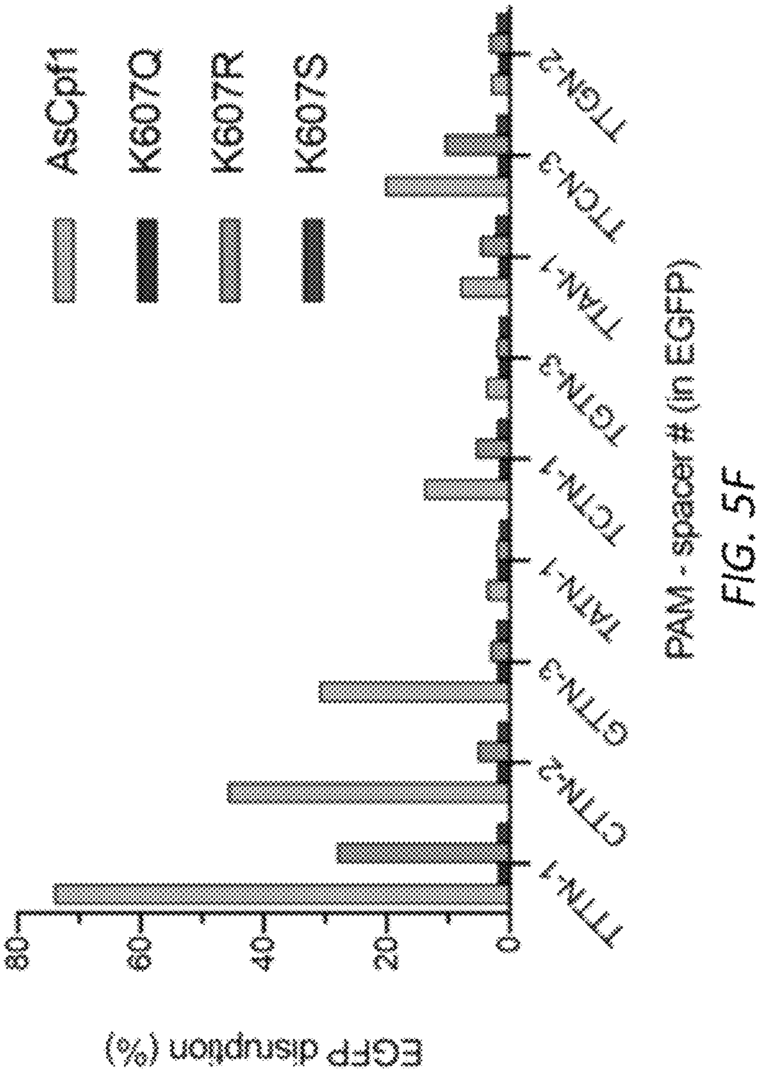
Figure 5H:
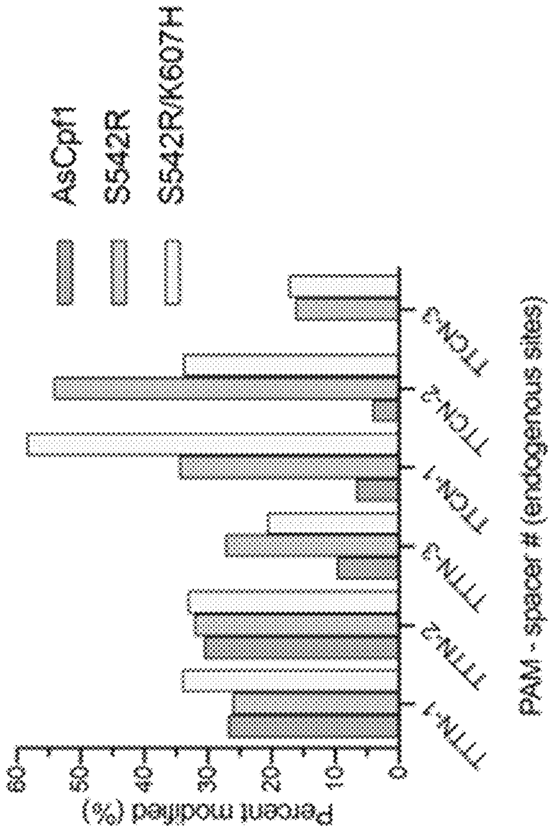
Figure 5G:
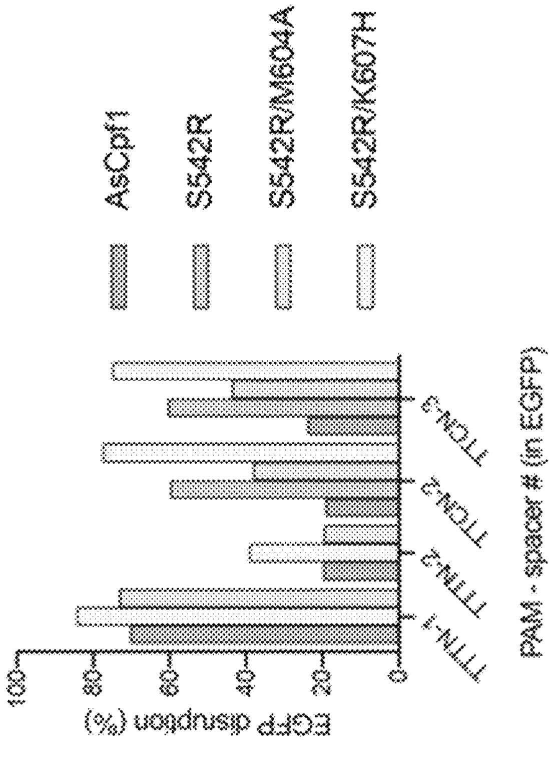

M604/K607: Residue M604 is positioned in the DNA minor groove near the $N_1$ position of the PAM and the $A_2$ nucleotide of the non-PAM target DNA strand. Residue K607 is also positioned in the minor groove and forms a network with $T_3$ and $T_2$ (of the PAM) and $A_3$ of the non-PAM DNA strand. Multiple different substitutions at K607 alone appear to negatively impact the activity of AsCpf1 (FIG. 5*f*), but combining a K607H substitution together with the S542R mutation leads to a variant with increased activity against sites harboring canonical TTTN or non-canonical TTCN PAMs (as judged by the EGFP disruption assay or by the mutagenesis of endogenous human gene target sites, in FIGS. 5*g* and 5*h*, respectively). Similarly, an M604A substitution combined with an S542R substitution improves activity against target sites harboring canonical TTTN or non-canonical TTCN PAMs when assayed using the EGFP disruption assay (FIG. 5*g*).

Figure 6A:
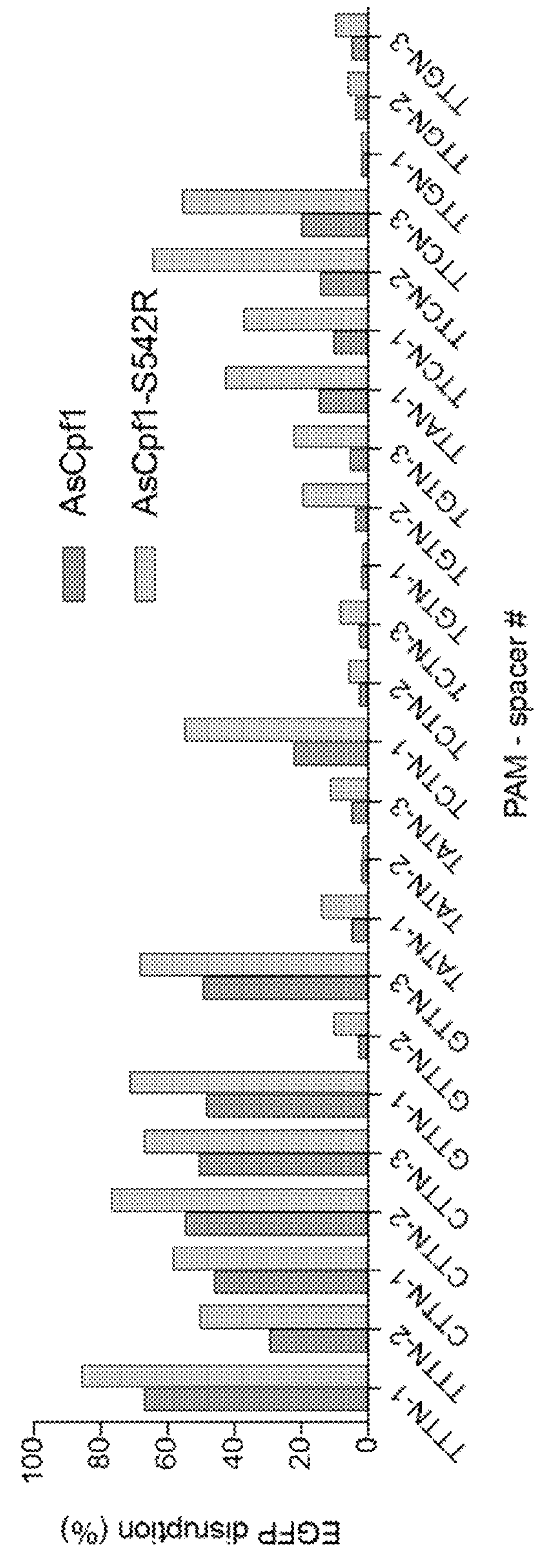
FIGS. 6A-6B: PAM recognition profiles of wild-type AsCpf1 and the AsCpf1-S542R variant. The activities of these nucleases in the human cell-based EGFP disruption assay were determined with crRNAs targeted to sites bearing either a canonical TTTN PAM or a non-canonical PAM with a single base difference (panel A) or double or triple base differences (panel B). Where possible, three sites for each non-canonical PAM were examined, with the exception of ATTN and TTAN due to lack of sufficient target sites in the EGFP reporter gene. n=1.
Figure 6B:
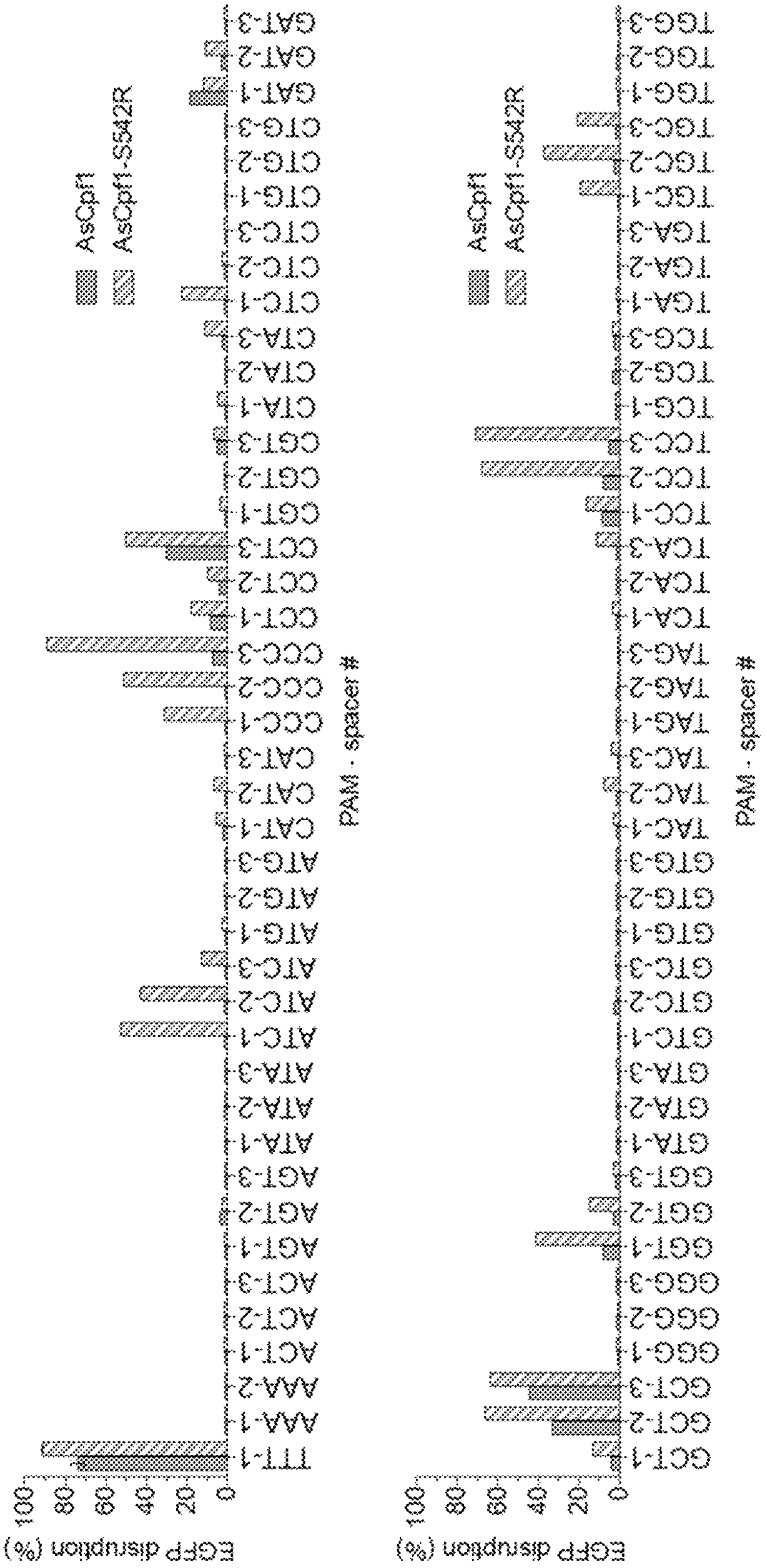
Figure 7B:
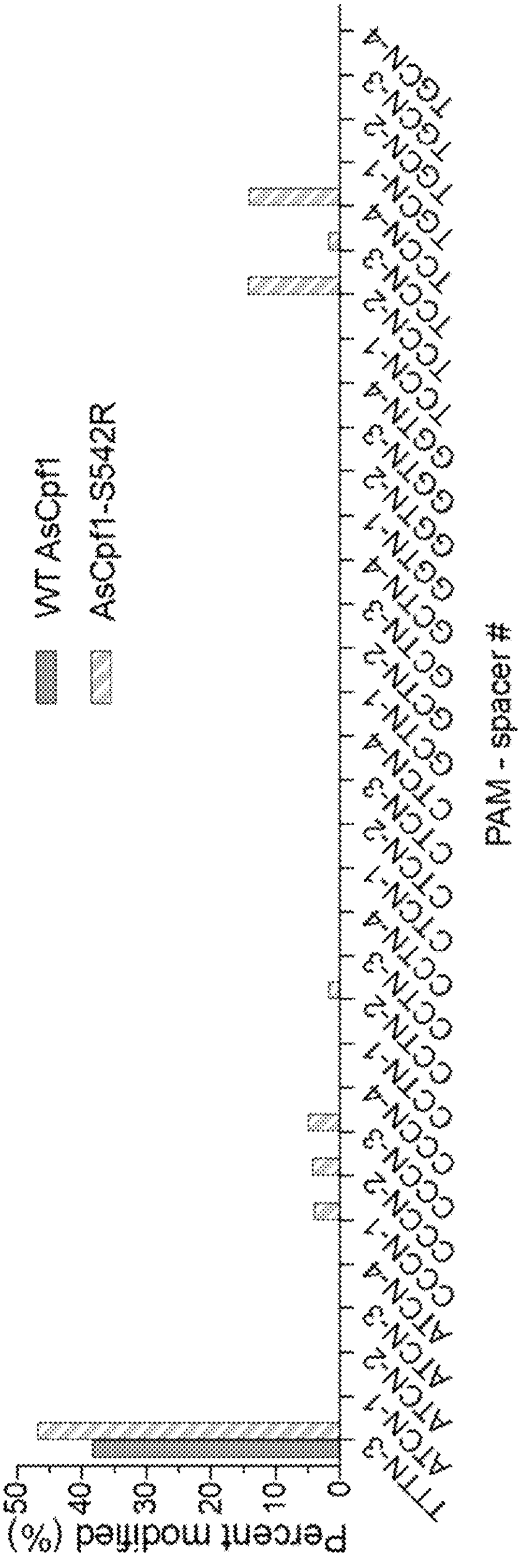

To further test the relaxed PAM specificity phenotype resulting from introduction of the S542R mutation, we compared the EGFP disruption activity of wild-type AsCpf1 with that of AsCpf1-S542R across target sites in EGFP that harbor a PAM with a single base difference relative to the canonical sequence (including the four non-canonical PAMs that we hypothesized might be recognized by the S542R variant) (FIG. 6A). In these experiments, we observed increased activities of the AsCpf1-S542R variant against target sites bearing multiple non-canonical PAM sites, including PAMs beyond the four hypothesized by our base-specific contact model (suggesting a general improvement in PAM binding affinity and a related relaxation in PAM specificity). To further examine the potential of the S542 mutant to expand AsCpf1 targeting range, we compared wild-type AsCpf1 to the S542R variant on a series of EGFP target sites with PAMs that harbor 2 or 3 base differences relative to the canonical site (FIG. 6B). The S542R mutant maintained at least the same level of activity observed with wild-type AsCpf1 at all sites, and dramatically improved activity (in some cases several fold) against many sites with PAMs harboring two or three substitutions (FIG. 6B). Our results with the EGFP disruption assay suggest that the AsCpf1-S542R variant can recognize sites harboring the following PAMs: TTTN, CTTN, GTTN, TCTN, TGTN, TTAN, TTCN, ATCN, CCCN, CCTN, GCTN, GGTN, TCCN, and TGCN. We next tested the S542R variant on endogenous human gene target sites bearing PAMs with one (FIG. 7A) and 2- or 3 base substitutions (FIG. 7B). These experiments again revealed that the S542R variant can cleave a wider range of mismatched PAM motifs but the spectrum of these sites was not as broad as what we observed in the EGFP disruption assay. Based on the results of our experiments with these endogenous human gene target sites, we conclude that the AsCpf1-S542R variant can cleave sites that harbor the following PAMs: TTTN, ATTN, CTTN, GTTN, TCTN, TTCN, CCCN, and TCCN.

The observation that a single substitution at S542 could expand the PAM recognition specificity of AsCpf1 suggested that it might be possible to further increase targeting range by adding single or multiple mutations to this variant. As shown in FIG. 5 and described in detail above, we found that amino acid substitutions at S170, E174, K548, N551, and K607 (alone or in combinations), resulted in somewhat altered PAM recognition specificities. Thus, we sought to explore whether various other combinations of substitutions at these positions together with the S542R mutation might further improve the targeting range of AsCpf1. First, we determined that combinations of substitutions that include S542R/K548R, S542R/N551R, and K548R/N551R could in most cases improve activity relative to the S542R substitution alone on target sites harboring canonical TTTN or non-canonical GTTN PAMs (FIG. 8A). Next, using the EGFP disruption assay, we determined across a larger number of target sites with more diverse PAM sequences that: 1) that variants harboring either the single S170R or E174R substitutions could for many target sites outperform the S542R substitution, 2) the E174R/S542R, S542R/K548R, and S542R/N551R variants perform as well or better than the S542R alone across a range of different target sites, and 3) that the E174R/S542R/K548R triple substitution variant conveyed the highest level of activity among a large series of AsCpf1 variants we tested against a range of target sites harboring canonical TTTN and non-canonical CTTN, GTTN, TATN, TCTN, TGTN, TTAN, TTCN, and TTGN PAM sites (FIGS. 8B And 8C).

Figure 9B:
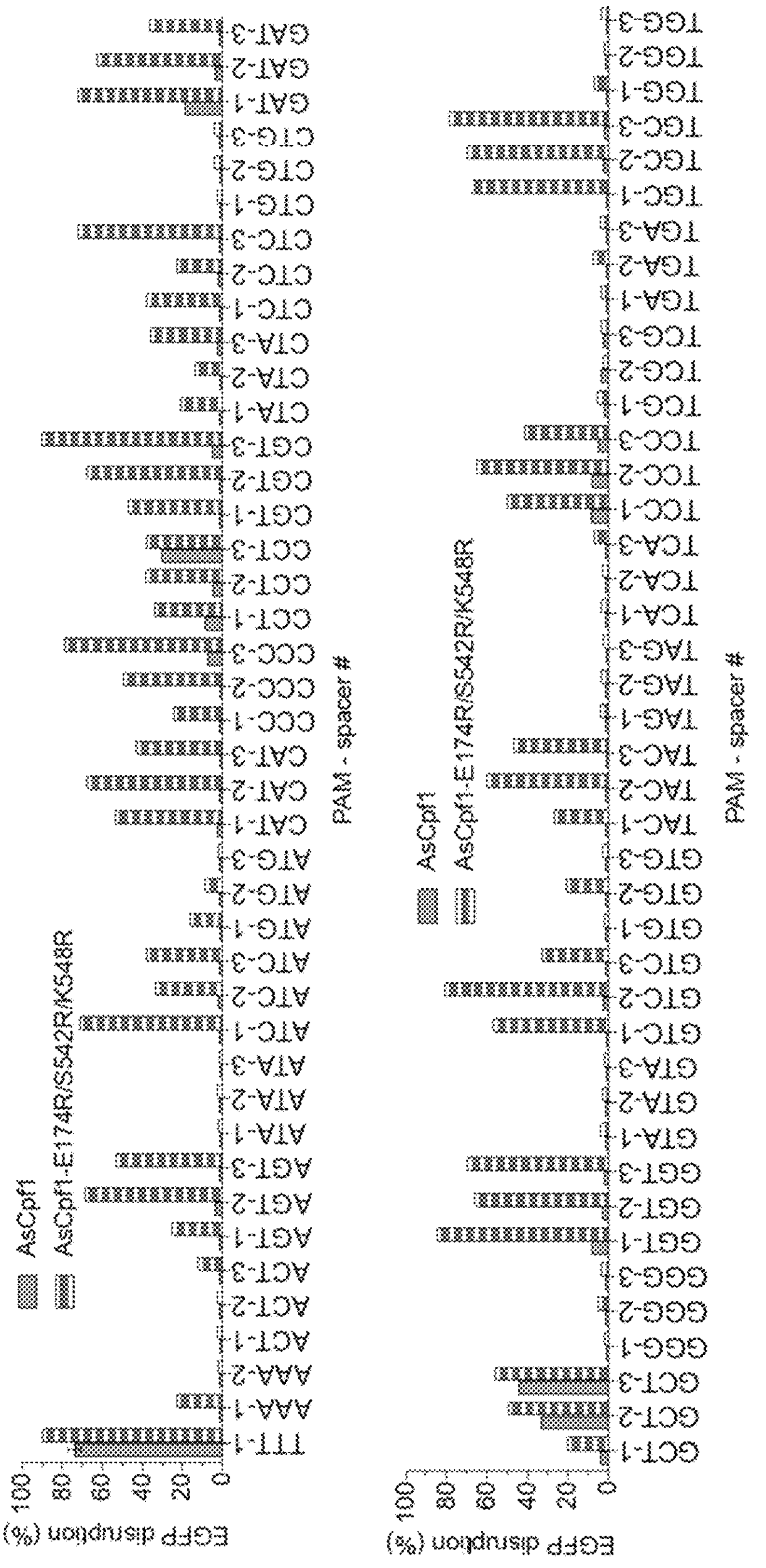

Further comparison of the AsCpf1 E174R/S542R/K548R variant to wild-type AsCpf1 and the AsCpf1-S542R variant on EGFP target sites bearing PAMs with single base differences (FIG. 9A) revealed that the E174R/S542R/K548R variant had higher EGFP disruption activity than both wild-type AsCpf1 and S542 on nearly all target sites with various PAM sites tested. Furthermore, when the E174R/S542R/K548R variant was compared to wild-type AsCpf1 on a series of EGFP sites with PAMs bearing two or three mismatches, substantial increases in EGFP disruption were observed for many of these sites (FIG. 9B). The E174R/S542R/K548R triple substitution variant also showed generally higher activities and on a wider range of variant PAMs than the S542R variant (compare FIG. 9B to FIG. 6B), including efficient recognition of sites harboring the following PAMs: TTTN, CTTN, GTTN, TATN, TCTN, TGTN, TTAN, TTCN, TTGN, AGTN, ATCN, CATN, CCCN, CCTN, CGTN, CTAN, CTCN, GATN, GCTN, GGTN, GTCN, TACN, TCCN, and TGCN.

Figure 10A:
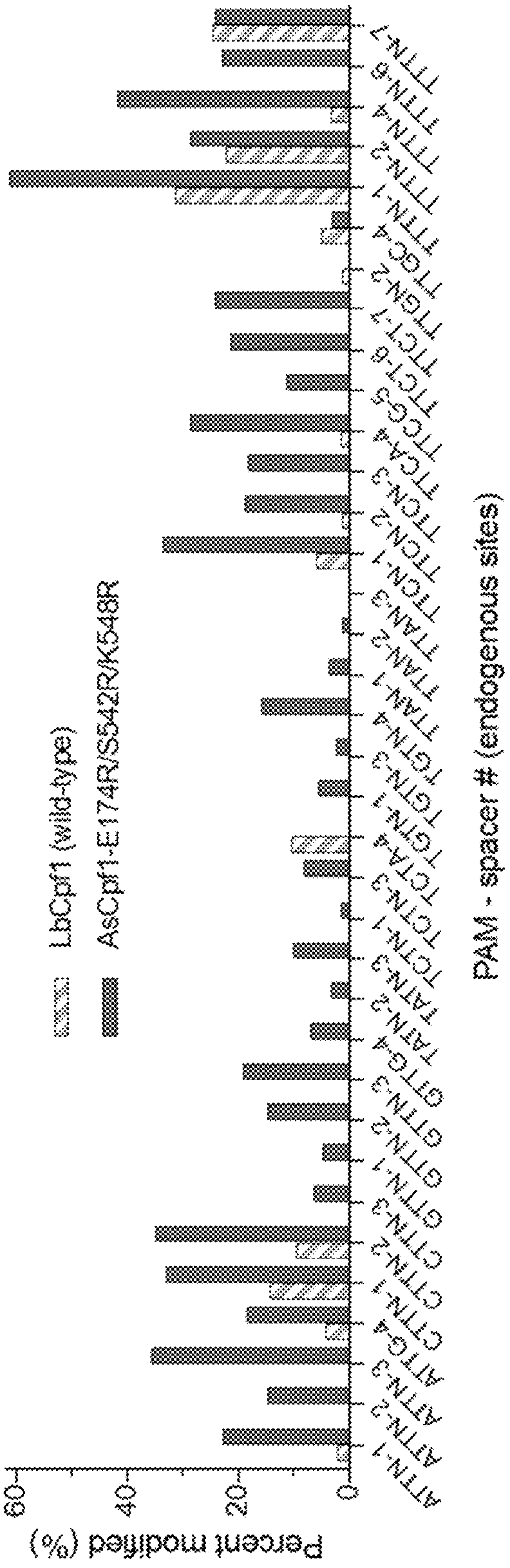
FIGS. 10A-10B: Comparison of the PAM recognition profiles of wild-type LbCpf1 and AsCpf1 variants. The ability of wild-type LbCpf1 to modify endogenous human gene target sites was compared to that of the AsCpf1 E174R/S542R/K548R variant. This experiment used crRNAs targeted to sites bearing either canonical TTTN PAMs and PAMs with single base differences (panel A), or PAMs with double or triple base differences (panel B).
Figure 10B:
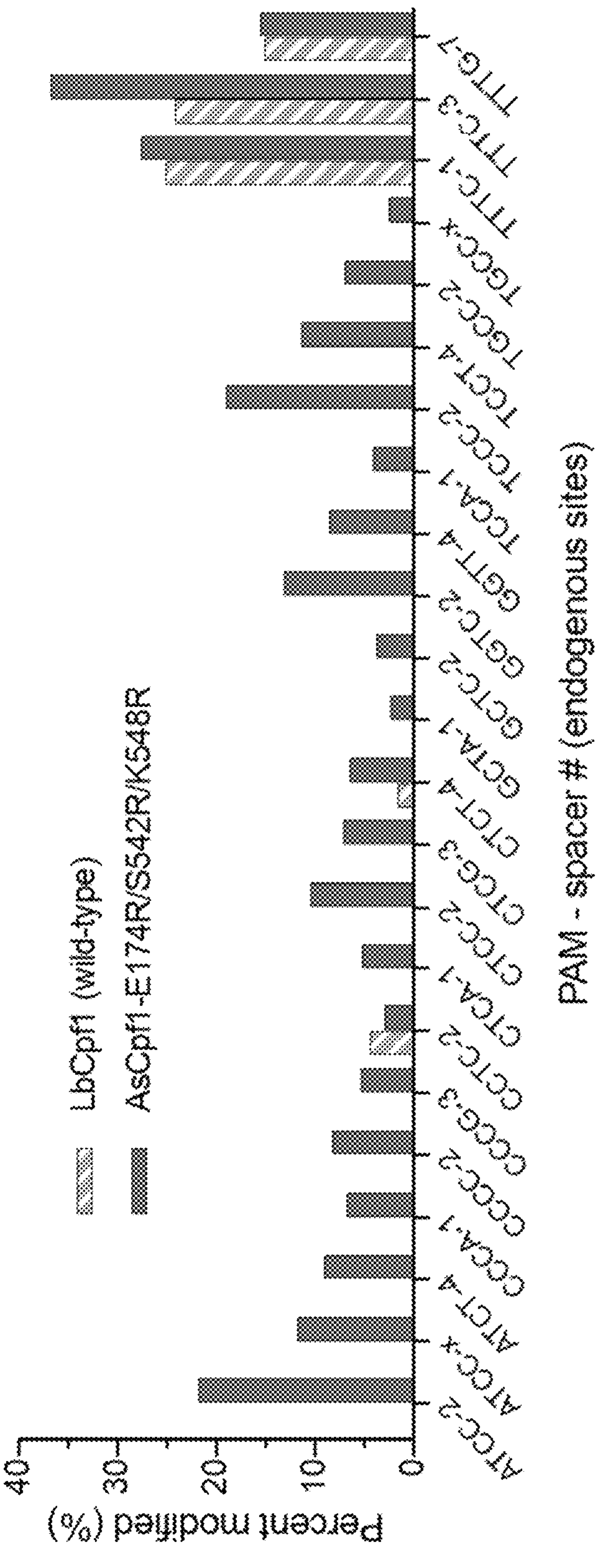

Because of the limitation of the EGFP disruption assay noted above for assessing Cpf1 nuclease activities, we next assessed the activity of our AsCpf1 E174R/S542R/K548R variant against a range of endogenous human gene target sites harboring PAMs with single base differences (FIG. 10A) or two or three base differences (FIG. 10B). These results demonstrate that AsCpf1 E174R/S542R/K548R can efficiently cleave sites bearing the following PAMs: TTTN, ATTN, CTTN, GTTN, TATN, TCTN, TGTN, TTCN, ATCN, CCCN, CCTN, CTCN, GCTN, GGTN, TCCN, and TGCN. It is important to note that AsCpf1-E174R/S542R/K548R was not tested on target sites with all possible PAMs. Significantly, target sites bearing most of these alternate PAMs could not be cleared even with wild-type LbCpf1, which has a more relaxed PAM preference than wild-type AsCpf1 (FIGS. 2 and 4). Furthermore, for the variant PAM sites that could be cleaved by wild-type LbCpf1, we observed that the AsCpf1-E174R/S542R/K548R variant consistently outperformed wild-type LbCpf1 as judged by efficiency of indel mutation induction. Interestingly, the AsCpf1-E174R/S542R/K548R variant also displayed improved activity against canonical TTTN PAM sites, even demonstrating substantial activity against the TTTN-6 site previously untargetable with AsCpf1 or LbCpf1 (FIGS. 10A and 10B). The TTTN-6 site bears a T at the first position of the PAM (for a TTTT PAM), suggesting that the triple substitution AsCpf1 variant may improve activity against sites bearing a T in the first position of the PAM. Thus, the AsCpf1-E174R/S542R/K548R variant substantially improves the targeting range of the Cpf1 platform for sites with non-canonical PAMs relative to wild-type AsCpf1 and LbCpf1 nucleases and generally show improved activities on sites with canonical PAMs as well.

Figure 11A:
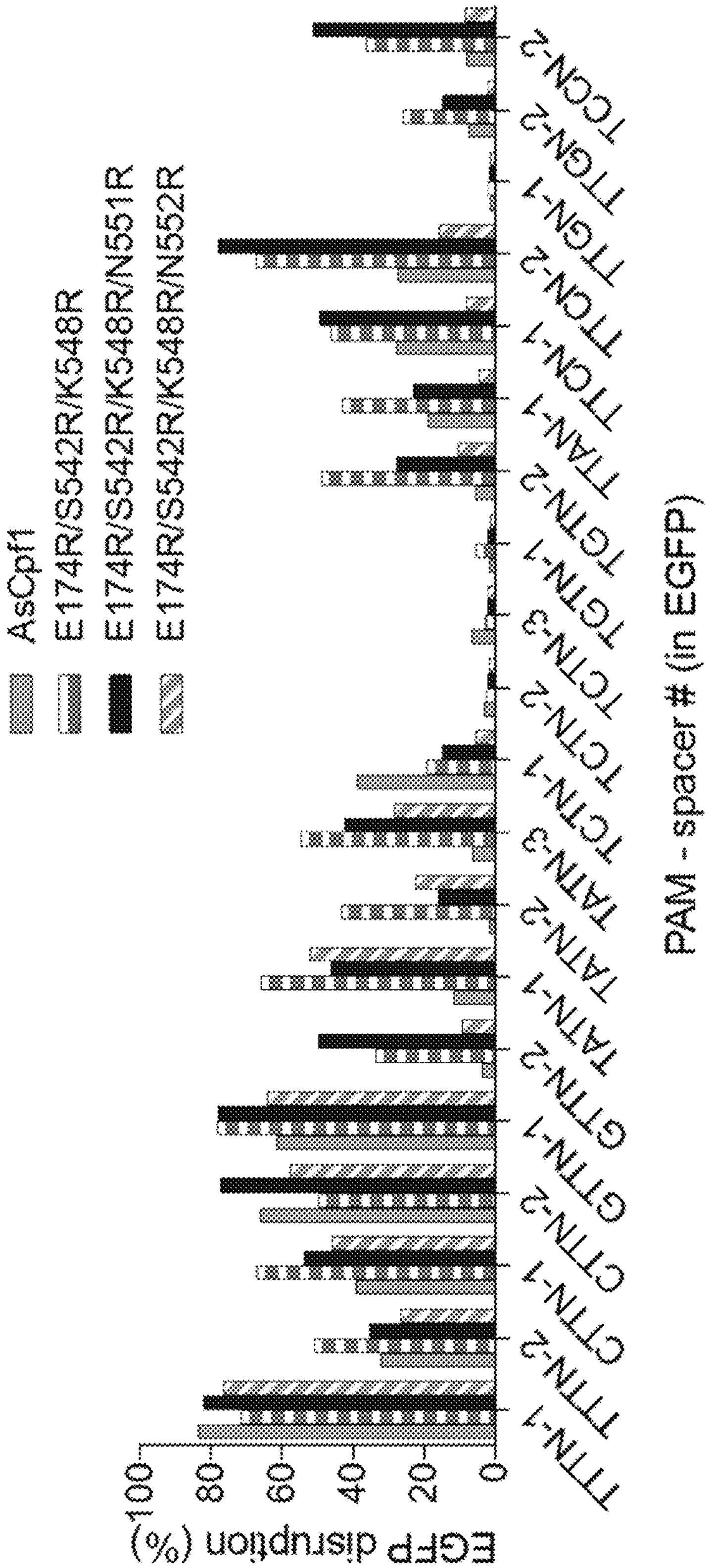
FIGS. 11A-11C: PAM recognition profiles of wild-type AsCpf1 and various engineered AsCpf1 variants. The activity of wild-type AsCpf1 was compared to the activities of AsCpf1 PAM variants using crRNAs targeted to sites bearing either canonical TTTN PAMs or PAMs with single, double, or triple base differences. Comparisons were performed (A) with the human cell-based EGFP disruption assay or (B) by assessing mutation frequencies (as judged by T7EI endonuclease assay) at endogenous human gene target sites. (C) The mutational activities of two AsCpf1 PAM variants were compared using crRNAs targeted to endogenous human gene sites bearing either canonical TTTN PAMs or PAMs bearing single, double, or triple base differences.
Figure 11B:
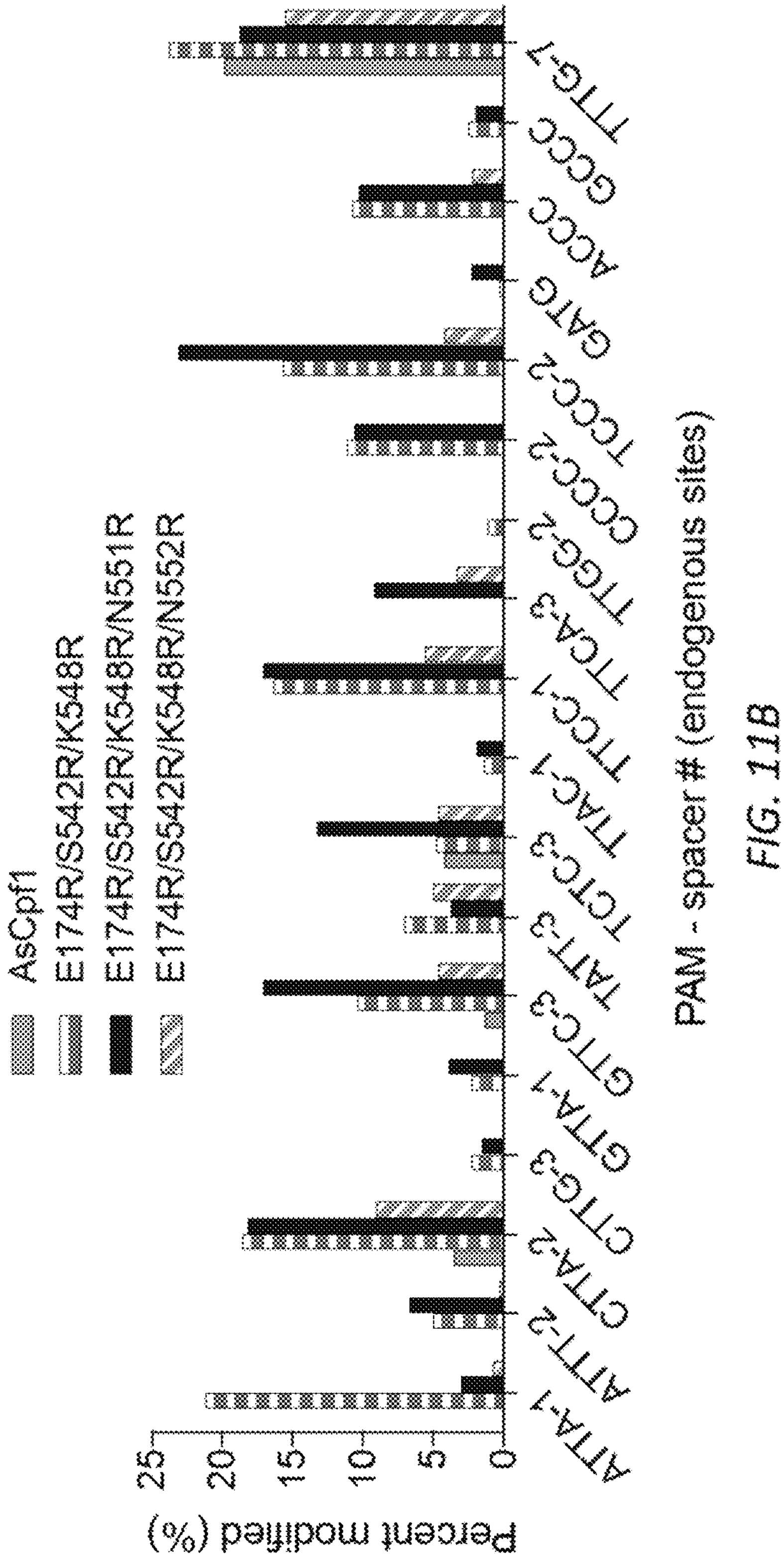
Figure 11C:
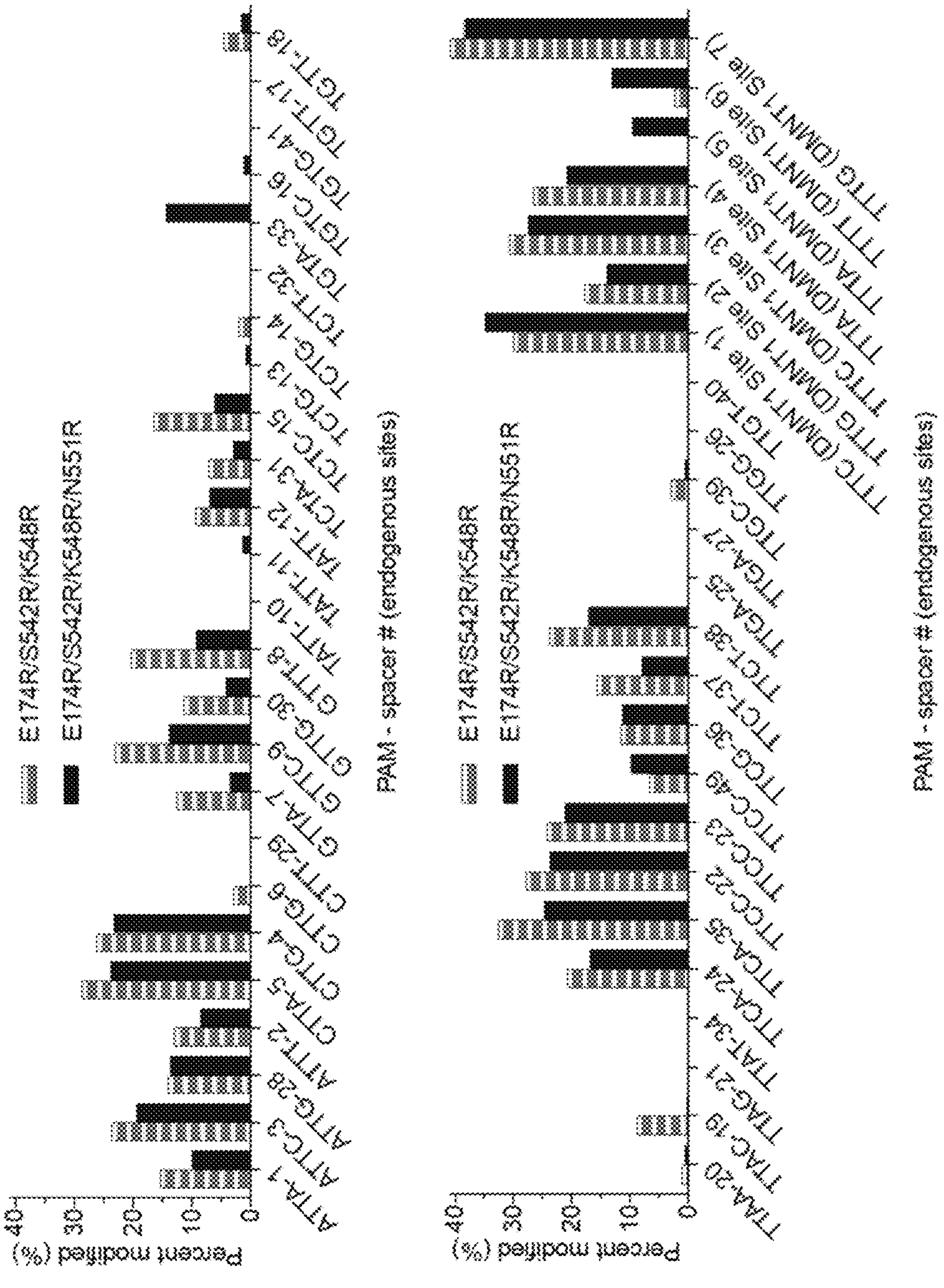

Next, to attempt to further relax the PAM specificity of our AsCpf1 PAM variants and/or improve the magnitude of activity at any given PAM, we added more amino acid substitutions to the E174R/S542R/K548R variant. First, we added the N551R or N552R substitution to generate quadruple substitution variants E174R/S542R/K548R/N551R and E174R/S542R/K548R/N552R, respectively. Comparison of these two quadruple substitution variants with wild-type AsCpf1 and the E174R/S542R/K548R variant revealed that the E174R/S542R/K548R/N551R variant could improve gene disruption activity at sites harboring various non-canonical PAMs bearing single, double, or triple differences as judged both by EGFP disruption assay or by their abilities to induce indel mutations in endogenous human gene target sites (FIGS. 11A and 11B, respectively). By contrast, the E174R/S542R/K548R/N552R quadruple substitution variant did not show improved activity in these same experiments and in many cases actually abrogated activity (FIGS. 11A and 11B). To further compare the PAM recognition specificities of the E174R/S542R/K548R and E174R/S542R/K548R/N551R variants, we examined their activities across an expanded larger number of endogenous human gene target sites that contained canonical or non-canonical (single base difference) PAMs. We observed comparable activity of both variants across the majority of sites, with a small number of cases in which one or the other variant exhibited slightly improved activity (FIG. 11C).

Figure 19A:
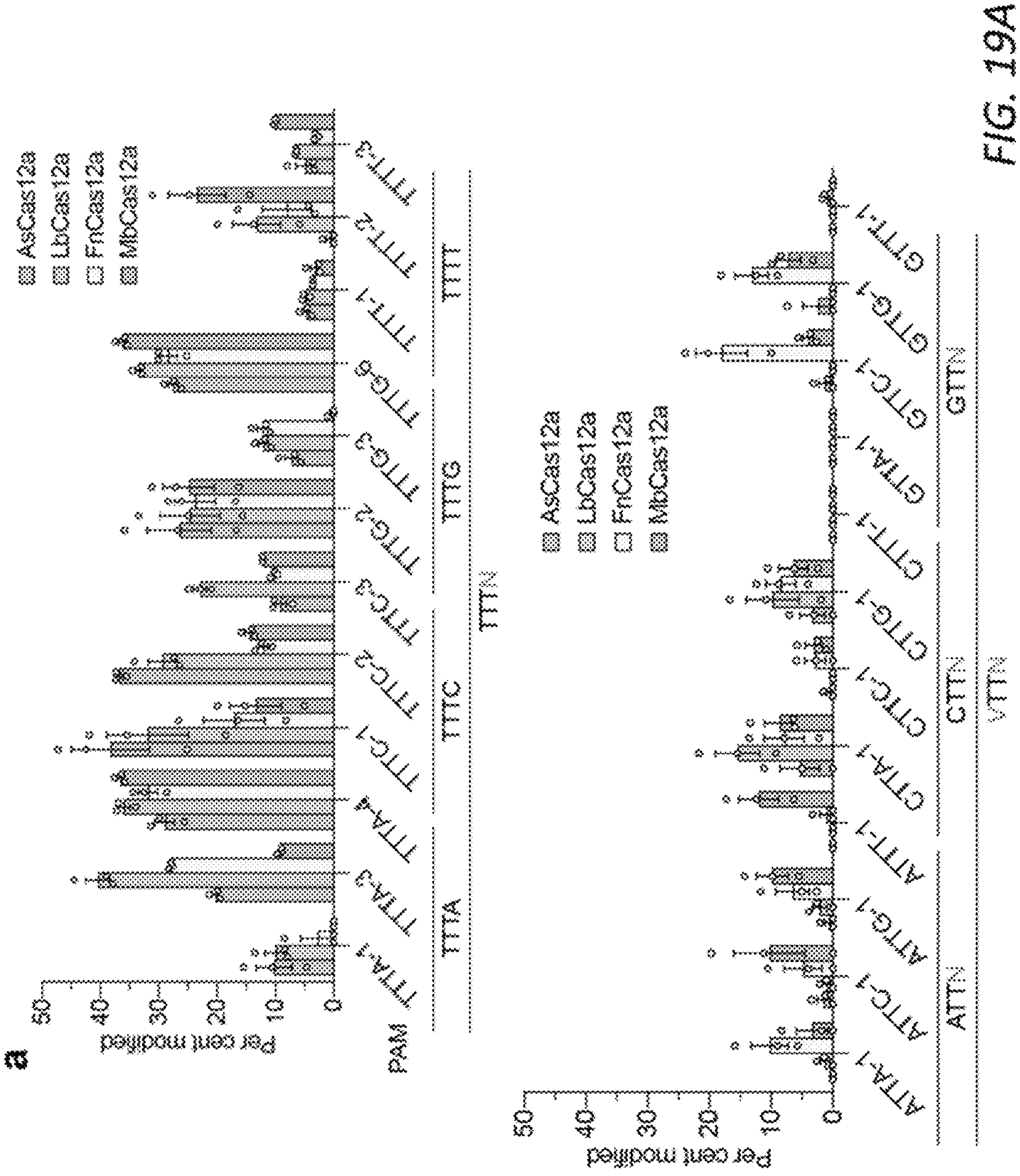
FIGS. 19A-19B: Activities of Cas12a orthologs in human cells. (A), Activities of Cas12a orthologs targeted to endogenous sites in human cells bearing TTTN or VTTN PAMs. Percent modification assessed by T7E1 assay; mean, s.e.m., and individual data points shown for n=3. (B), Summary of the activities of Cas12a orthologs against 24 sites with NTTN PAM sequences (mean activities from data in panel a shown).
Figure 19B:
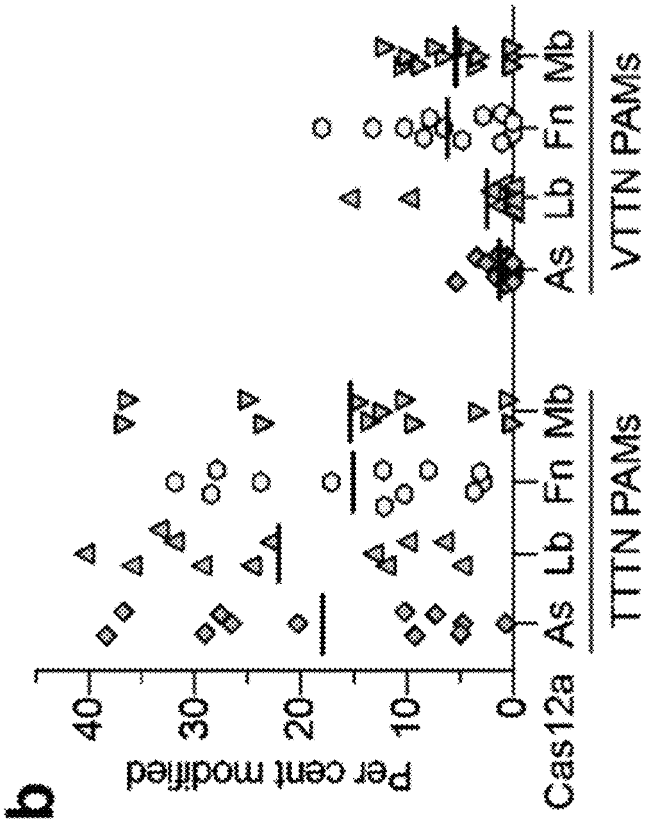

Example 1B. Further Characterization of AsCas12a Variants with Altered PAM Specificities and Improved On-Target Activities Prior characterizations of Cas12a orthologs in human cells revealed that As and LbCas12a were consistently more effective nucleases on sites with TTTV PAMs (Kim et al., Nat Biotechnol., 2016, 34:863-8), and that Fn and MbCas12a may possess relaxed PAM preferences of NTTN (Zetsche et al., Cell, 2015, 163:759-71). To more thoroughly assess the activities and PAM preferences of each ortholog, their genome editing activities using two sets of twelve crRNAs targeted to sites harboring TTTN or VTTN PAMs were examined in human cells (FIG. 19A). We observed similar gene disruption between the four orthologs on TTTN PAM sites, though target-specific differences were observed. Furthermore, Fn and Mb could more effectively target VTTN PAMs when compared to As and LbCas12a, but consistent with prior reports their mean activities on VTTN sites were too low to characterize these PAMs as bona fide targets (FIGS. 19A and 19B). These results support previous observations that Cas12a nucleases are mostly effective against sites harboring TTTV PAMs (Kim et al., Nat Biotechnol., 2016, 34:863-8), and that no naturally occurring Cas12a orthologs characterized to date have been shown to overcome this restrictive PAM requirement in human cells.

Figure 20A:
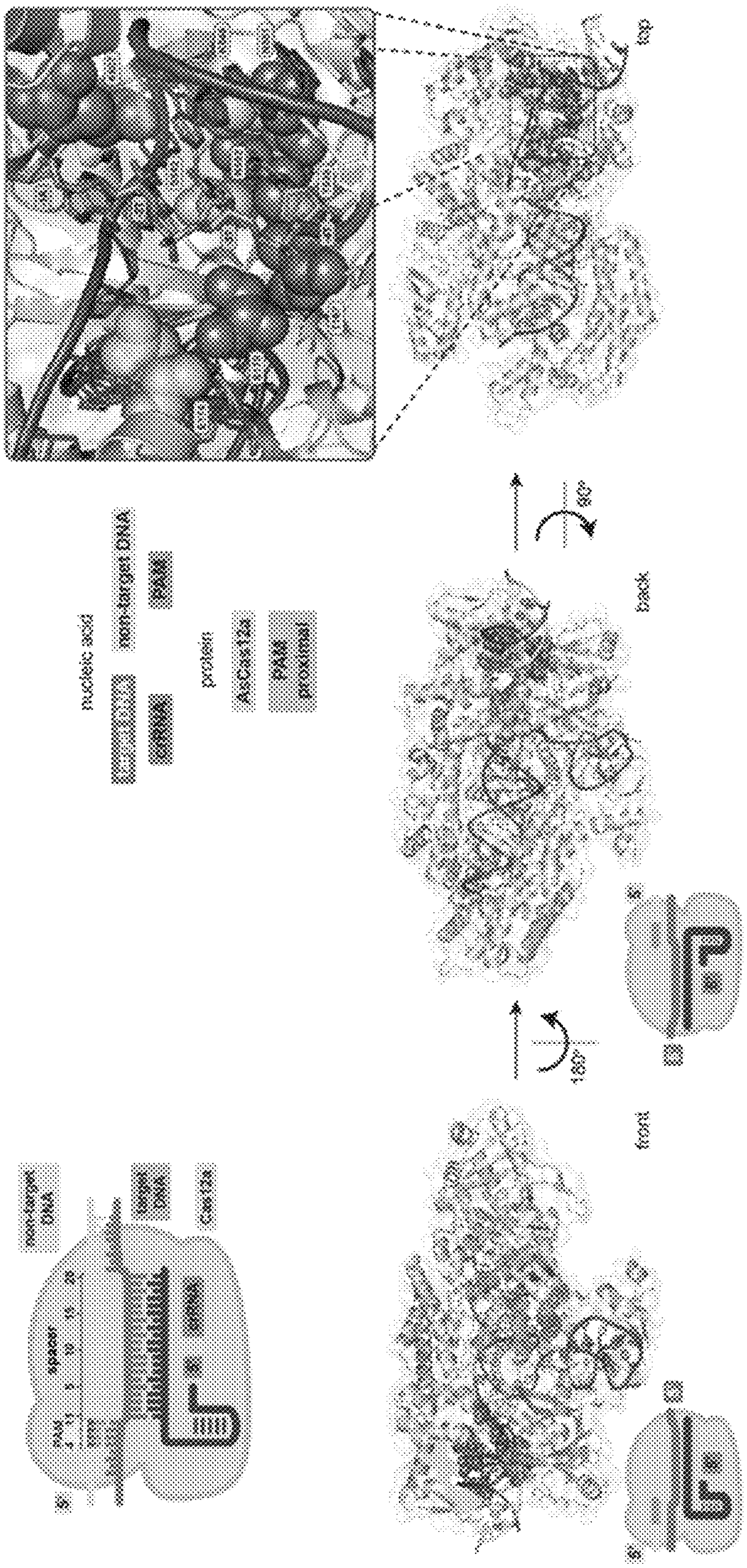
FIGS. 20A-20D: Engineering and characterization of AsCas12a variants. (A), Schematic and structural representations of Cas12a paired with a crRNA, and interacting with a putative target site encoding a prototypical TTTV PAM. In structural representations, amino acid residues proximal to PAM DNA bases are highlighted in green; images generated from PDBID:5B43 (Yamano et al., Cell. 2016 May 5; 165(4): 949-62) visualized in PyMOL (v 1.8.6.0). (B, C), Activities of AsCas12a variants bearing single amino acid substitutions when tested against endogenous sites in human cells bearing canonical (panel B) or non-canonical (panel C) PAMs. Percent modification assessed by T7E1 assay; mean, s.e.m., and individual data points shown for n=3. (D), Fold-change in the mean activities of AsCas12a variants compared to wild-type AsCas12a on sites bearing canonical and non-canonical PAMs. Fold-change compared to activity with wild-type AsCas12a calculated from the percent modification data from FIG. 15A.
Figure 20B:
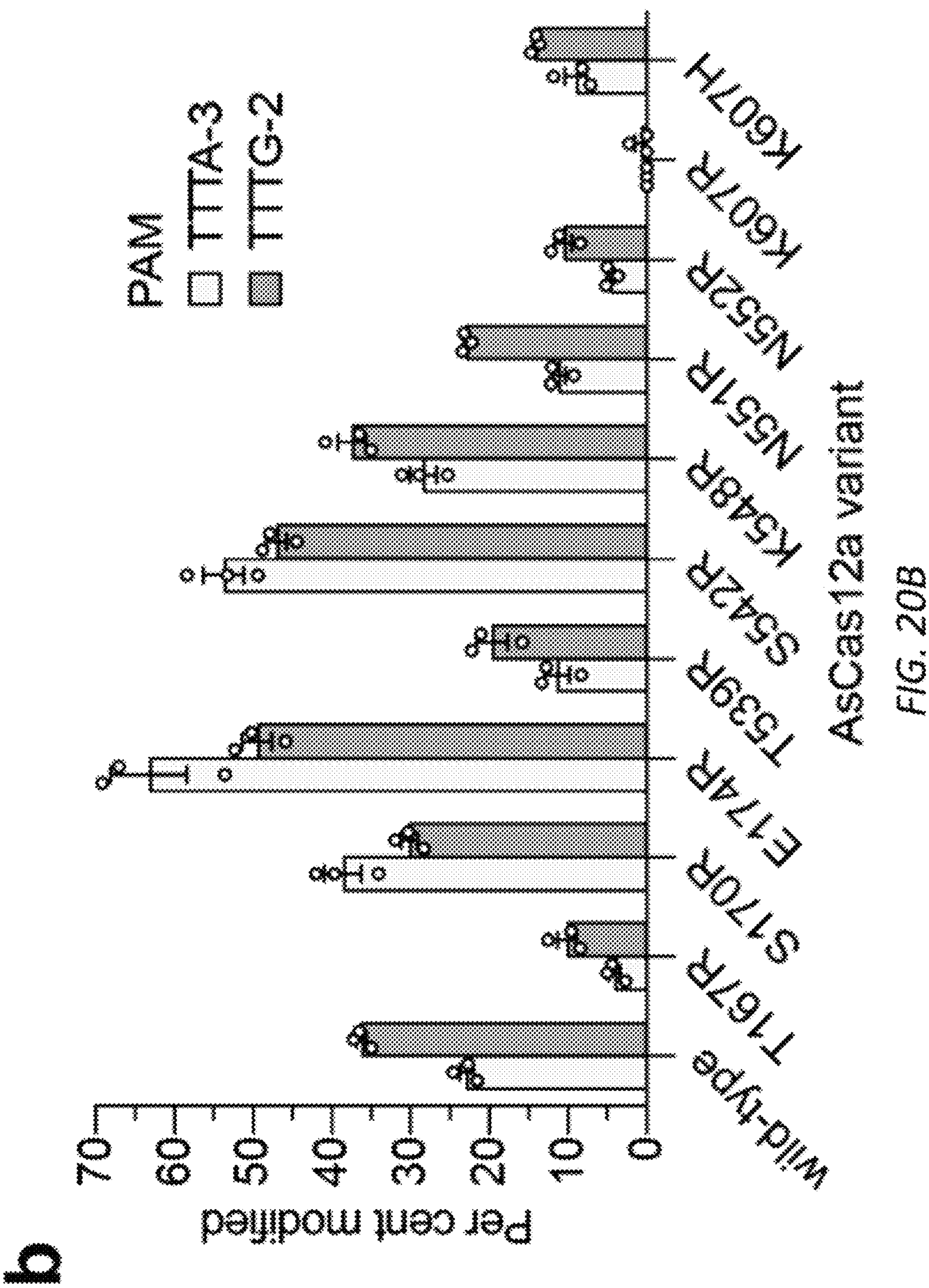
Figure 20C:
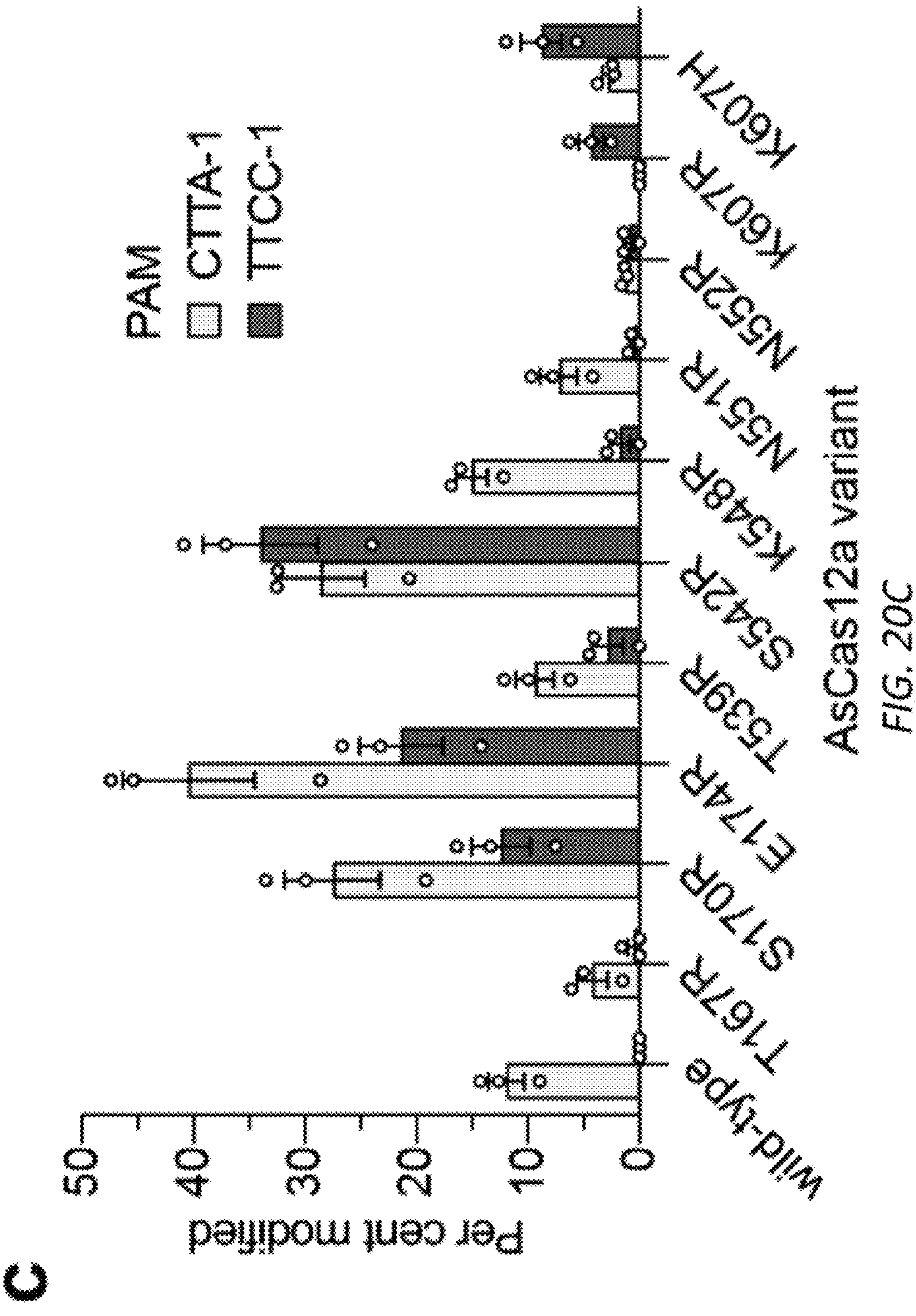

To expand the targeting range and broaden the utility of Cas12a nucleases, we leveraged structural studies of the AsCas12a ternary complex (Yamano et al., Cell. 2016 May 5:165(4):949-62) to engineer a single variant capable of recognizing both canonical and non-canonical PAMs. Residues in close spatial proximity to the PAM DNA bases were identified (FIG. 20A), and we hypothesized that substitution of these residues could alter or relax PAM recognition by creating novel base- or non-specific interactions. We first tested the activities of variants encoding single substitutions at these positions in human cells against sites encoding canonical and non-canonical PAMs. Compared to wild-type AsCas12a, four single substitution variants (S170R, E174R, S542R, K548R) displayed superior activity on canonical TTTA or TTTC PAM sites, while also enabling more efficient targeting of sites with non-canonical CTTA or TTCC PAMs (FIGS. 20B and 20C, respectively).

Figure 15A:
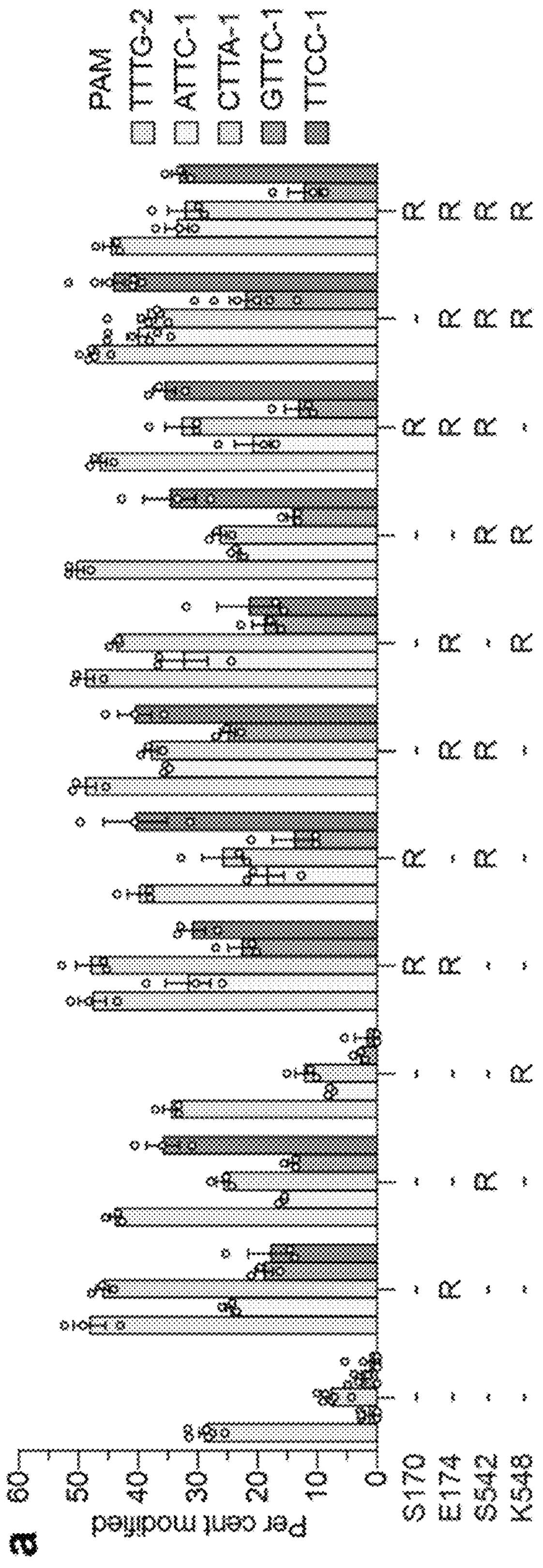
FIGS. 15A-15G: Engineering and characterization of an AsCas12a variant with expanded target range. (A), Modification of endogenous sites in human cells by AsCas12a variants bearing amino acid substitutions. Activities assessed by T7E1 assay; mean, s.e.m., and individual data points shown for $n \geq 3$. (B), PAM preference profiles for wild-type AsCas12a and the E174R/S542R/K548R variant, evaluated by the PAM determination assay (PAMDA). The $\log_{10}$ rate constants (k) are the mean of four replicates, two each against two distinct spacer sequences (see FIG. 21D). (C), Mean activity plots for E174R/S542R and E174R/S542R/K548R AsCas12a on non-canonical PAMs, where the black line represents the mean of 12 to 20 sites (dots) for each PAM class (see also FIGS. 23A, 23B and 23D). (D), Summary of the activities of wild-type, E174R/S542R, and E174R/S542R/K548R AsCas12a across 20 sites encoding non-canonical PAMs, one for each PAM of the VTTN, TTCN, and TATN classes (see also FIGS. 19A, 23A, and 23B: all sites numbered '1'). (E), Mean activity plots for AsCas12a, the E174R/S542R variant, and eAsCas12a on TTTN PAMs, where the black line represents the mean of 5 to 8 sites (dots) for each PAM class (see FIG. 23G). (F), Superimposition of the summaries of the human cell activities and PAMDA rate constants (k) for various targetable and non-targetable PAMs with eAsCas12a (E174R/S542R/K548R). Box and whisker plots shown for human cell activities determined by T7E1 assay. Tier 1 PAMs exhibit greater than 20% mean targeting in human cells and a PAMDA k greater than 0.01, and PAMs that meet a modest threshold of greater than 10% mean targeting in cells and a PAMDA k greater than 0.005 are considered tier 2 PAMs. (G), Calculation of the improvements in targeting range enabled by AsCas12a variants compared to wild-type AsCas12a, determined by enumerating complete PAM sequences within the indicated sequence feature and normalizing for element size. TSS, transcription start site; PAM sequences targetable by each AsCas12a variant are: wild-type, TTTV; eAsCas12a, see panel F and Extended Data FIG. 23I for PAM tiers: RVR, TATV; RR, TYCV.
Figure 20D:
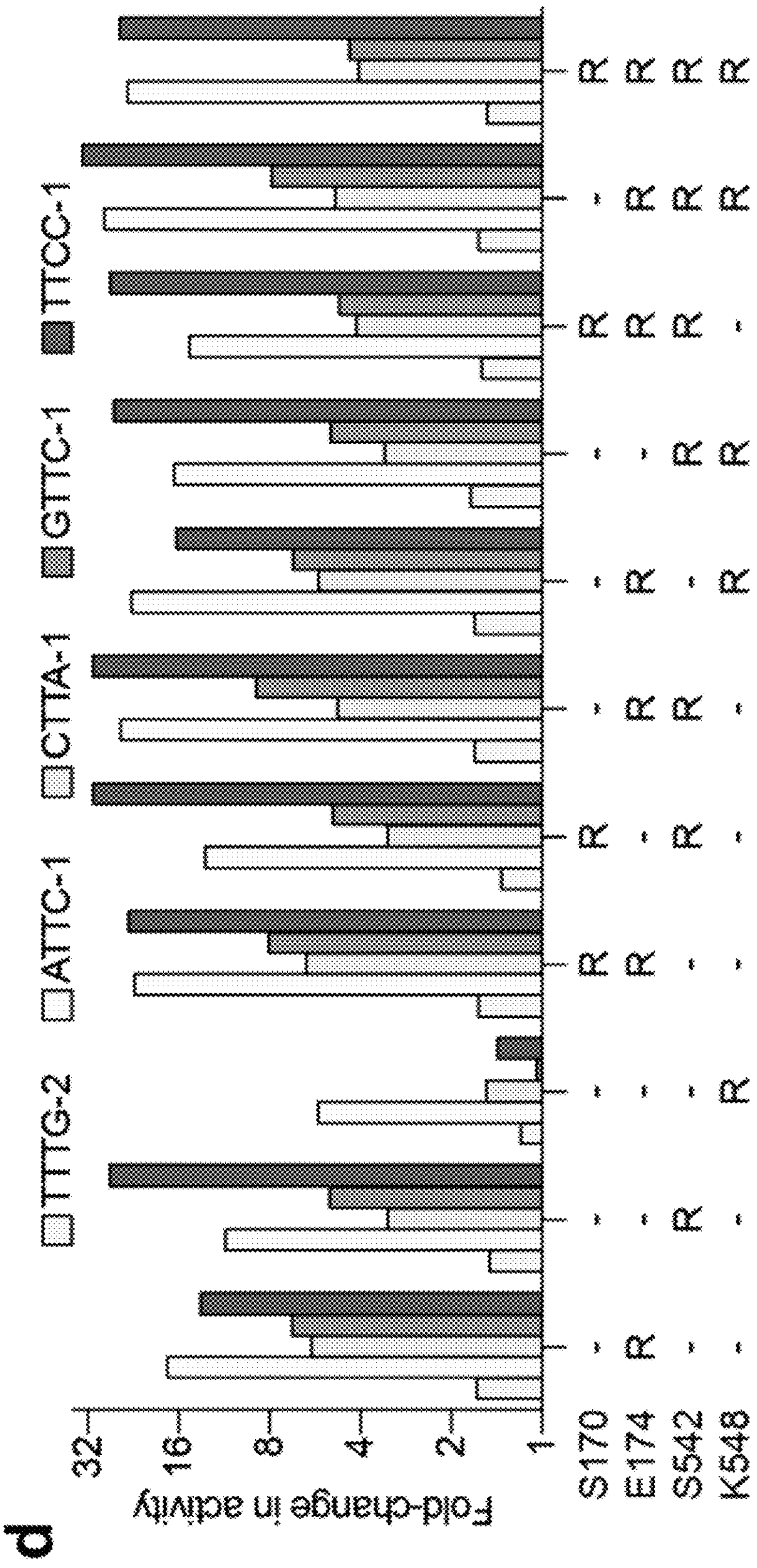

Combinatorial testing of these substitutions in human cells revealed substantial increases in activity compared to wild-type AsCas12a on four additional sites bearing non-canonical PAMs (ATTC, CTTA, GTTC, and TTCC), and recapitulated the observation of improved activity on a canonical TTTG PAM site (FIG. 15A). Some of the most prominent increases in activity and expansions in targeting range were observed when the E174R and S542R substitutions were combined, as E174R/S542R and E174R/S542R/K548R variants displayed between 4- and 32-fold improved activities on non-canonical PAM sites compared to AsCas12a, and nearly 2-fold enhanced activities on the canonical PAM site (FIG. 20D). Thus, we selected these two variants for further characterization.

To comprehensively profile the expanded PAM preferences of our AsCas12a variants, we optimized an unbiased in vitro high-throughput PAM determination assay (PAMDA; FIGS. 21A-21H). We first purified and assayed wild-type and E174R/S542R/K548R AsCas12a (FIG. 21A). The in vitro cleavage activities of these Cas12a nucleases were verified on plasmid substrates encoding two distinct spacer sequences with various targetable and non-targetable PAMs, corroborating previously observed improvements in activity in human cell assays (FIGS. 21B and 21C). We then adapted this workflow to perform the PAMDA by constructing two separate plasmid libraries encoding the same two spacer sequences, but now instead harboring a random 8-mer sequence in place of the PAM (FIG. 21D). Time-course cleavage reactions were performed on the two linearized plasmid libraries using AsCas12a/crRNA ribonucleoprotein (RNP) complexes, followed by PCR amplification and sequencing of the non-cleaved substrates to calculate the rates at which targetable PAMs are depleted (FIG. 21D). Strong correlations were observed between the PAM-specific rate constants (k; for depletion of the PAM from the population over time) on the most spacer proximal 4 nt PAM sequences between replicates and spacers across separate PAMDA experiments (FIGS. 21E and 21F, respectively). Binning of the count of $\log_{10}$ k values for each of the possible 256 4 nt PAMs for both wild-type and E174R/S542R/K548R AsCas12a suggested an approximate threshold for bona fide PAM recognition and targeting in the −2.25 $\log_{10}$ k range (FIG. 21G). Analysis of the depletion curves from the PAMDA data for the same PAM/spacer combinations used for optimization of the in vitro assay using static PAM substrates revealed consistent cleavage profiles (FIG. 21H).

Figure 15B:
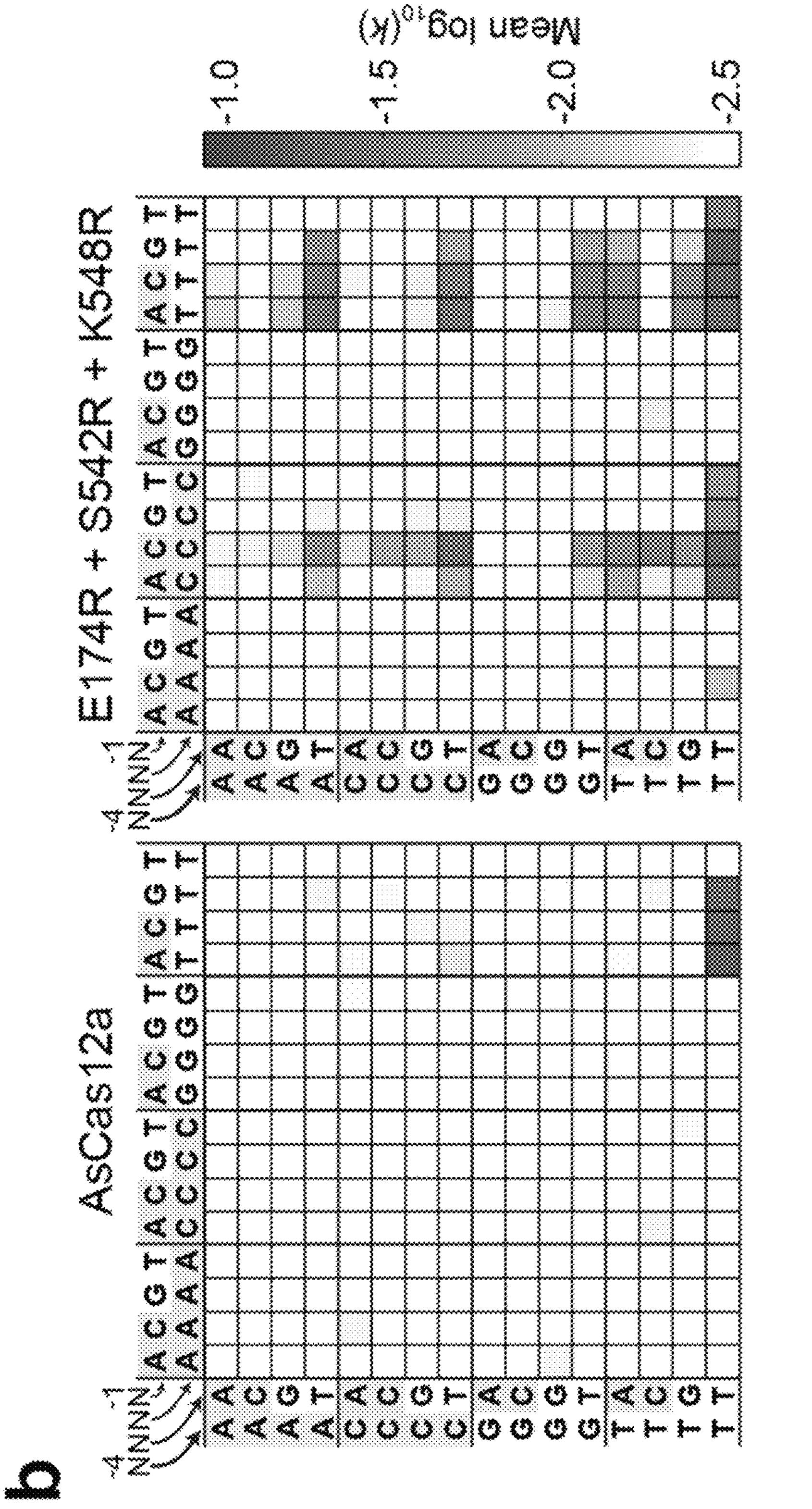

To perform the PAMDA, purified Cas12a nucleases are complexed with crRNAs to interrogate plasmid libraries harboring randomized 8 nt sequences in place of the PAM, enabling the calculation of in vitro rate constants (k) for depletion of targetable PAMs from the population. Plots of the mean $\log_{10}$ k values for wild-type AsCas12a on all possible 4 nt PAM sequences revealed that, as expected, targeting was only efficient on sites with TTTV PAMs (FIG. 15B). Conversely, the E174R/S542R/K548R variant displayed a dramatically broadened targeting of PAM classes that included TTTN and TTCN (TTYN); ATTV, CTTV, and GTTV (VTTV); TATV and TGTV (TRTV); and many additional PAMs (FIG. 15B). Importantly, this analysis also supported our observation that the variant maintains potent recognition of canonical TTTV PAMs.

Next, to gain a more complete understanding of the targeting range improvements conferred by each substitution, we deployed the PAMDA on the single and double substitution intermediate variants necessary to generate E174R/S542R/K548R (FIG. 22A). Consistent with our human cell assay data (FIG. 15A), this analysis revealed that the E174R/S542R variant also displayed improved activities across a broad range of PAMs. A comparison of the mean $\log_{10}$ k PAMDA values for E174R/S542R and E174R/S542R/K548R on NNYN PAMs demonstrated that both variants possess expanded targeting ranges (FIG. 22B), suggesting that the E174R and S542R substitutions are responsible for much of the broadened targeting range. Interestingly, the identities of these residues are not shared across Cas12a orthologs, but exist in regions where the flanking amino acids are strictly conserved (FIG. 22C)

Figure 15C:
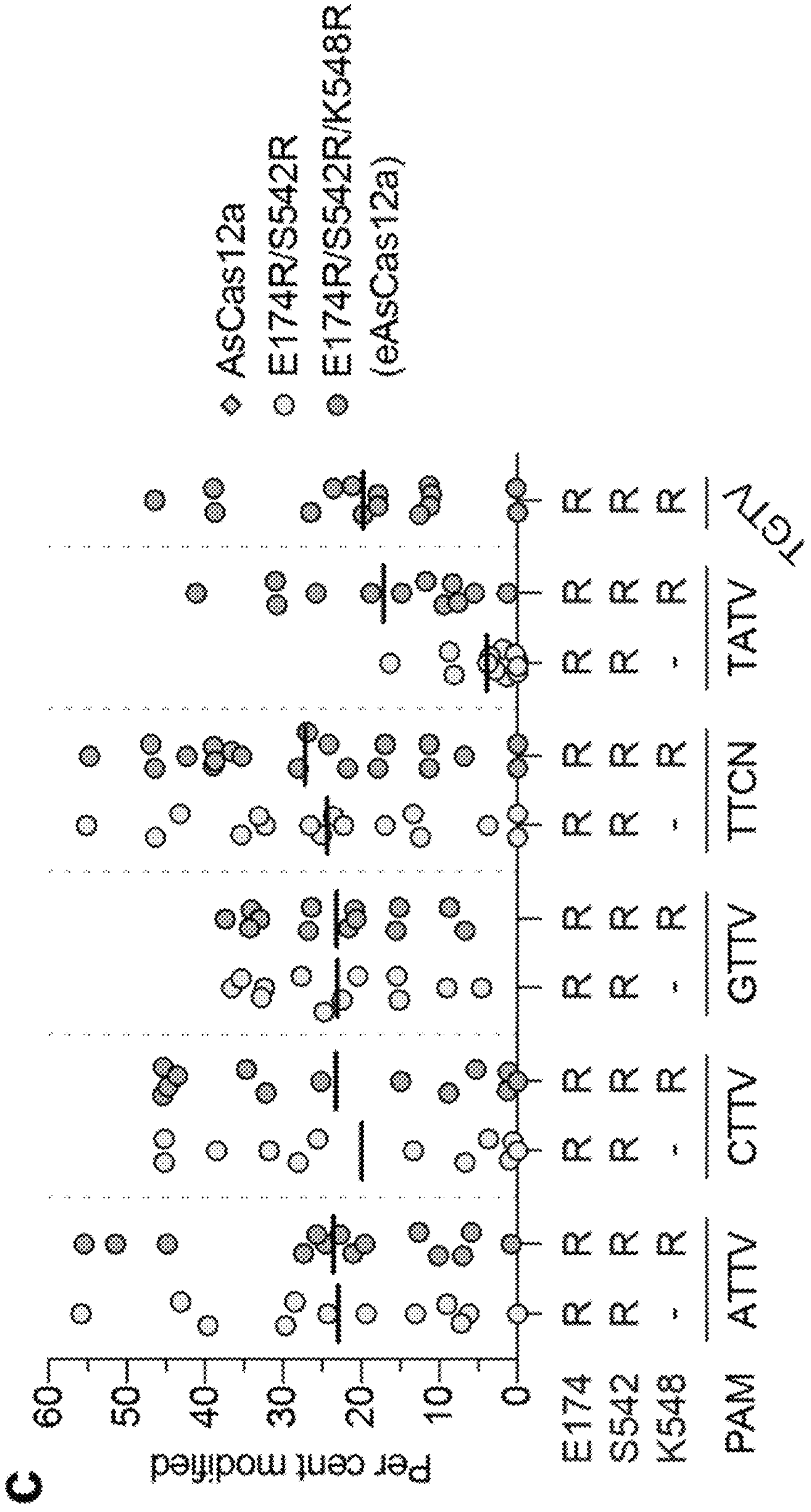
Figures 15D, 15E:
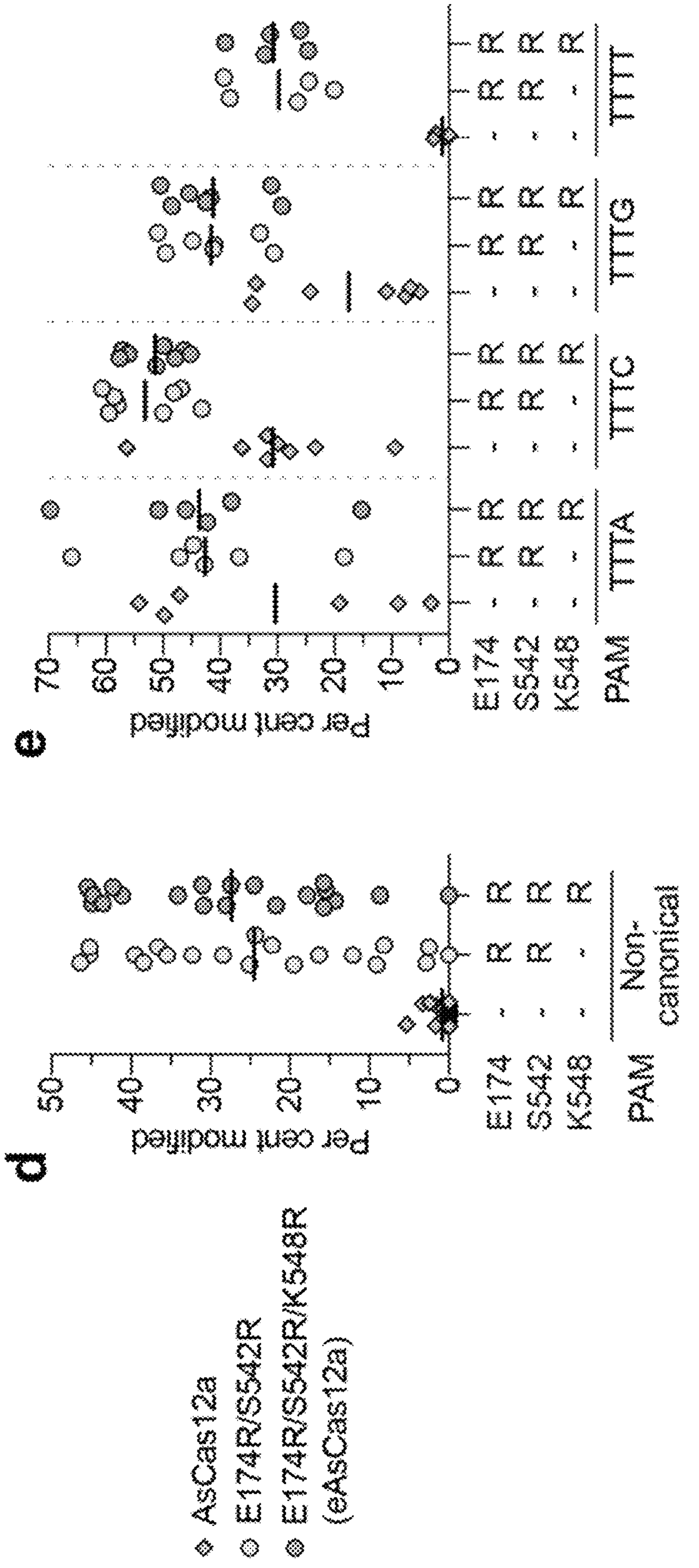
Figure 23A:
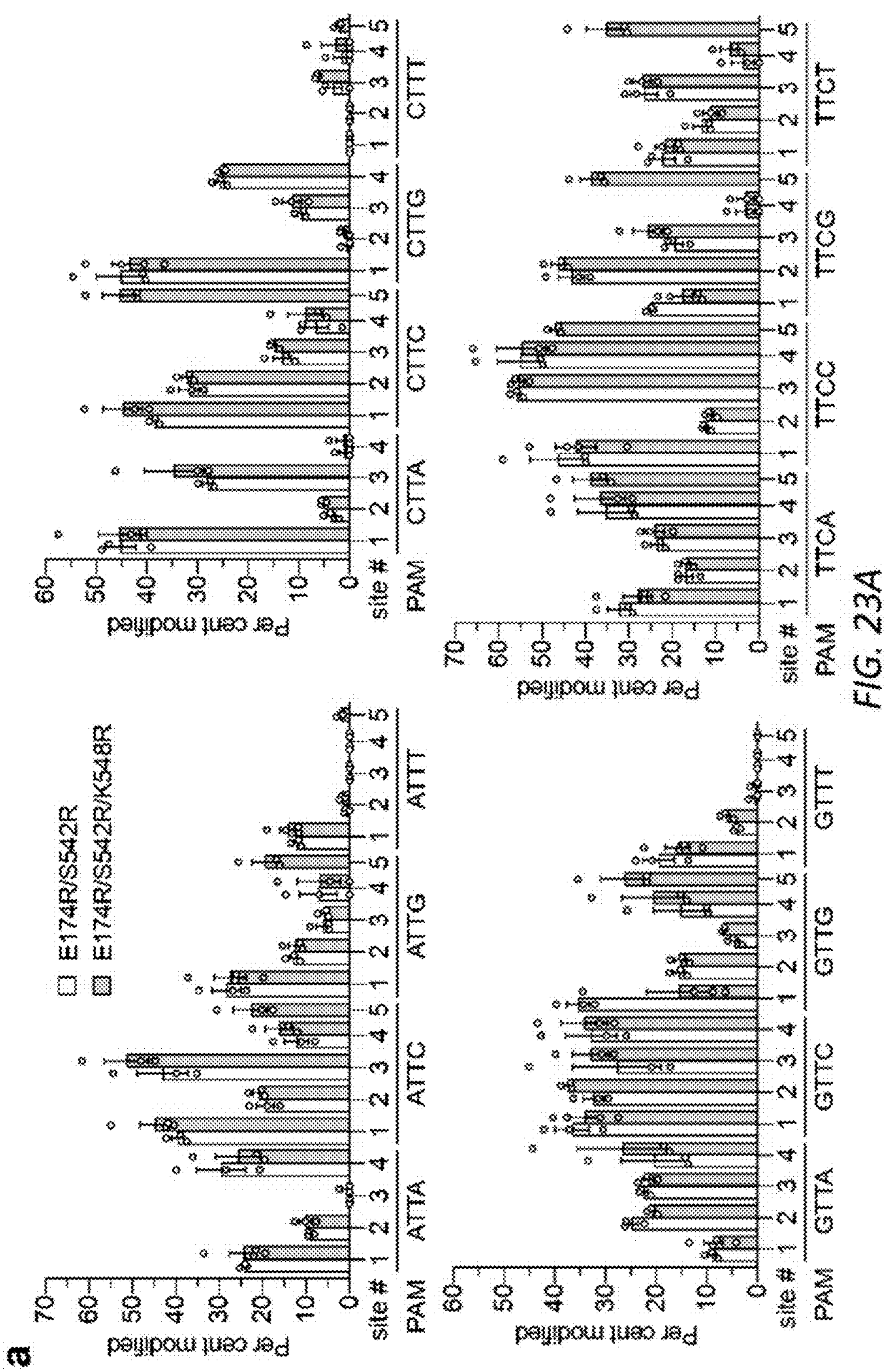
Figure 23F:
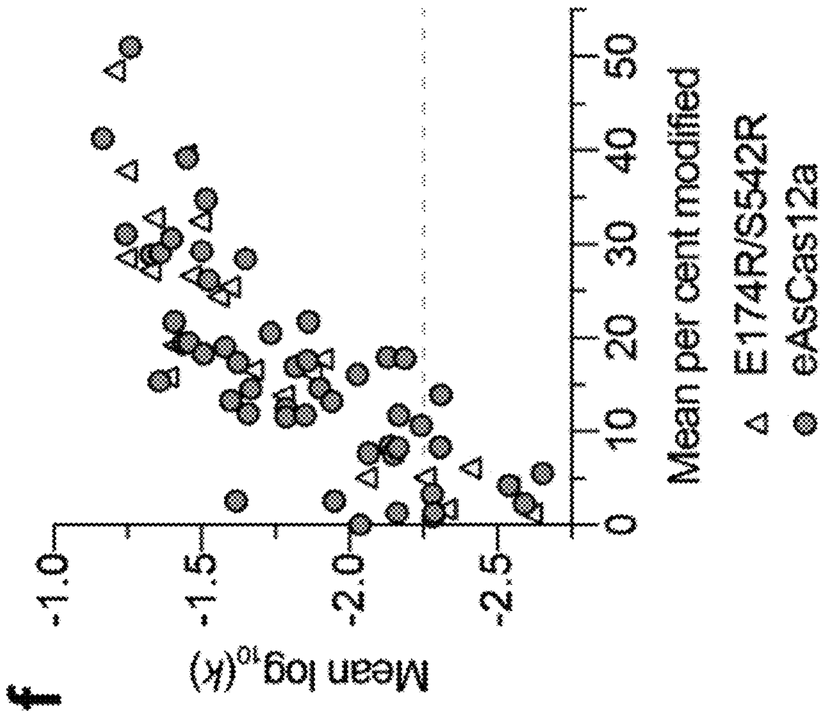

To further explore the targeting range improvements exhibited by the E174R/S542R and E174R/S542R/K548R variants in human cells, we characterized their activities on sites that the PAMDA identified as targetable or non-targetable, including 75 VTTN and TTCN sites harboring PAMs that should now mostly be accessible with either variant (VTTT as negative controls; FIG. 23A), and 17 sites with TATN PAMs where TATV sites should be effectively targeted only with E174R/S542R/K548R (FIG. 23B). As predicted by the PAMDA results for the variants, we observed consistent and robust targeting with E174R/S542R and E174R/S542R/K548R on sites with VTTV and TTCN PAMs, ineffective modification of VTTT sites, and only effective targeting of TATV sites with the E174R/S542R/K548R variant (FIGS. 15C, 23A and 23B). Importantly, both variants were far more effective at targeting these non-canonical PAM sites as compared to wild-type AsCas12a (FIGS. 15D, 19A, and 23C). Because the PAMDA results for the E174R/S542R/K548R variant indicated that it could also potentially recognize an expanded range of PAMs beyond those that we already tested, we examined 15 sites harboring TGTV PAMs and 83 other sites in human cells bearing alternate PAMs at or near a mean $\log_{10}$ (k) PAMDA threshold of −2.25 (FIGS. 23D and 23E, respectively). We observed robust modification of many of the sites harboring these additional non-canonical PAMs, and also a strong correlation between the mean human cell activities and PAMDA ks for most PAMs (FIG. 23F).

One additional observation from the PAMDA was that the E174R/S542R and E174R/S542R/K548R variants could now target TTTT PAMs previously inaccessible with wild-type AsCas12a (FIG. 22A). To determine whether these variants could effectively target sites with non-canonical TTTT PAMs, while also maintaining activity on canonical TTTV PAMs, we compared their activities on 25 additional TTTN sites in human cells (FIG. 23G). Consistent with our earlier findings (FIG. 15A), we observed a roughly 2-fold increase in modification of sites bearing each TTTV PAM, as well as greatly improved targeting of sites encoding TTTT PAMs (FIG. 15E). These results suggest that variants bearing the combination of E174R and S542R not only dramatically improve targeting range, but can also surprisingly enhance targeting of sites with TTTN PAMs (FIG. 23H).

Figure 15F:
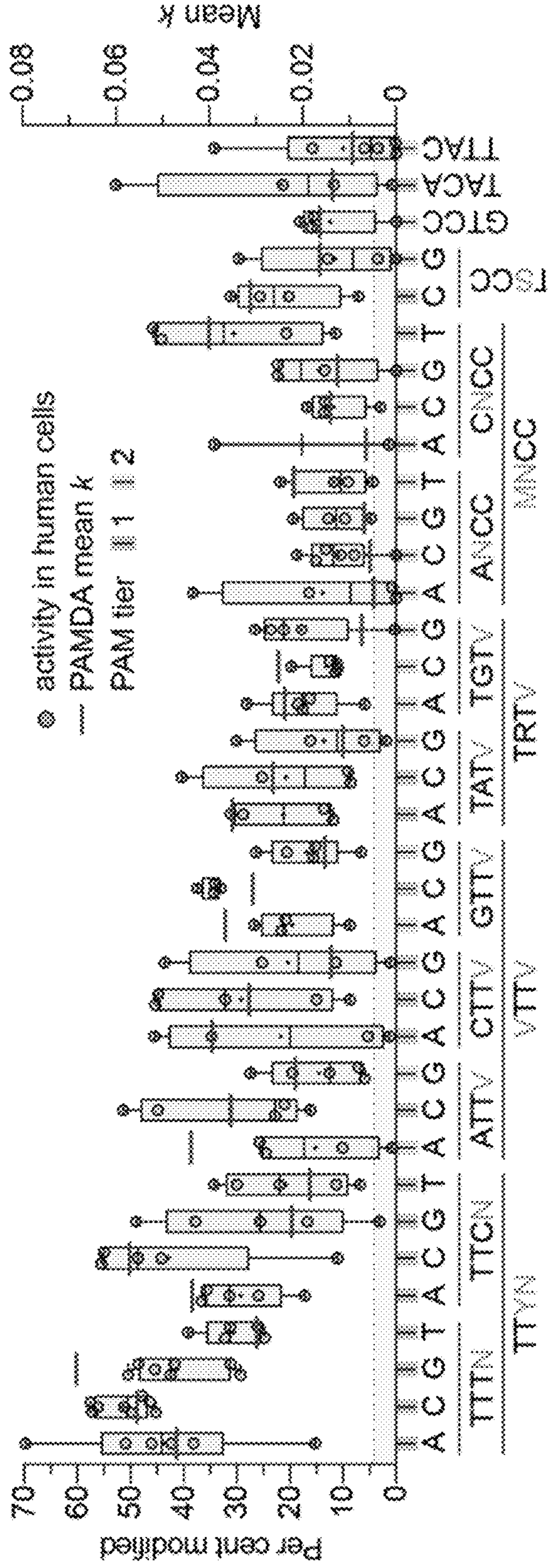

Overall, the E174R/S542R/K548R variant, henceforth referred to as enhanced AsCas12a (eAsCas12A), enables a dramatic expansion in targeting range and improvement of on-target activity. PAMs now accessible with eAsCas12a can be binned into confidence tiers based on consistency between PAMDA and human cell data (FIGS. 15F and 23I). We observed a strong correlation between the mean percent modification in human cells and the in vitro determined mean PAMDA ks (FIG. 23F), suggesting that the PAMDA is reasonably predictive of targetable and non-targetable PAMs in human cells. It is worth noting that the PAMDA data was generated from libraries encoding two separate spacer sequences, and it therefore possible that the PAM preference profiles observed from these libraries may not represent PAM rankings across all spacer sequences (though we did observe a good correlation between the two spacer libraries examined; FIG. 21F)

Thus, we classify PAMs that meet a stringent threshold of greater than 20% mean targeting in human cells across all sites examined and a PAMDA k greater than 0.01 as 'tier 1' PAMs (TTYN, CTTV, RTTC, TATM, CTCC, TCCC, and TACA), and PAMs that meet a medium targeting threshold of greater than 10% mean targeting in cells and a PAMDA k greater than 0.005 as 'tier 2' PAMs (RTTS, TATA, TGTV, ANCC, CVCC, TGCC, GTCC, TTAC) (FIG. 23I). Discrepant PAMs (poor correlation between human cell data and PAMDA data) and those with a mean modification in human cells of less than 10% are classified as 'tier 3' PAMs and are not recommended for most genome editing applications given our current data. For applications where targeting range may not be limiting and efficiency is the primary objective, we recommend prioritizing PAMs within tier 1 or 2 based on their PAMDA and human cell rankings (FIG. 23I).

Figure 15G:
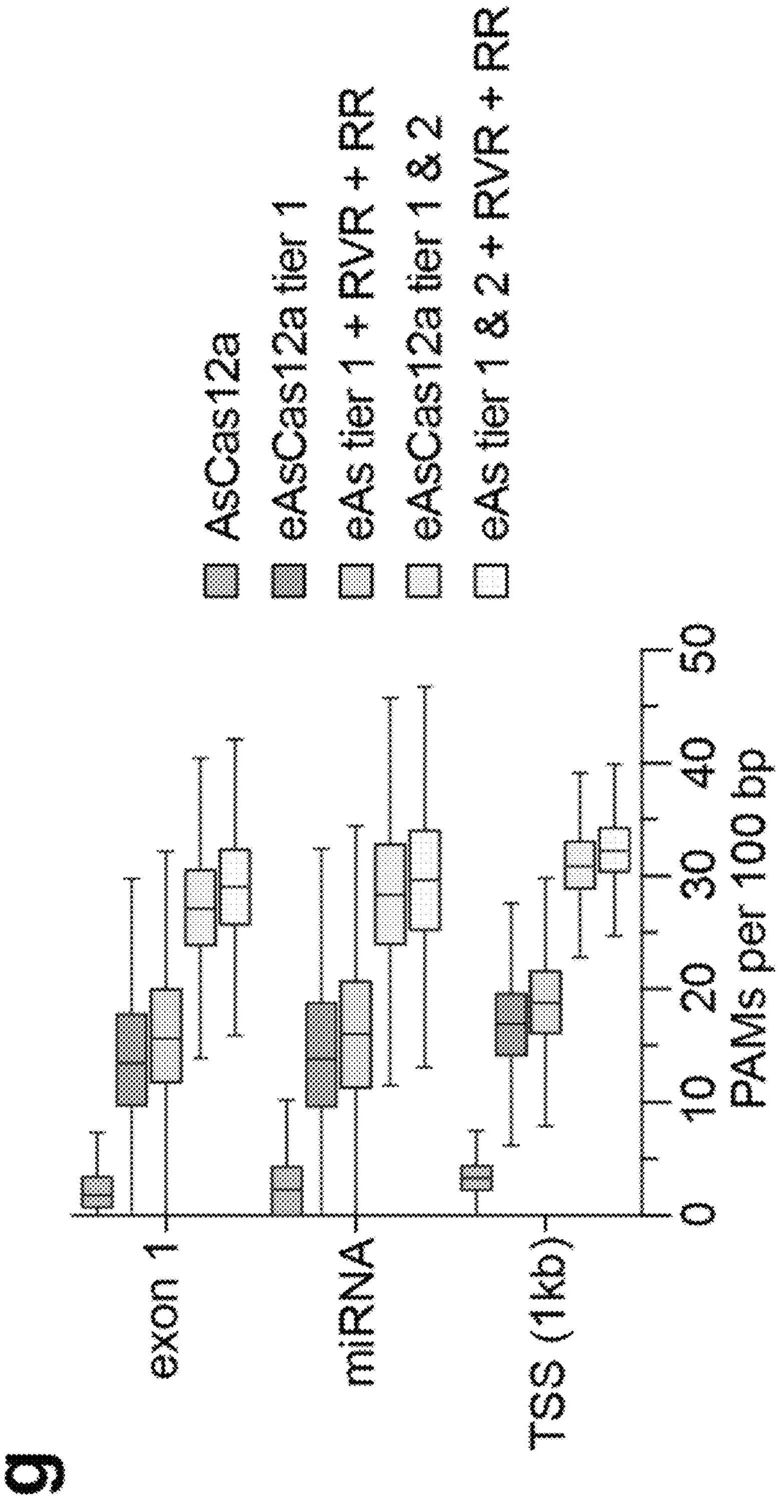

Taken together, eAsCas12a and other AsCas12a variants improve targeting by over 8-fold, enabling higher resolution targeting of coding and non-coding regions of the genome (FIG. 15G).

Improved On-Target Activity with eAsCas12a

Figure 16A:
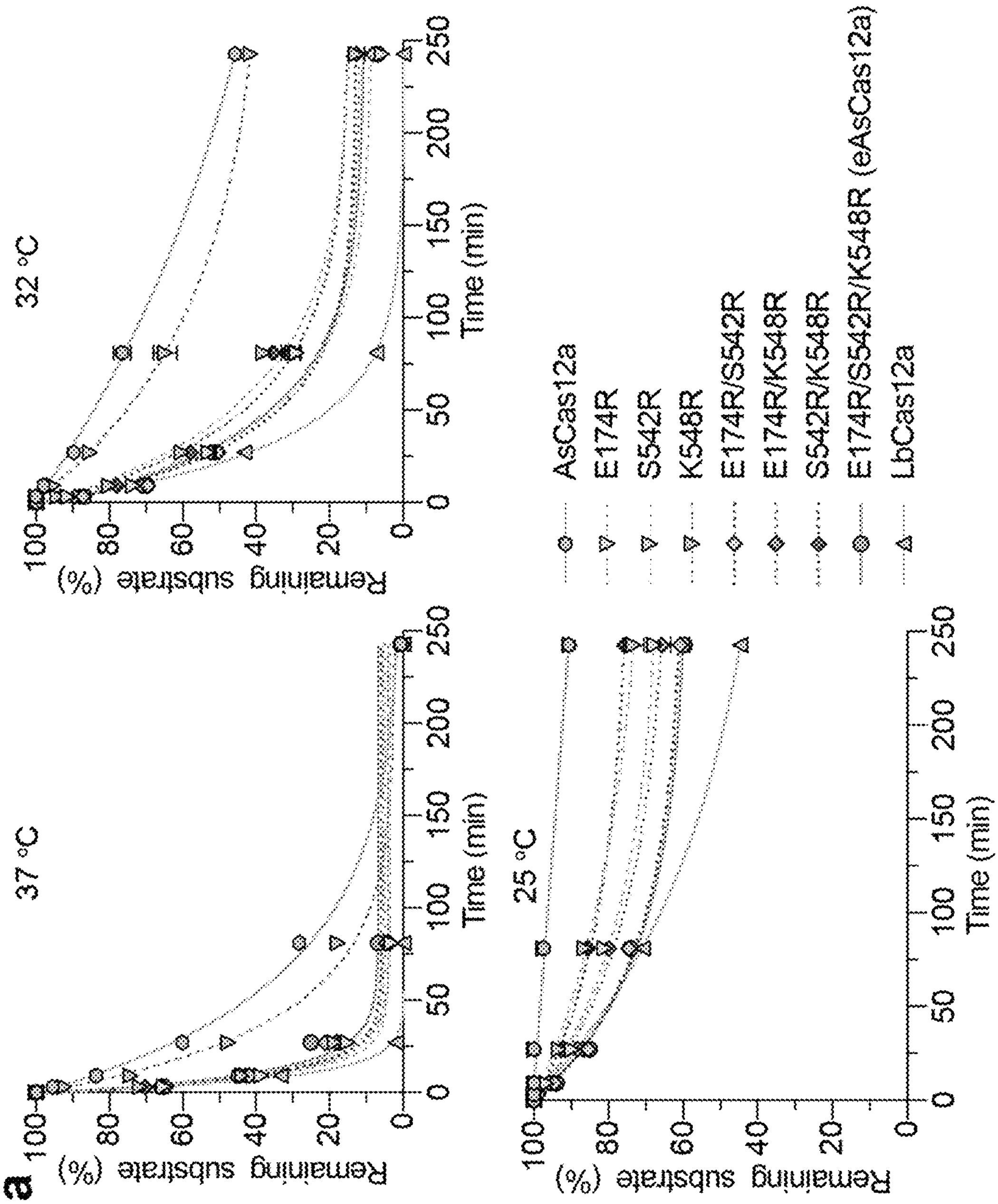

Beyond targeting range, another critical property of genome editing nucleases is potent on-target activity. We therefore sought to better understand which substitutions contribute to our observations of enhanced targeting efficiencies with eAsCas12a, as to the best of our knowledge, no amino acid substitutions have been described that increase the editing efficiencies of CRISPR nucleases. Thus, we first determined whether eAsCas12a or its derivative variants could revert DNA cleavage deficiencies at lower temperatures previously described for wild-type AsCas12a (Moreno-Mateos et al., Nat Commun., 2017, 8:2024). Comparative in vitro cleavage reactions at 37, 32, and 25° C. revealed that eAsCas12a nearly eliminates the temperature-dependent cleavage differences observed between AsCas12a and LbCas12a, and that the phenotypic recovery is largely attributable to the E174R and S542R substitutions (FIG. 16A).

A unique property of Cas12a nucleases is their ability to process individual crRNAs out of poly-crRNA transcripts (Fonfara et al., Nature, 2016, 532:517-21), simplifying multiplex targeting in cells (Zetsche et al., Nat Biotechnol., 2017, 35:31-34; Tak et al., Nat Methods, 2017, 14:1163-1166). To assess whether the enhanced activities of eAsCas12a could be extended to multiplex targeting, we compared the activities of As, eAs and LbCas12a when programmed with poly-crRNA arrays each encoding three crRNAs targeted to separate genes in human cells (FIGS. 18A-18C). In most cases, we observed superior targeting with eAsCas12a when poly-crRNA arrays were expressed from an RNA polymerase-III promoter, presumably due eAsCas12a's enhanced activity on sites with canonical PAMs (FIGS. 18A and 18B). This improvement of multiplex targeting was also observed when the poly-crRNA was expressed from an RNA polymerase-II promoter, expanding the scope of multiplex editing applications (FIG. 18C). We also designed multiplex arrays encoding two sets of proximally targeted crRNAs to generate small genomic deletions. Pairs of crRNAs were expressed from poly-crRNA transcripts or by instead transfecting pools of single crRNA plasmids into cells, and we again observed improved multiplex targeting with eAsCas12a (FIG. 18D).

Example 4 provides additional evidence to support the observation that the E174R substitution enhances on target activity.

Example 2. Variants of LbCpf1 with Altered PAM Specificity

Figure 12A:
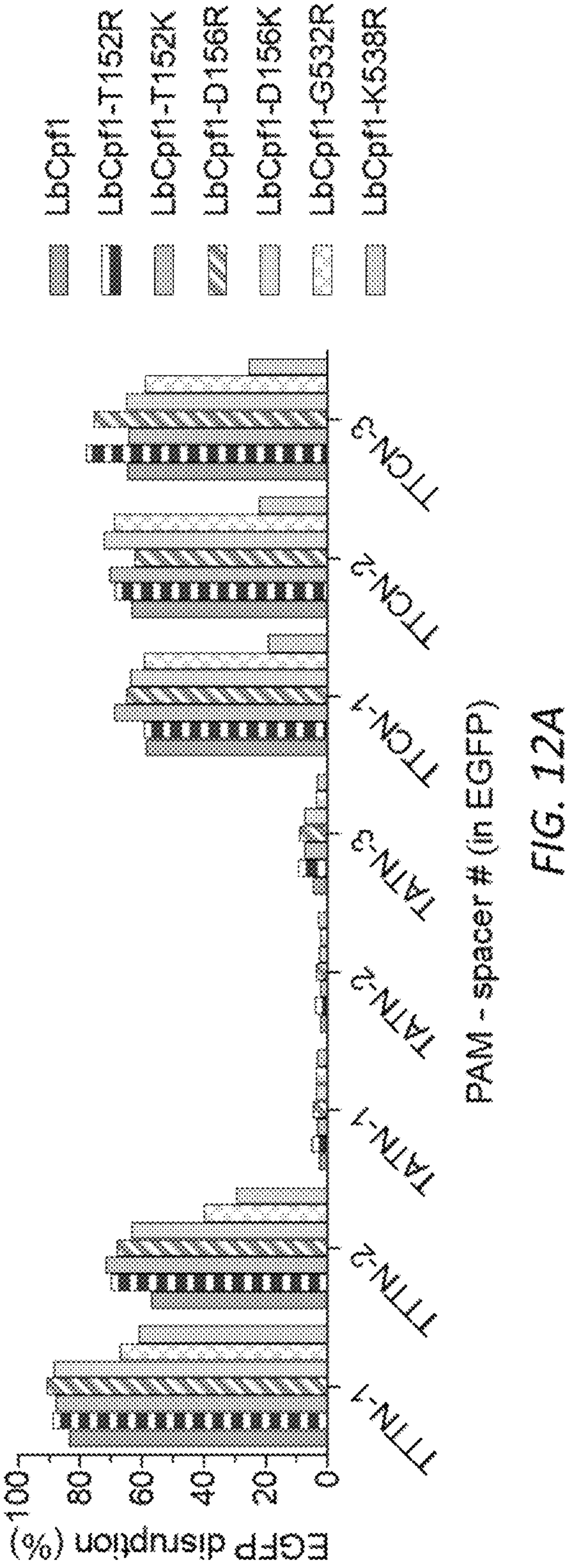
FIGS. 12A-12B: PAM recognition profiles of wild-type LbCpf1 and engineered LbCpf1 variants. (A) The activity of wild-type LbCpf1 and variants bearing various single amino acid substitutions were using the human cell-based EGFP disruption assay with crRNAs targeted to sites bearing either a canonical TTTN PAM or a PAM with a single base difference. (B) The activity of wild-type LbCpf1 was also compared to the LbCpf1-D156R/G532R/K538R variant using the human cell-based EGFP disruption assay with crRNAs targeted to sites bearing either a canonical TTTN PAM or a PAM with a single base difference. n=1.
Figure 12B:
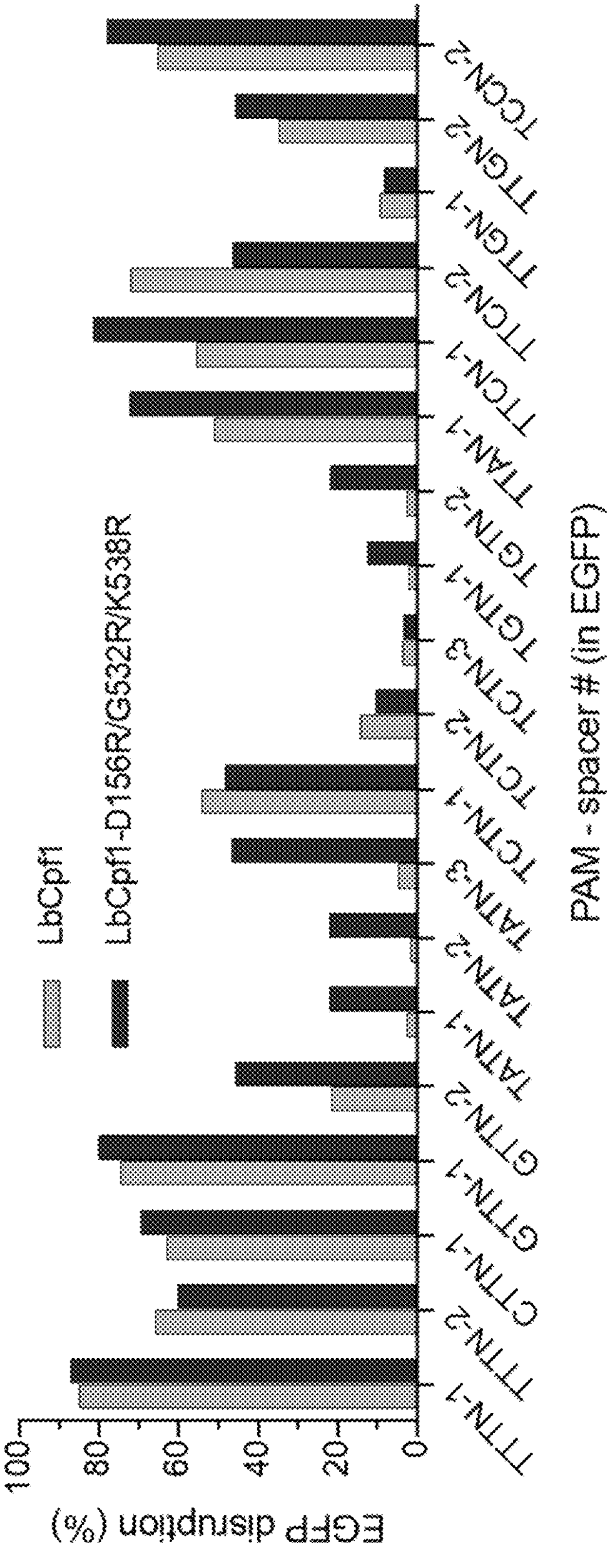

Because AsCpf1 and LbCpf1 share a high degree of homology across the residues in the vicinity of the protein-DNA contacts surrounding the PAM (based on three-dimensional crystal structures and a primary sequence alignment, see Table 1), we made LbCpf1 PAM variants that would harbor residues at residues corresponding to the positions we mutated in AsCpf1. Single substitutions at positions T152, D156, G532, and K538 in LbCpf1 (that correspond to residues S170, E174, S542, and K548 in AsCpf1) revealed only modest increases in EGFP disruption activity against sites with non-canonical PAMs (FIG. 12A) when compared to their corresponding AsCpf1 variants (FIG. 5). However, the triple substitution LbCpf1-D156R/G532R/K538R variant (analogous to AsCpf1-E174R/S542R/K548R) exhibited a slightly more substantial increase in targeting of sites with non-canonical PAMs compared with wild-type LbCpf1 in the EGFP disruption assay (FIG. 12B).

Example 3. Variants of FnCpf1 with Altered PAM Specificity

Previous reports have suggested that FnCpf1 does not work, or has poor activity in human cells (Zetsche, *Cell* 2015; Kim, *Nature Biotechnology* 2016). Because AsCpf1 and FnCpf1 share a high degree of homology, we first sought to test whether wild-type FnCpf1 does indeed function in human cells, and then whether we could relax the previously reported PAM specificity of TTN (Zetsche, *Cell* 2015).

Figure 13A:
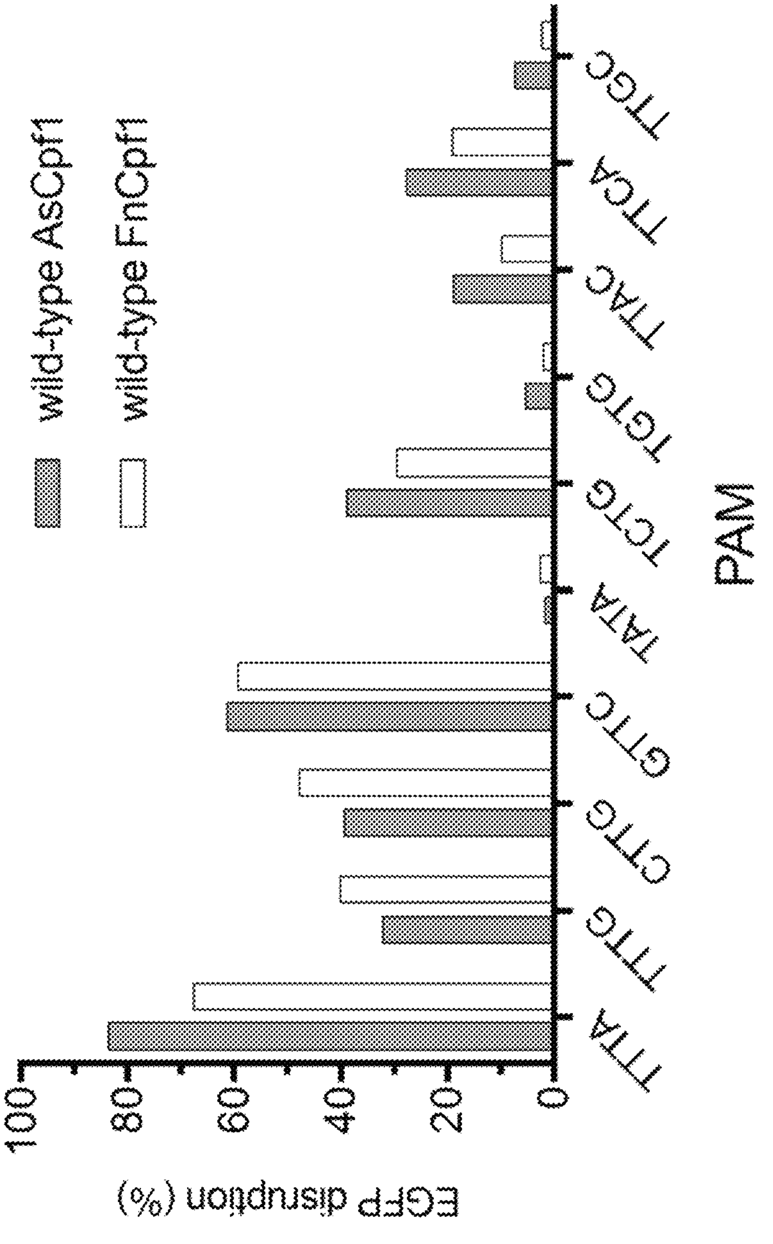
FIGS. 13A-13C: PAM recognition profiles of wild-type FnCpf1 and engineered LbCpf1 variants. (A) The activity of wild-type FnCpf1 using the human cell-based EGFP disruption assay with crRNAs targeted to sites bearing either a canonical TTN PAM or a PAM with a single base difference. (B) The activity of wild-type FnCpf1, AsCpf1, and LbCpf1 against endogenous human cell target sites with crRNAs targeted to sites bearing TTTN PAMs. (C) Comparison of the activity of wild-type FnCpf1 to engineered FnCpf1 PAM variants using the human cell-based EGFP disruption assay with crRNAs targeted to sites bearing either a canonical TTTN PAM or a PAM with a single base difference. n=1.
Figure 13B:
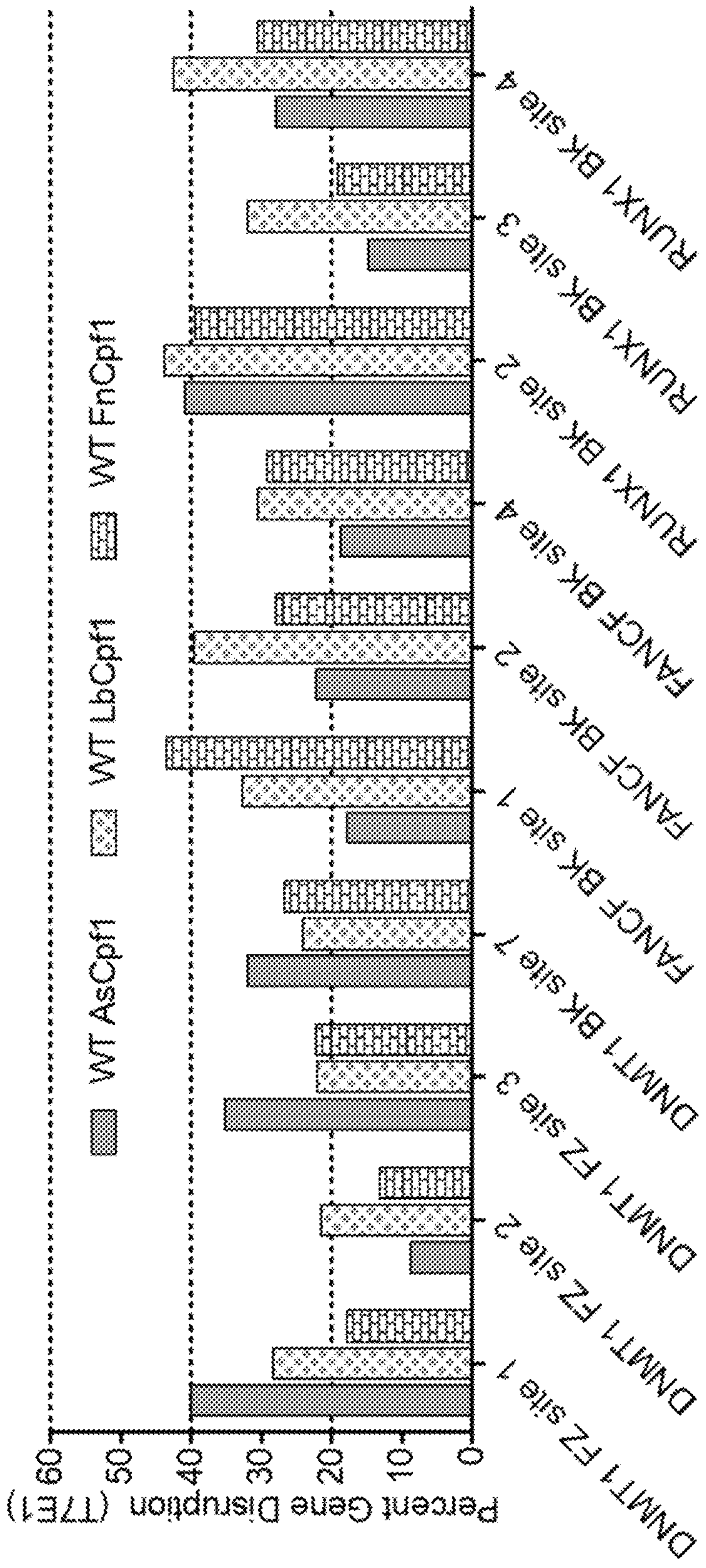

To examine the activity of FnCpf1 in human cells, we tested its activity in our human cell EGFP disruption assay against target sites that contain PAMs of the form NTTN, TNTN, and TTNN (FIG. 13A). Our results reveal that wild-type FnCpf1 can indeed mediate robust EGFP disruption in human cells against NTTN sites, with some detectable activity against TCTN and TTCN sites (FIG. 13A). Next, we compared the endogenous gene disruption activity of FnCpf1 to AsCpf1 and LbCpf1 at 10 different endogenous target sites bearing TTTN PAMs. In many cases, we observed comparable activity of FnCpf1 to AsCpf1 and LbCpf1, demonstrating that FnCpf1 does indeed function robustly in human cells (FIG. 13B).

Figure 13C:
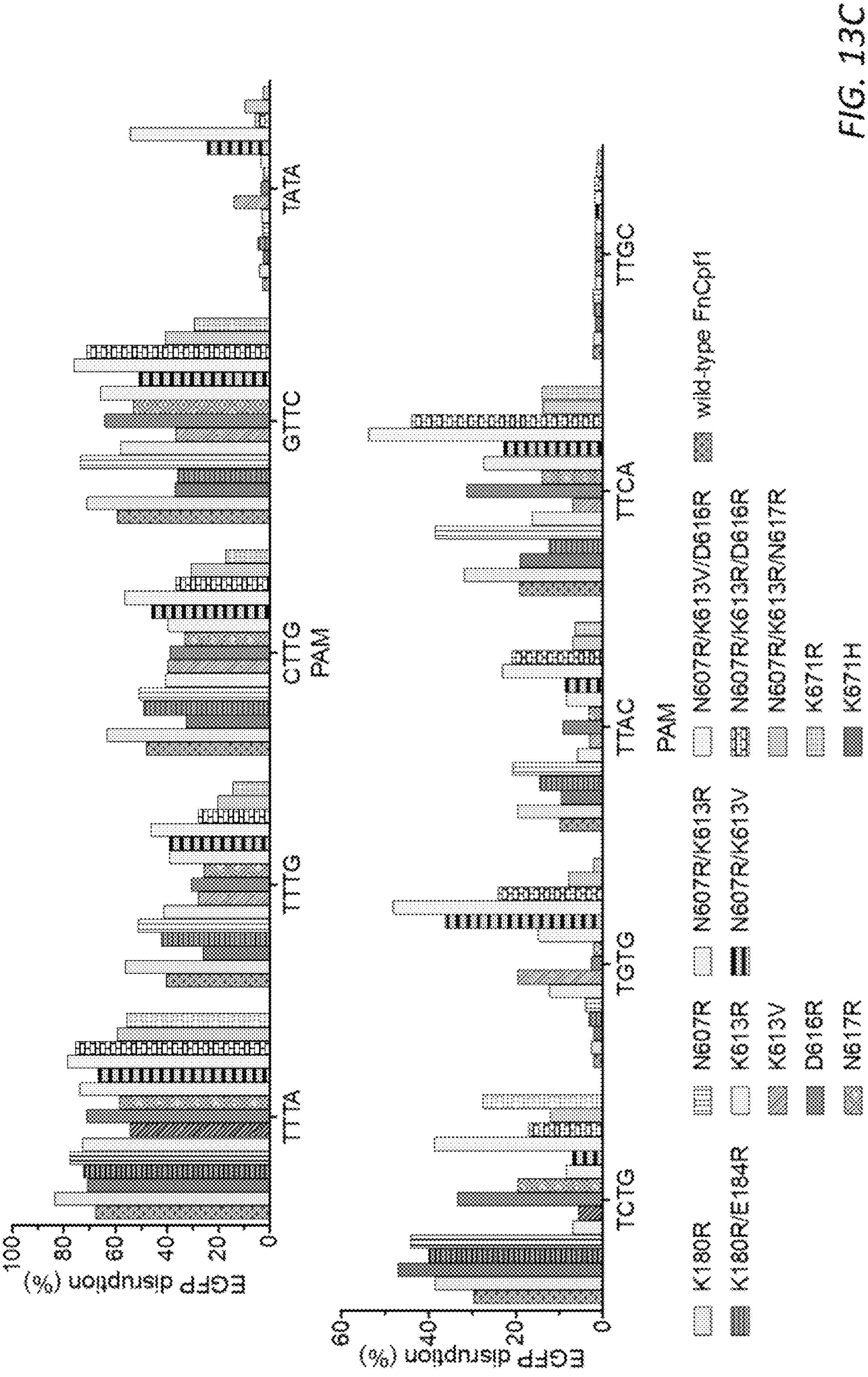

Because FnCpf1 functions in human cells, we sought to determine whether we could generate FnCpf1 PAM variants by creating variants of FnCpf1 bearing substitutions at residues homologous to positions of AsCpf1 that led to altered PAM specificity (Table 1). Of the substitutions that we examined, single substitutions of K180R, N607R, and D616R led to increases in activity over wild-type AsCpf1 at TTTN, TNTN, and NTTN PAM sites (FIG. 13C). Additionally, a K671H mutation could increase activity against a TCTN PAM site. We also observed that variants bearing combinations of substitutions including N607R/K613R, N607R/K613V. N607R/K613V/D616R, or N607R/K613R/D616R improved activity over wild-type FnCpf1 at certain PAMs of the form TTTN, CTTN, GTTN, TATN, TCTN, TCTN, TTAN, of TTCN (FIG. 13C).

Example 4. Additional Variants of AsCpf1 with Altered PAM Specificities

Gao et al. recently published additional Cpf1 variants with altered PAM specificity (Gao et al., "Engineered Cpf1

Enzymes with Altered PAM Specificities," bioRxiv 091611; doi: https://doi.org/10.1101/091611). These variants, with their claimed activities on canonical and/or non-canonical PAMs are as follows:

1) AsCpf1-S542R/K548V/N552R—functions against TATV PAM sites
2) AsCpf1-S542R/K607R—functions optimally against TYCV PAM sites, but displays loss of activity against canonical TTTV sites.

Figure 14A:
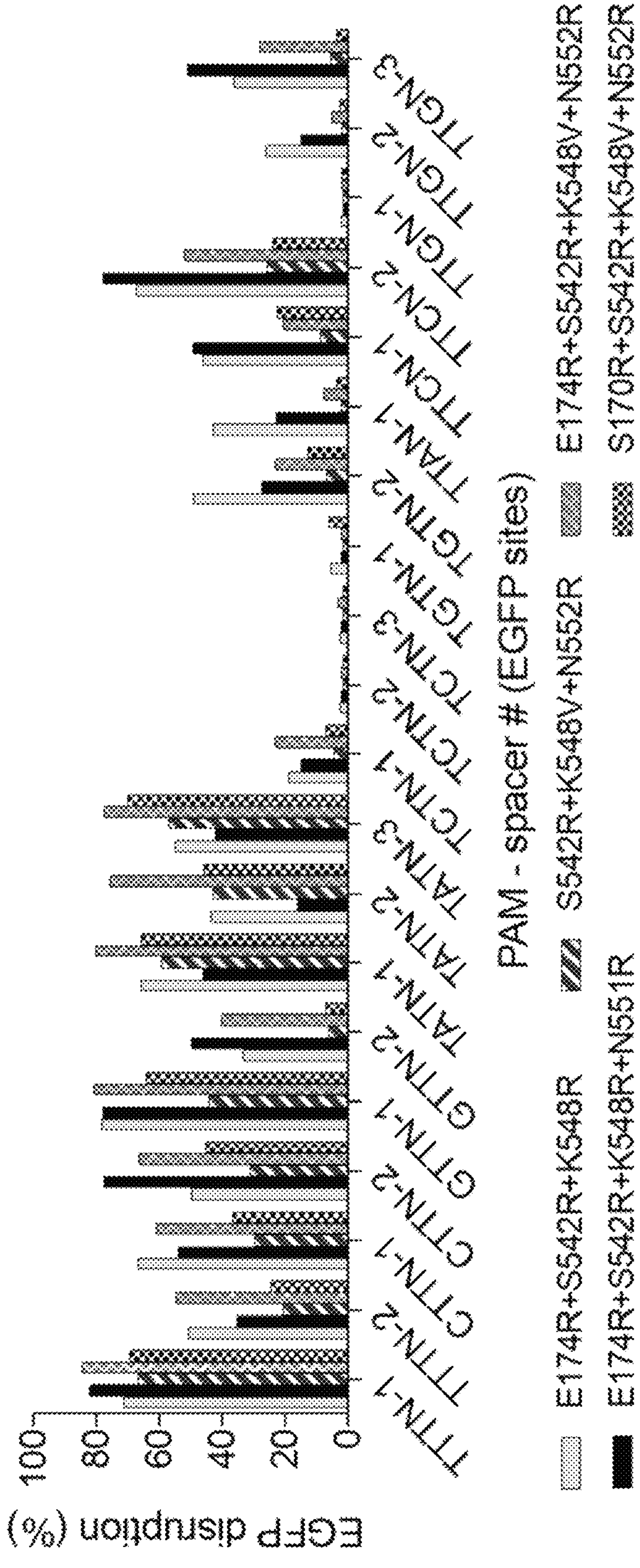
FIGS. 14A-14C: Comparison of PAM recognition profiles of AsCpf1 variants described in this application with different AsCpf1 variants disclosed in other work. (A, B) The activities of a number of our engineered AsCpf1 PAM recognition variants were compared to the S542R/K548V/N552R (panel A) and S542R/K607R (panel B) PAM recognition variants using the human cell-based EGFP disruption assay with crRNAs targeted to sites bearing either canonical TTTN PAMs or PAMs with single or double base differences. (C) Additional comparisons of our AsCpf1 variants to the S542R/K607R variant were performed by examining the abilities of these nucleases to mutagenize endogenous human gene sites with crRNAs targeted to sites with either canonical TTTN PAMs or PAMs with single, double, or triple base differences.

To benchmark the triple and quadruple substitution AsCpf1 variants described herein (E174R/S542R/K548R and E174R/S542R/K548R/N551R, respectively) against the S542R/K548V/N552R variant, we compared the activity of these three variants using the EGFP disruption assay on target sites bearing canonical TTTN, TATN (reported to be recognized by the S542R/K548V/N552R variant), and PAMs with single or double base differences (FIG. 14A). For all sites tested, we observed that our triple and quadruple substitution variants outperformed the S542R/K548V/N552R variant at TTTV, TATN, and other non-canonical CTTN, GTTN, TCTN, TGTN, TTAN, TTCN, TTGN, and TCCN PAMs (FIG. 14A). Next, based on our previous observations that S170R or E174R substitutions can increase the activity of AsCpf1 variants when combined with other substitutions, we explored whether the addition of either of these substitutions to the S542R/K548V/N552R variant could also improve its activity. In comparing the S170R/S542R/K548V/N552R and E174R/S542R/K548V/N552R quadruple substitution variants to the parental S542R/K548V/N552R, we observed that the addition of the S170R or E174R substitutions substantially improved activity (with the effect of E174R being greater than S170R, yet the addition of S170R also produces improvements; FIG. 14A).

Figure 14B:
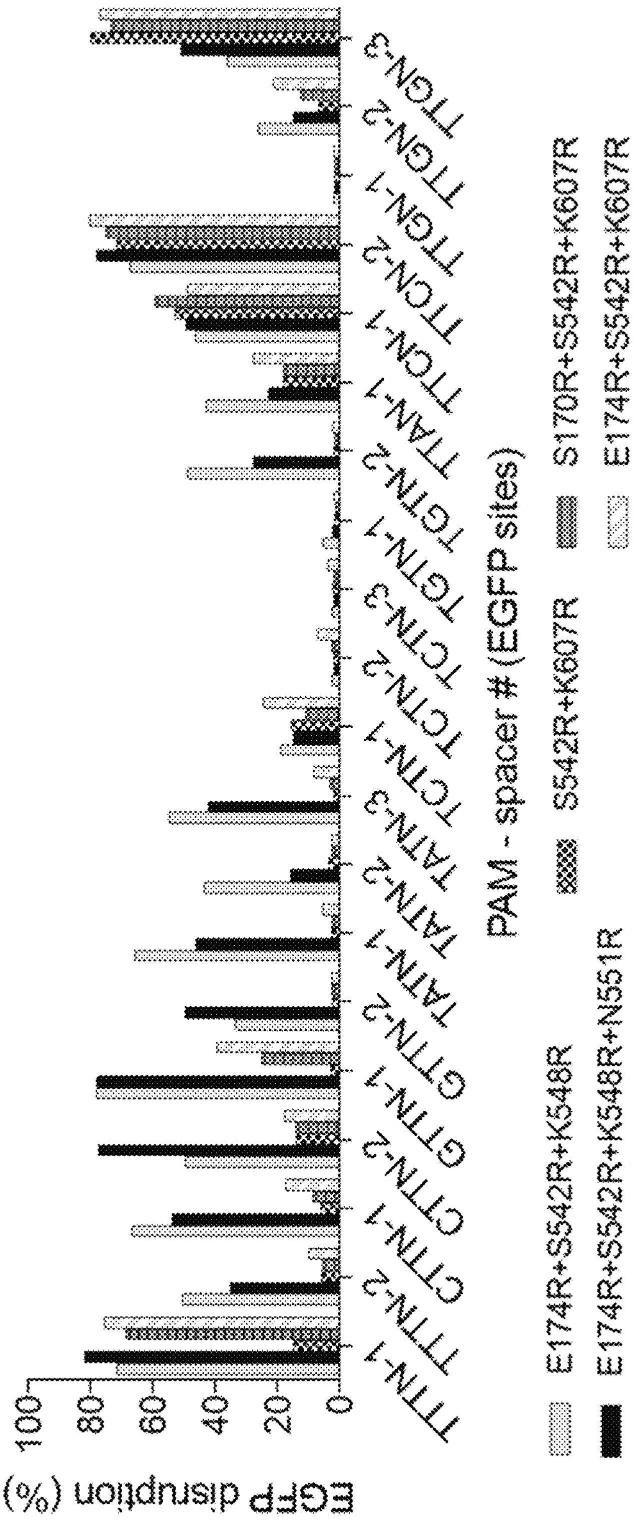
Figure 14C:
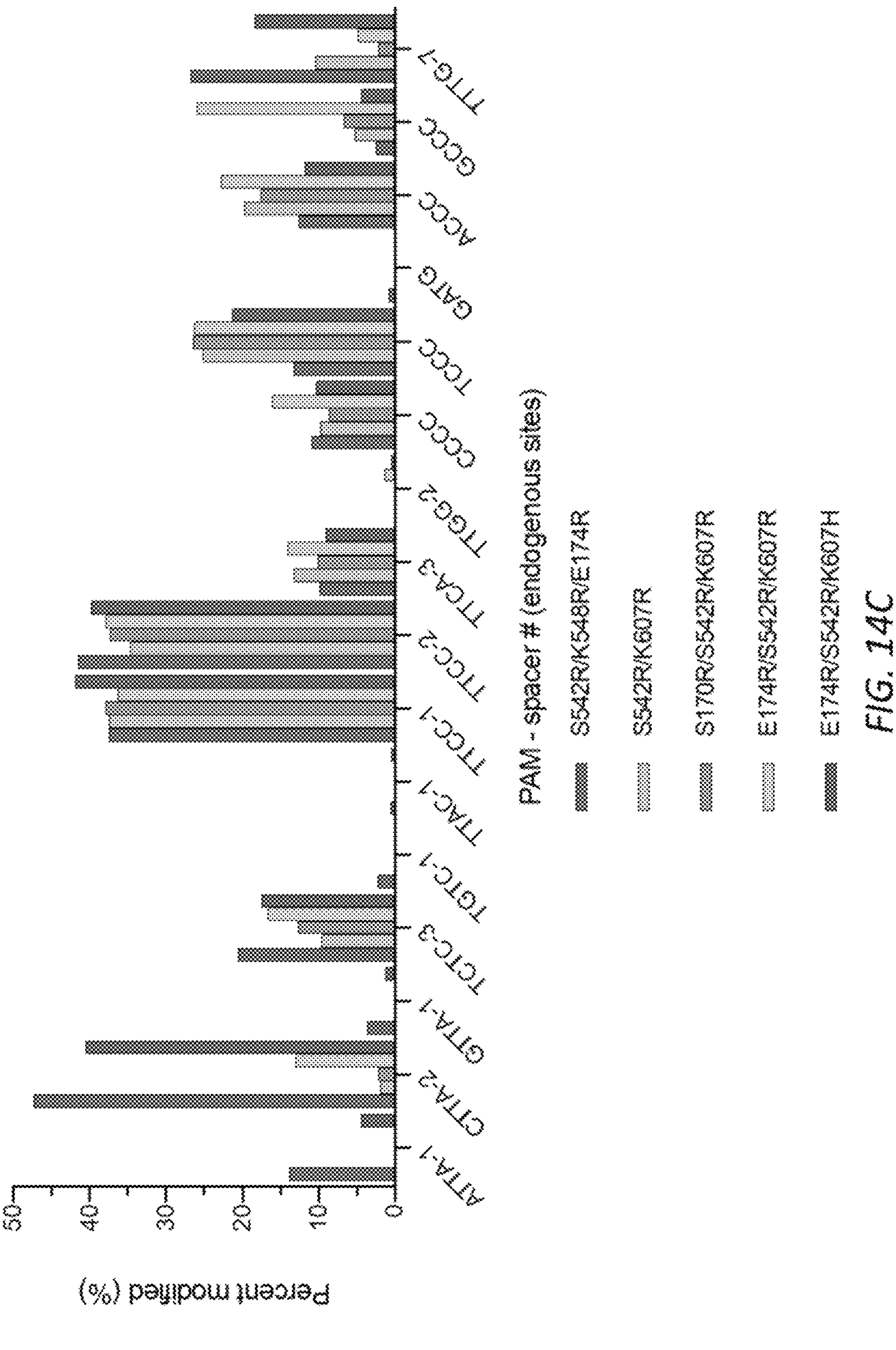

We also compared the activity of our triple and quadruple substitution AsCpf1 variants (E174R/S542R/K548R and E174R/S542R/K548R/N551R, respectively) against the S542R/K607R variant across a number of target sites in EGFP bearing the canonical TTTN PAM sequence or PAMs with a single base difference. For all of these sites, our triple and quadruple substitution variants (E174R/S542R/K548R and E174R/S542R/K548R/N551R) had roughly equal or higher levels of EGFP disruption activity when compared to the S542R/607R variant (FIG. 14B). S542R/K607R only outperformed our triple and quadruple variants on a target site with a TCCN PAM. Therefore, we added either the S170R or E174R substitutions to the S542R/K607R variant to create triple substitution S170R/S542R/K607R and E174R/S542R/K607R variants. These additional triple substitution variants performed as well or better than the S542R/K607R variant at all sites tested, notably working as well on sites with a TCCN PAM (FIG. 14B). Finally, we compared one of our triple substitution variants (E174R/S542R/K548R) with the S542R/K607R variant at a series of endogenous human gene target sites in U2OS cells bearing non-canonical PAMs (with 1, 2, or 3 base differences in the PAM). At all sites tested other than those bearing NCCC PAMs, our E174R/S542R/K548R variant performed as well as or better than the S542R/K607R variant (FIG. 14C). For the NCCC PAM sites where the S542R/K607R variant displayed higher gene disruption activity, we compared this variant to our S170R/S542R/K607R. E174R/S542R/K607R, and E174R/S542R/K607H variants and observed that in all cases, one of our triple substitution variants outperformed the S542R/K607H variant (FIG. 14C).

Example 4B. Improving the On-Target Activities of AsCas12a PAM Variants

Figure 16B:
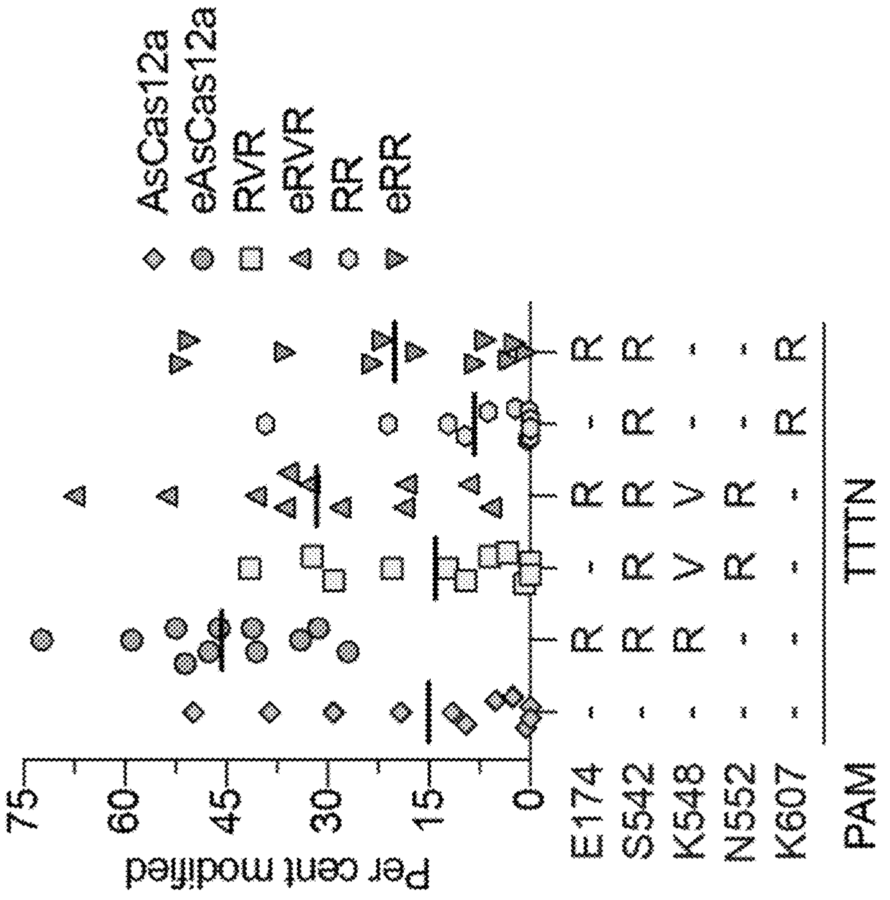

Since our results suggest that E174R and S542R lead to enhanced activities of eAsCas12a in human cells, we hypothesized that the inclusion of E174R in previously described AsCas12a variants that already encode S542R could also improve their activities. Thus, the E174R substitution was combined with the RVR (S542R/K548V/N552R) and RR (S542R/K607R) variants to create enhanced versions of these nucleases (eRVR and eRR, respectively). Comparison of the activities of the eAsCas12a. RVR, eRVR, RR, and eRR variants against 11 sites with TTTN PAMs in human cells (FIG. 24A) revealed that while the previously published RVR and RR variants have similar or weaker activities compared to wild-type AsCas12a, the addition of E174R to create the eRVR and eRR variants led to greater than 2-fold increases in their activities (albeit still lower than eAsCas12a; FIG. 16B). These results reinforce the observation that variants bearing the combination of E174R and S542R can improve on-target activity.

Next, because our PAMDA assessment of eAsCas12a revealed recognition of the primary PAMs previously reported as accessible by the RVR and RR variants (TATV and TYCV PAMs, respectively; FIG. 15B), we compared eAsCas12a to the published and enhanced versions of these nucleases at such sites in human cells. Across 12 TATN sites (FIG. 24B), we observed that eAsCas12a displayed roughly equivalent activity to the RVR variant (FIG. 16C). Interestingly, the addition of E174R to RVR led to a 2-fold improvement in activity, suggesting eRVR as the optimal variant for applications where targeting TATN sites is the primary objective (FIG. 16C). We then assessed eAsCas12a, RR, and eRR on 29 sites bearing TYCN PAMs in human cells (FIG. 24C). eAsCas12a exhibited higher modification compared to RR across the 18 TTCN sites, whereas the eRR variant containing E174R had comparable activity to eAsCas12a (FIG. 16D). Further comparison of these variants on 11 TCCN sites revealed that while the RR variant is a more effective nuclease compared to eAsCas12a on sites with TCCN PAMs, once again the E174R-containing eRR variant resulted in the most robust modification across all TCCN sites (FIG. 16D).

Figure 16E:
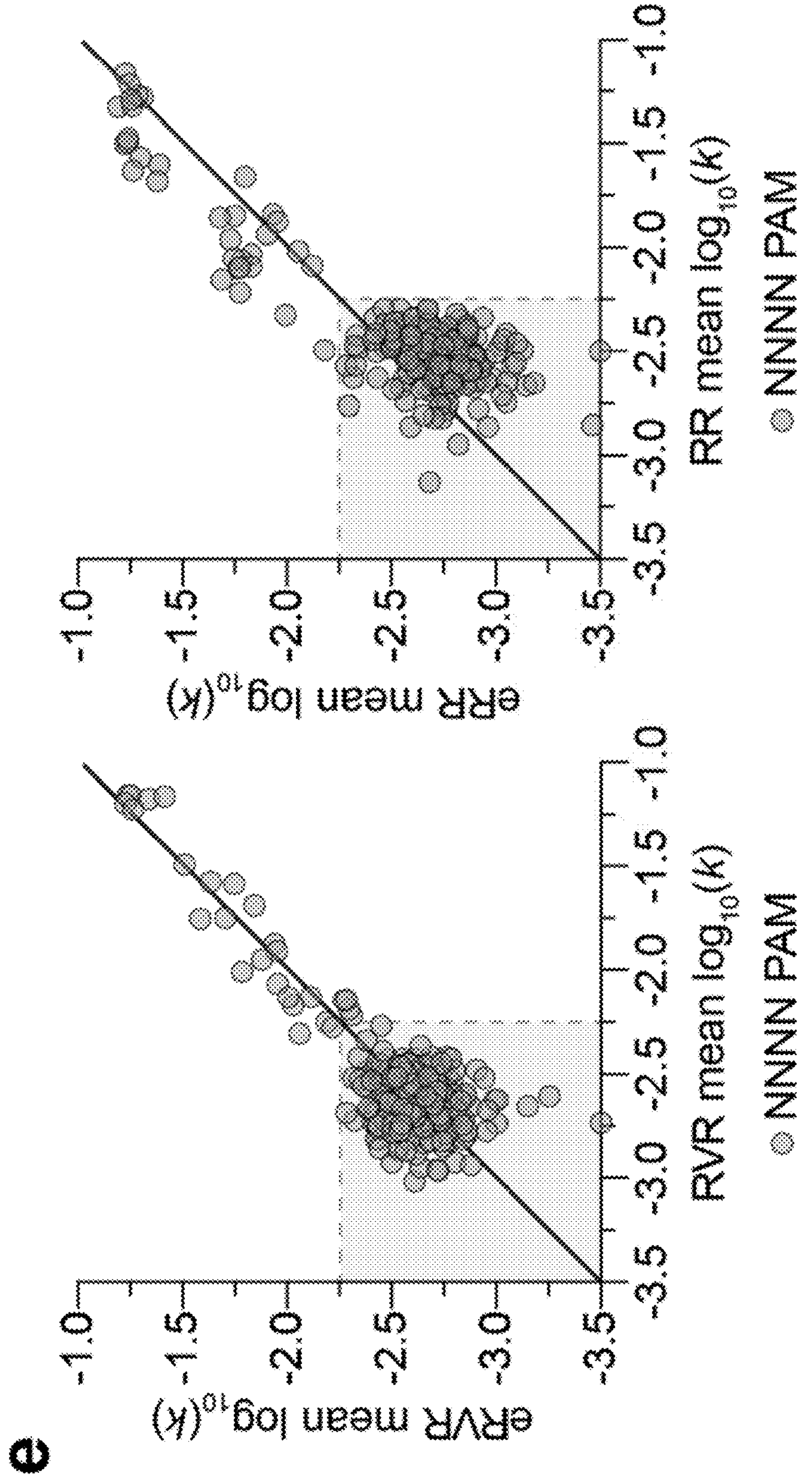
Figure 24A:
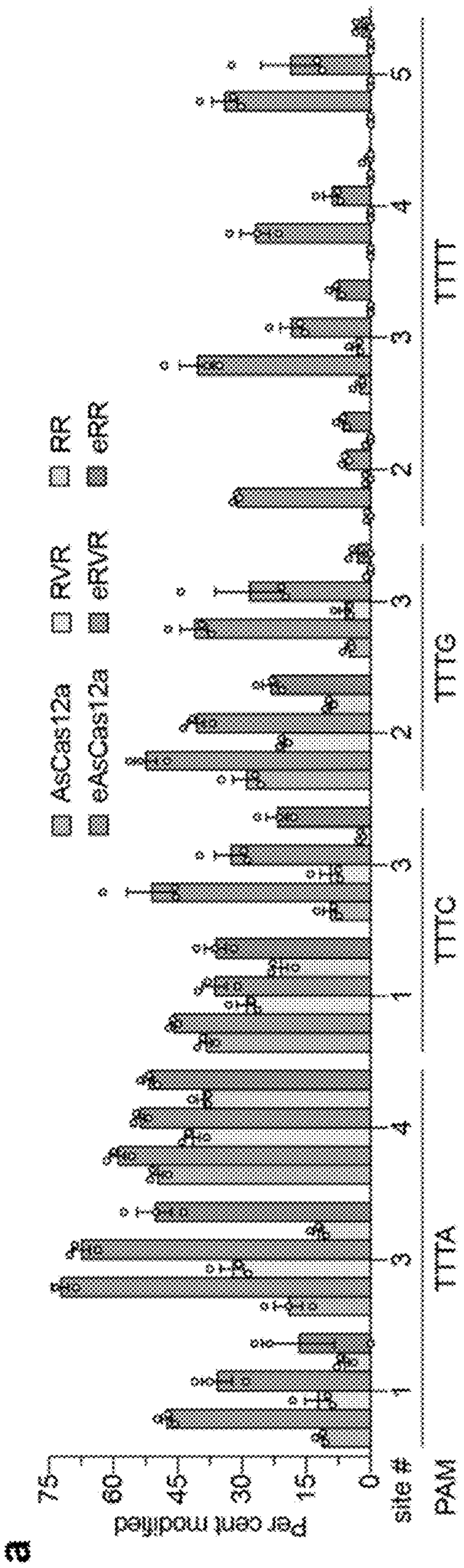
Figure 24B:
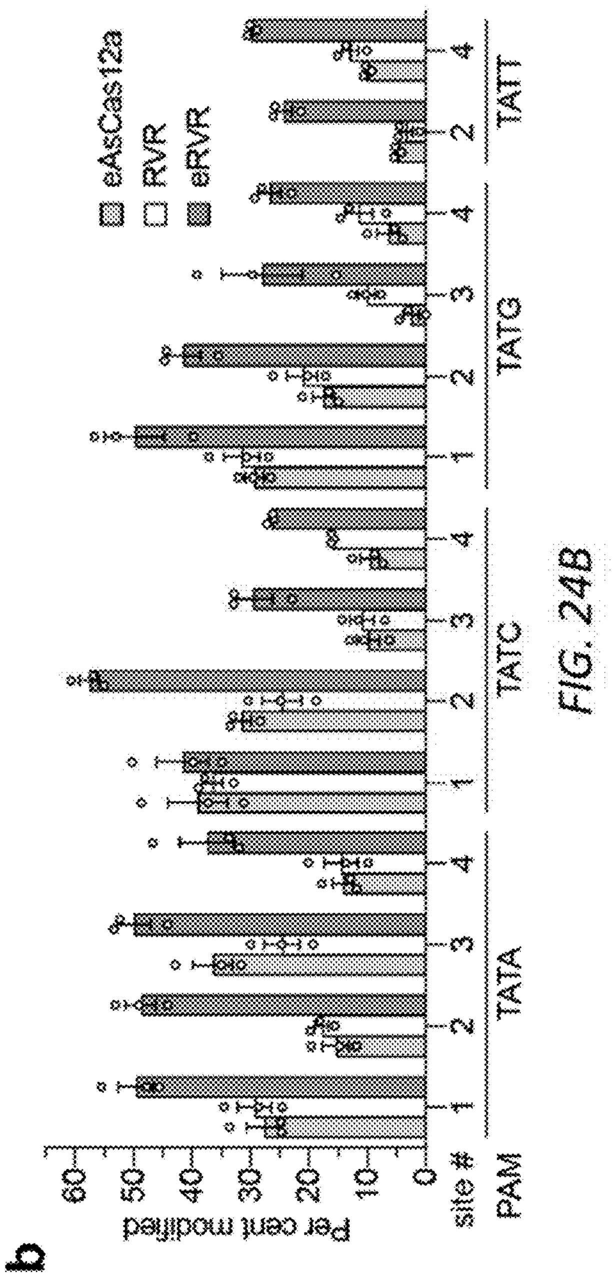
Figure 24C:
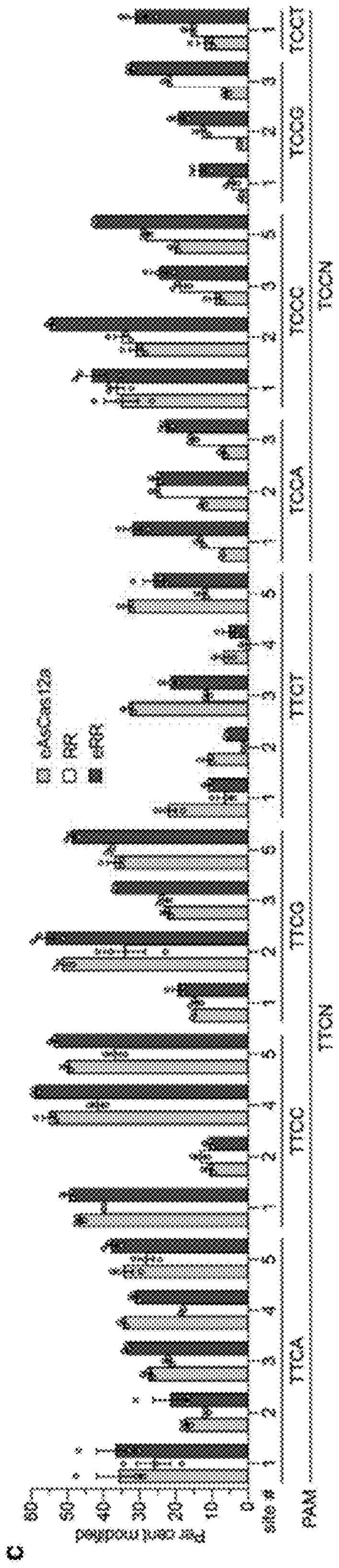
Figure 24D:
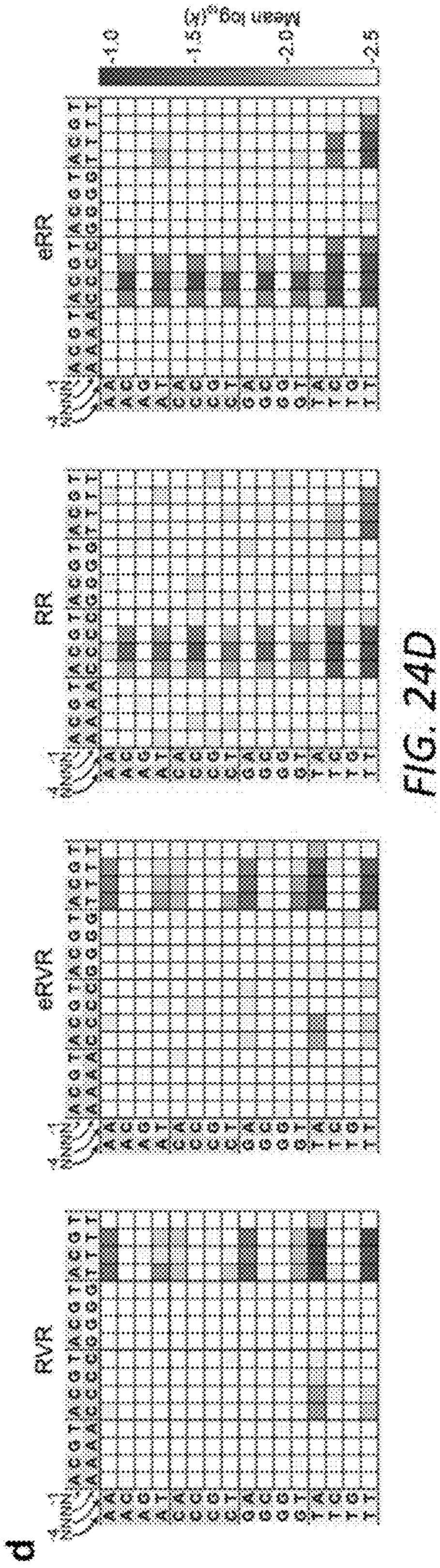
Figure 24E:
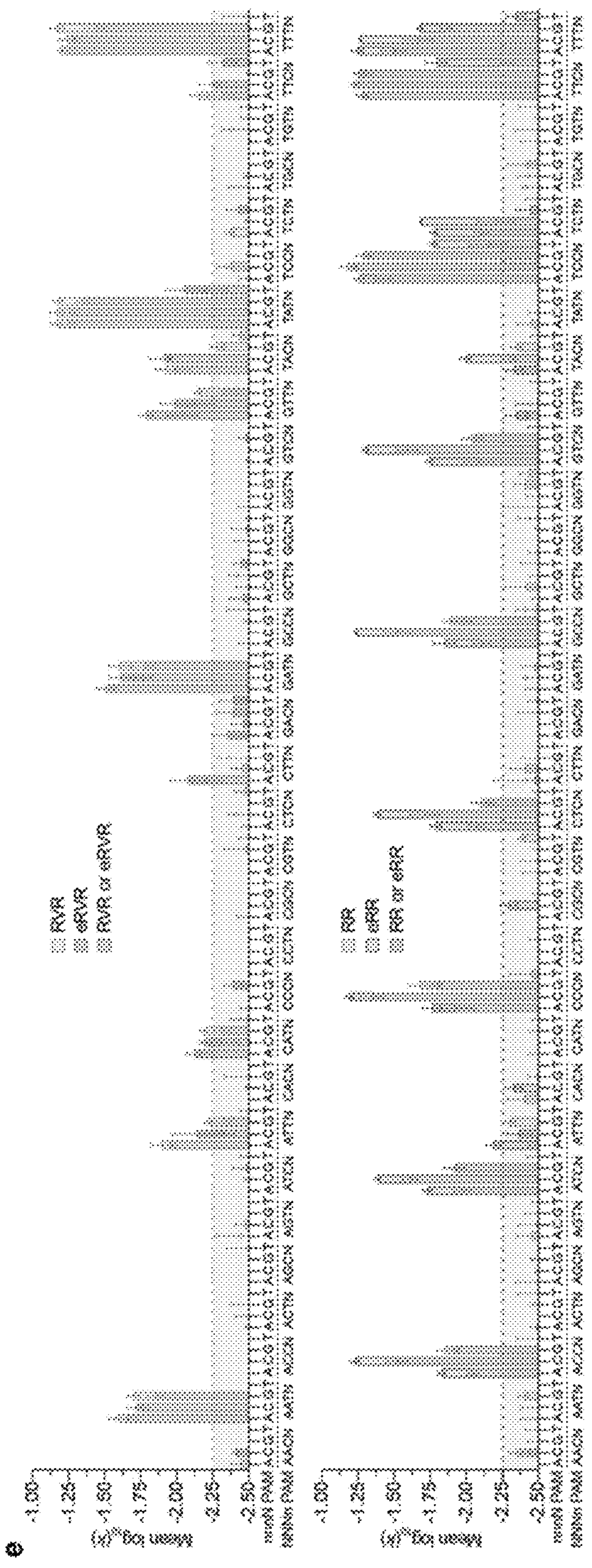

To determine whether the targeting range of the enhanced eRVR and eRR variants had been altered by the addition of E174R, we applied the PAMDA to the RVR, RR, and their enhanced variants (FIG. 24D). Consistent with our human cell data, we observed that the eRVR and eRR nucleases had similar targeting range to their parental RVR and RR variants, but that their on-target potency was improved by the addition of the E174R substitution (FIGS. 16E and 24E). Taken together, these results demonstrate that the E174R and S542R substitutions not only improve targeting range, but that they can also improve the on-target activities of AsCas12a nucleases.

Example 5. Enhancing the Genome-Wide Specificity of eAsCas12a

Figure 17A:
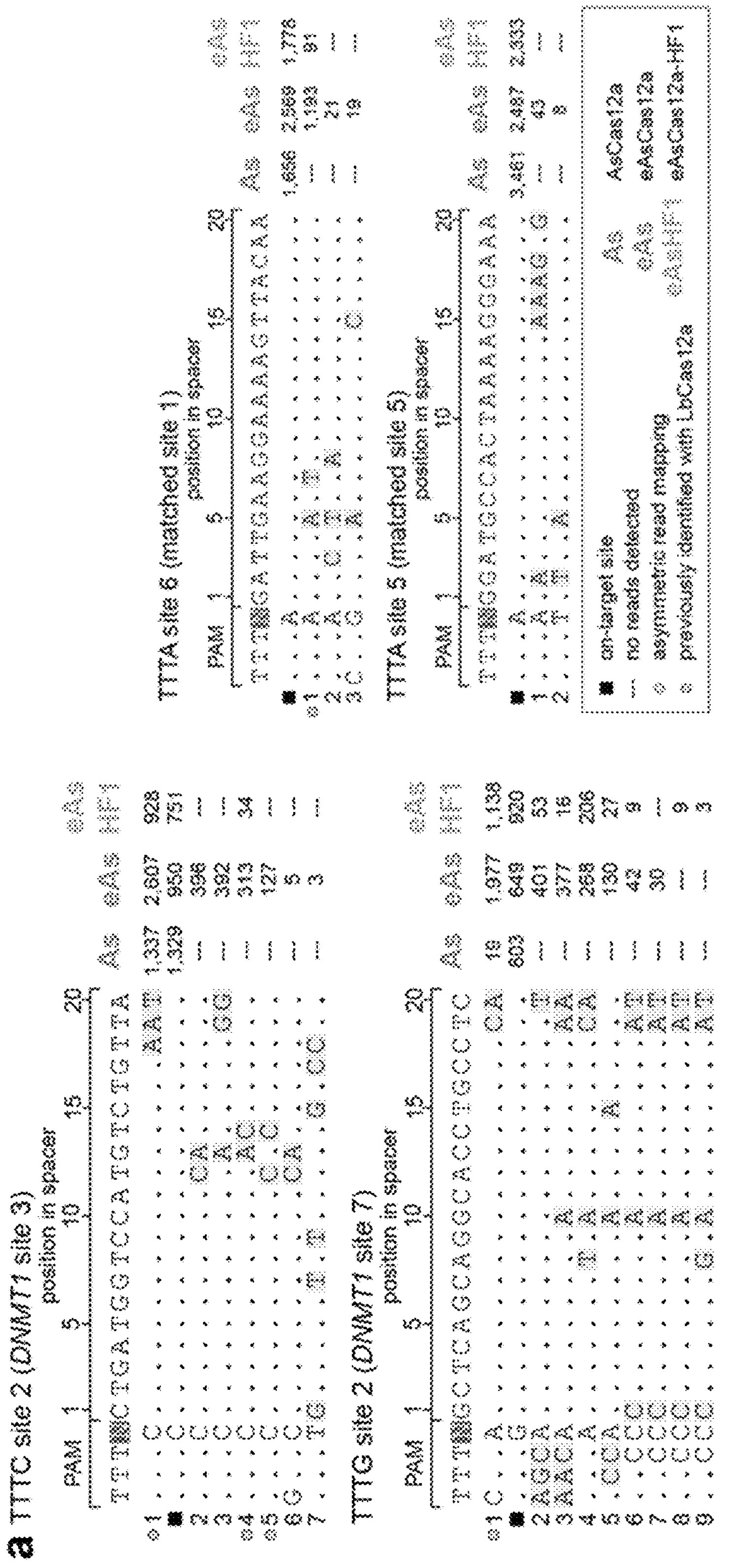
Figure 17C:
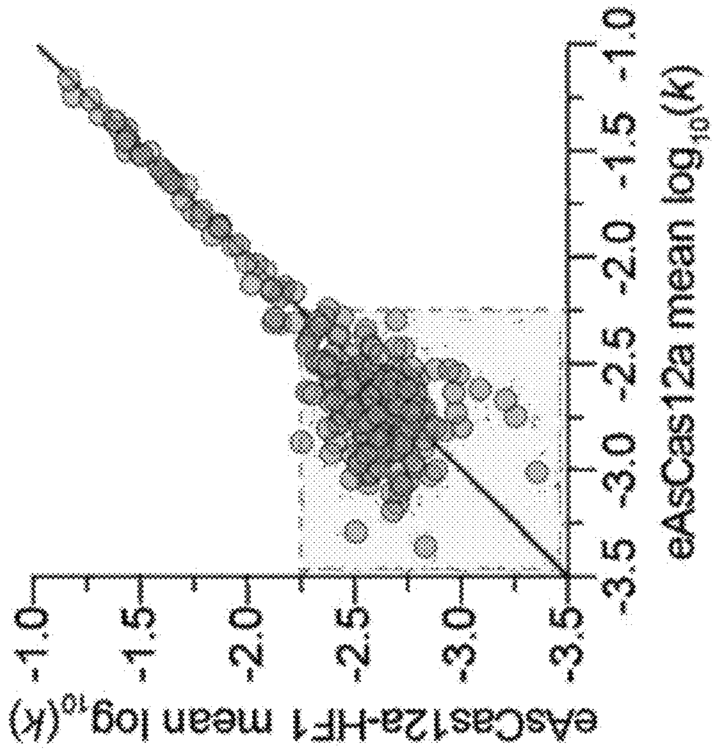
Figure 17B:
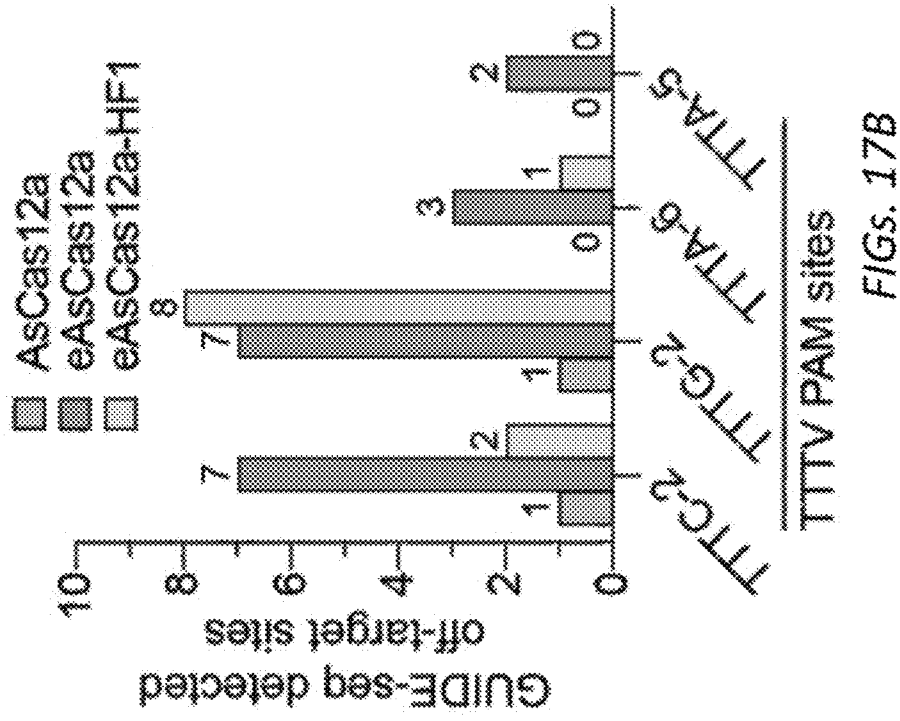
Figure 17D:
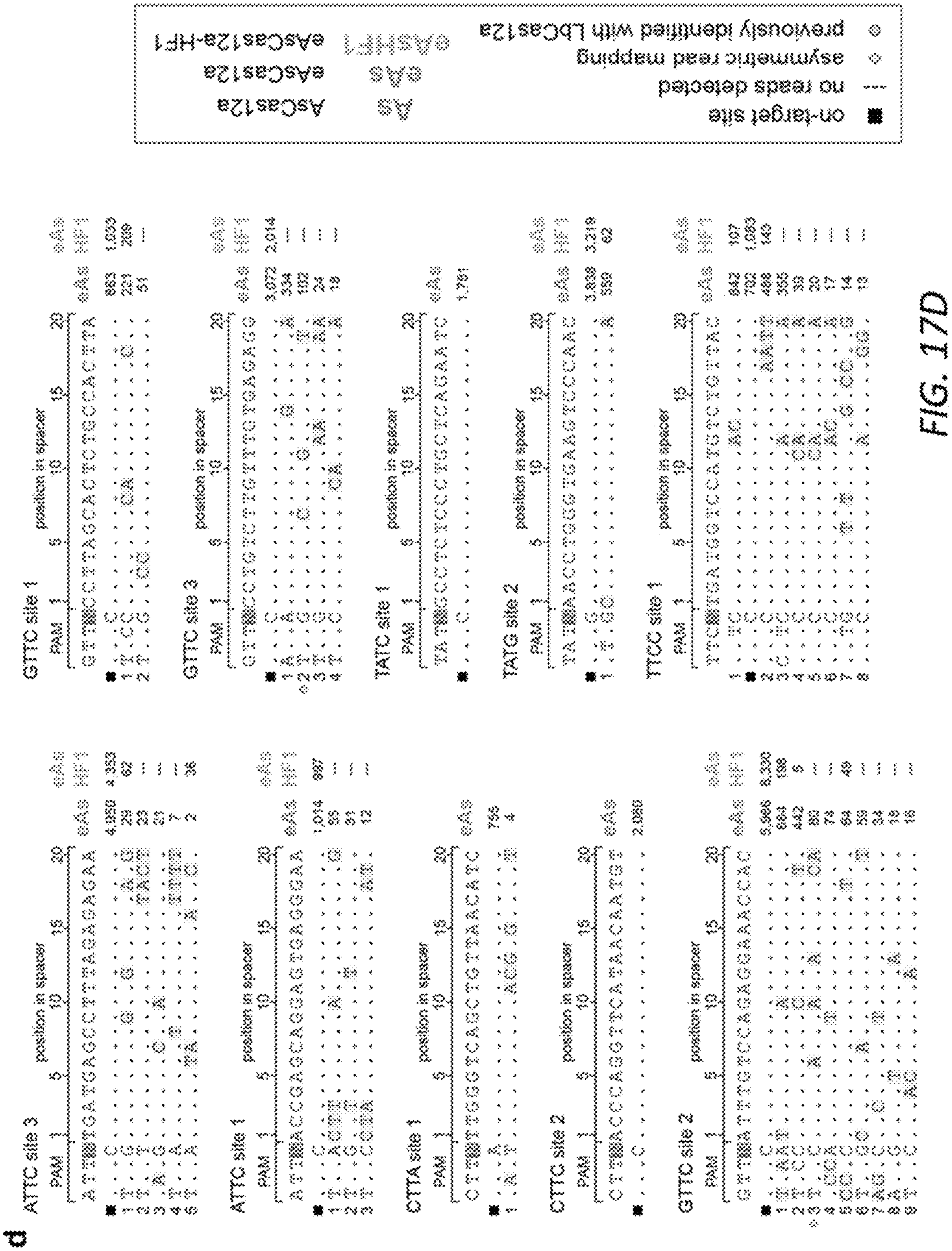

Given that eAsCas12a exhibits enhanced activity and relaxed PAM recognition compared to wild-type AsCas12a, we sought to compare the specificities of these nucleases as their ability to distinguish on- from off-target sites is critical for both research and therapeutic applications. In this regard, we and others have previously shown that wild-type Cas12a nucleases possess robust genome-wide specificities and are relatively intolerant of mismatched off-target sites that harbor single or double mismatches in the immediately PAM proximal, middle, and PAM distal regions of the spacer (Kleinstiver et al., Nat Biotechnol., 2016, 34:869-74; Kim et al., Nat Biotechnol., 2016, 34:863-8; WO2018/022634). Therefore, we used the genome-wide, unbiased identification of DSBs enabled by sequencing (GUIDE-seq) method (Tsai et al., Nat Biotechnol., 2015, 33:187-197) to compare the genome-wide specificities of As and eAsCas12a on four sites with TTTV PAMs (FIGS. 25A-25D). Few off-targets were detected by GUIDE-seq with wild-type AsCas12a, and we observed an increase in the number of off-targets for eAsCas12a (FIGS. 17A and 17B). Many of the off-targets observed for eAsCas12a were either previously identified in GUIDE-seq experiments with LbCas12a (Kleinstiver et al., Nat Biotechnol., 2016, 34:869-74), contained mismatches in positions known to be tolerant of nucleotide substitutions (Kleinstiver et al., Nat Biotechnol., 2016, 34:869-74; Kim et al., Nat Biotechnol., 2016, 34:863-8), or encoded now-targetable non-canonical PAMs (FIG. 17A).

Figure 25D:
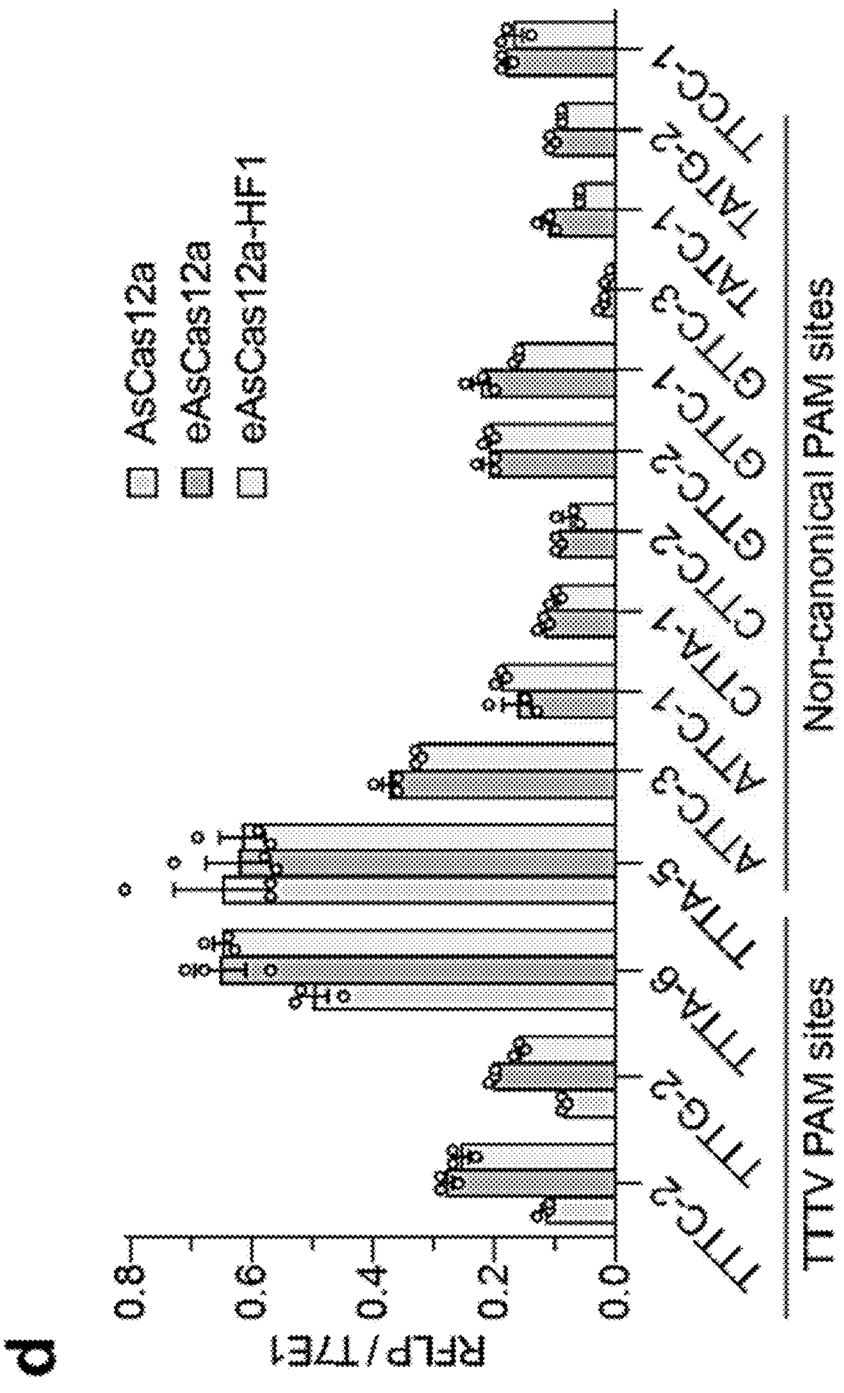
Figure 25E:
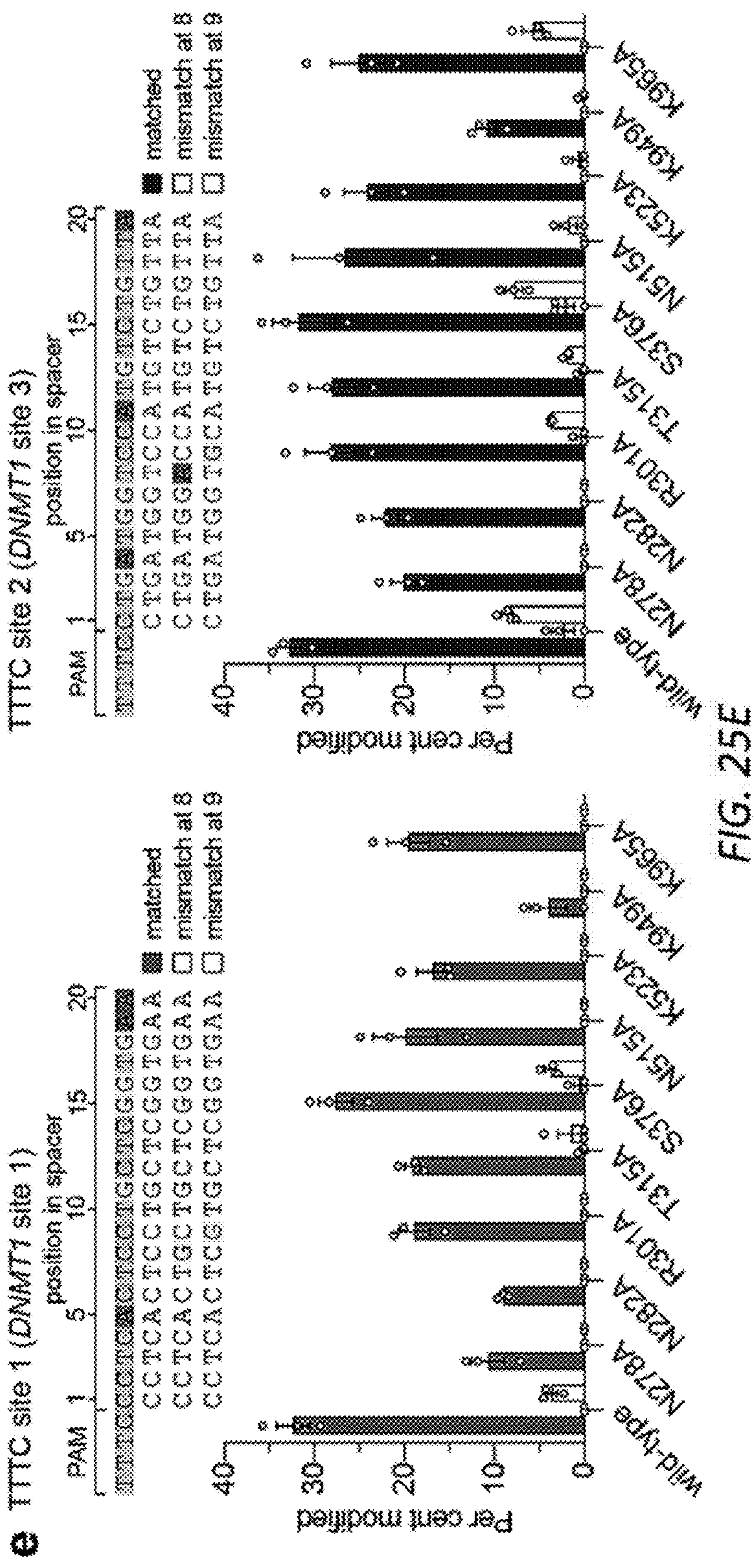
Figure 25F:
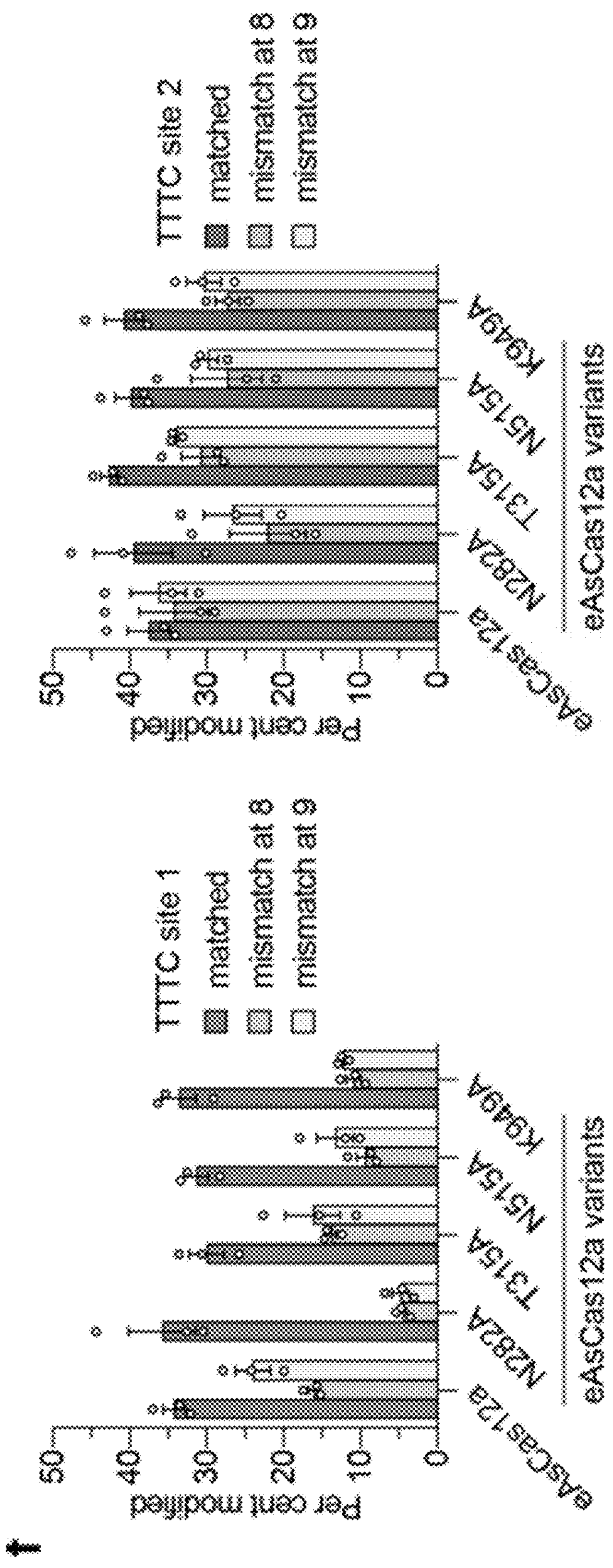
Figure 25G:
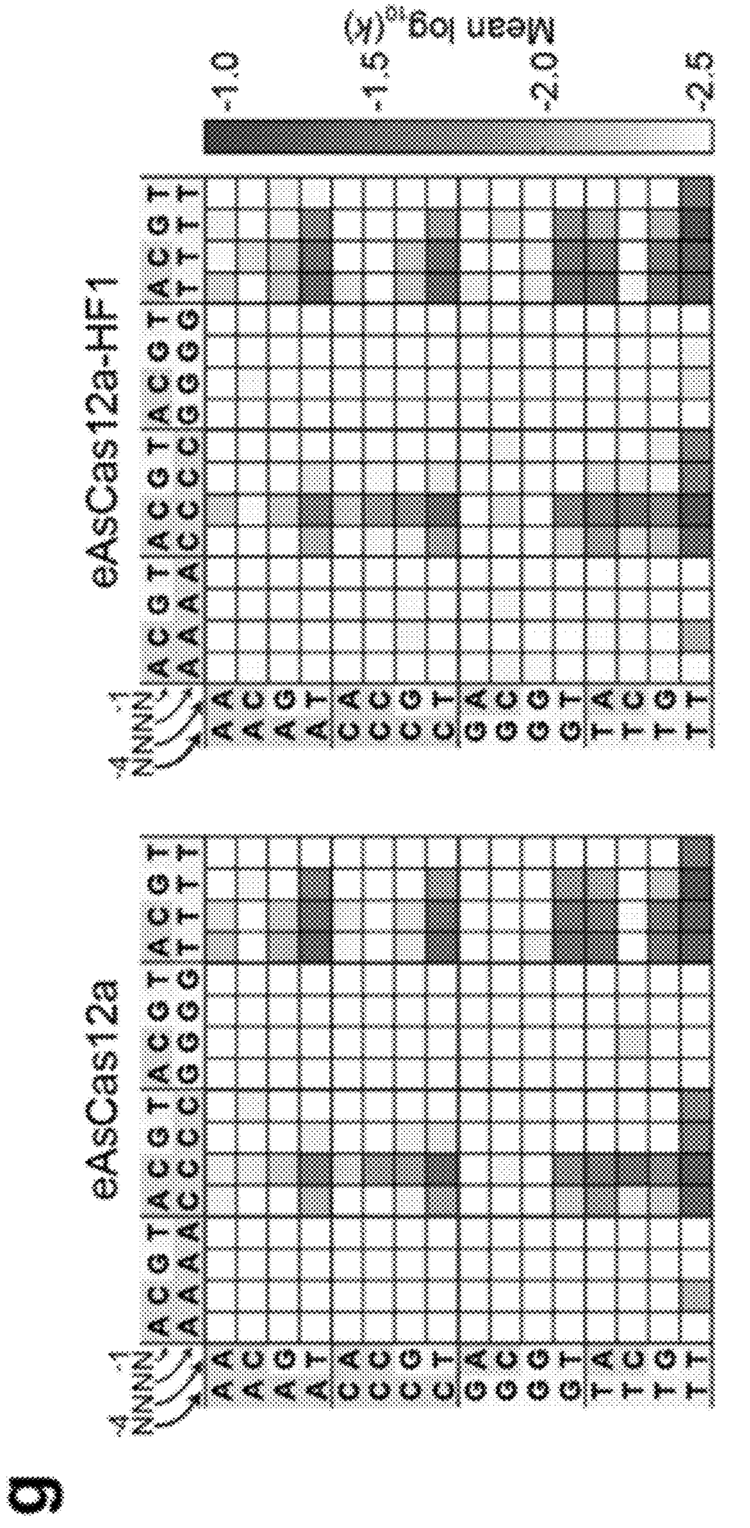
Figure 25H:
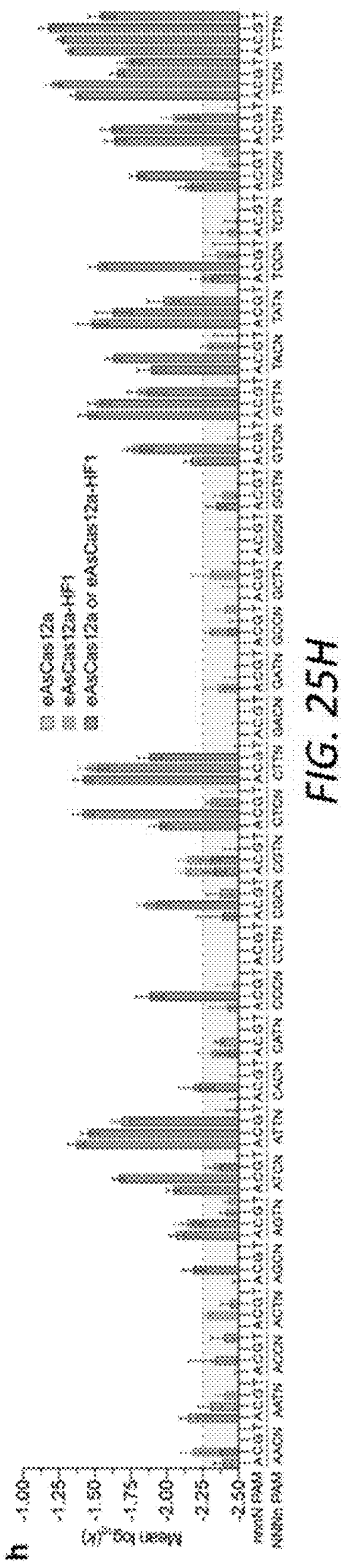
Figure 25I:
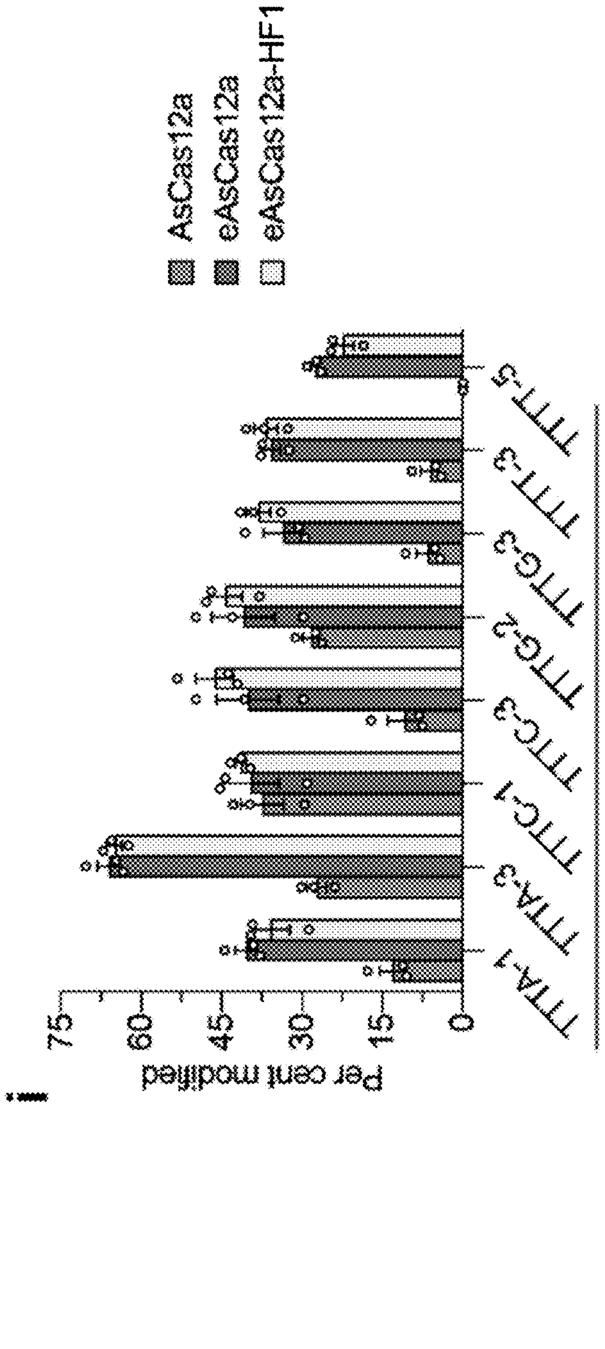
Figure 25J:
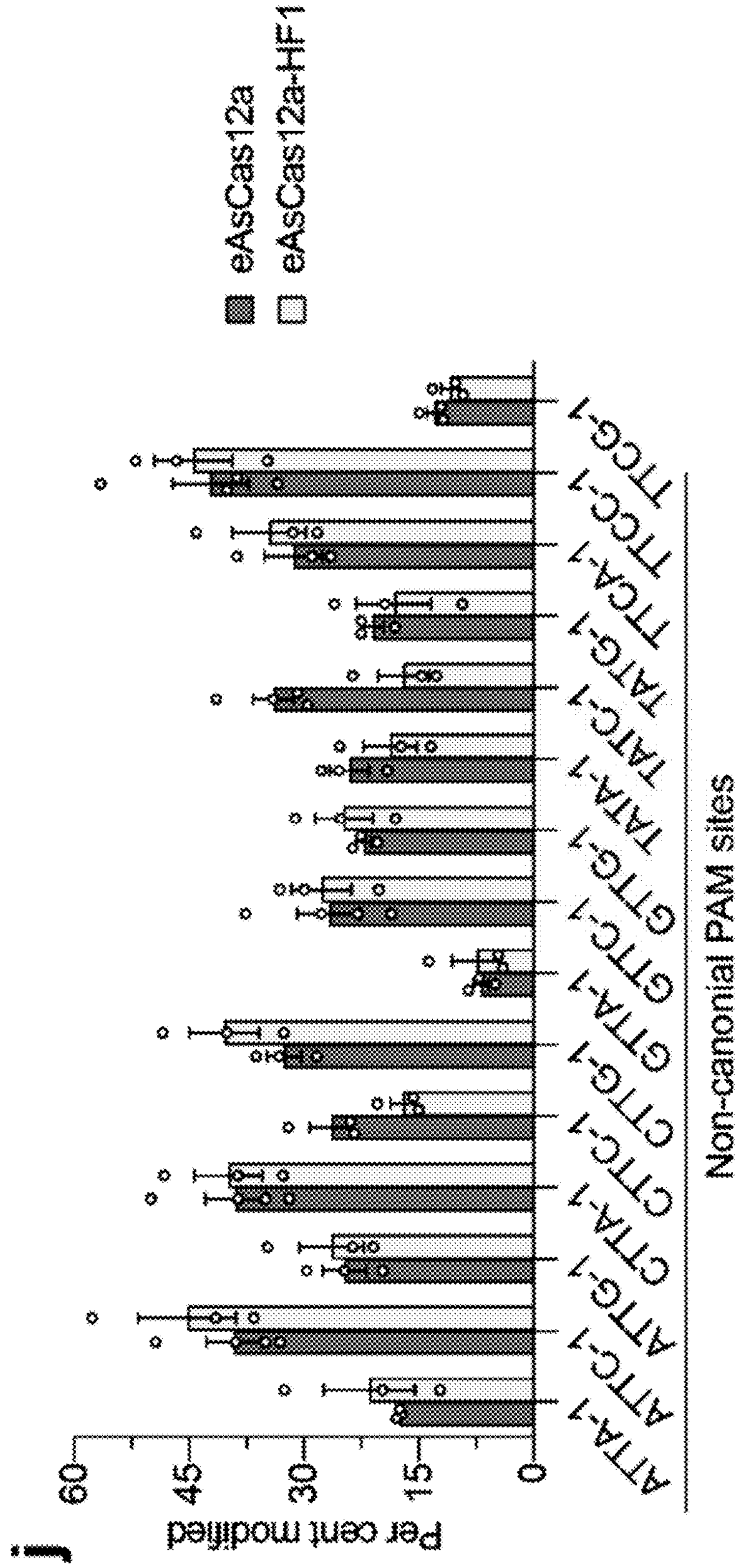

To explore whether a directed evolution method could be used to improve the fidelity of eAsCas12a, we examined the impact of amino acid substitutions at residues in AsCas12a predicted to make non-specific contacts to DNA. We assayed the single-mismatch tolerance of nine different putative high-fidelity (HF) substitutions (including the previously described K949A variant), and observed that while some substitutions improved the single mismatch tolerance profile of AsCas12a across two sites, many also reduced activity with the matched crRNA (FIG. 25E). We combined the most promising substitutions with eAsCas12a, and observed that the N282A version of eAsCas12a (named eAsCas12a-HF1) yielded the most desirable improvements in single mismatch intolerance and maintenance of on-target activity (FIG. 25F). Assessment of eAsCas12a and eAsCas12a-HF1 using the PAMDA revealed nearly identical PAM preference profiles (FIGS. 25G and 25H), suggesting that the N282A HF mutation does not alter PAM recognition or targeting range (FIG. 17C).

Next, to determine whether eAsCas12a-HFI can improve genome-wide specificity, we performed GUIDE-seq using the same four previously examined TTTV PAM targeted crRNAs. Compared to eAsCas12a, we observed a reduction in both the number and frequency at which off-targets were detected with eAsCas12a-HF1 for 3 out of 4 crRNAs (FIGS. 17A and 17B), where their specificity profiles now more closely resembled that observed for wild-type AsCas12a. Additional GUIDE-seq experiments were performed to compare eAsCas12a and eAsCas12a-HF1 across sites with non-canonical PAMs (FIGS. 17D and 25B-25D), and we again observed reductions in the number and frequency of off-targets with eAsCas12a-HF1 compared to eAsCas12a (FIGS. 17E and 17F, respectively).

Figure 25K:
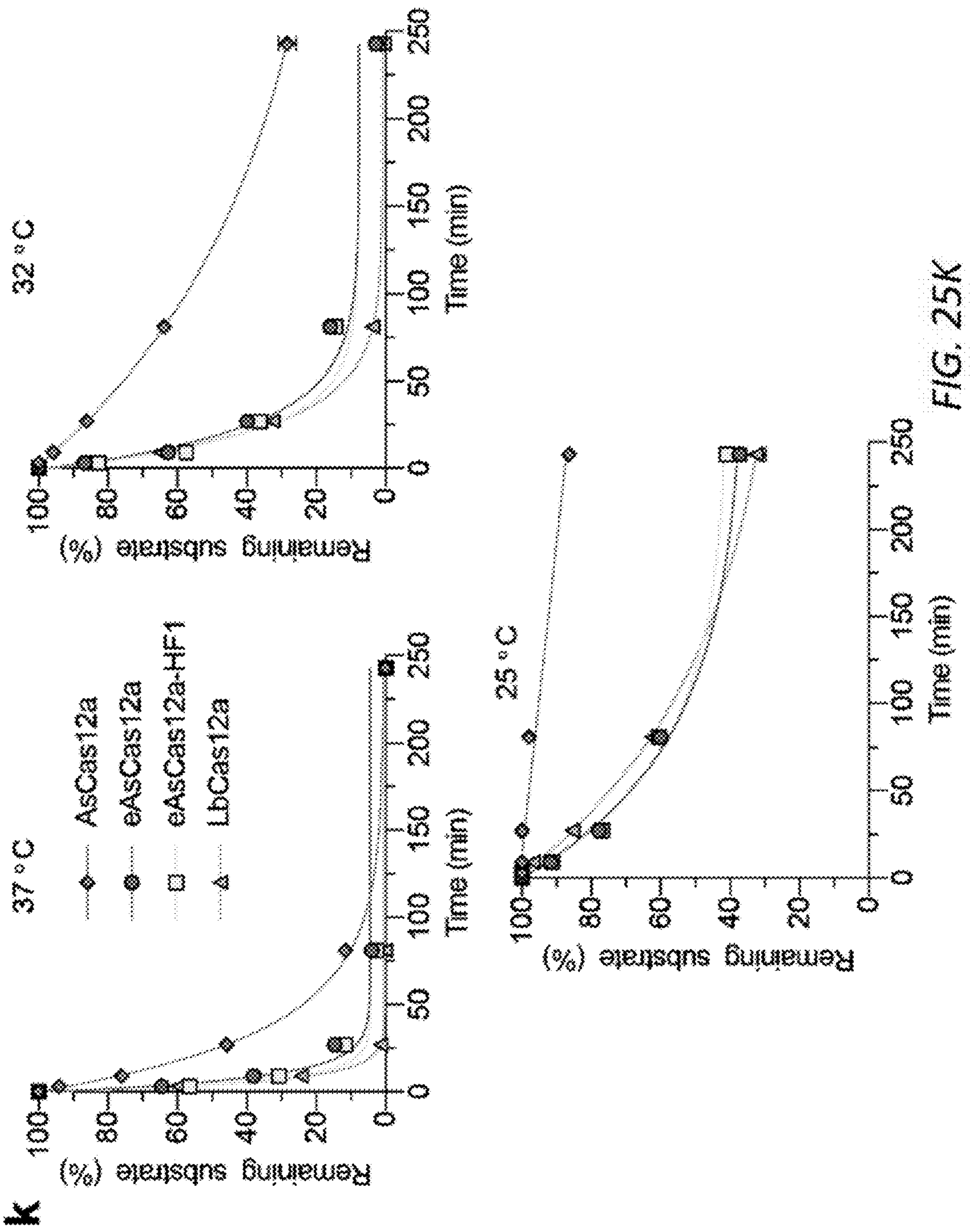

We then compared the on-target activities of eAsCas12a and eAsCas12a-HF1 across canonical and non-canonical PAM sites (FIGS. 251 and 25J, respectively) to examine whether the N282A substitution impacts targeting efficiency. We observed similar gene modification across 8 TTTN PAM sites (again with nearly 3-fold greater efficiency relative to wild-type AsCas12a; FIG. 17G), and comparable activities between eAsCas12a and eAsCas12a-HF1 on 15 sites bearing non-canonical PAMs (FIG. 17H). Moreover, in vitro cleavage assays to assess temperature tolerance revealed similar cleavage profiles between eAsCas12a, eAsCas12a-HF1, and LbCas12a at 37, 32, and 25° C. (FIG. 25K). Together, these results demonstrate that eAsCas12a-HF1 can improve genome-wide specificity while maintaining important targeting range, increased activity, and temperature tolerance properties.

Figure 26A:
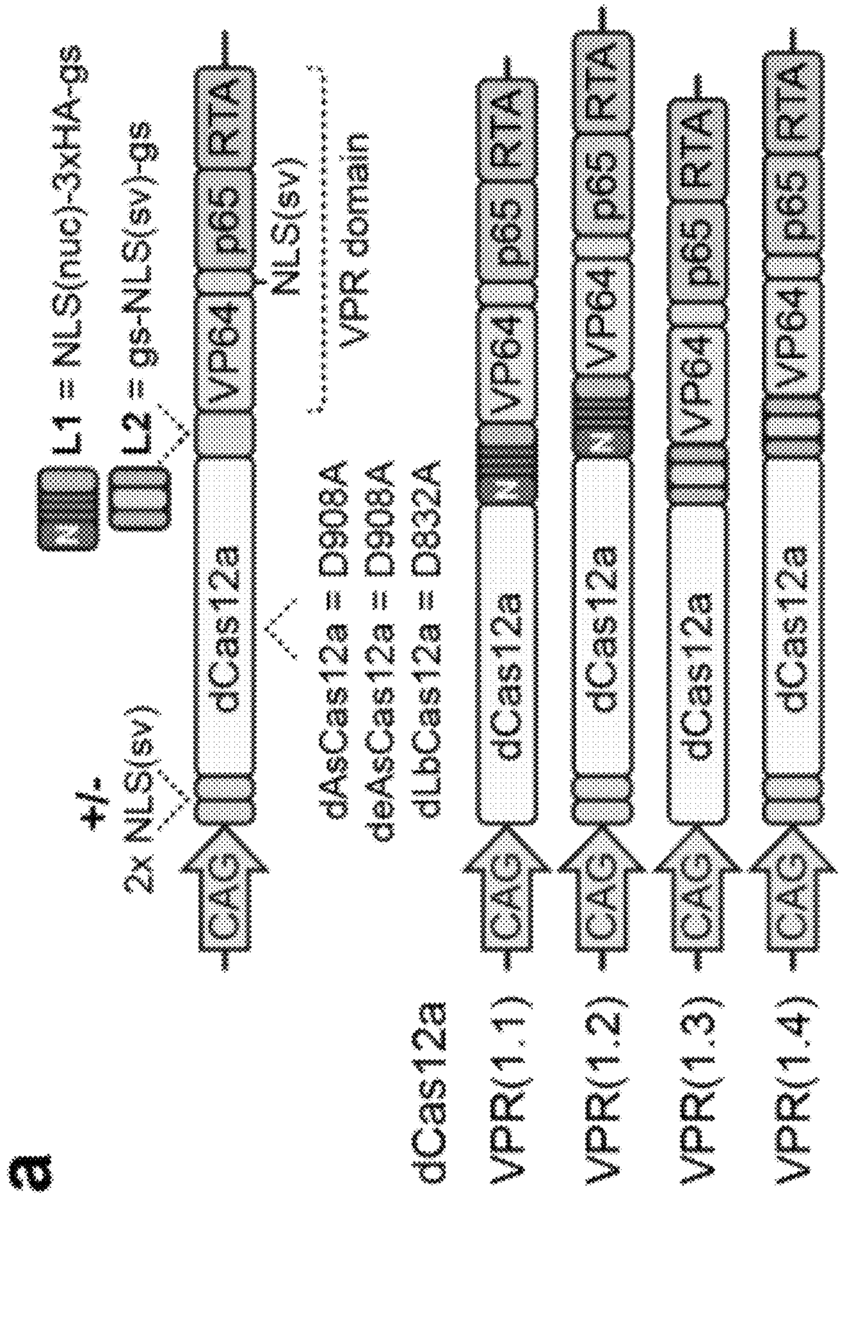
Figure 26E:
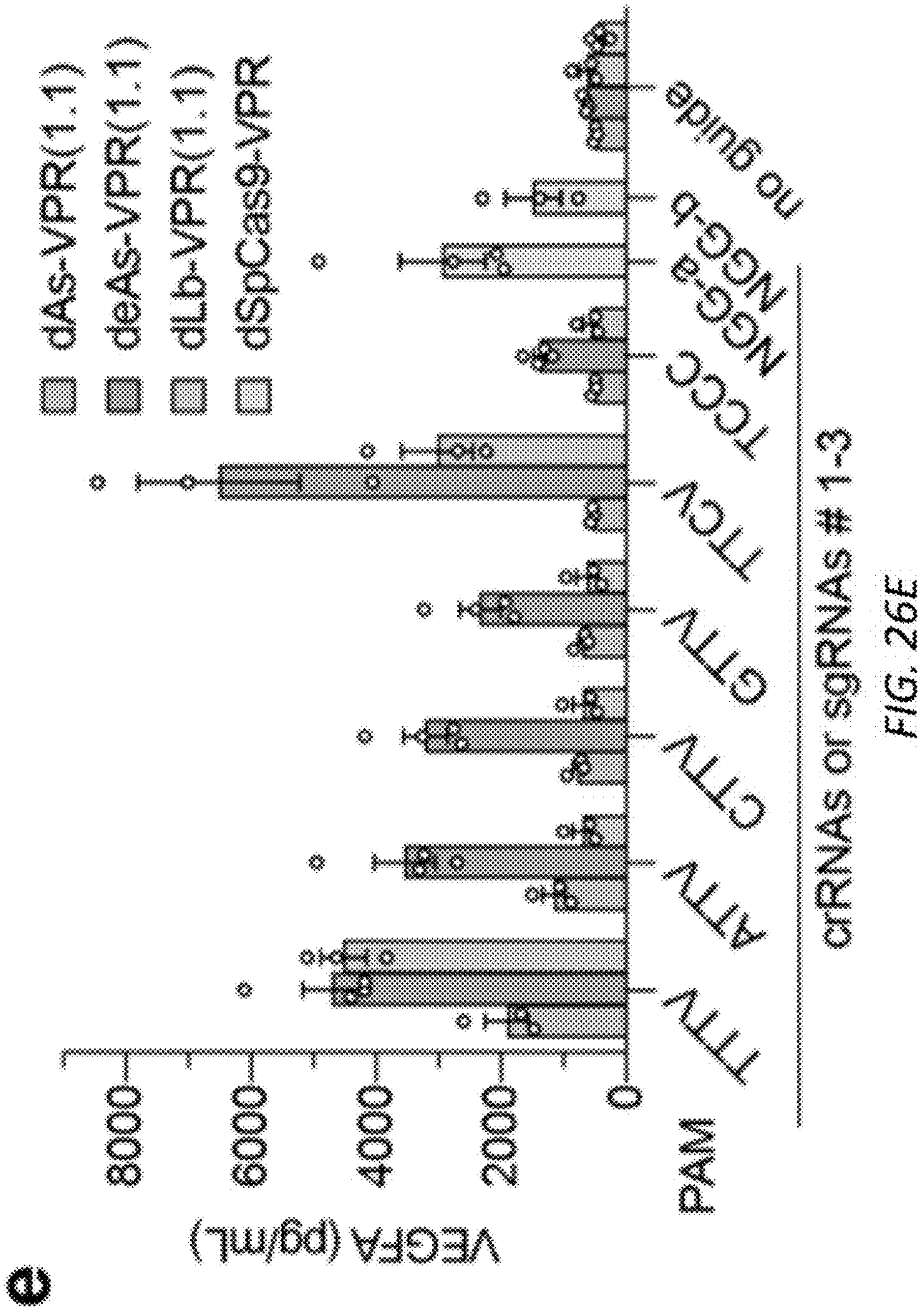
Figure 26F:
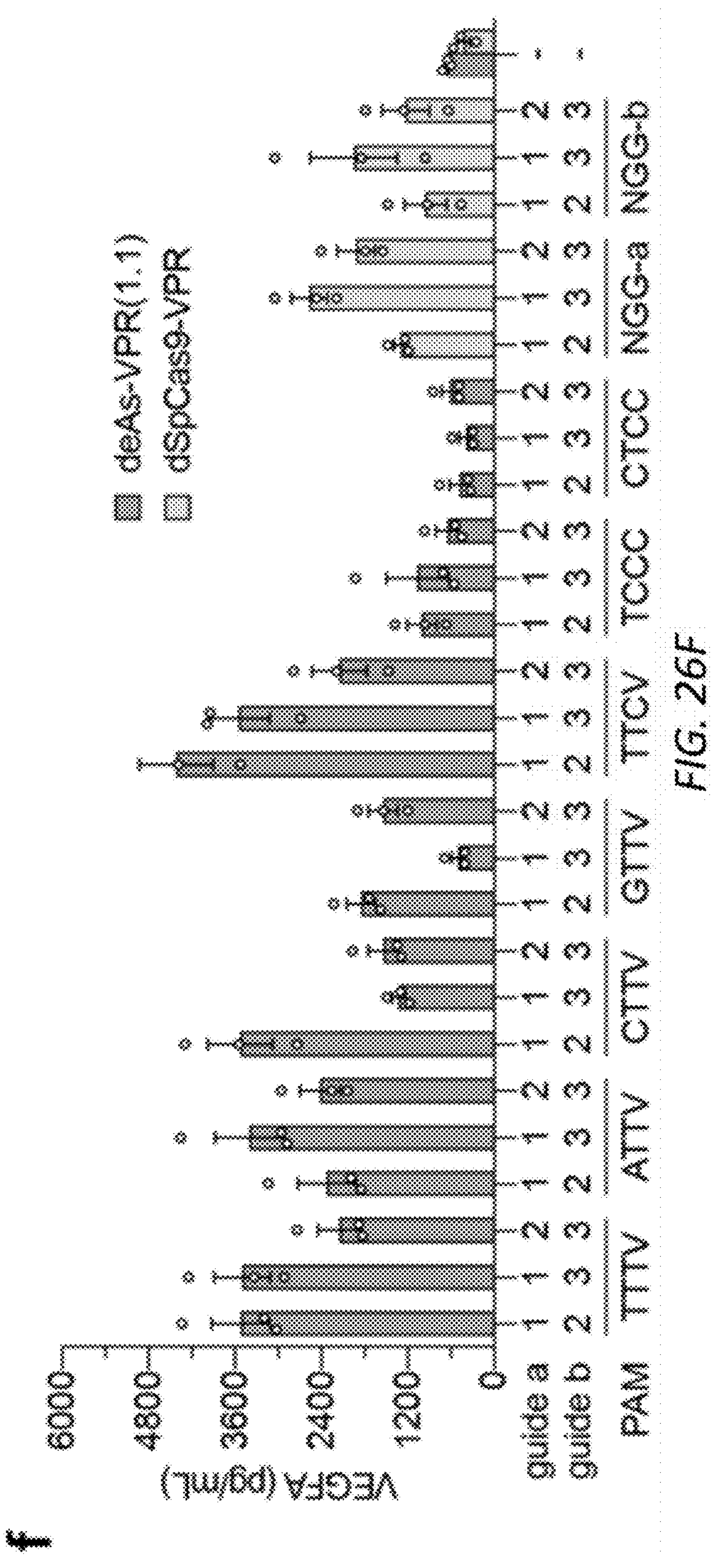

Example 6. Leveraging the Enhanced Properties of eAsCas12a for Gene Activation and Epigenome Editing Applications Another prominent adaptation of CRISPR-Cas12a has been for epigenome editing, where fusions of DNase inactive Cas12a (dCas12a) to heterologous effectors have been shown to modulate gene expression. We previously demonstrated that dLbCas12a fusions to the synthetic VPR transactivation domain (a combination of VP64, p65, and Rta; Chavez et al., Nat Methods., 2015, 12:326-8) mediated more potent gene activation compared to equivalent dAsCas12a fusions in human cells (Tak et al., Nat Methods, 2017, 14:1163-1166). To explore whether eAsCas12a could improve epigenome editing compared to LbCas12a effectors, we first designed and tested different configurations of dAs, deAs, and dLbCas12a fusions to VPR (FIG. 26A). Comparisons of their activities on canonical TTTV and non-canonical TTCV PAM sites proximal to the VEGFA promoter established an optimal dCas12a-VPR fusion architecture (version 1.1; FIGS. 26B-26D, and also revealed that deAs-VPR effectors facilitated greater VEGFA production relative to dAs and dLbCas12a fusions when using crRNAs targeted to canonical or non-canonical sites (FIG. 26E). In experiments comparing deAs-VPR to the prototypical dSpCas9-VPR fusion (targeting separate but nearby sites), we observed comparable or better gene activation with deAs-VPR (FIGS. 26B-C and 26E-F).

Figure 18E:
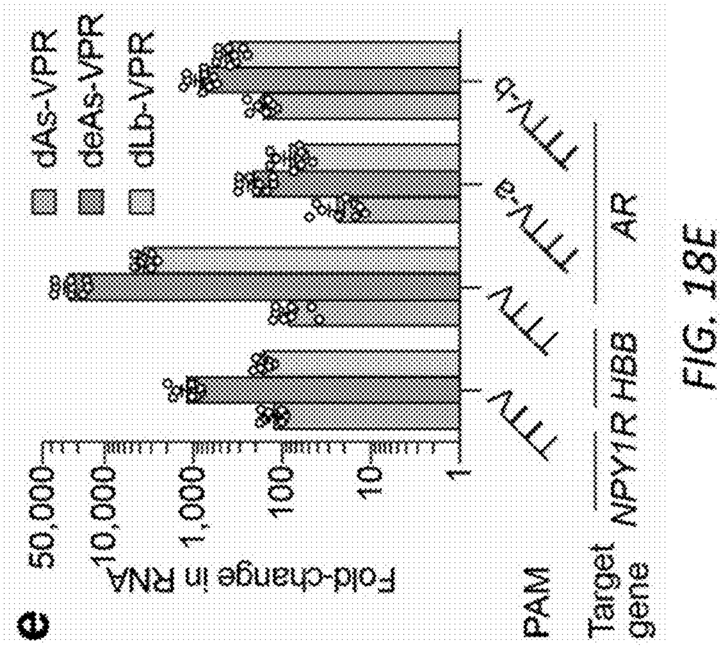

Additional experiments with dAs, deAs, and dLb-VPR fusions targeted to sites in the promoters of three additional endogenous genes (NPYIR, HBB, and AR) once again revealed the most potent gene activation with deAs-VPR when using pools of canonical PAM (FIG. 18E) or non-canonical PAM targeting crRNAs (FIGS. 18F and 18G). The deAs-VPR fusion achieved between 10 to 10,000-fold gene activation, frequently outperforming dAs or dLbCas12a-VPR by more than 10-100 fold.

Collectively, the deAsCas12a fusion to VPR can mediate robust gene activation at equivalent or greater efficiencies compared to published dLbCas12a-VPR fusions when targeted to canonical TTTV PAM sites, and also offers the novel capability to activate genes by targeting non-canonical PAM sites accessible only with this eAsCas12a variant. These results recapitulate the enhanced activity and improved targeting range properties of eAsCas12a, and provide potent and broadly targetable gene-activation technologies that may also be adaptable for other epigenome editing applications.

Example 7. Variants of AsCas12a and LbCas12a for Base Editing Applications

The ability to perform precise single base editing events has recently been demonstrated using engineered SpCas9 base editor (BE) constructs (see, e.g., Komor et al., Nature. 2016 May 19:533(7603):420-4; Nishida et al., Science. 2016 Sep. 16:353(6305); Kim et al., Nat Biotechnol. 2017 April; 35(4):371-376; Komor et al., Sci Adv. 2017 Aug. 30:3(8): eaao4774; and Gaudelli et al., Nature. 2017 Nov. 23:551 (7681):464-471), which exploit the formation of SpCas9-gRNA formed R-loops that cause ssDNA accessibility of the non-target DNA strand. The fusion of heterologous cytidine or adenine deaminase enzymatic domains to SpCas9 can therefore act on the exposed ssDNA strand, leading to the efficient introduction of C to T, or A to G, respectively. Because cellular base-excision repair (BER) employs uracil DNA glycosylase (UDG; also known as uracil N-glycosylase, or UNG) to excise uracil bases, this endogenous process can effectively reverse edits generated by cytidine BEs because the deamination of cytidine leads to a uracil intermediate. Therefore, to improve the efficiency of cytidine BEs, heterologous effector domains such as uracil glycosylase inhibitor (UGI) can also be fused to SpCas9 to inhibit UDG, subverting the initiation of BER and increasing the effectiveness of cytidine BEs.

Figure 18H:
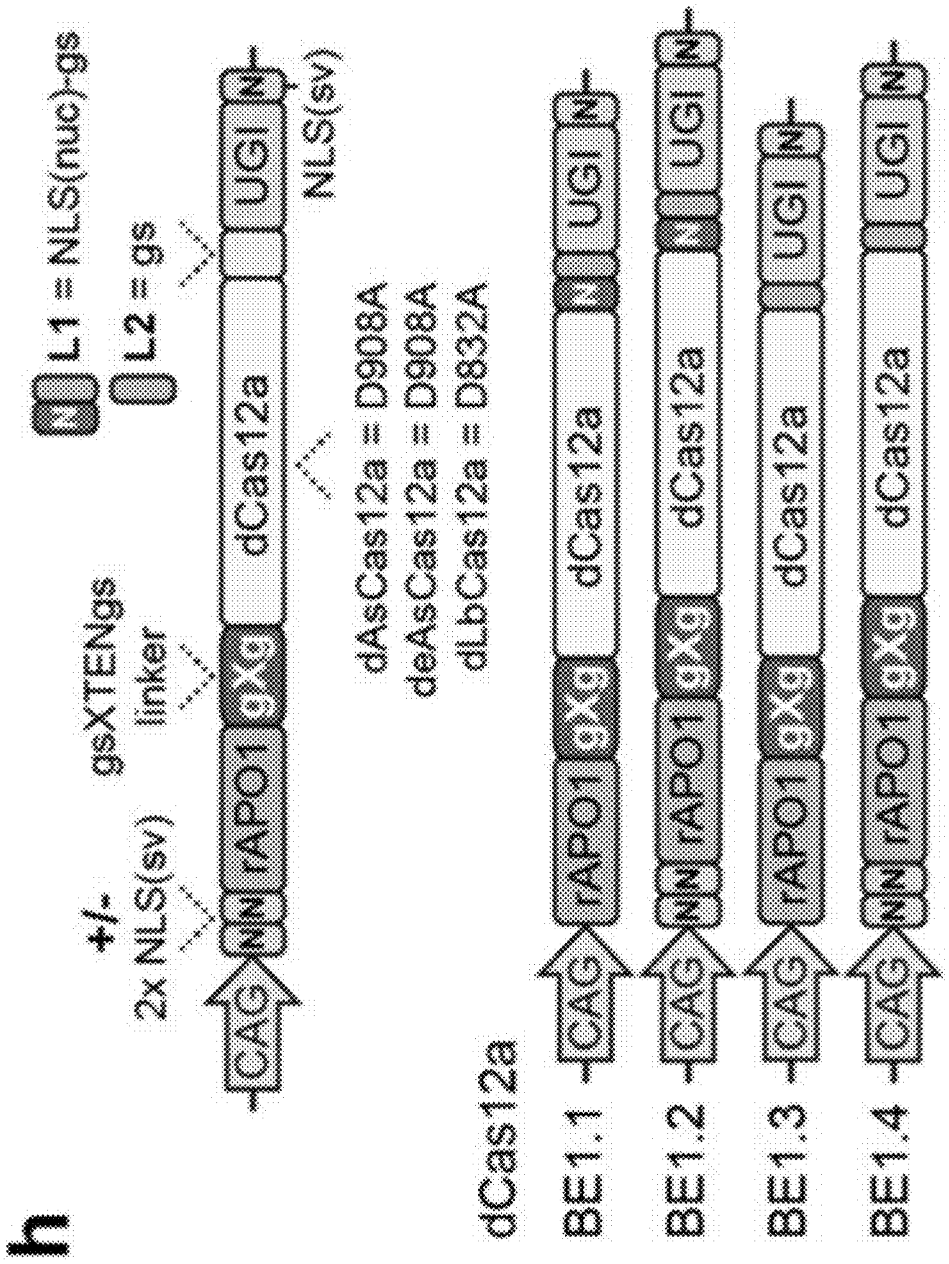
Figure 18I:
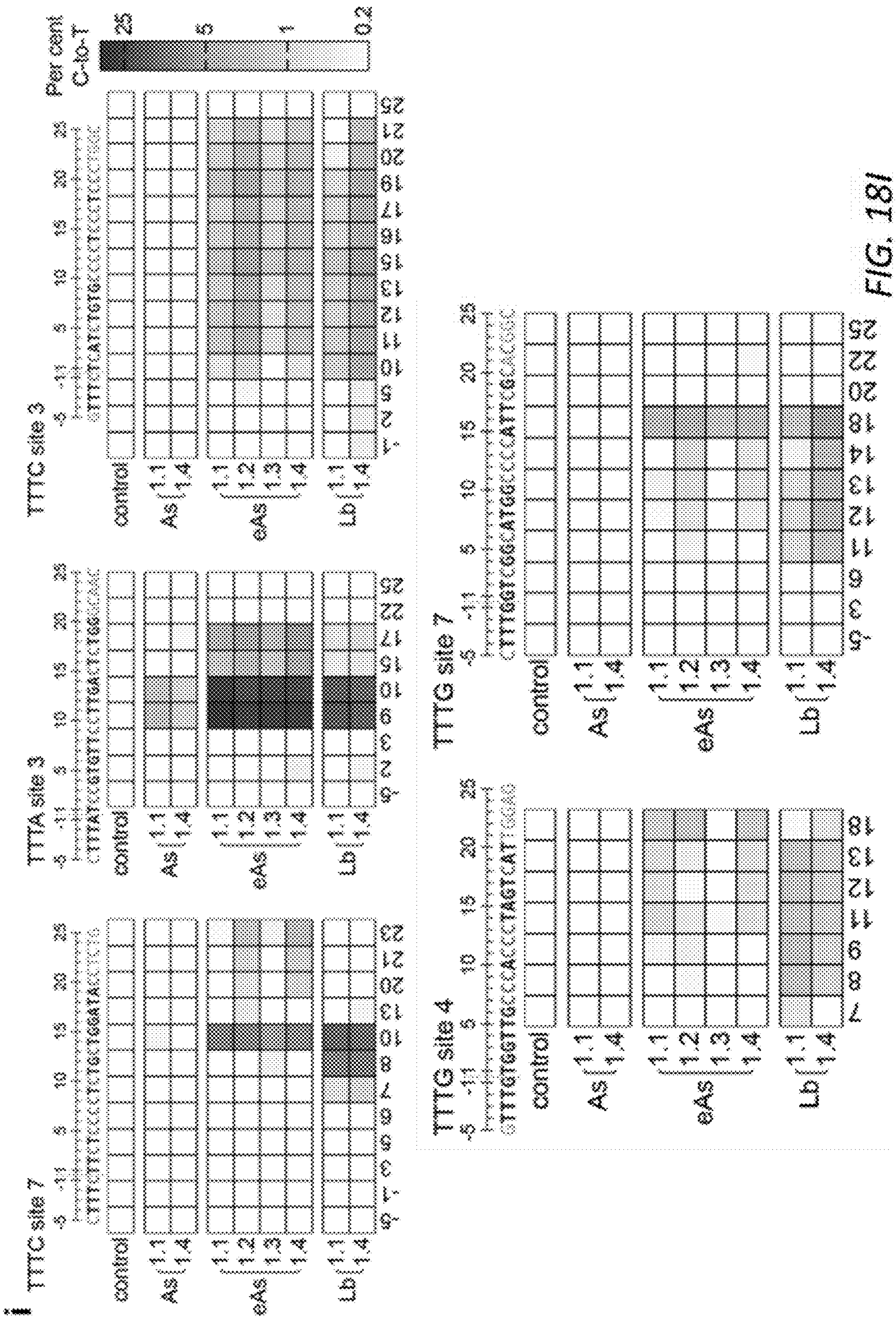
Figure 18I:
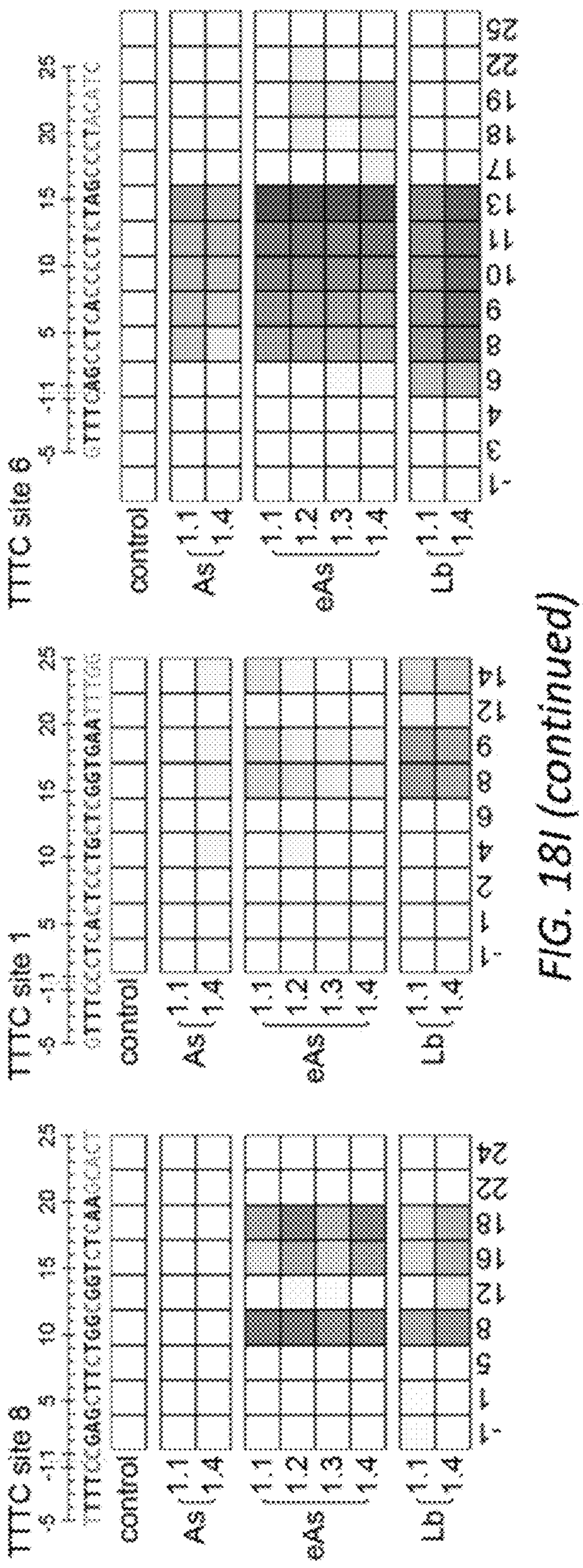
Figure 18J:
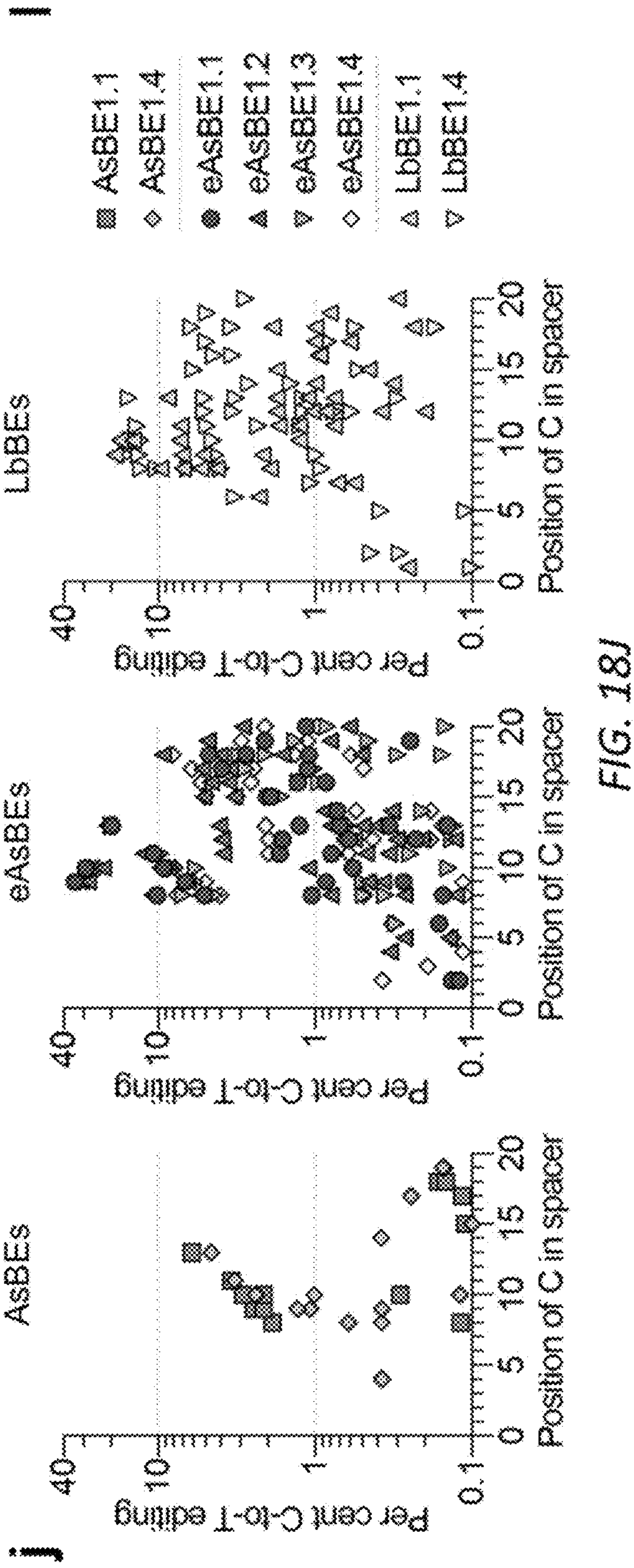
Figure 18K:
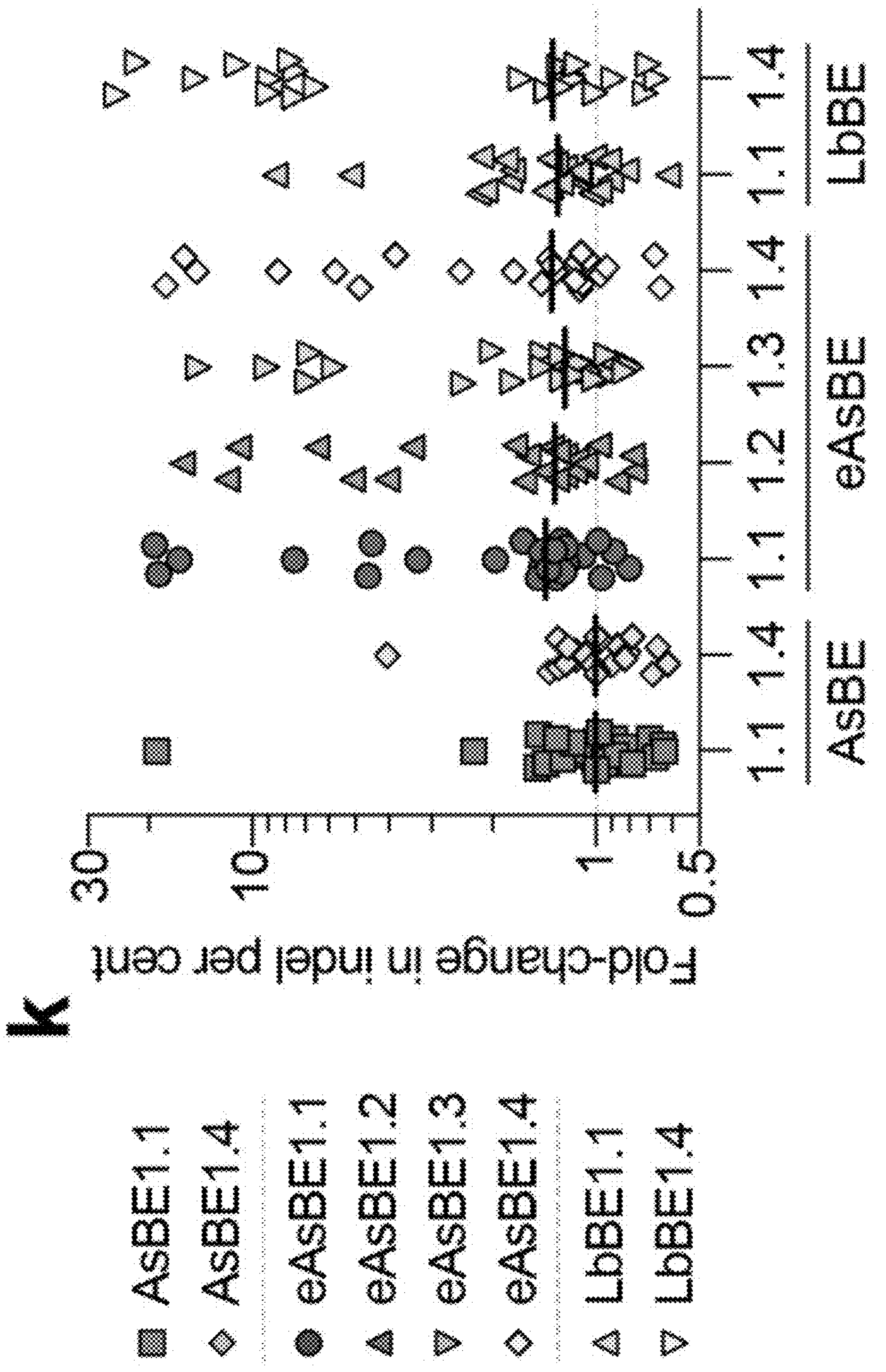
Figure 27A:
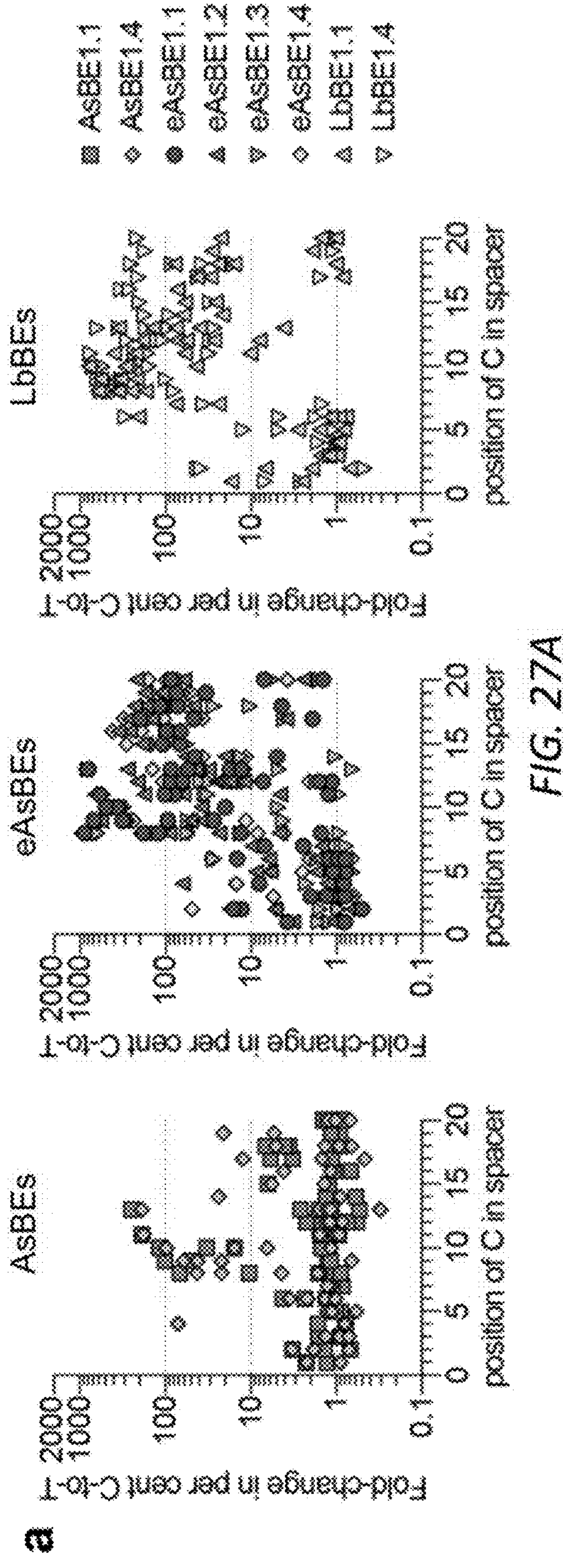
Figure 27B:
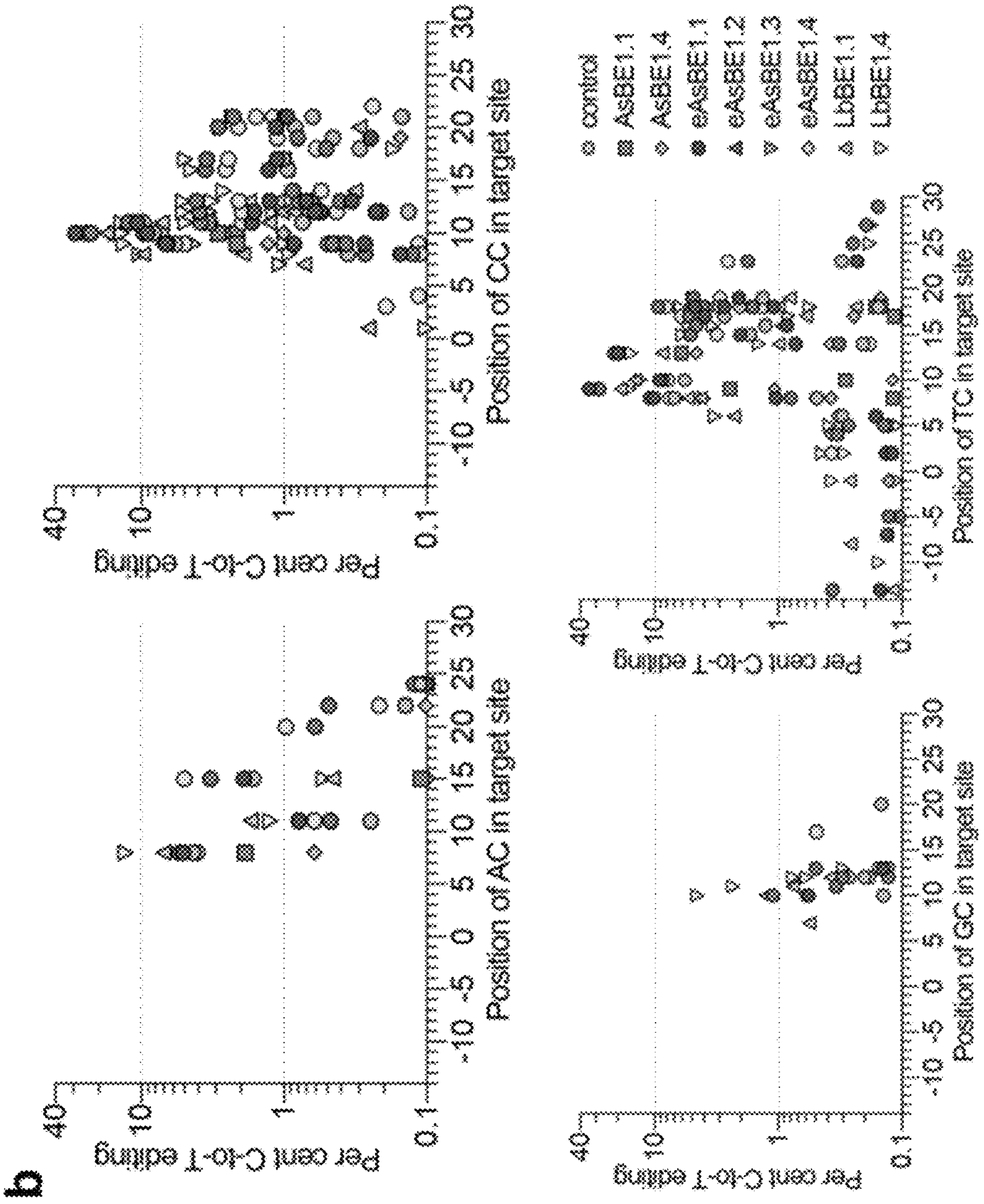
Figure 27C:
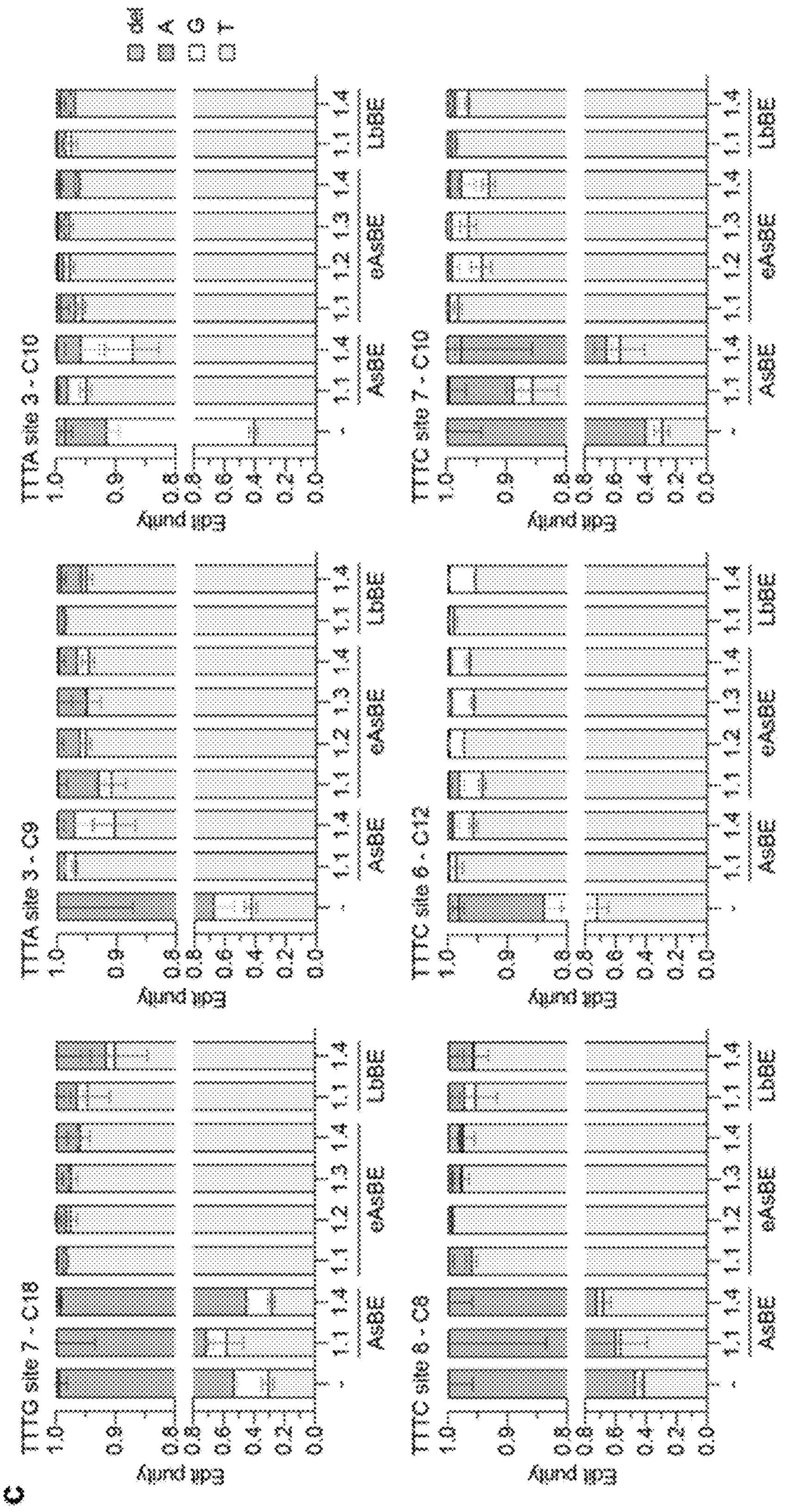
Figure 27D:
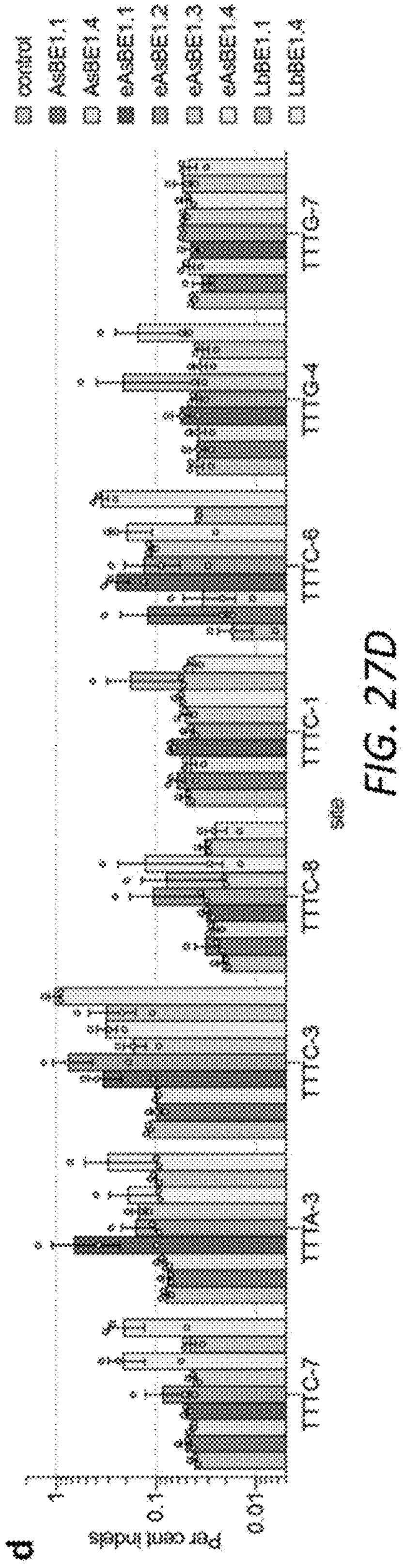

Because our prior observations suggested that eAsCas12a (E174R/S542R/K548R) possesses enhanced activity, we therefore wondered whether eAsCas12a could enable the development of putative AsCas12a base-editors (AsBEs). To test this hypothesis, we cloned four different DNase inactive eAsBE architectures (BE-1.1-1.4; FIG. 18H) that included an N-terminal fusion of rAPOBEC1, a D908A substitution to abrogate nuclease-mediated DNA hydrolysis activity, and a C-terminal fusion of UGI, and compared their activities to wild-type AsBE1.1 and 1.4 using eight different crRNAs. We observed minimal (<1%) C-to-T editing with AsBEs across all Cs for 7 of 8 sites (FIG. 18I). Interestingly, eAsBE fusions demonstrated far greater absolute levels of C-to-T conversion across the same eight sites (range of 2-34% editing; FIGS. 18I and 18J), dramatically improving editing relative to AsBEs (FIG. 27A). Assessment of two equivalent LbBE architectures (range of 2-19% C-to-T editing) revealed comparable levels of C-to-T editing relative to eAsBEs (FIGS. 18I and 18J). For all constructs, editing efficiencies varied by target site and BE architecture (FIG. 18I), and similar to observations with SpCas9BEs the presence of a G 5' of a C appeared to dampen C-to-T editing (FIG. 27B). Desirable edit purities (predominantly C-to-T as the major product) were observed with Cas12a-BEs for positions edited at high efficiencies (FIG. 27C). Low levels of indels were observed for Cas12a-BEs presumably due to the inactivation of their DNase activity (FIG. 18K and FIG. 27D). Taken together, these results demonstrate that the enhanced activities of eAsCas12a enable C-to-T editing at levels previously unachievable with AsBEs and at comparable efficacy to LbBEs, and expand the potential of CRISPR base-editing reagents.

Example 8. Variants of AsCas12a for DNA Detection

An additional recently described application of CRISPR-Cas12a nucleases is based on the observation that Cas12a molecules exhibit target-programmed non-specific DNase activity (Chen et al., Science, 2018, doi: 10.1126/science.aar6245), a property that has been leveraged for the sensitive detection specific DNA molecules in solution(Chen et al., Science, 2018, doi: 10.1126/science.aar6245; Gootenberg et al., Science, 2018, doi: 10.1126/science.aaq0179). When the Cas12a-crRNA complex is bound to a target DNA, the catalytic RuvC DNase active site adopts a hyper-active conformation that indiscriminately digests nearby DNA. A synthetic quenched fluorophore DNA-reporter molecule can be added to the solution, facilitating quantification of Cas12a-DNase activity that liberates the fluorescent reporter (East-Seletsky, Nature, 2016, 538:270-273). Thus, the expanded targeting range and improved activities of eAsCas12a could potentially improve DNA detection methodologies by enhancing sensitivity, facilitating detection of DNA molecules with non-canonical PAMs, or by enabling detection of variant alleles for diagnostic purposes.

Therefore, we sought to compare the collateral trans-DNase activities of wild-type AsCas12a and eAsCas12a to assess the compatibility of our engineered variant with DNA detection workflows. We assembled Cas12-crRNA complexes in vitro and programmed them with activating (matching the reporter molecule) or non-activating (control) DNA substrates prior to the addition of the reporter molecule. We also varied the PAM encoded on the activating DNA substrate to determine whether the expanded targeting range of eAsCas12a recapitulates in this in vitro assay. In experiments with wild-type AsCas12a, we observed robust detection in the presence of the matched substrate encoding a canonical TTTA PAM site, and greatly reduced activity when programmed with a substrate bearing a non-canonical ACCT PAM (FIG. 28A). Next, both eAsCas12a and eAsCas12-HF1 exhibited comparable levels of detection to wild-type AsCas12a on the TTTA PAM substrate (FIG. 28B), but could also robustly detect a non-canonical CTTA PAM substrate (as expected given the expanded the PAM preference profile of eAsCas12a (FIG. 15B). Surprisingly, the eAsCas12a enzyme was also able to detect a DNA substrate bearing a non-targetable ACCT PAM (FIG. 28B), suggesting potential differences in PAM requirements for prototypical target DNA cleavage or for non-specific trans-DNase activities. These results demonstrate that both eAsCas12a and eAsCas12a-HF1 are potent engineered nucleases for DNA detection that offer targeting range and potentially specificity advantages over wild-type AsCas12a.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated CRISPR from *Prevotella* and *Francisella* 1 (Cpf1) protein from Lachnospiraceae bacterium ND2006 (LbCpf1), comprising an amino acid sequence having at least 95% sequence identity to the amino acid sequence of SEQ ID NO:11, with the following mutations:

a) T152R or T152K, and/or b) D156R or D156K, relative to SEQ ID NO:11.

2. The isolated protein of claim 1, further comprising one or more mutations at a position selected from the group consisting of D832, E925, R1138, D1148, D1180, G532, K538, and combinations thereof.

3. The isolated protein of claim 2, where the one or more mutations is selected from the group consisting of D832A, E925A, R1138A, D1148A, D1180A, G532R, K538R, and combinations thereof.

4. The isolated protein of claim 3, comprising the following mutations: D156R, G532R, and K538R.

5. A fusion protein comprising the isolated protein of claim 1, fused to a heterologous functional domain, with an optional intervening linker, wherein the linker does not interfere with activity of the fusion protein.

6. The fusion protein of claim 5, wherein the heterologous functional domain is a transcriptional activation domain.

7. The fusion protein of claim 6, wherein the transcriptional activation domain is VP16, VP64, Rta, NF-κB p65, or a VPR fusion.

8. The fusion protein of claim 5, wherein the heterologous functional domain is a transcriptional silencer or transcriptional repression domain.

9. The fusion protein of claim 8, wherein the transcriptional repression domain is a Krueppel-associated box (KRAB) domain, ERF repressor domain (ERD), or mSin3A interaction domain (SID).

10. The fusion protein of claim 8, wherein the transcriptional silencer is Heterochromatin Protein 1 (HP1).

11. The fusion protein of claim 5, wherein the heterologous functional domain is an enzyme that modifies the methylation state of DNA.

12. The fusion protein of claim 11, wherein the enzyme that modifies the methylation state of DNA is a DNA methyltransferase (DNMT) or a TET protein.

13. The fusion protein of claim 12, wherein the TET protein is TET1.

14. The fusion protein of claim 5, wherein the heterologous functional domain is an enzyme that modifies a histone subunit.

15. The fusion protein of claim 14, wherein the enzyme that modifies a histone subunit is a histone acetyltransferase (HAT), histone deacetylase (HDAC), histone methyltransferase (HMT), or histone demethylase.

16. The fusion protein of claim 5, wherein the heterologous functional domain is a biological tether.

17. The fusion protein of claim 16, wherein the biological tether is MS2, Csy4 or lambda N protein.

18. The fusion protein of claim 5, wherein the heterologous functional domain is FokI.

19. The fusion protein of claim 5, wherein the heterologous functional domain is a deaminase.

20. The fusion protein of claim 19, wherein the deaminase is a cytidine deaminase.

21. The fusion protein of claim 20, wherein the cytidine deaminase is selected from the group consisting of APOBEC1, APOBEC2, APOBEC3A, APOBEC3B, APOBEC3C, APOBEC3D/E, APOBEC3F, APOBEC3G, APOBEC3H, APOBEC4, activation-induced cytidine deaminase (AID), cytosine deaminase 1 (CDA1), CDA2, and cytosine deaminase acting on tRNA (CDAT).

22. The fusion protein of claim 19, wherein deaminase is an adenosine deaminase.

23. The fusion protein of claim 22, wherein the adenosine deaminase is selected from the group consisting of adenosine deaminase 1 (ADA1), ADA2; adenosine deaminase acting on RNA 1 (ADAR1), ADAR2, ADAR3; adenosine deaminase acting on tRNA 1 (ADAT1), ADAT2, ADAT3; and naturally occurring or engineered tRNA-specific adenosine deaminase (TadA).

24. The fusion protein of claim 5, wherein the heterologous functional domain is an enzyme, domain, or peptide that inhibits or enhances endogenous DNA repair or base excision repair (BER) pathways.

25. The fusion protein of claim 24, wherein the enzyme, domain, or peptide that inhibits or enhances endogenous DNA repair or base excision repair (BER) pathways is uracil DNA glycosylase inhibitor (UGI) that inhibits uracil DNA glycosylase (UDG, also known as uracil N-glycosylase, or UNG); or Gam from the bacteriophage Mu.

26. An isolated nucleic acid encoding the protein of claim 1.

27. A vector comprising the isolated nucleic acid of claim 26.

28. The vector of claim 27, wherein the isolated nucleic acid comprises the following mutations:

a) T152R or T152K, and/or b) D156R or D156K, relative to SEQ ID NO: 11.

29. An isolated host cell comprising the nucleic acid of claim 27.

30. The isolated host cell of claim 29, wherein the host cell is a mammalian host cell.

* * * * *

SEQUENCE LISTING

```
<160> NUMBER OF SEQ ID NOS: 586

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: modified_base
<222> LOCATION: (25)..(25)
<223> OTHER INFORMATION: a, c, t, g, unknown or other
<220> FEATURE:
<221> NAME/KEY: misc_feature
<222> LOCATION: (25)..(25)
<223> OTHER INFORMATION: n is a, c, g, or t

<400> SEQUENCE: 1
tttngaccta ccgctcgaat agcgngg 27

<210> SEQ ID NO 2
<211> LENGTH: 1307
<212> TYPE: PRT
<213> ORGANISM: Acidaminococcus sp.

<400> SEQUENCE: 2

Met Thr Gln Phe Glu Gly Phe Thr Asn Leu Tyr Gln Val Ser Lys Thr
1 5 10 15

Leu Arg Phe Glu Leu Ile Pro Gln Gly Lys Thr Leu Lys His Ile Gln
20 25 30

Glu Gln Gly Phe Ile Glu Glu Asp Lys Ala Arg Asn Asp His Tyr Lys
35 40 45

Glu Leu Lys Pro Ile Ile Asp Arg Ile Tyr Lys Thr Tyr Ala Asp Gln
50 55 60

Cys Leu Gln Leu Val Gln Leu Asp Trp Glu Asn Leu Ser Ala Ala Ile
65 70 75 80

Asp Ser Tyr Arg Lys Glu Lys Thr Glu Glu Thr Arg Asn Ala Leu Ile
85 90 95

Glu Glu Gln Ala Thr Tyr Arg Asn Ala Ile His Asp Tyr Phe Ile Gly
100 105 110

Arg Thr Asp Asn Leu Thr Asp Ala Ile Asn Lys Arg His Ala Glu Ile
115 120 125

Tyr Lys Gly Leu Phe Lys Ala Glu Leu Phe Asn Gly Lys Val Leu Lys
130 135 140

Gln Leu Gly Thr Val Thr Thr Thr Glu His Glu Asn Ala Leu Leu Arg
145 150 155 160

Ser Phe Asp Lys Phe Thr Thr Tyr Phe Ser Gly Phe Tyr Glu Asn Arg
165 170 175

Lys Asn Val Phe Ser Ala Glu Asp Ile Ser Thr Ala Ile Pro His Arg
180 185 190

Ile Val Gln Asp Asn Phe Pro Lys Phe Lys Glu Asn Cys His Ile Phe
195 200 205

Thr Arg Leu Ile Thr Ala Val Pro Ser Leu Arg Glu His Phe Glu Asn
210 215 220

Val Lys Lys Ala Ile Gly Ile Phe Val Ser Thr Ser Ile Glu Glu Val
225 230 235 240

Phe Ser Phe Pro Phe Tyr Asn Gln Leu Leu Thr Gln Thr Gln Ile Asp
245 250 255

Leu Tyr Asn Gln Leu Leu Gly Gly Ile Ser Arg Glu Ala Gly Thr Glu
260 265 270

Lys Ile Lys Gly Leu Asn Glu Val Leu Asn Leu Ala Ile Gln Lys Asn

-continued 275 280 285

Asp Glu Thr Ala His Ile Ile Ala Ser Leu Pro His Arg Phe Ile Pro
290 295 300

Leu Phe Lys Gln Ile Leu Ser Asp Arg Asn Thr Leu Ser Phe Ile Leu
305 310 315 320

Glu Glu Phe Lys Ser Asp Glu Glu Val Ile Gln Ser Phe Cys Lys Tyr
325 330 335

Lys Thr Leu Leu Arg Asn Glu Asn Val Leu Glu Thr Ala Glu Ala Leu
340 345 350

Phe Asn Glu Leu Asn Ser Ile Asp Leu Thr His Ile Phe Ile Ser His
355 360 365

Lys Lys Leu Glu Thr Ile Ser Ser Ala Leu Cys Asp His Trp Asp Thr
370 375 380

Leu Arg Asn Ala Leu Tyr Glu Arg Arg Ile Ser Glu Leu Thr Gly Lys
385 390 395 400

Ile Thr Lys Ser Ala Lys Glu Lys Val Gln Arg Ser Leu Lys His Glu
405 410 415

Asp Ile Asn Leu Gln Glu Ile Ile Ser Ala Ala Gly Lys Glu Leu Ser
420 425 430

Glu Ala Phe Lys Gln Lys Thr Ser Glu Ile Leu Ser His Ala His Ala
435 440 445

Ala Leu Asp Gln Pro Leu Pro Thr Thr Leu Lys Lys Gln Glu Glu Lys
450 455 460

Glu Ile Leu Lys Ser Gln Leu Asp Ser Leu Leu Gly Leu Tyr His Leu
465 470 475 480

Leu Asp Trp Phe Ala Val Asp Glu Ser Asn Glu Val Asp Pro Glu Phe
485 490 495

Ser Ala Arg Leu Thr Gly Ile Lys Leu Glu Met Glu Pro Ser Leu Ser
500 505 510

Phe Tyr Asn Lys Ala Arg Asn Tyr Ala Thr Lys Lys Pro Tyr Ser Val
515 520 525

Glu Lys Phe Lys Leu Asn Phe Gln Met Pro Thr Leu Ala Ser Gly Trp
530 535 540

Asp Val Asn Lys Glu Lys Asn Asn Gly Ala Ile Leu Phe Val Lys Asn
545 550 555 560

Gly Leu Tyr Tyr Leu Gly Ile Met Pro Lys Gln Lys Gly Arg Tyr Lys
565 570 575

Ala Leu Ser Phe Glu Pro Thr Glu Lys Thr Ser Glu Gly Phe Asp Lys
580 585 590

Met Tyr Tyr Asp Tyr Phe Pro Asp Ala Ala Lys Met Ile Pro Lys Cys
595 600 605

Ser Thr Gln Leu Lys Ala Val Thr Ala His Phe Gln Thr His Thr Thr
610 615 620

Pro Ile Leu Leu Ser Asn Asn Phe Ile Glu Pro Leu Glu Ile Thr Lys
625 630 635 640

Glu Ile Tyr Asp Leu Asn Asn Pro Glu Lys Glu Pro Lys Lys Phe Gln
645 650 655

Thr Ala Tyr Ala Lys Lys Thr Gly Asp Gln Lys Gly Tyr Arg Glu Ala
660 665 670

Leu Cys Lys Trp Ile Asp Phe Thr Arg Asp Phe Leu Ser Lys Tyr Thr
675 680 685

Lys Thr Thr Ser Ile Asp Leu Ser Ser Leu Arg Pro Ser Ser Gln Tyr
690 695 700

-continued

```
Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys  Ser Lys Arg Thr Gly  Ile Ala Glu
        995                 1000                1005

Lys Ala  Val Tyr Gln Gln Phe  Glu Lys Met Leu Ile  Asp Lys Leu
    1010                1015                1020

Asn Cys  Leu Val Leu Lys Asp  Tyr Pro Ala Glu Lys  Val Gly Gly
    1025                1030                1035

Val Leu  Asn Pro Tyr Gln Leu  Thr Asp Gln Phe Thr  Ser Phe Ala
    1040                1045                1050

Lys Met  Gly Thr Gln Ser Gly  Phe Leu Phe Tyr Val  Pro Ala Pro
    1055                1060                1065

Tyr Thr  Ser Lys Ile Asp Pro  Leu Thr Gly Phe Val  Asp Pro Phe
    1070                1075                1080

Val Trp  Lys Thr Ile Lys Asn  His Glu Ser Arg Lys  His Phe Leu
    1085                1090                1095

Glu Gly  Phe Asp Phe Leu His  Tyr Asp Val Lys Thr  Gly Asp Phe
    1100                1105                1110
```

-continued

Ile Leu His Phe Lys Met Asn Arg Asn Leu Ser Phe Gln Arg Gly
1115 1120 1125

Leu Pro Gly Phe Met Pro Ala Trp Asp Ile Val Phe Glu Lys Asn
1130 1135 1140

Glu Thr Gln Phe Asp Ala Lys Gly Thr Pro Phe Ile Ala Gly Lys
1145 1150 1155

Arg Ile Val Pro Val Ile Glu Asn His Arg Phe Thr Gly Arg Tyr
1160 1165 1170

Arg Asp Leu Tyr Pro Ala Asn Glu Leu Ile Ala Leu Leu Glu Glu
1175 1180 1185

Lys Gly Ile Val Phe Arg Asp Gly Ser Asn Ile Leu Pro Lys Leu
1190 1195 1200

Leu Glu Asn Asp Asp Ser His Ala Ile Asp Thr Met Val Ala Leu
1205 1210 1215

Ile Arg Ser Val Leu Gln Met Arg Asn Ser Asn Ala Ala Thr Gly
1220 1225 1230

Glu Asp Tyr Ile Asn Ser Pro Val Arg Asp Leu Asn Gly Val Cys
1235 1240 1245

Phe Asp Ser Arg Phe Gln Asn Pro Glu Trp Pro Met Asp Ala Asp
1250 1255 1260

Ala Asn Gly Ala Tyr His Ile Ala Leu Lys Gly Gln Leu Leu Leu
1265 1270 1275

Asn His Leu Lys Glu Ser Lys Asp Leu Lys Leu Gln Asn Gly Ile
1280 1285 1290

Ser Asn Gln Asp Trp Leu Ala Tyr Ile Gln Glu Leu Arg Asn
1295 1300 1305

<210> SEQ ID NO 3
<211> LENGTH: 1246
<212> TYPE: PRT
<213> ORGANISM: Unknown
<220> FEATURE:
<223> OTHER INFORMATION: Lachnospiraceae bacterium

<400> SEQUENCE: 3

Met Leu Lys Asn Val Gly Ile Asp Arg Leu Asp Val Glu Lys Gly Arg
1 5 10 15

Lys Asn Met Ser Lys Leu Glu Lys Phe Thr Asn Cys Tyr Ser Leu Ser
20 25 30

Lys Thr Leu Arg Phe Lys Ala Ile Pro Val Gly Lys Thr Gln Glu Asn
35 40 45

Ile Asp Asn Lys Arg Leu Leu Val Glu Asp Glu Lys Arg Ala Glu Asp
50 55 60

Tyr Lys Gly Val Lys Lys Leu Leu Asp Arg Tyr Tyr Leu Ser Phe Ile
65 70 75 80

Asn Asp Val Leu His Ser Ile Lys Leu Lys Asn Leu Asn Asn Tyr Ile
85 90 95

Ser Leu Phe Arg Lys Lys Thr Arg Thr Glu Lys Glu Asn Lys Glu Leu
100 105 110

Glu Asn Leu Glu Ile Asn Leu Arg Lys Glu Ile Ala Lys Ala Phe Lys
115 120 125

Gly Asn Glu Gly Tyr Lys Ser Leu Phe Lys Lys Asp Ile Ile Glu Thr
130 135 140

Ile Leu Pro Glu Phe Leu Asp Asp Lys Asp Glu Ile Ala Leu Val Asn
145 150 155 160

```
Ser Phe Asn Gly Phe Thr Thr Ala Phe Thr Gly Phe Phe Asp Asn Arg
                165                 170                 175

Glu Asn Met Phe Ser Glu Glu Ala Lys Ser Thr Ser Ile Ala Phe Arg
            180                 185                 190

Cys Ile Asn Glu Asn Leu Thr Arg Tyr Ile Ser Asn Met Asp Ile Phe
        195                 200                 205

Glu Lys Val Asp Ala Ile Phe Asp Lys His Glu Val Gln Glu Ile Lys
    210                 215                 220

Glu Lys Ile Leu Asn Ser Asp Tyr Asp Val Glu Asp Phe Phe Glu Gly
225                 230                 235                 240

Glu Phe Phe Asn Phe Val Leu Thr Gln Glu Gly Ile Asp Val Tyr Asn
                245                 250                 255

Ala Ile Ile Gly Gly Phe Val Thr Glu Ser Gly Glu Lys Ile Lys Gly
            260                 265                 270

Leu Asn Glu Tyr Ile Asn Leu Tyr Asn Gln Lys Thr Lys Gln Lys Leu
        275                 280                 285

Pro Lys Phe Lys Pro Leu Tyr Lys Gln Val Leu Ser Asp Arg Glu Ser
    290                 295                 300

Leu Ser Phe Tyr Gly Glu Gly Tyr Thr Ser Asp Glu Glu Val Leu Glu
305                 310                 315                 320

Val Phe Arg Asn Thr Leu Asn Lys Asn Ser Glu Ile Phe Ser Ser Ile
                325                 330                 335

Lys Lys Leu Glu Lys Leu Phe Lys Asn Phe Asp Glu Tyr Ser Ser Ala
            340                 345                 350

Gly Ile Phe Val Lys Asn Gly Pro Ala Ile Ser Thr Ile Ser Lys Asp
        355                 360                 365

Ile Phe Gly Glu Trp Asn Val Ile Arg Asp Lys Trp Asn Ala Glu Tyr
    370                 375                 380

Asp Asp Ile His Leu Lys Lys Lys Ala Val Val Thr Glu Lys Tyr Glu
385                 390                 395                 400

Asp Asp Arg Arg Lys Ser Phe Lys Lys Ile Gly Ser Phe Ser Leu Glu
                405                 410                 415

Gln Leu Gln Glu Tyr Ala Asp Ala Asp Leu Ser Val Val Glu Lys Leu
            420                 425                 430

Lys Glu Ile Ile Ile Gln Lys Val Asp Glu Ile Tyr Lys Val Tyr Gly
        435                 440                 445

Ser Ser Glu Lys Leu Phe Asp Ala Asp Phe Val Leu Glu Lys Ser Leu
    450                 455                 460

Lys Lys Asn Asp Ala Val Val Ala Ile Met Lys Asp Leu Leu Asp Ser
465                 470                 475                 480

Val Lys Ser Phe Glu Asn Tyr Ile Lys Ala Phe Phe Gly Glu Gly Lys
                485                 490                 495

Glu Thr Asn Arg Asp Glu Ser Phe Tyr Gly Asp Phe Val Leu Ala Tyr
            500                 505                 510

Asp Ile Leu Leu Lys Val Asp His Ile Tyr Asp Ala Ile Arg Asn Tyr
        515                 520                 525

Val Thr Gln Lys Pro Tyr Ser Lys Asp Lys Phe Lys Leu Tyr Phe Gln
    530                 535                 540

Asn Pro Gln Phe Met Gly Gly Trp Asp Lys Asp Lys Glu Thr Asp Tyr
545                 550                 555                 560

Arg Ala Thr Ile Leu Arg Tyr Gly Ser Lys Tyr Tyr Leu Ala Ile Met
                565                 570                 575

Asp Lys Lys Tyr Ala Lys Cys Leu Gln Lys Ile Asp Lys Asp Asp Val
```

-continued

```
            580                 585                 590

Asn Gly Asn Tyr Glu Lys Ile Asn Tyr Lys Leu Leu Pro Gly Pro Asn
        595                 600                 605

Lys Met Leu Pro Lys Val Phe Phe Ser Lys Lys Trp Met Ala Tyr Tyr
    610                 615                 620

Asn Pro Ser Glu Asp Ile Gln Lys Ile Tyr Lys Asn Gly Thr Phe Lys
625                 630                 635                 640

Lys Gly Asp Met Phe Asn Leu Asn Asp Cys His Lys Leu Ile Asp Phe
                645                 650                 655

Phe Lys Asp Ser Ile Ser Arg Tyr Pro Lys Trp Ser Asn Ala Tyr Asp
            660                 665                 670

Phe Asn Phe Ser Glu Thr Glu Lys Tyr Lys Asp Ile Ala Gly Phe Tyr
        675                 680                 685

Arg Glu Val Glu Glu Gln Gly Tyr Lys Val Ser Phe Glu Ser Ala Ser
    690                 695                 700

Lys Lys Glu Val Asp Lys Leu Val Glu Glu Gly Lys Leu Tyr Met Phe
705                 710                 715                 720

Gln Ile Tyr Asn Lys Asp Phe Ser Asp Lys Ser His Gly Thr Pro Asn
                725                 730                 735

Leu His Thr Met Tyr Phe Lys Leu Leu Phe Asp Glu Asn Asn His Gly
            740                 745                 750

Gln Ile Arg Leu Ser Gly Gly Ala Glu Leu Phe Met Arg Arg Ala Ser
        755                 760                 765

Leu Lys Lys Glu Glu Leu Val Val His Pro Ala Asn Ser Pro Ile Ala
    770                 775                 780

Asn Lys Asn Pro Asp Asn Pro Lys Lys Thr Thr Thr Leu Ser Tyr Asp
785                 790                 795                 800

Val Tyr Lys Asp Lys Arg Phe Ser Glu Asp Gln Tyr Glu Leu His Ile
                805                 810                 815

Pro Ile Ala Ile Asn Lys Cys Pro Lys Asn Ile Phe Lys Ile Asn Thr
            820                 825                 830

Glu Val Arg Val Leu Leu Lys His Asp Asp Asn Pro Tyr Val Ile Gly
        835                 840                 845

Ile Asp Arg Gly Glu Arg Asn Leu Leu Tyr Ile Val Val Val Asp Gly
    850                 855                 860

Lys Gly Asn Ile Val Glu Gln Tyr Ser Leu Asn Glu Ile Ile Asn Asn
865                 870                 875                 880

Phe Asn Gly Ile Arg Ile Lys Thr Asp Tyr His Ser Leu Leu Asp Lys
                885                 890                 895

Lys Glu Lys Glu Arg Phe Glu Ala Arg Gln Asn Trp Thr Ser Ile Glu
            900                 905                 910

Asn Ile Lys Glu Leu Lys Ala Gly Tyr Ile Ser Gln Val Val His Lys
        915                 920                 925

Ile Cys Glu Leu Val Glu Lys Tyr Asp Ala Val Ile Ala Leu Glu Asp
    930                 935                 940

Leu Asn Ser Gly Phe Lys Asn Ser Arg Val Lys Val Glu Lys Gln Val
945                 950                 955                 960

Tyr Gln Lys Phe Glu Lys Met Leu Ile Asp Lys Leu Asn Tyr Met Val
                965                 970                 975

Asp Lys Lys Ser Asn Pro Cys Ala Thr Gly Gly Ala Leu Lys Gly Tyr
            980                 985                 990

Gln Ile Thr Asn Lys Phe Glu Ser  Phe Lys Ser Met Ser  Thr Gln Asn
        995                 1000                1005
```

```
Gly Phe  Ile Phe Tyr Ile Pro  Ala Trp Leu Thr Ser  Lys Ile Asp
    1010                 1015                 1020

Pro Ser  Thr Gly Phe Val Asn  Leu Leu Lys Thr Lys  Tyr Thr Ser
    1025                 1030                 1035

Ile Ala  Asp Ser Lys Lys Phe  Ile Ser Ser Phe Asp  Arg Ile Met
    1040                 1045                 1050

Tyr Val  Pro Glu Glu Asp Leu  Phe Glu Phe Ala Leu  Asp Tyr Lys
    1055                 1060                 1065

Asn Phe  Ser Arg Thr Asp Ala  Asp Tyr Ile Lys Lys  Trp Lys Leu
    1070                 1075                 1080

Tyr Ser  Tyr Gly Asn Arg Ile  Arg Ile Phe Arg Asn  Pro Lys Lys
    1085                 1090                 1095

Asn Asn  Val Phe Asp Trp Glu  Glu Val Cys Leu Thr  Ser Ala Tyr
    1100                 1105                 1110

Lys Glu  Leu Phe Asn Lys Tyr  Gly Ile Asn Tyr Gln  Gln Gly Asp
    1115                 1120                 1125

Ile Arg  Ala Leu Leu Cys Glu  Gln Ser Asp Lys Ala  Phe Tyr Ser
    1130                 1135                 1140

Ser Phe  Met Ala Leu Met Ser  Leu Met Leu Gln Met  Arg Asn Ser
    1145                 1150                 1155

Ile Thr  Gly Arg Thr Asp Val  Asp Phe Leu Ile Ser  Pro Val Lys
    1160                 1165                 1170

Asn Ser  Asp Gly Ile Phe Tyr  Asp Ser Arg Asn Tyr  Glu Ala Gln
    1175                 1180                 1185

Glu Asn  Ala Ile Leu Pro Lys  Asn Ala Asp Ala Asn  Gly Ala Tyr
    1190                 1195                 1200

Asn Ile  Ala Arg Lys Val Leu  Trp Ala Ile Gly Gln  Phe Lys Lys
    1205                 1210                 1215

Ala Glu  Asp Glu Lys Leu Asp  Lys Val Lys Ile Ala  Ile Ser Asn
    1220                 1225                 1230

Lys Glu  Trp Leu Glu Tyr Ala  Gln Thr Ser Val Lys  His
    1235                 1240                 1245


<210> SEQ ID NO 4
<211> LENGTH: 1300
<212> TYPE: PRT
<213> ORGANISM: Francisella tularensis

<400> SEQUENCE: 4

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
```

-continued

```
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
        515                 520                 525

Leu Leu Asp Gln Thr Asn Asn Leu Leu His Lys Leu Lys Ile Phe His
    530                 535                 540
```

Ile Ser Gln Ser Glu Asp Lys Ala Asn Ile Leu Asp Lys Asp Glu His
545 550 555 560

Phe Tyr Leu Val Phe Glu Glu Cys Tyr Phe Glu Leu Ala Asn Ile Val
565 570 575

Pro Leu Tyr Asn Lys Ile Arg Asn Tyr Ile Thr Gln Lys Pro Tyr Ser
580 585 590

Asp Glu Lys Phe Lys Leu Asn Phe Glu Asn Ser Thr Leu Ala Asn Gly
595 600 605

Trp Asp Lys Asn Lys Glu Pro Asp Asn Thr Ala Ile Leu Phe Ile Lys
610 615 620

Asp Asp Lys Tyr Tyr Leu Gly Val Met Asn Lys Lys Asn Asn Lys Ile
625 630 635 640

Phe Asp Asp Lys Ala Ile Lys Glu Asn Lys Gly Glu Gly Tyr Lys Lys
645 650 655

Ile Val Tyr Lys Leu Leu Pro Gly Ala Asn Lys Met Leu Pro Lys Val
660 665 670

Phe Phe Ser Ala Lys Ser Ile Lys Phe Tyr Asn Pro Ser Glu Asp Ile
675 680 685

Leu Arg Ile Arg Asn His Ser Thr His Thr Lys Asn Gly Ser Pro Gln
690 695 700

Lys Gly Tyr Glu Lys Phe Glu Phe Asn Ile Glu Asp Cys Arg Lys Phe
705 710 715 720

Ile Asp Phe Tyr Lys Gln Ser Ile Ser Lys His Pro Glu Trp Lys Asp
725 730 735

Phe Gly Phe Arg Phe Ser Asp Thr Gln Arg Tyr Asn Ser Ile Asp Glu
740 745 750

Phe Tyr Arg Glu Val Glu Asn Gln Gly Tyr Lys Leu Thr Phe Glu Asn
755 760 765

Ile Ser Glu Ser Tyr Ile Asp Ser Val Val Asn Gln Gly Lys Leu Tyr
770 775 780

Leu Phe Gln Ile Tyr Asn Lys Asp Phe Ser Ala Tyr Ser Lys Gly Arg
785 790 795 800

Pro Asn Leu His Thr Leu Tyr Trp Lys Ala Leu Phe Asp Glu Arg Asn
805 810 815

Leu Gln Asp Val Val Tyr Lys Leu Asn Gly Glu Ala Glu Leu Phe Tyr
820 825 830

Arg Lys Gln Ser Ile Pro Lys Lys Ile Thr His Pro Ala Lys Glu Ala
835 840 845

Ile Ala Asn Lys Asn Lys Asp Asn Pro Lys Lys Glu Ser Val Phe Glu
850 855 860

Tyr Asp Leu Ile Lys Asp Lys Arg Phe Thr Glu Asp Lys Phe Phe Phe
865 870 875 880

His Cys Pro Ile Thr Ile Asn Phe Lys Ser Ser Gly Ala Asn Lys Phe
885 890 895

Asn Asp Glu Ile Asn Leu Leu Leu Lys Glu Lys Ala Asn Asp Val His
900 905 910

Ile Leu Ser Ile Asp Arg Gly Glu Arg His Leu Ala Tyr Tyr Thr Leu
915 920 925

Val Asp Gly Lys Gly Asn Ile Ile Lys Gln Asp Thr Phe Asn Ile Ile
930 935 940

Gly Asn Asp Arg Met Lys Thr Asn Tyr His Asp Lys Leu Ala Ala Ile
945 950 955 960

-continued

```
Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn  Ala Ile Val Val Phe  Glu Asp Leu
        995                 1000                 1005

Asn Phe  Gly Phe Lys Arg Gly  Arg Phe Lys Val Glu  Lys Gln Val
    1010                 1015                 1020

Tyr Gln  Lys Leu Glu Lys Met  Leu Ile Glu Lys Leu  Asn Tyr Leu
    1025                 1030                 1035

Val Phe  Lys Asp Asn Glu Phe  Asp Lys Thr Gly Gly  Val Leu Arg
    1040                 1045                 1050

Ala Tyr  Gln Leu Thr Ala Pro  Phe Glu Thr Phe Lys  Lys Met Gly
    1055                 1060                 1065

Lys Gln  Thr Gly Ile Ile Tyr  Tyr Val Pro Ala Gly  Phe Thr Ser
    1070                 1075                 1080

Lys Ile  Cys Pro Val Thr Gly  Phe Val Asn Gln Leu  Tyr Pro Lys
    1085                 1090                 1095

Tyr Glu  Ser Val Ser Lys Ser  Gln Glu Phe Phe Ser  Lys Phe Asp
    1100                 1105                 1110

Lys Ile  Cys Tyr Asn Leu Asp  Lys Gly Tyr Phe Glu  Phe Ser Phe
    1115                 1120                 1125

Asp Tyr  Lys Asn Phe Gly Asp  Lys Ala Ala Lys Gly  Lys Trp Thr
    1130                 1135                 1140

Ile Ala  Ser Phe Gly Ser Arg  Leu Ile Asn Phe Arg  Asn Ser Asp
    1145                 1150                 1155

Lys Asn  His Asn Trp Asp Thr  Arg Glu Val Tyr Pro  Thr Lys Glu
    1160                 1165                 1170

Leu Glu  Lys Leu Leu Lys Asp  Tyr Ser Ile Glu Tyr  Gly His Gly
    1175                 1180                 1185

Glu Cys  Ile Lys Ala Ala Ile  Cys Gly Glu Ser Asp  Lys Lys Phe
    1190                 1195                 1200

Phe Ala  Lys Leu Thr Ser Val  Leu Asn Thr Ile Leu  Gln Met Arg
    1205                 1210                 1215

Asn Ser  Lys Thr Gly Thr Glu  Leu Asp Tyr Leu Ile  Ser Pro Val
    1220                 1225                 1230

Ala Asp  Val Asn Gly Asn Phe  Phe Asp Ser Arg Gln  Ala Pro Lys
    1235                 1240                 1245

Asn Met  Pro Gln Asp Ala Asp  Ala Asn Gly Ala Tyr  His Ile Gly
    1250                 1255                 1260

Leu Lys  Gly Leu Met Leu Leu  Gly Arg Ile Lys Asn  Asn Gln Glu
    1265                 1270                 1275

Gly Lys  Lys Leu Asn Leu Val  Ile Lys Asn Glu Glu  Tyr Phe Glu
    1280                 1285                 1290

Phe Val  Gln Asn Arg Asn Asn
    1295                 1300
```

<210> SEQ ID NO 5
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

-continued tacccatacg atgttccaga ttacgcttat ccctacgacg tgcctgatta tgcataccca 60
tatgatgtcc ccgactatgc c 81

<210> SEQ ID NO 6
<211> LENGTH: 4059
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 6
atgacacagt tcgagggctt taccaacctg tatcaggtga gcaagacact gcggtttgag 60
ctgatcccac agggcaagac cctgaagcac atccaggagc agggcttcat cgaggaggac 120
aaggcccgca atgatcacta caaggagctg aagcccatca tcgatcggat ctacaagacc 180
tatgccgacc agtgcctgca gctggtgcag ctggattggg agaacctgag cgccgccatc 240
gactcctata gaaaggagaa aaccgaggag acaaggaacg ccctgatcga ggagcaggcc 300
acatatcgca atgccatcca cgactacttc atcggccgga cagacaacct gaccgatgcc 360
atcaataaga gacacgccga gatctacaag ggcctgttca aggccgagct gtttaatggc 420
aaggtgctga agcagctggg caccgtgacc acaaccgagc acgagaacgc cctgctgcgg 480
agcttcgaca agtttacaac ctacttctcc ggcttttatg agaacaggaa gaacgtgttc 540
agcgccgagg atatcagcac agccatccca caccgcatcg tgcaggacaa cttccccaag 600
tttaaggaga attgtcacat cttcacacgc ctgatcaccg ccgtgcccag cctgcgggag 660
cactttgaga acgtgaagaa ggccatcggc atcttcgtga gcacctccat cgaggaggtg 720
ttttccttcc ctttttataa ccagctgctg acacagaccc agatcgacct gtataaccag 780
ctgctgggag gaatctctcg ggaggcaggc accgagaaga tcaagggcct gaacgaggtg 840
ctgaatctgg ccatccagaa gaatgatgag acagcccaca tcatcgcctc cctgccacac 900
agattcatcc ccctgtttaa gcagatcctg tccgatagga acaccctgtc tttcatcctg 960
gaggagttta agagcgacga ggaagtgatc cagtccttct gcaagtacaa gacactgctg 1020
agaaacgaga acgtgctgga gacagccgag gccctgttta acgagctgaa cagcatcgac 1080
ctgacacaca tcttcatcag ccacaagaag ctggagacaa tcagcagcgc cctgtgcgac 1140
cactgggata cactgaggaa tgccctgtat gagcggagaa tctccgagct gacaggcaag 1200
atcaccaagt ctgccaagga gaaggtgcag cgcagcctga agcacgagga tatcaacctg 1260
caggagatca tctctgccgc aggcaaggag ctgagcgagg ccttcaagca gaaaaccagc 1320
gagatcctgt cccacgcaca cgccgccctg gatcagccac tgcctacaac cctgaagaag 1380
caggaggaga aggagatcct gaagtctcag ctggacagcc tgctgggcct gtaccacctg 1440
ctggactggt ttgccgtgga tgagtccaac gaggtggacc ccgagttctc tgcccggctg 1500
accggcatca agctggagat ggagccttct ctgagcttct acaacaaggc cagaaattat 1560
gccaccaaga agccctactc cgtggagaag ttcaagctga actttcagat gcctacactg 1620
gcctctggct gggacgtgaa taaggagaag aacaatggcg ccatcctgtt tgtgaagaac 1680
ggcctgtact atctgggcat catgccaaag cagaagggca ggtataaggc cctgagcttc 1740
gagcccacag agaaaaccag cgagggcttt gataagatgt actatgacta cttccctgat 1800
gccgccaaga tgatcccaaa gtgcagcacc cagctgaagg ccgtgacagc ccactttcag 1860
acccacacaa cccccatcct gctgtccaac aatttcatcg agcctctgga gatcacaaag 1920

-continued

```
gagatctacg acctgaacaa tcctgagaag gagccaaaga agtttcagac agcctacgcc   1980
aagaaaaccg gcgaccagaa gggctacaga gaggccctgt gcaagtggat cgacttcaca   2040
agggattttc tgtccaagta taccaagaca acctctatcg atctgtctag cctgcggcca   2100
tcctctcagt ataaggacct gggcgagtac tatgccgagc tgaatcccct gctgtaccac   2160
atcagcttcc agagaatcgc cgagaaggag atcatggatg ccgtggagac aggcaagctg   2220
tacctgttcc agatctataa caaggacttt gccaagggcc accacggcaa gcctaatctg   2280
cacacactgt attggaccgg cctgttttct ccagagaacc tggccaagac aagcatcaag   2340
ctgaatggcc aggccgagct gttctaccgc cctaagtcca ggatgaagag gatggcacac   2400
cggctgggag agaagatgct gaacaagaag ctgaaggatc agaaaacccc aatccccgac   2460
accctgtacc aggagctgta cgactatgtg aatcacagac tgtcccacga cctgtctgat   2520
gaggccaggg ccctgctgcc caacgtgatc accaaggagg tgtctcacga gatcatcaag   2580
gataggcgct ttaccagcga caagttcttt ttccacgtgc ctatcacact gaactatcag   2640
gccgccaatt ccccatctaa gttcaaccag agggtgaatg cctacctgaa ggagcacccc   2700
gagacaccta tcatcggcat cgatcggggc gagagaaacc tgatctatat cacagtgatc   2760
gactccaccg gcaagatcct ggagcagcgg agcctgaaca ccatccagca gtttgattac   2820
cagaagaagc tggacaacag ggagaaggag agggtggcag caaggcaggc ctggtctgtg   2880
gtgggcacaa tcaaggatct gaagcagggc tatctgagcc aggtcatcca cgagatcgtg   2940
gacctgatga tccactacca ggccgtggtg gtgctggaga acctgaattt cggctttaag   3000
agcaagagga ccggcatcgc cgagaaggcc gtgtaccagc agttcgagaa gatgctgatc   3060
gataagctga attgcctggt gctgaaggac tatccagcag agaaagtggg aggcgtgctg   3120
aacccatacc agctgacaga ccagttcacc tcctttgcca agatgggcac ccagtctggc   3180
ttcctgtttt acgtgcctgc cccatataca tctaagatcg atcccctgac cggcttcgtg   3240
gaccccttcg tgtggaaaac catcaagaat cacgagagcc gcaagcactt cctggagggc   3300
ttcgactttc tgcactacga cgtgaaaacc ggcgacttca tcctgcactt taagatgaac   3360
agaaatctgt ccttccagag gggcctgccc ggctttatgc ctgcatggga tatcgtgttc   3420
gagaagaacg agacacagtt tgacgccaag ggcacccctt tcatcgccgg caagagaatc   3480
gtgccagtga tcgagaatca cagattcacc ggcagatacc gggacctgta tcctgccaac   3540
gagctgatcg ccctgctgga ggagaagggc atcgtgttca gggatggctc caacatcctg   3600
ccaaagctgc tggagaatga cgattctcac gccatcgaca ccatggtggc cctgatccgc   3660
agcgtgctgc agatgcggaa ctccaatgcc gccacaggcg aggactatat caacagcccc   3720
gtgcgcgatc tgaatggcgt gtgcttcgac tcccggtttc agaacccaga gtggcccatg   3780
gacgccgatg ccaatggcgc ctaccacatc gccctgaagg gccagctgct gctgaatcac   3840
ctgaaggaga gcaaggatct gaagctgcag aacggcatct ccaatcagga ctggctggcc   3900
tacatccagg agctgcgcaa caaaaggccg gcggccacga aaaaggccgg ccaggcaaaa   3960
aagaaaaagg gatcctaccc atacgatgtt ccagattacg cttatcccta cgacgtgcct   4020
gattatgcat acccatatga tgtccccgac tatgcctaa                          4059
```

<210> SEQ ID NO 7
<211> LENGTH: 16
<212> TYPE: PRT
<213> ORGANISM: Unknown
<220> FEATURE:

<223> OTHER INFORMATION: Description of Unknown: Nucleoplasmin NLS
peptide

<400> SEQUENCE: 7

Lys Arg Pro Ala Ala Thr Lys Lys Ala Gly Gln Ala Lys Lys Lys Lys
1 5 10 15

<210> SEQ ID NO 8
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 8

Tyr Pro Tyr Asp Val Pro Asp Tyr Ala Tyr Pro Tyr Asp Val Pro Asp
1 5 10 15

Tyr Ala Tyr Pro Tyr Asp Val Pro Asp Tyr Ala
20 25

<210> SEQ ID NO 9
<211> LENGTH: 1352
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 9

Met Thr Gln Phe Glu Gly Phe Thr Asn Leu Tyr Gln Val Ser Lys Thr
1 5 10 15

Leu Arg Phe Glu Leu Ile Pro Gln Gly Lys Thr Leu Lys His Ile Gln
20 25 30

Glu Gln Gly Phe Ile Glu Glu Asp Lys Ala Arg Asn Asp His Tyr Lys
35 40 45

Glu Leu Lys Pro Ile Ile Asp Arg Ile Tyr Lys Thr Tyr Ala Asp Gln
50 55 60

Cys Leu Gln Leu Val Gln Leu Asp Trp Glu Asn Leu Ser Ala Ala Ile
65 70 75 80

Asp Ser Tyr Arg Lys Glu Lys Thr Glu Glu Thr Arg Asn Ala Leu Ile
85 90 95

Glu Glu Gln Ala Thr Tyr Arg Asn Ala Ile His Asp Tyr Phe Ile Gly
100 105 110

Arg Thr Asp Asn Leu Thr Asp Ala Ile Asn Lys Arg His Ala Glu Ile
115 120 125

Tyr Lys Gly Leu Phe Lys Ala Glu Leu Phe Asn Gly Lys Val Leu Lys
130 135 140

Gln Leu Gly Thr Val Thr Thr Thr Glu His Glu Asn Ala Leu Leu Arg
145 150 155 160

Ser Phe Asp Lys Phe Thr Thr Tyr Phe Ser Gly Phe Tyr Glu Asn Arg
165 170 175

Lys Asn Val Phe Ser Ala Glu Asp Ile Ser Thr Ala Ile Pro His Arg
180 185 190

Ile Val Gln Asp Asn Phe Pro Lys Phe Lys Glu Asn Cys His Ile Phe
195 200 205

Thr Arg Leu Ile Thr Ala Val Pro Ser Leu Arg Glu His Phe Glu Asn
210 215 220

Val Lys Lys Ala Ile Gly Ile Phe Val Ser Thr Ser Ile Glu Glu Val

-continued

```
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655
```

```
Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys  Ser Lys Arg Thr Gly  Ile Ala Glu
        995                 1000                 1005

Lys Ala  Val Tyr Gln Gln Phe  Glu Lys Met Leu Ile  Asp Lys Leu
    1010                 1015                 1020

Asn Cys  Leu Val Leu Lys Asp  Tyr Pro Ala Glu Lys  Val Gly Gly
    1025                 1030                 1035

Val Leu  Asn Pro Tyr Gln Leu  Thr Asp Gln Phe Thr  Ser Phe Ala
    1040                 1045                 1050

Lys Met  Gly Thr Gln Ser Gly  Phe Leu Phe Tyr Val  Pro Ala Pro
    1055                 1060                 1065
```

-continued

```
Tyr Thr  Ser Lys Ile Asp Pro  Leu Thr Gly Phe Val  Asp Pro Phe
    1070                 1075                 1080

Val Trp  Lys Thr Ile Lys Asn  His Glu Ser Arg Lys  His Phe Leu
    1085                 1090                 1095

Glu Gly  Phe Asp Phe Leu His  Tyr Asp Val Lys Thr  Gly Asp Phe
    1100                 1105                 1110

Ile Leu  His Phe Lys Met Asn  Arg Asn Leu Ser Phe  Gln Arg Gly
    1115                 1120                 1125

Leu Pro  Gly Phe Met Pro Ala  Trp Asp Ile Val Phe  Glu Lys Asn
    1130                 1135                 1140

Glu Thr  Gln Phe Asp Ala Lys  Gly Thr Pro Phe Ile  Ala Gly Lys
    1145                 1150                 1155

Arg Ile  Val Pro Val Ile Glu  Asn His Arg Phe Thr  Gly Arg Tyr
    1160                 1165                 1170

Arg Asp  Leu Tyr Pro Ala Asn  Glu Leu Ile Ala Leu  Leu Glu Glu
    1175                 1180                 1185

Lys Gly  Ile Val Phe Arg Asp  Gly Ser Asn Ile Leu  Pro Lys Leu
    1190                 1195                 1200

Leu Glu  Asn Asp Asp Ser His  Ala Ile Asp Thr Met  Val Ala Leu
    1205                 1210                 1215

Ile Arg  Ser Val Leu Gln Met  Arg Asn Ser Asn Ala  Ala Thr Gly
    1220                 1225                 1230

Glu Asp  Tyr Ile Asn Ser Pro  Val Arg Asp Leu Asn  Gly Val Cys
    1235                 1240                 1245

Phe Asp  Ser Arg Phe Gln Asn  Pro Glu Trp Pro Met  Asp Ala Asp
    1250                 1255                 1260

Ala Asn  Gly Ala Tyr His Ile  Ala Leu Lys Gly Gln  Leu Leu Leu
    1265                 1270                 1275

Asn His  Leu Lys Glu Ser Lys  Asp Leu Lys Leu Gln  Asn Gly Ile
    1280                 1285                 1290

Ser Asn  Gln Asp Trp Leu Ala  Tyr Ile Gln Glu Leu  Arg Asn Lys
    1295                 1300                 1305

Arg Pro  Ala Ala Thr Lys Lys  Ala Gly Gln Ala Lys  Lys Lys Lys
    1310                 1315                 1320

Gly Ser  Tyr Pro Tyr Asp Val  Pro Asp Tyr Ala Tyr  Pro Tyr Asp
    1325                 1330                 1335

Val Pro  Asp Tyr Ala Tyr Pro  Tyr Asp Val Pro Asp  Tyr Ala
    1340                 1345                 1350
```

<210> SEQ ID NO 10
<211> LENGTH: 3822
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
atgagcaagc tggagaagtt tacaaactgc tactccctgt ctaagaccct gaggttcaag     60

gccatccctg tgggcaagac ccaggagaac atcgacaata agcggctgct ggtggaggac    120

gagaagagag ccgaggatta taagggcgtg aagaagctgc tggatcgcta ctatctgtct    180

tttatcaacg acgtgctgca cagcatcaag ctgaagaatc tgaacaatta catcagcctg    240

ttccggaaga aaaccagaac cgagaaggag aataaggagc tggagaacct ggagatcaat    300

ctgcggaagg agatcgccaa ggccttcaag ggcaacgagg gctacaagtc cctgtttaag    360
```

-continued

```
aaggatatca tcgagacaat cctgccagag ttcctggacg ataaggacga gatcgccctg    420
gtgaacagct tcaatggctt taccacagcc ttcaccggct tctttgataa cagagagaat    480
atgttttccg aggaggccaa gagcacatcc atcgccttca ggtgtatcaa cgagaatctg    540
acccgctaca tctctaatat ggacatcttc gagaaggtgg acgccatctt tgataagcac    600
gaggtgcagg agatcaagga gaagatcctg aacagcgact atgatgtgga ggatttcttt    660
gagggcgagt tctttaactt tgtgctgaca caggagggca tcgacgtgta taacgccatc    720
atcggcggct tcgtgaccga gagcggcgag aagatcaagg gcctgaacga gtacatcaac    780
ctgtataatc agaaaaccaa gcagaagctg cctaagttta agccactgta taagcaggtg    840
ctgagcgatc gggagtctct gagcttctac ggcgagggct atacatccga tgaggaggtg    900
ctggaggtgt ttagaaacac cctgaacaag aacagcgaga tcttcagctc catcaagaag    960
ctggagaagc tgttcaagaa ttttgacgag tactctagcg ccggcatctt tgtgaagaac   1020
ggccccgcca tcagcacaat ctccaaggat atcttcggcg agtggaacgt gatccgggac   1080
aagtggaatg ccgagtatga cgatatccac ctgaagaaga aggccgtggt gaccgagaag   1140
tacgaggacg atcggagaaa gtccttcaag aagatcggct cctttttctct ggagcagctg   1200
caggagtacg ccgacgccga tctgtctgtg gtggagaagc tgaaggagat catcatccag   1260
aaggtggatg agatctacaa ggtgtatggc tcctctgaga agctgttcga cgccgatttt   1320
gtgctggaga agagcctgaa gaagaacgac gccgtggtgg ccatcatgaa ggacctgctg   1380
gattctgtga agagcttcga gaattacatc aaggccttct ttggcgaggg caaggagaca   1440
aacagggacg agtccttcta tggcgatttt gtgctggcct acgacatcct gctgaaggtg   1500
gaccacatct acgatgccat ccgcaattat gtgacccaga agccctactc taaggataag   1560
ttcaagctgt attttcagaa ccctcagttc atgggcggct gggacaagga taaggagaca   1620
gactatcggg ccaccatcct gagatacggc tccaagtact atctggccat catggataag   1680
aagtacgcca agtgcctgca gaagatcgac aaggacgatg tgaacggcaa ttacgagaag   1740
atcaactata agctgctgcc cggccctaat aagatgctgc caaaggtgtt cttttctaag   1800
aagtggatgg cctactataa ccccagcgag gacatccaga agatctacaa gaatggcaca   1860
ttcaagaagg gcgatatgtt taacctgaat gactgtcaca agctgatcga cttctttaag   1920
gatagcatct cccggtatcc aaagtggtcc aatgcctacg atttcaactt ttctgagaca   1980
gagaagtata aggacatcgc cggcttttac agagaggtgg aggagcaggg ctataaggtg   2040
agcttcgagt ctgccagcaa gaaggaggtg gataagctgg tggaggaggg caagctgtat   2100
atgttccaga tctataacaa ggacttttcc gataagtctc acggcacacc caatctgcac   2160
accatgtact tcaagctgct gtttgacgag aacaatcacg gacagatcag gctgagcgga   2220
ggagcagagc tgttcatgag gcgcgcctcc ctgaagaagg aggagctggt ggtgcaccca   2280
gccaactccc ctatcgccaa caagaatcca gataatccca agaaaaccac aaccctgtcc   2340
tacgacgtgt ataaggataa gaggttttct gaggaccagt acgagctgca catcccaatc   2400
gccatcaata agtgccccaa gaacatcttc aagatcaata cagaggtgcg cgtgctgctg   2460
aagcacgacg ataacccccta tgtgatcggc atcgataggg gcgagcgcaa tctgctgtat   2520
atcgtggtgg tggacggcaa gggcaacatc gtggagcagt attccctgaa cgagatcatc   2580
aacaacttca acggcatcag gatcaagaca gattaccact ctctgctgga caagaaggag   2640
aaggagaggt tcgaggcccg ccagaactgg acctccatcg agaatatcaa ggagctgaag   2700
```

-continued

```
gccggctata tctctcaggt ggtgcacaag atctgcgagc tggtggagaa gtacgatgcc   2760

gtgatcgccc tggaggacct gaactctggc tttaagaata gccgcgtgaa ggtggagaag   2820

caggtgtatc agaagttcga gaagatgctg atcgataagc tgaactacat ggtggacaag   2880

aagtctaatc cttgtgcaac aggcggcgcc ctgaagggct atcagatcac caataagttc   2940

gagagcttta agtccatgtc tacccagaac ggcttcatct tttacatccc tgcctggctg   3000

acatccaaga tcgatccatc taccggcttt gtgaacctgc tgaaaaccaa gtataccagc   3060

atcgccgatt ccaagaagtt catcagctcc tttgacagga tcatgtacgt gcccgaggag   3120

gatctgttcg agtttgccct ggactataag aacttctctc gcacagacgc cgattacatc   3180

aagaagtgga agctgtactc ctacggcaac cggatcagaa tcttccggaa tcctaagaag   3240

aacaacgtgt tcgactggga ggaggtgtgc ctgaccagcg cctataagga gctgttcaac   3300

aagtacggca tcaattatca gcagggcgat atcagagccc tgctgtgcga gcagtccgac   3360

aaggccttct actctagctt tatggccctg atgagcctga tgctgcagat gcggaacagc   3420

atcacaggcc gcaccgacgt ggattttctg atcagccctg tgaagaactc cgacggcatc   3480

ttctacgata gccggaacta tgaggcccag gagaatgcca tcctgccaaa gaacgccgac   3540

gccaatggcg cctataacat cgccagaaag gtgctgtggg ccatcggcca gttcaagaag   3600

gccgaggacg agaagctgga taaggtgaag atcgccatct ctaacaagga gtggctggag   3660

tacgcccaga ccagcgtgaa gcacaaaagg ccggcggcca cgaaaaaggc cggccaggca   3720

aaaaagaaaa agggatccta cccatacgat gttccagatt acgcttatcc ctacgacgtg   3780

cctgattatg catacccata tgatgtcccc gactatgcct aa                      3822
```

<210> SEQ ID NO 11
<211> LENGTH: 1273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160
```

-continued

```
Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
        515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
```

-continued

```
            580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
        675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
    770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
            820                 825                 830

Arg Gly Glu Arg Asn Leu Leu Tyr Ile Val Val Val Asp Gly Lys Gly
        835                 840                 845

Asn Ile Val Glu Gln Tyr Ser Leu Asn Glu Ile Ile Asn Asn Phe Asn
    850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
            900                 905                 910

Glu Leu Val Glu Lys Tyr Asp Ala Val Ile Ala Leu Glu Asp Leu Asn
        915                 920                 925

Ser Gly Phe Lys Asn Ser Arg Val Lys Val Glu Lys Gln Val Tyr Gln
    930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu  Thr Ser Lys Ile Asp  Pro Ser Thr
        995                 1000                 1005
```

```
Gly Phe  Val Asn Leu Leu Lys  Thr Lys Tyr Thr Ser  Ile Ala Asp
    1010                 1015                 1020

Ser Lys  Lys Phe Ile Ser Ser  Phe Asp Arg Ile Met  Tyr Val Pro
    1025                 1030                 1035

Glu Glu  Asp Leu Phe Glu Phe  Ala Leu Asp Tyr Lys  Asn Phe Ser
    1040                 1045                 1050

Arg Thr  Asp Ala Asp Tyr Ile  Lys Lys Trp Lys Leu  Tyr Ser Tyr
    1055                 1060                 1065

Gly Asn  Arg Ile Arg Ile Phe  Arg Asn Pro Lys Lys  Asn Asn Val
    1070                 1075                 1080

Phe Asp  Trp Glu Glu Val Cys  Leu Thr Ser Ala Tyr  Lys Glu Leu
    1085                 1090                 1095

Phe Asn  Lys Tyr Gly Ile Asn  Tyr Gln Gln Gly Asp  Ile Arg Ala
    1100                 1105                 1110

Leu Leu  Cys Glu Gln Ser Asp  Lys Ala Phe Tyr Ser  Ser Phe Met
    1115                 1120                 1125

Ala Leu  Met Ser Leu Met Leu  Gln Met Arg Asn Ser  Ile Thr Gly
    1130                 1135                 1140

Arg Thr  Asp Val Asp Phe Leu  Ile Ser Pro Val Lys  Asn Ser Asp
    1145                 1150                 1155

Gly Ile  Phe Tyr Asp Ser Arg  Asn Tyr Glu Ala Gln  Glu Asn Ala
    1160                 1165                 1170

Ile Leu  Pro Lys Asn Ala Asp  Ala Asn Gly Ala Tyr  Asn Ile Ala
    1175                 1180                 1185

Arg Lys  Val Leu Trp Ala Ile  Gly Gln Phe Lys Lys  Ala Glu Asp
    1190                 1195                 1200

Glu Lys  Leu Asp Lys Val Lys  Ile Ala Ile Ser Asn  Lys Glu Trp
    1205                 1210                 1215

Leu Glu  Tyr Ala Gln Thr Ser  Val Lys His Lys Arg  Pro Ala Ala
    1220                 1225                 1230

Thr Lys  Lys Ala Gly Gln Ala  Lys Lys Lys Lys Gly  Ser Tyr Pro
    1235                 1240                 1245

Tyr Asp  Val Pro Asp Tyr Ala  Tyr Pro Tyr Asp Val  Pro Asp Tyr
    1250                 1255                 1260

Ala Tyr  Pro Tyr Asp Val Pro  Asp Tyr Ala
    1265                 1270
```

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

```
Gly Gly Gly Ser
1
```

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Gly Gly Gly Gly Ser
1 5

<210> SEQ ID NO 14

<400> SEQUENCE: 14

000

<210> SEQ ID NO 15

<400> SEQUENCE: 15

000

<210> SEQ ID NO 16
<211> LENGTH: 7
<212> TYPE: PRT
<213> ORGANISM: Simian virus 40

<400> SEQUENCE: 16

Pro Lys Lys Lys Arg Arg Val
1 5

<210> SEQ ID NO 17
<211> LENGTH: 4038
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17
atgagcatct accaggagtt cgtcaacaag tattcactga gtaagacact gcggttcgag 60
ctgatcccac agggcaagac actggagaac atcaaggccc gaggcctgat tctggacgat 120
gagaagcggg caaaagacta taagaaagcc aagcagatca ttgataaata ccaccagttc 180
tttatcgagg aaattctgag ctccgtgtgc atcagtgagg atctgctgca gaattactca 240
gacgtgtact tcaagctgaa gaagagcgac gatgacaacc tgcagaagga cttcaagtcc 300
gccaaggaca ccatcaagaa acagattagc gagtacatca aggactccga aaagtttaaa 360
aatctgttca accagaatct gatcgatgct aagaaaggcc aggagtccga cctgatcctg 420
tggctgaaac agtctaagga caatgggatt gaactgttca aggctaactc cgatatcact 480
gatattgacg aggcactgga aatcatcaag agcttcaagg gatggaccac atactttaaa 540
ggcttccacg agaaccgcaa gaacgtgtac tccagcaacg acattcctac ctccatcatc 600
taccgaatcg tcgatgacaa tctgccaaag ttcctggaga acaaggccaa atatgaatct 660
ctgaaggaca aagctcccga ggcaattaat tacgaacaga tcaagaaaga tctggctgag 720
gaactgacat tcgatatcga ctataagact agcgaggtga accagagggt cttttccctg 780
gacgaggtgt ttgaaatcgc caatttcaac aattacctga accagtccgg cattactaaa 840
ttcaatacca tcattggcgg gaagtttgtg aacggggaga ataccaagcg caagggaatt 900
aacgaataca tcaatctgta tagccagcag atcaacgaca aaactctgaa gaaatacaag 960
atgtctgtgc tgttcaaaca gatcctgagt gataccgagt ccaagtcttt tgtcattgat 1020
aaactggaag atgactcaga cgtggtcact accatgcaga gcttttatga gcagatcgcc 1080
gctttcaaga cagtggagga aaaatctatt aaggaaactc tgagtctgct gttcgatgac 1140
ctgaaagccc agaagctgga cctgagtaag atctacttca aaaacgataa gagtctgaca 1200

```
gacctgtcac agcaggtgtt tgatgactat tccgtgattg ggaccgccgt cctggagtac   1260
attacacagc agatcgctcc aaagaacctg gataatccct ctaagaaaga gcaggaactg   1320
atcgctaaga aaaccgagaa ggcaaaatat ctgagtctgg aaacaattaa gctggcactg   1380
gaggagttca acaagcacag ggatattgac aaacagtgcc gctttgagga aatcctggcc   1440
aacttcgcag ccatccccat gatttttgat gagatcgccc agaacaaaga caatctggct   1500
cagatcagta ttaagtacca gaaccagggc aagaaagacc tgctgcaggc ttcagcagaa   1560
gatgacgtga aagccatcaa ggatctgctg gaccagacca acaatctgct gcacaagctg   1620
aaaatcttcc atattagtca gtcagaggat aaggctaata tcctggataa agacgaacac   1680
ttctacctgg tgttcgagga atgttacttc gagctggcaa acattgtccc cctgtataac   1740
aagattagga actacatcac acagaagcct tactctgacg agaagtttaa actgaacttc   1800
gaaaatagta ccctggccaa cgggtgggat aagaacaagg agcctgacaa cacagctatc   1860
ctgttcatca aggatgacaa gtactatctg ggagtgatga ataagaaaaa caataagatc   1920
ttcgatgaca aagccattaa ggagaacaaa ggggaaggat acaagaaaat cgtgtataag   1980
ctgctgcccg gcgcaaataa gatgctgcct aaggtgttct tcagcgccaa gagtatcaaa   2040
ttctacaacc catccgagga catcctgcgg attagaaatc actcaacaca tactaagaac   2100
gggagccccc agaagggata tgagaaattt gagttcaaca tcgaggattg caggaagttt   2160
attgacttct acaagcagag catctccaaa caccctgaat ggaaggattt tggcttccgg   2220
ttttccgaca cacagagata taactctatc gacgagttct accgcgaggt ggaaaatcag   2280
gggtataagc tgacttttga gaacatttct gaaagttaca tcgacagcgt ggtcaatcag   2340
ggaaagctgt acctgttcca gatctataac aaagattttt cagcatacag caagggcaga   2400
ccaaacctgc atacactgta ctggaaggcc ctgttcgatg agaggaatct gcaggacgtg   2460
gtctataaac tgaacggaga ggccgaactg ttttaccgga agcagtctat tcctaagaaa   2520
atcactcacc cagctaagga ggccatcgct aacaagaaca aggacaatcc taagaaagag   2580
agcgtgttcg aatacgatct gattaaggac aagcggttca ccgaagataa gttcttttc    2640
cattgtccaa tcaccattaa cttcaagtca agcggcgcta acaagttcaa cgacgagatc   2700
aatctgctgc tgaaggaaaa agcaaacgat gtgcacatcc tgagcattga ccgaggagag   2760
cggcatctgg cctactatac cctggtggat ggcaaaggga atatcattaa gcaggataca   2820
ttcaacatca ttggcaatga ccggatgaaa accaactacc acgataaact ggctgcaatc   2880
gagaaggata gagactcagc taggaaggac tggaagaaaa tcaacaacat taaggagatg   2940
aaggaaggct atctgagcca ggtggtccat gagattgcaa agctggtcat cgaatacaat   3000
gccattgtgg tgttcgagga tctgaacttc ggctttaaga gggggcgctt taaggtggaa   3060
aaacaggtct atcagaagct ggagaaaatg ctgatcgaaa agctgaatta cctggtgttt   3120
aaagataacg agttcgacaa gaccggaggc gtcctgagag cctaccagct gacagctccc   3180
tttgaaactt tcaagaaaat gggaaaacag acaggcatca tctactatgt gccagccgga   3240
ttcacttcca agatctgccc cgtgaccggc tttgtcaacc agctgtaccc taaatatgag   3300
tcagtgagca agtcccagga atttttcagc aagttcgata agatctgtta taatctggac   3360
aaggggtact tcgagttttc cttcgattac aagaacttcg gcgacaaggc cgctaagggg   3420
aaatggacca ttgcctcctt cggatctcgc ctgatcaact ttcgaaattc cgataaaaac   3480
cacaattggg acactaggga ggtgtaccca accaaggagc tggaaaagct gctgaaagac   3540
```

-continued

```
tactctatcg agtatggaca tggcgaatgc atcaaggcag ccatctgtgg cgagagtgat   3600

aagaaatttt tcgccaagct gacctcagtg ctgaatacaa tcctgcagat gcggaactca   3660

aagaccggga cagaactgga ctatctgatt agccccgtgg ctgatgtcaa cggaaacttc   3720

ttcgacagca gacaggcacc caaaaatatg cctcaggatg cagacgccaa cggggcctac   3780

cacatcgggc tgaagggact gatgctgctg ggccggatca agaacaatca ggaggggaag   3840

aagctgaacc tggtcattaa gaacgaggaa tacttcgagt ttgtccagaa tagaaataac   3900

aaaaggccgg cggccacgaa aaaggccggc caggcaaaaa agaaaaaggg atcctaccca   3960

tacgatgttc cagattacgc ttatccctac gacgtgcctg attatgcata cccatatgat   4020

gtccccgact atgcctaa                                                  4038


<210> SEQ ID NO 18
<211> LENGTH: 1345
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270
```

-continued

```
Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685
```

-continued

```
Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
            980                 985                 990

Ala Lys Leu Val Ile Glu Tyr Asn  Ala Ile Val Val Phe  Glu Asp Leu
        995                 1000                1005

Asn Phe  Gly Phe Lys Arg Gly  Arg Phe Lys Val Glu  Lys Gln Val
    1010                1015                1020

Tyr Gln  Lys Leu Glu Lys Met  Leu Ile Glu Lys Leu  Asn Tyr Leu
    1025                1030                1035

Val Phe  Lys Asp Asn Glu Phe  Asp Lys Thr Gly Gly  Val Leu Arg
    1040                1045                1050

Ala Tyr  Gln Leu Thr Ala Pro  Phe Glu Thr Phe Lys  Lys Met Gly
    1055                1060                1065

Lys Gln  Thr Gly Ile Ile Tyr  Tyr Val Pro Ala Gly  Phe Thr Ser
    1070                1075                1080

Lys Ile  Cys Pro Val Thr Gly  Phe Val Asn Gln Leu  Tyr Pro Lys
    1085                1090                1095

Tyr Glu  Ser Val Ser Lys Ser  Gln Glu Phe Phe Ser  Lys Phe Asp
```

```
    1100                1105                1110

Lys Ile  Cys Tyr Asn Leu Asp  Lys Gly Tyr Phe Glu  Phe Ser Phe
    1115                1120                1125

Asp Tyr  Lys Asn Phe Gly Asp  Lys Ala Ala Lys Gly  Lys Trp Thr
    1130                1135                1140

Ile Ala  Ser Phe Gly Ser Arg  Leu Ile Asn Phe Arg  Asn Ser Asp
    1145                1150                1155

Lys Asn  His Asn Trp Asp Thr  Arg Glu Val Tyr Pro  Thr Lys Glu
    1160                1165                1170

Leu Glu  Lys Leu Leu Lys Asp  Tyr Ser Ile Glu Tyr  Gly His Gly
    1175                1180                1185

Glu Cys  Ile Lys Ala Ala Ile  Cys Gly Glu Ser Asp  Lys Lys Phe
    1190                1195                1200

Phe Ala  Lys Leu Thr Ser Val  Leu Asn Thr Ile Leu  Gln Met Arg
    1205                1210                1215

Asn Ser  Lys Thr Gly Thr Glu  Leu Asp Tyr Leu Ile  Ser Pro Val
    1220                1225                1230

Ala Asp  Val Asn Gly Asn Phe  Phe Asp Ser Arg Gln  Ala Pro Lys
    1235                1240                1245

Asn Met  Pro Gln Asp Ala Asp  Ala Asn Gly Ala Tyr  His Ile Gly
    1250                1255                1260

Leu Lys  Gly Leu Met Leu Leu  Gly Arg Ile Lys Asn  Asn Gln Glu
    1265                1270                1275

Gly Lys  Lys Leu Asn Leu Val  Ile Lys Asn Glu Glu  Tyr Phe Glu
    1280                1285                1290

Phe Val  Gln Asn Arg Asn Asn  Lys Arg Pro Ala Ala  Thr Lys Lys
    1295                1300                1305

Ala Gly  Gln Ala Lys Lys Lys  Lys Gly Ser Tyr Pro  Tyr Asp Val
    1310                1315                1320

Pro Asp  Tyr Ala Tyr Pro Tyr  Asp Val Pro Asp Tyr  Ala Tyr Pro
    1325                1330                1335

Tyr Asp  Val Pro Asp Tyr Ala
    1340                1345
```

<210> SEQ ID NO 19
<211> LENGTH: 21
<212> TYPE: DNA
<213> ORGANISM: Simian virus 40

<400> SEQUENCE: 19
ccaaagaaaa agaggaaagt c 21

<210> SEQ ID NO 20
<211> LENGTH: 21
<212> TYPE: DNA
<213> ORGANISM: Simian virus 40

<400> SEQUENCE: 20
cctaaaaaga aacgaaaggt t 21

<210> SEQ ID NO 21
<211> LENGTH: 48
<212> TYPE: DNA
<213> ORGANISM: Unknown
<220> FEATURE:
<223> OTHER INFORMATION: Description of Unknown: Nucleoplasmin NLS peptide

<400> SEQUENCE: 21
aaaaggccgg cggccacgaa aaaggccggc caggcaaaaa agaaaaag 48

<210> SEQ ID NO 22
<211> LENGTH: 21
<212> TYPE: DNA
<213> ORGANISM: Simian virus 40

<400> SEQUENCE: 22
cccaagaaga agaggaaagt c 21

<210> SEQ ID NO 23
<211> LENGTH: 93
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 23
tctggtggtt cttctggtgg ttctagcggc agcgagactc ccgggacctc agagtccgcc 60
acacccgaaa gttccggagg gagtagcggc ggg 93

<210> SEQ ID NO 24
<211> LENGTH: 7
<212> TYPE: PRT
<213> ORGANISM: Simian virus 40

<400> SEQUENCE: 24

Pro Lys Lys Lys Arg Lys Val
1 5

<210> SEQ ID NO 25
<211> LENGTH: 31
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 25

Ser Gly Gly Ser Ser Gly Gly Ser Ser Gly Ser Glu Thr Pro Gly Thr
1 5 10 15

Ser Glu Ser Ala Thr Pro Glu Ser Ser Gly Gly Ser Ser Gly Gly
20 25 30

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 26
aaccagtgga ggcaagaggg cggc 24

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 27
aaccaagaca ggtcactgtt tcag 24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28
aaccacacct tcacctgggc cagg 24

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 29
aaccggtggc gcattgccac gaag 24

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30
aatagcattg cagagaggcg tatc 24

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 31
aatatgctgt ctgaagccat cgct 24

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 32
aataagtggc agagtgctaa ggga 24

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 33
aatatggagc ctgctccagg tggg 24

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 34
aatcagtacg cagagagtcg ccgt 24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 35
aatcctaact gagaccttac accg 24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 36
aatgcgccac cggttgatgt gatg 24

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 37
accccggctc tggctaaaga ggga 24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 38
accccctatt tctgacctcc caaa 24

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 39
acccagaggc tcaagtgagc agct 24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
accctagtca ttggaggtga catc 24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41
acccacgagg gcagagtgct gctt 24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
acccaataag tggcagagtg ctaa 24

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 43
agccgccctc ttgcctccac tggt 24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 44
agccatcgct tcctcctgaa aatg 24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45
agcctcaccc ctctagccct acat 24

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 46
agcctgctcc aggtggggaa taag 24

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 47
agtaacagac atggaccatc agga 24

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 48
agtaccagat tctgagcagg gaga 24

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 49
agtctccgtg aacgttccct tagc 24

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 50
agtctgtcct gaacctgatg acac 24

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 51
atcaggaaac attaacgtac tgat 24

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 52
atcagaatcc tcttcgatgc catt 24

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 53
atcctcacag cagccccttg agaa 24

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 54
atccaatcaa ctctatacga aaat 24

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 55
atccccaaca tgcactgatg ttgt 24

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 56
atccatcggc gctttggtcg gcat 24

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 57
attaacgtac tgatgttaac agct 24

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 58
attaacatta acaagaagca tttg 24

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 59
attattcaag tggcgcagat ctag 24

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 60
attagaagga gatgctcctg tctc 24

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 61
attcaccgag caggagtgag ggaa 24

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 62
attccccacc tggagcaggc tcca 24

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 63
attctgatga gcctttagag agaa 24

<210> SEQ ID NO 64

<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 64
attccctctt tagccagagc cggg 24

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 65
attcgcacgg ctctggagcg gcgg 24

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 66
attgggtcag ctgttaacat cagt 24

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 67
attgttatga acctgggtga agtc 24

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 68
attggaatcc tggagtgacc cctg 24

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 69
attggattga gaatagaatt cttc 24

<210> SEQ ID NO 70
<211> LENGTH: 24

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
attggaacat ccgcgaaatg atac 24

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
atttggctca gcaggcacct gcct 24

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
atttgctttc cacccacctt tccc 24

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
atttctgacc tcccaaacag ctac 24

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
atttcttctt tctgcactaa attg 24

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
atttcgcgga tgttccaatc agta 24

<210> SEQ ID NO 76
<211> LENGTH: 24
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 76
caccgtgcgc cgggccttgc agtg 24

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
caccgaggca tctctgcacc gagg 24

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ccccgcccaa agccgccctc ttgc 24

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
ccccgccttc agaagagggt gcat 24

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ccccagaggg ttctagaccc agag 24

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ccccagggcc agcccagcag ccaa 24

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
cgcacggctc tggagcggcg gctg 24

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
cgcattgcca cgaagcaggc caat 24

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
cgccgctcca gagccgtgcg aatg 24

<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
cgccaccggt tgatgtgatg ggag 24

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
cgccacatcc atcggcgctt tggt 24

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
cgccgatgga tgtggcgcag gtag 24

<210> SEQ ID NO 88
<211> LENGTH: 24
<212> TYPE: DNA
<213> ORGANISM: Artificial Sequence
<220> FEATURE:

<223> OTHER INFORMATION: Description of Artificial Sequence: Synthetic oligonucleotide

<400> SEQUENCE: 88
cgtcagcacc tgggaccccg ccac 24

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 89
cgtctccaag gtgaaagcgg aagt 24

<210> SEQ ID NO 90
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 90
ctcaaacggt ccccagaggg ttct 24

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 91
ctcaaaactc atgggatgtg attc 24

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 92
ctccgtgaac gttcccttag cact 24

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 93
ctccttctaa tgagaaacgg tgta 24

<210> SEQ ID NO 94
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 94
ctccactggt tgtgcagccg ccgc 24

<210> SEQ ID NO 95
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 95
ctccagagcc gtgcgaatgg ggcc 24

<210> SEQ ID NO 96
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 96
ctctggggaa cacgcccggt gtca 24

<210> SEQ ID NO 97
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 97
cttattgggt cagctgttaa catc 24

<210> SEQ ID NO 98
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 98
cttattcccc acctggagca ggct 24

<210> SEQ ID NO 99
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 99
cttactaatc agatggaagc tctt 24

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 100
cttacaccgt ttctcattag aagg 24

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 101
cttccgcttt caccttggag acgg 24

<210> SEQ ID NO 102
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 102
cttcacccag gttcataaca atgt 24

<210> SEQ ID NO 103
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 103
cttctccccg ctccaacgcc ctca 24

<210> SEQ ID NO 104
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 104
cttctaatga gaaacggtgt aagg 24

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 105
cttcgcgcac ctcatggaat ccct 24

<210> SEQ ID NO 106
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 106
cttgacaggc gagtaacaga catg 24

<210> SEQ ID NO 107
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 107
cttgttaatg ttaataactt gctt 24

<210> SEQ ID NO 108
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 108
cttggttaac tgagtgtgtc atca 24

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 109
cttggggagt cccagaggta tcca 24

<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 110
ctttggtcag gttggctgct gggc 24

<210> SEQ ID NO 111
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 111
ctttccctgg cctacctcac tggc 24

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 112
ctttagccag agccggggtg tgca 24

<210> SEQ ID NO 113
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 113
ctttagagag aaggctgtcc ttag 24

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 114
ctttggtcgg catggcccca ttcg 24

<210> SEQ ID NO 115
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 115
gcccggtgtc acgccacttg acag 24

<210> SEQ ID NO 116
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 116
gccccacgct tcaggcacga agga 24

<210> SEQ ID NO 117
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 117
gtcacgccac ttgacaggcg agta 24

<210> SEQ ID NO 118
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 118
gtcatcaggt tcaggacaga ctgc 24

<210> SEQ ID NO 119
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 119
gtccccagag ggttctagac ccag 24

<210> SEQ ID NO 120
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 120
gtccaggaga caggagcatc tcct 24

<210> SEQ ID NO 121
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 121
gtcccaggtg ctgacgtagg tagt 24

<210> SEQ ID NO 122
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 122
gtcctcccca ttggcctgct tcgt 24

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 123
gttactcgcc tgtcaagtgg cgtg 24

<210> SEQ ID NO 124
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 124
gttatgaacc tgggtgaagt ccca 24

<210> SEQ ID NO 125
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 125
gttaatgtta ataacttgct tcaa 24

<210> SEQ ID NO 126
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 126
gttaaccaag gtcagaacat tcac 24

<210> SEQ ID NO 127
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 127
gttcccttag cactctgcca ctta 24

<210> SEQ ID NO 128
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 128
gttcatttgt ccagaggaaa ccac 24

<210> SEQ ID NO 129
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 129
gttccctgtc ttgtttgtga gagg 24

<210> SEQ ID NO 130
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 130
gttcaggaca gactgcctcc ttcg 24

-continued

<210> SEQ ID NO 131
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 131
gttggggatt cctggtgcca gaaa 24

<210> SEQ ID NO 132
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 132
gttgggactt cacccaggtt cata 24

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 133
gttgagggcg ttggagcggg gaga 24

<210> SEQ ID NO 134
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 134
gttgattgga ttgagaatag aatt 24

<210> SEQ ID NO 135
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 135
gttgtgcagc cgccgctcca gagc 24

<210> SEQ ID NO 136
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 136
gtttcctgat ggtccatgtc tgtt 24

<210> SEQ ID NO 137
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 137
gtttgacttg ggatagtgga atag 24

<210> SEQ ID NO 138
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 138
gtttgggagg tcagaaatag gggg 24

<210> SEQ ID NO 139
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 139
gtttctcatt agaaggagat gctc 24

<210> SEQ ID NO 140
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 140
gtttcacctc ggtgcagaga tgcc 24

<210> SEQ ID NO 141
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 141
tacatctctc tttcttctcc cctc 24

<210> SEQ ID NO 142
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 142
tacaggcaaa gctgagcaaa agta 24

<210> SEQ ID NO 143

<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 143
tacaaacggc agaagctgga ggag 24

<210> SEQ ID NO 144
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 144
tacaagacca gcatgtactc acct 24

<210> SEQ ID NO 145
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 145
tacccacgtt cgtggcccca tctt 24

<210> SEQ ID NO 146
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 146
taccagattc tgagcaggga gagg 24

<210> SEQ ID NO 147
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 147
tacctcactg gccccacccc agag 24

<210> SEQ ID NO 148
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 148
tacctgcgcc acatccatcg gcgc 24

<210> SEQ ID NO 149
<211> LENGTH: 24

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 149
tatagagttg attggattga gaat 24

<210> SEQ ID NO 150
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 150
tatattcaag aaggttatct caag 24

<210> SEQ ID NO 151
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 151
tatatattca agaaggttat ctca 24

<210> SEQ ID NO 152
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 152
tatagacatg tcccatttgt ggga 24

<210> SEQ ID NO 153
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 153
tatcgcctct ccctgctcag aatc 24

<210> SEQ ID NO 154
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 154
tatctcaaga aactggcttg gaaa 24

<210> SEQ ID NO 155
<211> LENGTH: 24
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 155
tatccagttc agtcaagttt gcct 24

<210> SEQ ID NO 156
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 156
tatcccaagt caaacttctc ttca 24

<210> SEQ ID NO 157
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 157
tatgttcggg tgctgtgaac ttcc 24

<210> SEQ ID NO 158
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 158
tatgaacctg ggtgaagtcc caac 24

<210> SEQ ID NO 159
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 159
tatgtagctg tttgggaggt caga 24

<210> SEQ ID NO 160
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 160
tatgggacat tttcagaact ccaa 24

<210> SEQ ID NO 161
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
tattgggtca gctgttaaca tcag 24

<210> SEQ ID NO 162
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
tatttctgac ctcccaaaca gcta 24

<210> SEQ ID NO 163
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
tattctcaat ccaatcaact ctat 24

<210> SEQ ID NO 164
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
tattggtcga aatgcatgtc aatc 24

<210> SEQ ID NO 165
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
tccatgtctg ttactcgcct gtca 24

<210> SEQ ID NO 166
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
tccaggagac aggagcatct cctt 24

<210> SEQ ID NO 167
<211> LENGTH: 24
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 167
tccagtccca aatatgtagc tgtt 24

<210> SEQ ID NO 168
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
tccccagagg gttctagacc caga 24

<210> SEQ ID NO 169
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
tccccaaact ctccagtctg ttta 24

<210> SEQ ID NO 170
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
tcccgtcacc cctgtttctg gcac 24

<210> SEQ ID NO 171
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
tcccaggtgc tgacgtaggt agtg 24

<210> SEQ ID NO 172
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
tccctcttta gccagagccg gggt 24

<210> SEQ ID NO 173
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 173
tccgtgaacg ttcccttagc actc 24

<210> SEQ ID NO 174
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 174
tccgagcttc tggcggtctc aagc 24

<210> SEQ ID NO 175
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 175
tccgcacgta acctcacttt cctg 24

<210> SEQ ID NO 176
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 176
tcctgatggt ccatgtctgt tact 24

<210> SEQ ID NO 177
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 177
tgcacacagc aggcctttgg tcag 24

<210> SEQ ID NO 178
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 178
tgcagaaaga agaaattcaa tcct 24

<210> SEQ ID NO 179
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 179
tgccacttat tgggtcagct gtta 24

<210> SEQ ID NO 180
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 180
tgcctcgcat cagcgtgatc agca 24

<210> SEQ ID NO 181
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 181
tgcctccact ggttgtgcag ccgc 24

<210> SEQ ID NO 182
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 182
tgccgaccaa agcgccgatg gatg 24

<210> SEQ ID NO 183
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 183
tgtaatgaaa tggcagcttg tttc 24

<210> SEQ ID NO 184
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 184
tgtactttgt cctccggttc tgga 24

<210> SEQ ID NO 185
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 185
tgtacctcac cactgacatt aatt 24

<210> SEQ ID NO 186
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 186
tgtaaccaca gtcaagtagt taat 24

<210> SEQ ID NO 187
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 187
tgtaaggtct cagttaggat tgaa 24

<210> SEQ ID NO 188
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 188
tgtcaatctc ccagcgtctt tatc 24

<210> SEQ ID NO 189
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 189
tgtcttgttt gtgagaggaa ttca 24

<210> SEQ ID NO 190
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 190
tgtccagagg aaaccactgt tggg 24

<210> SEQ ID NO 191
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 191
tgtctattcc actatcccaa gtca 24

<210> SEQ ID NO 192
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 192
tgtccctcac ccatctccct gtga 24

<210> SEQ ID NO 193
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 193
tgtgcagccg ccgctccaga gccg 24

<210> SEQ ID NO 194
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 194
tgtgagagga attcaaactg aggc 24

<210> SEQ ID NO 195
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 195
tgtggcgcag gtagcgcgcc cact 24

<210> SEQ ID NO 196
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 196
tgtggttcca gaaccggagg acaa 24

<210> SEQ ID NO 197
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 197
tgtgatggga gcccttcttc ttct 24

<210> SEQ ID NO 198
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 198
ttacaggcaa agctgagcaa aagt 24

<210> SEQ ID NO 199
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 199
ttactcatct ctgccagacc acct 24

<210> SEQ ID NO 200
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 200
ttactgattc tggggtcaac atct 24

<210> SEQ ID NO 201
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 201
ttacaaatga atggcatcga agag 24

<210> SEQ ID NO 202
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 202
ttacaccgtt tctcattaga agga 24

<210> SEQ ID NO 203
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 203
ttactagggc aataagcaac acct 24

<210> SEQ ID NO 204
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 204
ttcagtctcc gtgaacgttc cctt 24

<210> SEQ ID NO 205
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 205
ttcacccagg ttcataacaa tgtt 24

<210> SEQ ID NO 206
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 206
ttcacccagc ttccctgtgg tggc 24

<210> SEQ ID NO 207
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 207
ttcaatccta actgagacct taca 24

<210> SEQ ID NO 208
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 208
ttcaccttgg agacggcgac tctc 24

<210> SEQ ID NO 209
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 209
ttcctgatgg tccatgtctg ttac 24

<210> SEQ ID NO 210
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 210
ttccctggcc tacctcactg gccc 24

<210> SEQ ID NO 211
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 211
ttccaaagcc cattccctct ttag 24

<210> SEQ ID NO 212
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 212
ttccattgtg caaaagactc cctt 24

<210> SEQ ID NO 213
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 213
ttccgagctt ctggcggtct caag 24

<210> SEQ ID NO 214
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 214
ttcgtggccc catctttctc aagg 24

<210> SEQ ID NO 215
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 215
ttcgagagtg aggacgtgtg tgtc 24

<210> SEQ ID NO 216
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 216
ttcggagcga aaaccaagac aggt 24

<210> SEQ ID NO 217
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 217
ttcgaccaat ttagtgcaga aaga 24

<210> SEQ ID NO 218
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 218
ttcgcacggc tctggagcgg cggc 24

<210> SEQ ID NO 219
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 219
ttctgccctc ccgtcacccc tgtt 24

<210> SEQ ID NO 220
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 220
ttctgccctt tactcatctc tgcc 24

<210> SEQ ID NO 221
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 221
ttctgacctc ccaaacagct acat 24

<210> SEQ ID NO 222

<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 222
ttctttcgac caatttagtg caga 24

<210> SEQ ID NO 223
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 223
ttctggcggt ctcaagcact acct 24

<210> SEQ ID NO 224
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 224
tttatttccc ttcagctaaa ataa 24

<210> SEQ ID NO 225
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 225
tttattttag ctgaagggaa ataa 24

<210> SEQ ID NO 226
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 226
tttatccgtg ttccttgact ctgg 24

<210> SEQ ID NO 227
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 227
tttaccttcg gagcgaaaac caag 24

<210> SEQ ID NO 228
<211> LENGTH: 24

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 228
tttaggatgc cactaaaagg gaaa 24

<210> SEQ ID NO 229
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 229
tttagattga aggaaaagtt acaa 24

<210> SEQ ID NO 230
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 230
tttccctcac tcctgctcgg tgaa 24

<210> SEQ ID NO 231
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 231
tttcctgatg gtccatgtct gtta 24

<210> SEQ ID NO 232
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 232
tttctcatct gtgcccctcc ctcc 24

<210> SEQ ID NO 233
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 233
tttcaccttg gagacggcga ctct 24

<210> SEQ ID NO 234
<211> LENGTH: 24
<212> TYPE: DNA

-continued

<213> ORGANISM: Artificial Sequence
<220> FEATURE:
<223> OTHER INFORMATION: Description of Artificial Sequence: Synthetic
oligonucleotide

<400> SEQUENCE: 234
tttcgctccg aaggtaaaag aaat 24

<210> SEQ ID NO 235
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 235
tttcagcctc acccctctag ccct 24

<210> SEQ ID NO 236
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 236
tttcttctcc cctctgctgg atac 24

<210> SEQ ID NO 237
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 237
tttccgagct tctggcggtc tcaa 24

<210> SEQ ID NO 238
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 238
tttgaggagt gttcagtctc cgtg 24

<210> SEQ ID NO 239
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 239
tttggctcag caggcacctg cctc 24

<210> SEQ ID NO 240
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 240
tttgtcctcc ggttctggaa ccac 24

<210> SEQ ID NO 241
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 241
tttgtggttg cccaccctag tcat 24

<210> SEQ ID NO 242
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 242
tttgtacttt gtcctccggt tctg 24

<210> SEQ ID NO 243
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 243
tttgggcggg gtccagttcc ggga 24

<210> SEQ ID NO 244
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 244
tttggtcggc atggccccat tcgc 24

<210> SEQ ID NO 245
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 245
ttttatttcc cttcagctaa aata 24

<210> SEQ ID NO 246
<211> LENGTH: 24
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 246
ttttcaggag gaagcgatgg cttc 24

<210> SEQ ID NO 247
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 247
ttttccgagc ttctggcggt ctca 24

<210> SEQ ID NO 248
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 248
ttttcgtata gagttgattg gatt 24

<210> SEQ ID NO 249
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 249
ttttgagcta aagtctggct gtag 24

<210> SEQ ID NO 250
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 250
tttgagagtc tggatgagaa atgc 24

<210> SEQ ID NO 251
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 251
tttctaccct cttctctgcc tttc 24

<210> SEQ ID NO 252
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 252
tttgctctag gaaccctcag cccc 24

<210> SEQ ID NO 253
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 253
tttctccaaa gccactaggc aggc 24

<210> SEQ ID NO 254
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 254
tttaggaaag caggagctat tcag 24

<210> SEQ ID NO 255
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 255
tttggaacca aatttggtga gtgc 24

<210> SEQ ID NO 256
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 256
attcaggaag caggggtcct ccag 24

<210> SEQ ID NO 257
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 257
attgggcttt ggaaccaaat ttgg 24

<210> SEQ ID NO 258
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 258
attccgtcat agggatagat cggg 24

<210> SEQ ID NO 259
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 259
cttgtttctc caaagccact aggc 24

<210> SEQ ID NO 260
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 260
cttcctgaat agctcctgct ttcc 24

<210> SEQ ID NO 261
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 261
cttatcagtc ctgaaaagaa cccc 24

<210> SEQ ID NO 262
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 262
gttgcatttg ctctccacct ccca 24

<210> SEQ ID NO 263
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 263
gttagcgcgc ggtgagggga gggg 24

<210> SEQ ID NO 264
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 264
gttccaaagc ccaatctaaa aaac 24

<210> SEQ ID NO 265
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 265
ttcaggaagc aggggtcctc cagg 24

<210> SEQ ID NO 266
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 266
ttcctggagg ccagcactca ccaa 24

<210> SEQ ID NO 267
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 267
ttcaggactg ataagagcgc gcag 24

<210> SEQ ID NO 268
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 268
ctccaaagcc actaggcagg cgtt 24

<210> SEQ ID NO 269
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 269
ctccaggaaa tctggagccc tggc 24

<210> SEQ ID NO 270
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 270

-continued

```
ctccctccct cgcctccacc ctgt                                              24


<210> SEQ ID NO 271
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271

tcccgccccc accgggccgg cctc                                              24


<210> SEQ ID NO 272
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272

tcccctcacc gcgcgctaac gcct                                              24


<210> SEQ ID NO 273
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273

tccctcgcct ccaccctgtt ggtt                                              24


<210> SEQ ID NO 274
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274

tttgtactga tggtatgggg ccaa                                              24


<210> SEQ ID NO 275
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275

tttgaagtcc aactcctaag ccag                                              24


<210> SEQ ID NO 276
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
```

-continued

```
tttgcaagtg tatttacgta atat                                            24


<210> SEQ ID NO 277
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277

attggccaac cctagggtgt ggct                                            24


<210> SEQ ID NO 278
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278

attgctacta aaaacatcct cctt                                            24


<210> SEQ ID NO 279
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279

attgggaaaa cgatcttcaa tatg                                            24


<210> SEQ ID NO 280
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280

cttagacctc accctgtgga gcca                                            24


<210> SEQ ID NO 281
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281

cttaggagtt ggacttcaaa ccct                                            24


<210> SEQ ID NO 282
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282

cttaccaagc tgtgattcca aata                                            24
```

<210> SEQ ID NO 283
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 283
tatgcccagc cctggctcct gccc 24

<210> SEQ ID NO 284
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 284
tatctcttgg ccccatacca tcag 24

<210> SEQ ID NO 285
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 285
tatcccaaag ctgaattatg gtag 24

<210> SEQ ID NO 286
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 286
tgtcatcact tagacctcac cctg 24

<210> SEQ ID NO 287
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 287
tgtactgatg gtatggggcc aaga 24

<210> SEQ ID NO 288
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 288
tgtagatgga tctcttcctg cgtc 24

<210> SEQ ID NO 289
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 289
ttcaaaccct cagccctccc tcta 24

<210> SEQ ID NO 290
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 290
ttccaaatat tacgtaaata cact 24

<210> SEQ ID NO 291
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 291
ttcagctttg ggatatgtag atgg 24

<210> SEQ ID NO 292
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 292
ctccctgctc ctgggagtag attg 24

<210> SEQ ID NO 293
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 293
ctccctctaa gatatatctc ttgg 24

<210> SEQ ID NO 294
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 294
ctccagaata tgcaaaatac ttac 24

```
<210> SEQ ID NO 295
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295

tacctgtcct tggctcttct ggca                                              24


<210> SEQ ID NO 296
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296

taccatcagt acaaattgct acta                                              24


<210> SEQ ID NO 297
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297

taccataatt cagctttggg atat                                              24


<210> SEQ ID NO 298
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298

tttcaagcct cgggaaactg ccct                                              24


<210> SEQ ID NO 299
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299

tttctttgtt tgcaggtcag tgcc                                              24


<210> SEQ ID NO 300
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300

tttgggctgg cgctcgagct ctcc                                              24


<210> SEQ ID NO 301
```

<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 301
attcctggtt tgggctggcg ctcg 24

<210> SEQ ID NO 302
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 302
attagtgcca ttattgtggc gaat 24

<210> SEQ ID NO 303
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 303
attctcggca ctggcgtgag agtt 24

<210> SEQ ID NO 304
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 304
cttccccgga gtcgaggact gtgg 24

<210> SEQ ID NO 305
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 305
cttcggccac aagatggcac tgac 24

<210> SEQ ID NO 306
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 306
cttataaagt gaggaaaaca aatt 24

<210> SEQ ID NO 307
<211> LENGTH: 24

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 307
ttccccggag tcgaggactg tggg 24

<210> SEQ ID NO 308
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 308
ttcggccaca agatggcact gacc 24

<210> SEQ ID NO 309
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 309
ttcccagcga gccctttgat tcct 24

<210> SEQ ID NO 310
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 310
ctccggggaa ggcagggcag tttc 24

<210> SEQ ID NO 311
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 311
ctccagccgg gtatgacttc ggcc 24

<210> SEQ ID NO 312
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 312
ctcctttctt tggcccactg agaa 24

<210> SEQ ID NO 313
<211> LENGTH: 24
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 313
tttcaggctg tgaaccttgg tggg 24

<210> SEQ ID NO 314
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 314
tttcctgctc cctcctcgcc aatg 24

<210> SEQ ID NO 315
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 315
tttgctagga atattgaagg gggc 24

<210> SEQ ID NO 316
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 316
attgcggcgg gctgcgggcc aggc 24

<210> SEQ ID NO 317
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 317
attacccatc cgcccccgga aact 24

<210> SEQ ID NO 318
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 318
attcctagca aagagggaac ggct 24

<210> SEQ ID NO 319
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 319
cttccccttc attgcggcgg gctg 24

<210> SEQ ID NO 320
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 320
cttccccttc attgcggcgg gctg 24

<210> SEQ ID NO 321
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 321
cttcccctgc ccccttcaat attc 24

<210> SEQ ID NO 322
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 322
gttcacagcc tgaaaattac ccat 24

<210> SEQ ID NO 323
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 323
gttacgtgcg gacagggcct gaga 24

<210> SEQ ID NO 324
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 324
gttggagcgg ggagaaggcc aggg 24

<210> SEQ ID NO 325
<211> LENGTH: 24
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 325
ttccacacgc ggctcgggcc cggg                                              24

<210> SEQ ID NO 326
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
ttcaggctgt gaaccttggt gggg                                              24

<210> SEQ ID NO 327
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
ttcctgctcc ctcctcgcca atgc                                              24

<210> SEQ ID NO 328
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
ttccccttca ttgcggcggg ctgc                                              24

<210> SEQ ID NO 329
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
ttcccctgcc cccttcaata ttcc                                              24

<210> SEQ ID NO 330
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
tccccttcat tgcggcgggc tgcg                                              24

<210> SEQ ID NO 331
<211> LENGTH: 24
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 331
tccctcctcg ccaatgcccc gcgg 24

<210> SEQ ID NO 332
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 332
tcccctgccc ccttcaatat tcct 24

<210> SEQ ID NO 333
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 333
ctcctcgcca atgccccgcg ggcg 24

<210> SEQ ID NO 334
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 334
ctccctcctc gccaatgccc cgcg 24

<210> SEQ ID NO 335
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 335
ctccaggatt ccaatagatc tgtg 24

<210> SEQ ID NO 336
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 336
agggtgtgca gacggcagtc act 23

<210> SEQ ID NO 337
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 337
agggagcagc gtcttcgaga gtg 23

<210> SEQ ID NO 338
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 338
tggggtgagt gagtgtgtgc gtg 23

<210> SEQ ID NO 339
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 339
aggggggcgg atgggtaatt ttc 23

<210> SEQ ID NO 340
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 340
aggggcattg gcgaggaggg agc 23

<210> SEQ ID NO 341
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 341
agggcaaaga gggaacggct ctc 23

<210> SEQ ID NO 342
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 342
tttatccgtg ttccttgact ctgg 24

<210> SEQ ID NO 343
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

```
<400> SEQUENCE: 343

tttccctcac tcctgctcgg tgaa                                          24

<210> SEQ ID NO 344
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344

tttctcatct gtgcccctcc ctcc                                          24

<210> SEQ ID NO 345
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345

tttcagcctc acccctctag ccct                                          24

<210> SEQ ID NO 346
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346

tttcttctcc cctctgctgg atac                                          24

<210> SEQ ID NO 347
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347

tttccgagct tctggcggtc tcaa                                          24

<210> SEQ ID NO 348
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348

tttgtggttg cccaccctag tcat                                          24

<210> SEQ ID NO 349
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
```

tttggtcggc atggccccat tcgc 24

<210> SEQ ID NO 350
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 350
ccagaatgca caaagtactg cac 23

<210> SEQ ID NO 351
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 351
gccaaagccc gagagagtgc c 21

<210> SEQ ID NO 352
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 352
gctgtgtctg taaactgatg gctaaca 27

<210> SEQ ID NO 353
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 353
ttgcattcta ctcaattgca ttctgtggg 29

<210> SEQ ID NO 354
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 354
ggagcagctg gtcagagggg 20

<210> SEQ ID NO 355
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 355

-continued

```
ccatagggaa gggggacact gg                                              22


<210> SEQ ID NO 356
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 356

ctgcctccta ttcatacaca cttacggg                                        28


<210> SEQ ID NO 357
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 357

ctctgttggt ggaaactccc tgacc                                           25


<210> SEQ ID NO 358
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 358

gggccgggaa agagttgctg                                                 20


<210> SEQ ID NO 359
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 359

gccctacatc tgctctccct cc                                              22


<210> SEQ ID NO 360
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 360

ccagcacaac ttactcgcac ttgac                                           25


<210> SEQ ID NO 361
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 361

catcaccaac ccacagccaa gg                                              22
```

<210> SEQ ID NO 362
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 362
cagctccaca aacttggtgc caaattc 27

<210> SEQ ID NO 363
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 363
ccgcaatgaa ggggaagctc gac 23

<210> SEQ ID NO 364
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 364
cgctgttcag gtctctgcta gaagtagg 28

<210> SEQ ID NO 365
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 365
ccagaccaga gaccactggg aag 23

<210> SEQ ID NO 366
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 366
gacaaatgta tcatgctatt ataagatgtt gac 33

<210> SEQ ID NO 367
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 367
ccatttactg agagtaatta taattgtgc 29

<210> SEQ ID NO 368
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 368
ccaaggacag gaatatctta taccctctgt 30

<210> SEQ ID NO 369
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 369
tgtcattgtc cttgtccttt agctaccg 28

<210> SEQ ID NO 370
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 370
caaaacagcc aagcttgcat gc 22

<210> SEQ ID NO 371
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 371
agctgccatc ggtatttcac accgcatacg tac 33

<210> SEQ ID NO 372
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 372
agctggcaac ggtatttcac accgcatacg tac 33

<210> SEQ ID NO 373
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 373
agctgatgcc ggtatttcac accgcatacg tac 33

<210> SEQ ID NO 374
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 374
agctggatgc ggtatttcac accgcatacg tac 33

<210> SEQ ID NO 375
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 375
agctgcgatc ggtatttcac accgcatacg tac 33

<210> SEQ ID NO 376
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (13)..(15)
<223> OTHER INFORMATION: a, c, t, g, unknown or other
<220> FEATURE:
<221> NAME/KEY: misc_feature
<222> LOCATION: (13)..(15)
<223> OTHER INFORMATION: n is a, c, g, or t
<220> FEATURE:
<221> NAME/KEY: modified_base
<222> LOCATION: (18)..(27)
<223> OTHER INFORMATION: a, c, t, g, unknown or other
<220> FEATURE:
<221> NAME/KEY: misc_feature
<222> LOCATION: (18)..(27)
<223> OTHER INFORMATION: n is a, c, g, or t

<400> SEQUENCE: 376
agaccggaat tcnnngtnnn nnnnnnngga atcccttctg cagcacctgg gcgcaggtca 60
cgaggcatg 69

<210> SEQ ID NO 377
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (13)..(15)
<223> OTHER INFORMATION: a, c, t, g, unknown or other
<220> FEATURE:
<221> NAME/KEY: misc_feature
<222> LOCATION: (13)..(15)
<223> OTHER INFORMATION: n is a, c, g, or t
<220> FEATURE:
<221> NAME/KEY: modified_base
<222> LOCATION: (18)..(27)
<223> OTHER INFORMATION: a, c, t, g, unknown or other
<220> FEATURE:
<221> NAME/KEY: misc_feature
<222> LOCATION: (18)..(27)

<223> OTHER INFORMATION: n is a, c, g, or t

<400> SEQUENCE: 377
agaccggaat tcnnngtnnn nnnnnnnctg atggtccatg tctgttactc gcgcaggtca 60
cgaggcatg 69

<210> SEQ ID NO 378
<211> LENGTH: 15
<212> TYPE: DNA
<213> ORGANISM: Artificial Sequence
<220> FEATURE:
<223> OTHER INFORMATION: Description of Artificial Sequence: Synthetic primer

<400> SEQUENCE: 378
cctcgtgacc tgcgc 15

<210> SEQ ID NO 379
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 379
aattctttag gaatcccttc tgcagcacct gggcatg 37

<210> SEQ ID NO 380
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 380
cccaggtgct gcagaaggga ttcctaaag 29

<210> SEQ ID NO 381
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 381
aattccttag gaatcccttc tgcagcacct gggcatg 37

<210> SEQ ID NO 382
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 382
cccaggtgct gcagaaggga ttcctaagg 29

<210> SEQ ID NO 383
<211> LENGTH: 37
<212> TYPE: DNA
<213> ORGANISM: Artificial Sequence
<220> FEATURE:

-continued

<223> OTHER INFORMATION: Description of Artificial Sequence: Synthetic
      oligonucleotide

<400> SEQUENCE: 383
aattcacctg gaatcccttc tgcagcacct gggcatg 37

<210> SEQ ID NO 384
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
cccaggtgct gcagaaggga ttccaggtg 29

<210> SEQ ID NO 385
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
aattctttac tgatggtcca tgtctgttac tcgcatg 37

<210> SEQ ID NO 386
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
cgagtaacag acatggacca tcagtaaag 29

<210> SEQ ID NO 387
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
aattccttac tgatggtcca tgtctgttac tcgcatg 37

<210> SEQ ID NO 388
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
cgagtaacag acatggacca tcagtaagg 29

<210> SEQ ID NO 389
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 389
aattcacctc tgatggtcca tgtctgttac tcgcatg 37

<210> SEQ ID NO 390
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 390
cgagtaacag acatggacca tcagaggtg 29

<210> SEQ ID NO 391
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 391
atggtgagca gagtgcccta tc 22

<210> SEQ ID NO 392
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 392
atggtccctg gcagtctcca aa 22

<210> SEQ ID NO 393
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 393
ccatcggact ctcataggtt gtc 23

<210> SEQ ID NO 394
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 394
gacctgtact tattgtctct catc 24

<210> SEQ ID NO 395
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 395
gcacgtggat cctgagaact 20

<210> SEQ ID NO 396
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 396
attggacagc aagaaagcga g 21

<210> SEQ ID NO 397
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 397
cattatgctg aggatttgga aagg 24

<210> SEQ ID NO 398
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 398
cttgagcaca cagagggcta ca 22

<210> SEQ ID NO 399
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 399
gctccagagc cgtgcgaatg g 21

<210> SEQ ID NO 400
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 400
gccctacatc tgctctccct cc 22

<210> SEQ ID NO 401
<211> LENGTH: 26
<212> TYPE: DNA
<213> ORGANISM: Artificial Sequence
<220> FEATURE:
<223> OTHER INFORMATION: Description of Artificial Sequence: Synthetic primer -continued

<400> SEQUENCE: 401
cagctgaccc aataagtggc agagtg 26

<210> SEQ ID NO 402
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 402
tcaggttggc tgctgggctg g 21

<210> SEQ ID NO 403
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 403
ccccagtggc tgctctggg 19

<210> SEQ ID NO 404
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 404
catcgatgtc ctccccattg gc 22

<210> SEQ ID NO 405
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 405
gctgtctgaa gccatcgctt cc 22

<210> SEQ ID NO 406
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 406
cagaggtatc cagcagaggg gag 23

<210> SEQ ID NO 407
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 407
ccttcggagc gaaaaccaag acag 24

<210> SEQ ID NO 408
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 408
caggcaggac gaatcacact gaatg 25

<210> SEQ ID NO 409
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 409
gctccagagc cgtgcgaatg g 21

<210> SEQ ID NO 410
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 410
gcacctcatg gaatcccttc tgc 23

<210> SEQ ID NO 411
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 411
gaagctggag gaggaagggc 20

<210> SEQ ID NO 412
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 412
cagcagcaag cagcactctg c 21

<210> SEQ ID NO 413
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 413
gccctcttgc ctccactggt tg 22

<210> SEQ ID NO 414
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 414
ccaatagcat tgcagagagg cgt 23

<210> SEQ ID NO 415
<211> LENGTH: 367
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 415
tgtacaaaaa agcaggcttt aaaggaacca attcagtcga ctggatccgg taccaaggtc 60
gggcaggaag agggcctatt tcccatgatt ccttcatatt tgcatatacg atacaaggct 120
gttagagaga taattagaat taatttgact gtaaacacaa agatattagt acaaaatacg 180
tgacgtagaa agtaataatt tcttgggtag tttgcagttt taaaattatg ttttaaaatg 240
gactatcata tgcttaccgt aacttgaaag tatttcgatt tcttggcttt atatatcttg 300
tggaaaggac gaaacaccgt aatttctact cttgtagatg gagacgatta atgcgtctcc 360
ttttttt 367

<210> SEQ ID NO 416
<211> LENGTH: 367
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 416
tgtacaaaaa agcaggcttt aaaggaacca attcagtcga ctggatccgg taccaaggtc 60
gggcaggaag agggcctatt tcccatgatt ccttcatatt tgcatatacg atacaaggct 120
gttagagaga taattagaat taatttgact gtaaacacaa agatattagt acaaaatacg 180
tgacgtagaa agtaataatt tcttgggtag tttgcagttt taaaattatg ttttaaaatg 240
gactatcata tgcttaccgt aacttgaaag tatttcgatt tcttggcttt atatatcttg 300
tggaaaggac gaaacaccga atttctacta agtgtagatg gagacgatta atgcgtctcc 360
ttttttt 367

<210> SEQ ID NO 417
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 417
tgtacaaaaa agcaggcttt aaaggaacca attcagtcga ctggatccgg taccaaggtc 60
gggcaggaag agggcctatt tcccatgatt ccttcatatt tgcatatacg atacaaggct 120
gttagagaga taattagaat taatttgact gtaaacacaa agatattagt acaaaatacg 180
tgacgtagaa agtaataatt tcttgggtag tttgcagttt taaaattatg ttttaaaatg 240
gactatcata tgcttaccgt aacttgaaag tatttcgatt tcttggcttt atatatcttg 300
tggaaaggac gaaacaccga atttctactg ttgtagatgg agacgattaa tgcgtctcct 360
tttttt 366

<210> SEQ ID NO 418
<211> LENGTH: 367
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 418
tgtacaaaaa agcaggcttt aaaggaacca attcagtcga ctggatccgg taccaaggtc 60
gggcaggaag agggcctatt tcccatgatt ccttcatatt tgcatatacg atacaaggct 120
gttagagaga taattagaat taatttgact gtaaacacaa agatattagt acaaaatacg 180
tgacgtagaa agtaataatt tcttgggtag tttgcagttt taaaattatg ttttaaaatg 240
gactatcata tgcttaccgt aacttgaaag tatttcgatt tcttggcttt atatatcttg 300
tggaaaggac gaaacaccga atttctactg tttgtagatg gagacgatta atgcgtctcc 360
ttttttt 367

<210> SEQ ID NO 419
<211> LENGTH: 120
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 419
taatacgact cactatagta atttctactc ttgtagatgg agacccatgc catagcgttg 60
ttcggaatat gaatttttga acagattcac caacacctag tggtctcctt taaaaagctt 120

<210> SEQ ID NO 420
<211> LENGTH: 120
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 420
taatacgact cactatagaa tttctactaa gtgtagatgg agacccatgc catagcgttg 60
ttcggaatat gaatttttga acagattcac caacacctag tggtctcctt taaaaagctt 120

<210> SEQ ID NO 421
<211> LENGTH: 4059
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 421
atgacacagt tcgagggctt taccaacctg tatcaggtga gcaagacact gcggtttgag 60

-continued

```
ctgatcccac agggcaagac cctgaagcac atccaggagc agggcttcat cgaggaggac    120
aaggcccgca atgatcacta caaggagctg aagcccatca tcgatcggat ctacaagacc    180
tatgccgacc agtgcctgca gctggtgcag ctggattggg agaacctgag cgccgccatc    240
gactcctata gaaaggagaa aaccgaggag acaaggaacg ccctgatcga ggagcaggcc    300
acatatcgca atgccatcca cgactacttc atcggccgga cagacaacct gaccgatgcc    360
atcaataaga gacacgccga gatctacaag ggcctgttca aggccgagct gtttaatggc    420
aaggtgctga agcagctggg caccgtgacc acaaccgagc acgagaacgc cctgctgcgg    480
agcttcgaca agtttacaac ctacttctcc ggcttttatg agaacaggaa gaacgtgttc    540
agcgccgagg atatcagcac agccatccca caccgcatcg tgcaggacaa cttccccaag    600
tttaaggaga attgtcacat cttcacacgc ctgatcaccg ccgtgcccag cctgcgggag    660
cactttgaga acgtgaagaa ggccatcggc atcttcgtga gcacctccat cgaggaggtg    720
ttttccttcc ctttttataa ccagctgctg acacagaccc agatcgacct gtataaccag    780
ctgctgggag gaatctctcg ggaggcaggc accgagaaga tcaagggcct gaacgaggtg    840
ctgaatctgg ccatccagaa gaatgatgag acagcccaca tcatcgcctc cctgccacac    900
agattcatcc ccctgtttaa gcagatcctg tccgatagga acaccctgtc tttcatcctg    960
gaggagttta agagcgacga ggaagtgatc cagtccttct gcaagtacaa gacactgctg   1020
agaaacgaga acgtgctgga gacagccgag gccctgttta acgagctgaa cagcatcgac   1080
ctgacacaca tcttcatcag ccacaagaag ctggagacaa tcagcagcgc cctgtgcgac   1140
cactgggata cactgaggaa tgccctgtat gagcggagaa tctccgagct gacaggcaag   1200
atcaccaagt ctgccaagga gaaggtgcag cgcagcctga agcacgagga tatcaacctg   1260
caggagatca tctctgccgc aggcaaggag ctgagcgagg ccttcaagca gaaaaccagc   1320
gagatcctgt cccacgcaca cgccgccctg gatcagccac tgcctacaac cctgaagaag   1380
caggaggaga aggagatcct gaagtctcag ctggacagcc tgctgggcct gtaccacctg   1440
ctggactggt ttgccgtgga tgagtccaac gaggtggacc ccgagttctc tgcccggctg   1500
accggcatca agctggagat ggagccttct ctgagcttct acaacaaggc cagaaattat   1560
gccaccaaga agccctactc cgtggagaag ttcaagctga actttcagat gcctacactg   1620
gcctctggct gggacgtgaa taaggagaag aacaatggcg ccatcctgtt tgtgaagaac   1680
ggcctgtact atctgggcat catgccaaag cagaagggca ggtataaggc cctgagcttc   1740
gagcccacag agaaaaccag cgagggcttt gataagatgt actatgacta cttccctgat   1800
gccgccaaga tgatcccaaa gtgcagcacc cagctgaagg ccgtgacagc ccactttcag   1860
acccacacaa cccccatcct gctgtccaac aatttcatcg agcctctgga gatcacaaag   1920
gagatctacg acctgaacaa tcctgagaag gagccaaaga agtttcagac agcctacgcc   1980
aagaaaaccg gcgaccagaa gggctacaga gaggccctgt gcaagtggat cgacttcaca   2040
agggattttc tgtccaagta taccaagaca acctctatcg atctgtctag cctgcggcca   2100
tcctctcagt ataaggacct gggcgagtac tatgccgagc tgaatcccct gctgtaccac   2160
atcagcttcc agagaatcgc cgagaaggag atcatggatg ccgtggagac aggcaagctg   2220
tacctgttcc agatctataa caaggacttt gccaagggcc accacggcaa gcctaatctg   2280
cacacactgt attggaccgg cctgttttct ccagagaacc tggccaagac aagcatcaag   2340
ctgaatggcc aggccgagct gttctaccgc cctaagtcca ggatgaagag gatggcacac   2400
cggctgggag agaagatgct gaacaagaag ctgaaggatc agaaaacccc aatccccgac   2460
```

accctgtacc aggagctgta cgactatgtg aatcacagac tgtcccacga cctgtctgat 2520
gaggccaggg ccctgctgcc caacgtgatc accaaggagg tgtctcacga gatcatcaag 2580
gataggcgct ttaccagcga caagttcttt ttccacgtgc ctatcacact gaactatcag 2640
gccgccaatt ccccatctaa gttcaaccag agggtgaatg cctacctgaa ggagcacccc 2700
gagacaccta tcatcggcat cgatcggggc gagagaaacc tgatctatat cacagtgatc 2760
gactccaccg gcaagatcct ggagcagcgg agcctgaaca ccatccagca gtttgattac 2820
cagaagaagc tggacaacag ggagaaggag agggtggcag caaggcaggc ctggtctgtg 2880
gtgggcacaa tcaaggatct gaagcagggc tatctgagcc aggtcatcca cgagatcgtg 2940
gacctgatga tccactacca ggccgtggtg gtgctggaga acctgaattt cggctttaag 3000
agcaagagga ccggcatcgc cgagaaggcc gtgtaccagc agttcgagaa gatgctgatc 3060
gataagctga attgcctggt gctgaaggac tatccagcag agaaagtggg aggcgtgctg 3120
aacccatacc agctgacaga ccagttcacc tcctttgcca agatgggcac ccagtctggc 3180
ttcctgtttt acgtgcctgc cccatataca tctaagatcg atcccctgac cggcttcgtg 3240
gaccccttcg tgtggaaaac catcaagaat cacgagagcc gcaagcactt cctggagggc 3300
ttcgactttc tgcactacga cgtgaaaacc ggcgacttca tcctgcactt taagatgaac 3360
agaaatctgt ccttccagag gggcctgccc ggctttatgc ctgcatggga tatcgtgttc 3420
gagaagaacg agacacagtt tgacgccaag ggcacccctt tcatcgccgg caagagaatc 3480
gtgccagtga tcgagaatca cagattcacc ggcagatacc gggacctgta tcctgccaac 3540
gagctgatcg ccctgctgga ggagaagggc atcgtgttca gggatggctc caacatcctg 3600
ccaaagctgc tggagaatga cgattctcac gccatcgaca ccatggtggc cctgatccgc 3660
agcgtgctgc agatgcggaa ctccaatgcc gccacaggcg aggactatat caacagcccc 3720
gtgcgcgatc tgaatggcgt gtgcttcgac tcccggtttc agaacccaga gtggcccatg 3780
gacgccgatg ccaatggcgc ctaccacatc gccctgaagg gccagctgct gctgaatcac 3840
ctgaaggaga gcaaggatct gaagctgcag aacggcatct ccaatcagga ctggctggcc 3900
tacatccagg agctgcgcaa caaaaggccg gcggccacga aaaaggccgg ccaggcaaaa 3960
aagaaaaagg gatcctaccc atacgatgtt ccagattacg cttatcccta cgacgtgcct 4020
gattatgcat acccatatga tgtccccgac tatgcctaa 4059

<210> SEQ ID NO 422
<211> LENGTH: 4059
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 422
atgacacagt tcgagggctt taccaacctg tatcaggtga gcaagacact gcggtttgag 60
ctgatcccac agggcaagac cctgaagcac atccaggagc agggcttcat cgaggaggac 120
aaggcccgca atgatcacta caaggagctg aagcccatca tcgatcggat ctacaagacc 180
tatgccgacc agtgcctgca gctggtgcag ctggattggg agaacctgag cgccgccatc 240
gactcctata gaaaggagaa aaccgaggag acaaggaacg ccctgatcga ggagcaggcc 300
acatatcgca atgccatcca cgactacttc atcggccgga cagacaacct gaccgatgcc 360
atcaataaga gacacgccga gatctacaag ggcctgttca aggccgagct gtttaatggc 420

-continued

```
aaggtgctga agcagctggg caccgtgacc acaaccgagc acgagaacgc cctgctgcgg    480
agcttcgaca agtttacaac ctacttctcc ggcttttata gaaacaggaa gaacgtgttc    540
agcgccgagg atatcagcac agccatccca caccgcatcg tgcaggacaa cttccccaag    600
tttaaggaga attgtcacat cttcacacgc ctgatcaccg ccgtgcccag cctgcgggag    660
cactttgaga acgtgaagaa ggccatcggc atcttcgtga gcacctccat cgaggaggtg    720
ttttccttcc ctttttataa ccagctgctg acacagaccc agatcgacct gtataaccag    780
ctgctgggag gaatctctcg ggaggcaggc accgagaaga tcaagggcct gaacgaggtg    840
ctgaatctgg ccatccagaa gaatgatgag acagcccaca tcatcgcctc cctgccacac    900
agattcatcc ccctgtttaa gcagatcctg tccgatagga acaccctgtc tttcatcctg    960
gaggagttta agagcgacga ggaagtgatc cagtccttct gcaagtacaa gacactgctg   1020
agaaacgaga acgtgctgga gacagccgag gccctgttta acgagctgaa cagcatcgac   1080
ctgacacaca tcttcatcag ccacaagaag ctggagacaa tcagcagcgc cctgtgcgac   1140
cactgggata cactgaggaa tgccctgtat gagcggagaa tctccgagct gacaggcaag   1200
atcaccaagt ctgccaagga gaaggtgcag cgcagcctga agcacgagga tatcaacctg   1260
caggagatca tctctgccgc aggcaaggag ctgagcgagg ccttcaagca gaaaaccagc   1320
gagatcctgt cccacgcaca cgccgccctg gatcagccac tgcctacaac cctgaagaag   1380
caggaggaga aggagatcct gaagtctcag ctggacagcc tgctgggcct gtaccacctg   1440
ctggactggt ttgccgtgga tgagtccaac gaggtggacc ccgagttctc tgcccggctg   1500
accggcatca agctggagat ggagccttct ctgagcttct acaacaaggc cagaaattat   1560
gccaccaaga agccctactc cgtggagaag ttcaagctga actttcagat gcctacactg   1620
gccagaggct gggacgtgaa taaggagaag aacaatggcg ccatcctgtt tgtgaagaac   1680
ggcctgtact atctgggcat catgccaaag cagaagggca ggtataaggc cctgagcttc   1740
gagcccacag agaaaaccag cgagggcttt gataagatgt actatgacta cttccctgat   1800
gccgccaaga tgatcccaaa gtgcagcacc cagctgaagg ccgtgacagc ccactttcag   1860
acccacacaa cccccatcct gctgtccaac aatttcatcg agcctctgga gatcacaaag   1920
gagatctacg acctgaacaa tcctgagaag gagccaaaga agtttcagac agcctacgcc   1980
aagaaaaccg gcgaccagaa gggctacaga gaggccctgt gcaagtggat cgacttcaca   2040
agggattttc tgtccaagta taccaagaca acctctatcg atctgtctag cctgcggcca   2100
tcctctcagt ataaggacct gggcgagtac tatgccgagc tgaatcccct gctgtaccac   2160
atcagcttcc agagaatcgc cgagaaggag atcatggatg ccgtggagac aggcaagctg   2220
tacctgttcc agatctataa caaggacttt gccaagggcc accacggcaa gcctaatctg   2280
cacacactgt attggaccgg cctgttttct ccagagaacc tggccaagac aagcatcaag   2340
ctgaatggcc aggccgagct gttctaccgc cctaagtcca ggatgaagag gatggcacac   2400
cggctgggag agaagatgct gaacaagaag ctgaaggatc agaaaacccc aatccccgac   2460
accctgtacc aggagctgta cgactatgtg aatcacagac tgtcccacga cctgtctgat   2520
gaggccaggg ccctgctgcc caacgtgatc accaaggagg tgtctcacga gatcatcaag   2580
gataggcgct ttaccagcga caagttcttt ttccacgtgc ctatcacact gaactatcag   2640
gccgccaatt ccccatctaa gttcaaccag agggtgaatg cctacctgaa ggagcacccc   2700
gagacaccta tcatcggcat cgatcggggc gagagaaacc tgatctatat cacagtgatc   2760
```

gactccaccg gcaagatcct ggagcagcgg agcctgaaca ccatccagca gtttgattac 2820
cagaagaagc tggacaacag ggagaaggag agggtggcag caaggcaggc ctggtctgtg 2880
gtgggcacaa tcaaggatct gaagcagggc tatctgagcc aggtcatcca cgagatcgtg 2940
gacctgatga tccactacca ggccgtggtg gtgctggaga acctgaattt cggctttaag 3000
agcaagagga ccggcatcgc cgagaaggcc gtgtaccagc agttcgagaa gatgctgatc 3060
gataagctga attgcctggt gctgaaggac tatccagcag agaaagtggg aggcgtgctg 3120
aacccatacc agctgacaga ccagttcacc tcctttgcca agatgggcac ccagtctggc 3180
ttcctgtttt acgtgcctgc cccatataca tctaagatcg atcccctgac cggcttcgtg 3240
gaccccttcg tgtggaaaac catcaagaat cacgagagcc gcaagcactt cctggagggc 3300
ttcgactttc tgcactacga cgtgaaaacc ggcgacttca tcctgcactt taagatgaac 3360
agaaatctgt ccttccagag gggcctgccc ggctttatgc ctgcatggga tatcgtgttc 3420
gagaagaacg agacacagtt tgacgccaag ggcacccctt tcatcgccgg caagagaatc 3480
gtgccagtga tcgagaatca cagattcacc ggcagatacc gggacctgta tcctgccaac 3540
gagctgatcg ccctgctgga ggagaagggc atcgtgttca gggatggctc caacatcctg 3600
ccaaagctgc tggagaatga cgattctcac gccatcgaca ccatggtggc cctgatccgc 3660
agcgtgctgc agatgcggaa ctccaatgcc gccacaggcg aggactatat caacagcccc 3720
gtgcgcgatc tgaatggcgt gtgcttcgac tcccggtttc agaacccaga gtggcccatg 3780
gacgccgatg ccaatggcgc ctaccacatc gccctgaagg gccagctgct gctgaatcac 3840
ctgaaggaga gcaaggatct gaagctgcag aacggcatct ccaatcagga ctggctggcc 3900
tacatccagg agctgcgcaa caaaaggccg gcggccacga aaaaggccgg ccaggcaaaa 3960
aagaaaaagg gatcctaccc atacgatgtt ccagattacg cttatcccta cgacgtgcct 4020
gattatgcat acccatatga tgtccccgac tatgcctaa 4059

<210> SEQ ID NO 423
<211> LENGTH: 4059
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 423
atgacacagt tcgagggctt taccaacctg tatcaggtga gcaagacact gcggtttgag 60
ctgatcccac agggcaagac cctgaagcac atccaggagc agggcttcat cgaggaggac 120
aaggcccgca atgatcacta caaggagctg aagcccatca tcgatcggat ctacaagacc 180
tatgccgacc agtgcctgca gctggtgcag ctggattggg agaacctgag cgccgccatc 240
gactcctata gaaaggagaa aaccgaggag acaaggaacg ccctgatcga ggagcaggcc 300
acatatcgca atgccatcca cgactacttc atcggccgga cagacaacct gaccgatgcc 360
atcaataaga gacacgccga gatctacaag ggcctgttca aggccgagct gtttaatggc 420
aaggtgctga agcagctggg caccgtgacc acaaccgagc acgagaacgc cctgctgcgg 480
agcttcgaca agtttacaac ctacttctcc ggcttttata gaaacaggaa gaacgtgttc 540
agcgccgagg atatcagcac agccatccca caccgcatcg tgcaggacaa cttccccaag 600
tttaaggaga attgtcacat cttcacacgc ctgatcaccg ccgtgcccag cctgcgggag 660
cactttgaga acgtgaagaa ggccatcggc atcttcgtga gcacctccat cgaggaggtg 720

-continued

```
ttttccttcc ctttttataa ccagctgctg acacagaccc agatcgacct gtataaccag    780
ctgctgggag gaatctctcg ggaggcaggc accgagaaga tcaagggcct gaacgaggtg    840
ctgaatctgg ccatccagaa gaatgatgag acagcccaca tcatcgcctc cctgccacac    900
agattcatcc ccctgtttaa gcagatcctg tccgatagga acaccctgtc tttcatcctg    960
gaggagttta agagcgacga ggaagtgatc cagtccttct gcaagtacaa gacactgctg   1020
agaaacgaga acgtgctgga gacagccgag gccctgttta acgagctgaa cagcatcgac   1080
ctgacacaca tcttcatcag ccacaagaag ctggagacaa tcagcagcgc cctgtgcgac   1140
cactgggata cactgaggaa tgccctgtat gagcggagaa tctccgagct gacaggcaag   1200
atcaccaagt ctgccaagga gaaggtgcag cgcagcctga agcacgagga tatcaacctg   1260
caggagatca tctctgccgc aggcaaggag ctgagcgagg ccttcaagca gaaaaccagc   1320
gagatcctgt cccacgcaca cgccgccctg gatcagccac tgcctacaac cctgaagaag   1380
caggaggaga aggagatcct gaagtctcag ctggacagcc tgctgggcct gtaccacctg   1440
ctggactggt ttgccgtgga tgagtccaac gaggtggacc ccgagttctc tgcccggctg   1500
accggcatca agctggagat ggagccttct ctgagcttct acaacaaggc cagaaattat   1560
gccaccaaga agccctactc cgtggagaag ttcaagctga actttcagat gcctacactg   1620
gccagaggct gggacgtgaa tagagagaag aacaatggcg ccatcctgtt tgtgaagaac   1680
ggcctgtact atctgggcat catgccaaag cagaagggca ggtataaggc cctgagcttc   1740
gagcccacag agaaaaccag cgagggcttt gataagatgt actatgacta cttccctgat   1800
gccgccaaga tgatcccaaa gtgcagcacc cagctgaagg ccgtgacagc ccactttcag   1860
acccacacaa cccccatcct gctgtccaac aatttcatcg agcctctgga gatcacaaag   1920
gagatctacg acctgaacaa tcctgagaag gagccaaaga agtttcagac agcctacgcc   1980
aagaaaaccg gcgaccagaa gggctacaga gaggccctgt gcaagtggat cgacttcaca   2040
agggattttc tgtccaagta taccaagaca acctctatcg atctgtctag cctgcggcca   2100
tcctctcagt ataaggacct gggcgagtac tatgccgagc tgaatcccct gctgtaccac   2160
atcagcttcc agagaatcgc cgagaaggag atcatggatg ccgtggagac aggcaagctg   2220
tacctgttcc agatctataa caaggacttt gccaagggcc accacggcaa gcctaatctg   2280
cacacactgt attggaccgg cctgttttct ccagagaacc tggccaagac aagcatcaag   2340
ctgaatggcc aggccgagct gttctaccgc cctaagtcca ggatgaagag gatggcacac   2400
cggctgggag agaagatgct gaacaagaag ctgaaggatc agaaaacccc aatccccgac   2460
accctgtacc aggagctgta cgactatgtg aatcacagac tgtcccacga cctgtctgat   2520
gaggccaggg ccctgctgcc caacgtgatc accaaggagg tgtctcacga gatcatcaag   2580
gataggcgct ttaccagcga caagttcttt ttccacgtgc ctatcacact gaactatcag   2640
gccgccaatt ccccatctaa gttcaaccag agggtgaatg cctacctgaa ggagcacccc   2700
gagacaccta tcatcggcat cgatcggggc gagagaaacc tgatctatat cacagtgatc   2760
gactccaccg gcaagatcct ggagcagcgg agcctgaaca ccatccagca gtttgattac   2820
cagaagaagc tggacaacag ggagaaggag agggtggcag caaggcaggc ctggtctgtg   2880
gtgggcacaa tcaaggatct gaagcagggc tatctgagcc aggtcatcca cgagatcgtg   2940
gacctgatga tccactacca ggccgtggtg gtgctggaga acctgaattt cggctttaag   3000
agcaagagga ccggcatcgc cgagaaggcc gtgtaccagc agttcgagaa gatgctgatc   3060
gataagctga attgcctggt gctgaaggac tatccagcag agaaagtggg aggcgtgctg   3120
```

```
aacccatacc agctgacaga ccagttcacc tcctttgcca agatgggcac ccagtctggc   3180

ttcctgtttt acgtgcctgc cccatataca tctaagatcg atcccctgac cggcttcgtg   3240

gaccccttcg tgtggaaaac catcaagaat cacgagagcc gcaagcactt cctggagggc   3300

ttcgactttc tgcactacga cgtgaaaacc ggcgacttca tcctgcactt taagatgaac   3360

agaaatctgt ccttccagag gggcctgccc ggctttatgc ctgcatggga tatcgtgttc   3420

gagaagaacg agacacagtt tgacgccaag ggcacccctt tcatcgccgg caagagaatc   3480

gtgccagtga tcgagaatca cagattcacc ggcagatacc gggacctgta tcctgccaac   3540

gagctgatcg ccctgctgga ggagaagggc atcgtgttca gggatggctc caacatcctg   3600

ccaaagctgc tggagaatga cgattctcac gccatcgaca ccatggtggc cctgatccgc   3660

agcgtgctgc agatgcggaa ctccaatgcc gccacaggcg aggactatat caacagcccc   3720

gtgcgcgatc tgaatggcgt gtgcttcgac tcccggtttc agaacccaga gtggcccatg   3780

gacgccgatg ccaatggcgc ctaccacatc gccctgaagg gccagctgct gctgaatcac   3840

ctgaaggaga gcaaggatct gaagctgcag aacggcatct ccaatcagga ctggctggcc   3900

tacatccagg agctgcgcaa caaaaggccg gcggccacga aaaaggccgg ccaggcaaaa   3960

aagaaaaagg gatcctaccc atacgatgtt ccagattacg cttatcccta cgacgtgcct   4020

gattatgcat acccatatga tgtccccgac tatgcctaa                          4059
```

<210> SEQ ID NO 424
<211> LENGTH: 4059
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 424

```
atgacacagt tcgagggctt taccaacctg tatcaggtga gcaagacact gcggtttgag     60

ctgatcccac agggcaagac cctgaagcac atccaggagc agggcttcat cgaggaggac    120

aaggcccgca atgatcacta caaggagctg aagcccatca tcgatcggat ctacaagacc    180

tatgccgacc agtgcctgca gctggtgcag ctggattggg agaacctgag cgccgccatc    240

gactcctata gaaaggagaa aaccgaggag acaaggaacg ccctgatcga ggagcaggcc    300

acatatcgca atgccatcca cgactacttc atcggccgga cagacaacct gaccgatgcc    360

atcaataaga gacacgccga gatctacaag ggcctgttca aggccgagct gtttaatggc    420

aaggtgctga agcagctggg caccgtgacc acaaccgagc acgagaacgc cctgctgcgg    480

agcttcgaca agtttacaac ctacttctcc ggcttttata gaaacaggaa gaacgtgttc    540

agcgccgagg atatcagcac agccatccca caccgcatcg tgcaggacaa cttccccaag    600

tttaaggaga attgtcacat cttcacacgc ctgatcaccg ccgtgcccag cctgcgggag    660

cactttgaga acgtgaagaa ggccatcggc atcttcgtga gcacctccat cgaggaggtg    720

ttttccttcc ctttttataa ccagctgctg acacagaccc agatcgacct gtataaccag    780

ctgctgggag gaatctctcg ggaggcaggc accgagaaga tcaagggcct gaacgaggtg    840

ctggccctgg ccatccagaa gaatgatgag acagcccaca tcatcgcctc cctgccacac    900

agattcatcc ccctgtttaa gcagatcctg tccgatagga acaccctgtc tttcatcctg    960

gaggagttta agagcgacga ggaagtgatc cagtccttct gcaagtacaa gacactgctg   1020

agaaacgaga acgtgctgga gacagccgag gccctgttta acgagctgaa cagcatcgac   1080
```

ctgacacaca tcttcatcag ccacaagaag ctggagacaa tcagcagcgc cctgtgcgac 1140
cactgggata cactgaggaa tgccctgtat gagcggagaa tctccgagct gacaggcaag 1200
atcaccaagt ctgccaagga gaaggtgcag cgcagcctga agcacgagga tatcaacctg 1260
caggagatca tctctgccgc aggcaaggag ctgagcgagg ccttcaagca gaaaaccagc 1320
gagatcctgt cccacgcaca cgccgccctg gatcagccac tgcctacaac cctgaagaag 1380
caggaggaga aggagatcct gaagtctcag ctggacagcc tgctgggcct gtaccacctg 1440
ctggactggt ttgccgtgga tgagtccaac gaggtggacc ccgagttctc tgcccggctg 1500
accggcatca agctggagat ggagccttct ctgagcttct acaacaaggc cagaaattat 1560
gccaccaaga agccctactc cgtggagaag ttcaagctga actttcagat gcctacactg 1620
gccagaggct gggacgtgaa tagagagaag aacaatggcg ccatcctgtt tgtgaagaac 1680
ggcctgtact atctgggcat catgccaaag cagaagggca ggtataaggc cctgagcttc 1740
gagcccacag agaaaaccag cgagggcttt gataagatgt actatgacta cttccctgat 1800
gccgccaaga tgatcccaaa gtgcagcacc cagctgaagg ccgtgacagc ccactttcag 1860
acccacacaa cccccatcct gctgtccaac aatttcatcg agcctctgga gatcacaaag 1920
gagatctacg acctgaacaa tcctgagaag gagccaaaga agtttcagac agcctacgcc 1980
aagaaaaccg gcgaccagaa gggctacaga gaggccctgt gcaagtggat cgacttcaca 2040
agggattttc tgtccaagta taccaagaca acctctatcg atctgtctag cctgcggcca 2100
tcctctcagt ataaggacct gggcgagtac tatgccgagc tgaatcccct gctgtaccac 2160
atcagcttcc agagaatcgc cgagaaggag atcatggatg ccgtggagac aggcaagctg 2220
tacctgttcc agatctataa caaggacttt gccaagggcc accacggcaa gcctaatctg 2280
cacacactgt attggaccgg cctgttttct ccagagaacc tggccaagac aagcatcaag 2340
ctgaatggcc aggccgagct gttctaccgc cctaagtcca ggatgaagag gatggcacac 2400
cggctgggag agaagatgct gaacaagaag ctgaaggatc agaaaacccc aatccccgac 2460
accctgtacc aggagctgta cgactatgtg aatcacagac tgtcccacga cctgtctgat 2520
gaggccaggg ccctgctgcc caacgtgatc accaaggagg tgtctcacga gatcatcaag 2580
gataggcgct ttaccagcga caagttcttt ttccacgtgc ctatcacact gaactatcag 2640
gccgccaatt ccccatctaa gttcaaccag agggtgaatg cctacctgaa ggagcacccc 2700
gagacaccta tcatcggcat cgatcggggc gagagaaacc tgatctatat cacagtgatc 2760
gactccaccg gcaagatcct ggagcagcgg agcctgaaca ccatccagca gtttgattac 2820
cagaagaagc tggacaacag ggagaaggag agggtggcag caaggcaggc ctggtctgtg 2880
gtgggcacaa tcaaggatct gaagcagggc tatctgagcc aggtcatcca cgagatcgtg 2940
gacctgatga tccactacca ggccgtggtg gtgctggaga acctgaattt cggctttaag 3000
agcaagagga ccggcatcgc cgagaaggcc gtgtaccagc agttcgagaa gatgctgatc 3060
gataagctga attgcctggt gctgaaggac tatccagcag agaaagtggg aggcgtgctg 3120
aacccatacc agctgacaga ccagttcacc tcctttgcca agatgggcac ccagtctggc 3180
ttcctgtttt acgtgcctgc cccatataca tctaagatcg atcccctgac cggcttcgtg 3240
gacccettcg tgtggaaaac catcaagaat cacgagagcc gcaagcactt cctggagggc 3300
ttcgactttc tgcactacga cgtgaaaacc ggcgacttca tcctgcactt taagatgaac 3360
agaaatctgt ccttccagag gggcctgccc ggctttatgc ctgcatggga tatcgtgttc 3420

-continued

```
gagaagaacg agacacagtt tgacgccaag ggcacccctt tcatcgccgg caagagaatc   3480

gtgccagtga tcgagaatca cagattcacc ggcagatacc gggacctgta tcctgccaac   3540

gagctgatcg ccctgctgga ggagaagggc atcgtgttca gggatggctc caacatcctg   3600

ccaaagctgc tggagaatga cgattctcac gccatcgaca ccatggtggc cctgatccgc   3660

agcgtgctgc agatgcggaa ctccaatgcc gccacaggcg aggactatat caacagcccc   3720

gtgcgcgatc tgaatggcgt gtgcttcgac tcccggtttc agaacccaga gtggcccatg   3780

gacgccgatg ccaatggcgc ctaccacatc gccctgaagg gccagctgct gctgaatcac   3840

ctgaaggaga gcaaggatct gaagctgcag aacggcatct ccaatcagga ctggctggcc   3900

tacatccagg agctgcgcaa caaaaggccg gcggccacga aaaaggccgg ccaggcaaaa   3960

aagaaaaagg gatcctaccc atacgatgtt ccagattacg cttatcccta cgacgtgcct   4020

gattatgcat acccatatga tgtccccgac tatgcctaa                          4059
```

<210> SEQ ID NO 425
<211> LENGTH: 4011
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 425

```
atggggacac agttcgaggg ctttaccaac ctgtatcagg tgagcaagac actgcggttt     60

gagctgatcc cacagggcaa gaccctgaag cacatccagg agcagggctt catcgaggag    120

gacaaggccc gcaatgatca ctacaaggag ctgaagccca tcatcgatcg gatctacaag    180

acctatgccg accagtgcct gcagctggtg cagctggatt gggagaacct gagcgccgcc    240

atcgactcct atagaaagga gaaaaccgag gagacaagga acgccctgat cgaggagcag    300

gccacatatc gcaatgccat ccacgactac ttcatcggcc ggacagacaa cctgaccgat    360

gccatcaata agagacacgc cgagatctac aagggcctgt tcaaggccga gctgtttaat    420

ggcaaggtgc tgaagcagct gggcaccgtg accacaaccg agcacgagaa cgccctgctg    480

cggagcttcg acaagtttac aacctacttc tccggctttt atgagaacag gaagaacgtg    540

ttcagcgccg aggatatcag cacagccatc ccacaccgca tcgtgcagga caacttcccc    600

aagtttaagg agaattgtca catcttcaca cgcctgatca ccgccgtgcc cagcctgcgg    660

gagcactttg agaacgtgaa gaaggccatc ggcatcttcg tgagcacctc catcgaggag    720

gtgttttcct tccctttta taaccagctg ctgacacaga cccagatcga cctgtataac    780

cagctgctgg gaggaatctc tcgggaggca ggcaccgaga agatcaaggg cctgaacgag    840

gtgctgaatc tggccatcca gaagaatgat gagacagccc acatcatcgc ctccctgcca    900

cacagattca tcccccctgtt taagcagatc ctgtccgata ggaacaccct gtctttcatc    960

ctggaggagt ttaagagcga cgaggaagtg atccagtcct tctgcaagta caagacactg   1020

ctgagaaacg agaacgtgct ggagacagcc gaggccctgt ttaacgagct gaacagcatc   1080

gacctgacac acatcttcat cagccacaag aagctggaga caatcagcag cgccctgtgc   1140

gaccactggg atacactgag gaatgccctg tatgagcgga gaatctccga gctgacaggc   1200

aagatcacca agtctgccaa ggagaaggtg cagcgcagcc tgaagcacga ggatatcaac   1260

ctgcaggaga tcatctctgc cgcaggcaag gagctgagcg aggccttcaa gcagaaaacc   1320

agcgagatcc tgtcccacgc acacgccgcc ctggatcagc cactgcctac aaccctgaag   1380
```

-continued

```
aagcaggagg agaaggagat cctgaagtct cagctggaca gcctgctggg cctgtaccac   1440
ctgctggact ggtttgccgt ggatgagtcc aacgaggtgg accccgagtt ctctgcccgg   1500
ctgaccggca tcaagctgga gatggagcct tctctgagct tctacaacaa ggccagaaat   1560
tatgccacca agaagcccta ctccgtggag aagttcaagc tgaactttca gatgcctaca   1620
ctggcctctg gctgggacgt gaataaggag aagaacaatg gcgccatcct gtttgtgaag   1680
aacggcctgt actatctggg catcatgcca aagcagaagg gcaggtataa ggccctgagc   1740
ttcgagccca cagagaaaac cagcgagggc tttgataaga tgtactatga ctacttccct   1800
gatgccgcca agatgatccc aaagtgcagc acccagctga aggccgtgac agcccacttt   1860
cagacccaca caacccccat cctgctgtcc aacaatttca tcgagcctct ggagatcaca   1920
aaggagatct acgacctgaa caatcctgag aaggagccaa agaagtttca gacagcctac   1980
gccaagaaaa ccggcgacca gaagggctac agagaggccc tgtgcaagtg gatcgacttc   2040
acaagggatt ttctgtccaa gtataccaag acaacctcta tcgatctgtc tagcctgcgg   2100
ccatcctctc agtataagga cctgggcgag tactatgccg agctgaatcc cctgctgtac   2160
cacatcagct tccagagaat cgccgagaag gagatcatgg atgccgtgga gacaggcaag   2220
ctgtacctgt tccagatcta taacaaggac tttgccaagg gccaccacgg caagcctaat   2280
ctgcacacac tgtattggac cggcctgttt tctccagaga acctggccaa gacaagcatc   2340
aagctgaatg gccaggccga gctgttctac cgccctaagt ccaggatgaa gaggatggca   2400
caccggctgg gagagaagat gctgaacaag aagctgaagg atcagaaaac cccaatcccc   2460
gacaccctgt accaggagct gtacgactat gtgaatcaca gactgtccca cgacctgtct   2520
gatgaggcca gggccctgct gcccaacgtg atcaccaagg aggtgtctca cgagatcatc   2580
aaggataggc gctttaccag cgacaagttc tttttccacg tgcctatcac actgaactat   2640
caggccgcca attccccatc taagttcaac cagagggtga atgcctacct gaaggagcac   2700
cccgagacac ctatcatcgg catcgatcgg ggcgagagaa acctgatcta tatcacagtg   2760
atcgactcca ccggcaagat cctggagcag cggagcctga acaccatcca gcagtttgat   2820
taccagaaga agctggacaa cagggagaag gagagggtgg cagcaaggca ggcctggtct   2880
gtggtgggca caatcaagga tctgaagcag ggctatctga gccaggtcat ccacgagatc   2940
gtggacctga tgatccacta ccaggccgtg gtggtgctgg agaacctgaa tttcggcttt   3000
aagagcaaga ggaccggcat cgccgagaag gccgtgtacc agcagttcga gaagatgctg   3060
atcgataagc tgaattgcct ggtgctgaag gactatccag cagagaaagt gggaggcgtg   3120
ctgaacccat accagctgac agaccagttc acctcctttg ccaagatggg cacccagtct   3180
ggcttcctgt tttacgtgcc tgccccatat acatctaaga tcgatcccct gaccggcttc   3240
gtggacccct tcgtgtggaa aaccatcaag aatcacgaga gccgcaagca cttcctggag   3300
ggcttcgact ttctgcacta cgacgtgaaa accggcgact tcatcctgca ctttaagatg   3360
aacagaaatc tgtccttcca gaggggcctg cccggcttta tgcctgcatg ggatatcgtg   3420
ttcgagaaga acgagacaca gtttgacgcc aagggcaccc ctttcatcgc cggcaagaga   3480
atcgtgccag tgatcgagaa tcacagattc accggcagat accgggacct gtatcctgcc   3540
aacgagctga tcgccctgct ggaggagaag ggcatcgtgt tcagggatgg ctccaacatc   3600
ctgccaaagc tgctggagaa tgacgattct cacgccatcg acacgatggt ggccctgatc   3660
cgcagcgtgc tgcagatgcg gaactccaat gccgccacag gcgaggacta tatcaacagc   3720
cccgtgcgcg atctgaatgg cgtgtgcttc gactcccggt ttcagaaccc agagtggcca   3780
```

atggacgccg atgccaatgg cgcctaccac atcgccctga agggccagct gctgctgaat 3840
cacctgaagg agagcaagga tctgaagctg cagaacggca tctccaatca ggactggctg 3900
gcctacatcc aggagctgcg caacaaaagg ccggcggcca cgaaaaaggc cggccaggca 3960
aaaaagaaaa agggagcggc cgcactcgag caccaccacc accaccactg a 4011

<210> SEQ ID NO 426
<211> LENGTH: 3780
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 426
atggggagca aactggaaaa atttacgaat tgttatagcc tgtccaagac cctgcgtttc 60
aaagccatcc ccgttggcaa aacccaggag aatattgata ataaacgtct gctggttgag 120
gatgaaaaaa gagcagaaga ctataaggga gtcaaaaaac tgctggatcg gtactacctg 180
agctttataa atgacgtgct gcatagcatt aaactgaaaa atctgaataa ctatattagt 240
ctgttccgca agaaaacccg aacagagaaa gaaaataaag agctggaaaa cctggagatc 300
aatctgcgta aagagatcgc aaaagctttt aaaggaaatg aaggttataa aagcctgttc 360
aaaaaagaca ttattgaaac catcctgccg gaatttctgg atgataaaga cgagatagcg 420
ctcgtgaaca gcttcaacgg gttcacgacc gccttcacgg gctttttcga taacagggaa 480
aatatgtttt cagaggaagc caaaagcacc tcgatagcgt tccgttgcat taatgaaaat 540
ttgacaagat atatcagcaa catggatatt ttcgagaaag ttgatgcgat ctttgacaaa 600
catgaagtgc aggagattaa ggaaaaaatt ctgaacagcg attatgatgt tgaggatttt 660
ttcgaggggg aatttttttaa ctttgtactg acacaggaag gtatagatgt gtataatgct 720
attatcggcg ggttcgttac cgaatccggc gagaaaatta agggtctgaa tgagtacatc 780
aatctgtata accaaaagac caaacagaaa ctgccaaaat tcaaaccgct gtacaagcaa 840
gtcctgagcg atcgggaaag cttgagcttt tacggtgaag gttataccag cgacgaggag 900
gtactggagg tctttcgcaa taccctgaac aagaacagcg aaattttcag ctccattaaa 960
aagctggaga aactgtttaa gaattttgac gagtacagca gcgcaggtat ttttgtgaag 1020
aacggacctg ccataagcac cattagcaag gatatttttg gagagtggaa tgttatccgt 1080
gataaatgga acgcggaata tgatgacata cacctgaaaa agaaggctgt ggtaactgag 1140
aaatatgaag acgatcgccg caaaagcttt aaaaaaatcg gcagctttag cctggagcag 1200
ctgcaggaat atgcggacgc cgacctgagc gtggtcgaga aactgaagga aattattatc 1260
caaaaagtgg atgagattta caaggtatat ggtagcagcg aaaaactgtt tgatgcggac 1320
ttcgttctgg aaaaaagcct gaaaaaaaat gatgctgttg ttgcgatcat gaaagacctg 1380
ctcgatagcg ttaagagctt tgaaaattac attaaagcat tctttggcga gggcaaagaa 1440
acaaacagag acgaaagctt ttatggcgac ttcgtcctgg cttatgacat cctgttgaag 1500
gtagatcata tatatgatgc aattcgtaat tacgtaaccc aaaagccgta cagcaaagat 1560
aagttcaaac tgtatttcca gaacccgcag tttatgggtg gctgggacaa agacaaggag 1620
acagactatc gcgccactat tctgcgttac ggcagcaagt actatctcgc catcatggac 1680
aaaaaatatg caaagtgtct gcagaaaatc gataaagacg acgtgaacgg aaattacgaa 1740
aagattaatt ataagctgct gccagggccc aacaagatgt taccgaaagt attttttttcc 1800

-continued aaaaaatgga tggcatacta taacccgagc gaggatatac agaagattta caaaaatggg 1860
accttcaaaa agggggatat gttcaatctg aatgactgcc acaaactgat cgattttttt 1920
aaagatagca tcagccgtta tcctaaatgg tcaaacgcgt atgattttaa tttctccgaa 1980
acggagaaat ataaagacat tgctggtttc tatcgcgaag tcgaagaaca gggttataaa 2040
gttagctttg aatcggccag caagaaagag gttgataaac tggtggagga gggtaagctg 2100
tatatgtttc agatttataa caaagacttt agcgacaaaa gccacggtac tcctaatctg 2160
catacgatgt actttaaact gctgtttgat gagaataacc acggccaaat ccgtctctcc 2220
ggtggagcag aactttttat gcggcgtgcg agcctaaaaa aggaagaact ggtggtgcat 2280
cccgccaaca gcccgattgc taacaaaaat ccagataatc ctaagaagac caccacactg 2340
tcgtacgatg tctataagga taaacgtttc tcggaagacc agtatgaatt gcatataccg 2400
atagcaatta ataaatgccc aaaaaacatt ttcaaaatca acactgaagt tcgtgtgctg 2460
ctgaaacatg atgataatcc gtatgtgatc ggaattgacc gtggggagag aaatctgctg 2520
tatattgtag tcgttgatgg caagggcaac atcgttgagc agtatagcct gaatgaaata 2580
attaataatt ttaacggtat acgtattaaa accgactatc atagcctgct ggataaaaag 2640
gagaaagagc gttttgaggc acgccaaaat tggacgagca tcgaaaacat caaggaactg 2700
aaggcaggat atatcagcca agtagtccat aaaatctgtg aactggtgga gaagtacgac 2760
gctgtcattg ccctggaaga cctcaatagc ggctttaaaa acagccgggt gaaggtggag 2820
aaacaggtat accaaaagtt tgaaaagatg ctcattgata agctgaacta tatggttgat 2880
aaaaagagca acccgtgcgc cactggcggt gcactgaaag ggtaccaaat taccaataaa 2940
tttgaaagct ttaaaagcat gagcacgcag aatgggttta ttttttatat accagcatgg 3000
ctgacgagca agattgaccc cagcactggt tttgtcaatc tgctgaaaac caaatacaca 3060
agcattgcgg atagcaaaaa atttatttcg agcttcgacc gtattatgta tgttccggag 3120
gaagatctgt ttgaatttgc cctggattat aaaaacttca gccgcaccga tgcagattat 3180
atcaaaaaat ggaagctgta cagttatggt aatcgtatac gtatcttccg taatccgaag 3240
aaaaacaatg tgttcgattg ggaagaggtc tgtctgacca gcgcgtataa agaactgttc 3300
aacaagtacg gaataaatta tcagcaaggt gacattcgcg cactgctgtg tgaacagtca 3360
gataaagcat tttatagcag ctttatggcg ctgatgagcc tgatgctcca gatgcgcaac 3420
agcataaccg gtcgcacaga tgttgacttt ctgatcagcc ctgtgaagaa tagcgacggc 3480
atcttctacg attccaggaa ctatgaagca caggaaaacg ctattctgcc taaaaatgcc 3540
gatgccaacg gcgcctataa tattgcacgg aaggttctgt gggcgattgg acagttcaag 3600
aaagcggaag atgagaagct ggataaggta aaaattgcta ttagcaataa ggaatggctg 3660
gagtacgcac agacatcggt taaacacggt agtaaaaggc cggcggccac gaaaaaggcc 3720
ggccaggcaa aaaagaaaaa gggagcggcc gcactcgagc accaccacca ccaccactga 3780

<210> SEQ ID NO 427
<211> LENGTH: 4011
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 427
atggggacac agttcgaggg ctttaccaac ctgtatcagg tgagcaagac actgcggttt 60

-continued

```
gagctgatcc cacagggcaa gaccctgaag cacatccagg agcagggctt catcgaggag    120
gacaaggccc gcaatgatca ctacaaggag ctgaagccca tcatcgatcg gatctacaag    180
acctatgccg accagtgcct gcagctggtg cagctggatt gggagaacct gagcgccgcc    240
atcgactcct atagaaagga gaaaaccgag gagacaagga acgccctgat cgaggagcag    300
gccacatatc gcaatgccat ccacgactac ttcatcggcc ggacagacaa cctgaccgat    360
gccatcaata agagacacgc cgagatctac aagggcctgt tcaaggccga gctgtttaat    420
ggcaaggtgc tgaagcagct gggcaccgtg accacaaccg agcacgagaa cgccctgctg    480
cggagcttcg acaagtttac aacctacttc tccggctttt atagaaacag gaagaacgtg    540
ttcagcgccg aggatatcag cacagccatc ccacaccgca tcgtgcagga caacttcccc    600
aagtttaagg agaattgtca catcttcaca cgcctgatca ccgccgtgcc cagcctgcgg    660
gagcactttg agaacgtgaa gaaggccatc ggcatcttcg tgagcacctc catcgaggag    720
gtgttttcct tccctttta taaccagctg ctgacacaga cccagatcga cctgtataac    780
cagctgctgg gaggaatctc tcgggaggca ggcaccgaga agatcaaggg cctgaacgag    840
gtgctgaatc tggccatcca gaagaatgat gagacagccc acatcatcgc ctccctgcca    900
cacagattca tcccctgtt taagcagatc ctgtccgata ggaacaccct gtctttcatc    960
ctggaggagt ttaagagcga cgaggaagtg atccagtcct tctgcaagta caagacactg   1020
ctgagaaacg agaacgtgct ggagacagcc gaggccctgt ttaacgagct gaacagcatc   1080
gacctgacac acatcttcat cagccacaag aagctggaga caatcagcag cgccctgtgc   1140
gaccactggg atacactgag gaatgccctg tatgagcgga gaatctccga gctgacaggc   1200
aagatcacca agtctgccaa ggagaaggtg cagcgcagcc tgaagcacga ggatatcaac   1260
ctgcaggaga tcatctctgc cgcaggcaag gagctgagcg aggccttcaa gcagaaaacc   1320
agcgagatcc tgtcccacgc acacgccgcc ctggatcagc cactgcctac aaccctgaag   1380
aagcaggagg agaaggagat cctgaagtct cagctggaca gcctgctggg cctgtaccac   1440
ctgctggact ggtttgccgt ggatgagtcc aacgaggtgg accccgagtt ctctgcccgg   1500
ctgaccggca tcaagctgga gatggagcct tctctgagct tctacaacaa ggccagaaat   1560
tatgccacca agaagcccta ctccgtggag aagttcaagc tgaactttca gatgcctaca   1620
ctggccagag gctgggacgt gaatagagag aagaacaatg gcgccatcct gtttgtgaag   1680
aacggcctgt actatctggg catcatgcca aagcagaagg gcaggtataa ggccctgagc   1740
ttcgagccca cagagaaaac cagcgagggc tttgataaga tgtactatga ctacttccct   1800
gatgccgcca agatgatccc aaagtgcagc acccagctga aggccgtgac agcccacttt   1860
cagacccaca caacccccat cctgctgtcc aacaatttca tcgagcctct ggagatcaca   1920
aaggagatct acgacctgaa caatcctgag aaggagccaa agaagtttca gacagcctac   1980
gccaagaaaa ccggcgacca gaagggctac agagaggccc tgtgcaagtg gatcgacttc   2040
acaagggatt ttctgtccaa gtataccaag acaacctcta tcgatctgtc tagcctgcgg   2100
ccatcctctc agtataagga cctgggcgag tactatgccg agctgaatcc cctgctgtac   2160
cacatcagct tccagagaat cgccgagaag gagatcatgg atgccgtgga gacaggcaag   2220
ctgtacctgt tccagatcta taacaaggac tttgccaagg gccaccacgg caagcctaat   2280
ctgcacacac tgtattggac cggcctgttt tctccagaga acctggccaa gacaagcatc   2340
aagctgaatg gccaggccga gctgttctac cgccctaagt ccaggatgaa gaggatggca   2400
```

-continued

```
caccggctgg gagagaagat gctgaacaag aagctgaagg atcagaaaac cccaatcccc   2460

gacaccctgt accaggagct gtacgactat gtgaatcaca gactgtccca cgacctgtct   2520

gatgaggcca gggccctgct gcccaacgtg atcaccaagg aggtgtctca cgagatcatc   2580

aaggataggc gctttaccag cgacaagttc tttttccacg tgcctatcac actgaactat   2640

caggccgcca attccccatc taagttcaac cagagggtga atgcctacct gaaggagcac   2700

cccgagacac ctatcatcgg catcgatcgg ggcgagagaa acctgatcta tatcacagtg   2760

atcgactcca ccggcaagat cctggagcag cggagcctga acaccatcca gcagtttgat   2820

taccagaaga agctggacaa cagggagaag gagagggtgg cagcaaggca ggcctggtct   2880

gtggtgggca caatcaagga tctgaagcag ggctatctga gccaggtcat ccacgagatc   2940

gtggacctga tgatccacta ccaggccgtg gtggtgctgg agaacctgaa tttcggcttt   3000

aagagcaaga ggaccggcat cgccgagaag gccgtgtacc agcagttcga gaagatgctg   3060

atcgataagc tgaattgcct ggtgctgaag gactatccag cagagaaagt gggaggcgtg   3120

ctgaacccat accagctgac agaccagttc acctcctttg ccaagatggg cacccagtct   3180

ggcttcctgt tttacgtgcc tgccccatat acatctaaga tcgatcccct gaccggcttc   3240

gtggacccct tcgtgtggaa aaccatcaag aatcacgaga gccgcaagca cttcctggag   3300

ggcttcgact ttctgcacta cgacgtgaaa accggcgact tcatcctgca ctttaagatg   3360

aacagaaatc tgtccttcca gaggggcctg cccggcttta tgcctgcatg ggatatcgtg   3420

ttcgagaaga acgagacaca gtttgacgcc aagggcaccc ctttcatcgc cggcaagaga   3480

atcgtgccag tgatcgagaa tcacagattc accggcagat accgggacct gtatcctgcc   3540

aacgagctga tcgccctgct ggaggagaag ggcatcgtgt tcagggatgg ctccaacatc   3600

ctgccaaagc tgctggagaa tgacgattct cacgccatcg acacgatggt ggccctgatc   3660

cgcagcgtgc tgcagatgcg gaactccaat gccgccacag gcgaggacta tatcaacagc   3720

cccgtgcgcg atctgaatgg cgtgtgcttc gactcccggt ttcagaaccc agagtggcca   3780

atggacgccg atgccaatgg cgcctaccac atcgccctga agggccagct gctgctgaat   3840

cacctgaagg agagcaagga tctgaagctg cagaacggca tctccaatca ggactggctg   3900

gcctacatcc aggagctgcg caacaaaagg ccggcggcca cgaaaaaggc cggccaggca   3960

aaaaagaaaa agggagcggc cgcactcgag caccaccacc accaccactg a            4011
```

<210> SEQ ID NO 428
<211> LENGTH: 4011
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 428

```
atggggacac agttcgaggg ctttaccaac ctgtatcagg tgagcaagac actgcggttt     60

gagctgatcc cacagggcaa gaccctgaag cacatccagg agcagggctt catcgaggag    120

gacaaggccc gcaatgatca ctacaaggag ctgaagccca tcatcgatcg gatctacaag    180

acctatgccg accagtgcct gcagctggtg cagctggatt gggagaacct gagcgccgcc    240

atcgactcct atagaaagga gaaaaccgag gagacaagga acgccctgat cgaggagcag    300

gccacatatc gcaatgccat ccacgactac ttcatcggcc ggacagacaa cctgaccgat    360

gccatcaata agagacacgc cgagatctac aagggcctgt tcaaggccga gctgtttaat    420
```

-continued

```
ggcaaggtgc tgaagcagct gggcaccgtg accacaaccg agcacgagaa cgccctgctg    480
cggagcttcg acaagtttac aacctacttc tccggctttt atagaaacag gaagaacgtg    540
ttcagcgccg aggatatcag cacagccatc ccacaccgca tcgtgcagga caacttcccc    600
aagtttaagg agaattgtca catcttcaca cgcctgatca ccgccgtgcc cagcctgcgg    660
gagcactttg agaacgtgaa gaaggccatc ggcatcttcg tgagcacctc catcgaggag    720
gtgttttcct tccctttttta taaccagctg ctgacacaga cccagatcga cctgtataac    780
cagctgctgg gaggaatctc tcgggaggca ggcaccgaga agatcaaggg cctgaacgag    840
gtgctgaatc tggccatcca gaagaatgat gagacagccc acatcatcgc ctccctgcca    900
cacagattca tcccccctgtt taagcagatc ctgtccgata ggaacaccct gtctttcatc    960
ctggaggagt ttaagagcga cgaggaagtg atccagtcct tctgcaagta caagacactg   1020
ctgagaaacg agaacgtgct ggagacagcc gaggccctgt ttaacgagct gaacagcatc   1080
gacctgacac acatcttcat cagccacaag aagctggaga caatcagcag cgccctgtgc   1140
gaccactggg atacactgag gaatgccctg tatgagcgga gaatctccga gctgacaggc   1200
aagatcacca agtctgccaa ggagaaggtg cagcgcagcc tgaagcacga ggatatcaac   1260
ctgcaggaga tcatctctgc cgcaggcaag gagctgagcg aggccttcaa gcagaaaacc   1320
agcgagatcc tgtcccacgc acacgccgcc ctggatcagc cactgcctac aaccctgaag   1380
aagcaggagg agaaggagat cctgaagtct cagctggaca gcctgctggg cctgtaccac   1440
ctgctggact ggtttgccgt ggatgagtcc aacgaggtgg accccgagtt ctctgcccgg   1500
ctgaccggca tcaagctgga gatggagcct tctctgagct tctacaacaa ggccagaaat   1560
tatgccacca agaagcccta ctccgtggag aagttcaagc tgaactttca gatgcctaca   1620
ctggccagag gctgggacgt gaataaggag aagaacaatg gcgccatcct gtttgtgaag   1680
aacggcctgt actatctggg catcatgcca aagcagaagg gcaggtataa ggccctgagc   1740
ttcgagccca cagagaaaac cagcgagggc tttgataaga tgtactatga ctacttccct   1800
gatgccgcca agatgatccc aaagtgcagc acccagctga aggccgtgac agcccacttt   1860
cagacccaca caacccccat cctgctgtcc aacaatttca tcgagcctct ggagatcaca   1920
aaggagatct acgacctgaa caatcctgag aaggagccaa agaagtttca gacagcctac   1980
gccaagaaaa ccggcgacca gaagggctac agagaggccc tgtgcaagtg gatcgacttc   2040
acaagggatt ttctgtccaa gtataccaag acaacctcta tcgatctgtc tagcctgcgg   2100
ccatcctctc agtataagga cctgggcgag tactatgccg agctgaatcc cctgctgtac   2160
cacatcagct tccagagaat cgccgagaag gagatcatgg atgccgtgga gacaggcaag   2220
ctgtacctgt tccagatcta taacaaggac tttgccaagg gccaccacgg caagcctaat   2280
ctgcacacac tgtattggac cggcctgttt tctccagaga acctggccaa gacaagcatc   2340
aagctgaatg gccaggccga gctgttctac cgccctaagt ccaggatgaa gaggatggca   2400
caccggctgg gagagaagat gctgaacaag aagctgaagg atcagaaaac cccaatcccc   2460
gacaccctgt accaggagct gtacgactat gtgaatcaca gactgtccca cgacctgtct   2520
gatgaggcca gggccctgct gcccaacgtg atcaccaagg aggtgtctca cgagatcatc   2580
aaggataggc gctttaccag cgacaagttc tttttccacg tgcctatcac actgaactat   2640
caggccgcca attccccatc taagttcaac cagagggtga atgcctacct gaaggagcac   2700
cccgagacac ctatcatcgg catcgatcgg ggcgagagaa acctgatcta tatcacagtg   2760
atcgactcca ccggcaagat cctggagcag cggagcctga acaccatcca gcagtttgat   2820
```

taccagaaga agctggacaa cagggagaag gagagggtgg cagcaaggca ggcctggtct 2880
gtggtgggca caatcaagga tctgaagcag ggctatctga gccaggtcat ccacgagatc 2940
gtggacctga tgatccacta ccaggccgtg gtggtgctgg agaacctgaa tttcggcttt 3000
aagagcaaga ggaccggcat cgccgagaag gccgtgtacc agcagttcga gaagatgctg 3060
atcgataagc tgaattgcct ggtgctgaag gactatccag cagagaaagt gggaggcgtg 3120
ctgaacccat accagctgac agaccagttc acctcctttg ccaagatggg cacccagtct 3180
ggcttcctgt tttacgtgcc tgccccatat acatctaaga tcgatcccct gaccggcttc 3240
gtggacccct tcgtgtggaa aaccatcaag aatcacgaga gccgcaagca cttcctggag 3300
ggcttcgact ttctgcacta cgacgtgaaa accggcgact tcatcctgca ctttaagatg 3360
aacagaaatc tgtccttcca gaggggcctg cccggcttta tgcctgcatg ggatatcgtg 3420
ttcgagaaga acgagacaca gtttgacgcc aagggcaccc ctttcatcgc cggcaagaga 3480
atcgtgccag tgatcgagaa tcacagattc accggcagat accgggacct gtatcctgcc 3540
aacgagctga tcgccctgct ggaggagaag ggcatcgtgt tcagggatgg ctccaacatc 3600
ctgccaaagc tgctggagaa tgacgattct cacgccatcg acacgatggt ggccctgatc 3660
cgcagcgtgc tgcagatgcg gaactccaat gccgccacag gcgaggacta tatcaacagc 3720
cccgtgcgcg atctgaatgg cgtgtgcttc gactcccggt ttcagaaccc agagtggcca 3780
atggacgccg atgccaatgg cgcctaccac atcgccctga agggccagct gctgctgaat 3840
cacctgaagg agagcaagga tctgaagctg cagaacggca tctccaatca ggactggctg 3900
gcctacatcc aggagctgcg caacaaaagg ccggcggcca cgaaaaaggc cggccaggca 3960
aaaaagaaaa agggagcggc cgcactcgag caccaccacc accaccactg a 4011

<210> SEQ ID NO 429
<211> LENGTH: 4011
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 429
atggggacac agttcgaggg ctttaccaac ctgtatcagg tgagcaagac actgcggttt 60
gagctgatcc cacagggcaa gaccctgaag cacatccagg agcagggctt catcgaggag 120
gacaaggccc gcaatgatca ctacaaggag ctgaagccca tcatcgatcg gatctacaag 180
acctatgccg accagtgcct gcagctggtg cagctggatt gggagaacct gagcgccgcc 240
atcgactcct atagaaagga gaaaaccgag gagacaagga acgccctgat cgaggagcag 300
gccacatatc gcaatgccat ccacgactac ttcatcggcc ggacagacaa cctgaccgat 360
gccatcaata agagacacgc cgagatctac aagggcctgt tcaaggccga gctgtttaat 420
ggcaaggtgc tgaagcagct gggcaccgtg accacaaccg agcacgagaa cgccctgctg 480
cggagcttcg acaagtttac aacctacttc tccggctttt atagaaacag gaagaacgtg 540
ttcagcgccg aggatatcag cacagccatc ccacaccgca tcgtgcagga caacttcccc 600
aagtttaagg agaattgtca catcttcaca cgcctgatca ccgccgtgcc cagcctgcgg 660
gagcactttg agaacgtgaa gaaggccatc ggcatcttcg tgagcacctc catcgaggag 720
gtgttttcct tcccttttta taaccagctg ctgacacaga cccagatcga cctgtataac 780
cagctgctgg gaggaatctc tcgggaggca ggcaccgaga agatcaaggg cctgaacgag 840

```
gtgctggccc tggccatcca gaagaatgat gagacagccc acatcatcgc ctccctgcca    900
cacagattca tccccctgtt taagcagatc ctgtccgata ggaacaccct gtctttcatc    960
ctggaggagt ttaagagcga cgaggaagtg atccagtcct tctgcaagta caagacactg   1020
ctgagaaacg agaacgtgct ggagacagcc gaggccctgt ttaacgagct gaacagcatc   1080
gacctgacac acatcttcat cagccacaag aagctggaga caatcagcag cgccctgtgc   1140
gaccactggg atacactgag gaatgccctg tatgagcgga gaatctccga gctgacaggc   1200
aagatcacca agtctgccaa ggagaaggtg cagcgcagcc tgaagcacga ggatatcaac   1260
ctgcaggaga tcatctctgc cgcaggcaag gagctgagcg aggccttcaa gcagaaaacc   1320
agcgagatcc tgtcccacgc acacgccgcc ctggatcagc cactgcctac aaccctgaag   1380
aagcaggagg agaaggagat cctgaagtct cagctggaca gcctgctggg cctgtaccac   1440
ctgctggact ggtttgccgt ggatgagtcc aacgaggtgg accccgagtt ctctgcccgg   1500
ctgaccggca tcaagctgga gatggagcct tctctgagct tctacaacaa ggccagaaat   1560
tatgccacca agaagcccta ctccgtggag aagttcaagc tgaactttca gatgcctaca   1620
ctggccagag gctgggacgt gaatagagag aagaacaatg gcgccatcct gtttgtgaag   1680
aacggcctgt actatctggg catcatgcca aagcagaagg gcaggtataa ggccctgagc   1740
ttcgagccca cagagaaaac cagcgagggc tttgataaga tgtactatga ctacttccct   1800
gatgccgcca agatgatccc aaagtgcagc acccagctga aggccgtgac agcccacttt   1860
cagacccaca caacccccat cctgctgtcc aacaatttca tcgagcctct ggagatcaca   1920
aaggagatct acgacctgaa caatcctgag aaggagccaa agaagtttca gacagcctac   1980
gccaagaaaa ccggcgacca gaagggctac agagaggccc tgtgcaagtg gatcgacttc   2040
acaagggatt ttctgtccaa gtataccaag acaacctcta tcgatctgtc tagcctgcgg   2100
ccatcctctc agtataagga cctgggcgag tactatgccg agctgaatcc cctgctgtac   2160
cacatcagct tccagagaat cgccgagaag gagatcatgg atgccgtgga gacaggcaag   2220
ctgtacctgt tccagatcta taacaaggac tttgccaagg gccaccacgg caagcctaat   2280
ctgcacacac tgtattggac cggcctgttt tctccagaga acctggccaa gacaagcatc   2340
aagctgaatg gccaggccga gctgttctac cgccctaagt ccaggatgaa gaggatggca   2400
caccggctgg gagagaagat gctgaacaag aagctgaagg atcagaaaac cccaatcccc   2460
gacaccctgt accaggagct gtacgactat gtgaatcaca gactgtccca cgacctgtct   2520
gatgaggcca gggccctgct gcccaacgtg atcaccaagg aggtgtctca cgagatcatc   2580
aaggataggc gctttaccag cgacaagttc tttttccacg tgcctatcac actgaactat   2640
caggccgcca attccccatc taagttcaac cagagggtga atgcctacct gaaggagcac   2700
cccgagacac ctatcatcgg catcgatcgg ggcgagagaa acctgatcta tatcacagtg   2760
atcgactcca ccggcaagat cctggagcag cggagcctga acaccatcca gcagtttgat   2820
taccagaaga agctggacaa cagggagaag gagagggtgg cagcaaggca ggcctggtct   2880
gtggtgggca caatcaagga tctgaagcag ggctatctga gccaggtcat ccacgagatc   2940
gtggacctga tgatccacta ccaggccgtg gtggtgctgg agaacctgaa tttcggcttt   3000
aagagcaaga ggaccggcat cgccgagaag gccgtgtacc agcagttcga gaagatgctg   3060
atcgataagc tgaattgcct ggtgctgaag gactatccag cagagaaagt gggaggcgtg   3120
ctgaacccat accagctgac agaccagttc acctcctttg ccaagatggg cacccagtct   3180
```

-continued ggcttcctgt tttacgtgcc tgccccatat acatctaaga tcgatcccct gaccggcttc 3240
gtggacccct tcgtgtggaa aaccatcaag aatcacgaga gccgcaagca cttcctggag 3300
ggcttcgact ttctgcacta cgacgtgaaa accggcgact tcatcctgca ctttaagatg 3360
aacagaaatc tgtccttcca gaggggcctg cccggcttta tgcctgcatg ggatatcgtg 3420
ttcgagaaga acgagacaca gtttgacgcc aagggcaccc ctttcatcgc cggcaagaga 3480
atcgtgccag tgatcgagaa tcacagattc accggcagat accgggacct gtatcctgcc 3540
aacgagctga tcgccctgct ggaggagaag ggcatcgtgt tcagggatgg ctccaacatc 3600
ctgccaaagc tgctggagaa tgacgattct cacgccatcg acacgatggt ggccctgatc 3660
cgcagcgtgc tgcagatgcg gaactccaat gccgccacag gcgaggacta tatcaacagc 3720
cccgtgcgcg atctgaatgg cgtgtgcttc gactcccggt ttcagaaccc agagtggcca 3780
atggacgccg atgccaatgg cgcctaccac atcgccctga agggccagct gctgctgaat 3840
cacctgaagg agagcaagga tctgaagctg cagaacggca tctccaatca ggactggctg 3900
gcctacatcc aggagctgcg caacaaaagg ccggcggcca cgaaaaaggc cggccaggca 3960
aaaaagaaaa agggagcggc cgcactcgag caccaccacc accaccactg a 4011

<210> SEQ ID NO 430
<211> LENGTH: 4257
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 430
atgctgttcc aggactttac ccacctgtat ccactgtcca agacagtgag atttgagctg 60
aagcccatcg ataggaccct ggagcacatc cacgccaaga acttcctgtc tcaggacgag 120
acaatggccg atatgcacca gaaggtgaaa gtgatcctgg acgattacca ccgcgacttc 180
atcgccgata tgatgggcga ggtgaagctg accaagctgg ccgagttcta tgacgtgtac 240
ctgaagtttc ggaagaaccc aaaggacgat gagctgcaga agcagctgaa ggatctgcag 300
gccgtgctga gaaaggagat cgtgaagccc atcggcaatg gcggcaagta taaggccggc 360
tacgacaggc tgttcggcgc caagctgttt aaggacggca aggagctggg cgatctggcc 420
aagttcgtga tcgcacagga gggagagagc tccccaaagc tggcccacct ggcccacttc 480
gagaagtttt ccacctattt cacaggcttt cacgataacc ggaagaatat gtattctgac 540
gaggataagc acaccgccat cgcctaccgc ctgatccacg agaacctgcc ccggtttatc 600
gacaatctgc agatcctgac cacaatcaag cagaagcact ctgccctgta cgatcagatc 660
atcaacgagc tgaccgccag cggcctggac gtgtctctgg ccagccacct ggatggctat 720
cacaagctgc tgacacagga gggcatcacc gcctacaata cactgctggg aggaatctcc 780
ggagaggcag gctctcctaa gatccagggc atcaacgagc tgatcaattc tcaccacaac 840
cagcactgcc acaagagcga gagaatcgcc aagctgaggc cactgcacaa gcagatcctg 900
tccgacggca tgagcgtgtc cttcctgccc tctaagtttg ccgacgatag cgagatgtgc 960
caggccgtga acgagttcta tcgccactac gccgacgtgt tcgccaaggt gcagagcctg 1020
ttcgacggct ttgacgatca ccagaaggat ggcatctacg tggagcacaa gaacctgaat 1080
gagctgtcca agcaggcctt cggcgacttt gcactgctgg gacgcgtgct ggacggatac 1140
tatgtggatg tggtgaatcc agagttcaac gagcggtttg ccaaggccaa gaccgacaat 1200

-continued

```
gccaaggcca agctgacaaa ggagaaggat aagttcatca agggcgtgca ctccctggcc   1260
tctctggagc aggccatcga gcactatacc gcaaggcacg acgatgagag cgtgcaggca   1320
ggcaagctgg gacagtactt caagcacggc ctggccggag tggacaaccc catccagaag   1380
atccacaaca atcacagcac catcaagggc tttctggaga gggagcgccc tgcaggagag   1440
agagccctgc caaagatcaa gtccggcaag aatcctgaga tgacacagct gaggcagctg   1500
aaggagctgc tggataacgc cctgaatgtg gcccacttcg ccaagctgct gaccacaaag   1560
accacactgg acaatcagga tggcaacttc tatggcgagt ttggcgtgct gtacgacgag   1620
ctggccaaga tccccaccct gtataacaag gtgagagatt acctgagcca gaagcctttc   1680
tccaccgaga agtacaagct gaactttggc aatccaacac tgctgaatgg ctgggacctg   1740
aacaaggaga aggataattt cggcgtgatc ctgcagaagg acggctgcta ctatctggcc   1800
ctgctggaca aggcccacaa gaaggtgttt gataacgccc ctaatacagg caagagcatc   1860
tatcagaaga tgatctataa gtacctggag gtgaggaagc agttccccaa ggtgttcttt   1920
tccaaggagg ccatcgccat caactaccac ccttctaagg agctggtgga gatcaaggac   1980
aagggccggc agagatccga cgatgagcgc ctgaagctgt atcggtttat cctggagtgt   2040
ctgaagatcc accctaagta cgataagaag ttcgagggcg ccatcggcga catccagctg   2100
tttaagaagg ataagaaggg cagagaggtg ccaatcagcg agaaggacct gttcgataag   2160
atcaacggca tcttttctag caagcctaag ctggagatgg aggacttctt tatcggcgag   2220
ttcaagaggt ataacccaag ccaggacctg gtggatcagt ataatatcta caagaagatc   2280
gactccaacg ataatcgcaa gaaggagaat ttctacaaca atcaccccaa gtttaagaag   2340
gatctggtgc ggtactatta cgagtctatg tgcaagcacg aggagtggga ggagagcttc   2400
gagttttcca agaagctgca ggacatcggc tgttacgtgg atgtgaacga gctgtttacc   2460
gagatcgaga cacggagact gaattataag atctccttct gcaacatcaa tgccgactac   2520
atcgatgagc tggtggagca gggccagctg tatctgttcc agatctacaa caaggacttt   2580
tccccaaagg cccacggcaa gcccaatctg cacaccctgt acttcaaggc cctgttttct   2640
gaggacaacc tggccgatcc tatctataag ctgaatggcg aggcccagat cttctacaga   2700
aaggcctccc tggacatgaa cgagacaaca atccacaggg ccggcgaggt gctggagaac   2760
aagaatcccg ataatcctaa gaagagacag ttcgtgtacg acatcatcaa ggataagagg   2820
tacacacagg acaagttcat gctgcacgtg ccaatcacca tgaactttgg cgtgcagggc   2880
atgacaatca aggagttcaa taagaaggtg aaccagtcta tccagcagta tgacgaggtg   2940
aacgtgatcg gcatcgatcg gggcgagaga cacctgctgt acctgaccgt gatcaatagc   3000
aagggcgaga tcctggagca gtgttccctg aacgacatca ccacagcctc tgccaatggc   3060
acacagatga ccacacctta ccacaagatc ctggataaga gggagatcga gcgcctgaac   3120
gcccgggtgg gatggggcga gatcgagaca atcaaggagc tgaagtctgg ctatctgagc   3180
cacgtggtgc accagatcag ccagctgatg ctgaagtaca acgccatcgt ggtgctggag   3240
gacctgaatt tcggctttaa gaggggccgc tttaaggtgg agaagcagat ctatcagaac   3300
ttcgagaatg ccctgatcaa gaagctgaac cacctggtgc tgaaggacaa ggccgacgat   3360
gagatcggct cttacaagaa tgccctgcag ctgaccaaca atttcacaga tctgaagagc   3420
atcggcaagc agaccggctt cctgttttat gtgcccgcct ggaacacctc taagatcgac   3480
cctgagacag gctttgtgga tctgctgaag ccaagatacg agaacatcgc ccagagccag   3540
gccttctttg gcaagttcga caagatctgc tataatgccg acaaggatta cttcgagttt   3600
```

cacatcgact acgccaagtt taccgataag gccaagaata gccgccagat ctggacaatc 3660
tgttcccacg gcgacaagcg gtacgtgtac gataagacag ccaaccagaa taagggcgcc 3720
gccaagggca tcaacgtgaa tgatgagctg aagtccctgt tcgcccgcca ccacatcaac 3780
gagaagcagc ccaacctggt catggacatc tgccagaaca atgataagga gtttcacaag 3840
tctctgatgt acctgctgaa aaccctgctg gccctgcggt acagcaacgc ctcctctgac 3900
gaggatttca tcctgtcccc cgtggcaaac gacgagggcg tgttctttaa tagcgccctg 3960
gccgacgata cacagcctca gaatgccgat gccaacggcg cctaccacat cgccctgaag 4020
ggcctgtggc tgctgaatga gctgaagaac tccgacgatc tgaacaaggt gaagctggcc 4080
atcgacaatc agacctggct gaatttcgcc cagaacagga aaaggccggc ggccacgaaa 4140
aaggccggcc aggcaaaaaa gaaaaaggga tcctacccat acgatgttcc agattacgct 4200
tatccctacg acgtgcctga ttatgcatac ccatatgatg tccccgacta tgcctaa 4257

<210> SEQ ID NO 431
<211> LENGTH: 5658
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 431
atgacacagt tcgagggctt taccaacctg tatcaggtga gcaagacact gcggtttgag 60
ctgatcccac agggcaagac cctgaagcac atccaggagc agggcttcat cgaggaggac 120
aaggcccgca atgatcacta caaggagctg aagcccatca tcgatcggat ctacaagacc 180
tatgccgacc agtgcctgca gctggtgcag ctggattggg agaacctgag cgccgccatc 240
gactcctata gaaaggagaa aaccgaggag acaaggaacg ccctgatcga ggagcaggcc 300
acatatcgca atgccatcca cgactacttc atcggccgga cagacaacct gaccgatgcc 360
atcaataaga gacacgccga gatctacaag ggcctgttca aggccgagct gtttaatggc 420
aaggtgctga agcagctggg caccgtgacc acaaccgagc acgagaacgc cctgctgcgg 480
agcttcgaca agtttacaac ctacttctcc ggcttttatg agaacaggaa gaacgtgttc 540
agcgccgagg atatcagcac agccatccca caccgcatcg tgcaggacaa cttccccaag 600
tttaaggaga attgtcacat cttcacacgc ctgatcaccg ccgtgcccag cctgcgggag 660
cactttgaga acgtgaagaa ggccatcggc atcttcgtga gcacctccat cgaggaggtg 720
ttttccttcc ctttttataa ccagctgctg acacagaccc agatcgacct gtataaccag 780
ctgctgggag gaatctctcg ggaggcaggc accgagaaga tcaagggcct gaacgaggtg 840
ctgaatctgg ccatccagaa gaatgatgag acagcccaca tcatcgcctc cctgccacac 900
agattcatcc ccctgtttaa gcagatcctg tccgatagga acaccctgtc tttcatcctg 960
gaggagttta agagcgacga ggaagtgatc cagtccttct gcaagtacaa gacactgctg 1020
agaaacgaga acgtgctgga gacagccgag gccctgttta acgagctgaa cagcatcgac 1080
ctgacacaca tcttcatcag ccacaagaag ctggagacaa tcagcagcgc cctgtgcgac 1140
cactgggata cactgaggaa tgccctgtat gagcggagaa tctccgagct gacaggcaag 1200
atcaccaagt ctgccaagga gaaggtgcag cgcagcctga agcacgagga tatcaacctg 1260
caggagatca tctctgccgc aggcaaggag ctgagcgagg ccttcaagca gaaaaccagc 1320
gagatcctgt cccacgcaca cgccgccctg gatcagccac tgcctacaac cctgaagaag 1380

```
caggaggaga aggagatcct gaagtctcag ctggacagcc tgctgggcct gtaccacctg   1440
ctggactggt ttgccgtgga tgagtccaac gaggtggacc ccgagttctc tgcccggctg   1500
accggcatca agctggagat ggagccttct ctgagcttct acaacaaggc cagaaattat   1560
gccaccaaga agccctactc cgtggagaag ttcaagctga actttcagat gcctacactg   1620
gcctctggct gggacgtgaa taaggagaag aacaatggcg ccatcctgtt tgtgaagaac   1680
ggcctgtact atctgggcat catgccaaag cagaagggca ggtataaggc cctgagcttc   1740
gagcccacag agaaaaccag cgagggcttt gataagatgt actatgacta cttccctgat   1800
gccgccaaga tgatcccaaa gtgcagcacc cagctgaagg ccgtgacagc ccactttcag   1860
acccacacaa cccccatcct gctgtccaac aatttcatcg agcctctgga gatcacaaag   1920
gagatctacg acctgaacaa tcctgagaag gagccaaaga agtttcagac agcctacgcc   1980
aagaaaaccg gcgaccagaa gggctacaga gaggccctgt gcaagtggat cgacttcaca   2040
agggatttc tgtccaagta taccaagaca acctctatcg atctgtctag cctgcggcca   2100
tcctctcagt ataaggacct gggcgagtac tatgccgagc tgaatcccct gctgtaccac   2160
atcagcttcc agagaatcgc cgagaaggag atcatggatg ccgtggagac aggcaagctg   2220
tacctgttcc agatctataa caaggacttt gccaagggcc accacggcaa gcctaatctg   2280
cacacactgt attggaccgg cctgttttct ccagagaacc tggccaagac aagcatcaag   2340
ctgaatggcc aggccgagct gttctaccgc cctaagtcca ggatgaagag gatggcacac   2400
cggctgggag agaagatgct gaacaagaag ctgaaggatc agaaaacccc aatccccgac   2460
accctgtacc aggagctgta cgactatgtg aatcacagac tgtcccacga cctgtctgat   2520
gaggccaggg ccctgctgcc caacgtgatc accaaggagg tgtctcacga gatcatcaag   2580
gataggcgct ttaccagcga caagttcttt ttccacgtgc ctatcacact gaactatcag   2640
gccgccaatt ccccatctaa gttcaaccag agggtgaatg cctacctgaa ggagcacccc   2700
gagacaccta tcatcggcat cgcccggggc gagagaaacc tgatctatat cacagtgatc   2760
gactccaccg gcaagatcct ggagcagcgg agcctgaaca ccatccagca gtttgattac   2820
cagaagaagc tggacaacag ggagaaggag agggtggcag caaggcaggc ctggtctgtg   2880
gtgggcacaa tcaaggatct gaagcagggc tatctgagcc aggtcatcca cgagatcgtg   2940
gacctgatga tccactacca ggccgtggtg gtgctggaga acctgaattt cggctttaag   3000
agcaagagga ccggcatcgc cgagaaggcc gtgtaccagc agttcgagaa gatgctgatc   3060
gataagctga attgcctggt gctgaaggac tatccagcag agaaagtggg aggcgtgctg   3120
aacccatacc agctgacaga ccagttcacc tcctttgcca agatgggcac ccagtctggc   3180
ttcctgtttt acgtgcctgc cccatataca tctaagatcg atcccctgac cggcttcgtg   3240
gaccccttcg tgtggaaaac catcaagaat cacgagagcc gcaagcactt cctggagggc   3300
ttcgactttc tgcactacga cgtgaaaacc ggcgacttca tcctgcactt taagatgaac   3360
agaaatctgt ccttccagag gggcctgccc ggctttatgc ctgcatggga tatcgtgttc   3420
gagaagaacg agacacagtt tgacgccaag ggcacccctt tcatcgccgg caagagaatc   3480
gtgccagtga tcgagaatca cagattcacc ggcagatacc gggacctgta tcctgccaac   3540
gagctgatcg ccctgctgga ggagaagggc atcgtgttca gggatggctc caacatcctg   3600
ccaaagctgc tggagaatga cgattctcac gccatcgaca ccatggtggc cctgatccgc   3660
agcgtgctgc agatgcggaa ctccaatgcc gccacaggcg aggactatat caacagcccc   3720
```

-continued gtgcgcgatc tgaatggcgt gtgcttcgac tcccggtttc agaacccaga gtggcccatg 3780
gacgccgatg ccaatggcgc ctaccacatc gccctgaagg gccagctgct gctgaatcac 3840
ctgaaggaga gcaaggatct gaagctgcag aacggcatct ccaatcagga ctggctggcc 3900
tacatccagg agctgcgcaa caaaaggccg gcggccacga aaaaggccgg ccaggcaaaa 3960
aagaaaaagg gatcctaccc atacgatgtt ccagattacg cttatcccta cgacgtgcct 4020
gattatgcat acccatatga tgtccccgac tatgccggaa gcgaggccag cggttccgga 4080
cgggctgacg cattggacga ttttgatctg gatatgctgg gaagtgacgc cctcgatgat 4140
tttgaccttg acatgcttgg ttcggatgcc cttgatgact ttgacctcga catgctcggc 4200
agtgacgccc ttgatgattt cgacctggac atgctgatta actctagaag ttccggatct 4260
ccgaaaaaga aacgcaaagt tggtagccag tacctgcccg acaccgacga ccggcaccgg 4320
atcgaggaaa agcggaagcg gacctacgag acattcaaga gcatcatgaa gaagtccccc 4380
ttcagcggcc ccaccgaccc tagacctcca cctagaagaa tcgccgtgcc cagcagatcc 4440
agcgccagcg tgccaaaacc tgccccccag ccttacccct tcaccagcag cctgagcacc 4500
atcaactacg acgagttccc taccatggtg ttccccagcg gccagatctc tcaggcctct 4560
gctctggctc cagcccctcc tcaggtgctg cctcaggctc ctgctcctgc accagctcca 4620
gccatggtgt ctgcactggc tcaggcacca gcacccgtgc ctgtgctggc tcctggacct 4680
ccacaggctg tggctccacc agcccctaaa cctacacagg ccggcgaggg cacactgtct 4740
gaagctctgc tgcagctgca gttcgacgac gaggatctgg gagccctgct gggaaacagc 4800
accgatcctg ccgtgttcac cgacctggcc agcgtggaca acagcgagtt ccagcagctg 4860
ctgaaccagg gcatccctgt ggcccctcac accaccgagc ccatgctgat ggaatacccc 4920
gaggccatca cccggctcgt gacaggcgct cagaggcctc ctgatccagc tcctgcccct 4980
ctgggagcac caggcctgcc taatggactg ctgtctggcg acgaggactt cagctctatc 5040
gccgatatgg atttctcagc cttgctgggc tctggcagcg gcagccggga ttccagggaa 5100
gggatgtttt tgccgaagcc tgaggccggc tccgctatta gtgacgtgtt tgagggccgc 5160
gaggtgtgcc agccaaaacg aatccggcca tttcatcctc caggaagtcc atgggccaac 5220
cgcccactcc ccgccagcct cgcaccaaca ccaaccggtc cagtacatga gccagtcggg 5280
tcactgaccc cggcaccagt ccctcagcca ctggatccag cgcccgcagt gactcccgag 5340
gccagtcacc tgttggagga tcccgatgaa gagacgagcc aggctgtcaa agcccttcgg 5400
gagatggccg atactgtgat tccccagaag gaagaggctg caatctgtgg ccaaatggac 5460
ctttcccatc cgcccccaag ggccatctg gatgagctga caaccacact tgagtccatg 5520
accgaggatc tgaacctgga ctcacccctg accccggaat tgaacgagat tctggatacc 5580
ttcctgaacg acgagtgcct cttgcatgcc atgcatatca gcacaggact gtccatcttc 5640
gacacatctc tgttttaa 5658

<210> SEQ ID NO 432
<211> LENGTH: 1885
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 432

Met Thr Gln Phe Glu Gly Phe Thr Asn Leu Tyr Gln Val Ser Lys Thr
1 5 10 15

```
Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430
```

-continued

```
Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
```

```
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Ala Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys  Ser Lys Arg Thr Gly  Ile Ala Glu
        995                 1000                1005

Lys Ala  Val Tyr Gln Gln Phe  Glu Lys Met Leu Ile  Asp Lys Leu
    1010                 1015                 1020

Asn Cys  Leu Val Leu Lys Asp  Tyr Pro Ala Glu Lys  Val Gly Gly
    1025                 1030                 1035

Val Leu  Asn Pro Tyr Gln Leu  Thr Asp Gln Phe Thr  Ser Phe Ala
    1040                 1045                 1050

Lys Met  Gly Thr Gln Ser Gly  Phe Leu Phe Tyr Val  Pro Ala Pro
    1055                 1060                 1065

Tyr Thr  Ser Lys Ile Asp Pro  Leu Thr Gly Phe Val  Asp Pro Phe
    1070                 1075                 1080

Val Trp  Lys Thr Ile Lys Asn  His Glu Ser Arg Lys  His Phe Leu
    1085                 1090                 1095

Glu Gly  Phe Asp Phe Leu His  Tyr Asp Val Lys Thr  Gly Asp Phe
    1100                 1105                 1110

Ile Leu  His Phe Lys Met Asn  Arg Asn Leu Ser Phe  Gln Arg Gly
    1115                 1120                 1125

Leu Pro  Gly Phe Met Pro Ala  Trp Asp Ile Val Phe  Glu Lys Asn
    1130                 1135                 1140

Glu Thr  Gln Phe Asp Ala Lys  Gly Thr Pro Phe Ile  Ala Gly Lys
    1145                 1150                 1155

Arg Ile  Val Pro Val Ile Glu  Asn His Arg Phe Thr  Gly Arg Tyr
    1160                 1165                 1170

Arg Asp  Leu Tyr Pro Ala Asn  Glu Leu Ile Ala Leu  Leu Glu Glu
    1175                 1180                 1185

Lys Gly  Ile Val Phe Arg Asp  Gly Ser Asn Ile Leu  Pro Lys Leu
    1190                 1195                 1200

Leu Glu  Asn Asp Asp Ser His  Ala Ile Asp Thr Met  Val Ala Leu
    1205                 1210                 1215

Ile Arg  Ser Val Leu Gln Met  Arg Asn Ser Asn Ala  Ala Thr Gly
    1220                 1225                 1230

Glu Asp  Tyr Ile Asn Ser Pro  Val Arg Asp Leu Asn  Gly Val Cys
    1235                 1240                 1245

Phe Asp  Ser Arg Phe Gln Asn  Pro Glu Trp Pro Met  Asp Ala Asp
    1250                 1255                 1260
```

-continued

```
Ala Asn  Gly Ala Tyr His Ile  Ala Leu Lys Gly Gln  Leu Leu Leu
    1265                 1270                 1275

Asn His  Leu Lys Glu Ser Lys  Asp Leu Lys Leu Gln  Asn Gly Ile
    1280                 1285                 1290

Ser Asn  Gln Asp Trp Leu Ala  Tyr Ile Gln Glu Leu  Arg Asn Lys
    1295                 1300                 1305

Arg Pro  Ala Ala Thr Lys Lys  Ala Gly Gln Ala Lys  Lys Lys Lys
    1310                 1315                 1320

Gly Ser  Tyr Pro Tyr Asp Val  Pro Asp Tyr Ala Tyr  Pro Tyr Asp
    1325                 1330                 1335

Val Pro  Asp Tyr Ala Tyr Pro  Tyr Asp Val Pro Asp  Tyr Ala Gly
    1340                 1345                 1350

Ser Glu  Ala Ser Gly Ser Gly  Arg Ala Asp Ala Leu  Asp Asp Phe
    1355                 1360                 1365

Asp Leu  Asp Met Leu Gly Ser  Asp Ala Leu Asp Asp  Phe Asp Leu
    1370                 1375                 1380

Asp Met  Leu Gly Ser Asp Ala  Leu Asp Asp Phe Asp  Leu Asp Met
    1385                 1390                 1395

Leu Gly  Ser Asp Ala Leu Asp  Asp Phe Asp Leu Asp  Met Leu Ile
    1400                 1405                 1410

Asn Ser  Arg Ser Ser Gly Ser  Pro Lys Lys Lys Arg  Lys Val Gly
    1415                 1420                 1425

Ser Gln  Tyr Leu Pro Asp Thr  Asp Asp Arg His Arg  Ile Glu Glu
    1430                 1435                 1440

Lys Arg  Lys Arg Thr Tyr Glu  Thr Phe Lys Ser Ile  Met Lys Lys
    1445                 1450                 1455

Ser Pro  Phe Ser Gly Pro Thr  Asp Pro Arg Pro Pro  Pro Arg Arg
    1460                 1465                 1470

Ile Ala  Val Pro Ser Arg Ser  Ser Ala Ser Val Pro  Lys Pro Ala
    1475                 1480                 1485

Pro Gln  Pro Tyr Pro Phe Thr  Ser Ser Leu Ser Thr  Ile Asn Tyr
    1490                 1495                 1500

Asp Glu  Phe Pro Thr Met Val  Phe Pro Ser Gly Gln  Ile Ser Gln
    1505                 1510                 1515

Ala Ser  Ala Leu Ala Pro Ala  Pro Pro Gln Val Leu  Pro Gln Ala
    1520                 1525                 1530

Pro Ala  Pro Ala Pro Ala Pro  Ala Met Val Ser Ala  Leu Ala Gln
    1535                 1540                 1545

Ala Pro  Ala Pro Val Pro Val  Leu Ala Pro Gly Pro  Pro Gln Ala
    1550                 1555                 1560

Val Ala  Pro Pro Ala Pro Lys  Pro Thr Gln Ala Gly  Glu Gly Thr
    1565                 1570                 1575

Leu Ser  Glu Ala Leu Leu Gln  Leu Gln Phe Asp Asp  Glu Asp Leu
    1580                 1585                 1590

Gly Ala  Leu Leu Gly Asn Ser  Thr Asp Pro Ala Val  Phe Thr Asp
    1595                 1600                 1605

Leu Ala  Ser Val Asp Asn Ser  Glu Phe Gln Gln Leu  Leu Asn Gln
    1610                 1615                 1620

Gly Ile  Pro Val Ala Pro His  Thr Thr Glu Pro Met  Leu Met Glu
    1625                 1630                 1635

Tyr Pro  Glu Ala Ile Thr Arg  Leu Val Thr Gly Ala  Gln Arg Pro
    1640                 1645                 1650
```

-continued

```
Pro Asp  Pro Ala Pro Ala Pro  Leu Gly Ala Pro Gly  Leu Pro Asn
    1655                 1660                 1665

Gly Leu  Leu Ser Gly Asp Glu  Asp Phe Ser Ser Ile  Ala Asp Met
    1670                 1675                 1680

Asp Phe  Ser Ala Leu Leu Gly  Ser Gly Ser Gly Ser  Arg Asp Ser
    1685                 1690                 1695

Arg Glu  Gly Met Phe Leu Pro  Lys Pro Glu Ala Gly  Ser Ala Ile
    1700                 1705                 1710

Ser Asp  Val Phe Glu Gly Arg  Glu Val Cys Gln Pro  Lys Arg Ile
    1715                 1720                 1725

Arg Pro  Phe His Pro Pro Gly  Ser Pro Trp Ala Asn  Arg Pro Leu
    1730                 1735                 1740

Pro Ala  Ser Leu Ala Pro Thr  Pro Thr Gly Pro Val  His Glu Pro
    1745                 1750                 1755

Val Gly  Ser Leu Thr Pro Ala  Pro Val Pro Gln Pro  Leu Asp Pro
    1760                 1765                 1770

Ala Pro  Ala Val Thr Pro Glu  Ala Ser His Leu Leu  Glu Asp Pro
    1775                 1780                 1785

Asp Glu  Glu Thr Ser Gln Ala  Val Lys Ala Leu Arg  Glu Met Ala
    1790                 1795                 1800

Asp Thr  Val Ile Pro Gln Lys  Glu Glu Ala Ala Ile  Cys Gly Gln
    1805                 1810                 1815

Met Asp  Leu Ser His Pro Pro  Pro Arg Gly His Leu  Asp Glu Leu
    1820                 1825                 1830

Thr Thr  Thr Leu Glu Ser Met  Thr Glu Asp Leu Asn  Leu Asp Ser
    1835                 1840                 1845

Pro Leu  Thr Pro Glu Leu Asn  Glu Ile Leu Asp Thr  Phe Leu Asn
    1850                 1855                 1860

Asp Glu  Cys Leu Leu His Ala  Met His Ile Ser Thr  Gly Leu Ser
    1865                 1870                 1875

Ile Phe  Asp Thr Ser Leu Phe
    1880                 1885
```

<210> SEQ ID NO 433
<211> LENGTH: 5655
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 433

```
atgacacagt tcgagggctt taccaacctg tatcaggtga gcaagacact gcggtttgag     60

ctgatcccac agggcaagac cctgaagcac atccaggagc agggcttcat cgaggaggac    120

aaggcccgca atgatcacta caaggagctg aagcccatca tcgatcggat ctacaagacc    180

tatgccgacc agtgcctgca gctggtgcag ctggattggg agaacctgag cgccgccatc    240

gactcctata gaaaggagaa aaccgaggag acaaggaacg ccctgatcga ggagcaggcc    300

acatatcgca atgccatcca cgactacttc atcggccgga cagacaacct gaccgatgcc    360

atcaataaga gacacgccga gatctacaag ggcctgttca aggccgagct gtttaatggc    420

aaggtgctga agcagctggg caccgtgacc acaaccgagc acgagaacgc cctgctgcgg    480

agcttcgaca agtttacaac ctacttctcc ggcttttata gaaacaggaa gaacgtgttc    540

agcgccgagg atatcagcac agccatccca caccgcatcg tgcaggacaa cttccccaag    600
```

-continued

```
tttaaggaga attgtcacat cttcacacgc ctgatcaccg ccgtgcccag cctgcgggag    660
cactttgaga acgtgaagaa ggccatcggc atcttcgtga gcacctccat cgaggaggtg    720
ttttccttcc ctttttataa ccagctgctg acacagaccc agatcgacct gtataaccag    780
ctgctgggag gaatctctcg ggaggcaggc accgagaaga tcaagggcct gaacgaggtg    840
ctgaatctgg ccatccagaa gaatgatgag acagcccaca tcatcgcctc cctgccacac    900
agattcatcc ccctgtttaa gcagatcctg tccgatagga acaccctgtc tttcatcctg    960
gaggagttta agagcgacga ggaagtgatc cagtccttct gcaagtacaa gacactgctg   1020
agaaacgaga acgtgctgga gacagccgag gccctgttta acgagctgaa cagcatcgac   1080
ctgacacaca tcttcatcag ccacaagaag ctggagacaa tcagcagcgc cctgtgcgac   1140
cactgggata cactgaggaa tgccctgtat gagcggagaa tctccgagct gacaggcaag   1200
atcaccaagt ctgccaagga gaaggtgcag cgcagcctga agcacgagga tatcaacctg   1260
caggagatca tctctgccgc aggcaaggag ctgagcgagg ccttcaagca gaaaaccagc   1320
gagatcctgt cccacgcaca cgccgccctg gatcagccac tgcctacaac cctgaagaag   1380
caggaggaga aggagatcct gaagtctcag ctggacagcc tgctgggcct gtaccacctg   1440
ctggactggt ttgccgtgga tgagtccaac gaggtggacc ccgagttctc tgcccggctg   1500
accggcatca agctggagat ggagccttct ctgagcttct acaacaaggc cagaaattat   1560
gccaccaaga agccctactc cgtggagaag ttcaagctga actttcagat gcctacactg   1620
gccagaggct gggacgtgaa tagagagaag aacaatggcg ccatcctgtt tgtgaagaac   1680
ggcctgtact atctgggcat catgccaaag cagaagggca ggtataaggc cctgagcttc   1740
gagcccacag agaaaaccag cgagggcttt gataagatgt actatgacta cttccctgat   1800
gccgccaaga tgatcccaaa gtgcagcacc cagctgaagg ccgtgacagc ccactttcag   1860
acccacacaa cccccatcct gctgtccaac aatttcatcg agcctctgga gatcacaaag   1920
gagatctacg acctgaacaa tcctgagaag gagccaaaga agtttcagac agcctacgcc   1980
aagaaaaccg gcgaccagaa gggctacaga gaggccctgt gcaagtggat cgacttcaca   2040
agggattttc tgtccaagta taccaagaca acctctatcg atctgtctag cctgcggcca   2100
tcctctcagt ataaggacct gggcgagtac tatgccgagc tgaatcccct gctgtaccac   2160
atcagcttcc agagaatcgc cgagaaggag atcatggatg ccgtggagac aggcaagctg   2220
tacctgttcc agatctataa caaggacttt gccaagggcc accacggcaa gcctaatctg   2280
cacacactgt attggaccgg cctgttttct ccagagaacc tggccaagac aagcatcaag   2340
ctgaatggcc aggccgagct gttctaccgc cctaagtcca ggatgaagag gatggcacac   2400
cggctgggag agaagatgct gaacaagaag ctgaaggatc agaaaacccc aatccccgac   2460
accctgtacc aggagctgta cgactatgtg aatcacagac tgtcccacga cctgtctgat   2520
gaggccaggg ccctgctgcc caacgtgatc accaaggagg tgtctcacga gatcatcaag   2580
gataggcgct ttaccagcga caagttcttt ttccacgtgc ctatcacact gaactatcag   2640
gccgccaatt ccccatctaa gttcaaccag agggtgaatg cctacctgaa ggagcacccc   2700
gagacaccta tcatcggcat cgcccggggc gagagaaacc tgatctatat cacagtgatc   2760
gactccaccg gcaagatcct ggagcagcgg agcctgaaca ccatccagca gtttgattac   2820
cagaagaagc tggacaacag ggagaaggag agggtggcag caaggcaggc ctggtctgtg   2880
gtgggcacaa tcaaggatct gaagcagggc tatctgagcc aggtcatcca cgagatcgtg   2940
gacctgatga tccactacca ggccgtggtg gtgctggaga acctgaattt cggctttaag   3000
```

```
agcaagagga ccggcatcgc cgagaaggcc gtgtaccagc agttcgagaa gatgctgatc   3060
gataagctga attgcctggt gctgaaggac tatccagcag agaaagtggg aggcgtgctg   3120
aacccatacc agctgacaga ccagttcacc tcctttgcca agatgggcac ccagtctggc   3180
ttcctgtttt acgtgcctgc cccatataca tctaagatcg atcccctgac cggcttcgtg   3240
gaccccttcg tgtggaaaac catcaagaat cacgagagcc gcaagcactt cctggagggc   3300
ttcgactttc tgcactacga cgtgaaaacc ggcgacttca tcctgcactt taagatgaac   3360
agaaatctgt ccttccagag gggcctgccc ggctttatgc ctgcatggga tatcgtgttc   3420
gagaagaacg agacacagtt tgacgccaag ggcacccctt tcatcgccgg caagagaatc   3480
gtgccagtga tcgagaatca cagattcacc ggcagatacc gggacctgta tcctgccaac   3540
gagctgatcg ccctgctgga ggagaagggc atcgtgttca gggatggctc caacatcctg   3600
ccaaagctgc tggagaatga cgattctcac gccatcgaca ccatggtggc cctgatccgc   3660
agcgtgctgc agatgcggaa ctccaatgcc gccacaggcg aggactatat caacagcccc   3720
gtgcgcgatc tgaatggcgt gtgcttcgac tcccggtttc agaacccaga gtggcccatg   3780
gacgccgatg ccaatggcgc ctaccacatc gccctgaagg gccagctgct gctgaatcac   3840
ctgaaggaga gcaaggatct gaagctgcag aacggcatct ccaatcagga ctggctggcc   3900
tacatccagg agctgcgcaa caaaaggccg gcggccacga aaaaggccgg ccaggcaaaa   3960
aagaaaaagg gatcctaccc atacgatgtt ccagattacg cttatcccta cgacgtgcct   4020
gattatgcat acccatatga tgtccccgac tatgccggaa gcgaggccag cggttccgga   4080
cgggctgacg cattggacga ttttgatctg gatatgctgg gaagtgacgc cctcgatgat   4140
tttgaccttg acatgcttgg ttcggatgcc cttgatgact ttgacctcga catgctcggc   4200
agtgacgccc ttgatgattt cgacctggac atgctgatta actctagaag ttccggatct   4260
ccgaaaaaga aacgcaaagt tggtagccag tacctgcccg acaccgacga ccggcaccgg   4320
atcgaggaaa agcggaagcg gacctacgag acattcaaga gcatcatgaa gaagtccccc   4380
ttcagcggcc ccaccgaccc tagacctcca cctagaagaa tcgccgtgcc cagcagatcc   4440
agcgccagcg tgccaaaacc tgccccccag ccttacccct tcaccagcag cctgagcacc   4500
atcaactacg acgagttccc taccatggtg ttccccagcg gccagatctc tcaggcctct   4560
gctctggctc cagcccctcc tcaggtgctg cctcaggctc ctgctcctgc accagctcca   4620
gccatggtgt ctgcactggc tcaggcacca gcacccgtgc ctgtgctggc tcctggacct   4680
ccacaggctg tggctccacc agcccctaaa cctacacagg ccggcgaggg cacactgtct   4740
gaagctctgc tgcagctgca gttcgacgac gaggatctgg gagccctgct gggaaacagc   4800
accgatcctg ccgtgttcac cgacctggcc agcgtggaca acagcgagtt ccagcagctg   4860
ctgaaccagg gcatccctgt ggcccctcac accaccgagc ccatgctgat ggaatacccc   4920
gaggccatca cccggctcgt gacaggcgct cagaggcctc ctgatccagc tcctgcccct   4980
ctgggagcac caggcctgcc taatggactg ctgtctggcg acgaggactt cagctctatc   5040
gccgatatgg atttctcagc cttgctgggc tctggcagcg gcagccggga ttccagggaa   5100
gggatgtttt tgccgaagcc tgaggccggc tccgctatta gtgacgtgtt tgagggccgc   5160
gaggtgtgcc agccaaaacg aatccggcca tttcatcctc caggaagtcc atgggccaac   5220
cgcccactcc ccgccagcct cgcaccaaca ccaaccggtc cagtacatga gccagtcggg   5280
tcactgaccc cggcaccagt ccctcagcca ctggatccag cgcccgcagt gactcccgag   5340
```

```
gccagtcacc tgttggagga tcccgatgaa gagacgagcc aggctgtcaa agcccttcgg   5400

gagatggccg atactgtgat tccccagaag gaagaggctg caatctgtgg ccaaatggac   5460

ctttcccatc cgcccccaag gggccatctg gatgagctga caaccacact tgagtccatg   5520

accgaggatc tgaacctgga ctcacccctg accccggaat tgaacgagat tctggatacc   5580

ttcctgaacg acgagtgcct cttgcatgcc atgcatatca gcacaggact gtccatcttc   5640

gacacatctc tgttt                                                    5655


<210> SEQ ID NO 434
<211> LENGTH: 1885
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 434

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Arg Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300
```

-continued

```
Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Arg Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720
```

-continued

```
Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Ala Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys  Ser Lys Arg Thr Gly  Ile Ala Glu
        995                 1000                1005

Lys Ala  Val Tyr Gln Gln Phe  Glu Lys Met Leu Ile  Asp Lys Leu
    1010                1015                1020

Asn Cys  Leu Val Leu Lys Asp  Tyr Pro Ala Glu Lys  Val Gly Gly
    1025                1030                1035

Val Leu  Asn Pro Tyr Gln Leu  Thr Asp Gln Phe Thr  Ser Phe Ala
    1040                1045                1050

Lys Met  Gly Thr Gln Ser Gly  Phe Leu Phe Tyr Val  Pro Ala Pro
    1055                1060                1065

Tyr Thr  Ser Lys Ile Asp Pro  Leu Thr Gly Phe Val  Asp Pro Phe
    1070                1075                1080

Val Trp  Lys Thr Ile Lys Asn  His Glu Ser Arg Lys  His Phe Leu
    1085                1090                1095

Glu Gly  Phe Asp Phe Leu His  Tyr Asp Val Lys Thr  Gly Asp Phe
    1100                1105                1110

Ile Leu  His Phe Lys Met Asn  Arg Asn Leu Ser Phe  Gln Arg Gly
    1115                1120                1125

Leu Pro  Gly Phe Met Pro Ala  Trp Asp Ile Val Phe  Glu Lys Asn
```

```
    1130                1135                1140

Glu Thr  Gln Phe Asp Ala Lys  Gly Thr Pro Phe Ile  Ala Gly Lys
    1145                1150                1155

Arg Ile  Val Pro Val Ile Glu  Asn His Arg Phe Thr  Gly Arg Tyr
    1160                1165                1170

Arg Asp  Leu Tyr Pro Ala Asn  Glu Leu Ile Ala Leu  Leu Glu Glu
    1175                1180                1185

Lys Gly  Ile Val Phe Arg Asp  Gly Ser Asn Ile Leu  Pro Lys Leu
    1190                1195                1200

Leu Glu  Asn Asp Asp Ser His  Ala Ile Asp Thr Met  Val Ala Leu
    1205                1210                1215

Ile Arg  Ser Val Leu Gln Met  Arg Asn Ser Asn Ala  Ala Thr Gly
    1220                1225                1230

Glu Asp  Tyr Ile Asn Ser Pro  Val Arg Asp Leu Asn  Gly Val Cys
    1235                1240                1245

Phe Asp  Ser Arg Phe Gln Asn  Pro Glu Trp Pro Met  Asp Ala Asp
    1250                1255                1260

Ala Asn  Gly Ala Tyr His Ile  Ala Leu Lys Gly Gln  Leu Leu Leu
    1265                1270                1275

Asn His  Leu Lys Glu Ser Lys  Asp Leu Lys Leu Gln  Asn Gly Ile
    1280                1285                1290

Ser Asn  Gln Asp Trp Leu Ala  Tyr Ile Gln Glu Leu  Arg Asn Lys
    1295                1300                1305

Arg Pro  Ala Ala Thr Lys Lys  Ala Gly Gln Ala Lys  Lys Lys Lys
    1310                1315                1320

Gly Ser  Tyr Pro Tyr Asp Val  Pro Asp Tyr Ala Tyr  Pro Tyr Asp
    1325                1330                1335

Val Pro  Asp Tyr Ala Tyr Pro  Tyr Asp Val Pro Asp  Tyr Ala Gly
    1340                1345                1350

Ser Glu  Ala Ser Gly Ser Gly  Arg Ala Asp Ala Leu  Asp Asp Phe
    1355                1360                1365

Asp Leu  Asp Met Leu Gly Ser  Asp Ala Leu Asp Asp  Phe Asp Leu
    1370                1375                1380

Asp Met  Leu Gly Ser Asp Ala  Leu Asp Asp Phe Asp  Leu Asp Met
    1385                1390                1395

Leu Gly  Ser Asp Ala Leu Asp  Asp Phe Asp Leu Asp  Met Leu Ile
    1400                1405                1410

Asn Ser  Arg Ser Ser Gly Ser  Pro Lys Lys Lys Arg  Lys Val Gly
    1415                1420                1425

Ser Gln  Tyr Leu Pro Asp Thr  Asp Asp Arg His Arg  Ile Glu Glu
    1430                1435                1440

Lys Arg  Lys Arg Thr Tyr Glu  Thr Phe Lys Ser Ile  Met Lys Lys
    1445                1450                1455

Ser Pro  Phe Ser Gly Pro Thr  Asp Pro Arg Pro Pro  Pro Arg Arg
    1460                1465                1470

Ile Ala  Val Pro Ser Arg Ser  Ser Ala Ser Val Pro  Lys Pro Ala
    1475                1480                1485

Pro Gln  Pro Tyr Pro Phe Thr  Ser Ser Leu Ser Thr  Ile Asn Tyr
    1490                1495                1500

Asp Glu  Phe Pro Thr Met Val  Phe Pro Ser Gly Gln  Ile Ser Gln
    1505                1510                1515

Ala Ser  Ala Leu Ala Pro Ala  Pro Pro Gln Val Leu  Pro Gln Ala
    1520                1525                1530
```

```
Pro Ala  Pro Ala Pro Ala Pro  Ala Met Val Ser Ala  Leu Ala Gln
    1535                 1540                 1545

Ala Pro  Ala Pro Val Pro Val  Leu Ala Pro Gly Pro  Pro Gln Ala
    1550                 1555                 1560

Val Ala  Pro Pro Ala Pro Lys  Pro Thr Gln Ala Gly  Glu Gly Thr
    1565                 1570                 1575

Leu Ser  Glu Ala Leu Leu Gln  Leu Gln Phe Asp Asp  Glu Asp Leu
    1580                 1585                 1590

Gly Ala  Leu Leu Gly Asn Ser  Thr Asp Pro Ala Val  Phe Thr Asp
    1595                 1600                 1605

Leu Ala  Ser Val Asp Asn Ser  Glu Phe Gln Gln Leu  Leu Asn Gln
    1610                 1615                 1620

Gly Ile  Pro Val Ala Pro His  Thr Thr Glu Pro Met  Leu Met Glu
    1625                 1630                 1635

Tyr Pro  Glu Ala Ile Thr Arg  Leu Val Thr Gly Ala  Gln Arg Pro
    1640                 1645                 1650

Pro Asp  Pro Ala Pro Ala Pro  Leu Gly Ala Pro Gly  Leu Pro Asn
    1655                 1660                 1665

Gly Leu  Leu Ser Gly Asp Glu  Asp Phe Ser Ser Ile  Ala Asp Met
    1670                 1675                 1680

Asp Phe  Ser Ala Leu Leu Gly  Ser Gly Ser Gly Ser  Arg Asp Ser
    1685                 1690                 1695

Arg Glu  Gly Met Phe Leu Pro  Lys Pro Glu Ala Gly  Ser Ala Ile
    1700                 1705                 1710

Ser Asp  Val Phe Glu Gly Arg  Glu Val Cys Gln Pro  Lys Arg Ile
    1715                 1720                 1725

Arg Pro  Phe His Pro Pro Gly  Ser Pro Trp Ala Asn  Arg Pro Leu
    1730                 1735                 1740

Pro Ala  Ser Leu Ala Pro Thr  Pro Thr Gly Pro Val  His Glu Pro
    1745                 1750                 1755

Val Gly  Ser Leu Thr Pro Ala  Pro Val Pro Gln Pro  Leu Asp Pro
    1760                 1765                 1770

Ala Pro  Ala Val Thr Pro Glu  Ala Ser His Leu Leu  Glu Asp Pro
    1775                 1780                 1785

Asp Glu  Glu Thr Ser Gln Ala  Val Lys Ala Leu Arg  Glu Met Ala
    1790                 1795                 1800

Asp Thr  Val Ile Pro Gln Lys  Glu Glu Ala Ala Ile  Cys Gly Gln
    1805                 1810                 1815

Met Asp  Leu Ser His Pro Pro  Pro Arg Gly His Leu  Asp Glu Leu
    1820                 1825                 1830

Thr Thr  Thr Leu Glu Ser Met  Thr Glu Asp Leu Asn  Leu Asp Ser
    1835                 1840                 1845

Pro Leu  Thr Pro Glu Leu Asn  Glu Ile Leu Asp Thr  Phe Leu Asn
    1850                 1855                 1860

Asp Glu  Cys Leu Leu His Ala  Met His Ile Ser Thr  Gly Leu Ser
    1865                 1870                 1875

Ile Phe  Asp Thr Ser Leu Phe
    1880                 1885
```

<210> SEQ ID NO 435
<211> LENGTH: 5721
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 435

```
atgggcccaa agaaaaagag gaaagtcggc agtggaccta aaaagaaacg aaaggttggg     60
tcaggtacac agttcgaggg ctttaccaac ctgtatcagg tgagcaagac actgcggttt    120
gagctgatcc cacagggcaa gaccctgaag cacatccagg agcagggctt catcgaggag    180
gacaaggccc gcaatgatca ctacaaggag ctgaagccca tcatcgatcg gatctacaag    240
acctatgccg accagtgcct gcagctggtg cagctggatt gggagaacct gagcgccgcc    300
atcgactcct atagaaagga gaaaaccgag gagacaagga acgccctgat cgaggagcag    360
gccacatatc gcaatgccat ccacgactac ttcatcggcc ggacagacaa cctgaccgat    420
gccatcaata agagacacgc cgagatctac aagggcctgt tcaaggccga gctgtttaat    480
ggcaaggtgc tgaagcagct gggcaccgtg accacaaccg agcacgagaa cgccctgctg    540
cggagcttcg acaagtttac aacctacttc tccggctttt atagaaacag gaagaacgtg    600
ttcagcgccg aggatatcag cacagccatc ccacaccgca tcgtgcagga caacttcccc    660
aagtttaagg agaattgtca catcttcaca cgcctgatca ccgccgtgcc cagcctgcgg    720
gagcactttg agaacgtgaa gaaggccatc ggcatcttcg tgagcacctc catcgaggag    780
gtgttttcct tccctttta taaccagctg ctgacacaga cccagatcga cctgtataac    840
cagctgctgg gaggaatctc tcgggaggca ggcaccgaga agatcaaggg cctgaacgag    900
gtgctgaatc tggccatcca gaagaatgat gagacagccc acatcatcgc ctccctgcca    960
cacagattca tcccctgtt taagcagatc ctgtccgata ggaacaccct gtctttcatc   1020
ctggaggagt ttaagagcga cgaggaagtg atccagtcct tctgcaagta caagacactg   1080
ctgagaaacg agaacgtgct ggagacagcc gaggccctgt ttaacgagct gaacagcatc   1140
gacctgacac acatcttcat cagccacaag aagctggaga caatcagcag cgccctgtgc   1200
gaccactggg atacactgag gaatgccctg tatgagcgga gaatctccga gctgacaggc   1260
aagatcacca agtctgccaa ggagaaggtg cagcgcagcc tgaagcacga ggatatcaac   1320
ctgcaggaga tcatctctgc cgcaggcaag gagctgagcg aggccttcaa gcagaaaacc   1380
agcgagatcc tgtcccacgc acacgccgcc ctggatcagc cactgcctac aaccctgaag   1440
aagcaggagg agaaggagat cctgaagtct cagctggaca gcctgctggg cctgtaccac   1500
ctgctggact ggtttgccgt ggatgagtcc aacgaggtgg accccgagtt ctctgcccgg   1560
ctgaccggca tcaagctgga gatggagcct tctctgagct tctacaacaa ggccagaaat   1620
tatgccacca agaagcccta ctccgtggag aagttcaagc tgaactttca gatgcctaca   1680
ctggccagag gctgggacgt gaatagagag aagaacaatg gcgccatcct gtttgtgaag   1740
aacggcctgt actatctggg catcatgcca aagcagaagg gcaggtataa ggccctgagc   1800
ttcgagccca cagagaaaac cagcgagggc tttgataaga tgtactatga ctacttccct   1860
gatgccgcca agatgatccc aaagtgcagc acccagctga aggccgtgac agcccacttt   1920
cagacccaca caacccccat cctgctgtcc aacaatttca tcgagcctct ggagatcaca   1980
aaggagatct acgacctgaa caatcctgag aaggagccaa agaagtttca gacagcctac   2040
gccaagaaaa ccggcgacca gaagggctac agagaggccc tgtgcaagtg gatcgacttc   2100
acaagggatt ttctgtccaa gtataccaag acaacctcta tcgatctgtc tagcctgcgg   2160
ccatcctctc agtataagga cctgggcgag tactatgccg agctgaatcc cctgctgtac   2220
```

-continued

```
cacatcagct tccagagaat cgccgagaag gagatcatgg atgccgtgga gacaggcaag   2280
ctgtacctgt tccagatcta taacaaggac tttgccaagg gccaccacgg caagcctaat   2340
ctgcacacac tgtattggac cggcctgttt tctccagaga acctggccaa gacaagcatc   2400
aagctgaatg gccaggccga gctgttctac cgccctaagt ccaggatgaa gaggatggca   2460
caccggctgg gagagaagat gctgaacaag aagctgaagg atcagaaaac cccaatcccc   2520
gacaccctgt accaggagct gtacgactat gtgaatcaca gactgtccca cgacctgtct   2580
gatgaggcca gggccctgct gcccaacgtg atcaccaagg aggtgtctca cgagatcatc   2640
aaggataggc gctttaccag cgacaagttc tttttccacg tgcctatcac actgaactat   2700
caggccgcca attccccatc taagttcaac cagagggtga atgcctacct gaaggagcac   2760
cccgagacac ctatcatcgg catcgcccgg ggcgagagaa acctgatcta tatcacagtg   2820
atcgactcca ccggcaagat cctggagcag cggagcctga acaccatcca gcagtttgat   2880
taccagaaga agctggacaa cagggagaag gagagggtgg cagcaaggca ggcctggtct   2940
gtggtgggca caatcaagga tctgaagcag ggctatctga gccaggtcat ccacgagatc   3000
gtggacctga tgatccacta ccaggccgtg gtggtgctgg agaacctgaa tttcggcttt   3060
aagagcaaga ggaccggcat cgccgagaag gccgtgtacc agcagttcga gaagatgctg   3120
atcgataagc tgaattgcct ggtgctgaag gactatccag cagagaaagt gggaggcgtg   3180
ctgaacccat accagctgac agaccagttc acctcctttg ccaagatggg cacccagtct   3240
ggcttcctgt tttacgtgcc tgccccatat acatctaaga tcgatcccct gaccggcttc   3300
gtggacccct tcgtgtggaa aaccatcaag aatcacgaga gccgcaagca cttcctggag   3360
ggcttcgact ttctgcacta cgacgtgaaa accggcgact tcatcctgca ctttaagatg   3420
aacagaaatc tgtccttcca gaggggcctg cccggcttta tgcctgcatg ggatatcgtg   3480
ttcgagaaga acgagacaca gtttgacgcc aagggcaccc ctttcatcgc cggcaagaga   3540
atcgtgccag tgatcgagaa tcacagattc accggcagat accgggacct gtatcctgcc   3600
aacgagctga tcgccctgct ggaggagaag ggcatcgtgt tcagggatgg ctccaacatc   3660
ctgccaaagc tgctggagaa tgacgattct cacgccatcg acacgatggt ggccctgatc   3720
cgcagcgtgc tgcagatgcg gaactccaat gccgccacag gcgaggacta tatcaacagc   3780
cccgtgcgcg atctgaatgg cgtgtgcttc gactcccggt ttcagaaccc agagtggcca   3840
atggacgccg atgccaatgg cgcctaccac atcgccctga agggccagct gctgctgaat   3900
cacctgaagg agagcaagga tctgaagctg cagaacggca tctccaatca ggactggctg   3960
gcctacatcc aggagctgcg caacaaaagg ccggcggcca cgaaaaaggc cggccaggca   4020
aaaaagaaaa agggatccta cccatacgat gttccagatt acgcttatcc ctacgacgtg   4080
cctgattatg catacccata tgatgtcccc gactatgccg gaagcgaggc cagcggttcc   4140
ggacgggctg acgcattgga cgattttgat ctggatatgc tgggaagtga cgccctcgat   4200
gattttgacc ttgacatgct tggttcggat gcccttgatg actttgacct cgacatgctc   4260
ggcagtgacg cccttgatga tttcgacctg gacatgctga ttaactctag aagttccgga   4320
tctccgaaaa agaaacgcaa agttggtagc cagtacctgc ccgacaccga cgaccggcac   4380
cggatcgagg aaaagcggaa gcggacctac gagacattca agagcatcat gaagaagtcc   4440
cccttcagcg gccccaccga ccctagacct ccacctagaa gaatcgccgt gcccagcaga   4500
tccagcgcca gcgtgccaaa acctgccccc cagccttacc ccttcaccag cagcctgagc   4560
accatcaact acgacgagtt ccctaccatg gtgttcccca gcggccagat ctctcaggcc   4620
```

```
tctgctctgg ctccagcccc tcctcaggtg ctgcctcagg ctcctgctcc tgcaccagct   4680

ccagccatgg tgtctgcact ggctcaggca ccagcacccg tgcctgtgct ggctcctgga   4740

cctccacagg ctgtggctcc accagcccct aaacctacac aggccggcga gggcacactg   4800

tctgaagctc tgctgcagct gcagttcgac gacgaggatc tgggagccct gctgggaaac   4860

agcaccgatc ctgccgtgtt caccgacctg gccagcgtgg acaacagcga gttccagcag   4920

ctgctgaacc agggcatccc tgtggcccct cacaccaccg agcccatgct gatggaatac   4980

cccgaggcca tcacccggct cgtgacaggc gctcagaggc ctcctgatcc agctcctgcc   5040

cctctgggag caccaggcct gcctaatgga ctgctgtctg gcgacgagga cttcagctct   5100

atcgccgata tggatttctc agccttgctg ggctctggca gcggcagccg ggattccagg   5160

gaagggatgt tttgccgaa gcctgaggcc ggctccgcta ttagtgacgt gtttgagggc   5220

cgcgaggtgt gccagccaaa acgaatccgg ccatttcatc ctccaggaag tccatgggcc   5280

aaccgcccac tccccgccag cctcgcacca acaccaaccg gtccagtaca tgagccagtc   5340

gggtcactga ccccggcacc agtccctcag ccactggatc cagcgcccgc agtgactccc   5400

gaggccagtc acctgttgga ggatcccgat gaagagacga gccaggctgt caaagccctt   5460

cgggagatgg ccgatactgt gattccccag aaggaagagg ctgcaatctg tggccaaatg   5520

gacctttccc atccgccccc aaggggccat ctggatgagc tgacaaccac acttgagtcc   5580

atgaccgagg atctgaacct ggactcaccc ctgaccccgg aattgaacga gattctggat   5640

accttcctga acgacgagtg cctcttgcat gccatgcata tcagcacagg actgtccatc   5700

ttcgacacat ctctgtttta a                                                5721
```

<210> SEQ ID NO 436
<211> LENGTH: 5574
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 436

```
atgacacagt tcgagggctt taccaacctg tatcaggtga gcaagacact gcggtttgag     60

ctgatcccac agggcaagac cctgaagcac atccaggagc agggcttcat cgaggaggac    120

aaggcccgca atgatcacta caaggagctg aagcccatca tcgatcggat ctacaagacc    180

tatgccgacc agtgcctgca gctggtgcag ctggattggg agaacctgag cgccgccatc    240

gactcctata gaaaggagaa aaccgaggag acaaggaacg ccctgatcga ggagcaggcc    300

acatatcgca atgccatcca cgactacttc atcggccgga cagacaacct gaccgatgcc    360

atcaataaga gacacgccga gatctacaag ggcctgttca aggccgagct gtttaatggc    420

aaggtgctga agcagctggg caccgtgacc acaaccgagc acgagaacgc cctgctgcgg    480

agcttcgaca agtttacaac ctacttctcc ggcttttata gaaacaggaa gaacgtgttc    540

agcgccgagg atatcagcac agccatccca caccgcatcg tgcaggacaa cttccccaag    600

tttaaggaga attgtcacat cttcacacgc ctgatcaccg ccgtgcccag cctgcgggag    660

cactttgaga acgtgaagaa ggccatcggc atcttcgtga gcacctccat cgaggaggtg    720

ttttccttcc ctttttataa ccagctgctg acacagaccc agatcgacct gtataaccag    780

ctgctgggag gaatctctcg ggaggcaggc accgagaaga tcaagggcct gaacgaggtg    840

ctgaatctgg ccatccagaa gaatgatgag acagcccaca tcatcgcctc cctgccacac    900
```

```
agattcatcc ccctgtttaa gcagatcctg tccgatagga acaccctgtc tttcatcctg    960
gaggagttta agagcgacga ggaagtgatc cagtccttct gcaagtacaa gacactgctg   1020
agaaacgaga acgtgctgga gacagccgag gccctgttta acgagctgaa cagcatcgac   1080
ctgacacaca tcttcatcag ccacaagaag ctggagacaa tcagcagcgc cctgtgcgac   1140
cactgggata cactgaggaa tgccctgtat gagcggagaa tctccgagct gacaggcaag   1200
atcaccaagt ctgccaagga gaaggtgcag cgcagcctga agcacgagga tatcaacctg   1260
caggagatca tctctgccgc aggcaaggag ctgagcgagg ccttcaagca gaaaaccagc   1320
gagatcctgt cccacgcaca cgccgccctg gatcagccac tgcctacaac cctgaagaag   1380
caggaggaga aggagatcct gaagtctcag ctggacagcc tgctgggcct gtaccacctg   1440
ctggactggt ttgccgtgga tgagtccaac gaggtggacc ccgagttctc tgcccggctg   1500
accggcatca agctggagat ggagccttct ctgagcttct acaacaaggc cagaaattat   1560
gccaccaaga agccctactc cgtggagaag ttcaagctga actttcagat gcctacactg   1620
gccagaggct gggacgtgaa tagagagaag aacaatggcg ccatcctgtt tgtgaagaac   1680
ggcctgtact atctgggcat catgccaaag cagaagggca ggtataaggc cctgagcttc   1740
gagcccacag agaaaaccag cgagggcttt gataagatgt actatgacta cttccctgat   1800
gccgccaaga tgatcccaaa gtgcagcacc cagctgaagg ccgtgacagc ccactttcag   1860
acccacacaa cccccatcct gctgtccaac aatttcatcg agcctctgga gatcacaaag   1920
gagatctacg acctgaacaa tcctgagaag gagccaaaga agtttcagac agcctacgcc   1980
aagaaaaccg gcgaccagaa gggctacaga gaggccctgt gcaagtggat cgacttcaca   2040
agggattttc tgtccaagta taccaagaca acctctatcg atctgtctag cctgcggcca   2100
tcctctcagt ataaggacct gggcgagtac tatgccgagc tgaatcccct gctgtaccac   2160
atcagcttcc agagaatcgc cgagaaggag atcatggatg ccgtggagac aggcaagctg   2220
tacctgttcc agatctataa caaggacttt gccaagggcc accacggcaa gcctaatctg   2280
cacacactgt attggaccgg cctgttttct ccagagaacc tggccaagac aagcatcaag   2340
ctgaatggcc aggccgagct gttctaccgc cctaagtcca ggatgaagag gatggcacac   2400
cggctgggag agaagatgct gaacaagaag ctgaaggatc agaaaacccc aatccccgac   2460
accctgtacc aggagctgta cgactatgtg aatcacagac tgtcccacga cctgtctgat   2520
gaggccaggg ccctgctgcc caacgtgatc accaaggagg tgtctcacga gatcatcaag   2580
gataggcgct ttaccagcga caagttcttt ttccacgtgc ctatcacact gaactatcag   2640
gccgccaatt ccccatctaa gttcaaccag agggtgaatg cctacctgaa ggagcacccc   2700
gagacaccta tcatcggcat cgcccggggc gagagaaacc tgatctatat cacagtgatc   2760
gactccaccg gcaagatcct ggagcagcgg agcctgaaca ccatccagca gtttgattac   2820
cagaagaagc tggacaacag ggagaaggag agggtggcag caaggcaggc ctggtctgtg   2880
gtgggcacaa tcaaggatct gaagcagggc tatctgagcc aggtcatcca cgagatcgtg   2940
gacctgatga tccactacca ggccgtggtg gtgctggaga acctgaattt cggctttaag   3000
agcaagagga ccggcatcgc cgagaaggcc gtgtaccagc agttcgagaa gatgctgatc   3060
gataagctga attgcctggt gctgaaggac tatccagcag agaaagtggg aggcgtgctg   3120
aacccatacc agctgacaga ccagttcacc tcctttgcca agatgggcac ccagtctggc   3180
ttcctgtttt acgtgcctgc cccatataca tctaagatcg atcccctgac cggcttcgtg   3240
```

-continued

```
gaccccttcg tgtggaaaac catcaagaat cacgagagcc gcaagcactt cctggagggc   3300
ttcgactttc tgcactacga cgtgaaaacc ggcgacttca tcctgcactt taagatgaac   3360
agaaatctgt ccttccagag gggcctgccc ggctttatgc ctgcatggga tatcgtgttc   3420
gagaagaacg agacacagtt tgacgccaag ggcacccctt tcatcgccgg caagagaatc   3480
gtgccagtga tcgagaatca cagattcacc ggcagatacc gggacctgta tcctgccaac   3540
gagctgatcg ccctgctgga ggagaagggc atcgtgttca gggatggctc caacatcctg   3600
ccaaagctgc tggagaatga cgattctcac gccatcgaca cgatggtggc cctgatccgc   3660
agcgtgctgc agatgcggaa ctccaatgcc gccacaggcg aggactatat caacagcccc   3720
gtgcgcgatc tgaatggcgt gtgcttcgac tcccggtttc agaacccaga gtggccaatg   3780
gacgccgatg ccaatggcgc ctaccacatc gccctgaagg gccagctgct gctgaatcac   3840
ctgaaggaga gcaaggatct gaagctgcag aacggcatct ccaatcagga ctggctggcc   3900
tacatccagg agctgcgcaa cggtggaagc ggagggagtc ccaagaagaa gaggaaagtc   3960
gggggttccg gaggaagcga ggccagcggt tccggacggg ctgacgcatt ggacgatttt   4020
gatctggata tgctgggaag tgacgccctc gatgattttg accttgacat gcttggttcg   4080
gatgcccttg atgactttga cctcgacatg ctcggcagtg acgcccttga tgatttcgac   4140
ctggacatgc tgattaactc tagaagttcc ggatctccga aaaagaaacg caaagttggt   4200
agccagtacc tgcccgacac cgacgaccgg caccggatcg aggaaaagcg gaagcggacc   4260
tacgagacat tcaagagcat catgaagaag tcccccttca gcggccccac cgaccctaga   4320
cctccaccta gaagaatcgc cgtgcccagc agatccagcg ccagcgtgcc aaaacctgcc   4380
ccccagcctt accccttcac cagcagcctg agcaccatca actacgacga gttccctacc   4440
atggtgttcc ccagcggcca gatctctcag gcctctgctc tggctccagc ccctcctcag   4500
gtgctgcctc aggctcctgc tcctgcacca gctccagcca tggtgtctgc actggctcag   4560
gcaccagcac ccgtgcctgt gctggctcct ggacctccac aggctgtggc tccaccagcc   4620
cctaaaccta cacaggccgg cgagggcaca ctgtctgaag ctctgctgca gctgcagttc   4680
gacgacgagg atctgggagc cctgctggga aacagcaccg atcctgccgt gttcaccgac   4740
ctggccagcg tggacaacag cgagttccag cagctgctga accagggcat ccctgtggcc   4800
cctcacacca ccgagcccat gctgatggaa taccccgagg ccatcacccg gctcgtgaca   4860
ggcgctcaga ggcctcctga tccagctcct gcccctctgg gagcaccagg cctgcctaat   4920
ggactgctgt ctggcgacga ggacttcagc tctatcgccg atatggattt ctcagccttg   4980
ctgggctctg gcagcggcag ccgggattcc agggaaggga tgtttttgcc gaagcctgag   5040
gccggctccg ctattagtga cgtgtttgag ggccgcgagg tgtgccagcc aaaacgaatc   5100
cggccatttc atcctccagg aagtccatgg gccaaccgcc cactccccgc cagcctcgca   5160
ccaacaccaa ccggtccagt acatgagcca gtcgggtcac tgaccccggc accagtccct   5220
cagccactgg atccagcgcc cgcagtgact cccgaggcca gtcacctgtt ggaggatccc   5280
gatgaagaga cgagccaggc tgtcaaagcc cttcgggaga tggccgatac tgtgattccc   5340
cagaaggaag aggctgcaat ctgtggccaa atggaccttt cccatccgcc cccaaggggc   5400
catctggatg agctgacaac cacacttgag tccatgaccg aggatctgaa cctggactca   5460
cccctgaccc cggaattgaa cgagattctg gataccttcc tgaacgacga gtgcctcttg   5520
catgccatgc atatcagcac aggactgtcc atcttcgaca catctctgtt ttaa         5574
```

```
<210> SEQ ID NO 437
<211> LENGTH: 5637
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 437

atgggcccaa agaaaaagag gaaagtcggc agtggaccta aaaagaaacg aaaggttggg     60

tcaggtacac agttcgaggg ctttaccaac ctgtatcagg tgagcaagac actgcggttt    120

gagctgatcc cacagggcaa gaccctgaag cacatccagg agcagggctt catcgaggag    180

gacaaggccc gcaatgatca ctacaaggag ctgaagccca tcatcgatcg gatctacaag    240

acctatgccg accagtgcct gcagctggtg cagctggatt gggagaacct gagcgccgcc    300

atcgactcct atagaaagga gaaaaccgag gagacaagga acgccctgat cgaggagcag    360

gccacatatc gcaatgccat ccacgactac ttcatcggcc ggacagacaa cctgaccgat    420

gccatcaata agagacacgc cgagatctac aagggcctgt tcaaggccga gctgtttaat    480

ggcaaggtgc tgaagcagct gggcaccgtg accacaaccg agcacgagaa cgccctgctg    540

cggagcttcg acaagtttac aacctacttc tccggctttt atagaaacag gaagaacgtg    600

ttcagcgccg aggatatcag cacagccatc ccacaccgca tcgtgcagga caacttcccc    660

aagtttaagg agaattgtca catcttcaca cgcctgatca ccgccgtgcc cagcctgcgg    720

gagcactttg agaacgtgaa gaaggccatc ggcatcttcg tgagcacctc catcgaggag    780

gtgttttcct tccctttta taaccagctg ctgacacaga cccagatcga cctgtataac    840

cagctgctgg gaggaatctc tcgggaggca ggcaccgaga agatcaaggg cctgaacgag    900

gtgctgaatc tggccatcca gaagaatgat gagacagccc acatcatcgc ctccctgcca    960

cacagattca tccccctgtt taagcagatc ctgtccgata ggaacaccct gtctttcatc   1020

ctggaggagt ttaagagcga cgaggaagtg atccagtcct tctgcaagta caagacactg   1080

ctgagaaacg agaacgtgct ggagacagcc gaggccctgt ttaacgagct gaacagcatc   1140

gacctgacac acatcttcat cagccacaag aagctggaga caatcagcag cgccctgtgc   1200

gaccactggg atacactgag gaatgccctg tatgagcgga gaatctccga gctgacaggc   1260

aagatcacca agtctgccaa ggagaaggtg cagcgcagcc tgaagcacga ggatatcaac   1320

ctgcaggaga tcatctctgc cgcaggcaag gagctgagcg aggccttcaa gcagaaaacc   1380

agcgagatcc tgtcccacgc acacgccgcc ctggatcagc cactgcctac aaccctgaag   1440

aagcaggagg agaaggagat cctgaagtct cagctggaca gcctgctggg cctgtaccac   1500

ctgctggact ggtttgccgt ggatgagtcc aacgaggtgg accccgagtt ctctgcccgg   1560

ctgaccggca tcaagctgga gatggagcct tctctgagct tctacaacaa ggccagaaat   1620

tatgccacca agaagcccta ctccgtggag aagttcaagc tgaactttca gatgcctaca   1680

ctggccagag gctgggacgt gaatagagag aagaacaatg gcgccatcct gtttgtgaag   1740

aacggcctgt actatctggg catcatgcca aagcagaagg gcaggtataa ggccctgagc   1800

ttcgagccca cagagaaaac cagcgagggc tttgataaga tgtactatga ctacttccct   1860

gatgccgcca agatgatccc aaagtgcagc acccagctga aggccgtgac agcccacttt   1920

cagacccaca caacccccat cctgctgtcc aacaatttca tcgagcctct ggagatcaca   1980

aaggagatct acgacctgaa caatcctgag aaggagccaa agaagtttca gacagcctac   2040

gccaagaaaa ccggcgacca gaagggctac agagaggccc tgtgcaagtg gatcgacttc   2100
```

-continued

```
acaagggatt ttctgtccaa gtataccaag acaacctcta tcgatctgtc tagcctgcgg   2160
ccatcctctc agtataagga cctgggcgag tactatgccg agctgaatcc cctgctgtac   2220
cacatcagct tccagagaat cgccgagaag gagatcatgg atgccgtgga gacaggcaag   2280
ctgtacctgt tccagatcta taacaaggac tttgccaagg gccaccacgg caagcctaat   2340
ctgcacacac tgtattggac cggcctgttt tctccagaga acctggccaa gacaagcatc   2400
aagctgaatg gccaggccga gctgttctac cgccctaagt ccaggatgaa gaggatggca   2460
caccggctgg gagagaagat gctgaacaag aagctgaagg atcagaaaac cccaatcccc   2520
gacaccctgt accaggagct gtacgactat gtgaatcaca gactgtccca cgacctgtct   2580
gatgaggcca gggccctgct gcccaacgtg atcaccaagg aggtgtctca cgagatcatc   2640
aaggataggc gctttaccag cgacaagttc tttttccacg tgcctatcac actgaactat   2700
caggccgcca attccccatc taagttcaac cagagggtga atgcctacct gaaggagcac   2760
cccgagacac ctatcatcgg catcgcccgg ggcgagagaa acctgatcta tatcacagtg   2820
atcgactcca ccggcaagat cctggagcag cggagcctga acaccatcca gcagtttgat   2880
taccagaaga agctggacaa cagggagaag gagagggtgg cagcaaggca ggcctggtct   2940
gtggtgggca caatcaagga tctgaagcag ggctatctga gccaggtcat ccacgagatc   3000
gtggacctga tgatccacta ccaggccgtg gtggtgctgg agaacctgaa tttcggcttt   3060
aagagcaaga ggaccggcat cgccgagaag gccgtgtacc agcagttcga gaagatgctg   3120
atcgataagc tgaattgcct ggtgctgaag gactatccag cagagaaagt gggaggcgtg   3180
ctgaacccat accagctgac agaccagttc acctcctttg ccaagatggg cacccagtct   3240
ggcttcctgt tttacgtgcc tgccccatat acatctaaga tcgatcccct gaccggcttc   3300
gtggacccct tcgtgtggaa aaccatcaag aatcacgaga gccgcaagca cttcctggag   3360
ggcttcgact ttctgcacta cgacgtgaaa accggcgact tcatcctgca ctttaagatg   3420
aacagaaatc tgtccttcca gaggggcctg cccggcttta tgcctgcatg ggatatcgtg   3480
ttcgagaaga acgagacaca gtttgacgcc aagggcaccc ctttcatcgc cggcaagaga   3540
atcgtgccag tgatcgagaa tcacagattc accggcagat accgggacct gtatcctgcc   3600
aacgagctga tcgccctgct ggaggagaag ggcatcgtgt tcagggatgg ctccaacatc   3660
ctgccaaagc tgctggagaa tgacgattct cacgccatcg acacgatggt ggccctgatc   3720
cgcagcgtgc tgcagatgcg gaactccaat gccgccacag gcgaggacta tatcaacagc   3780
cccgtgcgcg atctgaatgg cgtgtgcttc gactcccggt ttcagaaccc agagtggcca   3840
atggacgccg atgccaatgg cgcctaccac atcgccctga agggccagct gctgctgaat   3900
cacctgaagg agagcaagga tctgaagctg cagaacggca tctccaatca ggactggctg   3960
gcctacatcc aggagctgcg caacggtgga agcggaggga gtcccaagaa gaagaggaaa   4020
gtcgggggtt ccggaggaag cgaggccagc ggttccggac gggctgacgc attggacgat   4080
tttgatctgg atatgctggg aagtgacgcc ctcgatgatt ttgaccttga catgcttggt   4140
tcggatgccc ttgatgactt tgacctcgac atgctcggca gtgacgccct tgatgatttc   4200
gacctggaca tgctgattaa ctctagaagt tccggatctc cgaaaaagaa acgcaaagtt   4260
ggtagccagt acctgcccga caccgacgac cggcaccgga tcgaggaaaa gcggaagcgg   4320
acctacgaga cattcaagag catcatgaag aagtccccct tcagcggccc caccgaccct   4380
agacctccac ctagaagaat cgccgtgccc agcagatcca gcgccagcgt gccaaaacct   4440
```

-continued gccccccagc cttacccctt caccagcagc ctgagcacca tcaactacga cgagttccct 4500
accatggtgt tccccagcgg ccagatctct caggcctctg ctctggctcc agcccctcct 4560
caggtgctgc ctcaggctcc tgctcctgca ccagctccag ccatggtgtc tgcactggct 4620
caggcaccag cacccgtgcc tgtgctggct cctggacctc cacaggctgt ggctccacca 4680
gcccctaaac ctacacaggc cggcgagggc acactgtctg aagctctgct gcagctgcag 4740
ttcgacgacg aggatctggg agccctgctg ggaaacagca ccgatcctgc cgtgttcacc 4800
gacctggcca gcgtggacaa cagcgagttc cagcagctgc tgaaccaggg catccctgtg 4860
gcccctcaca ccaccgagcc catgctgatg gaataccccg aggccatcac ccggctcgtg 4920
acaggcgctc agaggcctcc tgatccagct cctgcccctc tgggagcacc aggcctgcct 4980
aatggactgc tgtctggcga cgaggacttc agctctatcg ccgatatgga tttctcagcc 5040
ttgctgggct ctggcagcgg cagccgggat tccagggaag ggatgttttt gccgaagcct 5100
gaggccggct ccgctattag tgacgtgttt gagggccgcg aggtgtgcca gccaaaacga 5160
atccggccat ttcatcctcc aggaagtcca tgggccaacc gcccactccc cgccagcctc 5220
gcaccaacac caaccggtcc agtacatgag ccagtcgggt cactgacccc ggcaccagtc 5280
cctcagccac tggatccagc gcccgcagtg actcccgagg ccagtcacct gttggaggat 5340
cccgatgaag agacgagcca ggctgtcaaa gcccttcggg agatggccga tactgtgatt 5400
ccccagaagg aagaggctgc aatctgtggc caaatggacc tttcccatcc gcccccaagg 5460
ggccatctgg atgagctgac aaccacactt gagtccatga ccgaggatct gaacctggac 5520
tcacccctga ccccggaatt gaacgagatt ctggatacct tcctgaacga cgagtgcctc 5580
ttgcatgcca tgcatatcag cacaggactg tccatcttcg acacatctct gttttaa 5637

<210> SEQ ID NO 438
<211> LENGTH: 5073
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 438
atgggcagct cagagactgg cccagtggct gtggacccca cattgagacg gcggatcgag 60
ccccatgagt ttgaggtatt cttcgatccg agagagctcc gcaaggagac ctgcctgctt 120
tacgaaatta attggggggg ccggcactcc atttggcgac atacatcaca gaacactaac 180
aagcacgtcg aagtcaactt catcgagaag ttcacgacag aaagatattt ctgtccgaac 240
acaaggtgca gcattacctg gtttctcagc tggagcccat gcggcgaatg tagtagggcc 300
atcactgaat tcctgtcaag gtatccccac gtcactctgt ttatttacat cgcaaggctg 360
taccaccacg ctgacccccg caatcgacaa ggcctgcggg atttgatctc ttcaggtgtg 420
actatccaaa ttatgactga gcaggagtca ggatactgct ggagaaactt tgtgaattat 480
agcccgagta atgaagccca ctggcctagg tatccccatc tgtgggtacg actgtacgtt 540
cttgaactgt actgcatcat actgggcctg cctccttgtc tcaacattct gagaaggaag 600
cagccacagc tgacattctt taccatcgct cttcagtctt gtcattacca gcgactgccc 660
ccacacattc tctgggccac cgggttgaaa tctggtggtt cttctggtgg ttctagcggc 720
agcgagactc ccgggacctc agagtccgcc acacccgaaa gttccggagg gagtagcggc 780
gggtctacac agttcgaggg ctttaccaac ctgtatcagg tgagcaagac actgcggttt 840

-continued

```
gagctgatcc cacagggcaa gaccctgaag cacatccagg agcagggctt catcgaggag     900
gacaaggccc gcaatgatca ctacaaggag ctgaagccca tcatcgatcg gatctacaag     960
acctatgccg accagtgcct gcagctggtg cagctggatt gggagaacct gagcgccgcc    1020
atcgactcct atagaaagga gaaaaccgag gagacaagga acgccctgat cgaggagcag    1080
gccacatatc gcaatgccat ccacgactac ttcatcggcc ggacagacaa cctgaccgat    1140
gccatcaata agagacacgc cgagatctac aagggcctgt tcaaggccga gctgtttaat    1200
ggcaaggtgc tgaagcagct gggcaccgtg accacaaccg agcacgagaa cgccctgctg    1260
cggagcttcg acaagtttac aacctacttc tccggctttt atgagaacag gaagaacgtg    1320
ttcagcgccg aggatatcag cacagccatc ccacaccgca tcgtgcagga caacttcccc    1380
aagtttaagg agaattgtca catcttcaca cgcctgatca ccgccgtgcc cagcctgcgg    1440
gagcactttg agaacgtgaa gaaggccatc ggcatcttcg tgagcacctc catcgaggag    1500
gtgttttcct tccctttta taaccagctg ctgacacaga cccagatcga cctgtataac    1560
cagctgctgg gaggaatctc tcgggaggca ggcaccgaga agatcaaggg cctgaacgag    1620
gtgctgaatc tggccatcca gaagaatgat gagacagccc acatcatcgc ctccctgcca    1680
cacagattca tccccctgtt taagcagatc ctgtccgata ggaacaccct gtctttcatc    1740
ctggaggagt ttaagagcga cgaggaagtg atccagtcct tctgcaagta caagacactg    1800
ctgagaaacg agaacgtgct ggagacagcc gaggccctgt ttaacgagct gaacagcatc    1860
gacctgacac acatcttcat cagccacaag aagctggaga caatcagcag cgccctgtgc    1920
gaccactggg atacactgag gaatgccctg tatgagcgga gaatctccga gctgacaggc    1980
aagatcacca agtctgccaa ggagaaggtg cagcgcagcc tgaagcacga ggatatcaac    2040
ctgcaggaga tcatctctgc cgcaggcaag gagctgagcg aggccttcaa gcagaaaacc    2100
agcgagatcc tgtcccacgc acacgccgcc ctggatcagc cactgcctac aaccctgaag    2160
aagcaggagg agaaggagat cctgaagtct cagctggaca gcctgctggg cctgtaccac    2220
ctgctggact ggtttgccgt ggatgagtcc aacgaggtgg accccgagtt ctctgcccgg    2280
ctgaccggca tcaagctgga gatggagcct tctctgagct tctacaacaa ggccagaaat    2340
tatgccacca agaagcccta ctccgtggag aagttcaagc tgaactttca gatgcctaca    2400
ctggcctctg gctgggacgt gaataaggag aagaacaatg gcgccatcct gtttgtgaag    2460
aacggcctgt actatctggg catcatgcca aagcagaagg gcaggtataa ggccctgagc    2520
ttcgagccca cagagaaaac cagcgagggc tttgataaga tgtactatga ctacttccct    2580
gatgccgcca agatgatccc aaagtgcagc acccagctga aggccgtgac agcccacttt    2640
cagacccaca caacccccat cctgctgtcc aacaatttca tcgagcctct ggagatcaca    2700
aaggagatct acgacctgaa caatcctgag aaggagccaa agaagtttca gacagcctac    2760
gccaagaaaa ccggcgacca gaagggctac agagaggccc tgtgcaagtg gatcgacttc    2820
acaagggatt ttctgtccaa gtataccaag acaacctcta tcgatctgtc tagcctgcgg    2880
ccatcctctc agtataagga cctgggcgag tactatgccg agctgaatcc cctgctgtac    2940
cacatcagct tccagagaat cgccgagaag gagatcatgg atgccgtgga gacaggcaag    3000
ctgtacctgt tccagatcta taacaaggac tttgccaagg gccaccacgg caagcctaat    3060
ctgcacacac tgtattggac cggcctgttt tctccagaga acctggccaa gacaagcatc    3120
aagctgaatg gccaggccga gctgttctac cgccctaagt ccaggatgaa gaggatggca    3180
caccggctgg gagagaagat gctgaacaag aagctgaagg atcagaaaac cccaatcccc    3240
```

-continued gacaccctgt accaggagct gtacgactat gtgaatcaca gactgtccca cgacctgtct 3300
gatgaggcca gggccctgct gcccaacgtg atcaccaagg aggtgtctca cgagatcatc 3360
aaggataggc gctttaccag cgacaagttc tttttccacg tgcctatcac actgaactat 3420
caggccgcca attccccatc taagttcaac cagagggtga atgcctacct gaaggagcac 3480
cccgagacac ctatcatcgg catcgcccgg ggcgagagaa acctgatcta tatcacagtg 3540
atcgactcca ccggcaagat cctggagcag cggagcctga acaccatcca gcagtttgat 3600
taccagaaga agctggacaa cagggagaag gagagggtgg cagcaaggca ggcctggtct 3660
gtggtgggca caatcaagga tctgaagcag ggctatctga gccaggtcat ccacgagatc 3720
gtggacctga tgatccacta ccaggccgtg gtggtgctgg agaacctgaa tttcggcttt 3780
aagagcaaga ggaccggcat cgccgagaag gccgtgtacc agcagttcga gaagatgctg 3840
atcgataagc tgaattgcct ggtgctgaag gactatccag cagagaaagt gggaggcgtg 3900
ctgaacccat accagctgac agaccagttc acctcctttg ccaagatggg cacccagtct 3960
ggcttcctgt tttacgtgcc tgccccatat acatctaaga tcgatcccct gaccggcttc 4020
gtggacccct tcgtgtggaa aaccatcaag aatcacgaga gccgcaagca cttcctggag 4080
ggcttcgact ttctgcacta cgacgtgaaa accggcgact tcatcctgca ctttaagatg 4140
aacagaaatc tgtccttcca gaggggcctg cccggcttta tgcctgcatg ggatatcgtg 4200
ttcgagaaga acgagacaca gtttgacgcc aagggcaccc ctttcatcgc cggcaagaga 4260
atcgtgccag tgatcgagaa tcacagattc accggcagat accgggacct gtatcctgcc 4320
aacgagctga tcgccctgct ggaggagaag ggcatcgtgt tcagggatgg ctccaacatc 4380
ctgccaaagc tgctggagaa tgacgattct cacgccatcg acacgatggt ggccctgatc 4440
cgcagcgtgc tgcagatgcg gaactccaat gccgccacag gcgaggacta tatcaacagc 4500
cccgtgcgcg atctgaatgg cgtgtgcttc gactcccggt ttcagaaccc agagtggcca 4560
atggacgccg atgccaatgg cgcctaccac atcgccctga agggccagct gctgctgaat 4620
cacctgaagg agagcaagga tctgaagctg cagaacggca tctccaatca ggactggctg 4680
gcctacatcc aggagctgcg caacaaaagg ccggcggcca cgaaaaaggc cggccaggca 4740
aaaaagaaaa agggatcctc tggtggttct ggaggatctg gtggttctac taatctgtca 4800
gatattattg aaaaggagac cggtaagcaa ctggttatcc aggaatccat cctcatgctc 4860
ccagaggagg tggaagaagt cattgggaac aagccggaaa gcgatatact cgtgcacacc 4920
gcctacgacg agagcaccga cgagaatgtc atgcttctga ctagcgacgc ccctgaatac 4980
aagccttggg ctctggtcat acaggatagc aacggtgaga acaagattaa gatgctctct 5040
ggtggttctc ccaagaagaa gaggaaagtc taa 5073

<210> SEQ ID NO 439
<211> LENGTH: 4836
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 439
atgggcagct cagagactgg cccagtggct gtggacccca cattgagacg gcggatcgag 60
ccccatgagt ttgaggtatt cttcgatccg agagagctcc gcaaggagac ctgcctgctt 120
tacgaaatta attgggggggg ccggcactcc atttggcgac atacatcaca gaacactaac 180

-continued

```
aagcacgtcg aagtcaactt catcgagaag ttcacgacag aaagatattt ctgtccgaac    240
acaaggtgca gcattacctg gtttctcagc tggagcccat gcggcgaatg tagtagggcc    300
atcactgaat tcctgtcaag gtatccccac gtcactctgt ttatttacat cgcaaggctg    360
taccaccacg ctgacccccg caatcgacaa ggcctgcggg atttgatctc ttcaggtgtg    420
actatccaaa ttatgactga gcaggagtca ggatactgct ggagaaactt tgtgaattat    480
agcccgagta atgaagccca ctggcctagg tatccccatc tgtgggtacg actgtacgtt    540
cttgaactgt actgcatcat actgggcctg cctccttgtc tcaacattct gagaaggaag    600
cagccacagc tgacattctt taccatcgct cttcagtctt gtcattacca gcgactgccc    660
ccacacattc tctgggccac cgggttgaaa tctggtggtt cttctggtgg ttctagcggc    720
agcgagactc ccgggacctc agagtccgcc acacccgaaa gttccggagg gagtagcggc    780
gggtctagca agctggagaa gtttacaaac tgctactccc tgtctaagac cctgaggttc    840
aaggccatcc ctgtgggcaa gacccaggag aacatcgaca ataagcggct gctggtggag    900
gacgagaaga gagccgagga ttataagggc gtgaagaagc tgctggatcg ctactatctg    960
tcttttatca acgacgtgct gcacagcatc aagctgaaga atctgaacaa ttacatcagc   1020
ctgttccgga agaaaaccag aaccgagaag gagaataagg agctggagaa cctggagatc   1080
aatctgcgga aggagatcgc caaggccttc aagggcaacg agggctacaa gtccctgttt   1140
aagaaggata tcatcgagac aatcctgcca gagttcctgg acgataagga cgagatcgcc   1200
ctggtgaaca gcttcaatgg ctttaccaca gccttcaccg gcttctttga taacagagag   1260
aatatgtttt ccgaggaggc caagagcaca tccatcgcct tcaggtgtat caacgagaat   1320
ctgacccgct acatctctaa tatggacatc ttcgagaagg tggacgccat ctttgataag   1380
cacgaggtgc aggagatcaa ggagaagatc ctgaacagcg actatgatgt ggaggatttc   1440
tttgagggcg agttctttaa ctttgtgctg acacaggagg gcatcgacgt gtataacgcc   1500
atcatcggcg gcttcgtgac cgagagcggc gagaagatca agggcctgaa cgagtacatc   1560
aacctgtata atcagaaaac caagcagaag ctgcctaagt ttaagccact gtataagcag   1620
gtgctgagcg atcgggagtc tctgagcttc tacggcgagg gctatacatc cgatgaggag   1680
gtgctggagg tgtttagaaa caccctgaac aagaacagcg agatcttcag ctccatcaag   1740
aagctggaga agctgttcaa gaattttgac gagtactcta gcgccggcat ctttgtgaag   1800
aacggccccg ccatcagcac aatctccaag gatatcttcg gcgagtggaa cgtgatccgg   1860
gacaagtgga atgccgagta tgacgatatc cacctgaaga agaaggccgt ggtgaccgag   1920
aagtacgagg acgatcggag aaagtccttc aagaagatcg gctccttttc tctggagcag   1980
ctgcaggagt acgccgacgc cgatctgtct gtggtggaga agctgaagga gatcatcatc   2040
cagaaggtgg atgagatcta caaggtgtat ggctcctctg agaagctgtt cgacgccgat   2100
tttgtgctgg agaagagcct gaagaagaac gacgccgtgg tggccatcat gaaggacctg   2160
ctggattctg tgaagagctt cgagaattac atcaaggcct tctttggcga gggcaaggag   2220
acaaacaggg acgagtcctt ctatggcgat tttgtgctgg cctacgacat cctgctgaag   2280
gtggaccaca tctacgatgc catccgcaat tatgtgaccc agaagcccta ctctaaggat   2340
aagttcaagc tgtattttca gaaccctcag ttcatgggcg gctgggacaa ggataaggag   2400
acagactatc gggccaccat cctgagatac ggctccaagt actatctggc catcatggat   2460
aagaagtacg ccaagtgcct gcagaagatc gacaaggacg atgtgaacgg caattacgag   2520
```

-continued aagatcaact ataagctgct gcccggccct aataagatgc tgccaaaggt gttcttttct 2580
aagaagtgga tggcctacta taaccccagc gaggacatcc agaagatcta caagaatggc 2640
acattcaaga agggcgatat gtttaacctg aatgactgtc acaagctgat cgacttcttt 2700
aaggatagca tctcccggta tccaaagtgg tccaatgcct acgatttcaa cttttctgag 2760
acagagaagt ataaggacat cgccggcttt tacagagagg tggaggagca gggctataag 2820
gtgagcttcg agtctgccag caagaaggag gtggataagc tggtggagga gggcaagctg 2880
tatatgttcc agatctataa caaggacttt tccgataagt ctcacggcac acccaatctg 2940
cacaccatgt acttcaagct gctgtttgac gagaacaatc acggacagat caggctgagc 3000
ggaggagcag agctgttcat gaggcgcgcc tccctgaaga aggaggagct ggtggtgcac 3060
ccagccaact cccctatcgc caacaagaat ccagataatc ccaagaaaac cacaaccctg 3120
tcctacgacg tgtataagga taagaggttt tctgaggacc agtacgagct gcacatccca 3180
atcgccatca ataagtgccc caagaacatc ttcaagatca atacagaggt gcgcgtgctg 3240
ctgaagcacg acgataaccc ctatgtgatc ggcatcgcca ggggcgagcg caatctgctg 3300
tatatcgtgg tggtggacgg caagggcaac atcgtggagc agtattccct gaacgagatc 3360
atcaacaact tcaacggcat caggatcaag acagattacc actctctgct ggacaagaag 3420
gagaaggaga ggttcgaggc ccgccagaac tggacctcca tcgagaatat caaggagctg 3480
aaggccggct atatctctca ggtggtgcac aagatctgcg agctggtgga gaagtacgat 3540
gccgtgatcg ccctggagga cctgaactct ggctttaaga atagccgcgt gaaggtggag 3600
aagcaggtgt atcagaagtt cgagaagatg ctgatcgata agctgaacta catggtggac 3660
aagaagtcta atccttgtgc aacaggcggc gccctgaagg gctatcagat caccaataag 3720
ttcgagagct ttaagtccat gtctacccag aacggcttca tcttttacat ccctgcctgg 3780
ctgacatcca agatcgatcc atctaccggc tttgtgaacc tgctgaaaac caagtatacc 3840
agcatcgccg attccaagaa gttcatcagc tcctttgaca ggatcatgta cgtgcccgag 3900
gaggatctgt tcgagtttgc cctggactat aagaacttct ctcgcacaga cgccgattac 3960
atcaagaagt ggaagctgta ctcctacggc aaccggatca gaatcttccg gaatcctaag 4020
aagaacaacg tgttcgactg ggaggaggtg tgcctgacca gcgcctataa ggagctgttc 4080
aacaagtacg gcatcaatta tcagcagggc gatatcagag ccctgctgtg cgagcagtcc 4140
gacaaggcct tctactctag ctttatggcc ctgatgagcc tgatgctgca gatgcggaac 4200
agcatcacag gccgcaccga cgtggatttt ctgatcagcc ctgtgaagaa ctccgacggc 4260
atcttctacg atagccggaa ctatgaggcc caggagaatg ccatcctgcc aaagaacgcc 4320
gacgccaatg gcgcctataa catcgccaga aaggtgctgt gggccatcgg ccagttcaag 4380
aaggccgagg acgagaagct ggataaggtg aagatcgcca tctctaacaa ggagtggctg 4440
gagtacgccc agaccagcgt gaagcacaaa aggccggcgg ccacgaaaaa ggccggccag 4500
gcaaaaaaga aaaagggatc ctctggtggt tctggaggat ctggtggttc tactaatctg 4560
tcagatatta ttgaaaagga gaccggtaag caactggtta tccaggaatc catcctcatg 4620
ctcccagagg aggtggaaga agtcattggg aacaagccgg aaagcgatat actcgtgcac 4680
accgcctacg acgagagcac cgacgagaat gtcatgcttc tgactagcga cgcccctgaa 4740
tacaagcctt gggctctggt catacaggat agcaacggtg agaacaagat taagatgctc 4800
tctggtggtt ctcccaagaa gaagaggaaa gtctaa 4836

<210> SEQ ID NO 440
<211> LENGTH: 5073
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 440
atgggcagct cagagactgg cccagtggct gtggacccca cattgagacg gcggatcgag 60
ccccatgagt ttgaggtatt cttcgatccg agagagctcc gcaaggagac ctgcctgctt 120
tacgaaatta attgggggg ccggcactcc atttggcgac atacatcaca gaacactaac 180
aagcacgtcg aagtcaactt catcgagaag ttcacgacag aaagatattt ctgtccgaac 240
acaaggtgca gcattacctg gtttctcagc tggagcccat gcggcgaatg tagtagggcc 300
atcactgaat tcctgtcaag gtatccccac gtcactctgt ttatttacat cgcaaggctg 360
taccaccacg ctgacccccg caatcgacaa ggcctgcggg atttgatctc ttcaggtgtg 420
actatccaaa ttatgactga gcaggagtca ggatactgct ggagaaactt tgtgaattat 480
agcccgagta atgaagccca ctggcctagg tatccccatc tgtgggtacg actgtacgtt 540
cttgaactgt actgcatcat actgggcctg cctccttgtc tcaacattct gagaaggaag 600
cagccacagc tgacattctt taccatcgct cttcagtctt gtcattacca gcgactgccc 660
ccacacattc tctgggccac cgggttgaaa tctggtggtt cttctggtgg ttctagcggc 720
agcgagactc ccgggacctc agagtccgcc acacccgaaa gttccggagg gagtagcggc 780
gggtctacac agttcgaggg ctttaccaac ctgtatcagg tgagcaagac actgcggttt 840
gagctgatcc cacagggcaa gaccctgaag cacatccagg agcagggctt catcgaggag 900
gacaaggccc gcaatgatca ctacaaggag ctgaagccca tcatcgatcg gatctacaag 960
acctatgccg accagtgcct gcagctggtg cagctggatt gggagaacct gagcgccgcc 1020
atcgactcct atagaaagga gaaaaccgag gagacaagga acgccctgat cgaggagcag 1080
gccacatatc gcaatgccat ccacgactac ttcatcggcc ggacagacaa cctgaccgat 1140
gccatcaata agagacacgc cgagatctac aagggcctgt tcaaggccga gctgtttaat 1200
ggcaaggtgc tgaagcagct gggcaccgtg accacaaccg agcacgagaa cgccctgctg 1260
cggagcttcg acaagtttac aacctacttc tccggctttt atagaaacag gaagaacgtg 1320
ttcagcgccg aggatatcag cacagccatc ccacaccgca tcgtgcagga caacttcccc 1380
aagtttaagg agaattgtca catcttcaca cgcctgatca ccgccgtgcc cagcctgcgg 1440
gagcactttg agaacgtgaa gaaggccatc ggcatcttcg tgagcacctc catcgaggag 1500
gtgttttcct tccctttta taaccagctg ctgacacaga cccagatcga cctgtataac 1560
cagctgctgg gaggaatctc tcgggaggca ggcaccgaga agatcaaggg cctgaacgag 1620
gtgctgaatc tggccatcca gaagaatgat gagacagccc acatcatcgc ctccctgcca 1680
cacagattca tcccccctgtt taagcagatc ctgtccgata ggaacaccct gtctttcatc 1740
ctggaggagt ttaagagcga cgaggaagtg atccagtcct tctgcaagta caagacactg 1800
ctgagaaacg agaacgtgct ggagacagcc gaggccctgt ttaacgagct gaacagcatc 1860
gacctgacac acatcttcat cagccacaag aagctggaga caatcagcag cgccctgtgc 1920
gaccactggg atacactgag gaatgccctg tatgagcgga gaatctccga gctgacaggc 1980
aagatcacca agtctgccaa ggagaaggtg cagcgcagcc tgaagcacga ggatatcaac 2040
ctgcaggaga tcatctctgc cgcaggcaag gagctgagcg aggccttcaa gcagaaaacc 2100
agcgagatcc tgtcccacgc acacgccgcc ctggatcagc cactgcctac aaccctgaag 2160
aagcaggagg agaaggagat cctgaagtct cagctggaca gcctgctggg cctgtaccac 2220
ctgctggact ggtttgccgt ggatgagtcc aacgaggtgg accccgagtt ctctgcccgg 2280
ctgaccggca tcaagctgga gatggagcct tctctgagct tctacaacaa ggccagaaat 2340
tatgccacca agaagcccta ctccgtggag aagttcaagc tgaactttca gatgcctaca 2400
ctggccagag gctgggacgt gaatagagag aagaacaatg gcgccatcct gtttgtgaag 2460
aacggcctgt actatctggg catcatgcca aagcagaagg gcaggtataa ggccctgagc 2520
ttcgagccca cagagaaaac cagcgagggc tttgataaga tgtactatga ctacttccct 2580
gatgccgcca agatgatccc aaagtgcagc acccagctga aggccgtgac agcccacttt 2640
cagacccaca caaccccat cctgctgtcc aacaatttca tcgagcctct ggagatcaca 2700
aaggagatct acgacctgaa caatcctgag aaggagccaa agaagtttca gacagcctac 2760
gccaagaaaa ccggcgacca gaagggctac agagaggccc tgtgcaagtg gatcgacttc 2820
acaagggatt ttctgtccaa gtataccaag acaacctcta tcgatctgtc tagcctgcgg 2880
ccatcctctc agtataagga cctgggcgag tactatgccg agctgaatcc cctgctgtac 2940
cacatcagct tccagagaat cgccgagaag gagatcatgg atgccgtgga gacaggcaag 3000
ctgtacctgt tccagatcta taacaaggac tttgccaagg gccaccacgg caagcctaat 3060
ctgcacacac tgtattggac cggcctgttt tctccagaga acctggccaa gacaagcatc 3120
aagctgaatg gccaggccga gctgttctac cgccctaagt ccaggatgaa gaggatggca 3180
caccggctgg gagagaagat gctgaacaag aagctgaagg atcagaaaac cccaatcccc 3240
gacaccctgt accaggagct gtacgactat gtgaatcaca gactgtccca cgacctgtct 3300
gatgaggcca gggccctgct gcccaacgtg atcaccaagg aggtgtctca cgagatcatc 3360
aaggataggc gctttaccag cgacaagttc tttttccacg tgcctatcac actgaactat 3420
caggccgcca attccccatc taagttcaac cagagggtga atgcctacct gaaggagcac 3480
cccgagacac ctatcatcgg catcgcccgg ggcgagagaa acctgatcta tatcacagtg 3540
atcgactcca ccggcaagat cctggagcag cggagcctga acaccatcca gcagtttgat 3600
taccagaaga agctggacaa cagggagaag gagagggtgg cagcaaggca ggcctggtct 3660
gtggtgggca caatcaagga tctgaagcag ggctatctga gccaggtcat ccacgagatc 3720
gtggacctga tgatccacta ccaggccgtg gtggtgctgg agaacctgaa tttcggcttt 3780
aagagcaaga ggaccggcat cgccgagaag gccgtgtacc agcagttcga gaagatgctg 3840
atcgataagc tgaattgcct ggtgctgaag gactatccag cagagaaagt gggaggcgtg 3900
ctgaacccat accagctgac agaccagttc acctcctttg ccaagatggg cacccagtct 3960
ggcttcctgt tttacgtgcc tgccccatat acatctaaga tcgatcccct gaccggcttc 4020
gtggacccct tcgtgtggaa aaccatcaag aatcacgaga gccgcaagca cttcctggag 4080
ggcttcgact ttctgcacta cgacgtgaaa accggcgact tcatcctgca ctttaagatg 4140
aacagaaatc tgtccttcca gaggggcctg cccggcttta tgcctgcatg ggatatcgtg 4200
ttcgagaaga acgagacaca gtttgacgcc aagggcaccc ctttcatcgc cggcaagaga 4260
atcgtgccag tgatcgagaa tcacagattc accggcagat accgggacct gtatcctgcc 4320
aacgagctga tcgccctgct ggaggagaag ggcatcgtgt tcagggatgg ctccaacatc 4380
ctgccaaagc tgctggagaa tgacgattct cacgccatcg acacgatggt ggccctgatc 4440
cgcagcgtgc tgcagatgcg gaactccaat gccgccacag gcgaggacta tatcaacagc 4500
cccgtgcgcg atctgaatgg cgtgtgcttc gactcccggt ttcagaaccc agagtggcca 4560
atggacgccg atgccaatgg cgcctaccac atcgccctga agggccagct gctgctgaat 4620
cacctgaagg agagcaagga tctgaagctg cagaacggca tctccaatca ggactggctg 4680
gcctacatcc aggagctgcg caacaaaagg ccggcggcca cgaaaaaggc cggccaggca 4740
aaaaagaaaa agggatcctc tggtggttct ggaggatctg gtggttctac taatctgtca 4800
gatattattg aaaaggagac cggtaagcaa ctggttatcc aggaatccat cctcatgctc 4860
ccagaggagg tggaagaagt cattgggaac aagccggaaa gcgatatact cgtgcacacc 4920
gcctacgacg agagcaccga cgagaatgtc atgcttctga ctagcgacgc ccctgaatac 4980
aagccttggg ctctggtcat acaggatagc aacggtgaga acaagattaa gatgctctct 5040
ggtggttctc ccaagaagaa gaggaaagtc taa 5073

<210> SEQ ID NO 441
<211> LENGTH: 5133
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 441
atgggcccaa agaaaaagag gaaagtcggc agtggaccta aaaagaaacg aaaggttggg 60
tcaggtagct cagagactgg cccagtggct gtggacccca cattgagacg gcggatcgag 120
ccccatgagt ttgaggtatt cttcgatccg agagagctcc gcaaggagac ctgcctgctt 180
tacgaaatta attggggggg ccggcactcc atttggcgac atacatcaca gaacactaac 240
aagcacgtcg aagtcaactt catcgagaag ttcacgacag aaagatattt ctgtccgaac 300
acaaggtgca gcattacctg gtttctcagc tggagcccat gcggcgaatg tagtagggcc 360
atcactgaat tcctgtcaag gtatccccac gtcactctgt ttatttacat cgcaaggctg 420
taccaccacg ctgacccccg caatcgacaa ggcctgcggg atttgatctc ttcaggtgtg 480
actatccaaa ttatgactga gcaggagtca ggatactgct ggagaaactt tgtgaattat 540
agcccgagta atgaagccca ctggcctagg tatccccatc tgtgggtacg actgtacgtt 600
cttgaactgt actgcatcat actgggcctg cctccttgtc tcaacattct gagaaggaag 660
cagccacagc tgacattctt taccatcgct cttcagtctt gtcattacca gcgactgccc 720
ccacacattc tctgggccac cgggttgaaa tctggtggtt cttctggtgg ttctagcggc 780
agcgagactc ccgggacctc agagtccgcc acacccgaaa gttccggagg gagtagcggc 840
gggtctacac agttcgaggg ctttaccaac ctgtatcagg tgagcaagac actgcggttt 900
gagctgatcc cacagggcaa gaccctgaag cacatccagg agcagggctt catcgaggag 960
gacaaggccc gcaatgatca ctacaaggag ctgaagccca tcatcgatcg gatctacaag 1020
acctatgccg accagtgcct gcagctggtg cagctggatt gggagaacct gagcgccgcc 1080
atcgactcct atagaaagga gaaaaccgag gagacaagga acgccctgat cgaggagcag 1140
gccacatatc gcaatgccat ccacgactac ttcatcggcc ggacagacaa cctgaccgat 1200
gccatcaata agagacacgc cgagatctac aagggcctgt tcaaggccga gctgtttaat 1260
ggcaaggtgc tgaagcagct gggcaccgtg accacaaccg agcacgagaa cgccctgctg 1320
cggagcttcg acaagtttac aacctacttc tccggctttt atagaaacag gaagaacgtg 1380

-continued

```
ttcagcgccg aggatatcag cacagccatc ccacaccgca tcgtgcagga caacttcccc   1440
aagtttaagg agaattgtca catcttcaca cgcctgatca ccgccgtgcc cagcctgcgg   1500
gagcactttg agaacgtgaa gaaggccatc ggcatcttcg tgagcacctc catcgaggag   1560
gtgttttcct tccctttta taaccagctg ctgacacaga cccagatcga cctgtataac   1620
cagctgctgg gaggaatctc tcgggaggca ggcaccgaga agatcaaggg cctgaacgag   1680
gtgctgaatc tggccatcca gaagaatgat gagacagccc acatcatcgc ctccctgcca   1740
cacagattca tcccccctgtt taagcagatc ctgtccgata ggaacaccct gtctttcatc   1800
ctggaggagt ttaagagcga cgaggaagtg atccagtcct tctgcaagta caagacactg   1860
ctgagaaacg agaacgtgct ggagacagcc gaggccctgt ttaacgagct gaacagcatc   1920
gacctgacac acatcttcat cagccacaag aagctggaga caatcagcag cgccctgtgc   1980
gaccactggg atacactgag gaatgccctg tatgagcgga gaatctccga gctgacaggc   2040
aagatcacca agtctgccaa ggagaaggtg cagcgcagcc tgaagcacga ggatatcaac   2100
ctgcaggaga tcatctctgc cgcaggcaag gagctgagcg aggccttcaa gcagaaaacc   2160
agcgagatcc tgtcccacgc acacgccgcc ctggatcagc cactgcctac aaccctgaag   2220
aagcaggagg agaaggagat cctgaagtct cagctggaca gcctgctggg cctgtaccac   2280
ctgctggact ggtttgccgt ggatgagtcc aacgaggtgg accccgagtt ctctgcccgg   2340
ctgaccggca tcaagctgga gatggagcct tctctgagct tctacaacaa ggccagaaat   2400
tatgccacca agaagcccta ctccgtggag aagttcaagc tgaactttca gatgcctaca   2460
ctggccagag gctgggacgt gaatagagag aagaacaatg gcgccatcct gtttgtgaag   2520
aacggcctgt actatctggg catcatgcca aagcagaagg gcaggtataa ggccctgagc   2580
ttcgagccca cagagaaaac cagcgagggc tttgataaga tgtactatga ctacttccct   2640
gatgccgcca agatgatccc aaagtgcagc acccagctga aggccgtgac agcccacttt   2700
cagacccaca caaccccccat cctgctgtcc aacaatttca tcgagcctct ggagatcaca   2760
aaggagatct acgacctgaa caatcctgag aaggagccaa agaagtttca gacagcctac   2820
gccaagaaaa ccggcgacca gaagggctac agagaggccc tgtgcaagtg gatcgacttc   2880
acaagggatt ttctgtccaa gtataccaag acaacctcta tcgatctgtc tagcctgcgg   2940
ccatcctctc agtataagga cctgggcgag tactatgccg agctgaatcc cctgctgtac   3000
cacatcagct tccagagaat cgccgagaag gagatcatgg atgccgtgga gacaggcaag   3060
ctgtacctgt tccagatcta taacaaggac tttgccaagg gccaccacgg caagcctaat   3120
ctgcacacac tgtattggac cggcctgttt tctccagaga acctggccaa gacaagcatc   3180
aagctgaatg gccaggccga gctgttctac cgccctaagt ccaggatgaa gaggatggca   3240
caccggctgg gagagaagat gctgaacaag aagctgaagg atcagaaaac cccaatcccc   3300
gacaccctgt accaggagct gtacgactat gtgaatcaca gactgtccca cgacctgtct   3360
gatgaggcca gggccctgct gcccaacgtg atcaccaagg aggtgtctca cgagatcatc   3420
aaggataggc gctttaccag cgacaagttc tttttccacg tgcctatcac actgaactat   3480
caggccgcca attccccatc taagttcaac cagagggtga atgcctacct gaaggagcac   3540
cccgagacac ctatcatcgg catcgcccgg ggcgagagaa acctgatcta tatcacagtg   3600
atcgactcca ccggcaagat cctggagcag cggagcctga acaccatcca gcagtttgat   3660
taccagaaga agctggacaa cagggagaag gagagggtgg cagcaaggca ggcctggtct   3720
gtggtgggca caatcaagga tctgaagcag ggctatctga gccaggtcat ccacgagatc   3780
```

gtggacctga tgatccacta ccaggccgtg gtggtgctgg agaacctgaa tttcggcttt 3840
aagagcaaga ggaccggcat cgccgagaag gccgtgtacc agcagttcga gaagatgctg 3900
atcgataagc tgaattgcct ggtgctgaag gactatccag cagagaaagt gggaggcgtg 3960
ctgaacccat accagctgac agaccagttc acctcctttg ccaagatggg cacccagtct 4020
ggcttcctgt tttacgtgcc tgccccatat acatctaaga tcgatcccct gaccggcttc 4080
gtggacccct tcgtgtggaa aaccatcaag aatcacgaga gccgcaagca cttcctggag 4140
ggcttcgact ttctgcacta cgacgtgaaa accggcgact tcatcctgca ctttaagatg 4200
aacagaaatc tgtccttcca gaggggcctg cccggcttta tgcctgcatg ggatatcgtg 4260
ttcgagaaga acgagacaca gtttgacgcc aagggcaccc ctttcatcgc cggcaagaga 4320
atcgtgccag tgatcgagaa tcacagattc accggcagat accgggacct gtatcctgcc 4380
aacgagctga tcgccctgct ggaggagaag ggcatcgtgt tcagggatgg ctccaacatc 4440
ctgccaaagc tgctggagaa tgacgattct cacgccatcg acacgatggt ggccctgatc 4500
cgcagcgtgc tgcagatgcg gaactccaat gccgccacag gcgaggacta tatcaacagc 4560
cccgtgcgcg atctgaatgg cgtgtgcttc gactcccggt ttcagaaccc agagtggcca 4620
atggacgccg atgccaatgg cgcctaccac atcgccctga agggccagct gctgctgaat 4680
cacctgaagg agagcaagga tctgaagctg cagaacggca tctccaatca ggactggctg 4740
gcctacatcc aggagctgcg caacaaaagg ccggcggcca cgaaaaaggc cggccaggca 4800
aaaaagaaaa agggatcctc tggtggttct ggaggatctg gtggttctac taatctgtca 4860
gatattattg aaaaggagac cggtaagcaa ctggttatcc aggaatccat cctcatgctc 4920
ccagaggagg tggaagaagt cattgggaac aagccggaaa gcgatatact cgtgcacacc 4980
gcctacgacg agagcaccga cgagaatgtc atgcttctga ctagcgacgc ccctgaatac 5040
aagccttggg ctctggtcat acaggatagc aacggtgaga acaagattaa gatgctctct 5100
ggtggttctc ccaagaagaa gaggaaagtc taa 5133

<210> SEQ ID NO 442
<211> LENGTH: 5019
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 442
atgggcagct cagagactgg cccagtggct gtggacccca cattgagacg gcggatcgag 60
ccccatgagt ttgaggtatt cttcgatccg agagagctcc gcaaggagac ctgcctgctt 120
tacgaaatta attggggggg ccggcactcc atttggcgac atacatcaca gaacactaac 180
aagcacgtcg aagtcaactt catcgagaag ttcacgacag aaagatattt ctgtccgaac 240
acaaggtgca gcattacctg gtttctcagc tggagcccat gcggcgaatg tagtagggcc 300
atcactgaat tcctgtcaag gtatccccac gtcactctgt ttatttacat cgcaaggctg 360
taccaccacg ctgacccccg caatcgacaa ggcctgcggg atttgatctc ttcaggtgtg 420
actatccaaa ttatgactga gcaggagtca ggatactgct ggagaaactt tgtgaattat 480
agcccgagta atgaagccca ctggcctagg tatccccatc tgtgggtacg actgtacgtt 540
cttgaactgt actgcatcat actgggcctg cctccttgtc tcaacattct gagaaggaag 600
cagccacagc tgacattctt taccatcgct cttcagtctt gtcattacca gcgactgccc 660

```
ccacacattc tctgggccac cgggttgaaa tctggtggtt cttctggtgg ttctagcggc    720
agcgagactc ccgggacctc agagtccgcc acacccgaaa gttccggagg gagtagcggc    780
gggtctacac agttcgaggg ctttaccaac ctgtatcagg tgagcaagac actgcggttt    840
gagctgatcc cacagggcaa gaccctgaag cacatccagg agcagggctt catcgaggag    900
gacaaggccc gcaatgatca ctacaaggag ctgaagccca tcatcgatcg gatctacaag    960
acctatgccg accagtgcct gcagctggtg cagctggatt gggagaacct gagcgccgcc   1020
atcgactcct atagaaagga gaaaaccgag gagacaagga acgccctgat cgaggagcag   1080
gccacatatc gcaatgccat ccacgactac ttcatcggcc ggacagacaa cctgaccgat   1140
gccatcaata agagacacgc cgagatctac aagggcctgt tcaaggccga gctgtttaat   1200
ggcaaggtgc tgaagcagct gggcaccgtg accacaaccg agcacgagaa cgccctgctg   1260
cggagcttcg acaagtttac aacctacttc tccggctttt atagaaacag gaagaacgtg   1320
ttcagcgccg aggatatcag cacagccatc ccacaccgca tcgtgcagga caacttcccc   1380
aagtttaagg agaattgtca catcttcaca cgcctgatca ccgccgtgcc cagcctgcgg   1440
gagcactttg agaacgtgaa gaaggccatc ggcatcttcg tgagcacctc catcgaggag   1500
gtgttttcct tccctttta taaccagctg ctgacacaga cccagatcga cctgtataac    1560
cagctgctgg gaggaatctc tcgggaggca ggcaccgaga agatcaaggg cctgaacgag   1620
gtgctgaatc tggccatcca gaagaatgat gagacagccc acatcatcgc ctccctgcca   1680
cacagattca tcccccctgtt taagcagatc ctgtccgata ggaacaccct gtctttcatc   1740
ctggaggagt ttaagagcga cgaggaagtg atccagtcct tctgcaagta caagacactg   1800
ctgagaaacg agaacgtgct ggagacagcc gaggccctgt ttaacgagct gaacagcatc   1860
gacctgacac acatcttcat cagccacaag aagctggaga caatcagcag cgccctgtgc   1920
gaccactggg atacactgag gaatgccctg tatgagcgga gaatctccga gctgacaggc   1980
aagatcacca agtctgccaa ggagaaggtg cagcgcagcc tgaagcacga ggatatcaac   2040
ctgcaggaga tcatctctgc cgcaggcaag gagctgagcg aggccttcaa gcagaaaacc   2100
agcgagatcc tgtcccacgc acacgccgcc ctggatcagc cactgcctac aaccctgaag   2160
aagcaggagg agaaggagat cctgaagtct cagctggaca gcctgctggg cctgtaccac   2220
ctgctggact ggtttgccgt ggatgagtcc aacgaggtgg accccgagtt ctctgcccgg   2280
ctgaccggca tcaagctgga gatggagcct tctctgagct tctacaacaa ggccagaaat   2340
tatgccacca agaagcccta ctccgtggag aagttcaagc tgaactttca gatgcctaca   2400
ctggccagag gctgggacgt gaatagagag aagaacaatg gcgccatcct gtttgtgaag   2460
aacggcctgt actatctggg catcatgcca aagcagaagg gcaggtataa ggccctgagc   2520
ttcgagccca cagagaaaac cagcgagggc tttgataaga tgtactatga ctacttccct   2580
gatgccgcca agatgatccc aaagtgcagc acccagctga aggccgtgac agcccacttt   2640
cagacccaca caacccccat cctgctgtcc aacaatttca tcgagcctct ggagatcaca   2700
aaggagatct acgacctgaa caatcctgag aaggagccaa agaagtttca gacagcctac   2760
gccaagaaaa ccggcgacca gaagggctac agagaggccc tgtgcaagtg gatcgacttc   2820
acaagggatt ttctgtccaa gtataccaag acaacctcta tcgatctgtc tagcctgcgg   2880
ccatcctctc agtataagga cctgggcgag tactatgccg agctgaatcc cctgctgtac   2940
cacatcagct tccagagaat cgccgagaag gagatcatgg atgccgtgga gacaggcaag   3000
```

ctgtacctgt tccagatcta taacaaggac tttgccaagg gccaccacgg caagcctaat 3060
ctgcacacac tgtattggac cggcctgttt tctccagaga acctggccaa gacaagcatc 3120
aagctgaatg gccaggccga gctgttctac cgccctaagt ccaggatgaa gaggatggca 3180
caccggctgg gagagaagat gctgaacaag aagctgaagg atcagaaaac cccaatcccc 3240
gacaccctgt accaggagct gtacgactat gtgaatcaca gactgtccca cgacctgtct 3300
gatgaggcca gggccctgct gcccaacgtg atcaccaagg aggtgtctca cgagatcatc 3360
aaggataggc gctttaccag cgacaagttc tttttccacg tgcctatcac actgaactat 3420
caggccgcca attccccatc taagttcaac cagagggtga atgcctacct gaaggagcac 3480
cccgagacac ctatcatcgg catcgcccgg ggcgagagaa acctgatcta tatcacagtg 3540
atcgactcca ccggcaagat cctggagcag cggagcctga acaccatcca gcagtttgat 3600
taccagaaga agctggacaa cagggagaag gagagggtgg cagcaaggca ggcctggtct 3660
gtggtgggca caatcaagga tctgaagcag ggctatctga gccaggtcat ccacgagatc 3720
gtggacctga tgatccacta ccaggccgtg gtggtgctgg agaacctgaa tttcggcttt 3780
aagagcaaga ggaccggcat cgccgagaag gccgtgtacc agcagttcga gaagatgctg 3840
atcgataagc tgaattgcct ggtgctgaag gactatccag cagagaaagt gggaggcgtg 3900
ctgaacccat accagctgac agaccagttc acctcctttg ccaagatggg cacccagtct 3960
ggcttcctgt tttacgtgcc tgccccatat acatctaaga tcgatcccct gaccggcttc 4020
gtggacccct tcgtgtggaa aaccatcaag aatcacgaga gccgcaagca cttcctggag 4080
ggcttcgact ttctgcacta cgacgtgaaa accggcgact tcatcctgca ctttaagatg 4140
aacagaaatc tgtccttcca gaggggcctg cccggcttta tgcctgcatg ggatatcgtg 4200
ttcgagaaga acgagacaca gtttgacgcc aagggcaccc ctttcatcgc cggcaagaga 4260
atcgtgccag tgatcgagaa tcacagattc accggcagat accgggacct gtatcctgcc 4320
aacgagctga tcgccctgct ggaggagaag ggcatcgtgt tcagggatgg ctccaacatc 4380
ctgccaaagc tgctggagaa tgacgattct cacgccatcg acacgatggt ggccctgatc 4440
cgcagcgtgc tgcagatgcg gaactccaat gccgccacag gcgaggacta tatcaacagc 4500
cccgtgcgcg atctgaatgg cgtgtgcttc gactcccggt ttcagaaccc agagtggcca 4560
atggacgccg atgccaatgg cgcctaccac atcgccctga agggccagct gctgctgaat 4620
cacctgaagg agagcaagga tctgaagctg cagaacggca tctccaatca ggactggctg 4680
gcctacatcc aggagctgcg caactctggt ggttctggag gatctggtgg ttctactaat 4740
ctgtcagata ttattgaaaa ggagaccggt aagcaactgg ttatccagga atccatcctc 4800
atgctcccag aggaggtgga agaagtcatt gggaacaagc cggaaagcga tatactcgtg 4860
cacaccgcct acgacgagag caccgacgag aatgtcatgc ttctgactag cgacgcccct 4920
gaatacaagc cttgggctct ggtcatacag gatagcaacg gtgagaacaa gattaagatg 4980
ctctctggtg gttctcccaa gaagaagagg aaagtctaa 5019

<210> SEQ ID NO 443
<211> LENGTH: 5421
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 443

-continued

```
atgagcaagc tggagaagtt tacaaactgc tactccctgt ctaagaccct gaggttcaag     60
gccatccctg tgggcaagac ccaggagaac atcgacaata agcggctgct ggtggaggac    120
gagaagagag ccgaggatta taagggcgtg aagaagctgc tggatcgcta ctatctgtct    180
tttatcaacg acgtgctgca cagcatcaag ctgaagaatc tgaacaatta catcagcctg    240
ttccggaaga aaaccagaac cgagaaggag aataaggagc tggagaacct ggagatcaat    300
ctgcggaagg agatcgccaa ggccttcaag ggcaacgagg gctacaagtc cctgtttaag    360
aaggatatca tcgagacaat cctgccagag ttcctggacg ataaggacga gatcgccctg    420
gtgaacagct tcaatggctt taccacagcc ttcaccggct tctttgataa cagagagaat    480
atgttttccg aggaggccaa gagcacatcc atcgccttca ggtgtatcaa cgagaatctg    540
acccgctaca tctctaatat ggacatcttc gagaaggtgg acgccatctt tgataagcac    600
gaggtgcagg agatcaagga gaagatcctg aacagcgact atgatgtgga ggatttcttt    660
gagggcgagt tctttaactt tgtgctgaca caggagggca tcgacgtgta taacgccatc    720
atcggcggct tcgtgaccga gagcggcgag aagatcaagg gcctgaacga gtacatcaac    780
ctgtataatc agaaaaccaa gcagaagctg cctaagttta agccactgta taagcaggtg    840
ctgagcgatc gggagtctct gagcttctac ggcgagggct atacatccga tgaggaggtg    900
ctggaggtgt ttagaaacac cctgaacaag aacagcgaga tcttcagctc catcaagaag    960
ctggagaagc tgttcaagaa ttttgacgag tactctagcg ccggcatctt tgtgaagaac   1020
ggccccgcca tcagcacaat ctccaaggat atcttcggcg agtggaacgt gatccgggac   1080
aagtggaatg ccgagtatga cgatatccac ctgaagaaga aggccgtggt gaccgagaag   1140
tacgaggacg atcggagaaa gtccttcaag aagatcggct ccttttctct ggagcagctg   1200
caggagtacg ccgacgccga tctgtctgtg gtggagaagc tgaaggagat catcatccag   1260
aaggtggatg agatctacaa ggtgtatggc tcctctgaga agctgttcga cgccgatttt   1320
gtgctggaga agagcctgaa gaagaacgac gccgtggtgg ccatcatgaa ggacctgctg   1380
gattctgtga agagcttcga gaattacatc aaggccttct ttggcgaggg caaggagaca   1440
aacagggacg agtccttcta tggcgatttt gtgctggcct acgacatcct gctgaaggtg   1500
gaccacatct acgatgccat ccgcaattat gtgacccaga agccctactc taaggataag   1560
ttcaagctgt attttcagaa ccctcagttc atgggcggct gggacaagga taaggagaca   1620
gactatcggg ccaccatcct gagatacggc tccaagtact atctggccat catggataag   1680
aagtacgcca agtgcctgca gaagatcgac aaggacgatg tgaacggcaa ttacgagaag   1740
atcaactata agctgctgcc cggccctaat aagatgctgc caaaggtgtt cttttctaag   1800
aagtggatgg cctactataa ccccagcgag gacatccaga agatctacaa gaatggcaca   1860
ttcaagaagg gcgatatgtt taacctgaat gactgtcaca agctgatcga cttctttaag   1920
gatagcatct cccggtatcc aaagtggtcc aatgcctacg atttcaactt ttctgagaca   1980
gagaagtata aggacatcgc cggcttttac agagaggtgg aggagcaggg ctataaggtg   2040
agcttcgagt ctgccagcaa gaaggaggtg gataagctgg tggaggaggg caagctgtat   2100
atgttccaga tctataacaa ggacttttcc gataagtctc acggcacacc caatctgcac   2160
accatgtact tcaagctgct gtttgacgag aacaatcacg gacagatcag gctgagcgga   2220
ggagcagagc tgttcatgag gcgcgcctcc ctgaagaagg aggagctggt ggtgcaccca   2280
gccaactccc ctatcgccaa caagaatcca gataatccca agaaaaccac aaccctgtcc   2340
tacgacgtgt ataaggataa gaggttttct gaggaccagt acgagctgca catcccaatc   2400
```

-continued

```
gccatcaata agtgccccaa gaacatcttc aagatcaata cagaggtgcg cgtgctgctg   2460
aagcacgacg ataaccccta tgtgatcggc atcgccaggg gcgagcgcaa tctgctgtat   2520
atcgtggtgg tggacggcaa gggcaacatc gtggagcagt attccctgaa cgagatcatc   2580
aacaacttca acggcatcag gatcaagaca gattaccact ctctgctgga caagaaggag   2640
aaggagaggt tcgaggcccg ccagaactgg acctccatcg agaatatcaa ggagctgaag   2700
gccggctata tctctcaggt ggtgcacaag atctgcgagc tggtggagaa gtacgatgcc   2760
gtgatcgccc tggaggacct gaactctggc tttaagaata gccgcgtgaa ggtggagaag   2820
caggtgtatc agaagttcga gaagatgctg atcgataagc tgaactacat ggtggacaag   2880
aagtctaatc cttgtgcaac aggcggcgcc ctgaagggct atcagatcac caataagttc   2940
gagagcttta agtccatgtc tacccagaac ggcttcatct tttacatccc tgcctggctg   3000
acatccaaga tcgatccatc taccggcttt gtgaacctgc tgaaaaccaa gtataccagc   3060
atcgccgatt ccaagaagtt catcagctcc tttgacagga tcatgtacgt gcccgaggag   3120
gatctgttcg agtttgccct ggactataag aacttctctc gcacagacgc cgattacatc   3180
aagaagtgga agctgtactc ctacggcaac cggatcagaa tcttccggaa tcctaagaag   3240
aacaacgtgt tcgactggga ggaggtgtgc ctgaccagcg cctataagga gctgttcaac   3300
aagtacggca tcaattatca gcagggcgat atcagagccc tgctgtgcga gcagtccgac   3360
aaggccttct actctagctt tatggccctg atgagcctga tgctgcagat gcggaacagc   3420
atcacaggcc gcaccgacgt ggattttctg atcagccctg tgaagaactc cgacggcatc   3480
ttctacgata gccggaacta tgaggcccag gagaatgcca tcctgccaaa gaacgccgac   3540
gccaatggcg cctataacat cgccagaaag gtgctgtggg ccatcggcca gttcaagaag   3600
gccgaggacg agaagctgga taaggtgaag atcgccatct ctaacaagga gtggctggag   3660
tacgcccaga ccagcgtgaa gcacaaaagg ccggcggcca cgaaaaaggc cggccaggca   3720
aaaaagaaaa agggatccta cccatacgat gttccagatt acgcttatcc ctacgacgtg   3780
cctgattatg catacccata tgatgtcccc gactatgccg gaagcgaggc cagcggttcc   3840
ggacgggctg acgcattgga cgattttgat ctggatatgc tgggaagtga cgccctcgat   3900
gattttgacc ttgacatgct tggttcggat gcccttgatg actttgacct cgacatgctc   3960
ggcagtgacg cccttgatga tttcgacctg gacatgctga ttaactctag aagttccgga   4020
tctccgaaaa agaaacgcaa agttggtagc cagtacctgc ccgacaccga cgaccggcac   4080
cggatcgagg aaaagcggaa gcggacctac gagacattca agagcatcat gaagaagtcc   4140
cccttcagcg gccccaccga ccctagacct ccacctagaa gaatcgccgt gcccagcaga   4200
tccagcgcca gcgtgccaaa acctgccccc cagccttacc ccttcaccag cagcctgagc   4260
accatcaact acgacgagtt ccctaccatg gtgttcccca gcggccagat ctctcaggcc   4320
tctgctctgg ctccagcccc tcctcaggtg ctgcctcagg ctcctgctcc tgcaccagct   4380
ccagccatgg tgtctgcact ggctcaggca ccagcacccg tgcctgtgct ggctcctgga   4440
cctccacagg ctgtggctcc accagcccct aaacctacac aggccggcga gggcacactg   4500
tctgaagctc tgctgcagct gcagttcgac gacgaggatc tgggagccct gctgggaaac   4560
agcaccgatc ctgccgtgtt caccgacctg gccagcgtgg acaacagcga gttccagcag   4620
ctgctgaacc agggcatccc tgtggcccct cacaccaccg agcccatgct gatggaatac   4680
cccgaggcca tcacccggct cgtgacaggc gctcagaggc ctcctgatcc agctcctgcc   4740
```

```
cctctgggag caccaggcct gcctaatgga ctgctgtctg gcgacgagga cttcagctct   4800

atcgccgata tggatttctc agccttgctg ggctctggca gcggcagccg ggattccagg   4860

gaagggatgt tttgccgaa gcctgaggcc ggctccgcta ttagtgacgt gtttgagggc    4920

cgcgaggtgt gccagccaaa acgaatccgg ccatttcatc ctccaggaag tccatgggcc   4980

aaccgcccac tccccgccag cctcgcacca acaccaaccg gtccagtaca tgagccagtc   5040

gggtcactga ccccggcacc agtccctcag ccactggatc cagcgcccgc agtgactccc   5100

gaggccagtc acctgttgga ggatcccgat gaagagacga gccaggctgt caaagccctt   5160

cgggagatgg ccgatactgt gattccccag aaggaagagg ctgcaatctg tggccaaatg   5220

gacctttccc atccgccccc aaggggccat ctggatgagc tgacaaccac acttgagtcc   5280

atgaccgagg atctgaacct ggactcaccc ctgaccccgg aattgaacga gattctggat   5340

accttcctga acgacgagtg cctcttgcat gccatgcata tcagcacagg actgtccatc   5400

ttcgacacat ctctgtttta a                                             5421
```

```
<210> SEQ ID NO 444
<211> LENGTH: 1806
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 444

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240
```

```
Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
        515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655
```

-continued

```
Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
        675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
    770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Ala
            820                 825                 830

Arg Gly Glu Arg Asn Leu Leu Tyr Ile Val Val Val Asp Gly Lys Gly
        835                 840                 845

Asn Ile Val Glu Gln Tyr Ser Leu Asn Glu Ile Ile Asn Asn Phe Asn
    850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
            900                 905                 910

Glu Leu Val Glu Lys Tyr Asp Ala Val Ile Ala Leu Glu Asp Leu Asn
        915                 920                 925

Ser Gly Phe Lys Asn Ser Arg Val Lys Val Glu Lys Gln Val Tyr Gln
    930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu  Thr Ser Lys Ile Asp  Pro Ser Thr
        995                 1000                1005

Gly Phe  Val Asn Leu Leu Lys  Thr Lys Tyr Thr Ser  Ile Ala Asp
    1010                1015                1020

Ser Lys  Lys Phe Ile Ser Ser  Phe Asp Arg Ile Met  Tyr Val Pro
    1025                1030                1035

Glu Glu  Asp Leu Phe Glu Phe  Ala Leu Asp Tyr Lys  Asn Phe Ser
    1040                1045                1050

Arg Thr  Asp Ala Asp Tyr Ile  Lys Lys Trp Lys Leu  Tyr Ser Tyr
    1055                1060                1065

Gly Asn  Arg Ile Arg Ile Phe  Arg Asn Pro Lys Lys  Asn Asn Val
```

-continued

```
    1070                1075                1080

Phe Asp  Trp Glu Glu Val Cys  Leu Thr Ser Ala Tyr  Lys Glu Leu
    1085                1090                1095

Phe Asn  Lys Tyr Gly Ile Asn  Tyr Gln Gln Gly Asp  Ile Arg Ala
    1100                1105                1110

Leu Leu  Cys Glu Gln Ser Asp  Lys Ala Phe Tyr Ser  Ser Phe Met
    1115                1120                1125

Ala Leu  Met Ser Leu Met Leu  Gln Met Arg Asn Ser  Ile Thr Gly
    1130                1135                1140

Arg Thr  Asp Val Asp Phe Leu  Ile Ser Pro Val Lys  Asn Ser Asp
    1145                1150                1155

Gly Ile  Phe Tyr Asp Ser Arg  Asn Tyr Glu Ala Gln  Glu Asn Ala
    1160                1165                1170

Ile Leu  Pro Lys Asn Ala Asp  Ala Asn Gly Ala Tyr  Asn Ile Ala
    1175                1180                1185

Arg Lys  Val Leu Trp Ala Ile  Gly Gln Phe Lys Lys  Ala Glu Asp
    1190                1195                1200

Glu Lys  Leu Asp Lys Val Lys  Ile Ala Ile Ser Asn  Lys Glu Trp
    1205                1210                1215

Leu Glu  Tyr Ala Gln Thr Ser  Val Lys His Lys Arg  Pro Ala Ala
    1220                1225                1230

Thr Lys  Lys Ala Gly Gln Ala  Lys Lys Lys Lys Gly  Ser Tyr Pro
    1235                1240                1245

Tyr Asp  Val Pro Asp Tyr Ala  Tyr Pro Tyr Asp Val  Pro Asp Tyr
    1250                1255                1260

Ala Tyr  Pro Tyr Asp Val Pro  Asp Tyr Ala Gly Ser  Glu Ala Ser
    1265                1270                1275

Gly Ser  Gly Arg Ala Asp Ala  Leu Asp Asp Phe Asp  Leu Asp Met
    1280                1285                1290

Leu Gly  Ser Asp Ala Leu Asp  Asp Phe Asp Leu Asp  Met Leu Gly
    1295                1300                1305

Ser Asp  Ala Leu Asp Asp Phe  Asp Leu Asp Met Leu  Gly Ser Asp
    1310                1315                1320

Ala Leu  Asp Asp Phe Asp Leu  Asp Met Leu Ile Asn  Ser Arg Ser
    1325                1330                1335

Ser Gly  Ser Pro Lys Lys Lys  Arg Lys Val Gly Ser  Gln Tyr Leu
    1340                1345                1350

Pro Asp  Thr Asp Asp Arg His  Arg Ile Glu Glu Lys  Arg Lys Arg
    1355                1360                1365

Thr Tyr  Glu Thr Phe Lys Ser  Ile Met Lys Lys Ser  Pro Phe Ser
    1370                1375                1380

Gly Pro  Thr Asp Pro Arg Pro  Pro Pro Arg Arg Ile  Ala Val Pro
    1385                1390                1395

Ser Arg  Ser Ser Ala Ser Val  Pro Lys Pro Ala Pro  Gln Pro Tyr
    1400                1405                1410

Pro Phe  Thr Ser Ser Leu Ser  Thr Ile Asn Tyr Asp  Glu Phe Pro
    1415                1420                1425

Thr Met  Val Phe Pro Ser Gly  Gln Ile Ser Gln Ala  Ser Ala Leu
    1430                1435                1440

Ala Pro  Ala Pro Pro Gln Val  Leu Pro Gln Ala Pro  Ala Pro Ala
    1445                1450                1455

Pro Ala  Pro Ala Met Val Ser  Ala Leu Ala Gln Ala  Pro Ala Pro
    1460                1465                1470
```

-continued

Val Pro Val Leu Ala Pro Gly Pro Pro Gln Ala Val Ala Pro Pro
1475 1480 1485

Ala Pro Lys Pro Thr Gln Ala Gly Glu Gly Thr Leu Ser Glu Ala
1490 1495 1500

Leu Leu Gln Leu Gln Phe Asp Asp Glu Asp Leu Gly Ala Leu Leu
1505 1510 1515

Gly Asn Ser Thr Asp Pro Ala Val Phe Thr Asp Leu Ala Ser Val
1520 1525 1530

Asp Asn Ser Glu Phe Gln Gln Leu Leu Asn Gln Gly Ile Pro Val
1535 1540 1545

Ala Pro His Thr Thr Glu Pro Met Leu Met Glu Tyr Pro Glu Ala
1550 1555 1560

Ile Thr Arg Leu Val Thr Gly Ala Gln Arg Pro Pro Asp Pro Ala
1565 1570 1575

Pro Ala Pro Leu Gly Ala Pro Gly Leu Pro Asn Gly Leu Leu Ser
1580 1585 1590

Gly Asp Glu Asp Phe Ser Ser Ile Ala Asp Met Asp Phe Ser Ala
1595 1600 1605

Leu Leu Gly Ser Gly Ser Gly Ser Arg Asp Ser Arg Glu Gly Met
1610 1615 1620

Phe Leu Pro Lys Pro Glu Ala Gly Ser Ala Ile Ser Asp Val Phe
1625 1630 1635

Glu Gly Arg Glu Val Cys Gln Pro Lys Arg Ile Arg Pro Phe His
1640 1645 1650

Pro Pro Gly Ser Pro Trp Ala Asn Arg Pro Leu Pro Ala Ser Leu
1655 1660 1665

Ala Pro Thr Pro Thr Gly Pro Val His Glu Pro Val Gly Ser Leu
1670 1675 1680

Thr Pro Ala Pro Val Pro Gln Pro Leu Asp Pro Ala Pro Ala Val
1685 1690 1695

Thr Pro Glu Ala Ser His Leu Leu Glu Asp Pro Asp Glu Glu Thr
1700 1705 1710

Ser Gln Ala Val Lys Ala Leu Arg Glu Met Ala Asp Thr Val Ile
1715 1720 1725

Pro Gln Lys Glu Glu Ala Ala Ile Cys Gly Gln Met Asp Leu Ser
1730 1735 1740

His Pro Pro Pro Arg Gly His Leu Asp Glu Leu Thr Thr Thr Leu
1745 1750 1755

Glu Ser Met Thr Glu Asp Leu Asn Leu Asp Ser Pro Leu Thr Pro
1760 1765 1770

Glu Leu Asn Glu Ile Leu Asp Thr Phe Leu Asn Asp Glu Cys Leu
1775 1780 1785

Leu His Ala Met His Ile Ser Thr Gly Leu Ser Ile Phe Asp Thr
1790 1795 1800

Ser Leu Phe
1805

<210> SEQ ID NO 445
<211> LENGTH: 5130
<212> TYPE: DNA
<213> ORGANISM: Artificial Sequence
<220> FEATURE:
<223> OTHER INFORMATION: Description of Artificial Sequence: Synthetic polynucleotide -continued

<400> SEQUENCE: 445

```
atgggcccaa agaaaaagag gaaagtcggc agtggaccta aaaagaaacg aaaggttggg     60
tcaggtagct cagagactgg cccagtggct gtggacccca cattgagacg gcggatcgag    120
ccccatgagt ttgaggtatt cttcgatccg agagagctcc gcaaggagac ctgcctgctt    180
tacgaaatta attggggggg ccggcactcc atttggcgac atacatcaca gaacactaac    240
aagcacgtcg aagtcaactt catcgagaag ttcacgacag aaagatattt ctgtccgaac    300
acaaggtgca gcattacctg gtttctcagc tggagcccat gcggcgaatg tagtagggcc    360
atcactgaat tcctgtcaag gtatccccac gtcactctgt ttatttacat cgcaaggctg    420
taccaccacg ctgacccccg caatcgacaa ggcctgcggg atttgatctc ttcaggtgtg    480
actatccaaa ttatgactga gcaggagtca ggatactgct ggagaaactt tgtgaattat    540
agcccgagta atgaagccca ctggcctagg tatccccatc tgtgggtacg actgtacgtt    600
cttgaactgt actgcatcat actgggcctg cctccttgtc tcaacattct gagaaggaag    660
cagccacagc tgacattctt taccatcgct cttcagtctt gtcattacca gcgactgccc    720
ccacacattc tctgggccac cgggttgaaa tctggtggtt cttctggtgg ttctagcggc    780
agcgagactc ccgggacctc agagtccgcc acacccgaaa gttccggagg gagtagcggc    840
gggtctacac agttcgaggg ctttaccaac ctgtatcagg tgagcaagac actgcggttt    900
gagctgatcc cacagggcaa gaccctgaag cacatccagg agcagggctt catcgaggag    960
gacaaggccc gcaatgatca ctacaaggag ctgaagccca tcatcgatcg gatctacaag   1020
acctatgccg accagtgcct gcagctggtg cagctggatt gggagaacct gagcgccgcc   1080
atcgactcct atagaaagga gaaaaccgag gagacaagga acgccctgat cgaggagcag   1140
gccacatatc gcaatgccat ccacgactac ttcatcggcc ggacagacaa cctgaccgat   1200
gccatcaata agagacacgc cgagatctac aagggcctgt tcaaggccga gctgtttaat   1260
ggcaaggtgc tgaagcagct gggcaccgtg accacaaccg agcacgagaa cgccctgctg   1320
cggagcttcg acaagtttac aacctacttc tccggctttt atgagaacag gaagaacgtg   1380
ttcagcgccg aggatatcag cacagccatc ccacaccgca tcgtgcagga caacttcccc   1440
aagtttaagg agaattgtca catcttcaca cgcctgatca ccgccgtgcc cagcctgcgg   1500
gagcactttg agaacgtgaa gaaggccatc ggcatcttcg tgagcacctc catcgaggag   1560
gtgttttcct tccctttta taaccagctg ctgacacaga cccagatcga cctgtataac    1620
cagctgctgg gaggaatctc tcgggaggca ggcaccgaga agatcaaggg cctgaacgag   1680
gtgctgaatc tggccatcca gaagaatgat gagacagccc acatcatcgc ctccctgcca   1740
cacagattca tcccctgtt taagcagatc ctgtccgata ggaacaccct gtctttcatc    1800
ctggaggagt ttaagagcga cgaggaagtg atccagtcct tctgcaagta caagacactg   1860
ctgagaaacg agaacgtgct ggagacagcc gaggccctgt ttaacgagct gaacagcatc   1920
gacctgacac acatcttcat cagccacaag aagctggaga caatcagcag cgccctgtgc   1980
gaccactggg atacactgag gaatgccctg tatgagcgga gaatctccga gctgacaggc   2040
aagatcacca agtctgccaa ggagaaggtg cagcgcagcc tgaagcacga ggatatcaac   2100
ctgcaggaga tcatctctgc cgcaggcaag gagctgagcg aggccttcaa gcagaaaacc   2160
agcgagatcc tgtcccacgc acacgccgcc ctggatcagc cactgcctac aaccctgaag   2220
aagcaggagg agaaggagat cctgaagtct cagctggaca gcctgctggg cctgtaccac   2280
ctgctggact ggtttgccgt ggatgagtcc aacgaggtgg accccgagtt ctctgcccgg   2340
```

-continued

```
ctgaccggca tcaagctgga gatggagcct tctctgagct tctacaacaa ggccagaaat   2400
tatgccacca agaagcccta ctccgtggag aagttcaagc tgaactttca gatgcctaca   2460
ctggcctctg gctgggacgt gaataaggag aagaacaatg gcgccatcct gtttgtgaag   2520
aacggcctgt actatctggg catcatgcca aagcagaagg gcaggtataa ggccctgagc   2580
ttcgagccca cagagaaaac cagcgagggc tttgataaga tgtactatga ctacttccct   2640
gatgccgcca agatgatccc aaagtgcagc acccagctga aggccgtgac agcccacttt   2700
cagacccaca caaccccat cctgctgtcc aacaatttca tcgagcctct ggagatcaca   2760
aaggagatct acgacctgaa caatcctgag aaggagccaa agaagtttca gacagcctac   2820
gccaagaaaa ccggcgacca gaagggctac agagaggccc tgtgcaagtg gatcgacttc   2880
acaagggatt ttctgtccaa gtataccaag acaacctcta tcgatctgtc tagcctgcgg   2940
ccatcctctc agtataagga cctgggcgag tactatgccg agctgaatcc cctgctgtac   3000
cacatcagct tccagagaat cgccgagaag gagatcatgg atgccgtgga gacaggcaag   3060
ctgtacctgt tccagatcta taacaaggac tttgccaagg gccaccacgg caagcctaat   3120
ctgcacacac tgtattggac cggcctgttt tctccagaga acctggccaa gacaagcatc   3180
aagctgaatg gccaggccga gctgttctac cgccctaagt ccaggatgaa gaggatggca   3240
caccggctgg gagagaagat gctgaacaag aagctgaagg atcagaaaac cccaatcccc   3300
gacaccctgt accaggagct gtacgactat gtgaatcaca gactgtccca cgacctgtct   3360
gatgaggcca gggccctgct gcccaacgtg atcaccaagg aggtgtctca cgagatcatc   3420
aaggataggc gctttaccag cgacaagttc tttttccacg tgcctatcac actgaactat   3480
caggccgcca attccccatc taagttcaac cagagggtga atgcctacct gaaggagcac   3540
cccgagacac ctatcatcgg catcgcccgg ggcgagagaa acctgatcta tatcacagtg   3600
atcgactcca ccggcaagat cctggagcag cggagcctga acaccatcca gcagtttgat   3660
taccagaaga agctggacaa cagggagaag gagagggtgg cagcaaggca ggcctggtct   3720
gtggtgggca caatcaagga tctgaagcag ggctatctga gccaggtcat ccacgagatc   3780
gtggacctga tgatccacta ccaggccgtg gtggtgctgg agaacctgaa tttcggcttt   3840
aagagcaaga ggaccggcat cgccgagaag gccgtgtacc agcagttcga gaagatgctg   3900
atcgataagc tgaattgcct ggtgctgaag gactatccag cagagaaagt gggaggcgtg   3960
ctgaacccat accagctgac agaccagttc acctcctttg ccaagatggg cacccagtct   4020
ggcttcctgt tttacgtgcc tgccccatat acatctaaga tcgatcccct gaccggcttc   4080
gtggacccct tcgtgtggaa aaccatcaag aatcacgaga gccgcaagca cttcctggag   4140
ggcttcgact ttctgcacta cgacgtgaaa accggcgact tcatcctgca ctttaagatg   4200
aacagaaatc tgtccttcca gaggggcctg cccggcttta tgcctgcatg ggatatcgtg   4260
ttcgagaaga acgagacaca gtttgacgcc aagggcaccc ctttcatcgc cggcaagaga   4320
atcgtgccag tgatcgagaa tcacagattc accggcagat accgggacct gtatcctgcc   4380
aacgagctga tcgccctgct ggaggagaag ggcatcgtgt tcagggatgg ctccaacatc   4440
ctgccaaagc tgctggagaa tgacgattct cacgccatcg acacgatggt ggccctgatc   4500
cgcagcgtgc tgcagatgcg gaactccaat gccgccacag gcgaggacta tatcaacagc   4560
cccgtgcgcg atctgaatgg cgtgtgcttc gactcccggt ttcagaaccc agagtggcca   4620
atggacgccg atgccaatgg cgcctaccac atcgccctga agggccagct gctgctgaat   4680
```

-continued

```
cacctgaagg agagcaagga tctgaagctg cagaacggca tctccaatca ggactggctg   4740

gcctacatcc aggagctgcg caacaaaagg ccggcggcca cgaaaaaggc cggccaggca   4800

aaaaagaaaa agggatcctc tggtggttct ggaggatctg gtggttctac taatctgtca   4860

gatattattg aaaaggagac cggtaagcaa ctggttatcc aggaatccat cctcatgctc   4920

ccagaggagg tggaagaagt cattgggaac aagccggaaa gcgatatact cgtgcacacc   4980

gcctacgacg agagcaccga cgagaatgtc atgcttctga ctagcgacgc ccctgaatac   5040

aagccttggg ctctggtcat acaggatagc aacggtgaga acaagattaa gatgctctct   5100

ggtggttctc ccaagaagaa gaggaaagtc                                    5130
```

```
<210> SEQ ID NO 446
<211> LENGTH: 1710
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 446

Met Gly Pro Lys Lys Lys Arg Lys Val Gly Ser Gly Pro Lys Lys Lys
1               5                   10                  15

Arg Lys Val Gly Ser Gly Ser Ser Glu Thr Gly Pro Val Ala Val Asp
            20                  25                  30

Pro Thr Leu Arg Arg Arg Ile Glu Pro His Glu Phe Glu Val Phe Phe
        35                  40                  45

Asp Pro Arg Glu Leu Arg Lys Glu Thr Cys Leu Leu Tyr Glu Ile Asn
    50                  55                  60

Trp Gly Gly Arg His Ser Ile Trp Arg His Thr Ser Gln Asn Thr Asn
65                  70                  75                  80

Lys His Val Glu Val Asn Phe Ile Glu Lys Phe Thr Thr Glu Arg Tyr
                85                  90                  95

Phe Cys Pro Asn Thr Arg Cys Ser Ile Thr Trp Phe Leu Ser Trp Ser
            100                 105                 110

Pro Cys Gly Glu Cys Ser Arg Ala Ile Thr Glu Phe Leu Ser Arg Tyr
        115                 120                 125

Pro His Val Thr Leu Phe Ile Tyr Ile Ala Arg Leu Tyr His His Ala
    130                 135                 140

Asp Pro Arg Asn Arg Gln Gly Leu Arg Asp Leu Ile Ser Ser Gly Val
145                 150                 155                 160

Thr Ile Gln Ile Met Thr Glu Gln Glu Ser Gly Tyr Cys Trp Arg Asn
                165                 170                 175

Phe Val Asn Tyr Ser Pro Ser Asn Glu Ala His Trp Pro Arg Tyr Pro
            180                 185                 190

His Leu Trp Val Arg Leu Tyr Val Leu Glu Leu Tyr Cys Ile Ile Leu
        195                 200                 205

Gly Leu Pro Pro Cys Leu Asn Ile Leu Arg Arg Lys Gln Pro Gln Leu
    210                 215                 220

Thr Phe Phe Thr Ile Ala Leu Gln Ser Cys His Tyr Gln Arg Leu Pro
225                 230                 235                 240

Pro His Ile Leu Trp Ala Thr Gly Leu Lys Ser Gly Gly Ser Ser Gly
                245                 250                 255

Gly Ser Ser Gly Ser Glu Thr Pro Gly Thr Ser Glu Ser Ala Thr Pro
            260                 265                 270

Glu Ser Ser Gly Gly Ser Ser Gly Gly Ser Thr Gln Phe Glu Gly Phe
```

```
        275                 280                 285

Thr Asn Leu Tyr Gln Val Ser Lys Thr Leu Arg Phe Glu Leu Ile Pro
    290                 295                 300

Gln Gly Lys Thr Leu Lys His Ile Gln Glu Gln Gly Phe Ile Glu Glu
305                 310                 315                 320

Asp Lys Ala Arg Asn Asp His Tyr Lys Glu Leu Lys Pro Ile Ile Asp
                325                 330                 335

Arg Ile Tyr Lys Thr Tyr Ala Asp Gln Cys Leu Gln Leu Val Gln Leu
            340                 345                 350

Asp Trp Glu Asn Leu Ser Ala Ala Ile Asp Ser Tyr Arg Lys Glu Lys
        355                 360                 365

Thr Glu Glu Thr Arg Asn Ala Leu Ile Glu Glu Gln Ala Thr Tyr Arg
    370                 375                 380

Asn Ala Ile His Asp Tyr Phe Ile Gly Arg Thr Asp Asn Leu Thr Asp
385                 390                 395                 400

Ala Ile Asn Lys Arg His Ala Glu Ile Tyr Lys Gly Leu Phe Lys Ala
                405                 410                 415

Glu Leu Phe Asn Gly Lys Val Leu Lys Gln Leu Gly Thr Val Thr Thr
            420                 425                 430

Thr Glu His Glu Asn Ala Leu Leu Arg Ser Phe Asp Lys Phe Thr Thr
        435                 440                 445

Tyr Phe Ser Gly Phe Tyr Glu Asn Arg Lys Asn Val Phe Ser Ala Glu
    450                 455                 460

Asp Ile Ser Thr Ala Ile Pro His Arg Ile Val Gln Asp Asn Phe Pro
465                 470                 475                 480

Lys Phe Lys Glu Asn Cys His Ile Phe Thr Arg Leu Ile Thr Ala Val
                485                 490                 495

Pro Ser Leu Arg Glu His Phe Glu Asn Val Lys Lys Ala Ile Gly Ile
            500                 505                 510

Phe Val Ser Thr Ser Ile Glu Glu Val Phe Ser Phe Pro Phe Tyr Asn
        515                 520                 525

Gln Leu Leu Thr Gln Thr Gln Ile Asp Leu Tyr Asn Gln Leu Leu Gly
    530                 535                 540

Gly Ile Ser Arg Glu Ala Gly Thr Glu Lys Ile Lys Gly Leu Asn Glu
545                 550                 555                 560

Val Leu Asn Leu Ala Ile Gln Lys Asn Asp Glu Thr Ala His Ile Ile
                565                 570                 575

Ala Ser Leu Pro His Arg Phe Ile Pro Leu Phe Lys Gln Ile Leu Ser
            580                 585                 590

Asp Arg Asn Thr Leu Ser Phe Ile Leu Glu Glu Phe Lys Ser Asp Glu
        595                 600                 605

Glu Val Ile Gln Ser Phe Cys Lys Tyr Lys Thr Leu Leu Arg Asn Glu
    610                 615                 620

Asn Val Leu Glu Thr Ala Glu Ala Leu Phe Asn Glu Leu Asn Ser Ile
625                 630                 635                 640

Asp Leu Thr His Ile Phe Ile Ser His Lys Lys Leu Glu Thr Ile Ser
                645                 650                 655

Ser Ala Leu Cys Asp His Trp Asp Thr Leu Arg Asn Ala Leu Tyr Glu
            660                 665                 670

Arg Arg Ile Ser Glu Leu Thr Gly Lys Ile Thr Lys Ser Ala Lys Glu
        675                 680                 685

Lys Val Gln Arg Ser Leu Lys His Glu Asp Ile Asn Leu Gln Glu Ile
    690                 695                 700
```

-continued

```
Ile Ser Ala Ala Gly Lys Glu Leu Ser Glu Ala Phe Lys Gln Lys Thr
705                 710                 715                 720

Ser Glu Ile Leu Ser His Ala His Ala Ala Leu Asp Gln Pro Leu Pro
                725                 730                 735

Thr Thr Leu Lys Lys Gln Glu Glu Lys Glu Ile Leu Lys Ser Gln Leu
            740                 745                 750

Asp Ser Leu Leu Gly Leu Tyr His Leu Leu Asp Trp Phe Ala Val Asp
        755                 760                 765

Glu Ser Asn Glu Val Asp Pro Glu Phe Ser Ala Arg Leu Thr Gly Ile
    770                 775                 780

Lys Leu Glu Met Glu Pro Ser Leu Ser Phe Tyr Asn Lys Ala Arg Asn
785                 790                 795                 800

Tyr Ala Thr Lys Lys Pro Tyr Ser Val Glu Lys Phe Lys Leu Asn Phe
                805                 810                 815

Gln Met Pro Thr Leu Ala Ser Gly Trp Asp Val Asn Lys Glu Lys Asn
            820                 825                 830

Asn Gly Ala Ile Leu Phe Val Lys Asn Gly Leu Tyr Tyr Leu Gly Ile
        835                 840                 845

Met Pro Lys Gln Lys Gly Arg Tyr Lys Ala Leu Ser Phe Glu Pro Thr
    850                 855                 860

Glu Lys Thr Ser Glu Gly Phe Asp Lys Met Tyr Tyr Asp Tyr Phe Pro
865                 870                 875                 880

Asp Ala Ala Lys Met Ile Pro Lys Cys Ser Thr Gln Leu Lys Ala Val
                885                 890                 895

Thr Ala His Phe Gln Thr His Thr Thr Pro Ile Leu Leu Ser Asn Asn
            900                 905                 910

Phe Ile Glu Pro Leu Glu Ile Thr Lys Glu Ile Tyr Asp Leu Asn Asn
        915                 920                 925

Pro Glu Lys Glu Pro Lys Lys Phe Gln Thr Ala Tyr Ala Lys Lys Thr
    930                 935                 940

Gly Asp Gln Lys Gly Tyr Arg Glu Ala Leu Cys Lys Trp Ile Asp Phe
945                 950                 955                 960

Thr Arg Asp Phe Leu Ser Lys Tyr Thr Lys Thr Thr Ser Ile Asp Leu
                965                 970                 975

Ser Ser Leu Arg Pro Ser Ser Gln Tyr Lys Asp Leu Gly Glu Tyr Tyr
            980                 985                 990

Ala Glu Leu Asn Pro Leu Leu Tyr  His Ile Ser Phe Gln  Arg Ile Ala
        995                 1000                1005

Glu Lys  Glu Ile Met Asp Ala  Val Glu Thr Gly Lys  Leu Tyr Leu
    1010                1015                1020

Phe Gln  Ile Tyr Asn Lys Asp  Phe Ala Lys Gly His  His Gly Lys
    1025                1030                1035

Pro Asn  Leu His Thr Leu Tyr  Trp Thr Gly Leu Phe  Ser Pro Glu
    1040                1045                1050

Asn Leu  Ala Lys Thr Ser Ile  Lys Leu Asn Gly Gln  Ala Glu Leu
    1055                1060                1065

Phe Tyr  Arg Pro Lys Ser Arg  Met Lys Arg Met Ala  His Arg Leu
    1070                1075                1080

Gly Glu  Lys Met Leu Asn Lys  Lys Leu Lys Asp Gln  Lys Thr Pro
    1085                1090                1095

Ile Pro  Asp Thr Leu Tyr Gln  Glu Leu Tyr Asp Tyr  Val Asn His
    1100                1105                1110
```

-continued

Arg Leu Ser His Asp Leu Ser Asp Glu Ala Arg Ala Leu Leu Pro
1115 1120 1125

Asn Val Ile Thr Lys Glu Val Ser His Glu Ile Ile Lys Asp Arg
1130 1135 1140

Arg Phe Thr Ser Asp Lys Phe Phe Phe His Val Pro Ile Thr Leu
1145 1150 1155

Asn Tyr Gln Ala Ala Asn Ser Pro Ser Lys Phe Asn Gln Arg Val
1160 1165 1170

Asn Ala Tyr Leu Lys Glu His Pro Glu Thr Pro Ile Ile Gly Ile
1175 1180 1185

Ala Arg Gly Glu Arg Asn Leu Ile Tyr Ile Thr Val Ile Asp Ser
1190 1195 1200

Thr Gly Lys Ile Leu Glu Gln Arg Ser Leu Asn Thr Ile Gln Gln
1205 1210 1215

Phe Asp Tyr Gln Lys Lys Leu Asp Asn Arg Glu Lys Glu Arg Val
1220 1225 1230

Ala Ala Arg Gln Ala Trp Ser Val Val Gly Thr Ile Lys Asp Leu
1235 1240 1245

Lys Gln Gly Tyr Leu Ser Gln Val Ile His Glu Ile Val Asp Leu
1250 1255 1260

Met Ile His Tyr Gln Ala Val Val Val Leu Glu Asn Leu Asn Phe
1265 1270 1275

Gly Phe Lys Ser Lys Arg Thr Gly Ile Ala Glu Lys Ala Val Tyr
1280 1285 1290

Gln Gln Phe Glu Lys Met Leu Ile Asp Lys Leu Asn Cys Leu Val
1295 1300 1305

Leu Lys Asp Tyr Pro Ala Glu Lys Val Gly Gly Val Leu Asn Pro
1310 1315 1320

Tyr Gln Leu Thr Asp Gln Phe Thr Ser Phe Ala Lys Met Gly Thr
1325 1330 1335

Gln Ser Gly Phe Leu Phe Tyr Val Pro Ala Pro Tyr Thr Ser Lys
1340 1345 1350

Ile Asp Pro Leu Thr Gly Phe Val Asp Pro Phe Val Trp Lys Thr
1355 1360 1365

Ile Lys Asn His Glu Ser Arg Lys His Phe Leu Glu Gly Phe Asp
1370 1375 1380

Phe Leu His Tyr Asp Val Lys Thr Gly Asp Phe Ile Leu His Phe
1385 1390 1395

Lys Met Asn Arg Asn Leu Ser Phe Gln Arg Gly Leu Pro Gly Phe
1400 1405 1410

Met Pro Ala Trp Asp Ile Val Phe Glu Lys Asn Glu Thr Gln Phe
1415 1420 1425

Asp Ala Lys Gly Thr Pro Phe Ile Ala Gly Lys Arg Ile Val Pro
1430 1435 1440

Val Ile Glu Asn His Arg Phe Thr Gly Arg Tyr Arg Asp Leu Tyr
1445 1450 1455

Pro Ala Asn Glu Leu Ile Ala Leu Leu Glu Glu Lys Gly Ile Val
1460 1465 1470

Phe Arg Asp Gly Ser Asn Ile Leu Pro Lys Leu Leu Glu Asn Asp
1475 1480 1485

Asp Ser His Ala Ile Asp Thr Met Val Ala Leu Ile Arg Ser Val
1490 1495 1500

Leu Gln Met Arg Asn Ser Asn Ala Ala Thr Gly Glu Asp Tyr Ile

```
    1505                1510                1515

Asn Ser  Pro Val Arg Asp Leu  Asn Gly Val Cys Phe  Asp Ser Arg
    1520                1525                1530

Phe Gln  Asn Pro Glu Trp Pro  Met Asp Ala Asp Ala  Asn Gly Ala
    1535                1540                1545

Tyr His  Ile Ala Leu Lys Gly  Gln Leu Leu Leu Asn  His Leu Lys
    1550                1555                1560

Glu Ser  Lys Asp Leu Lys Leu  Gln Asn Gly Ile Ser  Asn Gln Asp
    1565                1570                1575

Trp Leu  Ala Tyr Ile Gln Glu  Leu Arg Asn Lys Arg  Pro Ala Ala
    1580                1585                1590

Thr Lys  Lys Ala Gly Gln Ala  Lys Lys Lys Lys Gly  Ser Ser Gly
    1595                1600                1605

Gly Ser  Gly Gly Ser Gly Gly  Ser Thr Asn Leu Ser  Asp Ile Ile
    1610                1615                1620

Glu Lys  Glu Thr Gly Lys Gln  Leu Val Ile Gln Glu  Ser Ile Leu
    1625                1630                1635

Met Leu  Pro Glu Glu Val Glu  Glu Val Ile Gly Asn  Lys Pro Glu
    1640                1645                1650

Ser Asp  Ile Leu Val His Thr  Ala Tyr Asp Glu Ser  Thr Asp Glu
    1655                1660                1665

Asn Val  Met Leu Leu Thr Ser  Asp Ala Pro Glu Tyr  Lys Pro Trp
    1670                1675                1680

Ala Leu  Val Ile Gln Asp Ser  Asn Gly Glu Asn Lys  Ile Lys Met
    1685                1690                1695

Leu Ser  Gly Gly Ser Pro Lys  Lys Lys Arg Lys Val
    1700                1705                1710


<210> SEQ ID NO 447
<211> LENGTH: 5130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 447

atgggcccaa agaaaaagag gaaagtcggc agtggaccta aaaagaaacg aaaggttggg     60

tcaggtagct cagagactgg cccagtggct gtggacccca cattgagacg gcggatcgag    120

ccccatgagt ttgaggtatt cttcgatccg agagagctcc gcaaggagac ctgcctgctt    180

tacgaaatta attggggggg ccggcactcc atttggcgac atacatcaca gaacactaac    240

aagcacgtcg aagtcaactt catcgagaag ttcacgacag aaagatattt ctgtccgaac    300

acaaggtgca gcattacctg gtttctcagc tggagcccat gcggcgaatg tagtagggcc    360

atcactgaat tcctgtcaag gtatccccac gtcactctgt ttatttacat cgcaaggctg    420

taccaccacg ctgacccccg caatcgacaa ggcctgcggg atttgatctc ttcaggtgtg    480

actatccaaa ttatgactga gcaggagtca ggatactgct ggagaaactt tgtgaattat    540

agcccgagta atgaagccca ctggcctagg tatccccatc tgtgggtacg actgtacgtt    600

cttgaactgt actgcatcat actgggcctg cctccttgtc tcaacattct gagaaggaag    660

cagccacagc tgacattctt taccatcgct cttcagtctt gtcattacca gcgactgccc    720

ccacacattc tctgggccac cgggttgaaa tctggtggtt cttctggtgg ttctagcggc    780

agcgagactc ccgggacctc agagtccgcc acacccgaaa gttccggagg gagtagcggc    840
```

-continued gggtctacac agttcgaggg ctttaccaac ctgtatcagg tgagcaagac actgcggttt 900
gagctgatcc cacagggcaa gaccctgaag cacatccagg agcagggctt catcgaggag 960
gacaaggccc gcaatgatca ctacaaggag ctgaagccca tcatcgatcg gatctacaag 1020
acctatgccg accagtgcct gcagctggtg cagctggatt gggagaacct gagcgccgcc 1080
atcgactcct atagaaagga gaaaaccgag gagacaagga acgccctgat cgaggagcag 1140
gccacatatc gcaatgccat ccacgactac ttcatcggcc ggacagacaa cctgaccgat 1200
gccatcaata agagacacgc cgagatctac aagggcctgt tcaaggccga gctgtttaat 1260
ggcaaggtgc tgaagcagct gggcaccgtg accacaaccg agcacgagaa cgccctgctg 1320
cggagcttcg acaagtttac aacctacttc tccggctttt atgccaacag gaagaacgtg 1380
ttcagcgccg aggatatcag cacagccatc ccacaccgca tcgtgcagga caacttcccc 1440
aagtttaagg agaattgtca catcttcaca cgcctgatca ccgccgtgcc cagcctgcgg 1500
gagcactttg agaacgtgaa gaaggccatc ggcatcttcg tgagcacctc catcgaggag 1560
gtgttttcct tccctttttta taaccagctg ctgacacaga cccagatcga cctgtataac 1620
cagctgctgg gaggaatctc tcgggaggca ggcaccgaga agatcaaggg cctgaacgag 1680
gtgctgaatc tggccatcca gaagaatgat gagacagccc acatcatcgc ctccctgcca 1740
cacagattca tcccccctgtt taagcagatc ctgtccgata ggaacaccct gtctttcatc 1800
ctggaggagt ttaagagcga cgaggaagtg atccagtcct tctgcaagta caagacactg 1860
ctgagaaacg agaacgtgct ggagacagcc gaggccctgt ttaacgagct gaacagcatc 1920
gacctgacac acatcttcat cagccacaag aagctggaga caatcagcag cgccctgtgc 1980
gaccactggg atacactgag gaatgccctg tatgagcgga gaatctccga gctgacaggc 2040
aagatcacca agtctgccaa ggagaaggtg cagcgcagcc tgaagcacga ggatatcaac 2100
ctgcaggaga tcatctctgc cgcaggcaag gagctgagcg aggccttcaa gcagaaaacc 2160
agcgagatcc tgtcccacgc acacgccgcc ctggatcagc cactgcctac aaccctgaag 2220
aagcaggagg agaaggagat cctgaagtct cagctggaca gcctgctggg cctgtaccac 2280
ctgctggact ggtttgccgt ggatgagtcc aacgaggtgg accccgagtt ctctgcccgg 2340
ctgaccggca tcaagctgga gatggagcct tctctgagct tctacaacaa ggccagaaat 2400
tatgccacca agaagcccta ctccgtggag aagttcaagc tgaactttca gatgcctaca 2460
ctggccgccg gctgggacgt gaataaggcc aagaacaatg gcgccatcct gtttgtgaag 2520
aacggcctgt actatctggg catcatgcca aagcagaagg gcaggtataa ggccctgagc 2580
ttcgagccca cagagaaaac cagcgagggc tttgataaga tgtactatga ctacttccct 2640
gatgccgcca agatgatccc aaagtgcagc acccagctga aggccgtgac agcccacttt 2700
cagacccaca caaccccccat cctgctgtcc aacaatttca tcgagcctct ggagatcaca 2760
aaggagatct acgacctgaa caatcctgag aaggagccaa agaagtttca gacagcctac 2820
gccaagaaaa ccggcgacca gaagggctac agagaggccc tgtgcaagtg gatcgacttc 2880
acaagggatt ttctgtccaa gtataccaag acaacctcta tcgatctgtc tagcctgcgg 2940
ccatcctctc agtataagga cctgggcgag tactatgccg agctgaatcc cctgctgtac 3000
cacatcagct tccagagaat cgccgagaag gagatcatgg atgccgtgga gacaggcaag 3060
ctgtacctgt tccagatcta taacaaggac tttgccaagg gccaccacgg caagcctaat 3120
ctgcacacac tgtattggac cggcctgttt tctccagaga acctggccaa gacaagcatc 3180
aagctgaatg gccaggccga gctgttctac cgccctaagt ccaggatgaa gaggatggca 3240
caccggctgg gagagaagat gctgaacaag aagctgaagg atcagaaaac cccaatcccc 3300
gacaccctgt accaggagct gtacgactat gtgaatcaca gactgtccca cgacctgtct 3360
gatgaggcca gggccctgct gcccaacgtg atcaccaagg aggtgtctca cgagatcatc 3420
aaggataggc gctttaccag cgacaagttc tttttccacg tgcctatcac actgaactat 3480
caggccgcca attccccatc taagttcaac cagagggtga atgcctacct gaaggagcac 3540
cccgagacac ctatcatcgg catcgcccgg ggcgagagaa acctgatcta tatcacagtg 3600
atcgactcca ccggcaagat cctggagcag cggagcctga acaccatcca gcagtttgat 3660
taccagaaga agctggacaa cagggagaag gagagggtgg cagcaaggca ggcctggtct 3720
gtggtgggca caatcaagga tctgaagcag ggctatctga gccaggtcat ccacgagatc 3780
gtggacctga tgatccacta ccaggccgtg gtggtgctgg agaacctgaa tttcggcttt 3840
aagagcaaga ggaccggcat cgccgagaag gccgtgtacc agcagttcga gaagatgctg 3900
atcgataagc tgaattgcct ggtgctgaag gactatccag cagagaaagt gggaggcgtg 3960
ctgaacccat accagctgac agaccagttc acctcctttg ccaagatggg cacccagtct 4020
ggcttcctgt tttacgtgcc tgccccatat acatctaaga tcgatcccct gaccggcttc 4080
gtggacccct tcgtgtggaa aaccatcaag aatcacgaga gccgcaagca cttcctggag 4140
ggcttcgact ttctgcacta cgacgtgaaa accggcgact tcatcctgca ctttaagatg 4200
aacagaaatc tgtccttcca gaggggcctg cccggcttta tgcctgcatg ggatatcgtg 4260
ttcgagaaga acgagacaca gtttgacgcc aagggcaccc ctttcatcgc cggcaagaga 4320
atcgtgccag tgatcgagaa tcacagattc accggcagat accgggacct gtatcctgcc 4380
aacgagctga tcgccctgct ggaggagaag ggcatcgtgt tcagggatgg ctccaacatc 4440
ctgccaaagc tgctggagaa tgacgattct cacgccatcg acacgatggt ggccctgatc 4500
cgcagcgtgc tgcagatgcg gaactccaat gccgccacag gcgaggacta tatcaacagc 4560
cccgtgcgcg atctgaatgg cgtgtgcttc gactcccggt ttcagaaccc agagtggcca 4620
atggacgccg atgccaatgg cgcctaccac atcgccctga agggccagct gctgctgaat 4680
cacctgaagg agagcaagga tctgaagctg cagaacggca tctccaatca ggactggctg 4740
gcctacatcc aggagctgcg caacaaaagg ccggcggcca cgaaaaaggc cggccaggca 4800
aaaaagaaaa agggatcctc tggtggttct ggaggatctg gtggttctac taatctgtca 4860
gatattattg aaaaggagac cggtaagcaa ctggttatcc aggaatccat cctcatgctc 4920
ccagaggagg tggaagaagt cattgggaac aagccggaaa gcgatatact cgtgcacacc 4980
gcctacgacg agagcaccga cgagaatgtc atgcttctga ctagcgacgc ccctgaatac 5040
aagccttggg ctctggtcat acaggatagc aacggtgaga acaagattaa gatgctctct 5100
ggtggttctc ccaagaagaa gaggaaagtc 5130

<210> SEQ ID NO 448
<211> LENGTH: 1710
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 448

Met Gly Pro Lys Lys Lys Arg Lys Val Gly Ser Gly Pro Lys Lys Lys
1 5 10 15

-continued

```
Arg Lys Val Gly Ser Gly Ser Ser Glu Thr Gly Pro Val Ala Val Asp
            20                  25                  30

Pro Thr Leu Arg Arg Arg Ile Glu Pro His Glu Phe Glu Val Phe Phe
        35                  40                  45

Asp Pro Arg Glu Leu Arg Lys Glu Thr Cys Leu Leu Tyr Glu Ile Asn
    50                  55                  60

Trp Gly Gly Arg His Ser Ile Trp Arg His Thr Ser Gln Asn Thr Asn
65                  70                  75                  80

Lys His Val Glu Val Asn Phe Ile Glu Lys Phe Thr Thr Glu Arg Tyr
                85                  90                  95

Phe Cys Pro Asn Thr Arg Cys Ser Ile Thr Trp Phe Leu Ser Trp Ser
            100                 105                 110

Pro Cys Gly Glu Cys Ser Arg Ala Ile Thr Glu Phe Leu Ser Arg Tyr
        115                 120                 125

Pro His Val Thr Leu Phe Ile Tyr Ile Ala Arg Leu Tyr His His Ala
    130                 135                 140

Asp Pro Arg Asn Arg Gln Gly Leu Arg Asp Leu Ile Ser Ser Gly Val
145                 150                 155                 160

Thr Ile Gln Ile Met Thr Glu Gln Glu Ser Gly Tyr Cys Trp Arg Asn
                165                 170                 175

Phe Val Asn Tyr Ser Pro Ser Asn Glu Ala His Trp Pro Arg Tyr Pro
            180                 185                 190

His Leu Trp Val Arg Leu Tyr Val Leu Glu Leu Tyr Cys Ile Ile Leu
        195                 200                 205

Gly Leu Pro Pro Cys Leu Asn Ile Leu Arg Arg Lys Gln Pro Gln Leu
    210                 215                 220

Thr Phe Phe Thr Ile Ala Leu Gln Ser Cys His Tyr Gln Arg Leu Pro
225                 230                 235                 240

Pro His Ile Leu Trp Ala Thr Gly Leu Lys Ser Gly Gly Ser Ser Gly
                245                 250                 255

Gly Ser Ser Gly Ser Glu Thr Pro Gly Thr Ser Glu Ser Ala Thr Pro
            260                 265                 270

Glu Ser Ser Gly Gly Ser Ser Gly Gly Ser Thr Gln Phe Glu Gly Phe
        275                 280                 285

Thr Asn Leu Tyr Gln Val Ser Lys Thr Leu Arg Phe Glu Leu Ile Pro
    290                 295                 300

Gln Gly Lys Thr Leu Lys His Ile Gln Glu Gln Gly Phe Ile Glu Glu
305                 310                 315                 320

Asp Lys Ala Arg Asn Asp His Tyr Lys Glu Leu Lys Pro Ile Ile Asp
                325                 330                 335

Arg Ile Tyr Lys Thr Tyr Ala Asp Gln Cys Leu Gln Leu Val Gln Leu
            340                 345                 350

Asp Trp Glu Asn Leu Ser Ala Ala Ile Asp Ser Tyr Arg Lys Glu Lys
        355                 360                 365

Thr Glu Glu Thr Arg Asn Ala Leu Ile Glu Glu Gln Ala Thr Tyr Arg
    370                 375                 380

Asn Ala Ile His Asp Tyr Phe Ile Gly Arg Thr Asp Asn Leu Thr Asp
385                 390                 395                 400

Ala Ile Asn Lys Arg His Ala Glu Ile Tyr Lys Gly Leu Phe Lys Ala
                405                 410                 415

Glu Leu Phe Asn Gly Lys Val Leu Lys Gln Leu Gly Thr Val Thr Thr
            420                 425                 430
```

-continued

```
Thr Glu His Glu Asn Ala Leu Leu Arg Ser Phe Asp Lys Phe Thr Thr
        435                 440                 445

Tyr Phe Ser Gly Phe Tyr Arg Asn Arg Lys Asn Val Phe Ser Ala Glu
    450                 455                 460

Asp Ile Ser Thr Ala Ile Pro His Arg Ile Val Gln Asp Asn Phe Pro
465                 470                 475                 480

Lys Phe Lys Glu Asn Cys His Ile Phe Thr Arg Leu Ile Thr Ala Val
                485                 490                 495

Pro Ser Leu Arg Glu His Phe Glu Asn Val Lys Lys Ala Ile Gly Ile
            500                 505                 510

Phe Val Ser Thr Ser Ile Glu Glu Val Phe Ser Phe Pro Phe Tyr Asn
        515                 520                 525

Gln Leu Leu Thr Gln Thr Gln Ile Asp Leu Tyr Asn Gln Leu Leu Gly
    530                 535                 540

Gly Ile Ser Arg Glu Ala Gly Thr Glu Lys Ile Lys Gly Leu Asn Glu
545                 550                 555                 560

Val Leu Asn Leu Ala Ile Gln Lys Asn Asp Glu Thr Ala His Ile Ile
                565                 570                 575

Ala Ser Leu Pro His Arg Phe Ile Pro Leu Phe Lys Gln Ile Leu Ser
            580                 585                 590

Asp Arg Asn Thr Leu Ser Phe Ile Leu Glu Glu Phe Lys Ser Asp Glu
        595                 600                 605

Glu Val Ile Gln Ser Phe Cys Lys Tyr Lys Thr Leu Leu Arg Asn Glu
    610                 615                 620

Asn Val Leu Glu Thr Ala Glu Ala Leu Phe Asn Glu Leu Asn Ser Ile
625                 630                 635                 640

Asp Leu Thr His Ile Phe Ile Ser His Lys Lys Leu Glu Thr Ile Ser
                645                 650                 655

Ser Ala Leu Cys Asp His Trp Asp Thr Leu Arg Asn Ala Leu Tyr Glu
            660                 665                 670

Arg Arg Ile Ser Glu Leu Thr Gly Lys Ile Thr Lys Ser Ala Lys Glu
        675                 680                 685

Lys Val Gln Arg Ser Leu Lys His Glu Asp Ile Asn Leu Gln Glu Ile
    690                 695                 700

Ile Ser Ala Ala Gly Lys Glu Leu Ser Glu Ala Phe Lys Gln Lys Thr
705                 710                 715                 720

Ser Glu Ile Leu Ser His Ala His Ala Ala Leu Asp Gln Pro Leu Pro
                725                 730                 735

Thr Thr Leu Lys Lys Gln Glu Glu Lys Glu Ile Leu Lys Ser Gln Leu
            740                 745                 750

Asp Ser Leu Leu Gly Leu Tyr His Leu Leu Asp Trp Phe Ala Val Asp
        755                 760                 765

Glu Ser Asn Glu Val Asp Pro Glu Phe Ser Ala Arg Leu Thr Gly Ile
    770                 775                 780

Lys Leu Glu Met Glu Pro Ser Leu Ser Phe Tyr Asn Lys Ala Arg Asn
785                 790                 795                 800

Tyr Ala Thr Lys Lys Pro Tyr Ser Val Glu Lys Phe Lys Leu Asn Phe
                805                 810                 815

Gln Met Pro Thr Leu Ala Arg Gly Trp Asp Val Asn Arg Glu Lys Asn
            820                 825                 830

Asn Gly Ala Ile Leu Phe Val Lys Asn Gly Leu Tyr Tyr Leu Gly Ile
        835                 840                 845

Met Pro Lys Gln Lys Gly Arg Tyr Lys Ala Leu Ser Phe Glu Pro Thr
```

```
    850                 855                 860

Glu Lys Thr Ser Glu Gly Phe Asp Lys Met Tyr Tyr Asp Tyr Phe Pro
865                 870                 875                 880

Asp Ala Ala Lys Met Ile Pro Lys Cys Ser Thr Gln Leu Lys Ala Val
                885                 890                 895

Thr Ala His Phe Gln Thr His Thr Thr Pro Ile Leu Leu Ser Asn Asn
            900                 905                 910

Phe Ile Glu Pro Leu Glu Ile Thr Lys Glu Ile Tyr Asp Leu Asn Asn
        915                 920                 925

Pro Glu Lys Glu Pro Lys Lys Phe Gln Thr Ala Tyr Ala Lys Lys Thr
    930                 935                 940

Gly Asp Gln Lys Gly Tyr Arg Glu Ala Leu Cys Lys Trp Ile Asp Phe
945                 950                 955                 960

Thr Arg Asp Phe Leu Ser Lys Tyr Thr Lys Thr Thr Ser Ile Asp Leu
                965                 970                 975

Ser Ser Leu Arg Pro Ser Ser Gln Tyr Lys Asp Leu Gly Glu Tyr Tyr
            980                 985                 990

Ala Glu Leu Asn Pro Leu Leu Tyr  His Ile Ser Phe Gln  Arg Ile Ala
        995                 1000                1005

Glu Lys  Glu Ile Met Asp Ala  Val Glu Thr Gly Lys  Leu Tyr Leu
    1010                 1015                1020

Phe Gln  Ile Tyr Asn Lys Asp  Phe Ala Lys Gly His  His Gly Lys
    1025                 1030                1035

Pro Asn  Leu His Thr Leu Tyr  Trp Thr Gly Leu Phe  Ser Pro Glu
    1040                 1045                1050

Asn Leu  Ala Lys Thr Ser Ile  Lys Leu Asn Gly Gln  Ala Glu Leu
    1055                 1060                1065

Phe Tyr  Arg Pro Lys Ser Arg  Met Lys Arg Met Ala  His Arg Leu
    1070                 1075                1080

Gly Glu  Lys Met Leu Asn Lys  Lys Leu Lys Asp Gln  Lys Thr Pro
    1085                 1090                1095

Ile Pro  Asp Thr Leu Tyr Gln  Glu Leu Tyr Asp Tyr  Val Asn His
    1100                 1105                1110

Arg Leu  Ser His Asp Leu Ser  Asp Glu Ala Arg Ala  Leu Leu Pro
    1115                 1120                1125

Asn Val  Ile Thr Lys Glu Val  Ser His Glu Ile Ile  Lys Asp Arg
    1130                 1135                1140

Arg Phe  Thr Ser Asp Lys Phe  Phe Phe His Val Pro  Ile Thr Leu
    1145                 1150                1155

Asn Tyr  Gln Ala Ala Asn Ser  Pro Ser Lys Phe Asn  Gln Arg Val
    1160                 1165                1170

Asn Ala  Tyr Leu Lys Glu His  Pro Glu Thr Pro Ile  Ile Gly Ile
    1175                 1180                1185

Ala Arg  Gly Glu Arg Asn Leu  Ile Tyr Ile Thr Val  Ile Asp Ser
    1190                 1195                1200

Thr Gly  Lys Ile Leu Glu Gln  Arg Ser Leu Asn Thr  Ile Gln Gln
    1205                 1210                1215

Phe Asp  Tyr Gln Lys Lys Leu  Asp Asn Arg Glu Lys  Glu Arg Val
    1220                 1225                1230

Ala Ala  Arg Gln Ala Trp Ser  Val Val Gly Thr Ile  Lys Asp Leu
    1235                 1240                1245

Lys Gln  Gly Tyr Leu Ser Gln  Val Ile His Glu Ile  Val Asp Leu
    1250                 1255                1260
```

```
Met Ile His Tyr Gln Ala Val Val Val Leu Glu Asn Leu Asn Phe
    1265                1270                1275

Gly Phe Lys Ser Lys Arg Thr Gly Ile Ala Glu Lys Ala Val Tyr
    1280                1285                1290

Gln Gln Phe Glu Lys Met Leu Ile Asp Lys Leu Asn Cys Leu Val
    1295                1300                1305

Leu Lys Asp Tyr Pro Ala Glu Lys Val Gly Gly Val Leu Asn Pro
    1310                1315                1320

Tyr Gln Leu Thr Asp Gln Phe Thr Ser Phe Ala Lys Met Gly Thr
    1325                1330                1335

Gln Ser Gly Phe Leu Phe Tyr Val Pro Ala Pro Tyr Thr Ser Lys
    1340                1345                1350

Ile Asp Pro Leu Thr Gly Phe Val Asp Pro Phe Val Trp Lys Thr
    1355                1360                1365

Ile Lys Asn His Glu Ser Arg Lys His Phe Leu Glu Gly Phe Asp
    1370                1375                1380

Phe Leu His Tyr Asp Val Lys Thr Gly Asp Phe Ile Leu His Phe
    1385                1390                1395

Lys Met Asn Arg Asn Leu Ser Phe Gln Arg Gly Leu Pro Gly Phe
    1400                1405                1410

Met Pro Ala Trp Asp Ile Val Phe Glu Lys Asn Glu Thr Gln Phe
    1415                1420                1425

Asp Ala Lys Gly Thr Pro Phe Ile Ala Gly Lys Arg Ile Val Pro
    1430                1435                1440

Val Ile Glu Asn His Arg Phe Thr Gly Arg Tyr Arg Asp Leu Tyr
    1445                1450                1455

Pro Ala Asn Glu Leu Ile Ala Leu Leu Glu Glu Lys Gly Ile Val
    1460                1465                1470

Phe Arg Asp Gly Ser Asn Ile Leu Pro Lys Leu Leu Glu Asn Asp
    1475                1480                1485

Asp Ser His Ala Ile Asp Thr Met Val Ala Leu Ile Arg Ser Val
    1490                1495                1500

Leu Gln Met Arg Asn Ser Asn Ala Ala Thr Gly Glu Asp Tyr Ile
    1505                1510                1515

Asn Ser Pro Val Arg Asp Leu Asn Gly Val Cys Phe Asp Ser Arg
    1520                1525                1530

Phe Gln Asn Pro Glu Trp Pro Met Asp Ala Asp Ala Asn Gly Ala
    1535                1540                1545

Tyr His Ile Ala Leu Lys Gly Gln Leu Leu Leu Asn His Leu Lys
    1550                1555                1560

Glu Ser Lys Asp Leu Lys Leu Gln Asn Gly Ile Ser Asn Gln Asp
    1565                1570                1575

Trp Leu Ala Tyr Ile Gln Glu Leu Arg Asn Lys Arg Pro Ala Ala
    1580                1585                1590

Thr Lys Lys Ala Gly Gln Ala Lys Lys Lys Lys Gly Ser Ser Gly
    1595                1600                1605

Gly Ser Gly Gly Ser Gly Gly Ser Thr Asn Leu Ser Asp Ile Ile
    1610                1615                1620

Glu Lys Glu Thr Gly Lys Gln Leu Val Ile Gln Glu Ser Ile Leu
    1625                1630                1635

Met Leu Pro Glu Glu Val Glu Glu Val Ile Gly Asn Lys Pro Glu
    1640                1645                1650
```

Ser Asp Ile Leu Val His Thr Ala Tyr Asp Glu Ser Thr Asp Glu
    1655                1660                1665

Asn Val Met Leu Leu Thr Ser Asp Ala Pro Glu Tyr Lys Pro Trp
    1670                1675                1680

Ala Leu Val Ile Gln Asp Ser Asn Gly Glu Asn Lys Ile Lys Met
    1685                1690                1695

Leu Ser Gly Gly Ser Pro Lys Lys Lys Arg Lys Val
    1700                1705                1710

<210> SEQ ID NO 449
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 449
tttnctgatg gtccatgtct gtta 24

<210> SEQ ID NO 450
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 450
tttcctgatg gtccatgtct gaat 24

<210> SEQ ID NO 451
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
tttcctgatg gtccatgtct gtta 24

<210> SEQ ID NO 452
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452
tttcctgatg gtccacatct gtta 24

<210> SEQ ID NO 453
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 453
tttcctgatg gtccatatct gtgg 24

<210> SEQ ID NO 454
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 454
tttcctgatg gtccatacct gtta 24

<210> SEQ ID NO 455
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 455
tttcctgatg gtccacgcct gtta 24

<210> SEQ ID NO 456
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 456
gttcctgatg gtccacatct gtta 24

<210> SEQ ID NO 457
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 457
ttttgtgatg tttcatgtgt ccta 24

<210> SEQ ID NO 458
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 458
tttngctcag caggcacctg cctc 24

<210> SEQ ID NO 459
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 459
cttagctcag caggcacctg ccca 24

<210> SEQ ID NO 460
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 460
tttggctcag caggcacctg cctc 24

<210> SEQ ID NO 461
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 461
agcagctcag caggcacctg cctt 24

<210> SEQ ID NO 462
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 462
aacagctcag cagacacctg ccaa 24

<210> SEQ ID NO 463
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 463
tttagctcag ctgacacctg ccca 24

<210> SEQ ID NO 464
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 464
tccagctcag cagacaccag cctc 24

<210> SEQ ID NO 465
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 465
ttcccctcag cagacacctg ccat 24

<210> SEQ ID NO 466
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 466
ttcccctcag cagacacctg ccat 24

<210> SEQ ID NO 467
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 467
ttcccctcag cagacacctg ccat 24

<210> SEQ ID NO 468
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 468
ttcccctcag cggacacctg ccat 24

<210> SEQ ID NO 469
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 469
tttngattga aggaaaagtt acaa 24

<210> SEQ ID NO 470
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 470
tttagattga aggaaaagtt acaa 24

<210> SEQ ID NO 471
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 471
tttagattaa tggaaaagtt acaa 24

<210> SEQ ID NO 472
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 472
tttagactta aagaaaagtt acaa 24

<210> SEQ ID NO 473
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 473
cttggattaa aggaaaagct acaa 24

<210> SEQ ID NO 474
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 474
tttnggatgc cactaaaagg gaaa 24

<210> SEQ ID NO 475
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 475
tttaggatgc cactaaaagg gaaa 24

-continued

<210> SEQ ID NO 476
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 476
tttagaatgc cactaaaaaa agag 24

<210> SEQ ID NO 477
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 477
ttttgtatac cactaaaagg gaaa 24

<210> SEQ ID NO 478
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 478
attntgatga gcctttagag agaa 24

<210> SEQ ID NO 479
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 479
attctgatga gcctttagag agaa 24

<210> SEQ ID NO 480
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 480
tttgtgatga gcgttgagag aaag 24

<210> SEQ ID NO 481
<211> LENGTH: 24
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 481
tttttgatga gcctttagag tact 24

<210> SEQ ID NO 482
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482
aatgtgatga cccattagag agaa 24

<210> SEQ ID NO 483
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
tttatgatga gtctttagag tttt 24

<210> SEQ ID NO 484
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484
tttatgatgt acctttagaa agca 24

<210> SEQ ID NO 485
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 485
attnaccgag caggagtgag ggaa 24

<210> SEQ ID NO 486
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486
attcaccgag caggagtgag ggaa 24

<210> SEQ ID NO 487
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 487
tttacttgag cagaagtgag ggag 24

<210> SEQ ID NO 488
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 488
tttgactgag caggattgag ggaa 24

<210> SEQ ID NO 489
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 489
tttcctagag caggagtgag gata 24

<210> SEQ ID NO 490
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 490
cttnttgggt cagctgttaa catc 24

<210> SEQ ID NO 491
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 491
cttattgggt cagctgttaa catc 24

<210> SEQ ID NO 492
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 492
cattttgggt cagcacgtga catt 24

<210> SEQ ID NO 493
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 493
cttnacccag gttcataaca atgt 24

<210> SEQ ID NO 494
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 494
cttcacccag gttcataaca atgt 24

<210> SEQ ID NO 495
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 495
gttnatttgt ccagaggaaa ccac 24

<210> SEQ ID NO 496
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 496
gttcatttgt ccagaggaaa ccac 24

<210> SEQ ID NO 497
<211> LENGTH: 24

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 497
ttaattttgt ccaaaggaaa ccac 24

<210> SEQ ID NO 498
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 498
ttccatttgt ccacaggaaa cctc 24

<210> SEQ ID NO 499
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 499
tttcatttga ccaaagaaaa ccca 24

<210> SEQ ID NO 500
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 500
gccaatttgt cctgaggaaa ccac 24

<210> SEQ ID NO 501
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 501
cctcatttgt ccagaggaaa ctac 24

<210> SEQ ID NO 502
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 502
tttgctttgt acagaggaaa ccat 24

<210> SEQ ID NO 503
<211> LENGTH: 24
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 503
agtcatctgt cctgaggaaa ccac 24

<210> SEQ ID NO 504
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 504
attgattttt ccagagaaaa ccac 24

<210> SEQ ID NO 505
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 505
tttcattact ccagaagaaa ccac 24

<210> SEQ ID NO 506
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 506
gttnccttag cactctgcca ctta 24

<210> SEQ ID NO 507
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 507
gttcccttag cactctgcca ctta 24

<210> SEQ ID NO 508
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 508
ttccccttag ccatctgcca ccta 24

<210> SEQ ID NO 509
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 509
tttgccccag cactctgcca ctta 24

<210> SEQ ID NO 510
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 510
gttncctgtc ttgtttgtga gagg 24

<210> SEQ ID NO 511
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 511
gttccctgtc ttgtttgtga gagg 24

<210> SEQ ID NO 512
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 512
attacctgtc ttgtttggga gaga 24

<210> SEQ ID NO 513
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 513
tttgcctgtc ctgtgtgtga gatg 24

<210> SEQ ID NO 514
<211> LENGTH: 24

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 514
tttgcctgtc ttgttaatga gaaa 24

<210> SEQ ID NO 515
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 515
tttccctgtc ttcattgtga gaga 24

<210> SEQ ID NO 516
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 516
tatngcctct ccctgctcag aatc 24

<210> SEQ ID NO 517
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 517
tatcgcctct ccctgctcag aatc 24

<210> SEQ ID NO 518
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 518
tatnaacctg ggtgaagtcc caac 24

<210> SEQ ID NO 519
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 519
tatgaacctg ggtgaagtcc caac 24

<210> SEQ ID NO 520
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 520
tttgcacctg ggtgaagtcc caaa 24

<210> SEQ ID NO 521
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: misc_feature
<222> LOCATION: (4)..(4)
<223> OTHER INFORMATION: n is a, c, g, or t

<400> SEQUENCE: 521
ttcntgatgg tccatgtctg ttac 24

<210> SEQ ID NO 522
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 522
tttctgatgg tccatacctg ttac 24

<210> SEQ ID NO 523
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 523
ttcctgatgg tccatgtctg ttac 24

<210> SEQ ID NO 524
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 524
ttcctgatgg tccatgtctg aatt 24

<210> SEQ ID NO 525
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 525
cttctgatgg tccatatctg ttaa 24

<210> SEQ ID NO 526
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 526
ttcctgatgg tccacatctg ttaa 24

<210> SEQ ID NO 527
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 527
ttcctgatgg tccacatctg ttaa 24

<210> SEQ ID NO 528
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 528
ttcctgatgg tccatacctg ttaa 24

<210> SEQ ID NO 529
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 529
tttgtgatgt ttcatgtgtc ctag 24

<210> SEQ ID NO 530
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 530
ttcctgatgg tccatatctg tggc 24

<210> SEQ ID NO 531
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 531
ctttcttctc ccctctgctg gatacctctg 30

<210> SEQ ID NO 532
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 532
ctttatccgt gttccttgac tctgggcaac 30

<210> SEQ ID NO 533
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 533
gtttctcatc tgtgcccctc cctccctggc 30

<210> SEQ ID NO 534
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 534
ttttccgagc ttctggcggt ctcaagcact 30

<210> SEQ ID NO 535
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 535
gtttccctca ctcctgctcg gtgaatttgg 30

<210> SEQ ID NO 536
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 536
gtttcagcct caccctcta gccctacatc 30

<210> SEQ ID NO 537
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 537
gtttgtggtt gcccacccta gtcattggag 30

<210> SEQ ID NO 538
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 538
ctttggtcgg catggcccca ttcgcacggc 30

<210> SEQ ID NO 539
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 539
ggaatccctt ctgcagcacc tgg 23

<210> SEQ ID NO 540
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 540
ctgatggtcc atgtctgtta ctc 23

<210> SEQ ID NO 541
<211> LENGTH: 21
<212> TYPE: PRT
<213> ORGANISM: Acidaminococcus sp.

<400> SEQUENCE: 541

Ser Phe Asp Lys Phe Thr Thr Tyr Phe Ser Gly Phe Tyr Glu Asn Arg
1 5 10 15

Lys Asn Val Phe Ser
20

<210> SEQ ID NO 542
<211> LENGTH: 21
<212> TYPE: PRT
<213> ORGANISM: Unknown
<220> FEATURE:
<223> OTHER INFORMATION: Lachnospiraceae bacterium

<400> SEQUENCE: 542

```
Ser Phe Asn Gly Phe Thr Thr Ala Phe Thr Gly Phe Phe Asp Asn Arg
1               5                   10                  15

Glu Asn Met Phe Ser
            20


<210> SEQ ID NO 543
<211> LENGTH: 21
<212> TYPE: PRT
<213> ORGANISM: Francisella tularensis

<400> SEQUENCE: 543

Ser Phe Lys Gly Trp Thr Thr Tyr Phe Lys Gly Phe His Glu Asn Arg
1               5                   10                  15

Lys Asn Val Tyr Ser
            20


<210> SEQ ID NO 544
<211> LENGTH: 21
<212> TYPE: PRT
<213> ORGANISM: Moraxella bovoculi

<400> SEQUENCE: 544

His Phe Glu Lys Phe Ser Thr Tyr Phe Thr Gly Phe His Asp Asn Arg
1               5                   10                  15

Lys Asn Met Tyr Ser
            20


<210> SEQ ID NO 545
<211> LENGTH: 21
<212> TYPE: PRT
<213> ORGANISM: Thiomicrospira sp.

<400> SEQUENCE: 545

Thr Phe Asn Asn Phe Thr Thr Tyr Phe Thr Gly Phe His Glu Asn Arg
1               5                   10                  15

Lys Asn Ile Tyr Ser
            20


<210> SEQ ID NO 546
<211> LENGTH: 21
<212> TYPE: PRT
<213> ORGANISM: Moraxella bovoculi

<400> SEQUENCE: 546

His Phe Glu Lys Phe Ser Thr Tyr Phe Thr Gly Phe His Asp Asn Arg
1               5                   10                  15

Lys Asn Met Tyr Ser
            20


<210> SEQ ID NO 547
<211> LENGTH: 22
<212> TYPE: PRT
<213> ORGANISM: Acidaminococcus sp.

<400> SEQUENCE: 547

Asn Phe Gln Met Pro Thr Leu Ala Ser Gly Trp Asp Val Asn Lys Glu
1               5                   10                  15

Lys Asn Asn Gly Ala Ile
            20


<210> SEQ ID NO 548
```

<211> LENGTH: 22
<212> TYPE: PRT
<213> ORGANISM: Unknown
<220> FEATURE:
<223> OTHER INFORMATION: Lachnospiraceae bacterium

<400> SEQUENCE: 548

Tyr Phe Gln Asn Pro Gln Phe Met Gly Gly Trp Asp Lys Asp Lys Glu
1               5                   10                  15

Thr Asp Tyr Arg Ala Thr
            20

<210> SEQ ID NO 549
<211> LENGTH: 22
<212> TYPE: PRT
<213> ORGANISM: Francisella tularensis

<400> SEQUENCE: 549

Asn Phe Glu Asn Ser Thr Leu Ala Asn Gly Trp Asp Lys Asn Lys Glu
1               5                   10                  15

Pro Asp Asn Thr Ala Ile
            20

<210> SEQ ID NO 550
<211> LENGTH: 22
<212> TYPE: PRT
<213> ORGANISM: Moraxella bovoculi

<400> SEQUENCE: 550

Asn Phe Gly Asn Pro Thr Leu Leu Asn Gly Trp Asp Leu Asn Lys Glu
1               5                   10                  15

Lys Asp Asn Phe Gly Val
            20

<210> SEQ ID NO 551
<211> LENGTH: 22
<212> TYPE: PRT
<213> ORGANISM: Thiomicrospira sp.

<400> SEQUENCE: 551

Asn Phe Asp Asn Asn Thr Leu Leu Ser Gly Trp Asp Ala Asn Lys Glu
1               5                   10                  15

Thr Ala Asn Ala Ser Ile
            20

<210> SEQ ID NO 552
<211> LENGTH: 22
<212> TYPE: PRT
<213> ORGANISM: Moraxella bovoculi

<400> SEQUENCE: 552

Asn Phe Gly Asn Pro Thr Leu Leu Asn Gly Trp Asp Leu Asn Lys Glu
1               5                   10                  15

Lys Asp Asn Phe Gly Val
            20

<210> SEQ ID NO 553
<211> LENGTH: 24
<212> TYPE: DNA
<213> ORGANISM: Acidaminococcus sp.

<400> SEQUENCE: 553
tttccctcac tcctgctcgg tgaa                                              24

<210> SEQ ID NO 554
<211> LENGTH: 20
<212> TYPE: DNA
<213> ORGANISM: Acidaminococcus sp.

<400> SEQUENCE: 554
cctcactcct gctcggtgaa 20

<210> SEQ ID NO 555
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 555
cctcactgct gctcggtgaa 20

<210> SEQ ID NO 556
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 556
cctcactcgt gctcggtgaa 20

<210> SEQ ID NO 557
<211> LENGTH: 24
<212> TYPE: DNA
<213> ORGANISM: Acidaminococcus sp.

<400> SEQUENCE: 557
tttcctgatg gtccatgtct gtta 24

<210> SEQ ID NO 558
<211> LENGTH: 20
<212> TYPE: DNA
<213> ORGANISM: Acidaminococcus sp.

<400> SEQUENCE: 558
ctgatggtcc atgtctgtta 20

<210> SEQ ID NO 559
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 559
ctgatggacc atgtctgtta 20

<210> SEQ ID NO 560
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 560
ctgatggtgc atgtctgtta 20

<210> SEQ ID NO 561
<211> LENGTH: 6
<212> TYPE: PRT
<213> ORGANISM: Unknown
<220> FEATURE:
<223> OTHER INFORMATION: Lachnospiraceae bacterium

<400> SEQUENCE: 561

Met Ser Lys Leu Glu Lys
1 5

<210> SEQ ID NO 562
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 562

His His His His His His
1 5

<210> SEQ ID NO 563
<211> LENGTH: 7
<212> TYPE: PRT
<213> ORGANISM: Acidaminococcus sp.

<400> SEQUENCE: 563

Gly Leu Phe Lys Ala Glu Leu
1 5

<210> SEQ ID NO 564
<211> LENGTH: 21
<212> TYPE: PRT
<213> ORGANISM: Acidaminococcus sp.

<400> SEQUENCE: 564

Ser Phe Asp Lys Phe Thr Thr Tyr Phe Ser Gly Phe Tyr Glu Asn Arg
1 5 10 15

Lys Asn Val Phe Ser
20

<210> SEQ ID NO 565
<211> LENGTH: 22
<212> TYPE: PRT
<213> ORGANISM: Acidaminococcus sp.

<400> SEQUENCE: 565

Asn Phe Gln Met Pro Thr Leu Ala Ser Gly Trp Asp Val Asn Lys Glu
1 5 10 15

Lys Asn Asn Gly Ala Ile
20

<210> SEQ ID NO 566
<211> LENGTH: 22
<212> TYPE: PRT
<213> ORGANISM: Acidaminococcus sp.

<400> SEQUENCE: 566

Tyr Asp Tyr Phe Pro Asp Ala Ala Lys Met Ile Pro Lys Cys Ser Thr

-continued

```
1               5                   10                  15

Gln Leu Lys Ala Val Thr
            20


<210> SEQ ID NO 567
<211> LENGTH: 5
<212> TYPE: PRT
<213> ORGANISM: Acidaminococcus sp.

<400> SEQUENCE: 567

Leu Ser Asn Asn Phe
1               5


<210> SEQ ID NO 568
<211> LENGTH: 9
<212> TYPE: PRT
<213> ORGANISM: Acidaminococcus sp.

<400> SEQUENCE: 568

Ser Lys Tyr Thr Lys Thr Thr Ser Ile
1               5


<210> SEQ ID NO 569
<211> LENGTH: 7
<212> TYPE: PRT
<213> ORGANISM: Unknown
<220> FEATURE:
<223> OTHER INFORMATION: Lachnospiraceae bacterium

<400> SEQUENCE: 569

Ser Leu Phe Lys Lys Asp Ile
1               5


<210> SEQ ID NO 570
<211> LENGTH: 21
<212> TYPE: PRT
<213> ORGANISM: Unknown
<220> FEATURE:
<223> OTHER INFORMATION: Lachnospiraceae bacterium

<400> SEQUENCE: 570

Ser Phe Asn Gly Phe Thr Thr Ala Phe Thr Gly Phe Phe Asp Asn Arg
1               5                   10                  15

Glu Asn Met Phe Ser
            20


<210> SEQ ID NO 571
<211> LENGTH: 22
<212> TYPE: PRT
<213> ORGANISM: Unknown
<220> FEATURE:
<223> OTHER INFORMATION: Lachnospiraceae bacterium

<400> SEQUENCE: 571

Tyr Phe Gln Asn Pro Gln Phe Met Gly Gly Trp Asp Lys Asp Lys Glu
1               5                   10                  15

Thr Asp Tyr Arg Ala Thr
            20


<210> SEQ ID NO 572
<211> LENGTH: 22
<212> TYPE: PRT
<213> ORGANISM: Unknown
<220> FEATURE:
<223> OTHER INFORMATION: Lachnospiraceae bacterium
```

<400> SEQUENCE: 572

Tyr Lys Leu Leu Pro Gly Pro Asn Lys Met Leu Pro Lys Val Phe Phe
1               5                   10                  15

Ser Lys Lys Trp Met Ala
            20

<210> SEQ ID NO 573
<211> LENGTH: 5
<212> TYPE: PRT
<213> ORGANISM: Unknown
<220> FEATURE:
<223> OTHER INFORMATION: Lachnospiraceae bacterium

<400> SEQUENCE: 573

Phe Ser Lys Lys Trp
1               5

<210> SEQ ID NO 574
<211> LENGTH: 9
<212> TYPE: PRT
<213> ORGANISM: Unknown
<220> FEATURE:
<223> OTHER INFORMATION: Lachnospiraceae bacterium

<400> SEQUENCE: 574

Ser Arg Tyr Pro Lys Trp Ser Asn Ala
1               5

<210> SEQ ID NO 575
<211> LENGTH: 7
<212> TYPE: PRT
<213> ORGANISM: Unknown
<220> FEATURE:
<223> OTHER INFORMATION: Lachnospiraceae bacterium

<400> SEQUENCE: 575

Ser Leu Phe Lys Lys Asp Ile
1               5

<210> SEQ ID NO 576
<211> LENGTH: 21
<212> TYPE: PRT
<213> ORGANISM: Unknown
<220> FEATURE:
<223> OTHER INFORMATION: Lachnospiraceae bacterium

<400> SEQUENCE: 576

Ser Phe Asn Gly Phe Thr Thr Ala Phe Thr Gly Phe Phe Asp Asn Arg
1               5                   10                  15

Glu Asn Met Phe Ser
            20

<210> SEQ ID NO 577
<211> LENGTH: 22
<212> TYPE: PRT
<213> ORGANISM: Unknown
<220> FEATURE:
<223> OTHER INFORMATION: Lachnospiraceae bacterium

<400> SEQUENCE: 577

Tyr Phe Gln Asn Pro Gln Phe Met Gly Gly Trp Asp Lys Asp Lys Glu
1               5                   10                  15

Thr Asp Tyr Arg Ala Thr
            20

<210> SEQ ID NO 578
<211> LENGTH: 22
<212> TYPE: PRT
<213> ORGANISM: Unknown
<220> FEATURE:
<223> OTHER INFORMATION: Lachnospiraceae bacterium

<400> SEQUENCE: 578

Tyr Lys Leu Leu Pro Gly Pro Asn Lys Met Leu Pro Lys Val Phe Phe
1               5                   10                  15

Ser Lys Lys Trp Met Ala
            20

<210> SEQ ID NO 579
<211> LENGTH: 5
<212> TYPE: PRT
<213> ORGANISM: Unknown
<220> FEATURE:
<223> OTHER INFORMATION: Lachnospiraceae bacterium

<400> SEQUENCE: 579

Phe Ser Lys Lys Trp
1               5

<210> SEQ ID NO 580
<211> LENGTH: 9
<212> TYPE: PRT
<213> ORGANISM: Unknown
<220> FEATURE:
<223> OTHER INFORMATION: Lachnospiraceae bacterium

<400> SEQUENCE: 580

Ser Arg Tyr Pro Lys Trp Ser Asn Ala
1               5

<210> SEQ ID NO 581
<211> LENGTH: 6
<212> TYPE: PRT
<213> ORGANISM: Francisella tularensis

<400> SEQUENCE: 581

Leu Lys Gln Ser Lys Asp
1               5

<210> SEQ ID NO 582
<211> LENGTH: 21
<212> TYPE: PRT
<213> ORGANISM: Francisella tularensis

<400> SEQUENCE: 582

Ser Phe Lys Gly Trp Thr Thr Tyr Phe Lys Gly Phe His Glu Asn Arg
1               5                   10                  15

Lys Asn Val Tyr Ser
            20

<210> SEQ ID NO 583
<211> LENGTH: 22
<212> TYPE: PRT
<213> ORGANISM: Francisella tularensis

<400> SEQUENCE: 583

Asn Phe Glu Asn Ser Thr Leu Ala Asn Gly Trp Asp Lys Asn Lys Glu
1               5                   10                  15

-continued

```
Pro Asp Asn Thr Ala Ile
            20


<210> SEQ ID NO 584
<211> LENGTH: 22
<212> TYPE: PRT
<213> ORGANISM: Francisella tularensis

<400> SEQUENCE: 584

Tyr Lys Leu Leu Pro Gly Ala Asn Lys Met Leu Pro Lys Val Phe Phe
1               5                   10                  15

Ser Ala Lys Ser Ile Lys
            20


<210> SEQ ID NO 585
<211> LENGTH: 5
<212> TYPE: PRT
<213> ORGANISM: Francisella tularensis

<400> SEQUENCE: 585

Arg Ile Arg Asn His
1               5


<210> SEQ ID NO 586
<211> LENGTH: 9
<212> TYPE: PRT
<213> ORGANISM: Francisella tularensis

<400> SEQUENCE: 586

Ser Lys His Pro Glu Trp Lys Asp Phe
1               5
```